US011672874B2

(12) United States Patent
Getts et al.

(10) Patent No.: US 11,672,874 B2
(45) Date of Patent: *Jun. 13, 2023

(54) METHODS AND COMPOSITIONS FOR GENOMIC INTEGRATION

(71) Applicant: Myeloid Therapeutics, Inc., Cambridge, MA (US)

(72) Inventors: Daniel Getts, Stow, MA (US); Yuxiao Wang, Belmont, MA (US); Namita Bisaria, Somerville, MA (US); Inna Shcherbakova, Holliston, MA (US); Socheata Ly, North Billerica, MA (US)

(73) Assignee: MYELOID THERAPEUTICS, INC., Cambridge, MA (US)

( * ) Notice: Subject to any disclaimer, the term of this patent is extended or adjusted under 35 U.S.C. 154(b) by 4 days.

This patent is subject to a terminal disclaimer.

(21) Appl. No.: 17/499,232

(22) Filed: Oct. 12, 2021

(65) Prior Publication Data
US 2023/0067484 A1 Mar. 2, 2023

Related U.S. Application Data

(63) Continuation-in-part of application No. PCT/US2020/049240, filed on Sep. 3, 2020.

(60) Provisional application No. 63/039,261, filed on Jun. 15, 2020, provisional application No. 62/908,800, filed on Oct. 1, 2019, provisional application No. 62/895,441, filed on Sep. 3, 2019.

(51) Int. Cl.
| | | |
|---|---|---|
| *C12N 15/85* | (2006.01) | |
| *A61K 31/713* | (2006.01) | |
| *C12N 15/11* | (2006.01) | |
| *A61K 31/711* | (2006.01) | |
| *C07K 16/32* | (2006.01) | |
| *A61K 38/17* | (2006.01) | |
| *A61K 39/395* | (2006.01) | |
| *C07K 14/725* | (2006.01) | |
| *C12N 9/12* | (2006.01) | |
| *A61K 38/45* | (2006.01) | |
| *C12N 9/22* | (2006.01) | |
| *A61K 38/46* | (2006.01) | |
| *C12N 15/90* | (2006.01) | |
| *C12N 15/113* | (2010.01) | |
| *A61K 48/00* | (2006.01) | |

(52) U.S. Cl.
CPC ............ *C12N 15/85* (2013.01); *A61K 31/711* (2013.01); *A61K 31/713* (2013.01); *A61K 38/1774* (2013.01); *A61K 38/45* (2013.01); *A61K 38/465* (2013.01); *A61K 39/39558* (2013.01); *C07K 14/7051* (2013.01); *C07K 16/32* (2013.01); *C12N 9/1276* (2013.01); *C12N 9/22* (2013.01); *C12N 15/11* (2013.01); *C12N 15/113* (2013.01); *C12N 15/907* (2013.01); *C12Y 207/07049* (2013.01); *A61K 48/00* (2013.01); *C07K 2319/03* (2013.01); *C07K 2319/09* (2013.01); *C07K 2319/30* (2013.01); *C07K 2319/33* (2013.01); *C12N 2310/14* (2013.01); *C12N 2310/20* (2017.05); *C12N 2320/31* (2013.01); *C12N 2800/80* (2013.01); *C12N 2800/90* (2013.01); *C12N 2830/50* (2013.01); *C12N 2840/203* (2013.01)

(58) Field of Classification Search
CPC ........ C12N 15/85; C12N 9/1276; C12N 9/22; C12N 15/11; C12N 15/113; C12N 15/907; C12N 2310/14; C12N 2310/20; C12N 2320/31; C12N 2800/80; C12N 2800/90; C12N 2830/50; C12N 2840/203; A61K 31/711; A61K 31/713; A61K 38/1774; A61K 38/45; A61K 38/465; A61K 39/39558; A61K 48/00; C12Y 207/07049; C07K 14/7051; C07K 16/32; C07K 2319/03; C07K 2319/09; C07K 2319/30; C07K 2319/33
USPC ...................................................... 424/93.21
See application file for complete search history.

(56) References Cited

U.S. PATENT DOCUMENTS

| | | |
|---|---|---|
| 5,633,234 A | 5/1997 | August et al. |
| 5,773,244 A | 6/1998 | Ares, Jr. et al. |
| 5,776,910 A | 7/1998 | Schreiber et al. |
| 6,150,160 A | 11/2000 | Kazazian, Jr. et al. |
| 6,210,963 B1 | 4/2001 | Haddada et al. |
| 6,806,080 B2 | 10/2004 | Kasahara et al. |
| 7,833,789 B2 | 11/2010 | Naldini et al. |
| 8,198,020 B2 | 6/2012 | Francois et al. |
| 8,709,412 B2 | 4/2014 | Jones et al. |
| 8,932,860 B2 | 1/2015 | Rozwadowski et al. |
| 9,045,541 B2 | 6/2015 | Eckelman et al. |
| 9,149,519 B2 | 10/2015 | Landau et al. |
| 9,206,479 B2 | 12/2015 | Maquat et al. |
| 9,221,908 B2 | 12/2015 | Frazier et al. |

(Continued)

FOREIGN PATENT DOCUMENTS

| | | |
|---|---|---|
| CA | 2850380 C | 8/2015 |
| EP | 2205750 B1 | 3/2012 |

(Continued)

OTHER PUBLICATIONS

Ade et al. Gene 2018, vol. 642, pp. 188-198. (Year: 2018).*

(Continued)

*Primary Examiner* — Janet L Epps-Smith
(74) *Attorney, Agent, or Firm* — Wilson Sonsini Goodrich & Rosati

(57) ABSTRACT

Methods and composition for modulating a target genome and stable integration of a transgene of interest into the genome of a cell are disclosed.

26 Claims, 70 Drawing Sheets

Specification includes a Sequence Listing.

(56) References Cited

U.S. PATENT DOCUMENTS

| | | | |
|---|---|---|---|
| 9,353,370 B2 | 5/2016 | Carninci et al. | |
| 9,481,892 B2 | 11/2016 | Schumann et al. | |
| 9,518,116 B2 | 12/2016 | Frazier et al. | |
| 9,663,575 B2 | 5/2017 | Eckelman et al. | |
| 9,745,368 B2 | 8/2017 | Milone et al. | |
| 9,845,345 B2 | 12/2017 | Ring et al. | |
| 10,034,900 B2 | 7/2018 | Senju | |
| 10,081,680 B2 | 9/2018 | Weiskopf et al. | |
| 10,106,609 B2 | 10/2018 | Yang et al. | |
| 10,125,193 B2 | 11/2018 | Cooper et al. | |
| 10,166,255 B2 | 1/2019 | Moriarity et al. | |
| 10,172,880 B2 | 1/2019 | Osborn et al. | |
| 10,174,095 B2 | 1/2019 | Brogdon et al. | |
| 10,174,309 B2 | 1/2019 | Grawunder | |
| 10,184,122 B2 | 1/2019 | Grunenwald et al. | |
| 10,189,903 B2 | 1/2019 | Jensen | |
| 10,214,591 B1 * | 2/2019 | Spadafora | C07K 16/34 |
| 10,259,859 B2 | 4/2019 | Pons et al. | |
| 10,259,873 B2 | 4/2019 | Frazier et al. | |
| 10,415,017 B2 | 9/2019 | O'Neill | |
| 10,428,143 B2 | 10/2019 | Krummel et al. | |
| 10,774,125 B2 | 9/2020 | Ring et al. | |
| 2002/0103152 A1 | 8/2002 | Kay et al. | |
| 2003/0121063 A1 | 6/2003 | Kazazian, Jr. et al. | |
| 2004/0053873 A1 | 3/2004 | Barman et al. | |
| 2005/0031628 A1 | 2/2005 | George et al. | |
| 2006/0188891 A1 | 8/2006 | Bickmore, Jr. et al. | |
| 2007/0037759 A1 | 2/2007 | Deininger et al. | |
| 2008/0254027 A1 | 10/2008 | Bernett et al. | |
| 2011/0045591 A1 * | 2/2011 | Schumann | C12N 15/85 |
| | | | 435/320.1 |
| 2011/0171729 A1 | 7/2011 | Wang et al. | |
| 2011/0250203 A1 | 10/2011 | Klitgaard et al. | |
| 2011/0287038 A1 | 11/2011 | Slawin et al. | |
| 2011/0293603 A1 | 12/2011 | Saraiva et al. | |
| 2012/0045389 A1 * | 2/2012 | Gassull Duro | C12N 7/00 |
| | | | 977/773 |
| 2014/0134142 A1 | 5/2014 | Smith et al. | |
| 2014/0140989 A1 | 5/2014 | Eckelman et al. | |
| 2014/0161805 A1 | 6/2014 | Jamieson et al. | |
| 2014/0242701 A1 | 8/2014 | Shiku et al. | |
| 2015/0057161 A1 | 2/2015 | Schultze et al. | |
| 2015/0274826 A1 | 10/2015 | Frazier et al. | |
| 2016/0137733 A1 | 5/2016 | Frazier et al. | |
| 2016/0250258 A1 | 9/2016 | Delaney et al. | |
| 2016/0251435 A1 | 9/2016 | Eckelman et al. | |
| 2017/0087185 A1 | 3/2017 | Crane et al. | |
| 2017/0151281 A1 | 6/2017 | Wagner et al. | |
| 2017/0151282 A1 | 6/2017 | Discher et al. | |
| 2017/0166657 A1 | 6/2017 | O'Neill et al. | |
| 2017/0226183 A1 | 8/2017 | Schiffer-Mannioui | |
| 2017/0233452 A1 | 8/2017 | McIvor et al. | |
| 2017/0246278 A1 | 8/2017 | Vera Valdes et al. | |
| 2017/0275665 A1 | 9/2017 | Silas et al. | |
| 2017/0283498 A1 | 10/2017 | Frazier et al. | |
| 2017/0292118 A1 | 10/2017 | Duchateau et al. | |
| 2017/0369890 A1 | 12/2017 | Henriksen | |
| 2018/0000899 A1 | 1/2018 | Francois et al. | |
| 2018/0057592 A1 | 3/2018 | Frazier et al. | |
| 2018/0104308 A1 | 4/2018 | Mamonkin et al. | |
| 2018/0105600 A1 | 4/2018 | Pons et al. | |
| 2018/0133252 A9 | 5/2018 | Wilson et al. | |
| 2018/0135032 A1 | 5/2018 | Izsvak et al. | |
| 2018/0142019 A1 | 5/2018 | Manning et al. | |
| 2018/0171021 A1 | 6/2018 | Karlsson et al. | |
| 2018/0186878 A1 | 7/2018 | Rosenthal | |
| 2018/0221503 A1 | 8/2018 | Kadiyala et al. | |
| 2018/0244748 A1 | 8/2018 | Gill et al. | |
| 2018/0250395 A1 | 9/2018 | Pietsch et al. | |
| 2018/0265890 A1 | 9/2018 | Qian et al. | |
| 2018/0319883 A1 | 11/2018 | Weiskopf et al. | |
| 2018/0325953 A1 | 11/2018 | Poznansky et al. | |
| 2018/0355011 A1 | 12/2018 | Lim et al. | |
| 2019/0010219 A1 | 1/2019 | Short | |
| 2019/0023761 A1 | 1/2019 | Pule et al. | |
| 2019/0038671 A1 | 2/2019 | Fan et al. | |
| 2019/0040453 A1 | 2/2019 | Bibillo et al. | |
| 2019/0055297 A1 | 2/2019 | Zhao et al. | |
| 2019/0062450 A1 | 2/2019 | De Palma et al. | |
| 2019/0070277 A1 | 3/2019 | O'Neill et al. | |
| 2019/0112373 A1 | 4/2019 | Manning et al. | |
| 2019/0119379 A1 | 4/2019 | Gottschalk et al. | |
| 2019/0119396 A1 | 4/2019 | Liu et al. | |
| 2019/0144522 A1 | 5/2019 | Bari et al. | |
| 2019/0144863 A1 | 5/2019 | Lee et al. | |
| 2019/0169266 A1 | 6/2019 | Pons et al. | |
| 2019/0169637 A1 | 6/2019 | Hudecek et al. | |
| 2019/0169638 A1 | 6/2019 | Izsvak et al. | |
| 2019/0185880 A1 | 6/2019 | Shedlock et al. | |
| 2019/0233496 A1 | 8/2019 | Rosenthal | |
| 2019/0240343 A1 | 8/2019 | Ahmed et al. | |
| 2019/0248892 A1 | 8/2019 | Frazier et al. | |
| 2019/0263928 A1 | 8/2019 | Watanabe et al. | |
| 2019/0275150 A1 | 9/2019 | Pincetic et al. | |
| 2019/0323037 A1 | 10/2019 | Buerckstuemmer et al. | |
| 2019/0336615 A1 | 11/2019 | Thompson et al. | |
| 2019/0345217 A1 | 11/2019 | Ma et al. | |
| 2020/0109398 A1 | 4/2020 | Rubens et al. | |
| 2020/0345774 A1 | 11/2020 | Getts et al. | |
| 2021/0222163 A1 | 7/2021 | Wu et al. | |
| 2021/0252053 A1 | 8/2021 | Wagner et al. | |
| 2021/0285009 A1 | 9/2021 | Schaffer et al. | |
| 2021/0299172 A1 | 9/2021 | Getts et al. | |

FOREIGN PATENT DOCUMENTS

| | | | |
|---|---|---|---|
| EP | 2626415 A2 | 8/2013 | |
| EP | 2242512 B1 | 4/2016 | |
| EP | 3197495 A1 | 8/2017 | |
| EP | 3350335 A1 | 7/2018 | |
| EP | 2956343 B1 | 12/2018 | |
| EP | 3414333 A1 | 12/2018 | |
| EP | 3504244 A1 | 7/2019 | |
| EP | 3519441 A1 | 8/2019 | |
| EP | 3574018 A2 | 12/2019 | |
| GB | 2572005 A | 9/2019 | |
| WO | WO-1995005835 A1 | 3/1995 | |
| WO | WO-02077029 A2 | 10/2002 | |
| WO | WO-2004050855 A2 | 6/2004 | |
| WO | WO-2007113572 A1 | 10/2007 | |
| WO | WO-2008011599 A2 | 1/2008 | |
| WO | WO-2012005763 A1 | 1/2012 | |
| WO | WO-2014153114 A1 | 9/2014 | |
| WO | WO-2016030501 A * | 3/2016 | ......... A61K 48/0058 |
| WO | WO-2016070136 A1 | 5/2016 | |
| WO | WO-2016126608 A1 | 8/2016 | |
| WO | WO-2016149254 A1 | 9/2016 | |
| WO | WO-2016172606 A1 | 10/2016 | |
| WO | WO-2016205749 A1 | 12/2016 | |
| WO | WO-2017025944 A2 | 2/2017 | |
| WO | WO-2017044487 A1 | 3/2017 | |
| WO | WO-2017050884 A1 | 3/2017 | |
| WO | WO-2017136633 A1 | 8/2017 | |
| WO | WO-2017172981 A2 | 10/2017 | |
| WO | WO-2017219027 A1 | 12/2017 | |
| WO | WO-2017219934 A1 | 12/2017 | |
| WO | WO-2018064076 A1 | 4/2018 | |
| WO | WO-2018073394 A1 | 4/2018 | |
| WO | WO-2018083126 A1 | 5/2018 | |
| WO | WO-2018107129 A1 | 6/2018 | |
| WO | WO-2018169948 A1 | 9/2018 | |
| WO | WO-2018170340 A1 | 9/2018 | |
| WO | WO-2018231871 A1 | 12/2018 | |
| WO | WO-2019005641 A1 | 1/2019 | |
| WO | WO-2019010551 A1 | 1/2019 | |
| WO | WO-2019020089 A1 | 1/2019 | |
| WO | WO-2019020090 A1 | 1/2019 | |
| WO | WO-2019032624 A1 | 2/2019 | |
| WO | WO-2019050948 A1 | 3/2019 | |
| WO | WO-2019051424 A2 | 3/2019 | |
| WO | WO-2019055946 A1 | 3/2019 | |
| WO | WO-2019067328 A1 | 4/2019 | |
| WO | WO-2019070704 A1 | 4/2019 | |
| WO | WO-2019070843 A1 | 4/2019 | |

(56) References Cited

FOREIGN PATENT DOCUMENTS

| | | |
|---|---|---|
| WO | WO-2019086512 A1 | 5/2019 |
| WO | WO-2019090175 A1 | 5/2019 |
| WO | WO-2019129146 A1 | 7/2019 |
| WO | WO-2019191332 A1 | 10/2019 |
| WO | WO-2019191334 A1 | 10/2019 |
| WO | WO-2019191340 A1 | 10/2019 |
| WO | WO-2020006049 A1 | 1/2020 |
| WO | WO-2020047124 A1 | 3/2020 |
| WO | WO-2020095044 A1 | 5/2020 |
| WO | WO-2020097193 A1 | 5/2020 |
| WO | WO-2020150534 A9 * 8/2020 ............. A61K 35/17 |
| WO | WO-2020223550 A1 | 11/2020 |
| WO | WO-2020252208 A2 | 12/2020 |
| WO | WO-2020257727 A1 | 12/2020 |
| WO | WO-2021016075 A1 | 1/2021 |
| WO | WO-2021046243 A2 | 3/2021 |
| WO | WO-2021102042 A1 | 5/2021 |
| WO | WO-2021119538 A1 | 6/2021 |
| WO | WO-2021178709 A1 | 9/2021 |
| WO | WO-2021178717 A2 | 9/2021 |
| WO | WO-2021178720 A2 | 9/2021 |
| WO | WO-2021178898 A1 | 9/2021 |

OTHER PUBLICATIONS

Callahan et al. Nucleic Acids Research, 2012, vol. 40, No. 2 813-827. (Year: 2012).*
Li et al. Nucleic Acids Research, 2006, vol. 34, No. 3 853-864. (Year: 2006).*
"Bucheton, et al., "The Molecular basis of I-R Hybrid Dysgenesis in *Drosophila melanogaster*: Identification, Cloning, and Properties of the I Factor" (1984) Cell vol. 38, 153-163".
"Chadwick, et al., "Safety of a single aerosol administration of escalating doses of the cationic lipid GL-67/DOPE/EMPE-PEG 5000 formulation to the lungs of normal volunteers" (1997) Gene Therapy vol. 4, 937-942".
"De Koning, et al., "Repetitive Elements May Comprise Over two=Thirds of the Human Genome" (2011) PLoS vol. 7, Issue 2, p. 1-12".
"Dewannieux, et al., Endogenous retroviruses: acquisition, amplification and taming of genome invaders (2013) Science Direct, Current Opinion in Virology, 3:646-656".
"Dewannieux, et al., "L1-mediated Retrotransposition of Murine B1 and B2 SINEs Recapitulated in Cultured Cells" (2005) J. Mol. Bio. 349, 241-247".
"Dewannieux, et al., "LINE-mediated retrotransposition of marked Alu sequences" (2003) Nature Genetics vol. 35, No. 1, pp. 41-48".
"Eickbush, et al., "Evolution of the R2 Retrotransposon Ribozyme and Its self-Cleavage Site" (2013) PLoS vol. 8, Issue 9, p. 1-16".
"Fingl et al., 1975, in "The Pharmacological Basis of Therapeutics", Ch. 1 pl".
"Fujiwara, et al., "Site-specific non-LTR retrotransposons" (2014) Microbiology Spectrum, p. 1-16".
"Gao, et al. "Cationic liposome-medicated gene transfer" (1995) Gene Therapy, 2, pp. 710-722".
"Gokhale, et al., "Antisense raf oligodeoxyribonucleotide is protected by liposomal encapsulation and inhibits Raf-1 protein expression in vitro and in vivo: implication for gene therapy of radioresistant cancer" (1997) Gene Therapy vol. 4, pp. 1289-1299".
"Goddard, et al. "A second dose of CFTR cDNA-liposome complex is as effective as the first does in restoring cAMP-dependent chloride secretion to null CF mice trachea" (1997) Gene Therapy vol. 4, pp. 1231-1236".
"Gorman, et al., "Efficient in vivo delivery of DNA to pulmonary cells using the novel lipid EDMPC" (1997) Gene Therapy vol. 4, pp. 953-992".
"Ivic, et al. "Molecular Reconstruction of Sleeping Beauty, a Tc1-like Transposon from Fish, and Its Transposition in Human Cells" (1997) Cell vol. 91, p. 501-510".

"Ivics, et al. "Transposon-medicated Genome Manipulations in Vertebrates" (2009) Nat Methods 6(6): 415-422".
"Luan, et al., "Reverse Transcription of R2Bm RNA Is Primed by a Nick at the Chromosomal Target Site: A Mechanism for Non-LTR Retrotransposition" (1993) Cell, vol. 72, pp. 595-605".
"Manoj, et al. "Targeted insertion of large genetic payloads using ca directed LINE-1 reverse transcriptase" (2021) Scientific Reports Nature Portfolio p. 1-9".
"Monahan, et al., "Direct intramuscular injection with recombinant AAV vectors results in sustained expression in a dog model of hemophilia" (1998) Gene Therapy, 5, p. 40-49".
"Ni, et al. "Transposon tools hopping in vertebrates" (2008) Briefings in Functional Genomics and proteomics, vol. 7, No. 6, pp. 444-453 (2008)".
"Onodera, et al., "Successful Peripheral T-Lymphocyte-Directed Gene Transfer for a Patient With Severe Combined Immune Deficiency Caused by Adenosine Deaminase Deficiency" (1998) Blood vol. 91, No. 1, p. 30-36".
"Takahashi, et al., "A new family of site-specific retrotransposons, SART1, is inserted into telomeric repeats of the silkworm, *Bombyx mori*" (1997) Nucleic acids Research, vol. 25, No. 8, pp. 1-7".
Ahl et al.: Retrotransposition and Crystal Structure of an Alu RNP in the Ribosome-Stalling Conformation. Mol Cell. 60(5):715-727 doi:10.1016/j.molcel.2015.10.003 (2015).
Ali, M. et al., "Induction of neoantigen-reactive T cells from healthy donors", Nature Protocols (2019).
Alvey C, Discher DE. 2017. Engineering macrophages to eat Cancer: from "marker of self" CD47 and phagocytosis to differentiation. Journal of Leukocyte Biology 102:31-40.
Alvey CM, Spinier KR, Irianto J, Pfeifer CR, Hayes B, Xia Y, Cho S, Dingal P, Hsu J, Smith L, Tewari M, Discher DE. 2017. SIRPA-Inhibited, Marrow-Derived macrophages engorge, accumulate, and differentiate in Antibody-Targeted regression of solid tumors. Current Biology 27:2065-2077.
Andreesen R, Scheibenbogen C, Brugger W, Krause S, Meerpohl HG, Leser HG, Engler H, Lohr GW. 1990. Adoptive transfer of tumor cytotoxic macrophages generated in vitro from circulating blood monocytes: a new approach to Cancer immunotherapy. Cancer Research 50:7450-7456.
Andreu N, Phelan J, de Sessions PF, Cliff JM, Clark TG, Hibberd ML. 2017. Primary macrophages and J774 cells respond differently to infection with *Mycobacterium tuberculosis*. Scientific Reports 7:42225.
Anzalone, et al. Search-and-replace genome editing without double-strand breaks or donor DNA. Nature 576, 149-157 (2019).
Batista FD, Iber D, Neuberger MS. 2001. B cells acquire antigen from target cells after synapse formation. Nature 411:489-494.
Baxter et al.: Engineering domain fusion chimeras from 1-Onul family LAGLIDADG homing endonucleases. Nucleic Acids Res. 40(16):7985-8000 doi:10.1093/nar/gks502 (2012).
Beningo KA, Wang YL. 2002. Fc-receptor-mediated phagocytosis is regulated by mechanical properties of the target. Journal of Cell Science 115:849-856.
"Berger, et al., Efficient Elutriation of monocytes within a closed system (Elutra™) Journal of Immunological Methods 298 (2005) 61-72".
Bhattacharjee, J., et al., "Monocytes isolated by positive and negative magnetic sorting techniques show different molecular characteristics and immunophenotypic behaviour", F100Research (2018) pp. 1-13.
Biglari, A., et al. Human monocytes expressing a CEA-specific chimeric CD64 receptor specifically target CEA-expressing tumour cells in vitro and in vivo, Gene Therapy (2006) 13, 602-610.
Bournazos, et al., "The Role and Function of Fcγ Receptors on Myeloid Cells" Microbiol Spectr (2016) 4(6).
Brooks SR, Kirkham PM, Freeberg L, Carter RH. 2004. Binding of cytoplasmic proteins to the CD19 intracellular domain is high affinity, competitive, and multimeric. The Journal of Immunology 172:7556-7564.
Bu JY, Shaw AS, Chan AC. 1995. Analysis of the interaction of ZAP-70 and syk protein-tyrosine kinases with the T-cell antigen receptor by plasmon resonance. PNAS 92:5106-5110.

(56) References Cited

OTHER PUBLICATIONS

"Calderwood, David, "Integrin Activation" Journal of Cell Science (2004) 117, pp. 657-666".

Chao MP, Alizadeh AA, Tang C, Myklebust JH, Varghese B, Gill S, Jan M, Cha AC, Chan CK, Tan BT, Park CY,Zhao F, Kohrt HE, Malumbres R, Briones J, Gascoyne RD, Lossos IS, Levy R, Weissman IL, Majeti R. 2010. Anti-CD47 antibody synergizes with rituximab to promote phagocytosis and eradicate non-Hodgkin lymphoma. Cell 142:699-713.

Chen J, Zhong MC, Guo H, Davidson D, Mishel S, Lu Y, Rhee I, Pe' rez-Quintero LA, Zhang S, Cruz-Munoz ME, Wu N, Vinh DC, Sinha M, Calderon V, Lowell CA, Danska JS, Veillette A. 2017. SLAMF7 is critical for phagocytosis of haematopoietic tumour cells via Mac-1 integrin. Nature 544:493-497.

Cros, et al., "Human CD14dim) Monocytes Patrol and Sense Nucleic Acids and viruses via TLR7 and TLR8 Receptors", Immunity 33, 375-386, Sep. 24, 2010.

Cross SE, Jin YS, Rao J, Gimzewski JK. 2007. Nanomechanical analysis of cells from cancer patients. Nature Nanotechnology 2:780-783.

Davis SJ, van der Merwe PA. 2006. The kinetic-segregation model: TCR triggering and beyond. Nature Immunology 7:803-809.

De Oliveria, S, et al., "Modification of Hematopoietic Stem/Progenitor Cells with CD19-Specific Chimeric Antigen Receptros as a Novel Approach for Cancer Immunotherapy" Human Gene Therapy 24:824-839 (Oct. 2013).

Deininger: Alu elements: know the SINEs. Genome Biol. 12(12):236, pp. 1-21 doi:10.1186/gb-2011-12-12-236 (2011).

Doucet et al.: A 3' Poly(A) Tract Is Required for LINE-1 Retrotransposition. Mol Cell 60(5):728-741 doi:10.1016/j.molcel.2015.10.012 (2015).

Douse et al.: TASOR is a pseudo-PARP that directs HUSH complex assembly and epigenetic transposon control. Nature Communications 11(4940):1-16 (2020).

Edelstein A, Amodaj N, Hoover K, Vale R, Stuurman N. 2010. Computer control of microscopes using mmanager. Current Protocols in Molecular Biology 14:Unit14.20.

Engel P, Zhou LJ, Ord DC, Sato S, Koller B, Tedder TF. 1995. Abnormal B lymphocyte development, activation, and differentiation in mice that lack or overexpress the CD19 signal transduction molecule. Immunity 3:39-50.

Senju, Satoru, et al., "Generation and genetic modification of dendritic cells derived from mouse embryonic stem cells derived from mouse embryonic stem cells", Blood, May 1, 2003, vol. 101, No. 9, pp. 3501-3508.

Faulkner et al.: L1 retrotransposition in the soma: a field jumping ahead. Mob DNA 9:22, pp. 1-18 doi:10.1186/s13100-018-0128-1 (2018).

Fesnak AD, June CH, Levine BL. 2016. Engineered T cells: the promise and challenges of cancer immunotherapy. Nature Reviews Cancer 16:566-581.

Floor et al.: Get in LINE: Competition for Newly Minted Retrotransposon Proteins at the Ribosome. Molecular Cell 60(5):712-714 http://dx.doi.org/10.1016/j.molcel.2015.11.014 (2015).

Flynn et al.: Mammalian Y RNAs are modified at discrete guanosine residues with N-glycans. bioRxiv 787614 doi:https://doi.org/10.1101/787614 [1-31] (2019).

Fraser, A., et al., "Development, functional characterization and validation of methodology for GMP-compliant manufacture of phagocytic macrophages: A novel cellular therapeutic for liver cirrhosis", Cyotherapy, 2017, ISSN 1465-3249.

Frassinelli et al.: The RNA editing enzyme ADAR2 restricts L1 mobility. RNA Biol, pp. 1-13 doi:10.1080/15476286.2021.1940020 (2021).

Freeman SA, Goyette J, Furuya W, Woods EC, Bertozzi CR, Bergmeier W, Hinz B, van der Merwe PA, Das R, Grinstein S. 2016. Integrins Form an Expanding Diffusional Barrier that Coordinates Phagocytosis. Cell 164: 128-140.

Freeman SA, Grinstein S. 2014. Phagocytosis: receptors, signal integration, and the cytoskeleton. Immunological Reviews 262:193-215.

Gardai SJ, McPhillips KA, Frasch SC, Janssen WJ, Starefeldt A, Murphy-Ullrich JE, Bratton DL, Oldenborg PA, Michalak M, Henson PM. 2005. Cell-surface calreticulin initiates clearance of viable or apoptotic cells through trans-activation of LRP on the phagocyte. Cell 123:321-334.

Geissmann, et al., "Blood Monocytes Consist of Two Principal Subsets with Distinct Migratory Properties", Immunity, vol. 19, pp. 71-82, July (2003).

Getts, Daniel R., "Microparticles bearing encephalitogenic peptides induce T-cell tolerance and ameliorate experimental autoimmune encephalomyelitis", Nat Biotechnol. Dec. 2012;30(12): 1217-1224.

Yeh et al.: In vivo base editing of post-mitotic sensory cells. Nat Commun. 9(1):2184, pp. 1-10 doi:10.1038/s41467-018-04580-3 (2018).

"Gordon, Siamon "Phagocytosis: An Immunobiologic Process" (2016) Immunity 44".

Goudot, C. et al., "Aryl Hydrocarbon Receptro Controls Monocyte Differentiation into Dendritic Cells versus Macrophages", Sep. 19, 2017 Immunity 47, 582-596.

Grechishnikova et al.: Conserved 3' UTR stem-loop structure in L1 and Alu transposons in human genome: possible role in retrotransposition. BMC Genomics 17(1):992, pp. 1-17 doi:10.1186/s12864-016-3344-4 (2016).

Hackett et al.: A Transposon and Transposase System for Human Application. Mol Ther. 18(4):674-683 doi:10.1038/mt.2010.2 (2010).

"Harburger, et al., "Integrin signalling at a glance" (2009) Journal of Cell Sciences 122".

Harshyne LA, Zimmer MI, Watkins SC, Barratt-Boyes SM. 2003. A Role for Class A Scavenger Receptor in Dendritic Cell Nibbling from Live Cells. The Journal of Immunology 170:2302-2309.

Harshyne LA, Watkins SC, Gambotto A, Barratt-Boyes SM. 2001. Dendritic cells acquire antigens from live cells for Cross-Presentation to CTL. The Journal of Immunology 166:3717-3723.

Haso W, Lee DW, Shah NN, Stetler-Stevenson M, Yuan CM, Pastan IH, Dimitrov DS, Morgan RA, FitzGerald DJ, Barrett DM, Wayne AS, Mackall CL, Orentas RJ. 2013. Anti-CD22-chimeric antigen receptors targeting B-cell precursor acute lymphoblastic leukemia. Blood 121:1165-1174.

"Huang, Min-Nung, et al., "Antigen-loaded monocyte administration induces potent therapeutic antitumor T cell responses", The Journal of Clinical Investigation, Jan. 6, 2020, pp. 1-15".

Hui E, Vale RD. 2014. In vitro membrane reconstitution of the T-cell receptor proximal signaling network. Nature Structural & Molecular Biology 21:133-142.

"Hui, et al., "T cell constimulatory receptor CD28 is a primary target for PD-1-mediated inhibition" (2017) Science 355(6332) p. 1428-1433".

"Sica, et al., "Fingolimod Immune Effects Beyond Its Sequestration Ability" Neuurol Ther (2019) 8:231-240".

"Silverstein, et al., "Mechanisms of Cell Signaling by The Scavenger Receptor CD36: Implications in Atherosclerosis and Thrombosis" Transactions of the American Clinical and Climatological Association, vol. 121 (2010), vol. 121".

"Ingersoll, Ph.D., Brooke, "Brief Report: Pilot Randomized Controlled Trial of Reciprocal Imitation Training for Teaching Elicited and Spontaneous Imitation to Children with Autism", J Autism Dev Disord. Sep. 2010; 40(9): 1154-1160".

International Search Report and Written Opinion for corresponding PCT/US2020/030837 dated Oct. 1, 2020.

Ivancevic et al.: LINEs between Species: Evolutionary Dynamics of LINE-1 Retrotransposons across the Eukaryotic Tree of Life. Genome Biol Evol. 8(11):3301-3322 doi:10.1093/gbe/evw243 (2016).

Jadus MR, Irwin MC, Irwin MR, Horansky RD, Sekhon S, Pepper KA, Kohn DB, Wepsic HT. 1996. Macrophages can recognize and kill tumor cells bearing the membrane isoform of macrophage colony-stimulating factor. Blood 87:5232-5241.

Jaeger et al.: TectoRNA: modular assembly units for the construction of RNA nano-objects. Nucleic Acids Res. 29(2):455-463 doi:10.1093/nar/29.2.455 (2001).

Jaiswal S, Jamieson CH, Pang WW, Park CY, Chao MP, Majeti R, Traver D, van Rooijen N, Weissman IL. 2009. CD47 is upregulated on circulating hematopoietic stem cells and leukemia cells to avoid phagocytosis. Cell 138:271-285.

(56) References Cited

OTHER PUBLICATIONS

Jamburuthugoda et al.: Identification of RNA binding motifs in the R2 retrotransposon-encoded reverse transcriptase. Nucleic Acids Res. 42(13):8405-8415 doi:10.1093/nar/gku514 (2014).

James JR, Vale RD. 2012. Biophysical mechanism of T-cell receptor triggering in a reconstituted system. Nature 487:64-69.

Joly E, Hudrisier D. 2003. What is trogocytosis and what is its purpose? Nature Immunology 4:815.

Kamber et al.: Inter-cellular CRISPR screens reveal regulators of cancer cell phagocytosis. Nature 597(7877):549-554 doi:10.1038/s41586-021-03879-4 (2021).

Kao G, Huang CC, Hedgecock EM, Hall DH, Wadsworth WG. 2006. The role of the laminin beta subunit in laminin heterotrimer assembly and basement membrane function and development in C. elegans. Developmental Biology 290:211-219.

"Kim, et al., "Monocyte Enrichment from Leukapheresis products by using the Elutra cell separator" Transfusion, vol. 47, Dec. 2007 pp. 2290-2296".

Kochenderfer JN, Feldman SA, Zhao Y, Xu H, Black MA, Morgan RA, Wilson WH, Rosenberg SA. 2009. Construction and preclinical evaluation of an anti-CD19 chimeric antigen receptor. Journal of Immunotherapy 32:689-702.

Lacerna LV, Stevenson GW, Stevenson HC. 1988. Adoptive cancer immunotherapy utilizing lymphokine activated killer cells and gamma interferon activated killer monocytes. Pharmacology & Therapeutics 38:453-465.

Larson et al.: Spliced integrated retrotransposed element (SpIRE) formation in the human genome. PLoS Biology 16(3):e2003067, pp. 1-37 (2018).

Lee S, Kivimae S, Dolor A, Szoka FC. 2016. Macrophage-based cell therapies: the long and winding road. Journal of Controlled Release 240:527-540.

Lim WA, June CH, Huang J, Hodes RJ. 2017. The Principles of Engineering Immune Cells to Treat Cancer. Cell 168:724-740.

Liu et al.: Ouroboros resembling competitive endogenous loop (ORCEL) in revealed through transcriptome sequencing dataset analysis. BMC Genomics 19(Suppl 2):171, pp. 87-95 doi:10.1186/s12864-018-4456-9 (2018).

Liu X, Pu Y, Cron K, Deng L, Kline J, Frazier WA, Xu H, Peng H, Fu YX, Xu MM. 2015. CD47 blockade triggers T cell-mediated destruction of immunogenic tumors. Nature Medicine 21:1209-1215.

Macia et al.: Engineered LINE-1 retrotransposition in nondividing human neurons. Genome Res. 27(3):335-348 doi:10.1101/gr.206805.116 (2017).

Majeti R, Chao MP, Alizadeh AA, Pang WW, Jaiswal S, Gibbs KD, van Rooijen N, Weissman IL. 2009. CD47 is an adverse prognostic factor and therapeutic antibody target on human acute myeloid leukemia stem cells. Cell 138:286-299.

"Matsuyoshi, Hidetake, et al., "Enchanced Priming of Antigen-Specific CTL's In Vivo by Embryonic Stem Cell-Derived Dendritic Cells Expressing Chemokine Along with Antigenic Protein: Application to Antitumor Vaccination", The Journal of Immunology (2004) 172:776-786".

Mayordomo JI, Zorina T, Storkus WJ, Zitvogel L, Celluzzi C, Falo LD, Melief CJ, Ildstad ST, Kast WM, Deleo AB. 1995. Bone marrow-derived dendritic cells pulsed with synthetic tumour peptides elicit protective and therapeutic antitumour immunity. Nature Medicine 1:1297-1302.

"Mcever, et al., "Selectins: initiators of leucocyte adhesion and signalling at the vascular wall" Cardovascular Research (2015) 107, pp. 331-339".

"Mildner, A., et al., "Distinct and Non-Redundant Roles of Microglia and Myeloid Subsets in Mouse Models of Alzheimer's Disease" Neurobiology of Disease, J. Neurosci., Aug. 3, 2011, 31(31):11159-11171".

Mita et al.: BRCA1 and S phase DNA repair pathways restrict LINE-1 retrotransposition in human cells. Nat Struct Mol Biol. 27(2):179-191 doi:10.1038/s41594-020-0374-z (2020).

Morrissey, M., et al., "Chimeric antigen receptros that trigger phagocytosis", eLife 2018, pp. 1/21.

Muckenfuss et al.: APOBEC3 proteins inhibit human LINE-1 retrotransposition. J Biol Chem. 281(31):22161-22172 doi:10.1074/jbc.M601716200 (2006).

Mukherjee, R. et al., "Non-Classical monocytes display inflammatory features: Validation in Sepsis and Systemic Lupus Erythematous", Scientific Reports, (2015) pp. 1-14.

"Murshid, et al., "Hsp90-peptide complexes stimulate antigen presentation through the class II pathway after binding scavenger receptor SREC-I" Immunobiology (2014) 219(12) pp. 924-931".

Novikova et al.: Engineering cooperative tecto-RNA complexes having programmable stoichiometries. Nucleic Acids Res. 39(7):2903-2917 doi:10.1093/nar/gkq1231 (2011).

Orechini et al.: ADAR1 restricts LINE-1 retrotransposition. Nucleic Acids Res. 45(1):155-168 doi:10.1093/nar/gkw834 (2017).

"Oviedo-Boyso, et al., "The Phosphoinositide-3-Kinase-Akt Signaling Pathway Is Important for *Staphylococcus aureus* Internalization by Endothelial Cells" (2011) Infection and Immunity, vol. 79, No. 11, p. 4569-4577".

Ozcan et al.: Programmable RNA targeting with the single-protein CRISPR effector Cas7-11. Nature 597(7878):720-725 doi: 10.1038/s41586-021-03886-5 (2021).

"Paslick, et al., "Identification and Characterization of a Novel Monocyte Subpopulation in Human Peripheral Blood", Article in Blood, Dec. 1989, 74: 2527-2534".

"Patel, et al, "The fate and lifespan of human monocyte subsets in steady state and systemic inflammation" J.Exp. Med. (2017), vol. 214, No. 7 p. 1913-1923".

PCT/US2020/049240 International Search Report and Written Opinion dated Mar. 26, 2021.

PCT/US2020/064686 International Search Report and Written Opinion dated Apr. 6, 2021.

Penberthy KK, Ravichandran KS. 2016. Apoptotic cell recognition receptors and scavenger receptors. Immunological Reviews 269:44-59.

Piskareva et al.: The carboxy-terminal segment of the human LINE-1 ORF2 protein is involved in RNA binding. FEBS Open Bio. 3:433-437 (2013).

Ralston KS, Solga MD, Mackey-Lawrence NM, Somlata, Bhattacharya A, Petri WA. 2014. Trogocytosis by Entamoeba histolytica contributes to cell killing and tissue invasion. Nature 508:526-530.

Richardson et al.: The Influence of LINE-1 and SINE Retrotransposons on Mammalian Genomes. Microbiol Spectr. 3(2):MDNA3-0061-2014, pp. 1-63 doi:10.1128/microbiolspec.MDNA3-0061-2014 (2015).

Roberts EW, Broz ML, Binnewies M, Headley MB, Nelson AE, Wolf DM, Kaisho T, Bogunovic D, Bhardwaj N, Krummel MF. 2016. Critical Role for CD103(+)/CD141(+) Dendritic Cells Bearing CCR7 for Tumor Antigen Trafficking and Priming of T Cell Immunity in Melanoma. Cancer Cell 30:324-336.

Roberts, Margo R., et al."Antigen-Specific Cytolysis by Neutrophils and NK Cells Expressing Chimeric Immune Receptros Bearing xx Signaling Domains", J Immunol 1998; 161:375-384.

Rosales, C. et al, "Phagocytosis: A Fundamental Process in Immunity", BioMed Research International, vol. 2017, Article ID 9042851, 18 pages.

Ruiz-Aguilar, S., et al., "Human CD16+ and CD16+ monocyte subsets display unique effector properties in inflammatory conditions in vivo", Journal of Leukocyte Biology, (2011) vol. 90, pp. 1119-1131.

Schlam D, Bagshaw RD, Freeman SA, Collins RF, Pawson T, Fairn GD, Grinstein S. 2015. Phosphoinositide 3-kinase enables phagocytosis of large particles by terminating actin assembly through Rac/Cdc42 GTPase-activating proteins. Nature Communications 6:8623.

Schlam, et al., "Phosphoinositide 3-kinase enables phagocytosis of large particles by terminating actin assembly through Rac/Cdc42 GRPase-activating proteins" (2015) Nature Communications.

Segel et al.: Mammalian retrovirus-like protein PEG10 packages its own mRNA and can be pseudotyped for mRNA delivery. Science 373(6557):882-889 doi:10.1126/science.abg6155 (2021).

Senju, et al., "Generation of dendritic cells and macrophages from human induced pluripotent stem cells aiming at cell therapy" Gene Therapy (2011) 18, 874-883.

(56) References Cited

OTHER PUBLICATIONS

Shein et al.: Recognition of 3'-end L1, Alu, processed pseudogenes, and mRNA stem-loops in the human genome using sequence-based and structure-based machine-learning models. Sci Rep. 9(1):7211, pp. 1-16 doi:10.1038/s41598-019-43403-3 (2019).
Shumann et al.: The impact of transposable element activity on therapeutically relevant human stem cells. Mob DNA 10:9, pp. 1-23 doi:10.1186/s13100-019-0151-x (2019).
Taylor et al.: A DNA-Based T Cell Receptor Reveals a Role for Receptor Clustering in Ligand Discrimination. Cell 169(1):108-119 doi:10.1016/j.cell.2017.03.006 (2017).
"Strauss, et al., "The immunophenotype of antigen presenting cells of the mononuclear phagocyte system in a normal human liver—A systematic review" Journal of Hepatology, (2015) vol. 62, pp. 458-468".
Tristan-Ramos et al.: The tumor suppressor microRNA let-7 inhibits human LINE-1 retrotransposition. Nat Commun. 11(1):5712 doi:10.1038/S41467-020-19430-4 [1-14] (2020).
Tseng D, Volkmer JP, Willingham SB, Contreras-Trujillo H, Fathman JW, Fernhoff NB, Seita J, Inlay MA, Weiskopf K, Miyanishi M, Weissman IL. 2013. Anti-CD47 antibody-mediated phagocytosis of cancer by macrophages primes an effective antitumor T-cell response. PNAS 110:11103-11108.
Tsutsui, et al. "The use of microbubbles to target drug delivery" Cardiovascular Ultrasound (2004) 2:23.
Tuveson DA, Carter RH, Soltoff SP, Fearon DT. 1993. CD19 of B cells as a surrogate kinase insert region to bindphosphatidylinositol 3-kinase. Science 260:986-989.
Wei et al.: Human L1 retrotransposition: cis preference versus trans complementation. Mol Cell Biol. 21 (4):1429-1439 doi:10.1128/MCB.21.4.1429-1439.2001 (2001).

Weischenfeldt J, Porse B. 2008. Bone Marrow-Derived Macrophages (BMM): Isolation and Applications. Cold Spring Harbor Protocols 2008:pdb.prot5080.
Xiao X, Ho M, Zhu Z, Pastan I, Dimitrov DS. 2009. Identification and characterization of fully human anti-CD22 monoclonal antibodies. mAbs 1:297-303.
Yesselman et al.: RNA tertiary structure energetics predicted by an ensemble model of the RNA double helix.bioRxiv 341107, pp. 1-31 DOI:10.1101/341107 (2018).
Yong, C., et al, "A role for multiple chimeric antigen receptor-expressing leukocytes in antigen-specific responses to cancer" (2016) Oncotarget, vol. 7, No. 23 pp. 34582-34598.
Zhang et al.: Homologous 2',5'-phosphodiesterases from disparate RNA viruses antagonize antiviral innate immunity. PNAS USA 110(32):13114-13119 doi:10.1073/pnas.1306917110 (2013).
Zhang et al.: The structure and retrotransposition mechanism of LTR-retrotransposons in the asexual yeast *Candida albicans*. Virulence 5(6):655-664 doi:10.4161/viru.32180 (2014).
Christian CM et al., Involvement of Conserved Amino Acids in the C-Terminal Region of LINE-1 ORF2p in Retrotransposition. Genetics. Mar. 2017;205(3):1139-1149. Epub Jan. 18, 2017.
Khazina E and Weichenrieder O. Human LINE-1 retrotransposition requires a metastable coiled coil and a positively charged N-terminus in L1ORF1p. eLIFE. Mar. 22, 2018;7:e34960.
Kines Kj et al., The endonuclease domain of the LINE-1 ORF2 protein can tolerate multiple mutations. Mobile DNA. Apr. 1, 20169;7:8.
Liu Q, et al. Nuclear localization of the ORF2 protein encoded by porcine circovirus type 2. Virology. Jun. 20, 2001;285(1):91-9.
Pascolo S. Messenger RNA-based vaccines. Expert Opin Biol Ther. Aug. 2004;4(8):1285-94.

\* cited by examiner

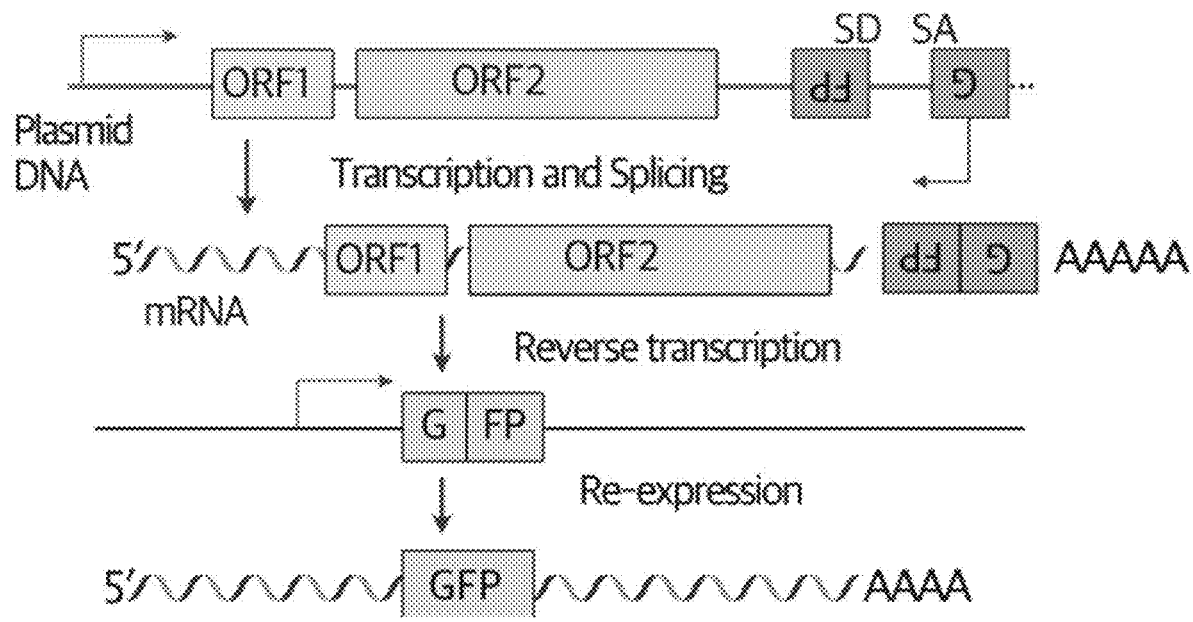
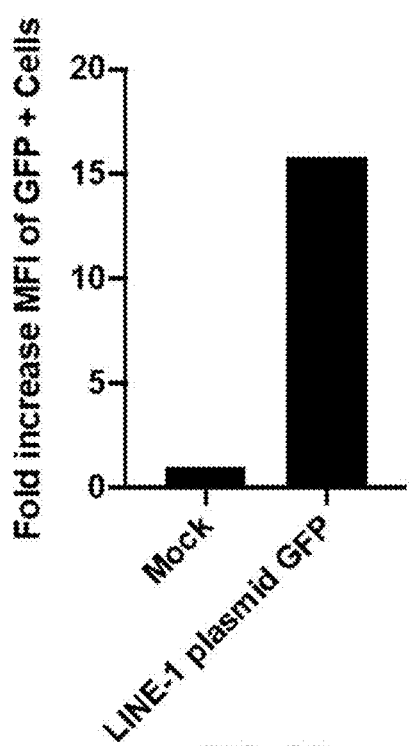
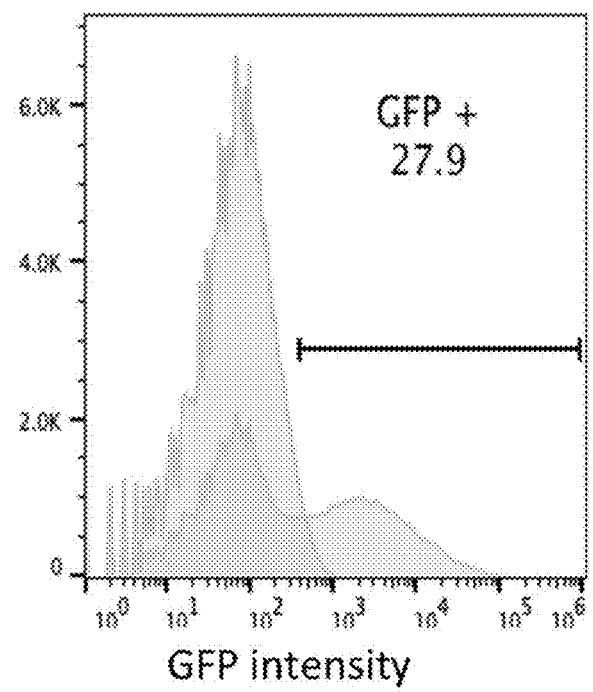
FIG. 8A
FIG. 8B
FIG. 8C

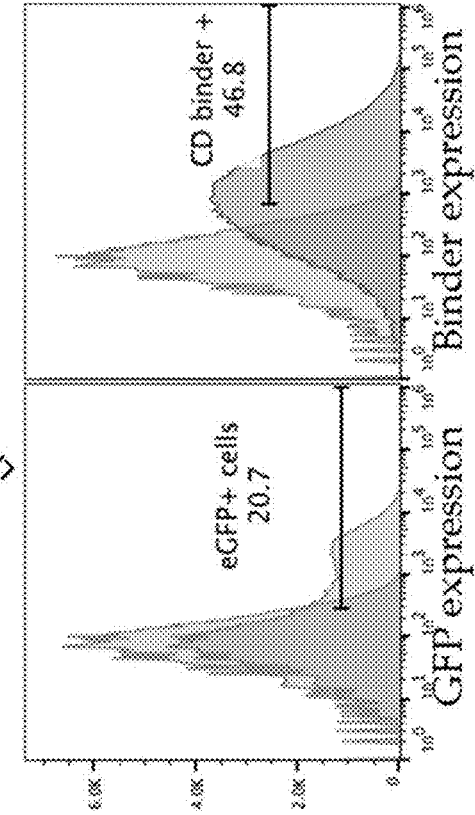
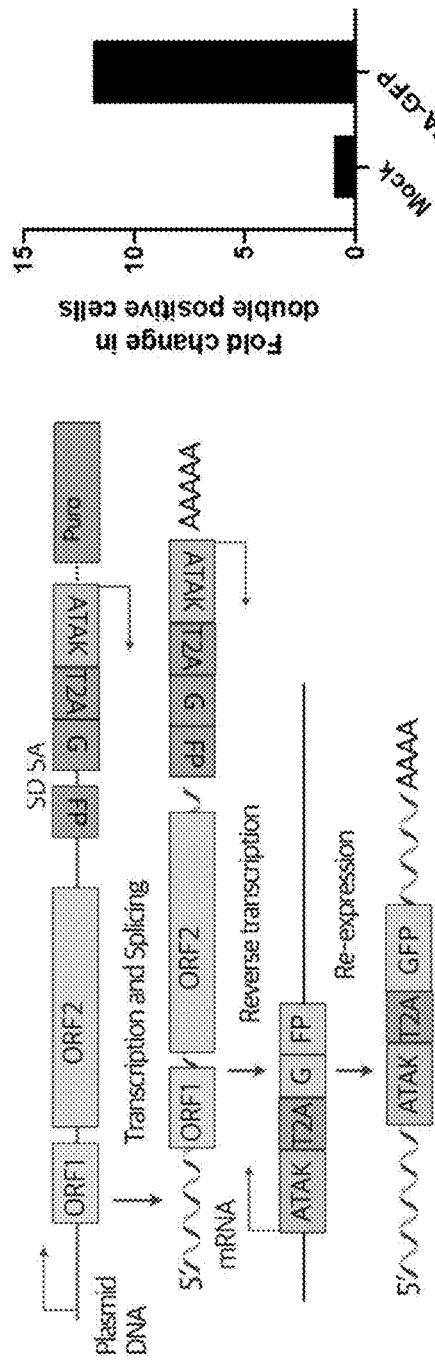
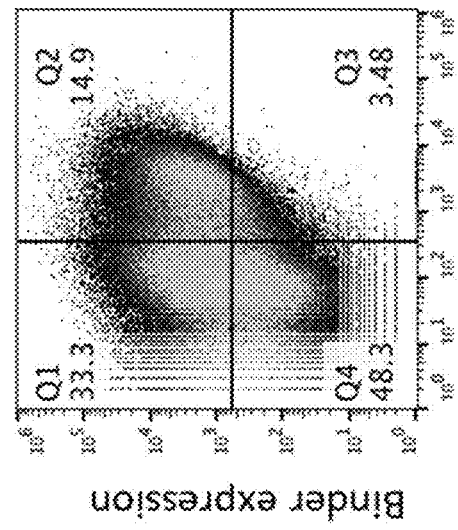
FIG. 10A
FIG. 10B
FIG. 10C
FIG. 10D

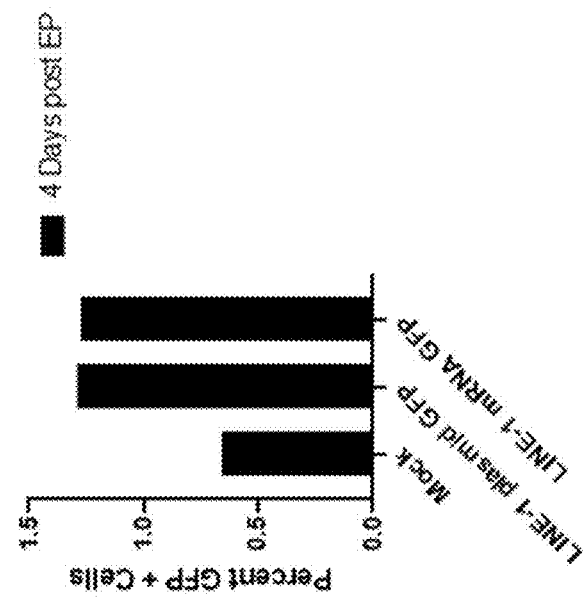
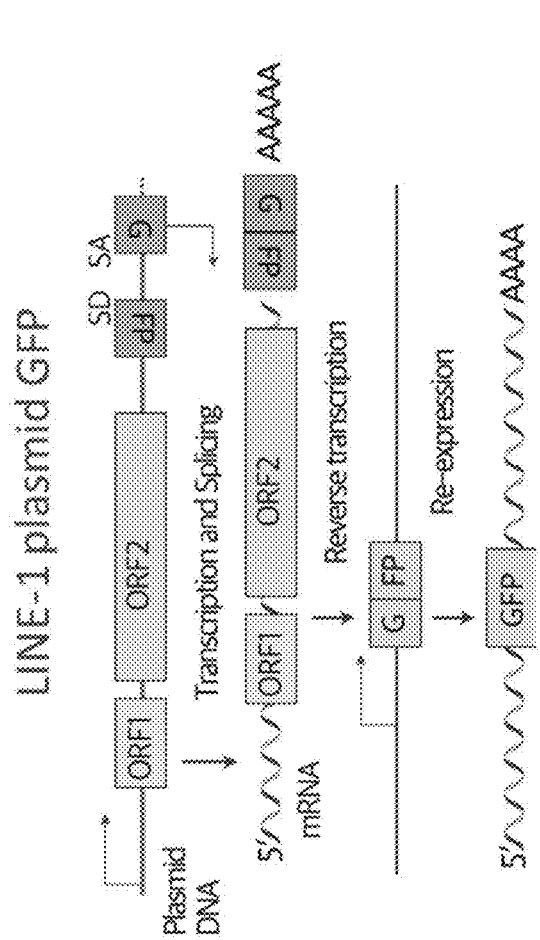
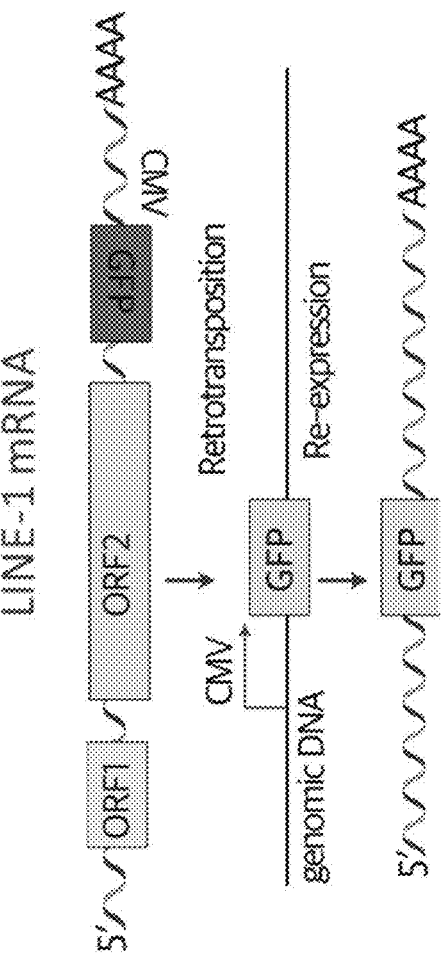
FIG. 17A
FIG. 17B

SEQUENCE LISTING

```
<160> NUMBER OF SEQ ID NOS: 85

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Met
            35                  40                  45

Gly Trp Ile Asn Thr His Thr Gly Glu Pro Thr Tyr Ala Asp Ser Phe
        50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
                100                 105                 110

Thr Val Thr Val
            115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
                20                  25                  30

Leu Ser Trp Phe Gln Gln Lys Pro Gly Lys Ala Pro Lys Thr Leu Ile
```

```
                35                  40                  45

Tyr Arg Ala Asn Arg Leu Glu Ser Gly Val Pro Ser Arg Phe Ser Gly
 50                  55                  60

Ser Gly Ser Gly Thr Asp Tyr Thr Leu Thr Ile Ser Ser Leu Gln Tyr
 65                  70                  75                  80

Glu Asp Phe Gly Ile Tyr Tyr Cys Gln Gln Tyr Asp Glu Ser Pro Trp
                 85                  90                  95

Thr Phe Gly Gly Gly Thr Lys Leu Glu Ile Lys
            100                 105

<210> SEQ ID NO 3
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Leu Tyr Cys Arg Arg Leu Lys Ile Gln Val Arg Lys Ala Ala Ile Thr
 1               5                  10                  15

Ser Tyr Glu Lys Ser Asp Gly Val Tyr Thr Gly Leu Ser Thr Arg Asn
                20                  25                  30

Gln Glu Thr Tyr Glu Thr Leu Lys His Glu Lys Pro Pro Gln
            35                  40                  45

<210> SEQ ID NO 4
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Tyr Glu Asp Met Arg Gly Ile Leu Tyr Ala Ala Pro Gln Leu Arg Ser
 1               5                  10                  15

Ile Arg Gly Gln Pro Gly Pro Asn His Glu Glu Asp Ala Asp Ser Tyr
                20                  25                  30

Glu Asn Met
        35

<210> SEQ ID NO 5
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Lys Val Ala Lys Lys Pro Thr Asn Lys Ala Pro His Pro Lys Gln
 1               5                  10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
            35                  40                  45

Glu Asp Gly Lys Glu Ser Arg Ile Ser Val Gln Glu Arg Gln
         50                  55                  60

<210> SEQ ID NO 6
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 7
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60

<210> SEQ ID NO 8
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
            100                 105                 110

Ser Gly Ser Gly Lys Pro Gly Ser Gly Glu Gly Ser Glu Val Gln Leu
        115                 120                 125

Val Glu
    130

<210> SEQ ID NO 9
<211> LENGTH: 108
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

Leu Val Gln Pro Gly Gly Ser Leu Arg Leu Ser Cys Ala Ala Ser Gly
1               5                   10                  15

Phe Asn Ile Lys Asp Thr Tyr Ile His Trp Val Arg Gln Ala Pro Gly
            20                  25                  30

Lys Gly Leu Glu Trp Val Ala Arg Ile Tyr Pro Thr Asn Gly Tyr Thr
        35                  40                  45

Arg Tyr Ala Asp Ser Val Lys Gly Arg Phe Thr Ile Ser Ala Asp Thr
    50                  55                  60

Ser Lys Asn Thr Ala Tyr Leu Gln Met Asn Ser Leu Arg Ala Glu Asp
65                  70                  75                  80

Thr Ala Val Tyr Tyr Cys Ser Arg Trp Gly Gly Asp Gly Phe Tyr Ala
                85                  90                  95

Met Asp Val Trp Gly Gln Gly Thr Leu Val Thr Val
            100                 105

```
<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10
```

Ser Ser Gly Gly Gly Gly Ser Gly Gly Gly Gly Ser Gly Gly Gly Gly
1               5                   10                  15

Ser

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Ser Gly Gly Gly Gly Ser Gly
1               5

```
<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

Ser Gly Gly Gly
1

```
<210> SEQ ID NO 13
<211> LENGTH: 4
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 13

Gly Ser Gly Ser
1

<210> SEQ ID NO 14
<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Trp Leu Gln Ser Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

```
His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Leu Lys Ile Gln Val Arg Lys Ala Ala Ile Thr Ser Tyr Glu Lys Ser
        355                 360                 365

Asp Gly Val Tyr Thr Gly Leu Ser Thr Arg Asn Gln Glu Thr Tyr Glu
    370                 375                 380

Thr Leu Lys His Glu Lys Pro Pro Gln Gly Ser Gly Ser Tyr Glu Asp
385                 390                 395                 400

Met Arg Gly Ile Leu Tyr Ala Ala Pro Gln Leu Arg Ser Ile Arg Gly
                405                 410                 415

Gln Pro Gly Pro Asn His Glu Glu Asp Ala Asp Ser Tyr Glu Asn Met
            420                 425                 430
```

<210> SEQ ID NO 15
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Trp Leu Gln Ser Leu Leu Leu Gly Thr Val Ala Cys Ser Ile
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Asp Val Asn Thr
        35                  40                  45

Ala Val Ala Trp Tyr Gln Gln Lys Pro Gly Lys Ala Pro Lys Leu Leu
    50                  55                  60

Ile Tyr Ser Ala Ser Phe Leu Tyr Ser Gly Val Pro Ser Arg Phe Ser
65                  70                  75                  80

Gly Ser Arg Ser Gly Thr Asp Phe Thr Leu Thr Ile Ser Ser Leu Gln
                85                  90                  95

Pro Glu Asp Phe Ala Thr Tyr Tyr Cys Gln Gln His Tyr Thr Thr Pro
            100                 105                 110

Pro Thr Phe Gly Gln Gly Thr Lys Val Glu Ile Lys Arg Thr Gly Ser
        115                 120                 125

Thr Ser Gly Ser Gly Lys Pro Gly Ser Gly Glu Gly Ser Glu Val Gln
130                 135                 140

Leu Val Glu Ser Gly Gly Gly Leu Val Gln Pro Gly Gly Ser Leu Arg
145                 150                 155                 160

Leu Ser Cys Ala Ala Ser Gly Phe Asn Ile Lys Asp Thr Tyr Ile His
                165                 170                 175

Trp Val Arg Gln Ala Pro Gly Lys Gly Leu Glu Trp Val Ala Arg Ile
            180                 185                 190

Tyr Pro Thr Asn Gly Tyr Thr Arg Tyr Ala Asp Ser Val Lys Gly Arg
        195                 200                 205

Phe Thr Ile Ser Ala Asp Thr Ser Lys Asn Thr Ala Tyr Leu Gln Met
    210                 215                 220

Asn Ser Leu Arg Ala Glu Asp Thr Ala Val Tyr Tyr Cys Ser Arg Trp
225                 230                 235                 240

Gly Gly Asp Gly Phe Tyr Ala Met Asp Val Trp Gly Gln Gly Thr Leu
                245                 250                 255
```

```
Val Thr Val Ser Ser Gly Gly Gly Ser Gly Ala Leu Ser Asn
            260                 265             270

Ser Ile Met Tyr Phe Ser His Phe Val Pro Val Phe Leu Pro Ala Lys
                275                 280                 285

Pro Thr Thr Thr Pro Ala Pro Arg Pro Pro Thr Pro Ala Pro Thr Ile
            290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Arg Arg Leu Lys Ile Gln Val Arg Lys Ala Ala Ile Thr Ser
            355                 360                 365

Tyr Glu Lys Ser Asp Gly Val Tyr Thr Gly Leu Ser Thr Arg Asn Gln
            370                 375                 380

Glu Thr Tyr Glu Thr Leu Lys His Glu Lys Pro Pro Gln Gly Ser Gly
385                 390                 395                 400

Ser Tyr Glu Asp Met Arg Gly Ile Leu Tyr Ala Ala Pro Gln Leu Arg
                405                 410                 415

Ser Ile Arg Gly Gln Pro Gly Pro Asn His Glu Glu Asp Ala Asp Ser
            420                 425                 430

Tyr Glu Asn Met
            435

<210> SEQ ID NO 16
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
        35                  40                  45

Tyr Gly Met Asn Trp Val Arg Gln Ala Pro Gly Lys Gly Leu Glu Trp
    50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
```

165                 170                 175
Gln Asp Ile Asn Ser Tyr Leu Ser Trp Phe Gln Gln Lys Pro Gly Lys
                180                 185                 190

Ala Pro Lys Thr Leu Ile Tyr Arg Ala Asn Arg Leu Glu Ser Gly Val
            195                 200                 205

Pro Ser Arg Phe Ser Gly Ser Gly Ser Gly Thr Asp Tyr Thr Leu Thr
        210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
                260                 265                 270

Phe Ser His Phe Val Pro Val Phe Leu Pro Ala Lys Pro Thr Thr Thr
            275                 280                 285

Pro Ala Pro Arg Pro Pro Thr Pro Ala Pro Thr Ile Ala Ser Gln Pro
        290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
                340                 345                 350

Lys Ile Gln Val Arg Lys Ala Ala Ile Thr Ser Tyr Glu Lys Ser Asp
            355                 360                 365

Gly Val Tyr Thr Gly Leu Ser Thr Arg Asn Gln Glu Thr Tyr Glu Thr
        370                 375                 380

Leu Lys His Glu Lys Pro Pro Gln Lys Val Ala Lys Pro Thr
385                 390                 395                 400

Asn Lys Ala Pro His Pro Lys Gln Glu Pro Gln Glu Ile Asn Phe Pro
                405                 410                 415

Asp Asp Leu Pro Gly Ser Asn Thr Ala Ala Pro Val Gln Glu Thr Leu
            420                 425                 430

His Gly Cys Gln Pro Val Thr Gln Glu Asp Gly Lys Glu Ser Arg Ile
        435                 440                 445

Ser Val Gln Glu Arg Gln
        450

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Trp Leu Gln Ser Leu Leu Leu Leu Gly Thr Val Ala Cys Ser Ile
1               5                   10                  15

Ser

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Leu Leu Pro Leu Ile Ile Gly Leu Ile Leu Gly Leu Leu Ala
1               5                   10                  15

Leu Val Leu Ile Ala Phe Cys Ile Ile
            20                  25

<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Tyr Cys Arg Leu Lys Ile Gln Val Arg Lys Ala Ala Ile Thr Ser
1               5                   10                  15

Tyr Glu Lys Ser Asp Gly Val Tyr Thr Gly Leu Ser Thr Arg Asn Gln
            20                  25                  30

Glu Thr Tyr Glu Thr Leu Lys His Glu Lys Pro Pro Gln
        35                  40                  45

<210> SEQ ID NO 21
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Arg Trp Lys Ser Lys Leu Tyr Ser Ile Val Cys Gly Lys Ser Thr
1               5                   10                  15

Pro Glu Lys Glu Gly Glu Leu Glu Gly Thr Thr Thr Lys Pro Leu Ala
            20                  25                  30

Pro Asn Pro Ser Phe Ser Pro Thr Pro Gly Phe Thr Pro Thr Leu Gly
        35                  40                  45

Phe Ser Pro Val Pro Ser Ser Thr Phe Thr Ser Ser Ser Thr Tyr Thr
    50                  55                  60

Pro Gly Asp Cys Pro Asn Phe Ala Ala Pro Arg Arg Glu Val Ala Pro
65                  70                  75                  80

Pro Tyr Gln Gly Ala Asp Pro Ile Leu Ala Thr Ala Leu Ala Ser Asp
                85                  90                  95

Pro Ile Pro Asn Pro Leu Gln Lys Trp Glu Asp Ser Ala His Lys Pro
            100                 105                 110

```
Gln Ser Leu Asp Thr Asp Pro Ala Thr Leu Tyr Ala Val Val Glu
        115                 120                 125

Asn Val Pro Pro Leu Arg Trp Lys Glu Phe Val Arg Arg Leu Gly Leu
    130                 135                 140

Ser Asp His Glu Ile Asp Arg Leu Glu Leu Gln Asn Gly Arg Cys Leu
145                 150                 155                 160

Arg Glu Ala Gln Tyr Ser Met Leu Ala Thr Trp Arg Arg Thr Pro
                165                 170                 175

Arg Arg Glu Ala Thr Leu Glu Leu Leu Gly Arg Val Leu Arg Asp Met
                180                 185                 190

Asp Leu Leu Gly Cys Leu Glu Asp Ile Glu Glu Ala Leu Cys Gly Pro
            195                 200                 205

Ala Ala Leu Pro Pro Ala Pro Ser Leu Leu Arg
        210                 215

<210> SEQ ID NO 22
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Pro Leu Cys Leu Gln Arg Glu Ala Lys Val Pro His Leu Pro Ala Asp
1               5                   10                  15

Lys Ala Arg Gly Thr Gln Gly Pro Glu Gln Gln His Leu Leu Ile Thr
                20                  25                  30

Ala Pro Ser Ser Ser Ser Ser Leu Glu Ser Ser Ala Ser Ala Leu
            35                  40                  45

Asp Arg Arg Ala Pro Thr Arg Asn Gln Pro Gln Ala Pro Gly Val Glu
    50                  55                  60

Ala Ser Gly Ala Gly Glu Ala Arg Ala Ser Thr Gly Ser Ser Asp Ser
65                  70                  75                  80

Ser Pro Gly Gly His Gly Thr Gln Val Asn Val Thr Cys Ile Val Asn
                85                  90                  95

Val Cys Ser Ser Ser Asp His Ser Ser Gln Cys Ser Ser Gln Ala Ser
            100                 105                 110

Ser Thr Met Gly Asp Thr Asp Ser Ser Pro Ser Glu Ser Pro Lys Asp
        115                 120                 125

Glu Gln Val Pro Phe Ser Lys Glu Glu Cys Ala Phe Arg Ser Gln Leu
    130                 135                 140

Glu Thr Pro Glu Thr Leu Leu Gly Ser Thr Glu Glu Lys Pro Leu Pro
145                 150                 155                 160

Leu Gly Val Pro Asp Ala Gly Met Lys Pro Ser
                165                 170

<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ser Asn Gly Tyr Ser Thr Asp Glu Asn Phe Arg Tyr Leu Ile Ser
1               5                   10                  15
```

Cys Phe Arg Ala Arg Val Lys Met Tyr Ile Gln Val Glu Pro Val Leu
                20                  25                  30

Asp Tyr Leu Thr Phe Leu Pro Ala Glu Val Lys Glu Gln Ile Gln Arg
            35                  40                  45

Thr Val Ala Thr Ser Gly Asn Met Gln Ala Val Glu Leu Leu Leu Ser
        50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Leu Leu
130                 135                 140

Thr Ile Glu Asp Arg Asn Arg Ile Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn
    210

<210> SEQ ID NO 24
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Trp Leu Gln Ser Leu Leu Leu Leu Gly Thr Val Ala Cys Ser Ile
1               5                   10                  15

Ser Glu Ile Gln Leu Val Gln Ser Gly Gly Gly Leu Val Lys Pro Gly
                20                  25                  30

Gly Ser Val Arg Ile Ser Cys Ala Ala Ser Gly Tyr Thr Phe Thr Asn
            35                  40                  45

Tyr Gly Met Asn Trp Val Arg Gln Ala Pro Gly Lys Gly Leu Glu Trp
        50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
130                 135                 140

Ser Gly Gly Gly Gly Ser Asp Ile Gln Met Thr Gln Ser Pro Ser Ser
145                 150                 155                 160

```
Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
    210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335

Cys Gly Val Leu Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
        355                 360                 365

Gly Val Tyr Thr Gly Leu Ser Thr Arg Asn Gln Glu Thr Tyr Glu Thr
    370                 375                 380

Leu Lys His Glu Lys Pro Pro Gln Gly Ser Gly Ser Met Ser Asn Gly
385                 390                 395                 400

Tyr Ser Thr Asp Glu Asn Phe Arg Tyr Leu Ile Ser Cys Phe Arg Ala
                405                 410                 415

Arg Val Lys Met Tyr Ile Gln Val Glu Pro Val Leu Asp Tyr Leu Thr
            420                 425                 430

Phe Leu Pro Ala Glu Val Lys Glu Gln Ile Gln Arg Thr Val Ala Thr
        435                 440                 445

Ser Gly Asn Met Gln Ala Val Glu Leu Leu Leu Ser Thr Leu Glu Lys
    450                 455                 460

Gly Val Trp His Leu Gly Trp Thr Arg Glu Phe Val Glu Ala Leu Arg
465                 470                 475                 480

Arg Thr Gly Ser Pro Leu Ala Ala Arg Tyr Met Asn Pro Glu Leu Thr
                485                 490                 495

Asp Leu Pro Ser Pro Ser Phe Glu Asn Ala His Asp Glu Tyr Leu Gln
            500                 505                 510

Leu Leu Asn Leu Leu Gln Pro Thr Leu Val Asp Lys Leu Leu Val Arg
        515                 520                 525

Asp Val Leu Asp Lys Cys Met Glu Glu Glu Leu Leu Thr Ile Glu Asp
    530                 535                 540

Arg Asn Arg Ile Ala Ala Ala Glu Asn Asn Gly Asn Glu Ser Gly Val
545                 550                 555                 560

Arg Glu Leu Leu Lys Arg Ile Val Gln Lys Glu Asn Trp Phe Ser Ala
                565                 570                 575
```

```
Phe Leu Asn Val Leu Arg Gln Thr Gly Asn Asn Glu Leu Val Gln Glu
            580                 585                 590

Leu Thr Gly Ser Asp Cys Ser Glu Ser Asn Ala Glu Ile Glu Asn
            595                 600                 605

<210> SEQ ID NO 25
<211> LENGTH: 615
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Trp Leu Gln Ser Leu Leu Leu Gly Thr Val Ala Cys Ser Ile
1               5                   10                  15

Ser Glu Ile Gln Leu Val Gln Ser Gly Gly Gly Leu Val Lys Pro Gly
                20                  25                  30

Gly Ser Val Arg Ile Ser Cys Ala Ala Ser Gly Tyr Thr Phe Thr Asn
            35                  40                  45

Tyr Gly Met Asn Trp Val Arg Gln Ala Pro Gly Lys Gly Leu Glu Trp
        50                  55                  60

Met Gly Trp Ile Asn Thr His Thr Gly Glu Pro Thr Tyr Ala Asp Ser
65                  70                  75                  80

Phe Lys Gly Arg Phe Thr Phe Ser Leu Asp Asp Ser Lys Asn Thr Ala
                85                  90                  95

Tyr Leu Gln Ile Asn Ser Leu Arg Ala Glu Asp Thr Ala Val Tyr Phe
            100                 105                 110

Cys Thr Arg Arg Gly Tyr Asp Trp Tyr Phe Asp Val Trp Gly Gln Gly
        115                 120                 125

Thr Thr Val Thr Val Ser Ser Gly Gly Gly Gly Ser Gly Gly Gly Gly
130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Ile Asn Ser Tyr Leu Ser Trp Phe Gln Gln Lys Pro Gly Lys
            180                 185                 190

Ala Pro Lys Thr Leu Ile Tyr Arg Ala Asn Arg Leu Glu Ser Gly Val
        195                 200                 205

Pro Ser Arg Phe Ser Gly Ser Gly Ser Gly Thr Asp Tyr Thr Leu Thr
210                 215                 220

Ile Ser Ser Leu Gln Tyr Glu Asp Phe Gly Ile Tyr Tyr Cys Gln Gln
225                 230                 235                 240

Tyr Asp Glu Ser Pro Trp Thr Phe Gly Gly Thr Lys Leu Glu Ile
                245                 250                 255

Lys Ser Gly Gly Gly Gly Ser Gly Ala Leu Ser Asn Ser Ile Met Tyr
            260                 265                 270

Phe Ser His Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Ile Tyr Ile Trp Ala Pro Leu Ala Gly Thr
                325                 330                 335
```

```
Cys Gly Val Leu Leu Ser Leu Val Ile Thr Leu Tyr Cys Arg Leu
            340                 345                 350

Lys Ile Gln Val Arg Lys Ala Ala Ile Thr Ser Tyr Glu Lys Ser Asp
            355                 360                 365

Gly Val Tyr Thr Gly Leu Ser Thr Arg Asn Gln Glu Thr Tyr Glu Thr
370                 375                 380

Leu Lys His Glu Lys Pro Pro Gln Gly Ser Gly Ser Gln Arg Trp Lys
385                 390                 395                 400

Ser Lys Leu Tyr Ser Ile Val Cys Gly Lys Ser Thr Pro Glu Lys Glu
                405                 410                 415

Gly Glu Leu Glu Gly Thr Thr Thr Lys Pro Leu Ala Pro Asn Pro Ser
            420                 425                 430

Phe Ser Pro Thr Pro Gly Phe Thr Pro Thr Leu Gly Phe Ser Pro Val
            435                 440                 445

Pro Ser Ser Thr Phe Thr Ser Ser Thr Tyr Thr Pro Gly Asp Cys
            450                 455                 460

Pro Asn Phe Ala Ala Pro Arg Arg Glu Val Ala Pro Pro Tyr Gln Gly
465                 470                 475                 480

Ala Asp Pro Ile Leu Ala Thr Ala Leu Ala Ser Asp Pro Ile Pro Asn
                485                 490                 495

Pro Leu Gln Lys Trp Glu Asp Ser Ala His Lys Pro Gln Ser Leu Asp
            500                 505                 510

Thr Asp Asp Pro Ala Thr Leu Tyr Ala Val Val Glu Asn Val Pro Pro
            515                 520                 525

Leu Arg Trp Lys Glu Phe Val Arg Arg Leu Gly Leu Ser Asp His Glu
            530                 535                 540

Ile Asp Arg Leu Glu Leu Gln Asn Gly Arg Cys Leu Arg Glu Ala Gln
545                 550                 555                 560

Tyr Ser Met Leu Ala Thr Trp Arg Arg Arg Thr Pro Arg Arg Glu Ala
                565                 570                 575

Thr Leu Glu Leu Leu Gly Arg Val Leu Arg Asp Met Asp Leu Leu Gly
            580                 585                 590

Cys Leu Glu Asp Ile Glu Glu Ala Leu Cys Gly Pro Ala Ala Leu Pro
            595                 600                 605

Pro Ala Pro Ser Leu Leu Arg
610                 615

<210> SEQ ID NO 26
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Trp Leu Gln Ser Leu Leu Leu Gly Thr Val Ala Cys Ser Ile
1               5                   10                  15

Ser Glu Ile Gln Leu Val Gln Ser Gly Gly Gly Leu Val Lys Pro Gly
            20                  25                  30

Gly Ser Val Arg Ile Ser Cys Ala Ala Ser Gly Tyr Thr Phe Thr Asn
            35                  40                  45

Tyr Gly Met Asn Trp Val Arg Gln Ala Pro Gly Lys Gly Leu Glu Trp
50                  55                  60

Met Gly Trp Ile Asn Thr His Thr Gly Glu Pro Thr Tyr Ala Asp Ser
```

```
            65                    70                    75                    80
       Phe Lys Gly Arg Phe Thr Phe Ser Leu Asp Asp Ser Lys Asn Thr Ala
                           85                    90                    95

Tyr Leu Gln Ile Asn Ser Leu Arg Ala Glu Asp Thr Ala Val Tyr Phe
                          100                   105                   110

Cys Thr Arg Arg Gly Tyr Asp Trp Tyr Phe Asp Val Trp Gly Gln Gly
                          115                   120                   125

Thr Thr Val Thr Val Ser Ser Gly Gly Gly Ser Gly Gly Gly Gly
           130                   135                   140

Ser Gly Gly Gly Gly Ser Asp Ile Gln Met Thr Gln Ser Pro Ser Ser
       145                   150                   155                   160

Leu Ser Ala Ser Val Gly Asp Arg Val Thr Ile Thr Cys Arg Ala Ser
                          165                   170                   175

Gln Asp Ile Asn Ser Tyr Leu Ser Trp Phe Gln Gln Lys Pro Gly Lys
                          180                   185                   190

Ala Pro Lys Thr Leu Ile Tyr Arg Ala Asn Arg Leu Glu Ser Gly Val
                          195                   200                   205

Pro Ser Arg Phe Ser Gly Ser Gly Ser Gly Thr Asp Tyr Thr Leu Thr
                          210                   215                   220

Ile Ser Ser Leu Gln Tyr Glu Asp Phe Gly Ile Tyr Tyr Cys Gln Gln
       225                   230                   235                   240

Tyr Asp Glu Ser Pro Trp Thr Phe Gly Gly Gly Thr Lys Leu Glu Ile
                          245                   250                   255

Lys Ser Gly Gly Gly Gly Ser Gly Ala Leu Ser Asn Ser Ile Met Tyr
                          260                   265                   270

Phe Ser His Phe Val Pro Val Phe Leu Pro Ala Lys Pro Thr Thr Thr
                          275                   280                   285

Pro Ala Pro Arg Pro Pro Thr Pro Ala Pro Thr Ile Ala Ser Gln Pro
                          290                   295                   300

Leu Ser Leu Arg Pro Glu Ala Cys Arg Pro Ala Ala Gly Gly Ala Val
       305                   310                   315                   320

His Thr Arg Gly Leu Asp Ile Tyr Ile Trp Ala Pro Leu Ala Gly Thr
                          325                   330                   335

Cys Gly Val Leu Leu Leu Ser Leu Val Ile Thr Leu Tyr Cys Arg Leu
                          340                   345                   350

Lys Ile Gln Val Arg Lys Ala Ala Ile Thr Ser Tyr Glu Lys Ser Asp
                          355                   360                   365

Gly Val Tyr Thr Gly Leu Ser Thr Arg Asn Gln Glu Thr Tyr Glu Thr
                          370                   375                   380

Leu Lys His Glu Lys Pro Pro Gln Gly Ser Gly Ser Pro Leu Cys Leu
       385                   390                   395                   400

Gln Arg Glu Ala Lys Val Pro His Leu Pro Ala Asp Lys Ala Arg Gly
                          405                   410                   415

Thr Gln Gly Pro Glu Gln Gln His Leu Leu Ile Thr Ala Pro Ser Ser
                          420                   425                   430

Ser Ser Ser Ser Leu Glu Ser Ala Ser Ala Leu Asp Arg Arg Ala
                          435                   440                   445

Pro Thr Arg Asn Gln Pro Gln Ala Pro Gly Val Glu Ala Ser Gly Ala
           450                   455                   460

Gly Glu Ala Arg Ala Ser Thr Gly Ser Ser Asp Ser Ser Pro Gly Gly
       465                   470                   475                   480

His Gly Thr Gln Val Asn Val Thr Cys Ile Val Asn Val Cys Ser Ser
                          485                   490                   495
```

-continued

```
Ser Asp His Ser Ser Gln Cys Ser Ser Gln Ala Ser Ser Thr Met Gly
            500                 505                 510

Asp Thr Asp Ser Ser Pro Ser Glu Ser Pro Lys Asp Glu Gln Val Pro
        515                 520                 525

Phe Ser Lys Glu Glu Cys Ala Phe Arg Ser Gln Leu Glu Thr Pro Glu
    530                 535                 540

Thr Leu Leu Gly Ser Thr Glu Glu Lys Pro Leu Pro Leu Val Pro
545                 550                 555                 560

Asp Ala Gly Met Lys Pro Ser
                565

<210> SEQ ID NO 27
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 30
<211> LENGTH: 86
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 30

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr Leu Tyr Cys
                85

<210> SEQ ID NO 31
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Ile Tyr
    50                  55                  60

Ile Trp Ala Pro Leu Ala Gly Thr Cys Gly Val Leu Leu Leu Ser Leu
65                  70                  75                  80

Val Ile Thr

<210> SEQ ID NO 32
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Gly Ser Thr
                100                 105                 110

Ser Gly Ser Gly Lys Pro Gly Ser Gly Glu Gly Ser Glu Val Gln Leu
            115                 120                 125

Val Glu Ser Ser Gly Gly Gly Ser Gly Gly Gly Ser Gly Gly
130                 135                 140

Gly Gly Ser Leu Val Gln Pro Gly Gly Ser Leu Arg Leu Ser Cys Ala
145                 150                 155                 160

Ala Ser Gly Phe Asn Ile Lys Asp Thr Tyr Ile His Trp Val Arg Gln
                165                 170                 175

Ala Pro Gly Lys Gly Leu Glu Trp Val Ala Arg Ile Tyr Pro Thr Asn
            180                 185                 190

Gly Tyr Thr Arg Tyr Ala Asp Ser Val Lys Gly Arg Phe Thr Ile Ser
        195                 200                 205

Ala Asp Thr Ser Lys Asn Thr Ala Tyr Leu Gln Met Asn Ser Leu Arg
    210                 215                 220

Ala Glu Asp Thr Ala Val Tyr Tyr Cys Ser Arg Trp Gly Gly Asp Gly
225                 230                 235                 240

Phe Tyr Ala Met Asp Val Trp Gly Gln Gly Thr Leu Val Thr Val
                245                 250                 255

<210> SEQ ID NO 33
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile

```
                195                 200                 205
Ser Ser Leu Gln Tyr Glu Asp Phe Gly Ile Tyr Tyr Cys Gln Gln Tyr
        210                 215                 220

Asp Glu Ser Pro Trp Thr Phe Gly Gly Gly Thr Lys Leu Glu Ile Lys
225                 230                 235                 240

<210> SEQ ID NO 34
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Tyr Leu Ile Ile Gly Ile Cys Gly Gly Ser Leu Leu Met Val
1               5                   10                  15

Phe Val Ala Leu Leu Val Phe Tyr Ile Thr
            20                  25

<210> SEQ ID NO 35
<211> LENGTH: 1075
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
taatacgact cactataggg agaaagacgc caccatgggc aagaagcaaa atcgcaagac      60
ggggaattcc aagacacaat ccgctagccc accacctaaa gagcgttcta gctcccctgc    120
tactgagcag tcctggatgg aaaacgactt cgatgaactc cgggaagagg gatttaggcg    180
atccaactat tcagaactcc gcgaagatat ccagacaaag gggaaggaag tcgagaattt    240
cgagaagaac ctcgaggagt gcatcacccg tatcacaaac actgagaaat gtctcaaaga    300
actcatggaa cttaagacaa aagccaggga gcttcgagag gagtgtcgga gtctgagatc    360
caggtgtgac cagctcgagg agcgcgtgag cgcgatggaa gacgagatga acgagatgaa    420
aagagagggc aaattcaggg agaagcgcat taagaggaac gaacagagtc tgcaggagat    480
ttgggattac gtcaagaggc ctaacctgcg gttgatcggc gtccccgaga gcgacgtaga    540
aaacgggact aaactggaga atacacttca agacatcatt caagaaaatt ttccaaacct    600
ggctcggcaa gctaatgtgc aaatccaaga gatccaacgc acaccccagc ggtatagctc    660
tcggcgtgcc accctaggc atattatcgt gcgctttact aaggtggaga tgaaagagaa    720
gatgctgcga gccgctcggg aaagggaag ggtgactttg aagggcaaac ctattcggct    780
gacggttgac cttagcgccg agacactcca ggcacgccgg aatgggcc ccatctttaa    840 tatcctgaag gagaagaact ccagccacg aatctcttac cctgcaaagt tgagttttat    900
ctccgagggt gagattaagt atttcatcga taaacagatg ctgcgagact tcgtgacaac    960
tcgcccagct ctcaaggaac tgctcaaaga ggctcttaat atggagcgca ataatagata   1020
tcaacccttg cagaaccacg caaagatgga ttataaggat gacgatgata aatga         1075

<210> SEQ ID NO 36
<211> LENGTH: 5751
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 36

| | | | | | | |
|---|---|---|---|---|---|---|
| taatacgact | cactataggg | agaaagacgc | caccatgaca | ggttcaaata | gtcacattac | 60 |
| gattctcact | ctgaatataa | atgggctgaa | ttctgcaatt | aaacggcaca | ggcttgcttc | 120 |
| ctggataaag | tctcaagacc | cctcagtgtg | ctgtattcag | gaaacgcatc | tcacgtgcag | 180 |
| ggacacccat | cggctgaaaa | taaaggctg | gcggaagatc | taccaagcca | atggaaaaca | 240 |
| aaagaaggct | ggggtggcga | tacttgtaag | cgataaaaca | gactttaaac | caactaagat | 300 |
| caaacgggac | aaagagggcc | attacatcat | ggtaaagggt | agtattcaac | aagaggagct | 360 |
| gactatcctg | aatatttatg | cacctaatac | tggagccccc | agattcataa | agcaagtgtt | 420 |
| gagtgacctt | caacgcgacc | tcgactccca | cactctgatc | atgggagact | ttaacacccc | 480 |
| gctgtccact | ctcgacagat | ctactagaca | gaaagtcaac | aaggatacac | aggaactgaa | 540 |
| cagtgctctc | caccaagcgg | accttatcga | catctacaga | acactccacc | ccaaaagcac | 600 |
| agaatatacc | ttcttttcag | cccctcacca | cacctattcc | aaaattgacc | acattgtggg | 660 |
| gagtaaagcc | cttctctcca | aatgtaaacg | gaccgaaatt | atcactaact | atctctccga | 720 |
| ccacagtgca | ataaaacttg | aattgcgaat | taagaatctc | actcaaagta | gatccacgac | 780 |
| atggaaactg | aacaatctcc | tcttgaatga | ctactgggtg | cataacgaaa | tgaaggctga | 840 |
| aataaagatg | ttctttgaga | ccaacgaaaa | caaagacacc | acgtaccaga | atctctggga | 900 |
| cgctttcaaa | gcagtgtgtc | gaggaaaatt | tattgcactg | aatgcttaca | agcggaagca | 960 |
| ggaaagatcc | aaaatagaca | ccctgactag | ccaacttaaa | gaactggaaa | agcaagagca | 1020 |
| aactcatagc | aaagctagcc | gtcgccaaga | aattacgaaa | atcagagctg | aactgaagga | 1080 |
| aattgagaca | cagaaaaccc | tgcaaaagat | aaatgaaagc | cgcagctggt | tctttgaacg | 1140 |
| catcaacaaa | atcgataggc | cacttgctcg | ccttatcaag | aagaaagggg | agaagaatca | 1200 |
| aatcgacact | ataagaatg | ataaaggcga | tataaccacc | gatcccacag | aaattcaaac | 1260 |
| aaccatacgc | gaatactaca | aacacctcta | cgccaataaa | ctcgaaaatc | tcgaggaaat | 1320 |
| ggatacattc | ctcgacacgt | acacccttcc | caggctgaac | caggaagaag | ttgaatcact | 1380 |
| gaatcggcct | atcacgggga | gtgaaatagt | agctatcatc | aattcactcc | ctaccaagaa | 1440 |
| gtcacccgga | cctgatggat | tcaccgccga | attctaccag | agatacatgg | aagaactggt | 1500 |
| gcccttcttg | ctgaaacttt | tccaaagtat | tgagaaagag | ggaatacttc | caaactcatt | 1560 |
| ttatgaggca | tccatcattc | tgatcccgaa | gcccggcagg | gacacgacca | agaaagagaa | 1620 |
| ttttcgacca | atctcattga | tgaacattga | tgcaaagatc | ctcaataaaa | tactggcaaa | 1680 |
| tcggattcag | cagcacataa | agaagctgat | ccaccatgat | caagtaggct | tcatccccgg | 1740 |
| tatgcaaggt | tggttcaata | tacgaaaatc | aatcaatgtt | atccagcata | taaaccgggc | 1800 |
| caaagacaag | aaccacatga | ttattagtat | cgatgctgag | aaagcctttg | acaaaataca | 1860 |
| acaacccttc | atgctgaaaa | cattgaataa | gctgggaatt | gatggcacct | acttcaaaat | 1920 |
| catcagagcc | atatatgaca | aaccaacagc | aaatatcatt | ctgaatggtc | agaaattgga | 1980 |
| agcattcccc | ttgaaaaccg | gcacacggca | gggttgccct | ctgtcaccac | tcctcttcaa | 2040 |
| catcgtgttg | gaagttcttg | cccgcgcaat | ccggcaggaa | aaggaaatca | agggcattca | 2100 |
| actgggcaaa | gaggaagtta | aattgagcct | gtttgcagac | gacatgatcg | tctatttgga | 2160 |
| aaaccccata | gttagtgcac | aaaatctgct | gaagttgatc | agtaatttct | ccaaagtgag | 2220 |
| tgggtacaaa | atcaatgtgc | aaaagagcca | agctttcttg | tacaccaaca | acaggcaaac | 2280 |

```
tgagtctcaa atcatgggcg aactcccctt cgtgattgca tccaagcgga tcaaatacct    2340
ggggattcaa ttgactcgtg atgtgaagga cctcttcaag gagaactaca acccctgct    2400 caaggaaatc aaagaggaca caaacaaatg gaagaacatt ccatgctctt gggtgggaag    2460
gatcaatatc gtcaaaatgg ccatcctgcc caaggtaatt tacaggttca atgctatacc    2520
catcaagctc cccatgacat tcttcacaga acttgaaaag acgacgctga agttcatttg    2580
gaaccagaaa cgtgccagga ttgctaaatc tattctctcc caaagaaaca aagctggcgg    2640
aatcacactc ccagacttca aactttacta caaggcgacc gtgacgaaaa cggcttggta    2700
ctggtaccaa aacagggata tagatcaatg aaccgaacg gagcccagcg aaattatgcc    2760
tcatatatac aactatctga tctttgacaa accggagaag aacaagcaat ggggaaagga    2820
tagtctgttt aataaatggt gctgggaaaa ctggctcgca atctgtagga agctgaaact    2880
ggatccattc ttgacgcctt atacaaagat aaattcccga tggattaaag atctcaacgt    2940
gaaacccaaa acaattaaaa ccctcgagga aacctgggt attacgattc aggacattgg    3000
ggtgggaaag gacttcatgt ccaaaacccc aaaagcgatg gcaaccaaag acaaaatcga    3060
caaatgggat ctcataaaac ttaagtcatt ttgcacagct aaagaaacga caattagggt    3120
gaaccgacaa ccgaccactt gggagaaaat cttcgcaaca tacagttctg acaaaggcct    3180
gatttccagg atctacaatg aattgaaaca aatttacaag aagaagacga caaccctat    3240 aaagaaatgg ccaaggaca tgaacagaca cttctctaag aagacattt atgcagccaa    3300 gaaacacatg aagaaatgca gctcttcact ggcaatcagg gaaatgcaaa tcaaaacaac    3360
aatgagatat catctcacac ccgtcagaat ggccatcatt aagaagagcg aaacaaccg    3420 gtgctggcgt ggttgcggag aaatcggtac tctccttcac tgttggtggg actgtaaact    3480
cgttcaacca ctgtggaagt ctgtgtggcg gttcctcaga gatctggaac tcgaaatccc    3540
atttgaccca gccatccctc tcctgggtat atacccgaat gagtataaat cctgctgcta    3600
taaagacacc tgcacaagga tgtttattgc agctctcttc acaatcgcga agacgtggaa    3660
ccaacccaaa tgtccgacta tgattgactg gattaagaag atgtggcaca tatacactat    3720
ggaatactat gctgcgatca agaacgatga gttcatatca tttgtgggca catggatgaa    3780
actcgaaacc atcatactct ctaaattgag tcaagaacag aaaactaaac accgtatatt    3840
ttccctgatc ggtgggaatt agctacaaag acgatgacga caaggaccat ggagacggtg    3900
agagacacaa aaaattccaa cacactattg caatgaaaat aaatttcctt tattagccag    3960
aagtcagatg ctcaagggc ttcatgatgt ccccataatt tttggcagag ggaaaaagat    4020
ctcagtggta tttgtgagcc agggcattgg ccttctgata ggcagcctgc acctgaggag    4080
tgcggccgct ttacttgtac agctcgtcca tgccgagagt gatcccggcg gcggtcacga    4140
actccagcag gaccatgtga tcgcgcttct cgttggggtc tttgctcagg gcggactggg    4200
tgctcaggta gtggttgtcg ggcagcagca cggggccgtc gccgatgggg tgttctgct    4260 ggtagtggtc ggcgagctgc acgctgccgt cctcgatgtt gtggcggatc ttgaagttca    4320
ccttgatgcc gttcttctgc ttgtcggcca tgatatagac gttgtggctg ttgtagttgt    4380
actccagctt gtgccccagg atgttgccgt cctccttgaa gtcgatgccc ttcagctcga    4440
tgcggttcac cagggtgtcg ccctcgaact tcacctcggc gcgggtcttg tagttgccgt    4500
cgtccttgaa gaagatggtg cgctcctgga cgtagccttc gggcatggcg gacttgaaga    4560
agtcgtgctg cttcatgtgg tcggggtagc ggctgaagca ctgcacgccg taggtcaggg    4620
```

| | | | |
|---|---|---|---|
| tggtcacgag ggtgggccag ggcacgggca gcttgccggt ggtgcagatg aacttcaggg | 4680 |
| tcagcttgcc gtaggtggca tcgccctcgc cctcgccgga cacgctgaac ttgtggccgt | 4740 |
| ttacgtcgcc gtccagctcg accaggatgg gcaccacccc ggtgaacagc tcctcgccct | 4800 |
| tgctcaccat ggtggcggga tctgacggtt cactaaacca gctctgctta tatagacctc | 4860 |
| ccaccgtaca cgcctaccgc ccatttgcgt caatggggcg gagttgttac gacattttgg | 4920 |
| aaagtcccgt tgattttggt gccaaaacaa actcccattg acgtcaatgg ggtgagact | 4980 |
| tggaaatccc cgtgagtcaa accgctatcc acgcccattg atgtactgcc aaaaccgcat | 5040 |
| caccatggta atagcgatga ctaatacgta gatgtactgc caagtaggaa agtcccataa | 5100 |
| ggtcatgtac tgggcataat gccaggcggg ccatttaccg tcattgacgt caatagggg | 5160 |
| cgtacttggc atatgataca cttgatgtac tgccaagtgg gcagtttacc gtaaatactc | 5220 |
| cacccattga cgtcaatgga aagtccctat tggcgttact atgggaacat acgtcattat | 5280 |
| tgacgtcaat gggcggggt cgttgggcgg tcagccaggc gggccattta ccgtaagtta | 5340 |
| tgtaacgacg tctcagctga caatgagatc acatggacac aggaagggga atatcacact | 5400 |
| ctggggactg tggtgggtc ggggagggg ggagggatag cattgggaga tatacctaat | 5460 |
| gctagatgac acattagtgg gtgcagcgca ccagcatggc acatgtatac atatgtaact | 5520 |
| aacctgcaca atgtgcacat gtaccctaaa acttagagta taatggatcc gcaggcctct | 5580 |
| gctagcttga ctgactgaga tacagcgtac cttcagctca cagacatgat aagatacatt | 5640 |
| gatgagtttg gacaaaccac aactagaatg cagtgaaaaa aatgctttat ttgtgaaatt | 5700 |
| tgtgatgcta ttgctttatt tgtaaccatt ataagctgca ataaacaagt t | 5751 |

<210> SEQ ID NO 37
<211> LENGTH: 18285
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

| | |
|---|---|
| cggccgcggg gggaggagcc aagatggccg aataggaaca gctccggtct acagctccca | 60 |
| gcgtgagcga cgcagaagac ggtgatttct gcatttccat ctgaggtacc gggttcatct | 120 |
| cactagggag tgccagacag tgggcgcagg ccagtgtgtg tgcgcaccgt gcgcgagccg | 180 |
| aagcagggcg aggcattgcc tcacctggga agcgcaaggg gtcagggagt tccctttccg | 240 |
| agtcaaagaa aggggtgacg gacgcacctg gaaaatcggg tcactcccac ccgaatattg | 300 |
| cgcttttcag accggcttaa gaaacggcgc accacgagac tatatcccac acctggctcg | 360 |
| gagggtccta cgcccacgga atctcgctga ttgctagcac agcagtctga gatcaaactg | 420 |
| caaggcggca acgaggctgg gggaggggcg cccgccattg cccaggcttg cttaggtaaa | 480 |
| caaagcagca gggaagctcg aactgggtgg agcccaccac agctcaagga ggcctgcctg | 540 |
| cctctgtagg ctccacctct ggggcaggg cacagacaaa caaaaagaca gcagtaacct | 600 |
| ctgcagactt aagtgtccct gtctgacagc tttgaagaga gcagtggttc tcccagcacg | 660 |
| cagctggaga tctgagaacg ggcagactgc ctcctcaagt gggtccctga cccctgaccc | 720 |
| ccgagcagcc taactgggag gcacccccca gcagggcac actgacacct cacacggcag | 780 |
| ggtattccaa cagacctgca gctgagggtc ctgtctgtta aaggaaaac taacaaccag | 840 |
| aaaggacatc tacaccgaaa acccatctgt acatcaccat catcaaagac caaaagtaga | 900 |

```
taaaaccaca aagatgggga aaaaacagaa cagaaaaact ggaaactcta aaacgcagag    960
cgcctctcct cctccaaagg aacgcagttc ctcaccagca acagaacaaa gctggatgga   1020
gaatgatttt tgatgagctga gagaagaagg cttcagacga tcaaattact ctgagctacg   1080
ggaggacatt caaaccaaag gcaagaagt tgaaaactt gaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgagaaggga gtttagaga   1320
aaaaagaata aaaagaaatg agcaaagcct ccaagaaata tgggactatg tgaaaagacc   1380
aaatctacgt ctgattggtg tacctgaaag tgatgtggag aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca agttgaaat aaggaaaaaa atgttaaggg cagccagaga   1620
gaaaggtcgg gttaccctca aggaaagcc catcagacta acagcggatc tctcggcaga   1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca agaaggcca   2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacacccca ctgtcaacat tagacagatc   2460
aacgagacag aaagtcaaca aggatacccca ggaattgaac tcagctctgc accaagcaga   2520
cctaatagac atctacagaa ctctccaccc caaatcaaca gaatatacat tttttcagc   2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga caacctgct   2760
cctgaatgac tactgggtac ataacgaaat gaaggcagaa ataaagatgt tctttgaaac   2820
caacgagaac aaagacacca cataccgaat tctctgggac gcattcaaag cagtgtgtag   2880
agggaaattt atagcactaa atgcctacaa gagaaagcag gaaagatcca aaattgacac   2940
cctaacatca caattaaaag aactagaaaa gcaagagcaa acacattcaa agctagcag   3000
aaggcaagaa ataactaaaa tcagagcaga actgaaggaa atagagacac aaaaaaccct   3060
tcaaaaaatc aatgaatcca ggagctggtt ttttgaaagg atcaacaaaa ttgatagacc   3120
gctagcaaga ctaataaaga aaaaagaga gaagaatcaa atagacacaa taaaaaatga   3180
taaaggggat atcaccaccg atcccacaga aatacaaact accatcagag aatactacaa   3240
acacctctac gcaaataaac tagaaaatct agaagaaatg gatacattcc tcgacacata   3300
```

```
cactctccca agactaaacc aggaagaagt tgaatctctg aatcgaccaa taacaggctc    3360
tgaaattgtg gcaataatca atagtttacc aaccaaaaag agtccaggac cagatggatt    3420
cacagccgaa ttctaccaga ggtacaagga ggaactggta ccattccttc tgaaactatt    3480
ccaatcaata gaaaagagg gaatcctccc taactcattt tatgaggcca gcatcattct    3540
gataccaaag ccgggcagag acacaaccaa aaagagaat tttagaccaa tatccttgat    3600
gaacattgat gcaaaaatcc tcaataaaat actggcaaac cgaatccagc agcacatcaa    3660
aaagcttatc caccatgatc aagtgggctt catccctggg atgcaaggct ggttcaatat    3720
acgcaaatca ataaatgtaa tccagcatat aaacagagcc aaagacaaaa accacatgat    3780
tatctcaata gatgcagaaa aagcctttga caaaattcaa caaccccttca tgctaaaaac    3840 tctcaataaa ttaggtattg atgggacgta tttcaaaata ataagagcta tctatgacaa    3900
acccacagcc aatatcatac tgaatgggca aaaactggaa gcattccctt tgaaaaccgg    3960
cacaagacag ggatgccctc tctcaccgct cctattcaac atagtgttgg aagttctggc    4020
cagggcaatc aggcaggaga aggaaataaa gggtattcaa ttaggaaaag aggaagtcaa    4080
attgtccctg tttgcagacg acatgattgt ttatctagaa aaccccatcg tctcagccca    4140
aaatctcctt aagctgataa gcaacttcag caaagtctca ggatacaaaa tcaatgtaca    4200
aaaatcacaa gcattcttat acaccaacaa cagacaaaca gagagccaaa tcatgggtga    4260
actcccattc acaattgctt caaagagaat aaaataccta ggaatccaac ttacaaggga    4320
tgtgaaggac ctcttcaagg agaactacaa accactgctc aaggaaataa agaggagac    4380 aaacaaatgg aagaacattc catgctcatg ggtaggaaga atcaatatcg tgaaaatggc    4440
catactgccc aaggtaattt acagattcaa tgccatcccc atcaagctac caatgacttt    4500
cttcacagaa ttggaaaaaa ctactttaaa gttcatatgg aaccaaaaaa gagcccgcat    4560
tgccaagtca atcctaagcc aaaagaacaa agctggaggc atcacactac ctgacttcaa    4620
actatactac aaggctacag taaccaaaac agcatggtac tggtaccaaa acagagatat    4680
agatcaatgg aacagaacag agccctcaga ataatgccg catatctaca actatctgat    4740
ctttgacaaa cctgagaaaa acaagcaatg gggaaaggat tccctattta ataaatggtg    4800
ctgggaaaac tggctagcca tatgtagaaa gctgaaactg gatcccttcc ttacaccta    4860 tacaaaaatc aattcaagat ggattaaaga tttaaacgtt aaacctaaaa ccataaaaac    4920
cctagaagaa aacctaggca ttaccattca ggacataggc gtgggcaagg acttcatgtc    4980
caaaacacca aaagcaatgg caacaaaaga caaaattgac aaatgggatc taattaaact    5040
aaagagcttc tgcacagcaa agaaactac catcagagtg aacaggcaac ctacaacatg    5100
ggagaaaatt tttgcaacct actcatctga caaagggcta atatccagaa tctacaatga    5160
actcaaacaa atttacaaga aaaaacaaa caaccccatc aaaaagtggg cgaaggacat    5220
gaacagacac ttctcaaaag aagacattta tgcagccaaa aaacacatga gaaatgctc    5280 atcatcactg gccatcagag aaatgcaaat caaaaccact atgagatatc atctcacacc    5340
agttagaatg gcaatcatta aaagtcagg aaacaacagg tgctggagag gatgcggaga    5400
aataggaaca cttttacact gttggtggga ctgtaaacta gttcaaccat tgtggaagtc    5460
agtgtggcga ttcctcaggg atctagaact agaaatacca tttgacccag ccatcccatt    5520
actgggtata tacccaaatg agtataaatc atgctgctat aaagacacat gcacacgtat    5580
gtttattgcg gcactattca caatagcaaa gacttggaac caacccaaat gtccaacaat    5640
```

```
gatagactgg attaagaaaa tgtggcacat atacaccatg aatactatg cagccataaa    5700 aaatgatgag ttcatatcct ttgtagggac atggatgaaa ttggaaacca tcattctcag    5760
taaactatcg caagaacaaa aaaccaaaca ccgcatattc tcactcatag gtgggaattg    5820
aacaatgaga tcacatggac acaggaaggg gaatatcaca ctctggggac tgtggtgggg    5880 tcggggagg ggggagggat agcattggga gatatatccta atgctagatg acacattagt    5940
gggtgcagcg caccagcatg gcacatgtat acggatccga attctcgacg gatcgatccg    6000
aacaaacgac ccaacacccg tgcgttttat tctgtctttt tattgccgat cccctcagaa    6060
gaactcgtca agaaggcgat agaaggcgat gcgctgcgaa tcgggagcgg cgataccgta    6120
aagcacgagg aagcggtcag cccattcgcc gccaagctct tcagcaatat cacgggtagc    6180
caacgctatg tcctgatagc ggtcggccgc tttacttgta cagctcgtcc atgccgagag    6240
tgatcccggc ggcggtcacg aactccagca ggaccatgtg atcgcgcttc tcgttggggt    6300
ctttgctcag ggcggactgg gtgctcaggt agtggttgtc gggcagcagc acggggccgt    6360
cgccgatggg ggtgttctgc tggtagtggt cggccaggtg agtccaggag atgtttcagc    6420
actgttgcct ttagtctcga ggcaacttag acaactgagt attgatctga gcacagcagg    6480
gtgtgagctg tttgaagata ctggggttgg gggtgaagaa actgcagagg actaactggg    6540
ctgagaccca gtggcaatgt tttagggcct aaggaatgcc tctgaaaatc tagatggaca    6600
actttgactt tgagaaaaga gaggtggaaa tgaggaaaat gacttttctt tattagattt    6660
cggtagaaag aactttcatc tttccccctat ttttgttatt cgttttaaaa catctatctg    6720
gaggcaggac aagtatggtc attaaaaaga tgcaggcaga aggcatatat tggctcagtc    6780
aaagtgggga actttggtgg ccaaacatac attgctaagg ctattcctat atcagctgga    6840
cacatataaa atgctgctaa tgcttcatta caaacttata tcctttaatt ccagatgggg    6900
gcaaagtatg tccagggggtg aggaacaatt gaaacatttg ggctggagta gattttgaaa    6960
gtcagctctg tgtgtgtgtg tgtgtgtgtg tgtgtgagag cgtgtgtttc ttttaacgtt    7020
ttcagcctac agcatacagg gttcatggtg gcaagaagat aacaagattt aaattatggc    7080
cagtgactag tgctgcaaga agaacaacta cctgcattta atgggaaagc aaaatctcag    7140
gctttgaggg aagttaacat aggcttgatt ctgggtggaa gctgggtgtg tagttatctg    7200
gaggccaggc tggagctctc agctcactat gggttcatct ttattgtctc ctttcatctc    7260
aacagctgca cgctgccgtc ctcgatgttg tggcggatct tgaagttcac cttgatgccg    7320
ttcttctgct tgtcggccat gatatagacg ttgtggctgt tgtagttgta ctccagcttg    7380
tgccccagga tgttgccgtc ctccttgaag tcgatgccct tcagctcgat gcggttcacc    7440
agggtgtcgc cctcgaactt cacctcggcg cgggtcttgt agttgccgtc gtccttgaag    7500
aagatggtgc gctcctggac gtagccttcg ggcatggcgg acttgaagaa gtcgtgctgc    7560
ttcatgtggt cggggtagcg gctgaagcac tgcacgccgt aggtcagggt ggtcacgagg    7620
gtgggccagg gcacgggcag cttgccggtg gtgcagatga acttcagggt cagcttgccg    7680
taggtggcat cgccctcgcc ctcgccggac acgctgaact tgtggccgtt tacgtcgccg    7740
tccagctcga ccaggatggg caccaccccg gtgaacagct cctcgccctt gctcaccatg    7800
gtggcgaatt cgaagcttga gctcgagatc tgagtccggt agcgctagcg gatctgacgg    7860
ttcactaaac cagctctgct tatatagacc tcccaccgta cacgcctacc gcccatttgc    7920
gtcaatgggg cggagttgtt acgacatttt ggaaagtccc gttgattttg gtgccaaaac    7980
aaactcccat tgacgtcaat ggggtggaga cttggaaatc cccgtgagtc aaaccgctat    8040
```

```
ccacgcccat tgatgtactg ccaaaaccgc atcaccatgg taatagcgat gactaatacg    8100
tagatgtact gccaagtagg aaagtcccat aaggtcatgt actgggcata atgccaggcg    8160
ggccatttac cgtcattgac gtcaataggg ggcgtacttg gcatatgata cacttgatgt    8220
actgccaagt gggcagttta ccgtaaatac tccacccatt gacgtcaatg gaaagtccct    8280
attggcgtta ctatgggaac atacgtcatt attgacgtca atgggcgggg gtcgttgggc    8340
ggtcagccag gcgggccatt taccgtaagt tatgtaacgc ggaactccat atatgggcta    8400
tgaactaatg accccgtaat tgattactat tagcccgggg gatccagaca tgataagata    8460
cattgatgag tttggacaaa ccacaactag aatgcagtga aaaaaatgct ttatttgtga    8520
aatttgtgat gctattgctt tatttgtaac cattataagc tgcaataaac aagttaacaa    8580
caacaattgc attcatttta tgtttcaggt tcaggggggag gtgtgggagg ttttttaaag    8640
caagtaaaac ctctacaaat gtggtatggc tgattatgat ccggctgcct cgcgcgtttc    8700
ggtgatgacg gtgaaaacct ctgacacatg cagctcccgg agacggtcac agcttgtctg    8760
taagcggatg ccgggagcag acaagcccgt cagggcgcgt cagcgggtgt tggcgggtgt    8820
cggggcgcag ccatgaggtc gatcgactct agaggatcga tccccgcccc ggacgaacta    8880
aacctgacta cgacatctct gccccttctt cgcggggcag tgcatgtaat cccttcagtt    8940
ggttggtaca acttgccaac tgggccctgt tccacatgtg acacgggggg ggaccaaaca    9000
caaaggggtt ctctgactgt agttgacatc cttataaatg gatgtgcaca tttgccaaca    9060
ctgagtggct ttcatcctgg agcagacttt gcagtctgtg gactgcaaca caacattgcc    9120
tttatgtgta actcttggct gaagctctta caccaatgct gggggacatg tacctcccag    9180
gggcccagga agactacggg aggctacacc aacgtcaatc agaggggcct gtgtagctac    9240
cgataagcgg accctcaaga gggcattagc aatagtgttt ataaggcccc cttgttaacc    9300
ctaaacgggt agcatatgct tcccgggtag tagtatatac tatccagact aaccctaatt    9360
caatagcata tgttacccaa cgggaagcat atgctatcga attagggtta gtaaaagggt    9420
cctaaggaac agcgatatct cccacccccat gagctgtcac ggttttattt acatgggtc    9480 aggattccac gagggtagtg aaccatttta gtcacaaggg cagtggctga agatcaagga    9540
gcgggcagtg aactctcctg aatcttcgcc tgcttcttca ttctccttcg tttagctaat    9600
agaataactg ctgagttgtg aacagtaagg tgtatgtgag gtgctcgaaa acaaggtttc    9660
aggtgacgcc cccagaataa aatttggacg ggggggttcag tggtggcatt gtgctatgac    9720
accaatataa ccctcacaaa ccccttgggc aataaatact agtgtaggaa tgaaacattc    9780
tgaatatctt taacaataga aatccatggg gtggggacaa gccgtaaaga ctggatgtcc    9840
atctcacacg aatttatggc tatgggcaac acataatcct agtgcaatat gatactgggg    9900
ttattaagat gtgtcccagg cagggaccaa gacaggtgaa ccatgttgtt acactctatt    9960
tgtaacaagg ggaaagagag tggacgccga cagcagcgga ctccactggt tgtctctaac    10020 accccgaaa attaaacggg gctccacgcc aatgggccc ataaacaaag acaagtggcc    10080
actctttttt ttgaaattgt ggagtggggg cacgcgtcag ccccacacg ccgcctgcg    10140 gttttggact gtaaaataag ggtgtaataa cttggctgat tgtaacccg ctaaccactg    10200 cggtcaaacc acttgcccac aaaaccacta atggcacccc gggaatacc tgcataagta    10260 ggtgggcggg ccaagatagg ggcgcgattg ctgcgatctg gaggacaaat tacacacact    10320
tgcgcctgag cgccaagcac agggttgttg gtcctcatat tcacgaggtc gctgagagca    10380
```

```
cggtgggcta atgttgccat gggtagcata tactacccaa atatctggat agcatatgct   10440
atcctaatct atatctgggt agcataggct atcctaatct atatctgggt agcatatgct   10500
atcctaatct atatctgggt agtatatgct atcctaattt atatctgggt agcataggct   10560
atcctaatct atatctgggt agcatatgct atcctaatct atatctgggt agtatatgct   10620
atcctaatct gtatccgggt agcatatgct atcctaatag agattagggt agtatatgct   10680
atcctaattt atatctgggt agcatatact acccaaatat ctggatagca tatgctatcc   10740
taatctatat ctgggtagca tatgctatcc taatctatat ctgggtagca taggctatcc   10800
taatctatat ctgggtagca tatgctatcc taatctatat ctgggtagta tatgctatcc   10860
taatttatat ctgggtagca taggctatcc taatctatat ctgggtagca tatgctatcc   10920
taatctatat ctgggtagta tatgctatcc taatctgtat ccgggtagca tatgctatcc   10980
tcatgcatat acagtcagca tatgataccc agtagtagag tgggagtgct atcctttgca   11040
tatgccgcca cctcccaagg gggcgtgaat tttcgctgct tgtccttttc ctgcatgctg   11100
gttgctccca ttcttaggtg aatttaagga ggccaggcta aagccgtcgc atgtctgatt   11160
gctcaccagg taaatgtcgc taatgttttc aacgcgaga aggtgttgag cgcggagctg   11220
agtgacgtga aacatgggt atgcccaatt gccccatgtt gggaggacga aaatggtgac   11280
aagacagatg gccagaaata caccaacagc acgcatgatg tctactgggg atttattctt   11340
tagtgcgggg gaatacacgg cttttaatac gattgagggc gtctcctaac aagttacatc   11400
actcctgccc ttcctcaccc tcatctccat cacctccttc atctccgtca tctccgtcat   11460 cacccctccgc ggcagcccct tccaccatag gtggaaacca gggaggcaaa tctactccat   11520
cgtcaaagct gcacacagtc accctgatat tgcaggtagg agcgggcttt gtcataacaa   11580
ggtccttaat cgcatccttc aaaacctcag caaatatatg agtttgtaaa agaccatga   11640 aataacagac aatggactcc cttagcgggc caggttgtgg gccgggtcca ggggccattc   11700 caaagggag acgactcaat ggtgtaagac gacattgtgg aatagcaagg gcagttcctc   11760
gccttaggtt gtaaagggag gtcttactac ctccatatac gaacacaccg gcgacccaag   11820
ttccttcgtc ggtagtcctt tctacgtgac tcctagccag gagagctctt aaaccttctg   11880
caatgttctc aaatttcggg ttggaacctc cttgaccacg atgctttcca aaccaccctc   11940
cttttttgcg cctgcctcca tcaccctgac cccggggtcc agtgcttggg ccttctcctg   12000
ggtcatctgc ggggccctgc tctatcgctc ccgggggcac gtcaggctca ccatctgggc   12060
caccttcttg gtggtattca aaataatcgg cttcccctac agggtggaaa atggccttc    12120 tacctggagg gggcctgcgc ggtggagacc cggatgatga tgactgacta ctgggactcc   12180
tgggcctctt ttctccacgt ccacgacctc tcccctggc tctttcacga cttccccccc    12240
tggctctttc acgtcctcta cccggcggc ctccactacc tcctcgaccc cggcctccac   12300
tacctcctcg accccggcct ccactgcctc ctcgacccg gctccacct cctgctcctg    12360 cccctcctgc tctgcccct cctctgctc ctgccctcc tgccctcct gctcctgccc    12420 ctcctgcccc tcctgctcct gccctcctg ccctcctgc tctgccct cctgcccctc    12480 ctcctgctcc tgcccctcct gccctcctc tgctcctgc ccctcctgcc cctcctgctc    12540 ctgccctcc tgccctcct gctcctgccc ctcctgcccc tcctgctcct gccctcctg    12600 ctcctgcccc tcctgctcct gccctcctg ctccctgccc tcctgcccct cctgcccctc    12660
ctcctgctct tgccctcct gctcctgccc ctcctgcccc tcctgccctt cctgctcctg    12720
cccctcctcc tgctcctgcc cctcctgccc ctcctgcccc tcctcctgct cctgcccctc    12780
```

```
ctgcccctcc tcctgctcct gcccctcctc ctgctcctgc ccctcctgcc cctcctgccc   12840
ctcctcctgc tcctgcccct cctgcccctc ctcctgctcc tgcccctcct cctgctcctg   12900
cccctcctgc ccctcctgcc cctcctcctg ctcctgcccc tcctcctgct cctgcccctc   12960
ctgcccctcc tgcccctcct gcccctcctc ctgctcctgc ccctcctcct gctcctgccc   13020
ctcctgctcc tgcccctccc gctcctgctc ctgctcctgt tccaccgtgg gtcccttgc   13080 agccaatgca acttggacgt ttttggggtc tccggacacc atctctatgt cttggccctg   13140
atcctgagcc gcccggggct cctggtcttc cgcctcctcg tcctcgtcct cttccccgtc   13200
ctcgtccatg gttatcaccc cctcttcttt gaggtccact gccgccggag ccttctggtc   13260
cagatgtgtc tcccttctct cctaggccat ttccaggtcc tgtacctggc ccctcgtcag   13320
acatgattca cactaaaaga gatcaataga catctttatt agacgacgct cagtgaatac   13380
agggagtgca gactcctgcc ccctccaaca gccccccac cctcatcccc ttcatggtcg   13440
ctgtcagaca gatccaggtc tgaaaattcc ccatcctccg aaccatcctc gtcctcatca   13500
ccaattactc gcagcccgga aaactcccgc tgaacatcct caagatttgc gtcctgagcc   13560
tcaagccagg cctcaaattc ctcgtccccc ttttgctgg acggtaggga tggggattct   13620
cgggacccct cctcttcctc ttcaaggtca ccagacagag atgctactgg ggcaacggaa   13680
gaaaagctgg gtgcggcctg tgaggatcag cttatcgatg ataagctgtc aaacatgaga   13740
attcttgaag acgaaagggc ctcgtgatac gcctattttt ataggttaat gtcatgataa   13800
taatggtttc ttagacgtca ggtggcactt ttcggggaaa tgtgcgcgga acccctattt   13860
gtttattttt ctaaatacat tcaaatatgt atccgctcat gagacaataa ccctgataaa   13920
tgcttcaata atattgaaaa aggaagagta tgagtattca acatttccgt gtcgccctta   13980 ttccctttt tgcggcattt tgccttcctg tttttgctca cccagaaacg ctggtgaaag   14040
taaaagatgc tgaagatcag ttgggtgcac gagtgggtta catcgaactg gatctcaaca   14100
gcggtaagat ccttgagagt tttcgccccg aagaacgttt tccaatgatg agcacttta   14160 aagttctgct atgtggcgcg gtattatccc gtgttgacgc cgggcaagag caactcggtc   14220
gccgcataca ctattctcag aatgacttgg ttgagtactc accagtcaca gaaaagcatc   14280
ttacggatgg catgacagta agagaattat gcagtgctgc cataaccatg agtgataaca   14340
ctgcggccaa cttacttctg acaacgatcg gaggaccgaa ggagctaacc gcttttttgc   14400
acaacatggg ggatcatgta actcgccttg atcgttggga accggagctg aatgaagcca   14460
taccaaacga cgagcgtgac accacgatgc ctgcagcaat ggcaacaacg ttgcgcaaac   14520
tattaactgg cgaactactt actctagctt cccggcaaca attaatagac tggatggagg   14580
cggataaagt tgcaggacca cttctgcgct cggcccttcc ggctggctgg tttattgctg   14640
ataaatctgg agccggtgag cgtgggtctc gcggtatcat tgcagcactg gggccagatg   14700
gtaagccctc ccgtatcgta gttatctaca cgacggggag tcaggcaact atggatgaac   14760
gaaatagaca gatcgctgag ataggtgcct cactgattaa gcattggtaa ctgtcagacc   14820
aagtttactc atatatactt tagattgatt taaaacttca ttttttaattt aaaaggatct   14880 aggtgaagat cctttttgat aatctcatga ccaaaatccc ttaacgtgag ttttcgttcc   14940
actgagcgtc agacccgta gaaaagatca aggatcttc ttgagatcct ttttttctgc   15000
gcgtaatctg ctgcttgcaa acaaaaaaac caccgctacc agcggtggtt tgtttgccgg   15060
atcaagagct accaactctt tttccgaagg taactggctt cagcagagcg cagataccaa   15120
```

```
atactgtcct tctagtgtag ccgtagttag gccaccactt caagaactct gtagcaccgc   15180
ctacatacct cgctctgcta atcctgttac cagtggctgc tgccagtggc gataagtcgt   15240
gtcttaccgg gttggactca agacgatagt taccggataa ggcgcagcgg tcgggctgaa   15300
cggggggttc gtgcacacag cccagcttgg agcgaacgac ctacaccgaa ctgagatacc   15360
tacagcgtga gctatgagaa agcgccacgc ttcccgaagg gagaaaggcg gacaggtatc   15420
cggtaagcgg cagggtcgga acaggagagc gcacgaggga gcttccaggg ggaaacgcct   15480
ggtatcttta tagtcctgtc gggtttcgcc acctctgact tgagcgtcga ttttgtgat    15540 gctcgtcagg ggggcggagc ctatggaaaa acgccagcaa cgcggccttt ttacggttcc   15600
tggccttttg ctggcctttt gctcacatgt tctttcctgc gttatcccct gattctgtgg   15660
ataaccgtat taccgccttt gagtgagctg ataccgctcg ccgcagccga acgaccgagc   15720
gcagcgagtc agtgagcgag gaagcggaag agcgcctgat gcggtatttt ctccttacgc   15780
atctgtgcgg tatttcacac cgcatatggt gcactctcag tacaatctgc tctgatgccg   15840
catagttaag ccagctgtgg aatgtgtgtc agttaggggt ggaaagtcc ccaggctccc     15900 cagcaggcag aagtatgcaa agcatgcatc tcaattagtc agcaaccagg tgtggaaagt   15960
ccccaggctc cccagcaggc agaagtatgc aaagcatgca tctcaattag tcagcaacca   16020
tagtcccgcc cctaactccg cccatcccgc cctaactccg cccagttccg cccattctc    16080 cgccccatgg ctgactaatt ttttttattt atgcagaggc cgaggccgcc tcggcctctg   16140
agctattcca gaagtagtga ggaggctttt ttggaggcct aggcttttgc aaaaagcttg   16200
catgcctgca ggtcggccgc cacgaccggt gccgccacca tcccctgacc cacgcccctg   16260
acccctcaca aggagacgac cttccatgac cgagtacaag cccacggtgc gcctcgccac   16320
ccgcgacgac gtccccgggc cgtacgcac cctcgccgcc gcgttcgccg actacccgc      16380 cacgcgccac accgtcgacc cggaccgcca catcgagcgg gtcaccgagc tgcaagaact   16440
cttcctcacg cgcgtcgggc tcgacatcgg caaggtgtgg gtcgcggacg acggcgccgc   16500
ggtggcggtc tggaccacgc cggagagcgt cgaagcgggg gcggtgttcg ccgagatcgg   16560
cccgcgcatg gccgagttga gcggttcccg gctggccgcg cagcaacaga tggaaggcct   16620
cctggcgccg caccggccca aggagcccgc gtggttcctg gccaccgtcg gcgtctcgcc   16680
cgaccaccag ggcaagggtc tgggcagcgc cgtcgtgctc cccggagtgg aggcggccga   16740
gcgcgccggg gtgcccgcct tcctggagac ctccgcgccc cgcaacctcc ccttctacga   16800
gcggctcggc ttcaccgtca ccgccgacgt cgaggtgccc gaaggaccgc gcacctggtg   16860
catgacccgc aagcccggtg cctgacgccc gccccacgac ccgcagcgcc cgaccgaaag   16920
gagcgcacga ccccatggct ccgaccgaag ccgacccggg cggccccgcc gaccccgcac   16980
ccgcccccga ggcccaccga ctctagagga tcataatcag ccataccaca tttgtagagg   17040
ttttacttgc tttaaaaaac ctcccacacc tccccctgaa cctgaaacat aaaatgaatg   17100
caattgttgt tgttaacttg tttattgcag cttataatgg ttacaaataa agcaatagca   17160
tcacaaattt cacaaataaa gcatttttt cactgcattc tagttgtggt ttgtccaaac    17220
tcatcaatgt atcttatcat gtctggatca ctcgccgata gtggaaaccg acgccccagc   17280
actcgtccga gggcaaagga ataggggaga tgggggaggc taactgaaac acggaaggag   17340
acaataccgg aaggaacccg cgctatgacg gcaataaaaa gacagaataa aacgcacggg   17400
tgttgggtcg tttgttcata aacgcggggt tcggtcccag ggctggcact ctgtcgatac   17460
cccaccgaga ccccattggg gccaatacgc ccgcgtttct tccttttccc cacccccaccc  17520
```

```
cccaagttcg ggtgaaggcc cagggctcgc agccaacgtc ggggcggcag gccctgccat    17580
agccactggc cccgtgggtt agggacgggg tcccccatgg ggaatggttt atggttcgtg    17640
ggggttatta ttttgggcgt tgcgtggggt ctggtccacg actggactga gcagacagac    17700
ccatggtttt tggatggcct gggcatggac cgcatgtact ggcgcgacac gaacaccggg    17760
cgtctgtggc tgccaaacac ccccgacccc caaaaaccac cgcgcggatt tctggcgtgc    17820
caagctagtc gaccaattct catgtttgac agcttatcat cgcagatccg ggcaacgttg    17880
ttgcattgct gcaggcgcag aactggtagg tatggaagat ctctagaagc tgggtaccag    17940
ctgctagcaa gcttgctagc ggccggctcg agtttactcc ctatcagtga tagagaacgt    18000
atgtcgagtt tactccctat cagtgataga gaacgatgtc gagtttactc cctatcagtg    18060
atagagaacg tatgtcgagt ttactcccta tcagtgatag agaacgtatg tcgagtttac    18120
tccctatcag tgatagagaa cgtatgtcga gtttatccct atcagtgata gagaacgtat    18180
gtcgagttta ctccctatca gtgatagaga acgtatgtcg aggtaggcgt gtacggtggg    18240
aggcctatat aagcagagct cgtttagtga accgtcagat cgccg                   18285

<210> SEQ ID NO 38
<211> LENGTH: 7264
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
taatacgact cactataggg agaagtactg ccaccatggg caagaagcaa atcgcaaga       60 cggggaattc caagacacaa tccgctagcc caccacctaa agagcgttct agctcccctg     120
ctactgagca gtcctggatg gaaaacgact tcgatgaact ccgggaagag ggatttaggc     180
gatccaacta ttcagaactc cgcgaagata tccagacaaa ggggaaggaa gtcgagaatt     240
tcgagaagaa cctcgaggag tgcatcaccc gtatcacaaa cactgagaaa tgtctcaaag     300
aactcatgga acttaagaca aaagccaggg agcttgagag ggagtgtcgg agtctgagat     360
ccaggtgtga ccagctcgag gagcgcgtga gcgcgatgga agacgagatg aacgagatga     420
aaagagaggg caaattcagg gagaagcgca ttaagaggaa cgaacagagt ctgcaggaga     480
tttgggatta cgtcaagagg cctaacctgc ggttgatcgg cgtccccgag agcgacgtag     540
aaaacgggac taaactggag aatacacttc aagacatcat tcaagaaaat tttccaaacc     600
tggctcggca agctaatgtg caaatccaag agatccaacg cacaccccag cggtatagct     660
ctcggcgtgc caccccctagg catattatcg tgcgctttac taaggtggag atgaaagaga     720
agatgctgcg agccgctcgg gaaaagggaa gggtgacttt gaagggcaaa cctattcggc     780
tgacggttga cctagcgcc gagacactcc aggcacgccg ggaatgggc cccatcttta      840 atatcctgaa ggagaagaac ttccagccac gaatctctta ccctgcaaag ttgagtttta     900
tctccgaggg tgagattaag tatttcatcg ataaacagat gctgcgagac ttcgtgacaa     960
ctcgcccagc tctcaaggaa ctgctcaaag aggctcttaa tatggagcgc aataatagat    1020
atcaacccct tgcagaaccac gcaaagatgt gagacagccg tcagaccatc aagactagga    1080
agaaactgca tcaactaatg agcaaaatca ccagctaaca tcatagtata catgaccggc    1140
tctaactcac atatcaccat ccttacactt aacattaacg gcctcaactc agctatcaag    1200
cgccatcggc tggccagctg gatcaaatca caggatccaa gcgtttgttg catccaagag    1260
```

```
acccacctga cctgtagaga tactcaccgc ctcaagatca agggatggcg aaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc   1500
tttatcaaac aggtcctgtc cgatctgcag cgagatctgg attctcatac gttgattatg   1560
ggtgatttca atacaccatt gagcaccctg gatcgcagca ccaggcaaaa ggtaaataaa   1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccac   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gatacctata ctctgccacg gcttaatcaa   2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga atctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc tctccctgaa agagattaag gaagatacta ataagtggaa gaatatcccc   3540
tgttcatggg ttggcagaat caacatagtg aagatggcaa tacttcctaa agtgatatat   3600
```

```
cgctttaacg ccatcccaat taaactgcct atgaccttct ttacggagct cgagaaaaca    3660
acccttaaat ttatatggaa tcaaaagaga gcaagaatag cgaagtccat cttgagccag    3720
aagaataagg ccggtgggat tactttgcct gattttaagt tgtattataa agccacagta    3780
actaagacag cctggtattg gtatcagaat agagacatcg accagtggaa tcggaccgaa    3840
ccatcagaga taatgcccca catctataat taccttatat tcgataagcc agaaaagaat    3900
aaacagtggg gcaaagacag cctcttcaac aagtggtgtt gggagaattg gctggccata    3960
tgccggaaac tcaagctcga cccctttctt acaccctaca ctaaaatcaa cagtaggtgg    4020
atcaaggact tgaatgtcaa gccaaagact ataagacac tggaagagaa tcttgggatc    4080
acaatacaag atataggcgt cggcaaagat tttatgtcaa agacgcccaa ggccatggcc    4140
actaaggata agattgataa gtgggacctt attaagctca aaagcttctg tactgccaag    4200
gagaccacga tcagagttaa taggcagccc actacatggg aaaagatttt cgccacttat    4260
tcatcagata aggggttgat aagcagaata tataacgagc tgaagcagat ctacaagaag    4320
aaaacgaata atcccatcaa gaagtgggca aaagatatga acaggcattt tagcaaagag    4380
gatatctacg ccgcgaagaa gcatatgaag aagtgtagtt caagcttggc cattcgtgag    4440
atgcagatta agacgaccat gcgataccac cttaccccag tgaggatggc aattatcaag    4500
aaatctggca ataatagatg ttggcggggc tgtggcagaga ttggcaccct gctccattgc    4560
tggtgggatt gcaagctggt gcagccgctt ggaaatcag tctggcgctt tctgagggac    4620
ctcgagcttg agattcccct cgatcccgca attcccttgc tcggaatcta tcctaacgaa    4680
tacaagagct gttgttacaa ggatacgtgt acccggatgt tcatcgcggc cttgtttacg    4740
atagctaaga cgtggaatca gcctaagtgc cccacaatga tcgattggat caagaaaatg    4800
tggcatattt ataccatgga gtattacgca gcaattaaga atgacgaatt tatttccttc    4860
gttgggacct ggatgaagct ggagactatt attctgagca agctgtctca ggagcaaaag    4920
acaaagcata gaatcttctc tctcattggt ggtaacgact acaaagacga tgacgacaag    4980
taaagcgctt ctagaagttg tctcctcctg cactgactga ctgatacaat cgatttctgg    5040
atccgcaggc ctaatcaacc tctggattac aaaatttgtg aaagattgac tggtattctt    5100
aactatgttg ctccttttac gctatgtgga tacgctgctt taatgccttt gtatcatgct    5160
attgcttccc gtatggcttt cattttctcc tccttgtata atcctggttg ctgtctctt    5220
tatgaggagt tgtggcccgt tgtcaggcaa cgtggcgtgg tgtgcactgt gtttgctgac    5280
gcaaccccca ctggttgggg cattgccacc acctgtcagc tcctttccgg gactttcgct    5340
ttccccctcc ctattgccac ggcggaactc atcgccgcct gccttgcccg ctgctggaca    5400
ggggctcggc tgttgggcac tgacaattcc gtggtgttgt cggggaagct gacgtccttt    5460
ccatggctgc tcgcctgtgt tgccacctgg attctgcgcg gacgtccttt ctgctacgtc    5520
ccttcggccc tcaatccagc ggaccttcct tcccgctgag agacacaaaa aattccaaca    5580
cactattgca atgaaaataa atttccttta ttagccagaa gtcagatgct caaggggctt    5640
catgatgtcc ccataatttt tggcagaggg aaaaagatct cagtggtatt tgtgagccag    5700
ggcattggc ttctgatagg cagcctgcac ctgaggagtg cggccgcttt acttgtacag    5760
ctcgtccatg ccgagagtga tcccggcggc ggtcacgaac tccagcagga ccatgtgatc    5820
gcgcttctcg ttggggtctt tgctcagggc ggactgggtg ctcaggtagt ggttgtcggg    5880
cagcagcacg gggccgtcgc cgatgggggt gttctgctgg tagtggtcgg cgagctgcac    5940
gctgccgtcc tcgatgttgt ggcggatctt gaagttcacc ttgatgccgt tcttctgctt    6000
```

```
gtcggccatg atatagacgt tgtggctgtt gtagttgtac tccagcttgt gccccaggat    6060
gttgccgtcc tccttgaagt cgatgccctt cagctcgatg cggttcacca gggtgtcgcc    6120
ctcgaacttc acctcggcgc gggtcttgta gttgccgtcg tccttgaaga agatggtgcg    6180
ctcctggacg tagccttcgg gcatggcgga cttgaagaag tcgtgctgct tcatgtggtc    6240
ggggtagcgg ctgaagcact gcacgccgta ggtcagggtg gtcacgaggg tgggccaggg    6300
cacgggcagc ttgccggtgg tgcagatgaa cttcagggtc agcttgccgt aggtggcatc    6360
gccctcgccc tcgccggaca cgctgaactt gtggccgttt acgtcgccgt ccagctcgac    6420
caggatgggc accaccccgg tgaacagctc ctcgcccttg ctcaccatgg tggcgggatc    6480
tgacggttca ctaaaccagc tctgcttata tagacctccc accgtacacg cctaccgccc    6540
atttgcgtca atggggcgga gttgttacga catttttggaa agtcccgttg attttggtgc    6600
caaaacaaac tcccattgac gtcaatgggg tggagacttg gaaatccccg tgagtcaaac    6660
cgctatccac gcccattgat gtactgccaa aaccgcatca ccatggtaat agcgatgact    6720
aatacgtaga tgtactgcca agtaggaaag tcccataagg tcatgtactg ggataatgc    6780 caggcgggcc atttaccgtc attgacgtca atagggggcg tacttggcat atgatacact    6840
tgatgtactg ccaagtgggc agtttaccgt aaatactcca cccattgacg tcaatggaaa    6900
gtccctattg gcgttactat gggaacatac gtcattattg acgtcaatgg gcggggtcg    6960 ttgggcggtc agccaggcgg gccatttacc gtaagttatg taacgggcct gctgccggct    7020
ctgcggcctc ttccgcgtct tcgccttcgc cctcagacga gtcggatctc cctttgggcc    7080
gcctccccgc ctgtctagct tgactgactg agatacagcg taccttcagc tcacagacat    7140
gataagatac attgatgagt ttggacaaac cacaactaga atgcagtgaa aaaaatgctt    7200
tatttgtgaa atttgtgatg ctattgcttt atttgtaacc attataagct gcaataaaca    7260
agtt                                                                 7264

<210> SEQ ID NO 39
<211> LENGTH: 18852
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
cggccgcggg gggaggagcc aagatggccg aataggaaca gctccggtct acagctccca      60
gcgtgagcga cgcagaagac ggtgatttct gcatttccat ctgaggtacc gggttcatct     120 cactaggag tgccagacag tgggcgcagg ccagtgtgtg tgcgcaccgt gcgcgagccg     180
aagcagggcg aggcattgcc tcacctggga agcgcaaggg gtcagggagt tccctttccg     240
agtcaaagaa aggggtgacg gacgcacctg gaaaatcggg tcactcccac ccgaatattg     300
cgcttttcag accggcttaa gaaacggcgc accacgagac tatatcccac acctggctcg     360
gagggtccta cgcccacgga atctcgctga ttgctagcac agcagtctga gatcaaactg     420
caaggcggca acgaggctgg gggaggggcg cccgccattg cccaggcttg cttaggtaaa     480
caaagcagca gggaagctcg aactgggtgg agcccaccac agctcaagga ggcctgcctg     540
cctctgtagg ctcacctct gggggcaggg cacagacaaa caaaaagaca gcagtaacct     600
ctgcagactt aagtgtccct gtctgacagc tttgaagaga gcagtggttc tcccagcacg     660
cagctggaga tctgagaacg ggcagactgc ctcctcaagt gggtccctga cccctgaccc     720
```

```
ccgagcagcc taactgggag gcaccccca gcagggcac actgacacct cacacggcag      780
ggtattccaa cagacctgca gctgagggtc ctgtctgtta aaggaaaac taacaaccag      840
aaggacatc tacaccgaaa acccatctgt acatcaccat catcaaagac caaaagtaga      900
taaaccaca aagatgggga aaaaacagaa cagaaaaact ggaaactcta aaacgcagag      960
cgcctctcct cctccaaagg aacgcagttc ctcaccagca acagaacaaa gctggatgga     1020
gaatgatttt tgatgagctga gagaagaagg cttcagacga tcaaattact ctgagctacg     1080
ggaggacatt caaaccaaag gcaagaagt tgaaaacttt gaaaaaaatt tagaagaatg      1140
tataactaga ataaccaata cagagaagtg cttaaaggag ctgatggagc tgaaaaccaa      1200
ggctcgagaa ctacgtgaag aatgcagaag cctcaggagc cgatgcgatc aactggaaga      1260
aagggtatca gcaatggaag atgaaatgaa tgaaatgaag cgagaaggga agtttagaga      1320
aaaaagaata aaagaaatg agcaaagcct ccaagaaata tgggactatg tgaaaagacc      1380
aaatctacgt ctgattggtg tacctgaaag tgatgtggag aatggaacca agttggaaaa      1440
cactctgcag gatattatcc aggagaactt ccccaatcta gcaaggcagg ccaacgttca     1500
gattcaggaa atacagagaa cgccacaaag atactcctcg agaagagcaa ctccaagaca     1560
cataattgtc agattcacca aagttgaaat gaaggaaaaa atgttaaggg cagccagaga     1620
gaaaggtcgg gttaccctca aaggaaagcc catcagacta acagcggatc tctcggcaga     1680
aaccctacaa gccagaagag agtgggggcc aatattcaac attcttaaag aaaagaattt     1740
tcaacccaga atttcatatc cagccaaact aagcttcata agtgaaggag aaataaaata     1800
ctttatagac aagcaaatgt tgagagattt tgtcaccacc aggcctgccc taaaagagct     1860
cctgaaggaa gcgctaaaca tggaaaggaa caaccggtac cagccgctgc aaaatcatgc     1920
caaaatgtaa agaccatcaa gactaggaag aaactgcatc aactaatgag caaaatcacc     1980
agctaacatc ataatgacag gatcaacttc acacataaca atattaactt taaatataaa     2040
tggactaaat tctgcaatta aaagacacag actggcaagt tggataaaga gtcaagaccc     2100
atcagtgtgc tgtattcagg aaacccatct cacgtgcaga gacacacata ggctcaaaat     2160
aaaaggatgg aggaagatct accaagccaa tggaaaacaa aaaaaggcag gggttgcaat     2220
cctagtctct gataaaacag actttaaacc aacaaagatc aaaagagaca agaaggcca      2280
ttacataatg gtaaagggat caattcaaca agaggagcta actatcctaa atatttatgc     2340
acccaataca ggagcaccca gattcataaa gcaagtcctc agtgacctac aaagagactt     2400
agactcccac acattaataa tgggagactt taacacccca ctgtcaacat tagacagatc     2460
aacgagacag aaagtcaaca aggatacca ggaattgaac tcagctctgc accaagcaga     2520
cctaatagac atctacagaa ctctccaccc caaatcaaca gaatatacat ttttttcagc     2580
accacaccac acctattcca aaattgacca catagttgga agtaaagctc tcctcagcaa     2640
atgtaaaaga acagaaatta taacaaacta tctctcagac cacagtgcaa tcaaactaga     2700
actcaggatt aagaatctca ctcaaagccg ctcaactaca tggaaactga caacctgct      2760
cctgaatgac tactgggtac ataacgaaat gaaggcagaa ataaagatgt tctttgaaac     2820
caacgagaac aaagacacca cataccagaa tctctggac gcattcaaag cagtgtgtag      2880
agggaaattt atagcactaa atgcctacaa gagaaagcag gaaagatcca aaattgacac     2940
cctaacatca caattaaaag aactagaaaa gcaagagcaa acacattcaa agctagcag      3000
aaggcaagaa ataactaaaa tcagagcaga actgaaggaa atagagacac aaaaaaccct     3060
```

-continued

```
tcaaaaaatc aatgaatcca ggagctggtt ttttgaaagg atcaacaaaa ttgatagacc    3120
gctagcaaga ctaataaaga aaaaagaga gaagaatcaa atagacacaa taaaaaatga    3180
taaaggggat atcaccaccg atcccacaga aatacaaact accatcagag aatactacaa    3240
acacctctac gcaaataaac tagaaaatct agaagaaatg gatacattcc tcgacacata    3300
cactctccca agactaaacc aggaagaagt tgaatctctg aatcgaccaa taacaggctc    3360
tgaaattgtg gcaataatca atagtttacc aaccaaaaag agtccaggac cagatggatt    3420
cacagccgaa ttctaccaga ggtacaagga ggaactggta ccattccttc tgaaactatt    3480
ccaatcaata gaaaaagagg gaatcctccc taactcattt tatgaggcca gcatcattct    3540
gataccaaag ccgggcagag acacaaccaa aaaagagaat tttagaccaa tatccttgat    3600
gaacattgat gcaaaaatcc tcaataaaat actggcaaac cgaatccagc agcacatcaa    3660
aaagcttatc caccatgatc aagtgggctt catccctggg atgcaaggct ggttcaatat    3720
acgcaaatca ataaatgtaa tccagcatat aaacagagcc aaagacaaaa accacatgat    3780
tatctcaata gatgcagaaa aagcctttga caaaattcaa caacccttca tgctaaaaac    3840
tctcaataaa ttaggtattg atgggacgta tttcaaaata ataagagcta tctatgacaa    3900
acccacagcc aatatcatac tgaatgggca aaaactggaa gcattccctt tgaaaaccgg    3960
cacaagacag ggatgccctc tctcaccgct cctattcaac atagtgttgg aagttctggc    4020
cagggcaatc aggcaggaga aggaaataaa gggtattcaa ttaggaaaag aggaagtcaa    4080
attgtccctg tttgcagacg acatgattgt ttatctagaa aaccccatcg tctcagccca    4140
aaatctcctt aagctgataa gcaacttcag caaagtctca ggatacaaaa tcaatgtaca    4200
aaaatcacaa gcattcttat acaccaacaa cagacaaaca gagagccaaa tcatgggtga    4260
actcccattc acaattgctt caaagagaat aaaatacta ggaatccaac ttacaaggga    4320
tgtgaaggac ctcttcaagg agaactacaa accactgctc aaggaaataa agaggagac    4380 aaacaaatgg aagaacattc catgctcatg ggtaggaaga atcaatatcg tgaaaatggc    4440
catactgccc aaggtaattt acagattcaa tgccatcccc atcaagctac caatgacttt    4500
cttcacagaa ttggaaaaaa ctactttaaa gttcatatgg aaccaaaaaa gagcccgcat    4560
tgccaagtca atcctaagcc aaaagaacaa agctggaggc atcacactac ctgacttcaa    4620
actatactac aaggctacag taaccaaaac agcatggtac tggtaccaaa acagagatat    4680
agatcaatgg aacagaacag agccctcaga aataatgccg catatctaca actatctgat    4740
ctttgacaaa cctgagaaaa acaagcaatg gggaaaggat tccctattta ataaatggtg    4800
ctgggaaaac tggctagcca tatgtagaaa gctgaaactg gatcccttcc ttacacctta    4860
tacaaaaatc aattcaagat ggattaaaga ttaaacgtt aaacctaaaa ccataaaaac    4920
cctagaagaa aacctaggca ttaccattca ggacatagg gtgggcaagg acttcatgtc    4980
caaaacacca aaagcaatgg caacaaaaga caaaattgac aaatgggatc taattaaact    5040
aaagagcttc tgcacagcaa aagaaactac catcagagtg aacaggcaac ctacaacatg    5100
ggagaaaatt tttgcaacct actcatctga caaagggcta atatccagaa tctacaatga    5160
actcaaacaa atttacaaga aaaaacaaa caaccccatc aaaaagtggg cgaaggacat    5220
gaacagacac ttctcaaaag aagacattta tgcagccaaa aacacatga agaaatgctc    5280 atcatcactg gccatcagag aaatgcaaat caaaaccact atgagatatc atctcacacc    5340
agttagaatg gcaatcatta aaagtcagg aacaacagg tgctggagag gatgcggaga    5400
aataggaaca cttttacact gttggtggga ctgtaaacta gttcaaccat tgtggaagtc    5460
```

-continued

```
agtgtggcga ttcctcaggg atctagaact agaaatacca tttgacccag ccatcccatt   5520
actgggtata tacccaaatg agtataaatc atgctgctat aaagacacat gcacacgtat   5580
gtttattgcg gcactattca caatagcaaa gacttggaac caacccaaat gtccaacaat   5640
gatagactgg attaagaaaa tgtggcacat atacaccatg gaatactatg cagccataaa   5700
aaatgatgag ttcatatcct ttgtagggac atggatgaaa ttggaaacca tcattctcag   5760
taaactatcg caagaacaaa aaaccaaaca ccgcatattc tcactcatag gtgggaattg   5820
aacaatgaga tcacatggac acaggaaggg gaatatcaca ctctggggac tgtggtgggg   5880
tcgggggagg ggggagggat agcattggga gatataccta atgctagatg acacattagt   5940
gggtgcagcg caccagcatg gcacatgtat acggatccga attctcgacg gatcgatccg   6000
aacaaacgac ccaacacccg tgcgttttat tctgtctttt tattgccgat cccctcagaa   6060
gaactcgtca agaaggcgat agaaggcgat gcgctgcgaa tcgggagcgg cgataccgta   6120
aagcacgagg aagcggtcag cccattcgcc gccaagctct tcagcaatat cacgggtagc   6180
caacgctatg tcctgatagc ggtcggccgc tcatgttctc gtaggagtcg gcgtcctctt   6240
cgtggttagg tccaggttgg cctctgatag accgcagctg aggagcggcg tacagaatgc   6300
ctctcatgtc ctcatagctg ccgctgcctt gtggaggctt ctcgtgcttc agtgtctcgt   6360
atgtctcttg attccgggtg ctcaggccgg tgtacacgcc atcagatttc tcgtagctgg   6420
tgatggcggc cttccgcact tggatcttca gccgtctgca gtacagggtg atgaccagag   6480
acagcagcag gacaccacat gtgccagcca gaggggccca aatgtagata tccaggcctc   6540
tggtatgcac agctccgcct gcagcaggtc tacaggcttc aggtctgaga gacagaggct   6600
ggctggcgat tgtaggagct ggtgtaggtg gtctaggagc gggtgttgtt gtaggcttgg   6660
cgggcagaaa cacgggcacg aagtggctga agtacatgat gctattgctc agggctccgc   6720
ttcctccgcc gcctgatttg atttccagct tggtgcctcc gccaaatgtc caagggctct   6780
cgtcgtactg ctggcagtag tagatgccga agtcctcgta ctgcaggctg ctgattgtca   6840
gggtgtagtc ggtgccagag ccgctgccag aaaatctgct tggcacgccg ctttccagtc   6900
tgttggcccg gtagatcagt gtcttagggg ccttgccagg cttctgctgg aaccagctca   6960
ggtagctgtt gatgtcctgg ctggctctac aggtgatggt cactctatcg cccacagagg   7020
cagacaggct gctagggctc tgtgtcatct ggatatcaga gccaccaccg ccagatccac   7080
cgccacctga tcctccgcct ccgctagaaa ctgtcactgt ggtgccctgg ccccacacat   7140
cgaagtacca gtcgtagcct cttctggtgc agaagtacac ggcggtatcc tcggctctca   7200
ggctgttgat ctgcaggtag gcggtgttct tgctgtcgtc caggctgaag gtgaatctgc   7260
ccttaaagct atcggcgtag gttggctcgc cggtgtgggg attgatccag cccatccact   7320
caaggccagg tgagtccagg agatgtttca gcactgttgc ctttagtctc gaggcaactt   7380
agacaactga gtattgatct gagcacagca gggtgtgagc tgtttgaaga tactggggtt   7440
gggggtgaag aaactgcaga ggactaactg ggctgagacc cagtggcaat gttttagggc   7500
ctaaggaatg cctctgaaaa tctagatgga caactttgac tttgagaaaa gagaggtgga   7560
aatgaggaaa atgacttttc tttattagat ttcggtagaa agaactttca tctttcccct   7620
atttttgtta ttcgttttaa aacatctatc tggaggcagg acaagtatgg tcattaaaaa   7680
gatgcaggca gaaggcatat attggctcag tcaaagtggg gaactttggt ggccaaacat   7740
acattgctaa ggctattcct atatcagctg gacacatata aaatgctgct aatgcttcat   7800
```

```
tacaaactta tatcctttaa ttccagatgg gggcaaagta tgtccagggg tgaggaacaa   7860
ttgaaacatt tgggctggag tagattttga aagtcagctc tgtgtgtgtg tgtgtgtgtg   7920
tgtgtgtgag agcgtgtgtt tcttttaacg ttttcagcct acagcataca gggttcatgg   7980
tggcaagaag ataacaagat ttaaattatg gccagtgact agtgctgcaa gaagaacaac   8040
tacctgcatt taatgggaaa gcaaaatctc aggctttgag ggaagttaac ataggcttga   8100
ttctgggtgg aagctgggtg tgtagttatc tggaggccag gctggagctc tcagctcact   8160
atgggttcat ctttattgtc tcctttttcc aggggcctgt cggacccagt tcatgccgta   8220
gttggtgaag gtgtagccgc tggcggcaca gctgattctg acagatccgc caggtttcac   8280
aagtccgccg ccagactgaa ccagctggat ctcagagatg ctacaggcca ctgttcccag   8340
cagcagcaga gactgcagcc acatctggtg gcgaattcga agcttgagct cgagatctga   8400
gtccggtagc gctagcggat ctgacggttc actaaaccag ctctgcttat atagacctcc   8460
caccgtacac gcctaccgcc catttgcgtc aatggggcgg agttgttacg acattttgga   8520
aagtcccgtt gattttggtg ccaaaacaaa ctcccattga cgtcaatggg gtggagactt   8580
ggaaatcccc gtgagtcaaa ccgctatcca cgcccattga tgtactgcca aaaccgcatc   8640
accatggtaa tagcgatgac taatacgtag atgtactgcc aagtaggaaa gtcccataag   8700
gtcatgtact gggcataatg ccaggcgggc catttaccgt cattgacgtc ataggggggc   8760
gtacttggca tatgatacac ttgatgtact gccaagtggg cagtttaccg taaatactcc   8820
acccattgac gtcaatggaa agtccctatt ggcgttacta tgggaacata cgtcattatt   8880
gacgtcaatg ggcgggggtc gttgggcggt cagccaggcg ggccatttac cgtaagttat   8940
gtaacgcgga actccatata tgggctatga actaatgacc ccgtaattga ttactattag   9000
cccgggggat ccagacatga taagatacat tgatgagttt ggacaaacca caactagaat   9060
gcagtgaaaa aaatgcttta tttgtgaaat ttgtgatgct attgctttat ttgtaaccat   9120
tataagctgc aataaacaag ttaacaacaa caattgcatt catttttatgt ttcaggttca   9180
gggggaggtg tgggaggttt tttaaagcaa gtaaaacctc tacaaatgtg gtatggctga   9240
ttatgatccg gctgcctcgc gcgtttcggt gatgacggtg aaaacctctg acacatgcag   9300
ctcccggaga cggtcacagc ttgtctgtaa gcggatgccg ggagcagaca gcccgtcag   9360
ggcgcgtcag cgggtgttgg cgggtgtcgg ggcgcagcca tgaggtcgat cgactctaga   9420
ggatcgatcc ccgccccgga cgaactaaac ctgactacga catctctgcc ccttcttcgc   9480
ggggcagtgc atgtaatccc ttcagttggt tggtacaact tgccaactgg gccctgttcc   9540
acatgtgaca cggggggggga ccaaacacaa aggggttctc tgactgtagt tgacatcctt   9600
ataaatggat gtgcacattt gccaacactg agtggctttc atcctggagc agactttgca   9660
gtctgtggac tgcaacacaa cattgccttt atgtgtaact cttggctgaa gctcttacac   9720
caatgctggg ggacatgtac ctcccagggg cccaggaaga ctacgggagg ctacaccaac   9780
gtcaatcaga ggggcctgtg tagctaccga taagcggacc ctcaagaggg cattagcaat   9840
agtgtttata aggcccccctt gttaaccccta acgggtagc atatgcttcc cgggtagtag   9900
tatatactat ccagactaac cctaattcaa tagcatatgt tacccaacgg gaagcatatg   9960
ctatcgaatt agggttagta aaagggtcct aaggaacagc gatatctccc accccatgag  10020
ctgtcacggt tttatttaca tggggtcagg attccacgag ggtagtgaac catttagtc  10080
acaagggcag tggctgaaga tcaaggagcg ggcagtgaac tctcctgaat cttcgcctgc  10140
ttcttcattc tccttcgttt agctaataga ataactgctg agttgtgaac agtaaggtgt  10200
```

```
atgtgaggtg ctcgaaaaca aggtttcagg tgacgccccc agaataaaat ttggacgggg   10260
ggttcagtgg tggcattgtg ctatgacacc aatataaccc tcacaaaccc cttgggcaat   10320
aaatactagt gtaggaatga aacattctga atatctttaa caatagaaat ccatggggtg   10380
gggacaagcc gtaaagactg gatgtccatc tcacacgaat ttatggctat gggcaacaca   10440
taatcctagt gcaatatgat actggggtta ttaagatgtg tcccaggcag ggaccaagac   10500
aggtgaacca tgttgttaca ctctatttgt aacaagggga aagagagtgg acgccgacag   10560
cagcggactc cactggttgt ctctaacacc cccgaaaatt aaacgggggct ccacgccaat   10620 ggggcccata aacaaagaca agtggccact cttttttttg aaattgtgga gtgggggcac   10680
gcgtcagccc ccacacgccg ccctgcggtt ttggactgta aaataagggt gtaataactt   10740
ggctgattgt aaccccgcta accactgcgg tcaaaccact tgcccacaaa accactaatg   10800
gcaccccggg gaatacctgc ataagtaggt gggcgggcca agataggggc gcgattgctg   10860
cgatctggag gacaaattac acacacttgc gcctgagcgc caagcacagg gttgttggtc   10920
ctcatattca cgaggtcgct gagagcacgg tgggctaatg ttgccatggg tagcatatac   10980
tacccaaata tctggatagc atatgctatc ctaatctata tctgggtagc ataggctatc   11040
ctaatctata tctgggtagc atatgctatc ctaatctata tctgggtagt atatgctatc   11100
ctaatttata tctgggtagc ataggctatc ctaatctata tctgggtagc atatgctatc   11160
ctaatctata tctgggtagt atatgctatc ctaatctgta tccgggtagc atatgctatc   11220
ctaatagaga ttagggtagt atatgctatc ctaatttata tctgggtagc atatactacc   11280
caaatatctg gatagcatat gctatcctaa tctatatctg ggtagcatat gctatcctaa   11340
tctatatctg ggtagcatag gctatcctaa tctatatctg ggtagcatat gctatcctaa   11400
tctatatctg ggtagtatat gctatcctaa tttatatctg ggtagcatag gctatcctaa   11460
tctatatctg ggtagcatat gctatcctaa tctatatctg ggtagtatat gctatcctaa   11520
tctgtatccg ggtagcatat gctatcctca tgcatataca gtcagcatat gatacccagt   11580
agtagagtgg gagtgctatc ctttgcatat gccgccacct cccaaggggg cgtgaatttt   11640
cgctgcttgt ccttttcctg catgctggtt gctcccattc ttaggtgaat ttaaggaggc   11700
caggctaaag ccgtcgcatg tctgattgct caccaggtaa atgtcgctaa tgttttccaa   11760
cgcgagaagg tgttgagcgc ggagctgagt gacgtgacaa catgggtatg cccaattgcc   11820
ccatgttggg aggacgaaaa tggtgacaag acagatggcc agaaatacac caacagcacg   11880
catgatgtct actggggatt tattcttag tgcgggggaa tacacggctt ttaatacgat   11940
tgagggcgtc tcctaacaag ttacatcact cctgcccttc ctcaccctca tctccatcac   12000
ctccttcatc tccgtcatct ccgtcatcac cctccgcggc agccccttcc accataggtg   12060
gaaaccaggg aggcaaatct actccatcgt caaagctgca cacagtcacc ctgatattgc   12120
aggtaggagc gggctttgtc ataacaaggt ccttaatcgc atccttcaaa acctcagcaa   12180
atatatgagt ttgtaaaaag accatgaaat aacagacaat ggactcccctt agcgggccag   12240 gttgtgggcc gggtccaggg gccattccaa aggggagacg actcaatggt gtaagacgac   12300
attgtggaat agcaagggca gttcctcgcc ttaggttgta aagggaggtc ttactacctc   12360
catatacgaa cacaccggcg acccaagttc cttcgtcggt agtcctttct acgtgactcc   12420
tagccaggag agctcttaaa ccttctgcaa tgttctcaaa tttcggggttg gaacctcctt   12480 gaccacgatg ctttccaaac caccctcctt ttttgcgcct gcctccatca ccctgacccc   12540
```

```
ggggtccagt gcttgggcct tctcctgggt catctgcggg gccctgctct atcgctcccg    12600
gggcacgtc  aggctcacca tctgggccac cttcttggtg gtattcaaaa taatcggctt    12660
cccctacagg gtggaaaaat ggccttctac ctggaggggg cctgcgcggt ggagacccgg    12720
atgatgatga ctgactactg ggactcctgg gcctcttttc tccacgtcca cgacctctcc    12780
ccctggctct ttcacgactt ccccccctgg ctctttcacg tcctctaccc cggcggcctc    12840
cactacctcc tcgaccccgg cctccactac ctcctcgacc ccggcctcca ctgcctcctc    12900
gaccccggcc tccacctcct gctcctgccc ctcctgctcc tgcccctcct cctgctcctg    12960
ccctcctgc  ccctcctgct cctgcccctc ctgcccctcc tgctcctgcc cctcctgccc    13020
ctcctgctcc tgcccctcct gcccctcctc ctgctcctgc ccctcctgcc cctcctcctg    13080
ctcctgcccc tcctgcccct cctgctcctg cccctcctgc ccctcctgct cctgcccctc    13140
ctgcccctcc tgctcctgcc cctcctgctc ctgcccctcc tgctcctgcc cctcctgctc    13200
ctgcccctcc tgcccctcct gctcctgcc  cctcctgct  cctgcccctc    13260
ctgcccctcc tgcccctcct gctcctgccc ctcctcctgc tcctgcccct cctgcccctc    13320
ctgcccctcc tcctgctcct gcccctcctg cccctcctcc tgctcctgcc cctcctcctg    13380
ctcctgcccc tcctgcccct cctgcccctc ctgctcctgc tgcccctcct gcccctcctc    13440
ctgctcctgc ccctcctcct gctcctgccc ctcctgcccc tcctgcccct cctcctgctc    13500
ctgcccctcc tcctgctcct gcccctcctg cccctcctgc cccctcctg   cctcctcctg    13560
ctcctgcccc tcctcctgct ctgcccctc ctgctcctgc ccctcccgct cctgctcctg    13620
ctcctgttcc accgtgggtc cctttgcagc caatgcaact tggacgtttt tggggtctcc    13680
ggacaccatc tctatgtctt ggccctgatc ctgagccgcc cggggctcct ggtcttccgc    13740
ctcctcgtcc tcgtcctctt cccgtcctc  gtccatggtt atcacccct  cttctttgag    13800
gtccactgcc gccggagcct tctggtccag atgtgtctcc cttctctcct aggccatttc    13860
caggtcctgt acctggcccc tcgtcagaca tgattcacac taaaagagat caatagacat    13920
ctttattaga cgacgctcag tgaatacagg gagtgcagac tcctgccccc tccaacagcc    13980
cccccaccct catccccttc atggtcgctg tcagacagat ccaggtctga aaattcccca    14040
tcctccgaac catcctcgtc ctcatcacca attactcgca gcccggaaaa ctcccgctga    14100
acatcctcaa gatttgcgtc ctgagcctca agccaggcct caaattcctc gtccccttt    14160
ttgctggacg taggatgg ggattctcgg gacccctcct cttcctcttc aaggtcacca     14220
gacagagatg ctactgggc  aacggaagaa aagctgggtg cggcctgtga ggatcagctt    14280
atcgatgata agctgtcaaa catgagaatt cttgaagacg aaagggcctc gtgatacgcc    14340
tatttttata ggttaatgtc atgataataa tggtttctta gacgtcaggt ggcacttttc    14400
ggggaaatgt gcgcggaacc cctatttgtt tattttcta  aatacattca aatatgtatc    14460
cgctcatgag acaataaccc tgataaatgc ttcaataata ttgaaaaagg aagagtatga    14520
gtattcaaca tttccgtgtc gcccttattc ccttttttgc ggcattttgc cttcctgttt    14580
ttgctcaccc agaaacgctg gtgaaagtaa aagatgctga agatcagttg ggtgcacgag    14640
tgggttacat cgaactggat ctcaacagcg gtaagatcct tgagagtttt cgccccgaag    14700
aacgttttcc aatgatgagc acttttaaag ttctgctatg tggcgcggta ttatcccgtg    14760
ttgacgccgg gcaagagcaa ctcggtcgcc gcatacacta ttctcagaat gacttggttg    14820
agtactcacc agtcacagaa aagcatctta cggatggcat gacagtaaga gaattatgca    14880
gtgctgccat aaccatgagt gataacactg cggccaactt acttctgaca acgatcggag    14940
```

```
gaccgaagga gctaaccgct tttttgcaca acatggggga tcatgtaact cgccttgatc    15000
gttgggaacc ggagctgaat gaagccatac caaacgacga gcgtgacacc acgatgcctg    15060
cagcaatggc aacaacgttg cgcaaactat taactggcga actacttact ctagcttccc    15120
ggcaacaatt aatagactgg atggaggcgg ataaagttgc aggaccactt ctgcgctcgg    15180
cccttccggc tggctggttt attgctgata aatctggagc cggtgagcgt gggtctcgcg    15240
gtatcattgc agcactgggg ccagatggta agccctcccg tatcgtagtt atctacacga    15300
cggggagtca ggcaactatg gatgaacgaa atagacagat cgctgagata ggtgcctcac    15360
tgattaagca ttggtaactg tcagaccaag tttactcata tactttag attgatttaa      15420 aacttcattt ttaatttaaa aggatctagg tgaagatcct ttttgataat ctcatgacca    15480
aaatccctta acgtgagttt tcgttccact gagcgtcaga ccccgtagaa aagatcaaag    15540
gatcttcttg agatcctttt tttctgcgcg taatctgctg cttgcaaaca aaaaaaccac    15600
cgctaccagc ggtggtttgt ttgccggatc aagagctacc aactcttttt ccgaaggtaa    15660
ctggcttcag cagagcgcag ataccaaata ctgtccttct agtgtagccg tagttaggcc    15720
accacttcaa gaactctgta gcaccgccta catacctcgc tctgctaatc ctgttaccag    15780
tggctgctgc cagtggcgat aagtcgtgtc ttaccgggtt ggactcaaga cgatagttac    15840
cggataaggc gcagcggtcg ggctgaacgg ggggttcgtg cacacagccc agcttggagc    15900
gaacgaccta caccgaactg agatacctac agcgtgagct atgagaaagc gccacgcttc    15960
ccgaagggag aaaggcggac aggtatccgg taagcggcag ggtcggaaca ggagagcgca    16020
cgagggagct ccaggggga acgcctggt atctttatag tcctgtcggg tttcgccacc      16080
tctgacttga gcgtcgattt ttgtgatgct cgtcaggggg gcggagccta tggaaaaacg    16140
ccagcaacgc ggccttttta cggttcctgg ccttttgctg gccttttgct cacatgttct    16200
ttcctgcgtt atcccctgat tctgtggata accgtattac cgcctttgag tgagctgata    16260
ccgctcgccg cagccgaacg accgagcgca gcgagtcagt gagcgaggaa gcggaagagc    16320
gcctgatgcg gtattttctc cttacgcatc tgtgcggtat ttcacaccgc atatggtgca    16380
ctctcagtac aatctgctct gatgccgcat agttaagcca gctgtggaat gtgtgtcagt    16440
tagggtgtgg aaagtcccca ggctccccag caggcagaag tatgcaaagc atgcatctca    16500
attagtcagc aaccaggtgt ggaaagtccc caggctcccc agcaggcaga agtatgcaaa    16560
gcatgcatct caattagtca gcaaccatag tcccgcccct aactccgccc atcccgcccc    16620
taactccgcc cagttccgcc cattctccgc cccatggctg actaatttt ttatttatg      16680 cagaggccga ggccgcctcg gcctctgagc tattccagaa gtagtgagga ggcttttttg    16740
gaggcctagg cttttgcaaa aagcttgcat gcctgcaggt cggccgccac gaccggtgcc    16800
gccaccatcc cctgacccac gccctgacc cctcacaagg agacgacctt ccatgaccga    16860
gtacaagccc acggtgcgcc tcgcacccg cgacgacgtc ccccgggccg tacgcaccct    16920
cgccgccgcg ttcgccgact accccgccac gcgccacacc gtcgaccgg accgccacat     16980 cgagcgggtc accgagctgc aagaactctt cctcacgcgc gtcgggctcg acatcggcaa    17040
ggtgtgggtc gcggacgacg gcgccgcggt ggcggtctgg accacgccgg agagcgtcga    17100
agcgggggcg gtgttcgccg agatcggccc cgcgcatggcc gagttgagcg gttcccggct    17160
ggccgcgcag caacagatgg aaggcctcct ggcgccgcac cggcccaagg agcccgcgtg    17220
gttcctggcc accgtcggcg tctcgcccga ccaccagggc aagggtctgg gcagcgccgt    17280
```

| | |
|---|---|
| cgtgctcccc ggagtggagg cggccgagcg cgccggggtg cccgccttcc tggagacctc | 17340 |
| cgcgccccgc aacctcccct tctacgagcg gctcggcttc accgtcaccg ccgacgtcga | 17400 |
| ggtgcccgaa ggaccgcgca cctggtgcat gacccgcaag cccggtgcct gacgcccgcc | 17460 |
| ccacgacccg cagcgcccga ccgaaaggag cgcacgaccc catggctccg accgaagccg | 17520 |
| acccgggcgg ccccgccgac cccgcacccg ccccgaggc ccaccgactc tagaggatca | 17580 |
| taatcagcca taccacattt gtagaggttt tacttgcttt aaaaaacctc ccacacctcc | 17640 |
| ccctgaacct gaaacataaa atgaatgcaa ttgttgttgt taacttgttt attgcagctt | 17700 |
| ataatggtta caaataaagc aatagcatca caaatttcac aaataaagca ttttttcac | 17760 |
| tgcattctag ttgtggtttg tccaaactca tcaatgtatc ttatcatgtc tggatcactc | 17820 |
| gccgatagtg gaaaccgacg ccccagcact cgtccgaggg caaaggaata ggggagatgg | 17880 |
| gggaggctaa ctgaaacacg gaaggagaca ataccggaag gaacccgcgc tatgacggca | 17940 |
| ataaaaagac agaataaaac gcacgggtgt tgggtcgttt gttcataaac gcggggttcg | 18000 |
| gtcccagggc tggcactctg tcgatacccc accgagaccc cattgggggcc aatacgcccg | 18060 |
| cgtttcttcc ttttccccac cccaccccc aagttcgggt gaaggcccag ggctcgcagc | 18120 |
| caacgtcggg gcggcaggcc ctgccatagc cactggcccc gtgggttagg gacggggtcc | 18180 |
| cccatgggga atggtttatg gttcgtgggg gttattattt tgggcgttgc gtggggtctg | 18240 |
| gtccacgact ggactgagca gacagaccca tggttttttgg atggcctggg catggaccgc | 18300 |
| atgtactggc gcgacacgaa caccgggcgt ctgtggctgc caaacacccc cgaccccccaa | 18360 |
| aaaccaccgc gcggatttct ggcgtgccaa gctagtcgac caattctcat gtttgacagc | 18420 |
| ttatcatcgc agatccgggc aacgttgttg cattgctgca ggcgcagaac tggtaggtat | 18480 |
| ggaagatctc tagaagctgg gtaccagctg ctagcaagct tgctagcggc cggctcgagt | 18540 |
| ttactcccta tcagtgatag agaacgtatg tcgagtttac tccctatcag tgatagagaa | 18600 |
| cgatgtcgag tttactccct atcagtgata gagaacgtat gtcgagttta ctccctatca | 18660 |
| gtgatagaga acgtatgtcg agtttactcc ctatcagtga tagagaacgt atgtcgagtt | 18720 |
| tatccctatc agtgatagag aacgtatgtc gagtttactc cctatcagtg atagagaacg | 18780 |
| tatgtcgagg taggcgtgta cggtgggagg cctatataag cagagctcgt ttagtgaacc | 18840 |
| gtcagatcgc cg | 18852 |

<210> SEQ ID NO 40
<211> LENGTH: 19625
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

| | |
|---|---|
| cggccgcggg gggaggagcc aagatggccg aataggaaca gctccggtct acagctccca | 60 |
| gcgtgagcga cgcagaagac ggtgatttct gcatttccat ctgaggtacc gggttcatct | 120 |
| cactagggag tgccagacag tgggcgcagg ccagtgtgtg tgcgcaccgt gcgcgagccg | 180 |
| aagcagggcg aggcattgcc tcacctggga agcgcaaggg gtcagggagt tcccttttccg | 240 |
| agtcaaagaa aggggtgacg gacgcacctg gaaaatcggg tcactcccac ccgaatattg | 300 |
| cgcttttcag accggcttaa gaaacggcgc accacgagac tatatcccac acctggctcg | 360 |
| gagggtccta cgcccacgga atctcgctga ttgctagcac agcagtctga gatcaaactg | 420 |

```
caaggcggca acgaggctgg gggaggggcg cccgccattg cccaggcttg cttaggtaaa    480
caaagcagca gggaagctcg aactgggtgg agcccaccac agctcaagga ggcctgcctg    540
cctctgtagg ctccacctct gggggcaggg cacagacaaa caaaaagaca gcagtaacct    600
ctgcagactt aagtgtccct gtctgacagc tttgaagaga gcagtggttc tcccagcacg    660
cagctggaga tctgagaacg ggcagactgc ctcctcaagt gggtccctga cccctgaccc    720
ccgagcagcc taactgggag cacccccca gcagggcac actgacacct cacacggcag      780
ggtattccaa cagacctgca gctgagggtc ctgtctgtta aaggaaaac taacaaccag     840
aaaggacatc tacaccgaaa acccatctgt acatcaccat catcaaagac caaaagtaga    900
taaaaccaca aagatgggga aaaacagaa cagaaaaact ggaaactcta aaacgcagag     960
cgcctctcct cctccaaagg aacgcagttc ctcaccagca acagaacaaa gctggatgga   1020
gaatgatttt gatgagctga gagaagaagg cttcagacga tcaaattact ctgagctacg   1080
ggaggacatt caaaccaaag gcaaagaagt tgaaactttt gaaaaaaatt tagaagaatg   1140
tataactaga ataaccaata cagagaagtg cttaaaggag ctgatggagc tgaaaaccaa   1200
ggctcgagaa ctacgtgaag aatgcagaag cctcaggagc cgatgcgatc aactggaaga   1260
aagggtatca gcaatggaag atgaaatgaa tgaaatgaag cgaaaggga gtttagaga    1320
aaaaagaata aaaagaaatg agcaaagcct ccaagaaata tgggactatg tgaaaagacc   1380
aaaatctacgt ctgattggtg tacctgaaag tgatgtggaa aatggaacca agttggaaaa   1440
cactctgcag gatattatcc aggagaactt ccccaatcta gcaaggcagg ccaacgttca   1500
gattcaggaa atacagagaa cgccacaaag atactcctcg agaagagcaa ctccaagaca   1560
cataattgtc agattcacca aagttgaaat gaaggaaaaa atgttaaggg cagccagaga   1620
gaaaggtcgg gttaccctca aaggaaagcc catcagacta cagcggatc tctcggcaga    1680
aaccctacaa gccagaagag agtgggggcc aatattcaac attcttaaag aaaagaattt   1740
tcaacccaga atttcatatc cagccaaact aagcttcata agtgaaggag aaataaaata   1800
ctttatagac aagcaaatgt tgagagattt tgtcaccacc aggcctgccc taaaagagct   1860
cctgaaggaa gcgctaaaca tggaaaggaa caaccggtac cagccgctgc aaaatcatgc   1920
caaaatgtaa agaccatcaa gactaggaag aaactgcatc aactaatgag caaaatcacc   1980
agctaacatc ataatgacag gatcaacttc acacataaca atattaactt taaatataaa   2040
tggactaaat tctgcaatta aaagacacag actggcaagt tggataaaga gtcaagaccc   2100
atcagtgtgc tgtattcagg aaacccatct cacgtgcaga gacacacata ggctcaaaat   2160
aaaaggatgg aggaagatct accaagccaa tggaaaacaa aaaaaggcag gggttgcaat   2220
cctagtctct gataaaacag actttaaacc aacaaagatc aaaagagaca agaaggcca    2280
ttacataatg gtaaagggat caattcaaca agaggagcta actatcctaa atatttatgc   2340
acccaataca ggagcaccca gattcataaa gcaagtcctc agtgacctac aaagagactt   2400
agactcccac acattaataa tgggagactt taacaccca ctgtcaacat tagacagatc    2460
aacgagacag aaagtcaaca aggatacca ggaattgaac tcagctctgc accaagcaga    2520
cctaatagac atctacagaa ctctccaccc caaatcaaca gaatatacat tttttcagc    2580
accacaccac acctattcca aaattgacca catagttgga agtaaagctc tcctcagcaa   2640
atgtaaaaga acagaaatta taacaaacta tctctcagac cacagtgcaa tcaaactaga   2700
actcaggatt aagaatctca ctcaaagccg ctcaactaca tggaaactga acaacctgct   2760
cctgaatgac tactgggtac ataacgaaat gaaggcagaa ataaagatgt tctttgaaac   2820
```

```
caacgagaac aaagacacca cataccagaa tctctgggac gcattcaaag cagtgtgtag    2880
agggaaattt atagcactaa atgcctacaa gagaaagcag gaaagatcca aaattgacac    2940
cctaacatca caattaaaag aactagaaaa gcaagagcaa acacattcaa aagctagcag    3000
aaggcaagaa ataactaaaa tcagagcaga actgaaggaa atagagacac aaaaaaccct    3060
tcaaaaaatc aatgaatcca ggagctggtt ttttgaaagg atcaacaaaa ttgatagacc    3120
gctagcaaga ctaataaaga aaaaagaga gaagaatcaa atagacacaa taaaaaatga    3180
taaaggggat atcaccaccg atcccacaga aatacaaact accatcagag aatactacaa    3240
acacctctac gcaaataaac tagaaaatct agaagaaatg gatacattcc tcgacacata    3300
cactctccca agactaaacc aggaagaagt tgaatctctg aatcgaccaa taacaggctc    3360
tgaaattgtg gcaataatca atagtttacc aaccaaaaag agtccaggac cagatggatt    3420
cacagccgaa ttctaccaga ggtacaagga ggaactggta ccattccttc tgaaactatt    3480
ccaatcaata gaaaaagagg gaatcctccc taactcattt tatgaggcca gcatcattct    3540
gataccaaag ccgggcagag acacaaccaa aaaagagaat tttagaccaa tatccttgat    3600
gaacattgat gcaaaaatcc tcaataaaat actggcaaac cgaatccagc agcacatcaa    3660
aaagcttatc caccatgatc aagtgggctt catccctggg atgcaaggct ggttcaatat    3720
acgcaaatca ataaatgtaa tccagcatat aaacagagcc aaagacaaaa accacatgat    3780
tatctcaata gatgcagaaa aagcctttga caaaattcaa caacccttca tgctaaaaac    3840
tctcaataaa ttaggtattg atgggacgta tttcaaaata ataagagcta tctatgacaa    3900
acccacagcc aatatcatac tgaatgggca aaaactggaa gcattccctt tgaaaaccgg    3960
cacaagacag ggatgccctc tctcaccgct cctattcaac atagtgttgg aagttctggc    4020
cagggcaatc aggcaggaga aggaaataaa gggtattcaa ttaggaaaag aggaagtcaa    4080
attgtccctg tttgcagacg acatgattgt ttatctagaa aacccatcg tctcagccca    4140 aaatctcctt aagctgataa gcaacttcag caaagtctca ggatacaaaa tcaatgtaca    4200
aaaatcacaa gcattcttat acaccaacaa cagacaaaca gagagccaaa tcatgggtga    4260
actcccattc acaattgctt caaagagaat aaaatatccta ggaatccaac ttacaaggga    4320
tgtgaaggac ctcttcaagg agaactacaa accactgctc aaggaaataa agaggagac    4380 aaacaaatgg aagaacattc catgctcatg ggtaggaaga atcaatatcg tgaaaatggc    4440
catactgccc aaggtaattt acagattcaa tgccatcccc atcaagctac caatgacttt    4500
cttcacagaa ttggaaaaaa ctactttaaa gttcatatgg aaccaaaaaa gagcccgcat    4560
tgccaagtca atcctaagcc aaaagaacaa agctggaggc atcacactac ctgacttcaa    4620
actatactac aaggctacag taaccaaaac agcatggtac tggtaccaaa acagagatat    4680
agatcaatgg aacagaacag agccctcaga ataatgccg catatctaca actatctgat    4740
ctttgacaaa cctgagaaaa acaagcaatg gggaaaggat tccctattta ataaatggtg    4800
ctgggaaaac tggctagcca tatgtagaaa gctgaaactg gatcccttcc ttacaccta    4860 tacaaaaatc aattcaagat ggattaaaga tttaaacgtt aaacctaaaa ccataaaaac    4920
cctagaagaa aacctaggca ttaccattca ggacataggc gtgggcaagg acttcatgtc    4980
caaaacacca aaagcaatgg caacaaaaga caaaattgac aaatgggatc taattaaact    5040
aaagagcttc tgcacagcaa aagaaactac catcagagtg aacaggcaac ctacaacatg    5100
ggagaaaatt tttgcaacct actcatctga caaagggcta atatccagaa tctacaatga    5160
```

```
actcaaacaa atttacaaga aaaaaacaaa caaccccatc aaaaagtggg cgaaggacat      5220
gaacagacac ttctcaaaag aagacattta tgcagccaaa aaacacatga agaaatgctc      5280
atcatcactg gccatcagag aaatgcaaat caaaaccact atgagatatc atctcacacc      5340
agttagaatg gcaatcatta aaaagtcagg aaacaacagg tgctggagag gatgcggaga      5400
aataggaaca cttttacact gttggtggga ctgtaaacta gttcaaccat tgtggaagtc      5460
agtgtggcga ttcctcaggg atctagaact agaaatacca tttgacccag ccatcccatt      5520
actgggtata tacccaaatg agtataaatc atgctgctat aaagacacat gcacacgtat      5580
gtttattgcg gcactattca caatagcaaa gacttggaac caacccaaat gtccaacaat      5640
gatagactgg attaagaaaa tgtggcacat atacaccatg gaatactatg cagccataaa      5700
aaatgatgag ttcatatcct ttgtagggac atggatgaaa ttggaaacca tcattctcag      5760
taaactatcg caagaacaaa aaccaaaca ccgcatattc tcactcatag gtgggaattg       5820
aacaatgaga tcacatggac acaggaaggg aatatcaca ctctggggac tgtggtgggg       5880
tcggggagg ggggagggat agcattggga gatataccta atgctagatg acacattagt       5940
gggtgcagcg caccagcatg gcacatgtat acggatccga attctcgacg gatcgatccg      6000
aacaaacgac ccaacacccg tgcgttttat tctgtctttt tattgccgat cccctcagaa      6060
gaactcgtca agaaggcgat agaaggcgat gcgctgcgaa tcgggagcgg cgataccgta      6120
aagcacgagg aagcggtcag cccattcgcc gccaagctct tcagcaatat cacgggtagc      6180
caacgctatg tcctgatagc ggtcggccgc tttacttgta cagctcgtcc atgccgagag      6240
tgatcccggc ggcggtcacg aactccagca ggaccatgtg atcgcgcttc tcgttggggt      6300
ctttgctcag gcggactgg gtgctcaggt agtggttgtc gggcagcagc acggggccgt       6360
cgccgatggg ggtgttctgc tggtagtggt cggccaggtg agtccaggag atgtttcagc      6420
actgttgcct ttagtctcga gcaacttag acaactgagt attgatctga gcacagcagg       6480
gtgtgagctg tttgaagata ctggggttgg gggtgaagaa actgcagagg actaactggg      6540
ctgagaccca gtggcaatgt tttagggcct aaggaatgcc tctgaaaatc tagatggaca      6600
actttgactt tgagaaaaga gaggtggaaa tgaggaaaat gacttttctt tattagattt      6660
cggtagaaag aactttcatc tttcccctat ttttgttatt cgttttaaaa catctatctg      6720
gaggcaggac aagtatggtc attaaaaaga tgcaggcaga aggcatatat tggctcagtc      6780
aaagtgggga actttggtgg ccaaacatac attgctaagg ctattcctat atcagctgga      6840
cacatataaa atgctgctaa tgcttcatta caaacttata tcctttaatt ccagatgggg      6900
gcaaagtatg tccaggggtg aggaacaatt gaaacatttg ggctggagta gattttgaaa      6960
gtcagctctg tgtgtgtgtg tgtgtgtgtg tgtgtgagag cgtgtgtttc ttttaacgtt      7020
ttcagcctac agcatacagg gttcatggtg gcaagaagat aacaagattt aaattatggc      7080
cagtgactag tgctgcaaga agaacaacta cctgcattta atgggaaagc aaaatctcag      7140
gctttgaggg aagttaacat aggcttgatt ctgggtggaa gctgggtgtg tagttatctg      7200
gaggccaggc tggagctctc agctcactat gggttcatct ttattgtctc ctttcatctc      7260
aacagctgca cgctgccgtc ctcgatgttg tggcggatct tgaagttcac cttgatgccg      7320
ttcttctgct tgtcggccat gatatagacg ttgtggctgt tgtagttgta ctccagcttg      7380
tgccccagga tgttgccgtc ctccttgaag tcgatgccct tcagctcgat gcggttcacc      7440
agggtgtcgc cctcgaactt cacctcgcg cgggtcttgt agttgccgtc gtccttgaag      7500
aagatggtgc gctcctggac gtagccttcg ggcatggcgg acttgaagaa gtcgtgctgc      7560
```

```
ttcatgtggt cggggtagcg gctgaagcac tgcacgccgt aggtcagggt ggtcacgagg    7620
gtgggccagg gcacgggcag cttgccggtg gtgcagatga acttcagggt cagcttgccg    7680
taggtggcat cgccctcgcc ctcgccggac acgctgaact tgtggccgtt tacgtcgccg    7740
tccagctcga ccaggatggg caccaccccg gtgaacagtc cctcgccctt gctcaccata    7800
gggccgggat tctcctccac gtcaccgcat gttagaagac ttcctctgcc ctccatgttc    7860
tcgtaggagt cggcgtcctc ttcgtggtta ggtccaggtt ggcctctgat agaccgcagc    7920
tgaggagcgg cgtacagaat gcctctcatg tcctcatagc tgccgctgcc ttgtggaggc    7980
ttctcgtgct tcagtgtctc gtatgtctct tgattccggg tgctcaggcc ggtgtacacg    8040
ccatcagatt tctcgtagct ggtgatggcg gccttccgca cttggatctt cagccgtctg    8100
cagtacaggg tgatgaccag agacagcagc aggacaccac atgtgccagc cagaggggcc    8160
caaatgtaga tatccaggcc tctggtatgc acagctccgc ctgcagcagg tctacaggct    8220
tcaggtctga gagacagagg ctggctggcg attgtaggag ctggtgtagg tggtctagga    8280
gcgggtgttg ttgtaggctt ggcgggcaga acacgggca cgaagtggct gaagtacatg     8340
atgctattgc tcagggctcc gcttcctccg ccgcctgatt tgatttccag cttggtgcct    8400
ccgccaaatg tccaagggct ctcgtcgtac tgctggcagt agtagatgcc gaagtcctcg    8460
tactgcaggc tgctgattgt cagggtgtag tcggtgccag agccgctgcc agaaaatctg    8520
cttggcacgc cgcttttccag tctgttggcc cggtagatca gtgtcttagg ggccttgcca   8580
ggcttctgct ggaaccagct caggtagctg ttgatgtcct ggctggctct acaggtgatg    8640
gtcactctat cgcccacaga ggcagacagg ctgctagggc tctgtgtcat ctggatatca    8700
gagccaccac cgccagatcc accgccacct gatcctccgc ctcgctaga aactgtcact     8760 gtggtgccct ggccccacac atcgaagtac cagtcgtagc ctcttctggt gcagaagtac    8820
acggcggtat cctcggctct caggctgttg atctgcaggt aggcggtgtt cttgctgtcg    8880
tccaggctga aggtgaatct gcccttaaag ctatcggcgt aggttggctc gccggtgtgg    8940
gtattgatcc agcccatcca ctcaaggcct ttttccagggg cctgtcggac ccagttcatg   9000
ccgtagttgg tgaaggtgta gccgctggcg gcacagctga ttctgacaga tccgccaggt    9060
ttcacaagtc cgccgccaga ctgaaccagc tggatctcag agatgctaca ggccactgtt    9120
cccagcagca gcagagactg cagccacatt cgaagcttga gctcgagatc tgagtccggt    9180
agcgctagcg gatctgacgg ttcactaaac cagctctgct tatatagacc tcccaccgta    9240
cacgcctacc gcccatttgc gtcaatgggg cggagttgtt acgacatttt ggaaagtccc    9300
gttgattttg gtgccaaaac aaactcccat tgacgtcaat ggggtggaga cttggaaatc    9360
cccgtgagtc aaaccgctat ccacgcccat tgatgtactg ccaaaaccgc atcaccatgg    9420
taatagcgat gactaatacg tagatgtact gccaagtagg aaagtcccat aaggtcatgt    9480
actgggcata atgccaggcg ggccatttac cgtcattgac gtcaataggg ggcgtacttg    9540
gcatatgata cacttgatgt actgccaagt gggcagttta ccgtaaatac tccacccatt    9600
gacgtcaatg gaaagtccct attggcgtta ctatgggaac atacgtcatt attgacgtca    9660
atgggcgggg gtcgttgggc ggtcagccag gcgggccatt taccgtaagt tatgtaacgc    9720
ggaactccat atatgggcta tgaactaatg accccgtaat tgattactat tagcccgggg    9780
gatccagaca tgataagata cattgatgag tttggacaaa ccacaactag aatgcagtga    9840
aaaaaatgct ttatttgtga aatttgtgat gctattgctt tatttgtaac cattataagc    9900
```

```
tgcaataaac aagttaacaa caacaattgc attcatttta tgtttcaggt tcaggggag      9960
gtgtgggagg ttttttaaag caagtaaaac ctctacaaat gtggtatggc tgattatgat     10020
ccggctgcct cgcgcgtttc ggtgatgacg gtgaaaacct ctgacacatg cagctcccgg     10080
agacggtcac agcttgtctg taagcggatg ccgggagcag acaagcccgt cagggcgcgt     10140
cagcgggtgt tggcgggtgt cggggcgcag ccatgaggtc gatcgactct agaggatcga     10200
tccccgcccc ggacgaacta aacctgacta cgacatctct gccccttctt cgcggggcag     10260
tgcatgtaat cccttcagtt ggttggtaca acttgccaac tgggccctgt tccacatgtg     10320
acacggggg ggaccaaaca caaaggggtt ctctgactgt agttgacatc cttataaatg      10380
gatgtgcaca tttgccaaca ctgagtggct ttcatcctgg agcagacttt gcagtctgtg     10440
gactgcaaca caacattgcc tttatgtgta actcttggct gaagctctta caccaatgct     10500
ggggggacatg tacctcccag gggcccagga agactacggg aggctacacc aacgtcaatc    10560
agagggggcct gtgtagctac cgataagcgg accctcaaga gggcattagc aatagtgttt    10620
ataaggcccc cttgttaacc ctaaacgggt agcatatgct tcccgggtag tagtatatac     10680
tatccagact aaccctaatt caatagcata tgttacccaa cgggaagcat atgctatcga     10740
attagggtta gtaaaagggt cctaaggaac agcgatatct cccaccccat gagctgtcac     10800
ggttttattt acatggggtc aggattccac gagggtagtg aaccatttta gtcacaaggg     10860
cagtggctga agatcaagga gcgggcagtg aactctcctg aatcttcgcc tgcttcttca    10920
ttctccttcg tttagctaat agaataactg ctgagttgtg aacagtaagg tgtatgtgag     10980
gtgctcgaaa acaaggtttc aggtgacgcc cccagaataa aatttggacg gggggttcag    11040
tggtggcatt gtgctatgac accaatataa ccctcacaaa ccccttgggc aataaatact    11100
agtgtaggaa tgaaacattc tgaatatctt taacaataga aatccatggg gtggggacaa    11160
gccgtaaaga ctggatgtcc atctcacacg aatttatggc tatgggcaac acataatcct    11220
agtgcaatat gatactgggg ttattaagat gtgtcccagg cagggaccaa gacaggtgaa    11280
ccatgttgtt acactctatt tgtaacaagg ggaaagagag tggacgccga cagcagcgga    11340
ctccactggt tgtctctaac accccgaaa attaaacggg gctccacgcc aatggggccc     11400
ataaacaaag acaagtggcc actcttttt ttgaaattgt ggagtggggg cacgcgtcag     11460
cccccacacg ccgccctgcg gttttggact gtaaaataag ggtgtaataa cttggctgat    11520
tgtaaccccg ctaaccactg cggtcaaacc acttgcccac aaaaccacta atggcacccc    11580
ggggaatacc tgcataagta ggtgggcggg ccaagatagg ggcgcgattg ctgcgatctg    11640
gaggacaaat tacacacact tgcgcctgag cgccaagcac agggttgttg gtcctcatat    11700
tcacgaggtc gctgagagca cggtgggcta atgttgccat gggtagcata tactacccaa    11760
atatctggat agcatatgct atcctaatct atatctgggt agcataggct atcctaatct    11820
atatctgggt agcatatgct atcctaatct atatctgggt agtatatgct atcctaattt    11880
atatctgggt agcataggct atcctaatct atatctgggt agcatatgct atcctaatct    11940
atatctgggt agtatatgct atcctaatct gtatccgggt agcatatgct atcctaatag    12000
agattagggt agtatatgct atcctaattt atatctgggt agcatatact acccaaatat    12060
ctggatagca tatgctatcc taatctatat ctgggtagca tatgctatcc taatctatat    12120
ctgggtagca taggctatcc taatctatat ctgggtagca tatgctatcc taatctatat    12180
ctgggtagta tatgctatcc taatttatat ctgggtagca taggctatcc taatctatat    12240
ctgggtagca tatgctatcc taatctatat ctgggtagta tatgctatcc taatctgtat    12300
```

```
ccgggtagca tatgctatcc tcatgcatat acagtcagca tatgataccc agtagtagag    12360
tgggagtgct atcctttgca tatgccgcca cctcccaagg gggcgtgaat tttcgctgct    12420
tgtccttttc ctgcatgctg gttgctccca ttcttaggtg aatttaagga ggccaggcta    12480
aagccgtcgc atgtctgatt gctcaccagg taaatgtcgc taatgttttc caacgcgaga    12540
aggtgttgag cgcggagctg agtgacgtga acatgggt atgcccaatt gccccatgtt      12600
gggaggacga aaatggtgac aagacagatg gccagaaata caccaacagc acgcatgatg    12660
tctactgggg atttattctt tagtgcgggg gaatacacgg cttttaatac gattgagggc    12720
gtctcctaac aagttacatc actcctgccc ttcctcaccc tcatctccat cacctccttc    12780
atctccgtca tctccgtcat caccctccgc ggcagcccct ccaccatag gtggaaacca     12840 gggaggcaaa tctactccat cgtcaaagct gcacacagtc accctgatat tgcaggtagg    12900
agcgggcttt gtcataacaa ggtccttaat cgcatccttc aaaacctcag caaatatatg    12960
agtttgtaaa aagaccatga aataacagac aatggactcc cttagcgggc caggttgtgg    13020
gccgggtcca ggggccattc caaaggggag acgactcaat ggtgtaagac gacattgtgg    13080
aatagcaagg gcagttcctc gccttaggtt gtaaagggag gtcttactac ctccatatac    13140
gaacacaccg gcgacccaag ttccttcgtc ggtagtcctt tctacgtgac tcctagccag    13200
gagagctctt aaaccttctg caatgttctc aaatttcggg ttggaacctc cttgaccacg    13260
atgctttcca aaccaccctc ctttttttgcg cctgcctcca tcaccctgac cccggggtcc    13320
agtgcttggg ccttctcctg ggtcatctgc ggggccctgc tctatcgctc ccgggggcac    13380
gtcaggctca ccatctgggc caccttcttg gtggtattca aaataatcgg cttcccctac    13440
agggtggaaa aatggccttc tacctggagg gggcctgcgc ggtggagacc cggatgatga    13500
tgactgacta ctgggactcc tgggcctctt ttctccacgt ccacgacctc tccccctggc    13560
tctttcacga cttccccccc tggctctttc acgtcctcta ccccggcggc ctccactacc    13620
tcctcgaccc cggcctccac tacctcctcg accccggcct ccactgcctc ctcgaccccg    13680
gcctccacct cctgctcctg cccctcctgc tcctgcccct cctcctgctc ctgccccctcc    13740 tgcccctcct gctcctgccc ctcctgcccc tcctgctcct gccccctcctg ccctcctgc    13800 tcctgcccct cctgcccctc ctcctgctcc tgccccctcct gcccctcctc ctgctcctgc    13860
ccctcctgcc cctcctgctc ctgccccctcc tgcccctcct gctcctgccc ctcctgcccc    13920
tcctgctcct gccccctcctg ctcctgcccc tcctgctcct gccccctcctg ctcctgcccc    13980 tcctgccccct cctgccccctc ctcctgctcc tgccccctcct gctcctgccc ctcctgcccc    14040 tcctgccccct cctgctcctg ccccctcctcc tgctcctgcc cctcctgccc ctcctgcccc    14100
tcctcctgct cctgccccctc ctgccccctcc tcctgctcct gccccctcctc ctgctcctgc    14160 ccctcctgcc cctcctgccc ctcctcctgc tcctgccccct cctgccccctc ctcctgctcc    14220 tgccccctcct cctgctcctg ccccctcctgc cctcctgcc cctcctcctg ctcctgcccc    14280
tcctcctgct cctgccccctc ctgccccctcc tgccccctcct gccccctcctc ctgctcctgc    14340 ccctcctcct gctcctgccc ctcctgctcc tgccccctccc gctcctgctc ctgctcctgt    14400
tccaccgtgg gtcccttgc agccaatgca acttggacgt ttttggggtc tccggacacc      14460
atctctatgt cttggccctg atcctgagcc gcccggggct cctggtcttc cgcctcctcg     14520
tcctcgtcct cttccccgtc ctcgtccatg gttatcaccc cctcttcttt gaggtccact     14580
gccgccggag ccttctggtc cagatgtgtc tcccttctct cctaggccat ttccaggtcc    14640
```

```
tgtacctggc ccctcgtcag acatgattca cactaaaaga gatcaataga catctttatt   14700
agacgacgct cagtgaatac agggagtgca gactcctgcc ccctccaaca gccccccac    14760
cctcatcccc ttcatggtcg ctgtcagaca gatccaggtc tgaaaattcc ccatcctccg   14820
aaccatcctc gtcctcatca ccaattactc gcagcccgga aaactcccgc tgaacatcct   14880
caagatttgc gtcctgagcc tcaagccagg cctcaaattc ctcgtcccccc ttttgctgg   14940
acggtaggga tggggattct cgggacccct cctcttcctc ttcaaggtca ccagacagag   15000
atgctactgg ggcaacggaa gaaaagctgg gtgcggcctg tgaggatcag cttatcgatg   15060
ataagctgtc aaacatgaga attcttgaag acgaaagggc ctcgtgatac gcctattttt    15120
ataggttaat gtcatgataa taatggtttc ttagacgtca ggtggcactt ttcggggaaa   15180
tgtgcgcgga accctatttt gtttatttttt ctaaatacat tcaaatatgt atccgctcat   15240
gagacaataa ccctgataaa tgcttcaata atattgaaaa aggaagagta tgagtattca   15300
acatttccgt gtcgccctta ttcccttttt tgcggcattt tgccttcctg ttttttgctca   15360
cccagaaacg ctggtgaaag taaaagatgc tgaagatcag ttgggtgcac gagtgggtta   15420
catcgaactg gatctcaaca gcggtaagat ccttgagagt tttcgccccg aagaacgttt    15480
tccaatgatg agcactttta aagttctgct atgtggcgcg gtattatccc gtgttgacgc    15540
cgggcaagag caactcggtc gccgcataca ctattctcag aatgacttgg ttgagtactc    15600
accagtcaca gaaaagcatc ttacggatgg catgacagta agagaattat gcagtgctgc    15660
cataaccatg agtgataaca ctgcggccaa cttacttctg acaacgatcg gaggaccgaa    15720
ggagctaacc gcttttttgc acaacatggg ggatcatgta actcgccttg atcgttggga    15780
accggagctg aatgaagcca taccaaacga cgagcgtgac accacgatgc ctgcagcaat   15840
ggcaacaacg ttgcgcaaac tattaactgg cgaactactt actctagctt cccggcaaca    15900
attaatagac tggatggagg cggataaagt tgcaggacca cttctgcgct cggcccttcc    15960
ggctggctgg tttattgctg ataaatctgg agccggtgag cgtgggtctc gcggtatcat    16020
tgcagcactg gggccagatg gtaagccctc ccgtatcgta gttatctaca cgacggggag   16080
tcaggcaact atggatgaac gaaatagaca gatcgctgag ataggtgcct cactgattaa   16140
gcattggtaa ctgtcagacc aagtttactc atatatactt tagattgatt taaaacttca    16200
ttttttaattt aaaaggatct aggtgaagat cctttttgat aatctcatga ccaaaatccc    16260
ttaacgtgag ttttcgttcc actgagcgtc agacccgta gaaaagatca aggatcttc     16320
ttgagatcct ttttttctgc gcgtaatctg ctgcttgcaa acaaaaaaac caccgctacc   16380
agcggtggtt tgtttgccgg atcaagagct accaactctt tttccgaagg taactggctt    16440
cagcagagcg cagataccaa atactgtcct tctagtgtag ccgtagttag gccaccactt   16500
caagaactct gtagcaccgc ctacatacct cgctctgcta atcctgttac cagtggctgc    16560
tgccagtggc gataagtcgt gtcttaccgg gttggactca agacgatagt taccggataa   16620
ggcgcagcgg tcgggctgaa cggggggttc gtgcacacag cccagcttgg agcgaacgac    16680
ctacaccgaa ctgagatacc tacagcgtga gctatgagaa agcgccacgc ttcccgaagg    16740
gagaaaggcg gacaggtatc cggtaagcgg cagggtcgga acaggagagc gcacgaggga    16800
gcttccaggg ggaaacgcct ggtatcttta tagtcctgtc gggtttcgcc acctctgact    16860
tgagcgtcga ttttttgtgat gctcgtcagg gggcggagc ctatgaaaa acgccagcaa    16920
cgcggccttt ttacggttcc tggccttttg ctggccttt gctcacatgt tctttcctgc    16980
gttatcccct gattctgtgg ataaccgtat taccgccttt gagtgagctg ataccgctcg    17040
```

-continued

```
ccgcagccga acgaccgagc gcagcgagtc agtgagcgag gaagcggaag agcgcctgat   17100
gcggtatttt ctccttacgc atctgtgcgg tatttcacac cgcatatggt gcactctcag   17160
tacaatctgc tctgatgccg catagttaag ccagctgtgg aatgtgtgtc agttagggtg   17220
tggaaagtcc ccaggctccc cagcaggcag aagtatgcaa agcatgcatc tcaattagtc   17280
agcaaccagg tgtggaaagt ccccaggctc cccagcaggc agaagtatgc aaagcatgca   17340
tctcaattag tcagcaacca tagtcccgcc cctaactccg cccatcccgc ccctaactcc   17400
gcccagttcc gcccattctc cgccccatgg ctgactaatt ttttttattt atgcagaggc   17460
cgaggccgcc tcgcctctg agctattcca gaagtagtga ggaggctttt ttggaggcct   17520
aggcttttgc aaaaagcttg catgcctgca ggtcggccgc cacgaccggt gccgccacca   17580
tcccctgacc cacgcccctg accctcaca aggagacgac cttccatgac cgagtacaag   17640
cccacggtgc gcctcgccac ccgcgacgac gtccccgggg ccgtacgcac cctcgccgcc   17700
gcgttcgccg actaccccgc cacgcgccac accgtcgacc cggaccgcca catcgagcgg   17760
gtcaccgagc tgcaagaact cttcctcacg cgcgtcgggc tcgacatcgg caaggtgtgg   17820
gtcgcggacg acgcgccgc ggtggcggtc tggaccacgc cggagagcgt cgaagcgggg   17880
gcggtgttcg ccgagatcgg cccgcgcatg gccgagttga gcggttcccg gctggccgcg   17940
cagcaacaga tggaaggcct cctggcgccg caccggccca aggagcccgc gtggttcctg   18000
gccaccgtcg gcgtctcgcc cgaccaccag ggcaagggtc tgggcagcgc cgtcgtgctc   18060
cccggagtgg aggcggccga gcgcgccggg gtgcccgcct tcctggagac ctccgcgccc   18120
cgcaacctcc ccttctacga gcggctcggc ttcaccgtca ccgccgacgt cgaggtgccc   18180
gaaggaccgc gcacctggtg catgacccgc aagcccggtg cctgacgccc gccccacgac   18240
ccgcagcgcc cgaccgaaag gagcgcacga ccccatggct ccgaccgaag ccgacccggg   18300
cggccccgcc gaccccgcac ccgccccgga ggcccaccga ctctagagga tcataatcag   18360
ccataccaca tttgtagagg ttttacttgc tttaaaaaac ctcccacacc tccccctgaa   18420
cctgaaacat aaaatgaatg caattgttgt tgttaacttg tttattgcag cttataatgg   18480
ttacaaataa agcaatagca tcacaaattt cacaaataaa gcattttttt cactgcattc   18540
tagttgtggt ttgtccaaac tcatcaatgt atcttatcat gtctggatca ctcgccgata   18600
gtggaaaccg acgccccagc actcgtccga gggcaaagga ataggggaga tggggaggc   18660 taactgaaac acggaaggag acaataccgg aaggaacccg cgctatgacg gcaataaaaa   18720
gacagaataa aacgcacggg tgttgggtcg tttgttcata aacgcggggt tcggtcccag   18780
ggctggcact ctgtcgatac cccaccgaga ccccattggg ccaatacgc ccgcgtttct   18840 tccttttccc cacccaccc cccaagttcg ggtgaaggcc cagggctcgc agccaacgtc   18900
ggggcggcag gccctgccat agccactggc cccgtgggtt agggacgggg tccccatgg   18960 ggaatggttt atggttcgtg ggggttatta ttttgggcgt tgcgtggggt ctggtccacg   19020
actggactga gcagacagac ccatggtttt tggatggcct gggcatggac cgcatgtact   19080
ggcgcgacac gaacaccggg cgtctgtggc tgccaaacac ccccgacccc caaaaaccac   19140
cgcgcggatt tctggcgtgc caagctagtc gaccaattct catgtttgac agcttatcat   19200
cgcagatccg ggcaacgttg ttgcattgct gcaggcgcag aactggtagg tatggaagat   19260
ctctagaagc tgggtaccag ctgctagcaa gcttgctagc ggccggctcg agtttactcc   19320
ctatcagtga tagagaacgt atgtcgagtt tactccctat cagtgataga gaacgatgtc   19380
```

```
gagtttactc cctatcagtg atagagaacg tatgtcgagt ttactcccta tcagtgatag      19440
agaacgtatg tcgagtttac tccctatcag tgatagagaa cgtatgtcga gtttatccct      19500
atcagtgata gagaacgtat gtcgagttta ctccctatca gtgatagaga acgtatgtcg      19560
aggtaggcgt gtacggtggg aggcctatat aagcagagct cgtttagtga accgtcagat      19620
cgccg                                                                 19625
```

<210> SEQ ID NO 41
<211> LENGTH: 19730
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
cggccgcggg gggaggagcc aagatggccg aataggaaca gctccggtct acagctccca        60
gcgtgagcga cgcagaagac ggtgatttct gcatttccat ctgaggtacc gggttcatct       120
cactagggag tgccagacag tgggcgcagg ccagtgtgtg tgcgcaccgt gcgcgagccg       180
aagcagggcg aggcattgcc tcacctggga agcgcaaggg gtcagggagt tccctttccg       240
agtcaaagaa aggggtgacg gacgcacctg gaaaatcggg tcactcccac ccgaatattg       300
cgcttttcag accggcttaa gaaacggcgc accacgagac tatatcccac acctggctcg       360
gagggtccta cgcccacgga atctcgctga ttgctagcac agcagtctga gatcaaactg       420
caaggcggca acgaggctgg gggaggggcg cccgccattg cccaggcttg cttaggtaaa       480
caaagcagca gggaagctcg aactgggtgg agccccaccac agctcaagga ggcctgcctg       540
cctctgtagg ctccacctct gggggcaggg cacagacaaa caaaaagaca gcagtaacct       600
ctgcagactt aagtgtccct gtctgacagc tttgaagaga gcagtggttc tcccagcacg       660
cagctggaga tctgagaacg ggcagactgc ctcctcaagt gggtccctga ccctgaccc        720 ccgagcagcc taactgggag gcaccccca gcagggggcac actgacacct cacacggcag      780
ggtattccaa cagacctgca gctgagggtc ctgtctgtta gaaggaaaac taacaaccag       840
aaaggacatc tacaccgaaa acccatctgt acatcaccat catcaaagac caaaagtaga       900
taaaaccaca aagatgggga aaaaacagaa cagaaaaact ggaaactcta aaacgcagag       960
cgcctctcct cctccaaagg aacgcagttc ctcaccagca acagaacaaa gctggatgga      1020
gaatgatttt gatgagctga gagaagaagg cttcagacga tcaaattact ctgagctacg      1080
ggaggacatt caaaccaaag gcaaagaagt tgaaactttt gaaaaaattt agaagaatg      1140 tataactaga ataaccaata cagagaagtg cttaaggag ctgatggagc tgaaaaccaa      1200
ggctcgagaa ctacgtgaag aatgcagaag cctcaggagc cgatgcgatc aactggaaga      1260
aagggtatca gcaatggaag atgaaatgaa tgaaatgaag cgagaaggga gtttagaga       1320 aaaaagaata aaaagaaatg agcaaagcct ccaagaaata tgggactatg tgaaaagacc      1380
aaatctacgt ctgattggtg tacctgaaag tgatgtggag aatggaacca agttggaaaa      1440
cactctgcag gatattatcc aggagaactt ccccaatcta gcaaggcagg ccaacgttca      1500
gattcaggaa atacagagaa cgccacaaag atactcctcg agaagagcaa ctccaagaca      1560
cataattgtc agattcacca agttgaaat gaaggaaaaa atgttaaggg cagccagaga      1620
gaaaggtcgg gttaccctca aggaaagcc catcagacta acagcggatc tctcggcaga      1680
aaccctacaa gccagaagag agtgggggcc aatattcaac attcttaaag aaaagaattt      1740
```

-continued

```
tcaacccaga atttcatatc cagccaaact aagcttcata agtgaaggag aaataaaata    1800
ctttatagac aagcaaatgt tgagagattt tgtcaccacc aggcctgccc taaaagagct    1860
cctgaaggaa gcgctaaaca tggaaaggaa caaccggtac cagccgctgc aaaatcatgc    1920
caaaatgtaa agaccatcaa gactaggaag aaactgcatc aactaatgag caaaatcacc    1980
agctaacatc ataatgacag gatcaacttc acacataaca atattaactt taaatataaa    2040
tggactaaat tctgcaatta aaagacacag actggcaagt tggataaaga gtcaagaccc    2100
atcagtgtgc tgtattcagg aaacccatct cacgtgcaga gacacacata ggctcaaaat    2160
aaaaggatgg aggaagatct accaagccaa tggaaaacaa aaaaggcag gggttgcaat     2220 cctagtctct gataaaacag actttaaacc aacaaagatc aaaagagaca agaaggcca     2280 ttacataatg gtaaagggat caattcaaca agaggagcta actatcctaa atatttatgc    2340
acccaataca ggagcaccca gattcataaa gcaagtcctc agtgacctac aaagagactt    2400
agactcccac acattaataa tgggagactt taacacccca ctgtcaacat tagacagatc    2460
aacgagacag aaagtcaaca aggatacccca ggaattgaac tcagctctgc accaagcaga    2520
cctaatagac atctacagaa ctctccaccc caaatcaaca gaatatacat tttttcagc     2580 accacaccac acctattcca aaattgacca catagttgga agtaaagctc tcctcagcaa    2640
atgtaaaaga acagaaatta taacaaacta tctctcagac cacagtgcaa tcaaactaga    2700
actcaggatt aagaatctca ctcaaagccg ctcaactaca tggaaactga caacctgct     2760 cctgaatgac tactgggtac ataacgaaat gaaggcagaa ataaagatgt tctttgaaac    2820
caacgagaac aaagacacca cataccagaa tctctgggac gcattcaaag cagtgtgtag    2880
agggaaattt atagcactaa atgcctacaa gagaaagcag gaaagatcca aaattgacac    2940
cctaacatca caattaaaag aactagaaaa gcaagagcaa acacattcaa aagctagcag    3000
aaggcaagaa ataactaaaa tcagagcaga actgaaggaa atagagacac aaaaaaccct    3060
tcaaaaaatc aatgaatcca ggagctggtt ttttgaaagg atcaacaaaa ttgatagacc    3120
gctagcaaga ctaataaaga aaaaagaga gaagaatcaa atagacacaa taaaaaatga    3180
taaaggggat atcaccaccg atcccacaga aatacaaact accatcagag aatactacaa    3240
acacctctac gcaaataaac tagaaaatct agaagaaatg gatacattcc tcgacacata    3300
cactctccca agactaaacc aggaagaagt tgaatctctg aatcgaccaa taacaggctc    3360
tgaaattgtg gcaataatca atagtttacc aaccaaaaag agtccaggac cagatggatt    3420
cacagccgaa ttctaccaga ggtacaagga ggaactggta ccattccttc tgaaactatt    3480
ccaatcaata gaaaagagg gaatcctccc taactcattt tatgaggcca gcatcattct    3540
gataccaaag ccgggcagag acacaaccaa aaaagagaat tttagaccaa tatccttgat    3600
gaacattgat gcaaaaatcc tcaataaaat actggcaaac cgaatccagc agcacatcaa    3660
aaagcttatc caccatgatc aagtgggctt catccctggg atgcaaggct ggttcaatat    3720
acgcaaatca ataaatgtaa tccagcatat aaacagagcc aaagacaaaa accacatgat    3780
tatctcaata gatgcagaaa agcctttga caaaattcaa caacccttca tgctaaaaac    3840
tctcaataaa ttaggtattg atgggacgta tttcaaaata ataagagcta tctatgacaa    3900
acccacagcc aatatcatac tgaatgggca aaaactggaa gcattccctt tgaaaccgg    3960 cacaagacag ggatgccctc tctcaccgct cctattcaac atagtgttgg aagttctggc    4020
cagggcaatc aggcaggaga aggaaataaa gggtattcaa ttaggaaaag aggaagtcaa    4080
attgtccctg tttgcagacg acatgattgt ttatctagaa aaccccatcg tctcagccca    4140
```

-continued

```
aaatctcctt aagctgataa gcaacttcag caaagtctca ggatacaaaa tcaatgtaca    4200
aaaatcacaa gcattcttat acaccaacaa cagacaaaca gagagccaaa tcatgggtga    4260
actcccattc acaattgctt caaagagaat aaaatccta ggaatccaac ttacaaggga     4320
tgtgaaggac ctcttcaagg agaactacaa accactgctc aaggaaataa agaggagac     4380 aaacaaatgg aagaacattc catgctcatg ggtaggaaga atcaatatcg tgaaaatggc    4440
catactgccc aaggtaattt acagattcaa tgccatcccc atcaagctac caatgacttt    4500
cttcacagaa ttggaaaaaa ctactttaaa gttcatatgg aaccaaaaaa gagcccgcat    4560
tgccaagtca atcctaagcc aaaagaacaa agctggaggc atcacactac ctgacttcaa    4620
actatactac aaggctacag taaccaaaac agcatggtac tggtaccaaa acagagatat    4680
agatcaatgg aacagaacag agccctcaga aataatgccg catatctaca actatctgat    4740
ctttgacaaa cctgagaaaa caagcaatg gggaaaggat tccctattta ataaatggtg     4800
ctgggaaaac tggctagcca tatgtagaaa gctgaaactg gatcccttcc ttacaccta    4860 tacaaaaatc aattcaagat ggattaaaga tttaaacgtt aaacctaaaa ccataaaaac    4920
cctagaagaa aacctaggca ttaccattca ggacataggc gtgggcaagg acttcatgtc    4980
caaaacacca aaagcaatgg caacaaaaga caaaattgac aaatgggatc taattaaact    5040
aaagagcttc tgcacagcaa agaaactac catcagagtg aacaggcaac ctacaacatg    5100
ggagaaaatt tttgcaacct actcatctga caagggcta atatccagaa tctacaatga     5160
actcaaacaa atttacaaga aaaaaacaaa caaccccatc aaaaagtggg cgaaggacat    5220
gaacagacac ttctcaaaag aagacattta tgcagccaaa aacacatga agaaatgctc      5280 atcatcactg gccatcagag aaatgcaaat caaaaccact atgagatatc atctcacacc    5340
agttagaatg gcaatcatta aaaagtcagg aaacaacagg tgctggagag gatgcggaga    5400
aataggaaca cttttacact gttggtggga ctgtaaacta gttcaaccat tgtggaagtc    5460
agtgtggcga ttcctcaggg atctagaact agaaatacca tttgacccag ccatcccatt    5520
actgggtata tacccaaatg agtataaatc atgctgctat aaagacacat gcacacgtat    5580
gtttattgcg gcactattca caatagcaaa gacttggaac caacccaaat gtccaacaat    5640
gatagactgg attaagaaaa tgtggcacat ataccacatg gaatactatg cagccataaa    5700
aaatgatgag ttcatatcct tgtagggac atggatgaaa ttggaaacca tcattctcag    5760
taaactatcg caagaacaaa aaaccaaaca ccgcatattc tcactcatag gtgggaattg    5820
aacaatgaga tcacatggac acaggaaggg gaatatcaca ctctggggac tgtggtgggg    5880 tcggggagg ggggagggat agcattggga gatataccta atgctagatg acacattagt     5940
gggtgcagcg caccagcatg gcacatgtat acggatccga attctcgacg gatcgatccg    6000
aacaaacgac ccaacacccg tgcgttttat tctgtctttt tattgccgat cccctcagaa     6060
gaactcgtca agaaggcgat agaaggcgat gcgctgcgaa tcgggagcgg cgataccgta    6120
aagcacgagg aagcggtcag cccattcgcc gccaagctct tcagcaatat cacgggtagc    6180
caacgctatg tcctgatagc ggtcggccgc tttacttgta cagctcgtcc atgccgagag    6240
tgatcccggc ggcggtcacg aactccagca ggaccatgtg atcgcgcttc tcgttggggt    6300
ctttgctcag gcggactgg gtgctcaggt agtggttgtc gggcagcagc acggggccgt     6360
cgccgatggg ggtgttctgc tggtagtggt cggccaggtg agtccaggag atgtttcagc    6420
actgttgcct ttagtctcga ggcaacttag acaactgagt attgatctga gcacagcagg    6480
```

```
gtgtgagctg tttgaagata ctggggttgg gggtgaagaa actgcagagg actaactggg    6540
ctgagaccca gtggcaatgt tttagggcct aaggaatgcc tctgaaaatc tagatggaca    6600
actttgactt tgagaaaaga gaggtggaaa tgaggaaaat gacttttctt tattagattt    6660
cggtagaaag aactttcatc tttcccctat ttttgttatt cgttttaaaa catctatctg    6720
gaggcaggac aagtatggtc attaaaaaga tgcaggcaga aggcatatat tggctcagtc    6780
aaagtgggga actttggtgg ccaaacatac attgctaagg ctattcctat atcagctgga    6840
cacatataaa atgctgctaa tgcttcatta caaacttata tcctttaatt ccagatgggg    6900
gcaaagtatg tccaggggtg aggaacaatt gaaacatttg gctggagta gattttgaaa     6960
gtcagctctg tgtgtgtgtg tgtgtgtgtg tgtgtgagag cgtgtgtttc ttttaacgtt    7020
ttcagcctac agcatacagg gttcatggtg gcaagaagat aacaagattt aaattatggc    7080
cagtgactag tgctgcaaga agaacaacta cctgcattta atgggaaagc aaaatctcag    7140
gctttgaggg aagttaacat aggcttgatt ctgggtggaa gctgggtgtg tagttatctg    7200
gaggccaggc tggagctctc agctcactat gggttcatct ttattgtctc ctttcatctc    7260
aacagctgca cgctgccgtc ctcgatgttg tggcggatct tgaagttcac cttgatgccg    7320
ttcttctgct tgtcggccat gatatagacg ttgtggctgt tgtagttgta ctccagcttg    7380
tgccccagga tgttgccgtc ctccttgaag tcgatgccct tcagctcgat gcggttcacc    7440
agggtgtcgc cctcgaactt cacctcggcg cgggtcttgt agttgccgtc gtccttgaag    7500
aagatggtgc gctcctggac gtagccttcg ggcatggcgg acttgaagaa gtcgtgctgc    7560
ttcatgtggt cggggtagcg gctgaagcac tgcacgccgt aggtcagggt ggtcacgagg    7620
gtgggccagg gcacgggcag cttgccggtg gtgcagatga acttcagggt cagcttgccg    7680
taggtggcat cgccctcgcc ctcgccggac acgctgaact tgtggccgtt tacgtcgccg    7740
tccagctcga ccaggatggg caccaccccg gtgaacagct cctcgccctt gctcaccata    7800
gggccgggat tctcctccac gtcaccgcat gttagaagac ttcctctgcc ctctcttgga    7860
ggcagggcct gcatgtgcag ggcatcgtag gtatccttgg tggctgtgct cagtccctgg    7920
tacagtccat cgtggccctt gcctcttctt ctctcgccct tcatgccgat ctcgctgtag    7980
gcctcggcca tcttgtcttt ctgcagctca ttatacaggc cctcttgagg attctttctc    8040
cgctggggct gccgcccat ctcaggatct ctgcctctcc gcttatccag cacgtcgtac     8100
tcttctcttc tccccaggtt cagctcgttg tacagctgat tctggccctg ctggtaagca    8160
ggagcgtcgg cggatctgct gaacttcact ctgcagtaca gggtgatgac cagagagagc    8220
agcagaacgc cacatgtgcc agccagaggg gcccaaatgt agatatccag gcctctggta    8280
tgcacagctc cgccagctgc aggtctacag gcttcaggtc tgagagacag aggctggctg    8340
gcgattgtag gagctggtgt aggtggtcta ggagcgggtg ttgttgtagg cttggcgggc    8400
agaaacacgg gcacgaagtg gctgaagtac atgatgctat tgctcagggc tccgcttcct    8460
ccgcctccgc tagaagaaac tgtgaccagg gtgccctgtc cccaaacatc catggcgtag    8520
aagccgtcgc ctccccatct agaacagtag tacacggcgg tgtcctcggc tctcaggctg    8580
ttcatctgca ggtaggcggt gttccttgct gtgtcggcgc tgatggtgaa tctgcccttc    8640
acgctatcgg cgtatctggt gtagccgttg gtggggtaga ttctggcgac ccattcaagt    8700
cccttttccag gggcctgtcg gacccagtgg atgtaggtgt ccttgatgtt gaagccgctg    8760
gcggcacaag acagtctcag agagccgcca ggctgaacaa gtcctccgcc agattcaacc    8820
agctgcacct cagatccttc gccagatcca ggctttccag agccgctggt gctgcctgtt    8880
```

```
ctcttgattt ccaccttggt gccctggcca aaggttggag gtgtggtgta gtgctgctgg    8940
cagtagtagg tggcgaagtc ctcaggctgc aggctagaga tggtcagggt gaagtcggtg    9000
ccagatctgc tgccgctgaa tctgcttggc acgccgctgt acagaaagct ggcgctgtag    9060
atcagcagct tagggggcttt tccaggcttc tgctgatacc aggccacggc ggtattcaca    9120
tcctggctgg ctctacaggt gatggtcact ctatcgccca cagaggcaga caggctgcta    9180
gggctctgtg tcatctggat gtcgctgatg ctgcaggcca ctgttcccag cagcagcaga    9240
gactgcagcc acattcgaag cttgagctcg agatctgagt ccggtagcgc tagcggatct    9300
gacggttcac taaaccagct ctgcttatat agacctccca ccgtacacgc ctaccgccca    9360
tttgcgtcaa tggggcggag ttgttacgac attttggaaa gtcccgttga ttttggtgcc    9420
aaaacaaact cccattgacg tcaatggggt ggagacttgg aaatcccgt gagtcaaacc    9480
gctatccacg cccattgatg tactgccaaa accgcatcac catggtaata gcgatgacta    9540
atacgtagat gtactgccaa gtaggaaagt cccataaggt catgtactgg gcataatgcc    9600
aggcgggcca tttaccgtca ttgacgtcaa tagggggcgt acttggcata tgatacactt    9660
gatgtactgc caagtgggca gtttaccgta aatactccac ccattgacgt caatggaaag    9720
tccctattgg cgttactatg ggaacatacg tcattattga cgtcaatggg cggggtcgt    9780
tgggcggtca gccaggcggg ccatttaccg taagttatgt aacgcggaac tccatatatg    9840
ggctatgaac taatgacccc gtaattgatt actattagcc cggggggatcc agacatgata    9900
agatacattg atgagtttgg acaaaccaca actagaatgc agtgaaaaaa atgctttatt    9960
tgtgaaattt gtgatgctat tgctttattt gtaaccatta taagctgcaa taaacaagtt   10020
aacaacaaca attgcattca ttttatgttt caggttcagg gggaggtgtg ggaggttttt   10080
taaagcaagt aaaacctcta caaatgtggt atggctgatt atgatccggc tgcctcgcgc   10140
gtttcggtga tgacggtgaa aacctctgac acatgcagct cccggagacg gtcacagctt   10200
gtctgtaagc ggatgccggg agcagacaag cccgtcaggg cgcgtcagcg ggtgttggcg   10260
ggtgtcgggg cgcagccatg aggtcgatcg actctagagg atcgatcccc gccccggacg   10320
aactaaacct gactacgaca tctctgcccc ttcttcgcgg ggcagtgcat gtaatccctt   10380
cagttggttg gtacaacttg ccaactgggc cctgttccac atgtgacacg ggggggggacc   10440
aaacacaaag gggttctctg actgtagttg acatccttat aaatggatgt gcacatttgc   10500
caacactgag tggctttcat cctggagcag actttgcagt ctgtggactg caacacaaca   10560
ttgcctttat gtgtaactct tggctgaagc tcttacacca atgctggggg acatgtacct   10620
cccaggggcc caggaagact acgggaggct acaccaacgt caatcagagg ggcctgtgta   10680
gctaccgata agcggaccct caagagggca ttagcaatag tgtttataag gccccttgt   10740
taaccctaaa cgggtagcat atgcttcccg ggtagtagta tatactatcc agactaaccc   10800
taattcaata gcatatgtta cccaacggga agcatatgct atcgaattag ggttagtaaa   10860
agggtcctaa ggaacagcga tatctcccac cccatgagct gtcacggttt tatttacatg   10920
gggtcaggat tccacgaggg tagtgaacca ttttagtcac aagggcagtg gctgaagatc   10980
aaggagcggg cagtgaactc tcctgaatct tcgcctgctt cttcattctc cttcgtttag   11040
ctaatagaat aactgctgag ttgtgaacag taaggtgtat gtgaggtgct cgaaaacaag   11100
gtttcaggtg acgcccccag aataaaattt ggacggggggg ttcagtggtg cattgtgct   11160
atgacaccaa tataaccctc acaaacccct tgggcaataa atactagtgt aggaatgaaa   11220
```

```
cattctgaat atctttaaca atagaaatcc atggggtggg gacaagccgt aaagactgga    11280
tgtccatctc acacgaattt atggctatgg gcaacacata atcctagtgc aatatgatac    11340
tggggttatt aagatgtgtc ccaggcaggg accaagacag gtgaaccatg ttgttacact    11400
ctatttgtaa caaggggaaa gagagtggac gccgacagca gcggactcca ctggttgtct    11460
ctaacacccc cgaaaattaa acggggctcc acgccaatgg ggcccataaa caaagacaag    11520
tggccactct ttttttgaa attgtggagt gggggcacgc gtcagccccc acacgccgcc    11580
ctgcggtttt ggactgtaaa ataagggtgt aataacttgg ctgattgtaa ccccgctaac    11640
cactgcggtc aaaccacttg cccacaaaac cactaatggc accccgggga atacctgcat    11700
aagtaggtgg gcgggccaag atagggcgc gattgctgcg atctggagga caaattacac     11760
acacttgcgc ctgagcgcca agcacagggt tgttggtcct catattcacg aggtcgctga    11820
gagcacggtg ggctaatgtt gccatgggta gcatatacta cccaaatatc tggatagcat    11880
atgctatcct aatctatatc tgggtagcat aggctatcct aatctatatc tgggtagcat    11940
atgctatcct aatctatatc tgggtagtat atgctatcct aatttatatc tgggtagcat    12000
aggctatcct aatctatatc tgggtagcat atgctatcct aatctatatc tgggtagtat    12060
atgctatcct aatctgtatc cgggtagcat atgctatcct aatagagatt agggtagtat    12120
atgctatcct aatttatatc tgggtagcat atactaccca aatatctgga tagcatatgc    12180
tatcctaatc tatatctggg tagcatatgc tatcctaatc tatatctggg tagcataggc    12240
tatcctaatc tatatctggg tagcatatgc tatcctaatc tatatctggg tagtatatgc    12300
tatcctaatt tatatctggg tagcataggc tatcctaatc tatatctggg tagcatatgc    12360
tatcctaatc tatatctggg tagtatatgc tatcctaatc tgtatccggg tagcatatgc    12420
tatcctcatg catatacagt cagcatatga tacccagtag tagagtggga gtgctatcct    12480
ttgcatatgc cgccacctcc caaggggcg tgaattttcg ctgcttgtcc ttttcctgca     12540
tgctggttgc tcccattctt aggtgaattt aaggaggcca ggctaaagcc gtcgcatgtc    12600
tgattgctca ccaggtaaat gtcgctaatg ttttccaacg cgagaaggtg ttgagcgcgg    12660
agctgagtga cgtgacaaca tgggtatgcc caattgcccc atgttgggag gacgaaaatg    12720
gtgacaagac agatggccag aaatacacca acagcacgca tgatgtctac tggggattta    12780
ttctttagtg cgggggaata cacggctttt aatacgattg agggcgtctc ctaacaagtt    12840
acatcactcc tgcccttcct caccctcatc tccatcacct ccttcatctc cgtcatctcc    12900
gtcatcaccc tccgcggcag ccccttccac cataggtgga aaccagggag gcaaatctac    12960
tccatcgtca agctgcaca cagtcaccct gatattgcag gtaggagcgg gctttgtcat     13020
aacaaggtcc ttaatcgcat ccttcaaaac ctcagcaaat atatgagttt gtaaaaagac    13080
catgaaataa cagacaatgg actcccttag cgggccaggt tgtgggccgg tccaggggc     13140
cattccaaag gggagacgac tcaatggtgt aagacgacat tgtggaatag caagggcagt    13200
tcctcgcctt aggttgtaaa gggaggtctt actacctcca tatacgaaca caccggcgac    13260
ccaagttcct tcgtcggtag tcctttctac gtgactccta gccaggagag ctcttaaacc    13320
ttctgcaatg ttctcaaatt tcgggttgga acctccttga ccacgatgct ttccaaacca    13380
ccctcctttt ttgcgcctgc ctccatcacc ctgaccccgg ggtccagtgc ttgggccttc    13440
tcctgggtca tctgcgggc cctgctctat cgctcccggg ggcacgtcag gctcaccatc    13500
tgggccacct tcttggtggt attcaaaata atcggcttcc cctacagggt ggaaaaatgg    13560
ccttctacct ggagggggcc tgcgcggtgg agacccggat gatgatgact gactactggg    13620
```

```
actcctgggc ctcttttctc cacgtccacg acctctcccc ctggctcttt cacgacttcc  13680 cccccctggct ctttcacgtc ctctacccccg gcggcctcca ctacctcctc gaccccggcc  13740
tccactacct cctcgacccc ggcctccact gcctcctcga cccggcctc cacctcctgc  13800 tcctgcccct cctgctcctg cccctcctcc tgctcctgcc cctcctgccc ctcctgctcc  13860
tgcccctcct gcccctcctg ctcctgcccc tcctgcccc ctgctcctg cccctcctgc  13920 ccctcctcct gctcctgccc ctcctgcccc tcctcctgct cctgcccctc ctgcccctcc  13980
tgctcctgcc cctcctgccc ctcctgctcc tgcccctcct gcccctcctg ctcctgcccc  14040
tcctgctcct gcccctcctg ctcctgcccc tcctgctcct gcccctcctg cccctcctgc  14100
ccctcctcct gctcctgccc ctcctgctcc tgcccctcct gcccctcctg cccctcctgc  14160
tcctgcccct cctgctcctc ctgcccctcc tgcccctcct gcccctcctc ctgctcctgc  14220
ccctcctgcc cctcctcctg ctcctgcccc tcctgcccct ctgcccctcc  14280
tgcccctcct cctgctcctg cccctcctgc cctcctcct gctcctgccc ctcctcctgc  14340
tcctgcccct cctgcccctc ctgcccctcc tcctgctcct gcccctcctc ctgctcctgc  14400
ccctcctgcc cctcctgccc ctcctgcccc tcctcctgct cctgcccctc ctcctgctcc  14460
tgcccctcct gctcctgccc ctcccgctcc tgctcctgct cctgttccac cgtgggtccc  14520
tttgcagcca atgcaacttg gacgtttttg gggtctccgg acaccatctc tatgtcttgg  14580
ccctgatcct gagccgcccg gggctcctgg tcttccgcct cctcgtcctc gtcctcttcc  14640
ccgtcctcgt ccatggttat caccccctct tctttgaggt ccactgccgc cggagccttc  14700
tggtccagat gtgtctccct tctctcctag gccatttcca ggtcctgtac ctggcccctc  14760
gtcagacatg attcacacta aaagagatca atagacatct ttattagacg acgctcagtg  14820
aatacaggga gtgcagactc ctgcccccctc caacagcccc cccaccctca tcccttcat  14880 ggtcgctgtc agacagatcc aggtctgaaa attccccatc ctccgaacca tcctcgtcct  14940
catcaccaat tactcgcagc ccggaaaact cccgctgaac atcctcaaga tttgcgtcct  15000
gagcctcaag ccaggcctca aattcctcgt ccccctttttt gctggacggt agggatgggg  15060
attctcggga ccccctcctct tcctcttcaa ggtcaccaga cagagatgct actggggcaa  15120
cggaagaaaa gctgggtgcg gcctgtgagg atcagcttat cgatgataag ctgtcaaaca  15180
tgagaattct tgaagacgaa agggcctcgt gatacgccta tttttatagg ttaatgtcat  15240
gataataatg gtttcttaga cgtcaggtgg cacttttcgg ggaaatgtgc gcggaacccc  15300
tatttgttta tttttctaaa tacattcaaa tatgtatccg ctcatgagac aataaccctg  15360
ataaatgctt caataatatt gaaaaggaa gagtatgagt attcaacatt ccgtgtcgc  15420 ccttattccc ttttttgcgg cattttgcct tcctgttttt gctcacccag aaacgctggt  15480
gaaagtaaaa gatgctgaag atcagttggg tgcacgagtg ggttacatcg aactggatct  15540
caacagcggt aagatccttg agagttttcg ccccgaagaa cgttttccaa tgatgagcac  15600
ttttaaagtt ctgctatgtg gcgcggtatt atcccgtgtt gacgccgggc aagagcaact  15660
cggtcgccgc atacactatt ctcagaatga cttggttgag tactcaccag tcacagaaaa  15720
gcatcttacg gatggcatga cagtaagaga attatgcagt gctgccataa ccatgagtga  15780
taacactgcg gccaacttac ttctgacaac gatcggagga ccgaaggagc taaccgcttt  15840
tttgcacaac atgggggatc atgtaactcg ccttgatcgt tgggaaccgg agctgaatga  15900
agccatacca aacgacgagc gtgacaccac gatgcctgca gcaatggcaa caacgttgcg  15960
```

```
caaactatta actggcgaac tacttactct agcttcccgg caacaattaa tagactggat    16020
ggaggcggat aaagttgcag gaccacttct gcgctcggcc cttccggctg gctggtttat    16080
tgctgataaa tctggagccg gtgagcgtgg gtctcgcggt atcattgcag cactggggcc    16140
agatggtaag ccctcccgta tcgtagttat ctacacgacg gggagtcagg caactatgga    16200
tgaacgaaat agacagatcg ctgagatagg tgcctcactg attaagcatt ggtaactgtc    16260
agaccaagtt tactcatata tactttagat tgatttaaaa cttcattttt aatttaaaag    16320
gatctaggtg aagatccttt ttgataatct catgaccaaa atcccttaac gtgagttttc    16380
gttccactga gcgtcagacc ccgtagaaaa gatcaaagga tcttcttgag atcctttttt    16440
tctgcgcgta atctgctgct tgcaaacaaa aaaaccaccg ctaccagcgg tggtttgttt    16500
gccggatcaa gagctaccaa ctctttttcc gaaggtaact ggcttcagca gagcgcagat    16560
accaaatact gtccttctag tgtagccgta gttaggccac cacttcaaga actctgtagc    16620
accgcctaca tacctcgctc tgctaatcct gttaccagtg gctgctgcca gtggcgataa    16680
gtcgtgtctt accgggttgg actcaagacg atagttaccg gataaggcgc agcggtcggg    16740
ctgaacgggg ggttcgtgca cacagcccag cttggagcga acgacctaca ccgaactgag    16800
atacctacag cgtgagctat gagaaagcgc cacgcttccc gaaggagaa aggcggacag    16860 gtatccggta agcggcaggg tcggaacagg agagcgcacg agggagcttc caggggggaaa    16920 cgcctggtat ctttatagtc ctgtcgggtt cgccacctc tgacttgagc gtcgatttt    16980 gtgatgctcg tcagggggc ggagcctatg gaaaaacgcc agcaacgcgg ccttttacg    17040 gttcctggcc ttttgctggc cttttgctca catgttcttt cctgcgttat cccctgattc    17100
tgtggataac cgtattaccg cctttgagtg agctgatacc gctcgccgca gccgaacgac    17160
cgagcgcagc gagtcagtga gcgaggaagc ggaagagcgc ctgatgcggt attttctcct    17220
tacgcatctg tgcggtattt cacaccgcat atggtgcact ctcagtacaa tctgctctga    17280
tgccgcatag ttaagccagc tgtggaatgt gtgtcagtta gggtgtggaa agtccccagg    17340 ctcccccagca ggcagaagta tgcaaagcat gcatctcaat tagtcagcaa ccaggtgtgg    17400
aaagtcccca ggctccccag caggcagaag tatgcaaagc atgcatctca attagtcagc    17460
aaccatagtc cgcccctaa ctccgcccat cccgcccta actccgccca gttccgccca    17520
ttctccgccc catggctgac taattttttt tatttatgca gaggccgagg ccgcctcggc    17580
ctctgagcta ttccagaagt agtgaggagg cttttttgga ggcctaggct tttgcaaaaa    17640
gcttgcatgc ctgcaggtcg gccgccacga ccggtgccgc caccatcccc tgacccacgc    17700
ccctgacccc tcacaaggag acgaccttcc atgaccgagt acaagcccac ggtgcgcctc    17760
gccacccgcg acgacgtccc cgggccgta cgcaccctcg ccgccgcgtt cgccgactac    17820
cccgccacgc gccacaccgt cgacccggac cgccacatcg agcgggtcac cgagctgcaa    17880
gaactcttcc tcacgcgcgt cgggctcgac atcggcaagg tgtgggtcgc ggacgacggc    17940
gccgcggtgg cggtctggac cacgccggag agcgtcgaag cggggcggt gttcgccgag    18000 atcggcccgc gcatggccga gttgagcggt tcccggctgg ccgcgcagca acagatggaa    18060
ggcctcctgg cgccgcaccg gcccaaggag cccgcgtggt cctggccac cgtcggcgtc    18120 tcgccgac accagggcaa gggtctgggc agcgccgtcg tgctccccgg agtggaggcg    18180
gccgagcgcg ccggggtgcc cgccttcctg gagacctccg cgcccgcaa cctccccttc    18240 tacgagcggc tcggcttcac cgtcaccgcc gacgtcgagg tgcccgaagg accgcgcacc    18300
tggtgcatga cccgcaagcc cggtgcctga cgcccgcccc acgacccgca gcgcccgacc    18360
```

```
gaaaggagcg cacgacccca tggctccgac cgaagccgac ccgggcggcc ccgccgaccc    18420
cgcacccgcc cccgaggccc accgactcta gaggatcata atcagccata ccacatttgt    18480
agaggtttta cttgctttaa aaaacctccc acacctcccc ctgaacctga aacataaaat    18540
gaatgcaatt gttgttgtta acttgtttat tgcagcttat aatggttaca aataaagcaa    18600
tagcatcaca aatttcacaa ataaagcatt tttttcactg cattctagtt gtggtttgtc    18660
caaactcatc aatgtatctt atcatgtctg atcactcgc cgatagtgga aaccgacgcc     18720
ccagcactcg tccgagggca aggaatagg ggagatgggg gaggctaact gaaacacgga     18780
aggagacaat accggaagga acccgcgcta tgacggcaat aaaagacag aataaaacgc     18840 acgggtgttg ggtcgtttgt tcataaacgc ggggttcggt cccagggctg cactctgtc    18900 gatacccccac cgagacccca ttggggccaa tacgcccgcg tttcttcctt ttccccaccc   18960
caccccccaa gttcgggtga aggcccaggg ctcgcagcca acgtcgggc ggcaggccct    19020 gccatagcca ctggcccgt gggttaggga cgggtcccc catggggaat ggtttatggt     19080 tcgtggggt tattattttg ggcgttgcgt ggggtctggt ccacgactgg actgagcaga    19140
cagacccatg gttttggat ggcctgggca tggaccgcat gtactggcgc gacacgaaca    19200
ccgggcgtct gtggctgcca acacccccg accccaaaa accaccgcgc ggatttctgg     19260
cgtgccaagc tagtcgacca attctcatgt ttgacagctt atcatcgcag atccgggcaa    19320
cgttgttgca ttgctgcagg cgcagaactg gtaggtatgg aagatctcta aagctgggt    19380 accagctgct agcaagcttg ctagcggccg gctcgagttt actccctatc agtgatagag    19440
aacgtatgtc gagtttactc cctatcagtg atagagaacg atgtcgagtt tactccctat    19500
cagtgataga gaacgtatgt cgagtttact cctatcagt gatagagaac gtatgtcgag    19560
tttactccct atcagtgata gagaacgtat gtcgagttta tccctatcag tgatagagaa    19620
cgtatgtcga gtttactccc tatcagtgat agagaacgta tgtcgaggta ggcgtgtacg    19680
gtgggaggcc tatataagca gagctcgttt agtgaaccgt cagatcgccg               19730
```

<210> SEQ ID NO 42
<211> LENGTH: 7291
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
taatacgact cactataggg agaagtactg ccaccatggg caagaagcaa aatcgcaaga     60
cggggaattc caagacacaa tccgctagcc caccacctaa agagcgttct agctcccctg    120
ctactgagca gtcctggatg gaaaacgact tcgatgaact ccgggaagag ggatttaggc    180
gatccaacta ttcagaactc cgcgaagata tccagacaaa ggggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagcatcat tcaagaaaat tttccaaacc    600
tggctcggca agctaatgtg caaatccaag agatccaacg cacaccccag cggtatagct    660
```

```
ctcggcgtgc caccoctagg catattatcg tgcgctttac taaggtggag atgaaagaga    720
agatgctgcg agccgctcgg gaaaagggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaacccct gcagaaccac gcaaagatgt gagacagccg tcagaccatc aagactagga   1080
agaaactgca tcaactaatg agcaaaatca ccagctaaca tcatagtata catgaccggc   1140
tctaactcac atatcaccat ccttacactt aacattaacg gcctcaactc agctatcaag   1200
cgccatcggc tggccagctg atcaaatca caggatccaa gcgtttgttg catccaagag   1260
acccacctga cctgtagaga tactcaccgc ctcaagatca agggatggcg aaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc   1500
tttatcaaac aggtcctgtc cgatctgcag cgagatctgg attctcatac gttgattatg   1560
ggtgatttca atacaccatt gagcaccctg gatcgcagca ccaggcaaaa ggtaaataaa   1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta tgggtccac    1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gatacctata ctctgccacg gcttaatcaa   2460
gaggaagtca gtccctcaa ccgcccaatt acaggaagcg agattgtggc cataattaac   2520
tccctgccga caaagaaatc tcctggtccg gacgggttta cagctgagtt ttatcaacgg   2580
tatatggaag agcttgtacc gtttctgctc aagctctttc agtctataga aaaggaaggc   2640
atcttgccca attccttcta cgaagcttct ataatactta ttcccaaacc aggacgcgat   2700
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
```

-continued

```
ggaacatatt ttaagattat tcgcgcaatt tacgataagc cgactgctaa cattatcctt     3060
aacggccaaa agctcgaggc cttccgctc aagactggaa cccgccaagg ctgtcccctc      3120
tccccgcttt tgtttaatat tgtactcgag gtgctggcta gggctattcg tcaagagaaa    3180
gagattaaag ggatacagct cgggaaggaa gaggtcaagc tttccttgtt cgccgatgat    3240
atgattgtgt acctggagaa tcctattgtg tctgctcaga accttcttaa acttatttct    3300
aactttagca aggtcagcgg ctataagatt aacgtccaga atctcaggc ctttctgtac     3360 acaaataatc gacagaccga atcccagata atgggtgagc ttccgtttgt catagccagc    3420
aaaaggataa agtatctcgg aatccagctg acacgagacg ttaaagattt gtttaaggaa    3480
aattacaagc ctctcctgaa agagattaag gaagatacta ataagtggaa gaatatcccc    3540
tgttcatggg ttggcagaat caacatagtg aagatggcaa tacttcctaa agtgatatat    3600
cgctttaacg ccatcccaat taaactgcct atgaccttct ttacgagct cgagaaaaca     3660 acccttaaat ttatatgaa tcaaaagaga gcaagaatag cgaagtccat cttgagccag     3720
aagaataagg ccggtgggat tactttgcct gattttaagt tgtattataa agccacagta    3780
actaagacag cctggtattg gtatcagaat agagacatcg accagtggaa tcggaccgaa    3840
ccatcagaga taatgcccca catctataat tacctttatat cgataagcc agaaaagaat    3900 aaacagtggg gcaaagacag cctcttcaac aagtggtgtt gggagaattg gctggccata    3960
tgccggaaac tcaagctcga ccccttcctt acacctaca ctaaaatcaa cagtaggtgg     4020
atcaaggact tgaatgtcaa gccaaagact ataagacac tggaagagaa tcttgggatc     4080 acaatcaag atataggcgt cggcaaagat tttatgtcaa agacgcccaa ggccatggcc     4140
actaaggata agattgataa gtgggacctt attaagctca aaagcttctg tactgccaag    4200
gagaccacga tcagagttaa taggcagccc actacatggg aaaagatttt cgccacttat    4260
tcatcagata aggggttgat aagcagaata tataacgagc tgaagcagat ctacaagaag    4320
aaaacgaata atcccatcaa gaagtgggca aagatatga acaggcattt tagcaaagag     4380
gatatctacg ccgcgaagaa gcatatgaag aagtgtagtt caagcttggc cattcgtgag    4440
atgcagatta agacgaccat gcgataccac cttacccccag tgaggatggc aattatcaag    4500
aaatctggca ataatagatg ttggcggggc tgtggcgaga ttggcacccct gctccattgc    4560 tggtgggatt gcaagctggt gcagccgctt tggaaatcag tctggcgctt tctgagggac    4620
ctcgagcttg agattccctt cgatcccgca attccctttgc tcggaatcta tcctaacgaa    4680
tacaagagct gttgttacaa ggatacgtgt acccggatgt tcatcgcggc cttgtttacg    4740
atagctaaga cgtggaatca gcctaagtgc cccacaatga tcgattggat caagaaaatg    4800
tggcatattt ataccatgga gtattacgca gcaattaaga atgacgaatt tatttccttc    4860
gttgggacct ggatgaagct ggagactatt attctgagca agctgtctca ggagcaaaag    4920
acaaagcata gaatcttctc tctcattggt ggtaacgact acaaagacga tgacgacaag    4980
cccgccgcca agagggtgaa gctggactaa agcgcttcta gaagttgtct cctcctgcac    5040
tgactgactg atacaatcga tttctggatc cgcaggccta atcaacctct ggattacaaa    5100
atttgtgaaa gattgactgg tattcttaac tatgttgctc cttttacgct atgtggatac    5160
gctgctttaa tgcctttgta tcatgctatt gcttcccgta tggctttcat tttctcctcc    5220
ttgtataaat cctggttgct gtctctttat gaggagttgt ggcccgttgt caggcaacgt    5280
ggcgtggtgt gcactgtgtt tgctgacgca acccccactg gttggggcat tgccaccacc    5340
tgtcagctcc tttccgggac tttcgctttc ccctccccta ttgccacggc ggaactcatc    5400
```

```
gccgcctgcc ttgcccgctg ctggacaggg gctcggctgt tgggcactga caattccgtg    5460
gtgttgtcgg ggaagctgac gtcctttcca tggctgctcg cctgtgttgc cacctggatt    5520
ctgcgcggga cgtccttctg ctacgtccct tcggccctca atccagcgga ccttccttcc    5580
cgctgagaga cacaaaaaat tccaacacac tattgcaatg aaaataaatt tcctttatta    5640
gccagaagtc agatgctcaa ggggcttcat gatgtcccca taattttttgg cagagggaaa    5700 aagatctcag tggtatttgt gagccagggc attggccttc tgataggcag cctgcacctg    5760
aggagtgcgg ccgctttact tgtacagctc gtccatgccg agagtgatcc cggcggcggt    5820
cacgaactcc agcaggacca tgtgatcgcg cttctcgttg gggtctttgc tcagggcgga    5880
ctgggtgctc aggtagtggt tgtcgggcag cagcacgggg ccgtcgccga tggggtgtt    5940 ctgctggtag tggtcggcga gctgcacgct gccgtcctcg atgttgtggc ggatcttgaa    6000
gttcaccttg atgccgttct tctgcttgtc ggccatgata tagacgttgt ggctgttgta    6060
gttgtactcc agcttgtgcc ccaggatgtt gccgtcctcc ttgaagtcga tgcccttcag    6120
ctcgatgcgg ttcaccaggg tgtcgccctc gaacttcacc tcggcgcggg tcttgtagtt    6180
gccgtcgtcc ttgaagaaga tggtgcgctc ctggacgtag ccttcgggca tggcggactt    6240
gaagaagtcg tgctgcttca tgtggtcggg gtagcggctg aagcactgca cgccgtaggt    6300
cagggtggtc acgagggtgg gccagggcac gggcagcttg ccggtggtgc agatgaactt    6360
cagggtcagc ttgccgtagg tggcatcgcc ctcgccctcg ccggacacgc tgaacttgtg    6420
gccgtttacg tcgccgtcca gctcgaccag gatgggcacc accccggtga acagctcctc    6480
gcccttgctc accatggtgg cgggatctga cggttcacta aaccagctct gcttatatag    6540
acctcccacc gtacacgcct accgcccatt tgcgtcaatg gggcggagtt gttacgacat    6600
tttggaaagt cccgttgatt ttggtgccaa acaaactcc cattgacgtc aatggggtgg    6660
agacttggaa atccccgtga gtcaaaccgc tatccacgcc cattgatgta ctgccaaaac    6720
cgcatcacca tggtaatagc gatgactaat acgtagatgt actgccaagt aggaaagtcc    6780
cataaggtca tgtactgggc ataatgccag gcgggccatt taccgtcatt gacgtcaata    6840
gggggcgtac ttggcatatg atacacttga tgtactgcca agtgggcagt ttaccgtaaa    6900
tactccaccc attgacgtca atggaaagtc cctattggcg ttactatggg aacatacgtc    6960
attattgacg tcaatgggcg ggggtcgttg ggcggtcagc caggcgggcc atttaccgta    7020
agttatgtaa cgggcctgct gccggctctg cggcctcttc cgcgtcttcg ccttcgccct    7080
cagacgagtc ggatctcccct ttgggccgcc tccccgcctg tctagcttga ctgactgaga    7140
tacagcgtac cttcagctca cagacatgat aagatacatt gatgagtttg gacaaaccac    7200
aactagaatg cagtgaaaaa aatgctttat ttgtgaaatt tgtgatgcta ttgctttatt    7260
tgtaaccatt ataagctgca ataaacaagt t                                   7291
```

<210> SEQ ID NO 43
<211> LENGTH: 7376
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
taatacgact cactataggg agaagtactg ccaccatggg caagaagcaa aatcgcaaga     60
cggggaattc caagacacaa tccgctagcc caccacctaa agagcgttct agctcccctg    120
```

```
ctactgagca gtcctggatg gaaaacgact tcgatgaact ccgggaagag ggatttaggc    180
gatccaacta ttcagaactc cgcgaagata tccagacaaa ggggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
tggctcggca agctaatgtg caaatccaag agatccaacg cacaccccag cggtatagct    660
ctcggcgtgc caccctagg catattatcg tgcgctttac taaggtggag atgaaagaga    720
agatgctgcg agccgctcgg gaaaagggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaacccTT gcagaaccac gcaaagatgt gagacagccg tcagaccatc aagactagga   1080
agaaactgca tcaactaatg agcaaaatca ccagctaaca tcatagtata catgaccggc   1140
tctaactcac atatcaccat ccttacactt aacattaacg gcctcaactc agctatcaag   1200
cgccatcggc tggccagctg gatcaaatca caggatccaa gcgtttgttg catccaagag   1260
acccacctga cctgtagaga tactcaccgc ctcaagatca agggatggcg aaagatttat   1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc   1500
tttatcaaac aggtcctgtc cgatctgcag cgagatctgg attctcatac gttgattatg   1560
ggtgatttca ataccattga gcaccctg gatcgcagca ccaggcaaaa ggtaaataaa   1620
gacacgcaag agctcaatag cgcactgcat caggcagatc tcattgatat ttatcgcact   1680
cttcatccta gagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccac   1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
agcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cacttttctg gataccttata ctctgccacg gcttaatcaa   2460
```

```
gaggaagtcg agtccctcaa ccgcccaatt acaggaagcg agattgtggc cataattaac    2520
tccctgccga caaagaaatc tcctggtccg gacgggttta cagctgagtt ttatcaacgg    2580
tatatggaag agcttgtacc gtttctgctc aagctctttc agtctataga aaaggaaggc    2640
atcttgccca attccttcta cgaagcttct ataatactta ttcccaaacc aggacgcgat    2700
accacaaaga aggaaaactt ccggcccatt agtctcatga atatcgacgc taaaatattg    2760
aacaagattc tcgccaacag aatccaacaa catattaaga aattgataca tcacgaccag    2820
gtggggttta tacctggcat gcagggctgg tttaacatcc ggaagagtat taacgtcatt    2880
caacacatta atagagctaa ggataagaat catatgatca tctctataga cgcggaaaag    2940
gcattcgata agattcagca gccatttatg ctcaagactc tgaacaaact cggcatcgac    3000
ggaacatatt ttaagattat tcgcgcaatt tacgataagc cgactgctaa cattatcctt    3060
aacggccaaa agctcgaggc ctttccgctc aagactggaa cccgccaagg ctgtcccctc    3120
tccccgcttt tgtttaatat tgtactcgag gtgctggcta gggctattcg tcaagagaaa    3180
gagattaaag ggatacagct cgggaaggaa gaggtcaagc tttccttgtt cgccgatgat    3240
atgattgtgt acctggagaa tcctattgtg tctgctcaga accttcttaa acttatttct    3300
aactttagca aggtcagcgg ctataagatt aacgtccaga aatctcaggc ctttctgtac    3360
acaaataatc gacagaccga atcccagata atgggtgagc ttccgtttgt catagccagc    3420
aaaaggataa agtatctcgg aatccagctg acacgagacg ttaaagattt gtttaaggaa    3480
aattacaagc ctctcctgaa agagattaag gaagatacta ataagtggaa gaatatcccc    3540
tgttcatggg ttggcagaat caacatagtg aagatggcaa tacttcctaa agtgatatat    3600
cgctttaacg ccatcccaat taaactgcct atgaccttct ttacggagct cgagaaaaca    3660
acccttaaat ttatatggaa tcaaaagaga gcaagaatag cgaagtccat cttgagccag    3720
aagaataagg ccggtgggat tactttgcct gattttaagt tgtattataa agccacagta    3780
actaagacag cctggtattg gtatcagaat agagacatcg accagtggaa tcggaccgaa    3840
ccatcagaga taatgcccca catctataat taccttatat tcgataagcc agaaaagaat    3900
aaacagtggg gcaaagacag cctcttcaac aagtggtgtt gggagaattg gctggccata    3960
tgccggaaac tcaagctcga cccctttctt acaccctaca ctaaaatcaa cagtaggtgg    4020
atcaaggact tgaatgtcaa gccaaagact ataaagacac tggaagagaa tcttgggatc    4080
acaatacaag atataggcgt cggcaaagat tttatgtcaa agacgcccaa ggccatggcc    4140
actaaggata agattgataa gtgggaccct attaagctca aaagcttctg tactgccaag    4200
gagaccacga tcagagttaa taggcagccc actacatggg aaaagatttt cgccacttat    4260
tcatcagata aggggttgat aagcagaata tataacgagc tgaagcagat ctacaagaag    4320
aaaacgaata atcccatcaa gaagtgggca aaagatatga acaggcattt tagcaaagag    4380
gatatctacg ccgcgaagaa gcatatgaag aagtgtagtt caagcttggc cattcgtgag    4440
atgcagatta agacgaccat gcgataccac cttaccccag tgaggatggc aattatcaag    4500
aaatctggca ataatagatg ttggcggggc tgtggcgaga ttggcacccct gctccattgc    4560 tggtgggatt gcaagctggt gcagccgctt tggaaatcag tctggcgctt tctgagggac    4620
ctcgagcttg agattccctt cgatcccgca attcccttgc tcggaatcta tcctaacgaa    4680
tacaagagct gttgttacaa ggatacgtgt acccggatgt tcatcgcggc cttgtttacg    4740
atagctaaga cgtggaatca gcctaagtgc cccacaatga tcgattggat caagaaaatg    4800
tggcatattt ataccatgga gtattacgca gcaattaaga atgacgaatt tatttccttc    4860
```

```
gttgggacct ggatgaagct ggagactatt attctgagca agctgtctca ggagcaaaag    4920
acaaagcata gaatcttctc tctcattggt ggtaacgact acaaagacga tgacgacaag    4980
taaagcggcc gggcgcggtg gctcacgcct gtaatcccag cactttggga ggccgaggcg    5040
ggaggatcgc agttcgagac cagcgcgaga ccccgtctct acaaaaatac aaaaattagc    5100
ttctagaagt tgtctcctcc tgcactgact gactgataca atcgatttct ggatccgcag    5160
gcctaatcaa cctctggatt acaaaatttg tgaaagattg actggtattc ttaactatgt    5220
tgctcctttt acgctatgtg gatacgctgc tttaatgcct ttgtatcatg ctattgcttc    5280
ccgtatggct ttcattttct cctccttgta taaatcctgg ttgctgtctc tttatgagga    5340
gttgtggccc gttgtcaggc aacgtggcgt ggtgtgcact gtgtttgctg acgcaacccc    5400
cactggttgg ggcattgcca ccacctgtca gctcctttcc gggactttcg ctttccccct    5460
ccctattgcc acggcggaac tcatcgccgc ctgccttgcc cgctgctgga cagggctcg    5520 gctgttgggc actgacaatt ccgtggtgtt gtcggggaag ctgacgtcct ttccatggct    5580
gctcgcctgt gttgccacct ggattctgcg cgggacgtcc ttctgctacg tcccttcggc    5640
cctcaatcca gcggaccttc cttcccgctg agagacacaa aaaattccaa cacactattg    5700
caatgaaaat aaatttcctt tattagccag aagtcagatg ctcaaggggc ttcatgatgt    5760
ccccataatt tttggcagag ggaaaaagat ctcagtggta tttgtgagcc agggcattgg    5820
ccttctgata ggcagcctgc acctgaggag tgcggccgct ttacttgtac agctcgtcca    5880
tgccgagagt gatcccggcg gcggtcacga actccagcag gaccatgtga tcgcgcttct    5940
cgttggggtc tttgctcagg gcggactggg tgctcaggta gtggttgtcg ggcagcagca    6000
cggggccgtc gccgatgggg gtgttctgct ggtagtggtc ggcgagctgc acgctgccgt    6060
cctcgatgtt gtggcggatc ttgaagttca ccttgatgcc gttcttctgc ttgtcggcca    6120
tgatatagac gttgtggctg ttgtagttgt actccagctt gtgccccagg atgttgccgt    6180
cctccttgaa gtcgatgccc ttcagctcga tgcggttcac cagggtgtcg ccctcgaact    6240
tcacctcggc gcgggtcttg tagttgccgt cgtccttgaa gaagatggtg cgctcctgga    6300
cgtagccttc gggcatggcg gacttgaaga agtcgtgctg cttcatgtgg tcggggtagc    6360
ggctgaagca ctgcacgccg taggtcaggg tggtcacgag ggtgggccag gcacgggca    6420 gcttgccggt ggtgcagatg aacttcaggg tcagcttgcc gtaggtggca tcgccctcgc    6480
cctcgccgga cacgctgaac ttgtggccgt ttacgtcgcc gtccagctcg accaggatgg    6540
gcaccacccc ggtgaacagc tcctcgccct tgctcaccat ggtggcggga tctgacggtt    6600
cactaaacca gctctgctta tatagacctc ccaccgtaca cgcctaccgc ccatttgcgt    6660
caatggggcg gagttgttac gacattttgg aaagtcccgt tgattttggt gccaaaacaa    6720
actcccattg acgtcaatgg ggtggagact tggaaatccc cgtgagtcaa accgctatcc    6780
acgcccattg atgtactgcc aaaaccgcat caccatggta atagcgatga ctaatacgta    6840
gatgtactgc caagtaggaa agtcccataa ggtcatgtac tgggcataat gccaggcggg    6900
ccatttaccg tcattgacgt caatagggggg cgtacttggc atatgataca cttgatgtac    6960
tgccaagtgg gcagtttacc gtaaatactc cacccattga cgtcaatgga aagtccctat    7020
tggcgttact atgggaacat acgtcattat tgacgtcaat gggcggggt cgttgggcgg    7080 tcagccaggc gggccattta ccgtaagtta tgtaacgggc ctgctgccgg ctctgcggcc    7140
tcttccgcgt cttcgccttc gccctcagac gagtcggatc tccctttggg ccgcctcccc    7200
```

| | |
|---|---|
| gcctgtctag cttgactgac tgagatacag cgtaccttca gctcacagac atgataagat | 7260 |
| acattgatga gtttggacaa accacaacta gaatgcagtg aaaaaaatgc tttatttgtg | 7320 |
| aaatttgtga tgctattgct ttatttgtaa ccattataag ctgcaataaa caagtt | 7376 |

<210> SEQ ID NO 44
<211> LENGTH: 14122
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

| | |
|---|---|
| taatacgact cactataggg agaagtactg ccaccatggg caagaagcaa atcgcaaga | 60 |
| cggggaattc caagacacaa tccgctagcc caccacctaa agagcgttct agctcccctg | 120 |
| ctactgagca gtcctggatg gaaaacgact tcgatgaact ccgggaagag ggatttaggc | 180 |
| gatccaacta ttcagaactc cgcgaagata tccagacaaa ggggaaggaa gtcgagaatt | 240 |
| tcgagaagaa cctcgaggag tgcatcaccc gtatcacaaa cactgagaaa tgtctcaaag | 300 |
| aactcatgga acttaagaca aaagccaggg agcttcgaga ggagtgtcgg agtctgagat | 360 |
| ccaggtgtga ccagctcgag gagcgcgtga gcgcgatgga agacgagatg aacgagatga | 420 |
| aaagagaggg caaattcagg gagaagcgca ttaagaggaa cgaacagagt ctgcaggaga | 480 |
| tttgggatta cgtcaagagg cctaacctgc ggttgatcgg cgtccccgag agcgacgtag | 540 |
| aaaacgggac taaactggag aatacacttc aagacatcat tcagaaaaat tttccaaacc | 600 |
| tggctcggca agctaatgtg caaatccaag agatccaacg cacaccccag cggtatagct | 660 |
| ctcggcgtgc caccctagg catattatcg tgcgctttac taaggtggag atgaaagaga | 720 |
| agatgctgcg agccgctcgg gaaaagggaa gggtgacttt gaagggcaaa cctattcggc | 780 |
| tgacggttga ccttagcgcc gagacactcc aggcacgccg gaatggggc cccatcttta | 840 |
| atatcctgaa ggagaagaac ttccagccac gaatctctta ccctgcaaag ttgagtttta | 900 |
| tctccgaggg tgagattaag tatttcatcg ataaacagat gctgcagac ttcgtgacaa | 960 |
| ctcgcccagc tctcaaggaa ctgctcaaag aggctcttaa tatggagcgc aataatagat | 1020 |
| atcaacccct gcagaaccac gcaaagatgt gagacagtta aaacagcctg tgggttgatc | 1080 |
| ccacccacag gcccattggg cgctagcact ctggtatcac ggtaccttg tgcgcctgtt | 1140 |
| ttatacccc tcccccaact gtaacttaga agtaacacac accgatcaac agtcagcgtg | 1200 |
| gcacaccagc cacgttttga tcaagcactt ctgttaccc ggactgagta tcaatagact | 1260 |
| gctcacgcgg ttgaaggaga aagcgttcgt tatccggcca actacttcga aaaacctagt | 1320 |
| aacaccgtga agttgcaga gtgtttcgct cagcactacc ccagtgtaga tcaggtcgat | 1380 |
| gagtcaccgc attccccacg ggcgaccgtg gcggtggctg cgttggcggc ctgcccatgg | 1440 |
| ggaaacccat gggacgctct aatacagaca tggtgcgaag agtctattga gctagttggt | 1500 |
| agtcctccgg cccctgaatg cggctaatcc taactgcgga gcacacaccc tcaagccaga | 1560 |
| gggcagtgtg tcgtaacggg caactctgca gcggaaccga ctactttggg tgtccgtgtt | 1620 |
| tcattttatt cctatactgg ctgcttatgg tgacaattga gagatcgtta ccatatagct | 1680 |
| attggattgg ccatccggtg actaatagag ctattatata tcccctttgtt gggtttatac | 1740 |
| cacttagctt gaaagaggtt aaaacattac aattcattgt taagttgaat acagcaaata | 1800 |
| catgaccggc tctaactcac atatcaccat ccttacactt aacattaacg gcctcaactc | 1860 |

```
agctatcaag cgccatcggc tggccagctg gatcaaatca caggatccaa gcgtttgttg   1920
catccaagag acccacctga cctgtagaga tactcaccgc ctcaagatca agggatggcg   1980
aaagatttat caggcgaacg gtaagcagaa gaaagccgga gtcgcaattc tggtctcaga   2040
caagacggat ttcaagccca ccaaaattaa gcgtgataag gaaggtcact atattatggt   2100
gaaaggcagc atacagcagg aagaacttac catattgaac atctacgcgc caaacaccgg   2160
cgcacctcgc tttatcaaac aggtcctgtc cgatctgcag cgagatctgg attctcatac   2220
gttgattatg ggtgatttca atacaccatt gagcaccctg gatcgcagca ccaggcaaaa   2280
ggtaaataaa gacacgcaag agctcaatag cgcactgcat caggcagatc tcattgatat   2340
ttatcgcact cttcatccta agagtaccga gtacacattc ttcagcgccc cacatcatac   2400
atactcaaag atcgatcata tcgtcggctc aaaggctctg ctgtcaaagt gcaagcgcac   2460
agagataatt acaaattacc tgtcagatca tagcgcgatc aagctcgagc tgagaatcaa   2520
gaacctgacc cagagccgga gtaccacttg gaagcttaat aacctgctgc tcaacgatta   2580
ttgggtccac aatgagatga aggcagagat taaaatgttc ttcgaaacaa atgagaataa   2640
ggatactacc tatcaaaacc tttgggatgc ctttaaggcc gtctgcagag gcaagttcat   2700
cgccctcaac gcctataaaa gaaaacaaga gagatctaag atcgatactc tcacctctca   2760
gctgaaggag ttggagaaac aggaacagac ccactccaag gcgtcaagac ggcaggagat   2820
cacaaagatt cgcgccgagt tgaaagagat cgaaacccaa aagactcttc agaaaattaa   2880
cgagtctcgt agttggttct tcgagcggat taataagata gacagacctc tggcacgact   2940
gattaagaag aagcgcgaaa gaaccagat tgataccatc aagaacgaca agggcgacat   3000
cactactgac ccgaccgaga tccagaccac tattcgggag tattataagc atttgtatgc   3060
taacaagctt gagaacctgg aagagatgga cactttctg gatacctata ctctgccacg   3120
gcttaatcaa gaggaagtcg agtccctcaa ccgcccaatt acaggaagcg agattgtggc   3180
cataattaac tccctgccga caaagaaatc tcctggtccg gacgggttta cagctgagtt   3240
ttatcaacgg tatatggaag agcttgtacc gtttctgctc aagctctttc agtctataga   3300
aaaggaaggc atcttgccca attccttcta cgaagcttct ataatactta ttcccaaacc   3360
aggacgcgat accacaaaga aggaaaactt ccggcccatt agtctcatga atatcgacgc   3420
taaaatattg aacaagattc tcgccaacag aatccaacaa catattaaga aattgataca   3480
tcacgaccag gtgggttta cctggcat gcagggctgg tttaacatcc ggaagagtat   3540
taacgtcatt caacacatta atagagctaa ggataagaat catatgatca tctctataga   3600
cgcggaaaag gcattcgata agattcagca gccatttatg ctcaagactc tgaacaaact   3660
cggcatcgac ggaacatatt ttaagattat tcgcgcaatt tacgataagc cgactgctaa   3720
cattatcctt aacggccaaa agctcgaggc ctttccgctc aagactggaa cccgccaagg   3780
ctgtcccctc tccccgcttt tgtttaatat tgtactcgag gtgctggcta gggctattcg   3840
tcaagagaaa gagattaaag ggatacagct cgggaaggaa gaggtcaagc tttccttgtt   3900
cgccgatgat atgattgtgt acctggagaa tcctattgtg tctgctcaga accttcttaa   3960
acttatttct aactttagca aggtcagcgg ctataagatt aacgtccaga aatctcaggc   4020 cttttctgtac acaaataatc gacagaccga atcccagata atgggtgagc ttccgtttgt   4080
catagccagc aaaaggataa agtatctcgg aatccagctg acacgagacg ttaaagattt   4140
gtttaaggaa aattacaagc ctctcctgaa agagattaag gaagatacta ataagtggaa   4200
gaatatcccc tgttcatggg ttggcagaat caacatagtg aagatggcaa tacttcctaa   4260
```

```
agtgatatat cgctttaacg ccatcccaat taaactgcct atgaccttct ttacggagct    4320
cgagaaaaca acccttaaat ttatatggaa tcaaaagaga gcaagaatag cgaagtccat    4380
cttgagccag aagaataagg ccggtggat tactttgcct gattttaagt tgtattataa     4440
agccacagta actaagacag cctggtattg gtatcagaat agagacatcg accagtggaa    4500
tcggaccgaa ccatcagaga taatgcccca catctataat taccttatat tcgataagcc    4560
agaaaagaat aaacagtggg gcaaagacag cctcttcaac aagtggtgtt gggagaattg    4620
gctggccata tgccggaaac tcaagctcga cccctttctt acaccctaca ctaaaatcaa    4680
cagtaggtgg atcaaggact tgaatgtcaa gccaaagact ataaagacac tggaagagaa    4740
tcttgggatc acaatacaag atataggcgt cggcaaagat tttatgtcaa agacgcccaa    4800
ggccatggcc actaaggata agattgataa gtgggacctt attaagctca aaagcttctg    4860
tactgccaag gagaccacga tcagagttaa taggcagccc actacatggg aaaagatttt    4920
cgccacttat tcatcagata aggggttgat aagcagaata tataacgagc tgaagcagat    4980
ctacaagaag aaaacgaata atcccatcaa gaagtgggca aaagatatga acaggcattt    5040
tagcaaagag gatatctacg ccgcgaagaa gcatatgaag aagtgtagtt caagcttggc    5100
cattcgtgag atgcagatta agacgaccat gcgataccac cttaccccag tgaggatggc    5160
aattatcaag aaatcggca ataatagatg ttggcgggc tgtggcgaga ttggcaccct      5220
gctccattgc tggtgggatt gcaagctggt gcagccgctt tggaaatcag tctggcgctt    5280
tctgagggac ctcgagcttg agattcccct cgatcccgca attccttgc tcggaatcta     5340 tcctaacgaa tacaagagct gttgttacaa ggatacgtgt acccggatgt tcatcgcggc    5400
cttgtttacg atagctaaga cgtggaatca gcctaagtgc cccacaatga tcgattggat    5460
caagaaaatg tggcatattt ataccatgga gtattacgca gcaattaaga atgacgaatt    5520
tatttccttc gttgggacct ggatgaagct ggagactatt attctgagca agctgtctca    5580
ggagcaaaag acaaagcata gaatcttctc tctcattggt ggtaacgact acaaagacga    5640
tgacgacaag taaagcgctt ctagaagttg tctcctcctg cactgactga ctgatacaat    5700
cgatttctgg atccgcaggc ctaatcaacc tctggattac aaaatttgtg aaagattgac    5760
tggtattctt aactatgttg ctccttttac gctatgtgga tacgctgctt taatgccttt    5820
gtatcatgct attgcttccc gtatggcttt catttctcc tccttgtata aatcctggtt     5880
gctgtctctt tatgaggagt tgtggcccgt tgtcaggcaa cgtggcgtgg tgtgcactgt    5940
gtttgctgac gcaaccccca ctggttgggg cattgccacc acctgtcagc tcctttccgg    6000
gactttcgct ttcccctcc ctattgccac ggcggaactc atcgccgcct gccttgcccg     6060
ctgctggaca gggctcggc tgttgggcac tgacaattc cgtggtgttgt cggggaagct      6120 gacgtccttt ccatggctgc tcgcctgtgt tgccacctgg attctgcgcg gacgtccttt     6180
ctgctacgtc ccttcggccc tcaatccagc ggaccttcct tcccgcgaac aaacgaccca    6240
acacccgtgc gttttattct gtcttttat tgccgatccc ctcagaagaa ctcgtcaaga     6300
aggcgataga aggcgatgcg ctgcgaatcg ggagcggcga taccgtaaag cacgaggaag    6360
cggtcagccc attcgccgcc aagctcttca gcaatatcac gggtagccaa cgctatgtcc    6420
tgatagcggt cggccgcttt acttgtacag ctcgtccatg ccgagagtga tcccggcggc    6480
ggtcacgaac tccagcagga ccatgtgatc gcgcttctcg ttgggtcttt gctcagggc     6540 ggactgggtg ctcaggtagt ggttgtcggg cagcagcacg gggccgtcgc cgatggggt     6600
```

```
gttctgctgg tagtggtcgg ccaggtgagt ccaggagatg tttcagcact gttgccttta    6660
gtctcgaggc aacttagaca actgagtatt gatctgagca cagcagggtg tgagctgttt    6720
gaagatactg gggttggggg tgaagaaact gcagaggact aactgggctg agacccagtg    6780
gcaatgtttt agggcctaag gaatgcctct gaaaatctag atggacaact ttgactttga    6840
gaaagagag gtggaaatga ggaaaatgac ttttctttat tagatttcgg tagaaagaac     6900
tttcatcttt cccctatttt tgttattcgt tttaaaacat ctatctggag caggacaag    6960
tatggtcatt aaaaagatgc aggcagaagg catatattgg ctcagtcaaa gtggggaact    7020
ttggtggcca acatacatt gctaaggcta ttcctatatc agctggacac atataaaatg     7080
ctgctaatgc ttcattacaa acttatatcc tttaattcca gatgggggca aagtatgtcc    7140
aggggtgagg aacaattgaa acatttgggc tggagtagat tttgaaagtc agctctgtgt    7200
gtgtgtgtgt gtgtgtgtgt gtgagagcgt gtgtttcttt taacgttttc agcctacagc    7260
atacagggtt catggtggca agaagataac aagatttaaa ttatggccag tgactagtgc    7320
tgcaagaaga acaactacct gcatttaatg ggaaagcaaa atctcaggct ttgagggaag    7380
ttaacatagg cttgattctg ggtggaagct gggtgtgtag ttatctggag gccaggctgg    7440
agctctcagc tcactatggg ttcatcttta ttgtctcctt tcatctcaac agctgcacgc    7500
tgccgtcctc gatgttgtgg cggatcttga agttcacctt gatgccgttc ttctgcttgt    7560
cggccatgat atagacgttg tggctgttgt agttgtactc cagcttgtgc cccaggatgt    7620
tgccgtcctc cttgaagtcg atgcccttca gctcgatgcg gttcaccagg gtgtcgccct    7680
cgaacttcac ctcggcgcgg gtcttgtagt tgccgtcgtc cttgaagaag atggtgcgct    7740
cctggacgta gccttcgggc atggcggact tgaagaagtc gtgctgcttc atgtggtcgg    7800
ggtagcggct gaagcactgc acgccgtagg tcagggtggt cacgagggtg gccagggca    7860
cgggcagctt gccggtggtg cagatgaact tcagggtcag cttgccgtag gtggcatcgc    7920
cctcgccctc gccggacacg ctgaacttgt ggccgtttac gtcgccgtcc agctcgacca    7980
ggatgggcac caccccggtg aacagctcct cgcccttgct caccatggtg gcgaattcga    8040
agcttgagca cgagatctga gtccggtagg cctagcggat ctgacggttc actaaaccag    8100
ctctgcttat atagacctcc caccgtacac gcctaccgcc catttgcgtc aatggggcgg    8160
agttgttacg acattttgga aagtcccgtt gattttggtg ccaaaacaaa ctcccattga    8220
cgtcaatggg gtggagactt ggaaatcccc gtgagtcaaa ccgctatcca cgcccattga    8280
tgtactgcca aaaccgcatc accatggtaa tagcgatgac taatacgtag atgtactgcc    8340
aagtaggaaa gtcccataag gtcatgtact gggcataatg ccaggcgggc catttaccgt    8400
cattgacgtc aataggggc gtacttggca tatgatacac ttgatgtact gccaagtggg    8460
cagtttaccg taaatactcc acccattgac gtcaatggaa agtccctatt ggcgttacta    8520
tgggaacata cgtcattatt gacgtcaatg ggcgggggtc gttgggcggt cagcaggcg    8580
ggccatttac cgtaagttat gtaacgggcc tgctgccggc tctgcggcct cttccgcgtc    8640
ttcgccttcg ccctcagacg agtcggatct ccctttgggc cgcctccccg cctgtctagc    8700
ttgactgact gagatacagc gtaccttcag ctcacagaca tgataagata cattgatgag    8760
tttggacaaa ccacaactag aatgcagtga aaaaaatgct ttatttgtga atttgtgat    8820
gctattgctt tatttgtaac cattataagc tgcaataaac aagttaacaa caacaattgc    8880
attcatttta tgtttcaggt tcaggggga gtgtgggagg ttttttaaag caagtaaaac    8940
ctctacaaat gtggtattgg cccatctcta tcggtatcgt agcataaccc cttggggcct    9000
```

```
ctaaacgggt cttgaggggt tttttgtgcc cctcgggccg gattgctatc taccggcatt    9060
ggcgcagaaa aaaatgcctg atgcgacgct gcgcgtctta tactcccaca tatgccagat    9120
tcagcaacgg atacggcttc cccaacttgc ccacttccat acgtgtcctc cttaccagaa    9180
atttatcctt aaggtcgtca gctatcctgc aggcgatctc tcgatttcga tcaagacatt    9240
cctttaatgg tcttttctgg acaccactag gggtcagaag tagttcatca aactttcttc    9300
cctccctaat ctcattggtt accttgggct atcgaaactt aattaagcga tctgcatctc    9360
aattagtcag caaccatagt cccgcccta actccgccca tcccgcccct aactccgccc      9420
agttccgccc attctccgcc ccatcgctga ctaattttt ttatttatgc agaggccgag      9480
gccgcctcgg cctctgagct attccagaag tagtgaggag cttttttgg aggcctaggc      9540 ttttgcaaag gaggtagcca acatgattga acaagatgga ttgcacgcag gttctcccgc    9600
cgcttgggtg gagaggctat tcggctatga ctgggcacaa cagacaatcg gctgctctga    9660
tgccgccgtg ttccggctgt cagcgcaggg gcgcccggtt cttttgtca agaccgacct      9720 gtccggtgcc ctgaatgaac tccaggacga ggcagcgcgg ctatcgtggc tggccacgac    9780
gggcgttcct tgcgcagctg tgctcgacgt tgtcactgaa gcgggaaggg actggctgct    9840
attgggcgaa gtgccggggc aggatctcct gtcatctcac cttgctcctg ccgagaaagt    9900
atccatcatg gctgatgcaa tgcggcggct gcatacgctt gatccggcta cctgcccatt    9960
cgaccaccaa gcgaaacatc gcatcgagcg agcacgtact cggatggaag ccggtcttgt    10020
cgatcaggat gatctggacg aagagcatca ggggctcgcg ccagccgaac tgttcgccag    10080
gctcaaggcg cggatgcccg acggcgagga tctcgtcgtg acccacggcg atgcctgctt    10140
gccgaatatc atggtggaaa atggccgctt ttctggattc atcgactgtg gccggctggg    10200
tgtggcggac cgctatcagg acatagcgtt ggctacccgt gatattgctg aagagcttgg    10260
cggcgaatgg gctgaccgct tcctcgtgct ttacggtatc gccgctcccg attcgcagcg    10320
catcgccttc tatcgccttc ttgacgagtt cttctagtat gtaagccctg tgccttctag    10380
ttgccagcca tctgttgttt gcccctcccc cgtgccttcc ttgaccctgg aaggtgccac    10440
tcccactgtc ctttcctaat aaaatgagga aattgcatcg cattgtctga gtaggtgtca    10500
ttctattctg gggggtgggg tggggcagga cagcaagggg gaggattggg aagacaatag    10560
caggcatgct ggggatgcgg tgggctctat ggttaattaa ccagtcaagt cagctacttg    10620
gcgagatcga cttgtctggg tttcgactac gctcagaatt gcgtcagtca agttcgatct    10680
ggtccttgct attgcacccg ttctccgatt acgagtttca tttaaatcat gtgagcaaaa    10740
ggccagcaaa aggccaggaa ccgtaaaaag gccgcgttgc tggcgttttt ccataggctc    10800
cgcccccctg acgagcatca caaaaatcga cgctcaagtc agaggtggcg aaacccgaca    10860
ggactataaa gataccaggc gtttccccct ggaagctccc tcgtgcgctc tcctgttccg    10920
accctgccgc ttaccggata cctgtccgcc tttctccctt cggaagcgt ggcgctttct      10980 catagctcac gctgtaggta tctcagttcg gtgtaggtcg ttcgctccaa gctgggctgt    11040
gtgcacgaac cccccgttca gcccgaccgc tgcgccttat ccgtaactac tcgtcttgag    11100
tccaacccgg taagacacga cttatcgcca ctggcagcag ccactggtaa caggattagc    11160
agagcgaggt atgtaggcgg tgctacagag ttcttgaagt ggtggcctaa ctacggctac    11220
actagaagaa cagtatttgg tatctgcgct ctgctgaagc cagttacctt cggaaaaaga    11280
gttggtagct cttgatccgg caaacaaacc accgctggta gcggtggttt ttttgtttgc    11340
```

-continued

```
aagcagcaga ttacgcgcag aaaaaaagga tctcaagaag atcctttgat cttttctacg   11400
gggtctgacg ctcagtggaa cgaaaactca cgttaaggga ttttggtcat gagattatca   11460
aaaaggatct tcacctagat cctttttaaat taaaaatgaa gttttaaatc aatctaaagt   11520
atatatgagt aaacttggtc tgacagttac caatgcttaa tcagtgaggc acctatctca   11580
gcgatctgtc tatttcgttc atccatagtt gcatttaaat ttccgaactc tccaaggccc   11640
tcgtcggaaa atcttcaaac ctttcgtccg atccatcttg caggctacct ctcgaacgaa   11700
ctatcgcaag tctcttggcc ggccttgcgc cttggctatt gcttggcagc gcctatcgcc   11760
aggtattact ccaatcccga atatccgaga tcgggatcac ccgagagaag ttcaacctac   11820
atcctcaatc ccgatctatc cgagatccga ggaatatcga atcggggcg cgcctggtgt    11880 accgagaacg atcctctcag tgcgagtctc gacgatccat atcgttgctt ggcagtcagc   11940
cagtcggaat ccagcttggg acccaggaag tccaatcgtc agatattgta ctcaagcctg   12000
gtcacggcag cgtaccgatc tgtttaaacc tagatattga tagtctgatc ggtcaacgta   12060
taatcgagtc ctagcttttg caaacatcta tcaagagaca ggatcagcag gaggctttcg   12120
catgagtatt caacatttcc gtgtcgccct tattcccttt tttgcggcat tttgccttcc   12180 tgttttttgct cacccagaaa cgctggtgaa agtaaaagat gctgaagatc agttgggtgc   12240
gcgagtgggt tacatcgaac tggatctcaa cagcggtaag atccttgaga gttttcgccc   12300
cgaagaacgc tttccaatga tgagcacttt taaagttctg ctatgtggcg cggtattatc   12360
ccgtattgac gccgggcaag agcaactcgg tcgccgcata cactattctc agaatgactt   12420
ggttgagtat tcaccagtca cagaaaagca tcttacggat ggcatgacag taagagaatt   12480
atgcagtgct gccataacca tgagtgataa cactgcggcc aacttacttc tgacaacgat   12540
tggaggaccg aaggagctaa ccgcttttt gcacaacatg ggggatcatg taactcgcct   12600
tgatcgttgg gaaccggagc tgaatgaagc cataccaaac gacgagcgtg acaccacgat   12660
gcctgtagca atggcaacaa ccttgcgtaa actattaact ggcgaactac ttactctagc   12720
ttcccggcaa cagttgatag actggatgga ggcggataaa gttgcaggac cacttctgcg   12780
ctcggccctt ccggctggct ggtttattgc tgataaatct ggagccggtg agcgtgggtc   12840
tcgcggtatc attgcagcac tggggccaga tggtaagccc tcccgtatcg tagttatcta   12900
cacgacgggg agtcaggcaa ctatggatga acgaaataga cagatcgctg agataggtgc   12960
ctcactgatt aagcattggt aaccgattct aggtgcattg gcgcagaaaa aaatgcctga   13020
tgcgacgctg cgcgtcttat actcccacat atgccagatt cagcaacgga tacgcttcc   13080 ccaacttgcc cacttccata cgtgtcctcc ttaccagaaa tttatcctta agatcgttta   13140
aactcgactc tggctctatc gaatctccgt cgtttcgagc ttacgcgaac agccgtggcg   13200
ctcatttgct cgtcgggcat cgaatctcgt cagctatcgt cagcttacct ttttggcagc   13260
gatcgcggct cccgacatct tggaccatta gctccacagg tatcttcttc cctctagtgg   13320
tcataacagc agcttcagct acctctcaat tcaaaaaacc cctcaagacc cgtttagagg   13380
ccccaagggg ttatgctatc aatcgttgcg ttacacacac aaaaaaccaa cacacatcca   13440
tcttcgatgg atagcgattt tattatctaa ctgctgatcg agtgtagcca gatctagtaa   13500
tcaattacgg ggtcattagt tcatagccca tatatggagt tccgcgttac ataacttacg   13560
gtaaatggcc cgcctggctg accgcccaac gacccccgcc cattgacgtc aataatgacg   13620
tatgttccca tagtaacgcc aatagggact ttccattgac gtcaatgggt ggagtattta   13680
cggtaaactg cccacttggc agtacatcaa gtgtatcata tgccaagtac gccccctatt   13740
```

-continued

| | | | |
|---|---|---|---|
| gacgtcaatg | acggtaaatg | gcccgcctgg | cattatgccc agtacatgac cttatgggac 13800 |
| tttcctactt | ggcagtacat | ctacgtatta | gtcatcgcta ttaccatgct gatgcggttt 13860 |
| tggcagtaca | tcaatgggcg | tggatagcgg | tttgactcac ggggatttcc aagtctccac 13920 |
| cccattgacg | tcaatgggag | tttgttttgg | caccaaaatc aacgggactt tccaaaatgt 13980 |
| cgtaacaact | ccgccccatt | gacgcaaatg | gcggtaggc gtgtacggtg ggaggtctat 14040 |
| ataagcagag | ctggtttagt | gaaccgtcag | atcagatctt tgtcgatcct accatccact 14100 |
| cgacacaccc | gccagcggcc | gc | 14122 |

<210> SEQ ID NO 45
<211> LENGTH: 14124
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 45

| | | | |
|---|---|---|---|
| taatacgact | cactataggg | agaagtactg | ccaccatggg caagaagcaa atcgcaaga 60 |
| cggggaattc | caagacacaa | tccgctagcc | caccacctaa agagcgttct agctcccctg 120 |
| ctactgagca | gtcctggatg | gaaaacgact | tcgatgaact ccgggaagag ggatttaggc 180 |
| gatccaacta | ttcagaactc | cgcgaagata | tccagacaaa ggggaaggaa gtcgagaatt 240 |
| tcgagaagaa | cctcgaggag | tgcatcaccc | gtatcacaaa cactgagaaa tgtctcaaag 300 |
| aactcatgga | acttaagaca | aaagccaggg | agcttcgaga ggagtgtcgg agtctgagat 360 |
| ccaggtgtga | ccagctcgag | gagcgcgtga | gcgcgatgga agacgagatg aacgagatga 420 |
| aaagagaggg | caaattcagg | gagaagcgca | ttaagaggaa cgaacagagt ctgcaggaga 480 |
| tttgggatta | cgtcaagagg | cctaacctgc | ggttgatcgg cgtccccgag agcgacgtag 540 |
| aaaacgggac | taaactggag | aatacacttc | aagacatcat tcaagaaaat tttccaaacc 600 |
| tggctcggca | agctaatgtg | caaatccaag | agatccaacg cacaccccag cggtatagct 660 |
| ctcggcgtgc | caccccctagg | catattatcg | tgcgctttac taaggtggag atgaaagaga 720 |
| agatgctgcg | agccgctcgg | gaaaagggaa | gggtgacttt gaagggcaaa cctattcggc 780 |
| tgacggttga | ccttagcgcc | gagacactcc | aggcacgccg ggaatggggc ccatctttta 840 |
| atatcctgaa | ggagaagaac | ttccagccac | gaatctctta ccctgcaaag ttgagtttta 900 |
| tctccgaggg | tgagattaag | tatttcatcg | ataaacagat gctgcgagac ttcgtgacaa 960 |
| ctcgcccagc | tctcaaggaa | ctgctcaaag | aggctcttaa tatggagcgc aataatagat 1020 |
| atcaacccttt | gcagaaccac | gcaaagatgt | gagacagtta aaacagctgt gggttgtcac 1080 |
| ccacccacag | ggtccactgg | gcgctagtac | actggtatct cggtacccttt gtacgcctgt 1140 |
| tttataccccc | ctccctgatt | tgcaacttag | aagcaacgca aaccagatca atagtaggtg 1200 |
| tgacatacca | gtcgcatctt | gatcaagcac | ttctgtatcc ccggaccgag tatcaataga 1260 |
| ctgtgcacac | ggttgaagga | gaaaacgtcc | gttacccggc taactacttc gagaagccta 1320 |
| gtaacgccat | tgaagttgca | gagtgtttcg | ctcagcactc ccccgtgta gatcaggtcg 1380 |
| atgagtcacc | gcattcccca | cgggcgaccg | tggcggtggc tgcgttggcg gcctgcctat 1440 |
| ggggtaaccc | ataggacgct | ctaatacgga | catggcgtga agagtctatt gagctagtta 1500 |
| gtagtcctcc | ggcccctgaa | tgcggctaat | cctaactgcg gagcacatac ccttaatcca 1560 |
| aagggcagtg | tgtcgtaacg | ggcaactctg | cagcggaacc gactactttg ggtgtccgtg 1620 |

-continued

```
tttcttttta ttcttgtatt ggctgcttat ggtgacaatt aaagaattgt taccatatag    1680
ctattggatt ggccatccag tgtcaaacag agctattgta tatctctttg ttggattcac    1740
acctctcact cttgaaacgt tacacaccct caattacatt atactgctga acacgaagcg    1800
tacatgaccg gctctaactc acatatcacc atccttacac ttaacattaa cggcctcaac    1860
tcagctatca agcgccatcg gctggccagc tggatcaaat cacaggatcc aagcgtttgt    1920
tgcatccaag agacccacct gacctgtaga gatactcacc gcctcaagat caagggatgg    1980
cgaaagattt atcaggcgaa cggtaagcag aagaaagccg gagtcgcaat tctggtctca    2040
gacaagacga atttcaagcc caccaaaatt aagcgtgata aggaaggtca ctatattatg    2100
gtgaaaggca gcatacagca ggaagaactt accatattga acatctacgc gccaaacacc    2160
ggcgcacctc gctttatcaa acaggtcctg tccgatctgc agcgagatct ggattctcat    2220
acgttgatta tgggtgattt caatacacca ttgagcaccc tggatcgcag caccaggcaa    2280
aaggtaaata aagacacgca agagctcaat agcgcactgc atcaggcaga tctcattgat    2340
atttatcgca ctcttcatcc taagagtacc gagtacacat tcttcagcgc cccacatcat    2400
acatactcaa agatcgatca tatcgtcggc tcaaaggctc tgctgtcaaa gtgcaagcgc    2460
acagagataa ttacaaatta cctgtcagat catagcgcga tcaagctcga gctgagaatc    2520
aagaacctga cccagagccg gagtaccact tggaagctta taacctgct gctcaacgat    2580 tattgggtcc acaatgagat gaaggcagag attaaaatgt tcttcgaaac aaatgagaat    2640
aaggatacta cctatcaaaa cctttgggat gcctttaagg ccgtctgcag aggcaagttc    2700
atcgccctca acgcctataa agaaaaacaa gagagatcta agatcgatac tctcacctct    2760
cagctgaagg agttggagaa acaggaacag acccactcca aggcgtcaag acggcaggag    2820
atcacaaaga ttcgcgccga gttgaaagag atcgaaaccc aaaagactct tcagaaaatt    2880
aacgagtctc gtagttggtt cttcgagcgg attaataaga tagacagacc tctggcacga    2940
ctgattaaga agaagcgcga aaagaaccag attgatacca tcaagaacga caagggcgac    3000
atcactactg acccgaccga gatccagacc actattcggg agtattataa gcatttgtat    3060
gctaacaagc ttgagaacct ggaagagatg gacactttc tggataccta tactctgcca    3120
cggcttaatc aagaggaagt cgagtccctc aaccgcccaa ttacaggaag cgagattgtg    3180
gccataatta actccctgcc gacaaagaaa tctcctggtc cggacgggtt tacagctgag    3240
ttttatcaac ggtatatgga agagcttgta ccgtttctgc tcaagctctt tcagtctata    3300
gaaaaggaag gcatcttgcc caattccttc tacgaagctt ctataatact tattcccaaa    3360
ccaggacgcg ataccacaaa gaaggaaaac ttccggccca ttagtctcat gaatatcgac    3420
gctaaaatat tgaacaagat tctcgccaac agaatccaac aacatattaa gaaattgata    3480
catcacgacc aggtggggtt tatacctggc atgcagggct ggtttaacat ccggaagagt    3540
attaacgtca ttcaacacat taatagagct aaggataaga atcatatgat catctctata    3600
gacgcggaaa aggcattcga taagattcag cagccattta tgctcaagac tctgaacaaa    3660
ctcggcatcg acggaacata tttttaagatt attcgcgcaa tttacgataa gccgactgct    3720
aacattatcc ttaacggcca aaagctcgag gcctttccgc tcaagactgg aacccgccaa    3780
ggctgtcccc tctccccgct tttgtttaat attgtactcg aggtgctggc tagggctatt    3840
cgtcaagaga aagagattaa agggatacag ctcgggaagg aagaggtcaa gctttccttg    3900
ttcgccgatg atatgattgt gtacctggag aatcctattg tgtctgctca gaaccttctt    3960
```

```
aaacttattt ctaactttag caaggtcagc ggctataaga ttaacgtcca gaaatctcag    4020
gcctttctgt acacaaataa tcgacagacc gaatcccaga taatgggtga gcttccgttt    4080
gtcatagcca gcaaaaggat aaagtatctc ggaatccagc tgacacgaga cgttaaagat    4140
ttgtttaagg aaaattacaa gcctctcctg aaagagatta aggaagatac taataagtgg    4200
aagaatatcc cctgttcatg ggttggcaga atcaacatag tgaagatggc aatacttcct    4260
aaagtgatat atcgctttaa cgccatccca attaaactgc ctatgacctt ctttacggag    4320
ctcgagaaaa caacccttaa atttatatgg aatcaaaaga gagcaagaat agcgaagtcc    4380
atcttgagcc agaagaataa ggccggtggg attacttttgc ctgattttaa gttgtattat    4440
aaagccacag taactaagac agcctggtat tggtatcaga atagagacat cgaccagtgg    4500
aatcggaccg aaccatcaga gataatgccc cacatctata attaccttat attcgataag    4560
ccagaaaaga ataaacagtg gggcaaagac agcctcttca acaagtggtg ttgggagaat    4620
tggctggcca tatgccggaa actcaagctc gaccccttcc ttacacccta cactaaaatc    4680
aacagtaggt ggatcaagga cttgaatgtc aagccaaaga ctataaagac actggaagag    4740
aatcttggga tcacaataca agatataggc gtcggcaaag attttatgtc aaagacgccc    4800
aaggccatgg ccactaagga taagattgat aagtgggacc ttattaagct caaaagcttc    4860
tgtactgcca aggagaccac gatcagagtt aataggcagc ccactacatg ggaaaagatt    4920
ttcgccactt attcatcaga taaggggttg ataagcagaa tatataacga gctgaagcag    4980
atctacaaga agaaaacgaa taatcccatc aagaagtggg caaaagatat gaacaggcat    5040
tttagcaaag aggatatcta cgccgcgaag aagcatatga agaagtgtag ttcaagcttg    5100
gccattcgtg agatgcagat taagacgacc atgcgatacc accttacccc agtgaggatg    5160
gcaattatca agaaatctgg caataataga tgttggcggg gctgtggcga gattggcacc    5220
ctgctccatt gctggtggga ttgcaagctg gtgcagccgc tttggaaatc agtctggcgc    5280
tttctgaggg acctcgagct tgagattccc ttcgatcccg caattccctt gctcggaatc    5340
tatcctaacg aatacaagag ctgttgttac aaggatacgt gtacccggat gttcatcgcg    5400
gccttgttta cgatagctaa gacgtggaat cagcctaagt gccccacaat gatcgattgg    5460
atcaagaaaa tgtggcatat ttataccatg gagtattacg cagcaattaa gaatgacgaa    5520
tttatttcct tcgttgggac ctggatgaag ctggagacta ttattctgag caagctgtct    5580
caggagcaaa agacaaagca tagaatcttc tctctcattg gtggtaacga ctacaaagac    5640
gatgacgaca gtaaagcgc ttctagaagt tgtctcctcc tgcactgact gactgataca    5700
atcgatttct ggatccgcag gcctaatcaa cctctggatt acaaaatttg tgaaagattg    5760
actggtattc ttaactatgt tgctcctttt acgctatgtg gatacgctgc tttaatgcct    5820
ttgtatcatg ctattgcttc ccgtatggct ttcattttct cctccttgta taaatcctgg    5880
ttgctgtctc tttatgagga gttgtggccc gttgtcaggc aacgtggcgt ggtgtgcact    5940
gtgtttgctg acgcaacccc cactggttgg ggcattgcca ccacctgtca gctcctttcc    6000
gggactttcg ctttccccct cccattgcc acggcggaac tcatcgccgc ctgccttgcc    6060
cgctgctgga caggggctcg gctgttgggc actgacaatt ccgtggtgtt gtcggggaag    6120
ctgacgtcct ttccatggct gctcgcctgt gttgccacct ggattctgcg cgggacgtcc    6180
ttctgctacg tccccttcggc cctcaatcca gcggaccttc cttcccgcga caaacgacc    6240 caacacccgt gcgttttatt ctgtcttttt attgccgatc cctcagaag aactcgtcaa    6300 gaaggcgata aaggcgatg cgctgcgaat cgggagcggc gataccgtaa agcacgagga    6360
```

```
agcggtcagc ccattcgccg ccaagctctt cagcaatatc acgggtagcc aacgctatgt      6420
cctgatagcg gtcggccgct ttacttgtac agctcgtcca tgccgagagt gatcccggcg      6480
gcggtcacga actccagcag gaccatgtga tcgcgcttct cgttggggtc tttgctcagg      6540
gcggactggg tgctcaggta gtggttgtcg ggcagcagca cggggccgtc gccgatgggg      6600
gtgttctgct ggtagtggtc ggccaggtga gtccaggaga tgtttcagca ctgttgcctt      6660
tagtctcgag gcaacttaga caactgagta ttgatctgag cacagcaggg tgtgagctgt      6720
ttgaagatac tggggttggg ggtgaagaaa ctgcagagga ctaactgggc tgagacccag      6780
tggcaatgtt ttagggccta aggaatgcct ctgaaaatct agatggacaa ctttgacttt      6840
gagaaaagag aggtggaaat gaggaaaatg acttttcttt attagatttc ggtagaaaga      6900
actttcatct ttcccctatt tttgttattc gttttaaaac atctatctgg aggcaggaca      6960
agtatggtca ttaaaaagat gcaggcagaa ggcatatatt ggctcagtca aagtggggaa      7020
ctttggtggc caaacataca ttgctaaggc tattcctata tcagctggac acatataaaa      7080
tgctgctaat gcttcattac aaacttatat cctttaattc cagatggggg caaagtatgt      7140
ccaggggtga ggaacaattg aaacatttgg gctggagtag attttgaaag tcagctctgt      7200
gtgtgtgtgt gtgtgtgtgt gtgtgagagc gtgtgtttct tttaacgttt tcagcctaca      7260
gcatacaggt tcatggtgg caagaagata acaagattta aattatggcc agtgactagt       7320
gctgcaagaa gaacaactac ctgcatttaa tgggaaagca aaatctcagg ctttgaggga      7380
agttaacata ggcttgattc tgggtggaag ctgggtgtgt agttatctgg aggccaggct      7440
ggagctctca gctcactatg ggttcatctt tattgtctcc tttcatctca acagctgcac      7500
gctgccgtcc tcgatgttgt ggcggatctt gaagttcacc ttgatgccgt tcttctgctt      7560
gtcggccatg atatagacgt tgtggctgtt gtagttgtac tccagcttgt gccccaggat      7620
gttgccgtcc tccttgaagt cgatgcccct cagctcgatg cggttcacca gggtgtcgcc      7680
ctcgaacttc acctcggcgc gggtcttgta gttgccgtcg tccttgaaga agatggtgcg      7740
ctcctggacg tagccttcgg gcatggcgga cttgaagaag tcgtgctgct tcatgtggtc      7800
ggggtagcgg ctgaagcact gcacgccgta ggtcaggtg gtcacgaggg tgggccaggg       7860
cacgggcagc ttgccggtgg tgcagatgaa cttcagggtc agcttgccgt aggtggcatc      7920
gccctcgccc tcgccggaca cgctgaactt gtggccgttt acgtcgccgt ccagctcgac      7980
caggatgggc accaccccgg tgaacagctc ctcgcccttg ctcaccatgg tggcgaattc      8040
gaagcttgag cacgagatct gagtccggta ggcctagcgg atctgacggt tcactaaacc      8100
agctctgctt atatagacct cccaccgtac acgcctaccg cccatttgcg tcaatggggc      8160
ggagttgtta cgacattttg gaaagtcccg ttgattttgg tgccaaaaca aactcccatt      8220
gacgtcaatg gggtggagac ttggaaatcc ccgtgagtca aaccgctatc cacgcccatt      8280
gatgtactgc caaaaccgca tcaccatggt aatagcgatg actaatacgt agatgtactg      8340
ccaagtagga aagtcccata aggtcatgta ctgggcataa tgccaggcgg ccatttacc      8400 gtcattgacg tcaataggg gcgtacttgg catatgatac acttgatgta ctgccaagtg       8460
ggcagtttac cgtaaatact ccacccattg acgtcaatgg aaagtcccta ttggcgttac      8520
tatgggaaca tacgtcatta ttgacgtcaa tgggcggggg tcgttgggcg gtcagccagg      8580
cgggccattt accgtaagtt atgtaacggg cctgctgccg gctctgcggc ctcttccgcg      8640
tcttcgcctt cgccctcaga cgagtcggat ctcccttggg gccgcctccc cgcctgtcta      8700
```

```
gcttgactga ctgagataca gcgtaccttc agctcacaga catgataaga tacattgatg    8760
agtttggaca aaccacaact agaatgcagt gaaaaaaatg ctttatttgt gaaatttgtg    8820
atgctattgc tttatttgta accattataa gctgcaataa acaagttaac aacaacaatt    8880
gcattcattt tatgtttcag gttcaggggg aggtgtggga ggtttttttaa agcaagtaaa    8940 acctctacaa atgtggtatt ggcccatctc tatcggtatc gtagcataac cccttggggc    9000
ctctaaacgg gtcttgaggg gttttttgtg cccctcgggc cggattgcta tctaccggca    9060
ttggcgcaga aaaaaatgcc tgatgcgacg ctgcgcgtct tatactccca catatgccag    9120
attcagcaac ggatacggct tccccaactt gcccacttcc atacgtgtcc tccttaccag    9180
aaatttatcc ttaaggtcgt cagctatcct gcaggcgatc tctcgatttc gatcaagaca    9240
ttcctttaat ggtcttttct ggacaccact agggtcaga agtagttcat caaactttct    9300
tccctcccta atctcattgg ttaccttggg ctatcgaaac ttaattaagc gatctgcatc    9360
tcaattagtc agcaaccata gtcccgcccc taactccgcc catcccgccc ctaactccgc    9420
ccagttccgc ccattctccg ccccatcgct gactaatttt ttttatttat gcagaggccg    9480
aggccgcctc ggcctctgag ctattccaga gtagtgagg aggctttttt ggaggcctag    9540
gcttttgcaa aggaggtagc caacatgatt gaacaagatg gattgcacgc aggttctccc    9600
gccgcttggg tggagaggct attcggctat gactgggcac aacagacaat cggctgctct    9660
gatgccgccg tgttccggct gtcagcgcag gggcgcccgg ttcttttttgt caagaccgac    9720 ctgtccggtg ccctgaatga actccaggac gaggcagcgc ggctatcgtg gctggccacg    9780
acgggcgttc cttgcgcagc tgtgctcgac gttgtcactg aagcgggaag ggactggctg    9840
ctattgggcg aagtgccggg gcaggatctc ctgtcatctc accttgctcc tgccgagaaa    9900
gtatccatca tggctgatgc aatgcggcgg ctgcatacgc ttgatccggc tacctgccca    9960
ttcgaccacc aagcgaaaca tcgcatcgag cgagcacgta ctcggatgga agccggtctt   10020
gtcgatcagg atgatctgga cgaagagcat caggggctcg cgccagccga actgttcgcc   10080
aggctcaagg cgcggatgcc cgacggcgag gatctcgtcg tgacccacgg cgatgcctgc   10140
ttgccgaata tcatggtgga aaatggccgc ttttctggat tcatcgactg tggccggctg   10200
ggtgtggcgg accgctatca ggacatagcg ttggctaccc gtgatattgc tgaagagctt   10260
ggcggcgaat gggctgaccg cttcctcgtg ctttacggta tcgccgctcc cgattcgcag   10320
cgcatcgcct tctatcgcct tcttgacgag ttcttctagt atgtaagccc tgtgccttct   10380
agttgccagc catctgttgt ttgccccctcc ccgtgccttt ccttgaccct ggaaggtgcc   10440
actcccactg tcctttccta ataaaatgag gaaattgcat cgcattgtct gagtaggtgt   10500
cattctattc tggggggtgg ggtggggcag gacagcaagg gggaggattg gaagacaat   10560 agcaggcatg ctggggatgc ggtgggctct atggttaatt aaccagtcaa gtcagctact   10620
tggcgagatc gacttgtctg ggtttcgact acgctcagaa ttgcgtcagt caagttcgat   10680
ctggtccttg ctattgcacc cgttctccga ttacgagttt catttaaatc atgtgagcaa   10740
aaggccagca aaaggccagg aaccgtaaaa aggccgcgtt gctggcgttt ttccataggc   10800
tccgcccccc tgacgagcat cacaaaaatc gacgctcaag tcagaggtgg cgaaacccga   10860
caggactata aagataccag gcgtttcccc ctggaagctc cctcgtgcgc tctcctgttc   10920
cgaccctgcc gcttaccgga tacctgtccg cctttctccc ttcgggaagc gtggcgcttt   10980
ctcatagctc acgctgtagg tatctcagtt cggtgtaggt cgttcgctcc aagctgggct   11040
gtgtgcacga accccccgtt cagcccgacc gctgcgcctt atccggtaac tatcgtcttg   11100
```

```
agtccaaccc ggtaagacac gacttatcgc cactggcagc agccactggt aacaggatta   11160
gcagagcgag gtatgtaggc ggtgctacag agttcttgaa gtggtggcct aactacggct   11220
acactagaag aacagtattt ggtatctgcg ctctgctgaa gccagttacc ttcggaaaaa   11280
gagttggtag ctcttgatcc ggcaaacaaa ccaccgctgg tagcgtggt ttttttgttt    11340 gcaagcagca gattacgcgc agaaaaaaag gatctcaaga agatcctttg atcttttcta   11400
cggggtctga cgctcagtgg aacgaaaact cacgttaagg gattttggtc atgagattat   11460
caaaaaggat cttcacctag atccttttaa attaaaaatg aagttttaaa tcaatctaaa   11520
gtatatatga gtaaacttgg tctgacagtt accaatgctt aatcagtgag gcacctatct   11580
cagcgatctg tctatttcgt tcatccatag ttgcatttaa atttccgaac tctccaaggc   11640
cctcgtcgga aaatcttcaa acctttcgtc cgatccatct tgcaggctac ctctcgaacg   11700
aactatcgca agtctcttgg ccggccttgc gccttggcta ttgcttggca gcgcctatcg   11760
ccaggtatta ctccaatccc gaatatccga gatcgggatc acccgagaga agttcaacct   11820
acatcctcaa tcccgatcta tccgagatcc gaggaatatc gaaatcgggg cgcgcctggt   11880
gtaccgagaa cgatcctctc agtgcgagtc tcgacgatcc atatcgttgc ttggcagtca   11940
gccagtcgga atccagcttg ggacccagga agtccaatcg tcagatattg tactcaagcc   12000
tggtcacggc agcgtaccga tctgtttaaa cctagatatt gatagtctga tcggtcaacg   12060
tataatcgag tcctagcttt tgcaaacatc tatcaagaga caggatcagc aggaggcttt   12120
cgcatgagta ttcaacattt ccgtgtcgcc cttattccct tttttgcggc attttgcctt   12180 cctgttttg ctcacccaga aacgctggtg aaagtaaaag atgctgaaga tcagttgggt    12240
gcgcgagtgg gttacatcga actggatctc aacagcggta agatccttga gagttttcgc   12300
cccgaagaac gctttccaat gatgagcact tttaaagttc tgctatgtgg cgcggtatta   12360
tcccgtattg acgccgggca agagcaactc ggtcgccgca tacactattc tcagaatgac   12420
ttggttgagt attcaccagt cacagaaaag catcttacgg atggcatgac agtaagagaa   12480
ttatgcagtg ctgccataac catgagtgat aacactgcgg ccaacttact tctgacaacg   12540
attggaggac cgaaggagct aaccgctttt ttgcacaaca tgggggatca tgtaactcgc   12600
cttgatcgtt gggaaccgga gctgaatgaa gccataccaa acgacgagcg tgacaccacg   12660
atgcctgtag caatggcaac aaccttgcgt aaactattaa ctggcgaact acttactcta   12720
gcttcccggc aacagttgat agactggatg gaggcggata agttgcagg accacttctg   12780 cgctcggccc ttccggctgg ctggtttatt gctgataaat ctggagccgg tgagcgtggg   12840
tctcgcggta tcattgcagc actggggcca gatggtaagc cctcccgtat cgtagttatc   12900
tacacgacgg ggagtcaggc aactatggat gaacgaaata gacagatcgc tgagataggt   12960
gcctcactga ttaagcattg gtaaccgatt ctaggtgcat tggcgcagaa aaaaatgcct   13020
gatgcgacgc tgcgcgtctt atactcccac atatgccaga ttcagcaacg gatacggctt   13080
ccccaacttg cccacttcca tacgtgtcct ccttaccaga aatttatcct taagatcgtt   13140
taaactcgac tctggctcta tcgaatctcc gtcgtttcga gcttacgcga acagccgtgg   13200
cgctcatttg ctcgtcgggc atcgaatctc gtcagctatc gtcagcttac cttttggca    13260 gcgatcgcgg ctcccgacat cttggaccat tagctccaca ggtatcttct tccctctagt   13320
ggtcataaca gcagcttcag ctacctctca attcaaaaaa cccctcaaga cccgtttaga   13380
ggccccaagg ggttatgcta tcaatcgttg cgttacacac acaaaaaacc aacacacatc   13440
```

-continued

| | |
|---|---|
| catcttcgat ggatagcgat tttattatct aactgctgat cgagtgtagc cagatctagt | 13500 |
| aatcaattac ggggtcatta gttcatagcc catatatgga gttccgcgtt acataactta | 13560 |
| cggtaaatgg cccgcctggc tgaccgccca acgaccccg cccattgacg tcaataatga | 13620 |
| cgtatgttcc catagtaacg ccaataggga ctttccattg acgtcaatgg gtggagtatt | 13680 |
| tacggtaaac tgcccacttg gcagtacatc aagtgtatca tatgccaagt acgcccccta | 13740 |
| ttgacgtcaa tgacggtaaa tggcccgcct ggcattatgc ccagtacatg accttatggg | 13800 |
| actttcctac ttggcagtac atctacgtat tagtcatcgc tattaccatg ctgatgcggt | 13860 |
| tttggcagta catcaatggg cgtggatagc ggtttgactc acggggattt ccaagtctcc | 13920 |
| accccattga cgtcaatggg agtttgtttt ggcaccaaaa tcaacgggac tttccaaaat | 13980 |
| gtcgtaacaa ctccgcccca ttgacgcaaa tgggcggtag gcgtgtacgg tgggaggtct | 14040 |
| atataagcag agctggttta gtgaaccgtc agatcagatc tttgtcgatc ctaccatcca | 14100 |
| ctcgacacac cgccagcgg ccgc | 14124 |

<210> SEQ ID NO 46
<211> LENGTH: 13439
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 46

| | |
|---|---|
| taatacgact cactataggg agaagtactg ccaccatggg caagaagcaa aatcgcaaga | 60 |
| cggggaattc caagacacaa tccgctagcc caccacctaa agagcgttct agctcccctg | 120 |
| ctactgagca gtcctggatg gaaaacgact tcgatgaact ccgggaagag ggatttaggc | 180 |
| gatccaacta ttcagaactc cgcgaagata tccagacaaa ggggaaggaa gtcgagaatt | 240 |
| tcgagaagaa cctcgaggag tgcatcaccc gtatcacaaa cactgagaaa tgtctcaaag | 300 |
| aactcatgga acttaagaca aaagccaggg agcttcgaga ggagtgtcgg agtctgagat | 360 |
| ccaggtgtga ccagctcgag gagcgcgtga gcgcgatgga agacgagatg aacgagatga | 420 |
| aaagagaggg caaattcagg gagaagcgca ttaagaggaa cgaacagagt ctgcaggaga | 480 |
| tttgggatta cgtcaagagg cctaacctgc ggttgatcgg cgtccccgag agcgacgtag | 540 |
| aaaacgggac taaactggag aatacacttc aagcatcat tcaagaaaat tttccaaacc | 600 |
| tggctcggca agctaatgtg caaatccaag agatccaacg cacacccag cggtatagct | 660 |
| ctcggcgtgc caccctagg catattatcg tgcgctttac taaggtggag atgaaagaga | 720 |
| agatgctgcg agccgctcgg aaaagggaa gggtgacttt gaagggcaaa cctattcggc | 780 |
| tgacggttga ccttagcgcc gagacactcc aggcacgccg ggaatggggc ccatctttta | 840 |
| atatcctgaa ggagaagaac ttccagccac gaatctctta ccctgcaaag ttgagtttta | 900 |
| tctccgaggg tgagattaag tatttcatcg ataaacagat gctgcgagac ttcgtgacaa | 960 |
| ctcgcccagc tctcaaggaa ctgctcaaag aggctcttaa tatggagcgc aataatagat | 1020 |
| atcaacccctt gcagaaccac gcaaagatgg gaagcggaca gtgtactaat tatgctctct | 1080 |
| tgaaattggc tggagatgtt gagagcaacc ctggacctat gaccggctct aactcacata | 1140 |
| tcaccatcct tacacttaac attaacggcc tcaactcagc tatcaagcgc atcggctggg | 1200 |
| ccagctggat caaatcacag gatccaagcg tttgttgcat ccaagagacc cacctgacct | 1260 |
| gtagagatac tcaccgcctc aagatcaagg gatggcgaaa gatttatcag gcgaacggta | 1320 |

-continued

```
agcagaagaa agccggagtc gcaattctgg tctcagacaa gacggatttc aagcccacca   1380
aaattaagcg tgataaggaa ggtcactata ttatggtgaa aggcagcata cagcaggaag   1440
aacttaccat attgaacatc tacgcgccaa acaccggcgc acctcgcttt atcaaacagg   1500
tcctgtccga tctgcagcga gatctggatt ctcatacgtt gattatgggt gatttcaata   1560
caccattgag caccctggat cgcagcacca ggcaaaaggt aaataaagac acgcaagagc   1620
tcaatagcgc actgcatcag gcagatctca ttgatattta tcgcactctt catcctaaga   1680
gtaccgagta cacattcttc agcgccccac atcatacata ctcaaagatc gatcatatcg   1740
tcggctcaaa ggctctgctg tcaaagtgca agcgcacaga gataattaca aattacctgt   1800
cagatcatag cgcgatcaag ctcgagctga gaatcaagaa cctgacccag agccggagta   1860
ccacttggaa gcttaataac ctgctgctca acgattattg ggtccacaat gagatgaagg   1920
cagagattaa aatgttcttc gaaacaaatg agaataagga tactacctat caaaaccttt   1980
gggatgcctt taaggccgtc tgcagaggca agttcatcgc cctcaacgcc tataaaagaa   2040
aacaagagag atctaagatc gatactctca cctctcagct gaaggagttg gagaaacagg   2100
aacagaccca ctccaaggcg tcaagacggc aggagatcac aaagattcgc gccgagttga   2160
aagagatcga aacccaaaag actcttcaga aaattaacga gtctcgtagt tggttcttcg   2220
agcggattaa taagatagac agacctctgg cacgactgat taagaagaag cgcgaaaaga   2280
accagattga taccatcaag aacgacaagg gcgacatcac tactgacccg accgagatcc   2340
agaccactat tcgggagtat tataagcatt tgtatgctaa caagcttgag aacctggaag   2400
agatggacac ttttctggat acctatactc tgccacggct taatcaagag gaagtcgagt   2460
ccctcaaccg cccaattaca ggaagcgaga ttgtggccat aattaactcc ctgccgacaa   2520
agaaatctcc tggtccggac gggtttacag ctgagtttta tcaacggtat atggaagagc   2580
ttgtaccgtt tctgctcaag ctctttcagt ctatagaaaa ggaaggcatc ttgcccaatt   2640
ccttctacga agcttctata atacttattc ccaaaccagg acgcgatacc acaaagaagg   2700
aaaacttccg gcccattagt ctcatgaata tcgacgctaa aatattgaac aagattctcg   2760
ccaacagaat ccaacaacat attaagaaat tgatacatca cgaccaggtg gggtttatac   2820
ctggcatgca gggctggttt aacatccgga agagtattaa cgtcattcaa cacattaata   2880
gagctaagga taagaatcat atgatcatct ctatagacgc ggaaaaggca ttcgataaga   2940
ttcagcagcc atttatgctc aagactctga acaaactcgg catcgacgga acatatttta   3000
agattattcg cgcaatttac gataagccga ctgctaacat tatccttaac ggccaaaagc   3060
tcgaggcctt tccgctcaag actggaaccc gccaaggctg tccctctcc ccgcttttgt   3120 ttaatattgt actcgaggtg ctggctaggg ctattcgtca agagaaagag attaaaggga   3180
tacagctcgg gaaggaagag gtcaagcttt ccttgttcgc cgatgatatg attgtgtacc   3240
tggagaatcc tattgtgtct gctcagaacc ttcttaaact tatttctaac tttagcaagg   3300
tcagcggcta agattaac gtccagaaat ctcaggcctt tctgtacaca aataatcgac   3360
agaccgaatc ccagataatg ggtgagcttc cgtttgtcat agccagcaaa aggataaagt   3420
atctcggaat ccagctgaca cgagacgtta aagatttgtt taaggaaaat tacaagcctc   3480
tcctgaaaga gattaaggaa gatactaata agtggaagaa tatccctgt tcatgggttg   3540 gcagaatcaa catagtgaag atggcaatac ttcctaaagt gatatatcgc tttaacgcca   3600
tcccaattaa actgccatg accttctta cggagctcga gaaacaacc cttaaattta   3660 tatggaatca aaagagagca agaatagcga agtccatctt gagccagaag aataaggccg   3720
```

```
gtgggattac tttgcctgat tttaagttgt attataaagc cacagtaact aagacagcct    3780
ggtattggta tcagaataga gacatcgacc agtggaatcg gaccgaacca tcagagataa    3840
tgccccacat ctataattac cttatattcg ataagccaga aaagaataaa cagtggggca    3900
aagacagcct cttcaacaag tggtgttggg agaattggct ggccatatgc cggaaactca    3960
agctcgaccc ctttcttaca ccctacacta aaatcaacag taggtggatc aaggacttga    4020
atgtcaagcc aaagactata aagacactgg aagagaatct tgggatcaca atacaagata    4080
taggcgtcgg caaagatttt atgtcaaaga cgcccaaggc catggccact aaggataaga    4140
ttgataagtg ggaccttatt aagctcaaaa gcttctgtac tgccaaggag accacgatca    4200
gagttaatag gcagcccact acatgggaaa agattttcgc cacttattca tcagataagg    4260
ggttgataag cagaatatat aacgagctga agcagatcta caagaagaaa cgaataatc     4320 ccatcaagaa gtgggcaaaa gatatgaaca ggcattttag caaagaggat atctacgccg    4380
cgaagaagca tatgaagaag tgtagttcaa gcttggccat tcgtgagatg cagattaaga    4440
cgaccatgcg ataccacctt accccagtga ggatggcaat tatcaagaaa tctggcaata    4500
atagatgttg gcggggctgt ggcgagattg gcaccctgct ccattgctgg tgggattgca    4560
agctggtgca gccgctttgg aaatcagtct ggcgcttttct gagggacctc gagcttgaga    4620
ttcccttcga tcccgcaatt cccttgctcg gaatctatcc taacgaatac aagagctgtt    4680
gttacaagga tacgtgtacc cggatgttca tcgcggcctt gtttacgata gctaagacgt    4740
ggaatcagcc taagtgcccc acaatgatcg attggatcaa gaaaatgtgg catatttata    4800
ccatggagta ttacgcagca attaagaatg acgaatttat ttccttcgtt gggacctgga    4860
tgaagctgga gactattatt ctgagcaagc tgtctcagga gcaaaagaca aagcatagaa    4920
tcttctctct cattggtggt aacgactaca agacgatga cgacaagtaa agcgcttcta    4980
gaagttgtct cctcctgcac tgactgactg atacaatcga tttctggatc cgcaggccta    5040
atcaacctct ggattacaaa atttgtgaaa gattgactgg tattcttaac tatgttgctc    5100
cttttacgct atgtggatac gctgctttaa tgcctttgta tcatgctatt gcttcccgta    5160
tggctttcat tttctcctcc ttgtataaat cctggttgct gtctctttat gaggagttgt    5220
ggcccgttgt caggcaacgt ggcgtggtgt gcactgtgtt tgctgacgca accccccactg   5280 gttgggcat tgccaccacc tgtcagctcc tttccgggac tttcgctttc ccctcccta     5340 ttgccacggc ggaactcatc gccgcctgcc ttgcccgctg ctggacaggg gctcggctgt    5400
tgggcactga caattccgtg gtgttgtcgg ggaagctgac gtccttttcca tggctgctcg    5460 cctgtgttgc cacctggatt ctgcgcggga cgtccttctg ctacgtccct tcggccctca    5520
atccagcgga ccttccttcc cgcgaacaaa cgacccaaca cccgtgcgtt ttattctgtc    5580
tttttattgc cgatccctc agaagaactc gtcaagaagg cgatagaagg cgatgcgctg    5640
cgaatcggga gcggcgatac cgtaaagcac gaggaagcgg tcagcccatt cgccgccaag    5700
ctcttcagca atatcacggg tagccaacgc tatgtcctga tagcggtcgg ccgctttact    5760
tgtacagctc gtccatgccg agagtgatcc cggcggcggt cacgaactcc agcaggacca    5820
tgtgatcgcg cttctcgttg ggtctttgc tcagggcgga ctgggtgctc aggtagtggt    5880
tgtcgggcag cagcacgggg ccgtcgccga tgggggtgtt ctgctggtag tggtcggcca    5940
ggtgagtcca ggagatgttt cagcactgtt gcctttagtc tcgaggcaac ttagacaact    6000
gagtattgat ctgagcacag cagggtgtga gctgtttgaa gatactgggg ttggggtga    6060
```

```
agaaactgca gaggactaac tgggctgaga cccagtggca atgttttagg gcctaaggaa    6120
tgcctctgaa aatctagatg gacaactttg actttgagaa aagagaggtg gaaatgagga    6180
aaatgacttt tctttattag atttcggtag aaagaacttt catctttccc ctattttgt     6240
tattcgtttt aaaacatcta tctggaggca ggacaagtat ggtcattaaa aagatgcagg    6300
cagaaggcat atattggctc agtcaaagtg gggaactttg gtggccaaac atacattgct    6360
aaggctattc ctatatcagc tggacacata taaaatgctg ctaatgcttc attacaaact    6420
tatatccttt aattccagat gggggcaaag tatgtccagg ggtgaggaac aattgaaaca    6480
tttgggctgg agtagatttt gaaagtcagc tctgtgtgtg tgtgtgtgtg tgtgtgtgtg    6540
agagcgtgtg tttcttttaa cgttttcagc ctacagcata cagggttcat ggtggcaaga    6600
agataacaag atttaaatta tggccagtga ctagtgctgc aagaagaaca actacctgca    6660
tttaatggga aagcaaaatc tcaggctttg agggaagtta acataggctt gattctgggt    6720
ggaagctggg tgtgtagtta tctggaggcc aggctggagc tctcagctca ctatgggttc    6780
atctttattg tctcctttca tctcaacagc tgcacgctgc cgtcctcgat gttgtggcgg    6840
atcttgaagt tcaccttgat gccgttcttc tgcttgtcgg ccatgatata gacgttgtgg    6900
ctgttgtagt tgtactccag cttgtgcccc aggatgttgc cgtcctcctt gaagtcgatg    6960
cccttcagct cgatgcggtt caccagggtg tcgccctcga acttcacctc ggcgcgggtc    7020
ttgtagttgc cgtcgtcctt gaagaagatg gtgcgctcct ggacgtagcc ttcgggcatg    7080
gcggacttga agaagtcgtg ctgcttcatg tggtcggggt agcggctgaa gcactgcacg    7140
ccgtaggtca gggtggtcac gagggtgggc cagggcacgg gcagcttgcc ggtggtgcag    7200
atgaacttca gggtcagctt gccgtaggtg gcatcgccct cgccctcgcc ggacacgctg    7260
aacttgtggc cgtttacgtc gccgtccagc tcgaccagga tgggcaccac cccggtgaac    7320
agctcctcgc ccttgctcac catggtggcg aattcgaagc ttgagcacga gatctgagtc    7380
cggtaggcct agcggatctg acggttcact aaaccagctc tgcttatata gacctcccac    7440
cgtacacgcc taccgcccat ttgcgtcaat ggggcggagt tgttacgaca ttttggaaag    7500
tcccgttgat tttggtgcca aaacaaactc ccattgacgt caatggggtg gagacttgga    7560
aatccccgtg agtcaaaccg ctatccacgc ccattgatgt actgccaaaa ccgcatcacc    7620
atggtaatag cgatgactaa tacgtagatg tactgccaag taggaaagtc ccataaggtc    7680
atgtactggg cataatgcca ggcgggccat ttaccgtcat tgacgtcaat aggggggcgta    7740
cttggcatat gatacacttg atgtactgcc aagtgggcag tttaccgtaa atactccacc    7800
cattgacgtc aatggaaagt ccctattggc gttactatgg aacatacgt cattattgac     7860
gtcaatgggc gggggtcgtt gggcggtcag ccaggcgggc catttaccgt aagttatgta    7920
acgggcctgc tgccggctct gcggcctctt ccgcgtcttc gccttcgccc tcagacgagt    7980
cggatctccc tttgggccgc ctccccgcct gtctagcttg actgactgag atacagcgta    8040
ccttcagctc acagacatga taagatacat tgatgagttt ggacaaacca caactagaat    8100
gcagtgaaaa aaatgcttta tttgtgaaat ttgtgatgct attgctttat ttgtaaccat    8160
tataagctgc aataaacaag ttaacaacaa caattgcatt catttatgt ttcaggttca     8220
gggggaggtg tgggaggttt tttaaagcaa gtaaaacctc tacaaatgtg gtattggccc    8280
atctctatcg gtatcgtagc ataacccctt ggggcctcta acgggtctt gaggggtttt     8340
ttgtgcccct cgggccggat tgctatctac cggcattggc gcagaaaaaa atgcctgatg    8400
cgacgctgcg cgtcttatac tcccacatat gccagattca gcaacggata cggcttcccc    8460
```

```
aacttgccca cttccatacg tgtcctcctt accagaaatt tatccttaag gtcgtcagct   8520
atcctgcagg cgatctctcg atttcgatca agacattcct ttaatggtct tttctggaca   8580
ccactagggg tcagaagtag ttcatcaaac tttcttccct ccctaatctc attggttacc   8640
ttgggctatc gaaacttaat taagcgatct gcatctcaat tagtcagcaa ccatagtccc   8700
gcccctaact ccgcccatcc cgccctaac tccgcccagt ccgcccatt ctccgcccca     8760 tcgctgacta atttttttta tttatgcaga ggccgaggcc gcctcggcct ctgagctatt   8820
ccagaagtag tgaggaggct tttttggagg cctaggcttt tgcaaaggag gtagccaaca   8880
tgattgaaca agatggattg cacgcaggtt ctcccgccgc ttgggtggag aggctattcg   8940
gctatgactg ggcacaacag acaatcggct gctctgatgc cgccgtgttc cggctgtcag   9000
cgcaggggcg cccggttctt tttgtcaaga ccgacctgtc cggtgccctg aatgaactcc   9060
aggacgaggc agcgcggcta tcgtggctgg ccacgacggg cgttccttgc gcagctgtgc   9120
tcgacgttgt cactgaagcg ggaagggact ggctgctatt gggcgaagtg ccggggcagg   9180
atctcctgtc atctcacctt gctcctgccg agaaagtatc catcatggct gatgcaatgc   9240
ggcggctgca tacgcttgat ccggctacct gcccattcga ccaccaagcg aaacatcgca   9300
tcgagcgagc acgtactcgg atggaagccg gtcttgtcga tcaggatgat ctggacgaag   9360
agcatcaggg gctcgcgcca gccgaactgt tcgccaggct caaggcgcgg atgcccgacg   9420
gcgaggatct cgtcgtgacc cacggcgatg cctgcttgcc gaatatcatg gtggaaaatg   9480
gccgcttttc tggattcatc gactgtggcc ggctgggtgt ggcggaccgc tatcaggaca   9540
tagcgttggc tacccgtgat attgctgaag agcttggcgg cgaatgggct gaccgcttcc   9600
tcgtgcttta cggtatcgcc gctcccgatt cgcagcgcat cgccttctat cgccttcttg   9660
acgagttctt ctagtatgta agccctgtgc cttctagttg ccagccatct gttgtttgcc   9720
cctcccccgt gccttccttg accctggaag gtgccactcc cactgtcctt tcctaataaa   9780
atgaggaaat tgcatcgcat tgtctgagta ggtgtcattc tattctgggg ggtggggtgg   9840
ggcaggacag caagggggag gattgggaag acaatagcag gcatgctggg gatgcggtgg   9900
gctctatggt taattaacca gtcaagtcag ctacttggcg agatcgactt gtctgggttt   9960
cgactacgct cagaattgcg tcagtcaagt tcgatctggt ccttgctatt gcacccgttc  10020
tccgattacg agtttcattt aaatcatgtg agcaaaaggc cagcaaaagg ccaggaaccg  10080
taaaaaggcc gcgttgctgg cgttttccca taggctccgc cccctgacg agcatcacaa   10140 aaatcgacgc tcaagtcaga ggtggcgaaa cccgacagga ctataaagat accaggcgtt  10200
tccccctgga agctccctcg tgcgctctcc tgttccgacc ctgccgctta ccggatacct  10260
gtccgccttt ctcccttcgg gaagcgtggc gctttctcat agctcacgct gtaggtatct  10320
cagttcggtg taggtcgttc gctccaagct gggctgtgtg cacgaacccc ccgttcagcc  10380
cgaccgctgc gccttatccg gtaactatcg tcttgagtcc aacccggtaa gacacgactt  10440
atcgccactg gcagcagcca ctggtaacag gattagcaga gcgaggtatg taggcggtgc  10500
tacagagttc ttgaagtggt ggcctaacta cggctacact agaagaacag tatttggtat  10560
ctgcgctctg ctgaagccag ttaccttcgg aaaaagagtt ggtagctctt gatccggcaa  10620
acaaaccacc gctggtagcg gtggtttttt tgtttgcaag cagcagatta cgcgcagaaa  10680
aaaaggatct caagaagatc ctttgatctt ttctacgggg tctgacgctc agtggaacga  10740
aaactcacgt taagggattt tggtcatgag attatcaaaa aggatcttca cctagatcct  10800
```

```
tttaaattaa aaatgaagtt ttaaatcaat ctaaagtata tatgagtaaa cttggtctga    10860
cagttaccaa tgcttaatca gtgaggcacc tatctcagcg atctgtctat ttcgttcatc    10920
catagttgca tttaaatttc cgaactctcc aaggccctcg tcggaaaatc ttcaaacctt    10980
tcgtccgatc catcttgcag gctacctctc gaacgaacta tcgcaagtct cttggccggc    11040
cttgcgcctt ggctattgct tggcagcgcc tatcgccagg tattactcca atcccgaata    11100
tccgagatcg ggatcacccg agagaagttc aacctacatc ctcaatcccg atctatccga    11160
gatccgagga atatcgaaat cggggcgcgc ctggtgtacc gagaacgatc ctctcagtgc    11220
gagtctcgac gatccatatc gttgcttggc agtcagccag tcggaatcca gcttgggacc    11280
caggaagtcc aatcgtcaga tattgtactc aagcctggtc acggcagcgt accgatctgt    11340
ttaaacctag atattgatag tctgatcggt caacgtataa tcgagtccta gcttttgcaa    11400
acatctatca agagacagga tcagcaggag ctttcgcat gagtattcaa catttccgtg    11460
tcgcccttat tcccttttt gcggcatttt gccttcctgt ttttgctcac ccagaaacgc    11520
tggtgaaagt aaaagatgct gaagatcagt tgggtgcgcg agtgggttac atcgaactgg    11580
atctcaacag cggtaagatc cttgagagtt ttcgccccga agaacgcttt ccaatgatga    11640
gcacttttaa agttctgcta tgtggcgcgg tattatcccg tattgacgcc gggcaagagc    11700
aactcggtcg ccgcatacac tattctcaga atgacttggt tgagtattca ccagtcacag    11760
aaaagcatct tacggatggc atgacagtaa gagaattatg cagtgctgcc ataaccatga    11820
gtgataacac tgcggccaac ttacttctga caacgattgg aggaccgaag gagctaaccg    11880
cttttttgca caacatgggg gatcatgtaa ctcgccttga tcgttgggaa ccggagctga    11940
atgaagccat accaaacgac gagcgtgaca ccacgatgcc tgtagcaatg gcaacaacct    12000
tgcgtaaact attaactggc gaactactta ctctagcttc ccggcaacag ttgatagact    12060
ggatggaggc ggataaagtt gcaggaccac ttctgcgctc ggcccttccg gctggctggt    12120
ttattgctga taaatctgga gccggtgagc gtgggtctcg cggtatcatt gcagcactgg    12180
ggccagatgg taagccctcc cgtatcgtag ttatctacac gacggggagt caggcaacta    12240
tggatgaacg aaatagacag atcgctgaga taggtgcctc actgattaag cattggtaac    12300
cgattctagg tgcattggcg cagaaaaaaa tgcctgatgc gacgctgcgc gtcttatact    12360
cccacatatg ccagattcag caacggtac ggcttcccca acttgcccac ttccatacgt    12420
gtcctcctta ccagaaattt atccttaaga tcgtttaaac tcgactctgg ctctatcgaa    12480
tctccgtcgt ttcgagctta cgcgaacagc cgtggcgctc atttgctcgt cgggcatcga    12540
atctcgtcag ctatcgtcag cttaccttt tggcagcgat cgcggctccc gacatcttgg    12600
accattagct ccacaggtat cttcttccct ctagtggtca taacagcagc ttcagctacc    12660
tctcaattca aaaaccccct caagacccgt ttagaggccc aaggggtta tgctatcaat    12720 cgttgcgtta cacacacaaa aaaccaacac acatccatct tcgatggata gcgattttat    12780
tatctaactg ctgatcgagt gtagccagat ctagtaatca attacggggt cattagttca    12840
tagcccatat atggagttcc gcgttacata acttacggta aatggcccgc ctggctgacc    12900
gcccaacgac ccccgcccat tgacgtcaat aatgacgtat gttcccatag taacgccaat    12960
agggactttc cattgacgtc aatgggtgga gtatttacgg taaactgccc acttggcagt    13020
acatcaagtg tatcatatgc caagtacgcc ccctattgac gtcaatgacg gtaaatggcc    13080
cgcctggcat tatgcccagt acatgacctt atgggacttt cctacttggc agtacatcta    13140
cgtattagtc atcgctatta ccatgctgat gcggttttgg cagtacatca atgggcgtgg    13200
```

-continued

```
atagcggttt gactcacggg gatttccaag tctccacccc attgacgtca atgggagttt     13260
gttttggcac caaaatcaac gggactttcc aaaatgtcgt aacaactccg ccccattgac     13320
gcaaatgggc ggtaggcgtg tacggtggga ggtctatata agcagagctg gtttagtgaa     13380
ccgtcagatc agatctttgt cgatcctacc atccactcga cacacccgcc agcggccgc      13439
```

<210> SEQ ID NO 47
<211> LENGTH: 13436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
taatacgact cactataggg agaagtactg ccaccatggg caagaagcaa aatcgcaaga       60
cggggaattc caagacacaa tccgctagcc caccacctaa agagcgttct agctcccctg      120
ctactgagca gtcctggatg gaaaacgact tcgatgaact ccgggaagag ggatttaggc      180
gatccaacta ttcagaactc cgcgaagata tccagacaaa ggggaaggaa gtcgagaatt      240
tcgagaagaa cctcgaggag tgcatcaccc gtatcacaaa cactgagaaa tgtctcaaag      300
aactcatgga acttaagaca aaagccaggg agcttcgaga ggagtgtcgg agtctgagat      360
ccaggtgtga ccagctcgag gagcgcgtga gcgcgatgga agacgagatg aacgagatga      420
aaagagaggg caaattcagg gagaagcgca ttaagaggaa cgaacagagt ctgcaggaga      480
tttgggatta cgtcaagagg cctaacctgc ggttgatcgg cgtccccgag agcgacgtag      540
aaaacgggac taaactggag aatacacttc aagacatcat tcaagaaaat tttccaaacc      600
tggctcggca agctaatgtg caaatccaag agatccaacg cacacccagc ggtatagct      660 ctcggcgtgc caccccctagg catattatcg tgcgctttac taaggtggag atgaaagaga      720
agatgctgcg agccgctcgg gaaaagggaa gggtgacttt gaagggcaaa cctattcggc      780
tgacggttga ccttagcgcc gagacactcc aggcacgccg ggaatggggc cccatctta      840 atatcctgaa ggagaagaac ttccagccac gaatctctta ccctgcaaag ttgagttta      900 tctccgaggg tgagattaag tatttcatcg ataaacagat gctgcgagac ttcgtgacaa      960
ctcgcccagc tctcaaggaa ctgctcaaag aggctcttaa tatggagcgc aataatagat     1020 atcaacccttt gcagaaccac gcaaagatgg gaagcggagc tactaacttc agcctgctga     1080
agcaggctgg agacgtggag gagaaccctg gacctatgac cggctctaac tcacatatca     1140
ccatccttac acttaacatt aacggcctca actcagctat caagcgccat cggctggcca     1200
gctggatcaa atcacaggat ccaagcgttt gttgcatcca agagacccac ctgacctgta     1260
gagatactca ccgcctcaag atcaagggat ggcgaaagat ttatcaggcg aacggtaagc     1320
agaagaaagc cggagtcgca attctggtct cagacaagac ggatttcaag cccaccaaaa     1380
ttaagcgtga taaggaaggt cactatatta tggtgaaagg cagcatacag caggaagaac     1440
ttaccatatt gaacatctac gcgccaaaca ccggcgcacc tcgctttatc aaacaggtcc     1500
tgtccgatct gcagcgagat ctggattctc atacgttgat tatgggtgat ttcaatacac     1560
cattgagcac cctggatcgc agcaccaggc aaaaggtaaa taagacacg caagagctca     1620 atagcgcact gcatcaggca gatctcattg atatttatcg cactcttcat cctaagagta     1680
ccgagtacac attcttcagc gccccacatc atacatactc aaagatcgat catatcgtcg     1740
gctcaaaggc tctgctgtca aagtgcaagc gcacagagat aattacaaat tacctgtcag     1800
```

```
atcatagcgc gatcaagctc gagctgagaa tcaagaacct gacccagagc cggagtacca    1860
cttggaagct taataacctg ctgctcaacg attattgggt ccacaatgag atgaaggcag    1920
agattaaaat gttcttcgaa acaaatgaga ataaggatac tacctatcaa aacctttggg    1980
atgcctttaa ggccgtctgc agaggcaagt tcatcgccct caacgcctat aaagaaaaac    2040
aagagagatc taagatcgat actctcacct ctcagctgaa ggagttggag aaacaggaac    2100
agacccactc caaggcgtca agacggcagg agatcacaaa gattcgcgcc gagttgaaag    2160
agatcgaaac ccaaaagact cttcagaaaa ttaacgagtc tcgtagttgg ttcttcgagc    2220
ggattaataa gatagacaga cctctggcac gactgattaa gaagaagcgc gaaaagaacc    2280
agattgatac catcaagaac gacaagggcg acatcactac tgacccgacc gagatccaga    2340
ccactattcg ggagtattat aagcatttgt atgctaacaa gcttgagaac ctggaagaga    2400
tggacacttt tctggatacc tatactctgc cacggcttaa tcaagaggaa gtcgagtccc    2460
tcaaccgccc aattacagga agcgagattg tggccataat taactccctg ccgacaaaga    2520
aatctcctgg tccggacggg tttacagctg agttttatca acggtatatg aagagcttg    2580 taccgttttct gctcaagctc tttcagtcta tagaaaagga aggcatcttg cccaattcct    2640
tctacgaagc ttctataata cttattccca aaccaggacg cgataccaca aagaaggaaa    2700
acttccggcc cattagtctc atgaatatcg acgctaaaat attgaacaag attctcgcca    2760
acagaatcca acaacatatt aagaaattga tacatcacga ccaggtgggg tttatacctg    2820
gcatgcaggg ctggttaac atccggaaga gtattaacgt cattcaacac attaatagag    2880
ctaaggataa gaatcatatg atcatctcta tagacgcgga aaaggcattc gataagattc    2940
agcagccatt tatgctcaag actctgaaca aactcggcat cgacggaaca tattttaaga    3000
ttattcgcgc aatttacgat aagccgactg ctaacattat ccttaacggc caaaagctcg    3060
aggcctttcc gctcaagact ggaacccgcc aaggctgtcc cctctcccg cttttgttta    3120 atattgtact cgaggtgctg gctagggcta ttcgtcaaga gaaagagatt aaagggatac    3180
agctcgggaa ggaagaggtc aagctttcct tgttcgccga tgatatgatt gtgtacctgg    3240
agaatcctat tgtgtctgct cagaaccttc ttaaacttat ttctaacttt agcaaggtca    3300
gcggctataa gattaacgtc cagaaatctc aggcctttct gtacacaaat aatcgacaga    3360
ccgaatccca gataatgggt gagcttccgt ttgtcatagc cagcaaaagg ataaagtatc    3420
tcggaatcca gctgacacga gacgttaaag atttgtttaa ggaaaattac aagcctctcc    3480
tgaaagagat taaggaagat actaataagt ggaagaatat ccctgttca tgggttggca    3540 gaatcaacat agtgaagatg gcaatacttc ctaaagtgat atatcgcttt aacgccatcc    3600 caattaaaact gcctatgacc ttctttacgg agctcgagaa acaaccctt aaatttatat    3660 ggaatcaaaa gagagcaaga atagcgaagt ccatcttgag ccagaagaat aaggccggtg    3720
ggattacttt gcctgatttt aagttgtatt ataaagccac agtaactaag acagcctggt    3780
attggtatca gaatagagac atcgaccagt ggaatcggac cgaaccatca gagataatgc    3840
cccacatcta taattacctt atattcgata agccagaaaa gaataaacag tggggcaaag    3900
acagcctctt caacaagtgg tgttgggaga attggctggc catatgccgg aaactcaagc    3960
tcgacccctt tcttacaccc tacactaaaa tcaacagtag gtggatcaag gacttgaatg    4020
tcaagccaaa gactataaag acactggaag agaatcttgg gatcacaata caagatatag    4080
gcgtcggcaa agattttatg tcaaagacgc ccaaggccat ggccactaag gataagattg    4140
```

```
ataagtggga ccttattaag ctcaaaagct tctgtactgc caaggagacc acgatcagag    4200
ttaataggca gcccactaca tgggaaaaga ttttcgccac ttattcatca gataagggt     4260 tgataagcag aatatataac gagctgaagc agatctacaa gaagaaaacg aataatccca    4320
tcaagaagtg ggcaaaagat atgaacaggc atttttagcaa agaggatatc tacgccgcga   4380
agaagcatat gaagaagtgt agttcaagct tggccattcg tgagatgcag attaagacga    4440
ccatgcgata ccaccttacc ccagtgagga tggcaattat caagaaatct ggcaataata   4500
gatgttggcg gggctgtggc gagattggca ccctgctcca ttgctggtgg gattgcaagc    4560
tggtgcagcc gctttggaaa tcagtctggc gctttctgag ggacctcgag cttgagattc    4620
ccttcgatcc cgcaattccc ttgctcggaa tctatcctaa cgaatacaag agctgttgtt    4680
acaaggatac gtgtacccgg atgttcatcg cggccttgtt tacgatagct aagacgtgga    4740
atcagcctaa gtgccccaca atgatcgatt ggatcaagaa aatgtggcat atttatacca    4800
tggagtatta cgcagcaatt aagaatgacg aatttatttc cttcgttggg acctggatga    4860
agctggagac tattattctg agcaagctgt ctcaggagca aaagacaaag catagaatct    4920
tctctctcat tggtggtaac gactacaaag acgatgacga caagtaaagc gcttctagaa    4980
gttgtctcct cctgcactga ctgactgata caatcgattc ctggatccgc aggcctaatc    5040
aacctctgga ttacaaaatt tgtgaaagat tgactggtat tcttaactat gttgctcctt    5100
ttacgctatg tggatacgct gctttaatgc ctttgtatca tgctattgct tcccgtatgg    5160
ctttcatttt ctcctccttg tataaatcct ggttgctgtc tctttatgag gagttgtggc    5220
ccgttgtcag gcaacgtggc gtggtgtgca ctgtgtttgc tgacgcaacc cccactggtt    5280
ggggcattgc caccacctgt cagctccttt ccgggacttt cgctttcccc ctccctattg    5340
ccacggcgga actcatcgcc gcctgccttg cccgctgctg gacagggcct cggctgttgg    5400
gcactgacaa ttccgtggtg ttgtcgggga agctgacgtc cttccatgg ctgctcgcct     5460 gtgttgccac ctggattctg cgcgggacgt ccttctgcta cgtcccttcg gccctcaatc    5520
cagcggacct tccttcccgc gaacaaacga cccaacaccc gtgcgtttta ttctgtcttt    5580
ttattgccga tcccctcaga agaactcgtc aagaaggcga tagaaggcga tgcgctgcga    5640
atcgggagcg gcgataccgt aaagcacgag gaagcggtca gcccattcgc cgccaagctc    5700
ttcagcaata tcacgggtag ccaacgctat gtcctgatag cggtcggccg ctttacttgt    5760
acagctcgtc catgccgaga gtgatcccgg cggcggtcac gaactccagc aggaccatgt    5820
gatcgcgctt ctcgttgggg tctttgctca gggcggactg ggtgctcagg tagtggttgt    5880
cgggcagcag cacggggccg tcgccgatgg gggtgttctg ctggtagtgg tcggccaggt    5940
gagtccagga gatgtttcag cactgttgcc tttagtctcg aggcaactta gacaactgag    6000
tattgatctg agcacagcag ggtgtgagct gtttgaagat actggggttg ggggtgaaga    6060
aactgcagag gactaactgg gctgagaccc agtggcaatg ttttagggcc taaggaatgc    6120
ctctgaaaat ctagatggac aactttgact ttgagaaaag agaggtggaa atgaggaaaa    6180
tgactttcct ttattagatt tcggtagaaa gaactttcat cttttcccta tttttgttat    6240
tcgtttaaaa acatctatct ggaggcagga caagtatggt cattaaaaag atgcaggcag    6300
aaggcatata ttggctcagt caaagtgggg aactttggtg gccaaacata cattgctaag    6360
gctattccta tatcagctgg acacatataa aatgctgcta atgcttcatt acaaacttat    6420
atcctttaat tccagatggg ggcaaagtat gtccaggggt gaggaacaat tgaaacattt    6480
gggctggagt agattttgaa agtcagctct gtgtgtgtgt gtgtgtgtgt gtgtgtgaga    6540
```

-continued

```
gcgtgtgttt cttttaacgt tttcagccta cagcatacag ggttcatggt ggcaagaaga   6600
taacaagatt taaattatgg ccagtgacta gtgctgcaag aagaacaact acctgcattt   6660
aatgggaaag caaaatctca ggctttgagg gaagttaaca taggcttgat tctgggtgga   6720
agctgggtgt gtagttatct ggaggccagg ctggagctct cagctcacta tgggttcatc   6780
tttattgtct cctttcatct caacagctgc acgctgccgt cctcgatgtt gtggcggatc   6840
ttgaagttca ccttgatgcc gttcttctgc ttgtcggcca tgatatagac gttgtggctg   6900
ttgtagttgt actccagctt gtgcccagg atgttgccgt cctccttgaa gtcgatgccc     6960
ttcagctcga tgcggttcac cagggtgtcg ccctcgaact tcacctcggc gcgggtcttg   7020
tagttgccgt cgtccttgaa gaagatggtg cgctcctgga cgtagccttc gggcatggcg   7080
gacttgaaga agtcgtgctg cttcatgtgg tcgggtagc ggctgaagca ctgcacgccg    7140
taggtcaggg tggtcacgag ggtgggccag ggcacgggca gcttgccggt ggtgcagatg   7200
aacttcaggg tcagcttgcc gtaggtggca tcgccctcgc cctcgccgga cacgctgaac   7260
ttgtggccgt ttacgtcgcc gtccagctcg accaggatgg gcaccacccc ggtgaacagc   7320
tcctcgccct tgctcaccat ggtggcgaat tcgaagcttg agcacgagat ctgagtccgg   7380
taggcctagc ggatctgacg gttcactaaa ccagctctgc ttatatagac ctcccaccgt   7440
acacgcctac cgcccatttg cgtcaatggg gcggagttgt tacgacattt tggaaagtcc   7500
cgttgatttt ggtgccaaaa caaactccca ttgacgtcaa tggggtggag acttggaaat   7560
ccccgtgagt caaaccgcta tccacgccca ttgatgtact gccaaaaccg catcaccatg   7620
gtaatagcga tgactaatac gtagatgtac tgccaagtag gaaagtccca taaggtcatg   7680
tactgggcat aatgccaggc gggccattta ccgtcattga cgtcaatagg gggcgtactt   7740
ggcatatgat acacttgatg tactgccaag tgggcagttt accgtaaata ctccacccat   7800
tgacgtcaat ggaaagtccc tattggcgtt actatgggaa catacgtcat tattgacgtc   7860
aatgggcggg ggtcgttggg cggtcagcca ggcgggccat ttaccgtaag ttatgtaacg   7920
ggcctgctgc cggctctgcg gcctcttccg cgtcttcgcc ttcgccctca gacgagtcgg   7980
atctcccttt gggccgcctc cccgcctgtc tagcttgact gactgagata cagcgtacct   8040
tcagctcaca gacatgataa gatacattga tgagtttgga caaaccacaa ctagaatgca   8100
gtgaaaaaaa tgctttattt gtgaaatttg tgatgctatt gctttatttg taaccattat   8160
aagctgcaat aaacaagtta acaacaacaa ttgcattcat tttatgtttc aggttcaggg   8220
ggaggtgtgg gaggtttttt aaagcaagta aaacctctac aaatgtggta ttggcccatc   8280
tctatcggta tcgtagcata acccctttggg gcctctaaac gggtcttgag ggttttttg   8340
tgcccctcgg gccggattgc tatctaccgg cattggcgca gaaaaaaatg cctgatgcga   8400
cgctgcgcgt cttatactcc cacatatgcc agattcagca acggatacgg cttccccaac   8460
ttgcccactt ccatacgtgt cctccttacc agaaatttat ccttaaggtc gtcagctatc   8520
ctgcaggcga tctctcgatt tcgatcaaga cattccttta atggtctttt ctggacacca   8580
ctaggggtca gaagtagttc atcaaacttt cttccctccc taatctcatt ggttaccttg   8640
ggctatcgaa acttaattaa gcgatctgca tctcaattag tcagcaacca tagtcccgcc   8700
cctaactccg cccatcccgc ccctaactcc gcccagttcc gcccattctc cgccccatcg   8760
ctgactaatt ttttttattt atgcagaggc cgaggccgcc tcggcctctg agctattcca   8820
gaagtagtga ggaggctttt ttggaggcct aggcttttgc aaaggaggta gccaacatga   8880
```

```
ttgaacaaga tggattgcac gcaggttctc ccgccgcttg ggtggagagg ctattcggct    8940
atgactgggc acaacagaca atcggctgct ctgatgccgc cgtgttccgg ctgtcagcgc    9000
aggggcgccc ggttcttttt gtcaagaccg acctgtccgg tgccctgaat gaactccagg    9060
acgaggcagc gcggctatcg tggctggcca cgacgggcgt tccttgcgca gctgtgctcg    9120
acgttgtcac tgaagcggga agggactggc tgctattggg cgaagtgccg gggcaggatc    9180
tcctgtcatc tcaccttgct cctgccgaga agtatccat catggctgat gcaatgcggc     9240
ggctgcatac gcttgatccg gctacctgcc cattcgacca ccaagcgaaa catcgcatcg    9300
agcgagcacg tactcggatg gaagccggtc ttgtcgatca ggatgatctg gacgaagagc    9360
atcaggggct cgcgccagcc gaactgttcg ccaggctcaa ggcgcggatg cccgacggcg    9420
aggatctcgt cgtgacccac ggcgatgcct gcttgccgaa tatcatggtg aaaatggcc    9480 gcttttctgg attcatcgac tgtggccggc tgggtgtggc ggaccgctat caggacatag    9540
cgttggctac ccgtgatatt gctgaagagc ttggcggcga atgggctgac cgcttcctcg    9600
tgctttacgg tatcgccgct cccgattcgc agcgcatcgc cttctatcgc cttcttgacg    9660
agttcttcta gtatgtaagc cctgtgcctt ctagttgcca gccatctgtt gtttgcccct    9720
cccccgtgcc ttccttgacc ctggaagtg ccactcccac tgtcctttcc taataaaatg     9780
aggaaattgc atcgcattgt ctgagtaggt gtcattctat tctgggggt ggggtggggc     9840 aggacagcaa gggggaggat tgggaagaca atagcaggca tgctgggat gcggtgggct     9900 ctatggttaa ttaaccagtc aagtcagcta cttggcgaga tcgacttgtc tgggtttcga    9960
ctacgctcag aattgcgtca gtcaagttcg atctggtcct tgctattgca cccgttctcc    10020
gattacgagt ttcatttaaa tcatgtgagc aaaaggccag caaaaggcca ggaaccgtaa    10080
aaaggccgcg ttgctggcgt ttttccatag gctccgcccc cctgacgagc atcacaaaaa    10140
tcgacgctca agtcagaggt ggcgaaaccc gacaggacta taaagatacc aggcgtttcc    10200
ccctggaagc tccctcgtgc gctctcctgt tccgaccctg ccgcttaccg gatacctgtc    10260
cgcctttctc ccttcgggaa gcgtggcgct ttctcatagc tcacgctgta ggtatctcag    10320
ttcggtgtag tcgttcgct ccaagctggg ctgtgtgcac gaaccccccg ttcagcccga     10380
ccgctgcgcc ttatccggta actatcgtct tgagtccaac ccggtaagac acgacttatc    10440
gccactggca gcagccactg gtaacaggat tagcagagcg aggtatgtag gcggtgctac    10500
agagttcttg aagtggtggc ctaactacgg ctacactaga agaacagtat ttggtatctg    10560
cgctctgctg aagccagtta ccttcggaaa aagagttggt agctcttgat ccggcaaaca    10620
aaccaccgct ggtagcggtg gttttttttgt ttgcaagcag cagattacgc gcagaaaaaa    10680
aggatctcaa gaagatcctt tgatcttttc tacgggtct gacgctcagt ggaacgaaaa     10740
ctcacgttaa gggattttgg tcatgagatt atcaaaaagg atcttcacct agatcctttt    10800
aaattaaaaa tgaagtttta aatcaatcta agtatatat gagtaaactt ggtctgacag     10860
ttaccaatgc ttaatcagtg aggcacctat ctcagcgatc tgtctatttc gttcatccat    10920
agttgcattt aaatttccga actctccaag gccctcgtcg aaaatcttc aaacctttcg     10980 tccgatccat cttgcaggct acctctcgaa cgaactatcg caagtctctt ggccggcctt    11040
gcgccttggc tattgcttgg cagcgcctat cgccaggtat tactccaatc cgaatatcc    11100 gagatcggga tcacccgaga gaagttcaac ctacatcctc aatcccgatc tatccgagat    11160
ccgaggaata tcgaaatcgg ggcgcgcctg gtgtaccgag aacgatcctc tcagtgcgag    11220
tctcgacgat ccatatcgtt gcttggcagt cagccagtcg gaatccagct tgggacccag    11280
```

```
gaagtccaat cgtcagatat tgtactcaag cctggtcacg gcagcgtacc gatctgttta   11340
aacctagata ttgatagtct gatcggtcaa cgtataatcg agtcctagct tttgcaaaca   11400
tctatcaaga gacaggatca gcaggaggct ttcgcatgag tattcaacat ttccgtgtcg   11460
cccttattcc cttttttgcg gcattttgcc ttcctgtttt tgctcaccca gaaacgctgg   11520
tgaaagtaaa agatgctgaa gatcagttgg gtgcgcgagt gggttacatc gaactggatc   11580
tcaacagcgg taagatcctt gagagttttc gccccgaaga acgctttcca atgatgagca   11640
cttttaaagt tctgctatgt ggcgcggtat tatcccgtat tgacgccggg caagagcaac   11700
tcggtcgccg catacactat tctcagaatg acttggttga gtattcacca gtcacagaaa   11760
agcatcttac ggatggcatg acagtaagag aattatgcag tgctgccata accatgagtg   11820
ataacactgc ggccaactta cttctgacaa cgattggagg accgaaggag ctaaccgctt   11880
ttttgcacaa catgggggat catgtaactc gccttgatcg ttgggaaccg gagctgaatg   11940
aagccatacc aaacgacgag cgtgacacca cgatgcctgt agcaatggca acaaccttgc   12000
gtaaactatt aactggcgaa ctacttactc tagcttcccg gcaacagttg atagactgga   12060
tggaggcgga taaagttgca ggaccacttc tgcgctcggc ccttccggct ggctggttta   12120
ttgctgataa atctggagcc ggtgagcgtg ggtctcgcgg tatcattgca gcactggggc   12180
cagatggtaa gccctcccgt atcgtagtta tctacacgac ggggagtcag gcaactatgg   12240
atgaacgaaa tagacagatc gctgagatag gtgcctcact gattaagcat tggtaaccga   12300
ttctaggtgc attggcgcag aaaaaaatgc ctgatgcgac gctgcgcgtc ttatactccc   12360
acatatgcca gattcagcaa cggatacggc ttccccaact gcccacttc catacgtgtc    12420 ctccttacca gaaatttatc cttaagatcg tttaaactcg actctggctc tatcgaatct   12480
ccgtcgtttc gagcttacgc gaacagccgt ggcgctcatt tgctcgtcgg gcatcgaatc   12540
tcgtcagcta tcgtcagctt accttttgg cagcgatcgc ggctcccgac atcttggacc   12600
attagctcca caggtatctt cttccctcta gtggtcataa cagcagcttc agctacctct   12660
caattcaaaa accccctcaa gacccgttta gaggccccaa ggggttatgc tatcaatcgt   12720
tgcgttacac acacaaaaaa ccaacacaca tccatcttcg atggatagcg attttattat   12780
ctaactgctg atcgagtgta gccagatcta gtaatcaatt acggggtcat tagttcatag   12840
cccatatatg gagttccgcg ttacataact tacggtaaat ggcccgcctg gctgaccgcc   12900
caacgacccc cgcccattga cgtcaataat gacgtatgtt cccatagtaa cgccaatagg   12960
gactttccat tgacgtcaat gggtggagta tttacggtaa actgcccact tggcagtaca   13020
tcaagtgtat catatgccaa gtacgccccc tattgacgtc aatgacggta aatggcccgc   13080
ctggcattat gcccagtaca tgaccttatg gactttcct acttggcagt acatctacgt   13140
attagtcatc gctattacca tgctgatgcg gttttggcag tacatcaatg ggcgtggata   13200
gcggtttgac tcacggggat ttccaagtct ccacccatt gacgtcaatg ggagtttgtt   13260
ttggcaccaa aatcaacggg actttccaaa atgtcgtaac aactccgccc cattgacgca   13320
aatgggcggt aggcgtgtac ggtgggaggt ctatataagc agagctggtt tagtgaaccg   13380
tcagatcaga tctttgtcga tcctaccatc cactcgacac acccgccagc ggccgc       13436
```

<210> SEQ ID NO 48
<211> LENGTH: 13433
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 48

```
taatacgact cactataggg agaagtactg ccaccatggg caagaagcaa aatcgcaaga      60
cggggaattc caagacacaa tccgctagcc caccacctaa agagcgttct agctcccctg     120
ctactgagca gtcctggatg gaaaacgact tcgatgaact ccgggaagag ggatttaggc     180
gatccaacta ttcagaactc cgcgaagata tccagacaaa ggggaaggaa gtcgagaatt     240
tcgagaagaa cctcgaggag tgcatcaccc gtatcacaaa cactgagaaa tgtctcaaag     300
aactcatgga acttaagaca aaagccaggg agcttcgaga ggagtgtcgg agtctgagat     360
ccaggtgtga ccagctcgag gagcgcgtga gcgcgatgga agacgagatg aacgagatga     420
aaagagaggg caaattcagg gagaagcgca ttaagaggaa cgaacagagt ctgcaggaga     480
tttgggatta cgtcaagagg cctaacctgc ggttgatcgg cgtccccgag agcgacgtag     540
aaaacgggac taaactggag aatacacttc aagacatcat tcaagaaaat tttccaaacc     600
tggctcggca agctaatgtg caaatccaag agatccaacg cacaccccag cggtatagct     660
ctcggcgtgc caccccctagg catattatcg tgcgctttac taaggtggag atgaaagaga     720
agatgctgcg agccgctcgg gaaaagggaa gggtgacttt gaagggcaaa cctattcggc     780
tgacggttga ccttagcgcc gagacactcc aggcacgccg ggaatggggc ccatctttta     840
atatcctgaa ggagaagaac ttccagccac gaatctctta ccctgcaaag ttgagtttta     900
tctccgaggg tgagattaag tatttcatcg ataaacagat gctgcgagac ttcgtgacaa     960
ctcgcccagc tctcaaggaa ctgctcaaag aggctcttaa tatggagcgc aataatagat    1020
atcaaccctt gcagaaccac gcaaagatgg gaagcggaga gggcagagga agtctgctaa    1080
catgcggtga cgtcgaggag aatcctggac ctatgaccgg ctctaactca catatcacca    1140
tccttacact taacattaac ggcctcaact cagctatcaa gcgccatcgg ctggccagct    1200
ggatcaaatc acaggatcca agcgtttgtt gcatccaaga gacccacctg acctgtagag    1260
atactcaccg cctcaagatc aagggatggc gaaagattta tcaggcgaac ggtaagcaga    1320
agaaagccgg agtcgcaatt ctggtctcag acaagacgga tttcaagccc accaaaatta    1380
agcgtgataa ggaaggtcac tatattatgg tgaaaggcag catacagcag gaagaactta    1440
ccatattgaa catctacgcg ccaaacaccg gcgcacctcg ctttatcaaa caggtcctgt    1500
ccgatctgca gcgagatctg gattctcata cgttgattat gggtgatttc aatacaccat    1560
tgagcaccct ggatcgcagc accaggcaaa aggtaaataa agacacgcaa gagctcaata    1620
gcgcactgca tcaggcagat ctcattgata tttatcgcac tcttcatcct aagagtaccg    1680
agtacacatt cttcagcgcc ccacatcata catactcaaa gatcgatcat atcgtcggct    1740
caaaggctct gctgtcaaag tgcaagcgca cagagataat tacaaattac ctgtcagatc    1800
atagcgcgat caagctcgag ctgagaatca agaacctgac ccagagccgg agtaccactt    1860
ggaagcttaa taacctgctg ctcaacgatt attgggtcca caatgagatg aaggcagaga    1920
ttaaaatgtt cttcgaaaca aatgagaata aggatactac ctatcaaaac ctttgggatg    1980
cctttaaggc cgtctgcaga ggcaagttca tcgccctcaa cgcctataaa agaaaacaag    2040
agagatctaa gatcgatact ctcacctctc agctgaagga gttggagaaa caggaacaga    2100
cccactccaa ggcgtcaaga cggcaggaga tcacaaagat tcgcgccgag ttgaagagaa    2160
tcgaaaccca aaagactctt cagaaaatta acgagtctcg tagttggttc ttcgagcgga    2220
```

| | |
|---|---|
| ttaataagat agacagacct ctggcacgac tgattaagaa gaagcgcgaa aagaaccaga | 2280 |
| ttgataccat caagaacgac aagggcgaca tcactactga cccgaccgag atccagacca | 2340 |
| ctattcggga gtattataag catttgtatg ctaacaagct tgagaacctg aagagatgg | 2400 |
| acactttct ggatacctat actctgccac ggcttaatca agaggaagtc gagtccctca | 2460 |
| accgcccaat tacaggaagc gagattgtgg ccataattaa ctccctgccg acaaagaaat | 2520 |
| ctcctggtcc ggacgggttt acagctgagt tttatcaacg gtatatggaa gagcttgtac | 2580 |
| cgtttctgct caagctcttt cagtctatag aaaaggaagg catcttgccc aattccttct | 2640 |
| acgaagcttc tataatactt attcccaaac caggacgcga taccacaaag aaggaaaact | 2700 |
| tccggcccat tagtctcatg aatatcgacg ctaaaatatt gaacaagatt ctcgccaaca | 2760 |
| gaatccaaca acatattaag aaattgatac atcacgacca ggtggggttt atacctggca | 2820 |
| tgcagggctg gtttaacatc cggaagagta ttaacgtcat tcaacacatt aatagagcta | 2880 |
| aggataagaa tcatatgatc atctctatag acgcggaaaa ggcattcgat aagattcagc | 2940 |
| agccatttat gctcaagact ctgaacaaac tcggcatcga cggaacatat tttaagatta | 3000 |
| ttcgcgcaat ttacgataag ccgactgcta acattatcct taacggccaa aagctcgagg | 3060 |
| cctttccgct caagactgga acccgccaag gctgtcccct ctccccgctt ttgtttaata | 3120 |
| ttgtactcga ggtgctggct agggctattc gtcaagagaa agagattaaa gggatacagc | 3180 |
| tcgggaagga agaggtcaag cttccttgt tcgccgatga tatgattgtg tacctggaga | 3240 |
| atcctattgt gtctgctcag aaccttctta aacttatttc taactttagc aaggtcagcg | 3300 |
| gctataagat taacgtccag aaatctcagg cctttctgta cacaaataat cgacagaccg | 3360 |
| aatcccagat aatgggtgag cttccgtttg tcatagccag caaaaggata aagtatctcg | 3420 |
| gaatccagct gacacgagac gttaaagatt tgtttaagga aaattacaag cctctcctga | 3480 |
| aagagattaa ggaagatact aataagtgga agaatatccc ctgttcatgg gttggcagaa | 3540 |
| tcaacatagt gaagatggca atacttccta aagtgatata tcgctttaac gccatcccaa | 3600 |
| ttaaactgcc tatgaccttc tttacggagc tcgagaaaac aacccttaaa tttatatgga | 3660 |
| atcaaaagag agcaagaata gcgaagtcca tcttgagcca gaagaataag gccggtggga | 3720 |
| ttactttgcc tgatttttaag ttgtattata agccacagt aactaagaca gcctggtatt | 3780 |
| ggtatcagaa tagagacatc gaccagtgga atcggaccga accatcagag ataatgcccc | 3840 |
| acatctataa ttaccttata ttcgataagc cagaaaagaa taaacagtgg ggcaaagaca | 3900 |
| gcctcttcaa caagtggtgt tgggagaatt ggctggccat atgccggaaa ctcaagctcg | 3960 |
| accccttct tacaccctac actaaaatca acagtaggtg gatcaaggac ttgaatgtca | 4020 |
| agccaaagac tataaagaca ctggaagaga atcttgggat cacaatacaa gatataggcg | 4080 |
| tcggcaaaga ttttatgtca aagacgccca aggccatggc cactaaggat aagattgata | 4140 |
| agtgggacct tattaagctc aaaagcttct gtactgccaa ggagaccacg atcagagtta | 4200 |
| ataggcagcc cactacatgg gaaaagattt tcgccactta ttcatcagat aagggggttga | 4260 |
| taagcagaat atataacgag ctgaagcaga tctacaagaa gaaaacgaat aatcccatca | 4320 |
| agaagtgggc aaaagatatg aacaggcatt ttagcaaaga ggatatctac gccgcgaaga | 4380 |
| agcatatgaa gaagtgtagt tcaagcttgg ccattcgtga gatgcagatt aagacgacca | 4440 |
| tgcgatacca ccttacccca gtgaggatgg caattatcaa gaaatctggc aataatagat | 4500 |
| gttggcgggg ctgtggcgag attggcaccc tgctccattg ctggtgggat tgcaagctgg | 4560 |
| tgcagccgct ttggaaatca gtctggcgct ttctgaggga cctcgagctt gagattccct | 4620 |

```
tcgatcccgc aattcccttg ctcggaatct atcctaacga atacaagagc tgttgttaca    4680
aggatacgtg tacccggatg ttcatcgcgg ccttgtttac gatagctaag acgtggaatc    4740
agcctaagtg ccccacaatg atcgattgga tcaagaaaat gtggcatatt tataccatgg    4800
agtattacgc agcaattaag aatgacgaat ttatttcctt cgttgggacc tggatgaagc    4860
tggagactat tattctgagc aagctgtctc aggagcaaaa gacaaagcat agaatcttct    4920
ctctcattgg tggtaacgac tacaaagacg atgacgacaa gtaaagcgct tctagaagtt    4980
gtctcctcct gcactgactg actgatacaa tcgatttctg gatccgcagg cctaatcaac    5040
ctctggatta caaatttgt gaaagattga ctggtattct taactatgtt gctccttta     5100 cgctatgtgg atacgctgct ttaatgcctt tgtatcatgc tattgcttcc cgtatggctt    5160
tcattttctc ctccttgtat aaatcctggt tgctgtctct ttatgaggag ttgtggcccg    5220
ttgtcaggca acgtggcgtg gtgtgcactg tgtttgctga cgcaaccccc actggttggg    5280
gcattgccac cacctgtcag ctcctttccg ggactttcgc tttcccctc cctattgcca    5340 cggcggaact catcgccgcc tgccttgccc gctgctggac aggggctcgg ctgttgggca    5400
ctgacaattc cgtggtgttg tcggggaagc tgacgtcctt tccatggctg ctcgcctgtg    5460
ttgccacctg gattctgcgc gggacgtcct tctgctacgt cccttcggcc ctcaatccag    5520
cggaccttcc ttcccgcgaa caaacgaccc aacacccgtg cgtttattc tgtcttttta     5580 ttgccgatcc cctcagaaga actcgtcaag aaggcgatag aaggcgatgc gctgcgaatc    5640
gggagcggcg ataccgtaaa gcacgaggaa gcggtcagcc cattcgccgc caagctcttc    5700
agcaatatca cgggtagcca acgctatgtc ctgatagcgg tcggccgctt tacttgtaca    5760
gctcgtccat gccgagagtg atcccggcgg cggtcacgaa ctccagcagg accatgtgat    5820
cgcgcttctc gttgggtct ttgctcaggg cggactgggt gctcaggtag tggttgtcgg    5880
gcagcagcac ggggccgtcg ccgatggggg tgttctgctg gtagtggtcg gccaggtgag    5940
tccaggagat gtttcagcac tgttgccttt agtctcgagg caacttagac aactgagtat    6000
tgatctgagc acagcagggt gtgagctgtt tgaagatact ggggttgggg gtgaagaaac    6060
tgcagaggac taactgggct gagacccagt ggcaatgttt tagggcctaa ggaatgcctc    6120
tgaaaatcta gatggacaac tttgactttg agaaaagaga ggtggaaatg aggaaaatga    6180
cttttcttta ttagatttcg gtagaaagaa ctttcatctt tcccctattt ttgttattcg    6240
ttttaaaaca tctatctgga ggcaggacaa gtatggtcat taaaaagatg caggcagaag    6300
gcatatattg gctcagtcaa agtggggaac tttggtggcc aaacatacat tgctaaggct    6360
attcctatat cagctggaca catataaaat gctgctaatg cttcattaca aacttatatc    6420
ctttaattcc agatggggc aaagtatgtc caggggtgag gaacaattga acatttggg     6480 ctggagtaga ttttgaaagt cagctctgtg tgtgtgtgtg tgtgtgtgtg tgtgagagcg    6540
tgtgtttctt ttaacgtttt cagcctacag catacagggt tcatggtggc aagaagataa    6600
caagatttaa attatggcca gtgactagtg ctgcaagaag aacaactacc tgcatttaat    6660
gggaaagcaa atctcaggc tttgagggaa gttaacatag gcttgattct gggtggaagc    6720
tgggtgtgta gttatctgga ggccaggctg gagctctcag ctcactatgg gttcatcttc    6780
attgtctcct ttcatctcaa cagctgcacg ctgccgtcct cgatgttgtg gcggatcttg    6840
aagttcacct tgatgccgtt cttctgcttg tcggccatga tatagacgtt gtggctgttg    6900
tagttgtact ccagcttgtg ccccaggatg ttgccgtcct ccttgaagtc gatgcccttc    6960
```

```
agctcgatgc ggttcaccag ggtgtcgccc tcgaacttca cctcggcgcg ggtcttgtag      7020
ttgccgtcgt ccttgaagaa gatggtgcgc tcctggacgt agccttcggg catggcggac      7080
ttgaagaagt cgtgctgctt catgtggtcg gggtagcggc tgaagcactg cacgccgtag      7140
gtcagggtgg tcacgagggt gggccagggc acgggcagct tgccggtggt gcagatgaac      7200
ttcagggtca gcttgccgta ggtggcatcg ccctcgccct cgccggacac gctgaacttg      7260
tggccgttta cgtcgccgtc cagctcgacc aggatgggca ccaccccggt gaacagctcc      7320
tcgcccttgc tcaccatggt ggcgaattcg aagcttgagc acgagatctg agtccggtag      7380
gcctagcgga tctgacggtt cactaaacca gctctgctta tatagacctc ccaccgtaca      7440
cgcctaccgc ccatttgcgt caatggggcg gagttgttac gacattttgg aaagtcccgt      7500
tgattttggt gccaaaacaa actcccattg acgtcaatgg ggtggagact tggaaatccc      7560
cgtgagtcaa accgctatcc acgccattg atgtactgcc aaaaccgcat caccatggta      7620
atagcgatga ctaatacgta gatgtactgc caagtaggaa agtcccataa ggtcatgtac      7680
tgggcataat gccaggcggg ccatttaccg tcattgacgt caatagggg cgtacttggc      7740 atatgataca cttgatgtac tgccaagtgg gcagtttacc gtaaatactc cacccattga      7800
cgtcaatgga aagtccctat tggcgttact atgggaacat acgtcattat tgacgtcaat      7860
gggcgggggt cgttgggcgg tcagccaggc gggccattta ccgtaagtta tgtaacgggc      7920
ctgctgccgg ctctgcggcc tcttccgcgt cttcgccttc gccctcagac gagtcggatc      7980
tccctttggg ccgcctcccc gcctgtctag cttgactgac tgagatacag cgtaccttca      8040
gctcacagac atgataagat acattgatga gtttggacaa accacaacta gaatgcagtg      8100
aaaaaaatgc tttatttgtg aaatttgtga tgctattgct ttatttgtaa ccattataag      8160
ctgcaataaa caagttaaca acaacaattg cattcatttt atgtttcagg ttcaggggga      8220
ggtgtgggag gttttttaaa gcaagtaaaa cctctacaaa tgtggtattg gcccatctct      8280
atcggtatcg tagcataacc ccttggggcc tctaaacggg tcttgagggg ttttttgtgc      8340
ccctcgggcc ggattgctat ctaccggcat ggcgcagaa aaaaatgcct gatgcgacgc      8400
tgcgcgtctt atactcccac atatgccaga ttcagcaacg gatacggctt ccccaacttg      8460
cccacttcca tacgtgtcct ccttaccaga aatttatcct taaggtcgtc agctatcctg      8520
caggcgatct ctcgatttcg atcaagacat tcctttaatg gtcttttctg gacaccacta      8580
ggggtcagaa gtagttcatc aaactttctt ccctccctaa tctcattggt taccttgggc      8640
tatcgaaact taattaagcg atctgcatct caattagtca gcaaccatag tcccgccct      8700 aactccgccc atcccgcccc taactccgcc cagttccgcc cattctccgc ccatcgctg      8760 actaattttt tttatttatg cagaggccga ggccgcctcg gcctctgagc tattccagaa      8820
gtagtgagga ggcttttttg gaggcctagg cttttgcaaa ggaggtagcc aacatgattg      8880
aacaagatgg attgcacgca ggttctcccg ccgcttgggt ggagaggcta ttcggctatg      8940
actgggcaca acagacaatc ggctgctctg atgccgccgt gttccggctg tcagcgcagg      9000
ggcgcccggt tctttttgtc aagaccgacc tgtccggtgc cctgaatgaa ctccaggacg      9060
aggcagcgcg gctatcgtgg ctggccacga cgggcgttcc ttgcgcagct gtgctcgacg      9120
ttgtcactga agcgggaagg gactggctgc tattgggcga agtgccgggg caggatctcc      9180
tgtcatctca ccttgctcct gccgagaaag tatccatcat ggctgatgca atgcggcggc      9240
tgcatacgct tgatccggct acctgcccat tcgaccacca agcgaaacat cgcatcgagc      9300
gagcacgtac tcggatggaa gccggtcttg tcgatcagga tgatctggac gaagagcatc      9360
```

```
aggggctcgc gccagccgaa ctgttcgcca ggctcaaggc gcggatgccc gacggcgagg    9420
atctcgtcgt gacccacggc gatgcctgct tgccgaatat catggtggaa aatggccgct    9480
tttctggatt catcgactgt ggccggctgg gtgtggcgga ccgctatcag gacatagcgt    9540
tggctacccg tgatattgct gaagagcttg gcggcgaatg ggctgaccgc ttcctcgtgc    9600
tttacggtat cgccgctccc gattcgcagc gcatcgcctt ctatcgcctt cttgacgagt    9660
tcttctagta tgtaagccct gtgccttcta gttgccagcc atctgttgtt tgcccctccc    9720
ccgtgccttc cttgaccctg gaaggtgcca ctcccactgt cctttcctaa taaaatgagg    9780
aaattgcatc gcattgtctg agtaggtgtc attctattct ggggggtggg gtggggcagg    9840
acagcaaggg ggaggattgg gaagacaata gcaggcatgc tggggatgcg gtgggctcta    9900
tggttaatta accagtcaag tcagctactt ggcgagatcg acttgtctgg gtttcgacta    9960
cgctcagaat tgcgtcagtc aagttcgatc tggtccttgc tattgcaccc gttctccgat   10020
tacgagtttc atttaaatca tgtgagcaaa aggccagcaa aaggccagga accgtaaaaa   10080
ggccgcgttg ctggcgtttt tccataggct ccgcccccct gacgagcatc acaaaaatcg   10140
acgctcaagt cagaggtggc gaaacccgac aggactataa agataccagg cgtttccccc   10200
tggaagctcc ctcgtgcgct ctcctgttcc gaccctgccg cttaccggat acctgtccgc   10260
ctttctccct tcgggaagcg tggcgctttc tcatagctca cgctgtaggt atctcagttc   10320
ggtgtaggtc gttcgctcca agctgggctg tgtgcacgaa ccccccgttc agcccgaccg   10380
ctgcgcctta tccggtaact atcgtcttga gtccaacccg gtaagacacg acttatcgcc   10440
actggcagca gccactggta acaggattag cagagcgagg tatgtaggcg gtgctacaga   10500
gttcttgaag tggtggccta actacggcta cactagaaga acagtatttg gtatctgcgc   10560
tctgctgaag ccagttacct tcggaaaaag agttggtagc tcttgatccg gcaaacaaac   10620
caccgctggt agcggtggtt tttttgtttg caagcagcag attacgcgca gaaaaaaagg   10680
atctcaagaa gatcctttga tcttttctac ggggtctgac gctcagtgga acgaaaactc   10740
acgttaaggg attttggtca tgagattatc aaaaaggatc ttcacctaga tccttttaaa   10800
ttaaaaatga agttttaaat caatctaaag tatatatgag taaacttggt ctgacagtta   10860
ccaatgctta atcagtgagg cacctatctc agcgatctgt ctatttcgtt catccatagt   10920
tgcatttaaa tttccgaact ctccaaggcc ctcgtcggaa atcttcaaa cctttcgtcc    10980 gatccatctt gcaggctacc tctcgaacga actatcgcaa gtctcttggc cggccttgcg   11040
ccttggctat tgcttggcag cgcctatcgc caggtattac tccaatcccg aatatccgag   11100
atcgggatca cccgagagaa gttcaaccta catcctcaat cccgatctat ccgagatccg   11160
aggaatatcg aaatcgggc gcgcctggtg taccgagaac gatcctctca gtgcgagtct   11220
cgacgatcca tatcgttgct tggcagtcag ccagtcggaa tccagcttgg gacccaggaa   11280
gtccaatcgt cagatattgt actcaagcct ggtcacggca gcgtaccgat ctgtttaaac   11340
ctagatattg atagtctgat cggtcaacgt ataatcgagt cctagctttt gcaaacatct   11400
atcaagagac aggatcagca ggaggctttc gcatgagtat tcaacatttc cgtgtcgccc   11460
ttattccctt ttttgcggca ttttgccttc ctgttttgtc tcacccagaa acgctggtga   11520
aagtaaaaga tgctgaagat cagttgggtg cgcgagtggg ttacatcgaa ctggatctca   11580
acagcggtaa gatccttgag agttttcgcc ccgaagaacg ctttccaatg atgagcactt   11640
ttaaagttct gctatgtggc gcggtattat cccgtattga cgccgggcaa gagcaactcg   11700
```

```
gtcgccgcat acactattct cagaatgact tggttgagta ttcaccagtc acagaaaagc    11760
atcttacgga tggcatgaca gtaagagaat tatgcagtgc tgccataacc atgagtgata    11820
acactgcggc caacttactt ctgacaacga ttggaggacc gaaggagcta accgcttttt    11880
tgcacaacat gggggatcat gtaactcgcc ttgatcgttg ggaaccggag ctgaatgaag    11940
ccataccaaa cgacgagcgt gacaccacga tgcctgtagc aatggcaaca accttgcgta    12000
aactattaac tggcgaacta cttactctag cttcccggca acagttgata gactggatgg    12060
aggcggataa agttgcagga ccacttctgc gctcggccct tccggctggc tggtttattg    12120
ctgataaatc tggagccggt gagcgtgggt ctcgcggtat cattgcagca ctggggccag    12180
atggtaagcc ctcccgtatc gtagttatct acacgacggg gagtcaggca actatggatg    12240
aacgaaatag acagatcgct gagataggtg cctcactgat taagcattgg taaccgattc    12300
taggtgcatt ggcgcagaaa aaaatgcctg atgcgacgct gcgcgtctta tactcccaca    12360
tatgccagat tcagcaacgg atacggcttc cccaacttgc ccacttccat acgtgtcctc    12420
cttaccagaa atttatcctt aagatcgttt aaactcgact ctggctctat cgaatctccg    12480
tcgtttcgag cttacgcgaa cagccgtggc gctcatttgc tcgtcgggca tcgaatctcg    12540
tcagctatcg tcagcttacc tttttggcag cgatcgcggc tcccgacatc ttggaccatt    12600
agctccacag gtatcttctt ccctctagtg gtcataacag cagcttcagc tacctctcaa    12660
ttcaaaaaac ccctcaagac ccgtttagag ccccaaggg gttatgctat caatcgttgc    12720
gttacacaca caaaaaacca acacacatcc atcttcgatg gatagcgatt ttattatcta    12780
actgctgatc gagtgtagcc agatctagta atcaattacg gggtcattag ttcatagccc    12840
atatatggag ttccgcgtta cataacttac ggtaaatggc ccgcctggct gaccgcccaa    12900
cgacccccgc ccattgacgt caataatgac gtatgttccc atagtaacgc caatagggac    12960
tttccattga cgtcaatggg tggagtattt acggtaaact gcccacttgg cagtacatca    13020
agtgtatcat atgccaagta cgccccctat tgacgtcaat gacggtaaat ggcccgcctg    13080
gcattatgcc cagtacatga ccttatggga ctttcctact tggcagtaca tctacgtatt    13140
agtcatcgct attaccatgc tgatgcggtt ttggcagtac atcaatgggc gtggatagcg    13200
gtttgactca cggggatttc caagtctcca ccccattgac gtcaatggga gtttgttttg    13260
gcaccaaaat caacgggact ttccaaaatg tcgtaacaac tccgccccat tgacgcaaat    13320
gggcggtagg cgtgtacggt gggaggtcta tataagcaga gctggtttag tgaaccgtca    13380
gatcagatct tgtcgatcc taccatccac tcgacacacc cgccagcggc cgc             13433
```

<210> SEQ ID NO 49
<211> LENGTH: 9241
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
taatacgact cactataggg agaagtactg ccaccatggg caagaagcaa aatcgcaaga      60
cggggaattc caagacacaa tccgctagcc accaccctaa agagcgttct agctcccctg     120
ctactgagca gtcctggatg gaaaacgact tcgatgaact ccgggaagag ggatttaggc     180
gatccaacta ttcagaactc cgcgaagata tccagacaaa ggggaaggaa gtcgagaatt     240
tcgagaagaa cctcgaggag tgcatcaccc gtatcacaaa cactgagaaa tgtctcaaag     300
```

```
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
tggctcggca agctaatgtg caaatccaag agatccaacg cacacccag cggtatagct      660
ctcggcgtgc cacccctagg catattatcg tgcgctttac taaggtggag atgaaagaga    720
agatgctgcg agccgctcgg gaaaagggaa gggtgacttt gaagggcaaa cctattcggc    780
tgacggttga ccttagcgcc gagacactcc aggcacgccg ggaatggggc cccatcttta    840
atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaacccett gcagaaccac gcaaagatgt gagacagccg tcagaccatc aagactagga    1080
agaaactgca tcaactaatg agcaaaatca ccagctaaca tcatagtata catgaccggc    1140
tctaactcac atatccaccat ccttacactt aacattaacg gcctcaactc agctatcaag   1200
cgccatcggc tggccagctg gatcaaatca caggatccaa gcgtttgttg catccaagag    1260
acccacctga cctgtagaga tactcaccgc ctcaagatca agggatggcg aaagattat     1320
caggcgaacg gtaagcagaa gaaagccgga gtcgcaattc tggtctcaga caagacggat   1380
ttcaagccca ccaaaattaa gcgtgataag gaaggtcact atattatggt gaaaggcagc   1440
atacagcagg aagaacttac catattgaac atctacgcgc caaacaccgg cgcacctcgc    1500
tttatcaaac aggtcctgtc cgatctgcag cgagatctgg attctcatac gttgattatg    1560
ggtgatttca ataccaccatt gagcaccctg gatcgcagca ccaggcaaaa ggtaaataaa    1620
gacacgcaag agctcaatag cgcactgcat caggcagatc tcattgatat ttatcgcact   1680
cttcatccta agagtaccga gtacacattc ttcagcgccc cacatcatac atactcaaag   1740
atcgatcata tcgtcggctc aaaggctctg ctgtcaaagt gcaagcgcac agagataatt   1800
acaaattacc tgtcagatca tagcgcgatc aagctcgagc tgagaatcaa gaacctgacc   1860
cagagccgga gtaccacttg gaagcttaat aacctgctgc tcaacgatta ttgggtccac    1920
aatgagatga aggcagagat taaaatgttc ttcgaaacaa atgagaataa ggatactacc   1980
tatcaaaacc tttgggatgc ctttaaggcc gtctgcagag gcaagttcat cgccctcaac   2040
gcctataaaa gaaaacaaga gagatctaag atcgatactc tcacctctca gctgaaggag   2100
ttggagaaac aggaacagac ccactccaag gcgtcaagac ggcaggagat cacaaagatt   2160
cgcgccgagt tgaaagagat cgaaacccaa aagactcttc agaaaattaa cgagtctcgt   2220
agttggttct tcgagcggat taataagata gacagacctc tggcacgact gattaagaag   2280
aagcgcgaaa agaaccagat tgataccatc aagaacgaca agggcgacat cactactgac   2340
ccgaccgaga tccagaccac tattcgggag tattataagc atttgtatgc taacaagctt   2400
gagaacctgg aagagatgga cactttctg gatacctata ctctgccacg gcttaatcaa    2460
gaggaagtcg agtccctcaa ccgcccaatt acaggaagcg agattgtggc cataattaac   2520
tccctgccga caaagaaatc tcctggtccg gacgggttta cagctgagtt ttatcaacgg   2580
tatatgaag agcttgtacc gtttctgctc aagctctttc agtctataga aaggaaggc    2640
atcttgccca attccttcta cgaagcttct ataatactta ttccaaaacc aggacgcgat   2700
```

```
accacaaaga aggaaaactt ccggcccatt agtctcatga atatcgacgc taaaatattg   2760
aacaagattc tcgccaacag aatccaacaa catattaaga aattgataca tcacgaccag   2820
gtggggttta tacctggcat gcagggctgg tttaacatcc ggaagagtat taacgtcatt   2880
caacacatta atagagctaa ggataagaat catatgatca tctctataga cgcggaaaag   2940
gcattcgata agattcagca gccatttatg ctcaagactc tgaacaaact cggcatcgac   3000
ggaacatatt ttaagattat tcgcgcaatt tacgataagc cgactgctaa cattatcctt   3060
aacggccaaa agctcgaggc ctttccgctc aagactggaa cccgccaagg ctgtcccctc   3120
tccccgcttt tgtttaatat tgtactcgag gtgctggcta gggctattcg tcaagagaaa   3180
gagattaaag ggatacagct cgggaaggaa gaggtcaagc tttccttgtt cgccgatgat   3240
atgattgtgt acctggagaa tcctattgtg tctgctcaga accttcttaa acttatttct   3300
aactttagca aggtcagcgg ctataagatt aacgtccaga aatctcaggc ctttctgtac   3360
acaaataatc gacagaccga atcccagata atgggtgagc ttccgtttgt catagccagc   3420
aaaaggataa agtatctcgg aatccagctg acacgagacg ttaaagattt gtttaaggaa   3480
aattacaagc ctctcctgaa agagattaag gaagatacta ataagtggaa gaatatcccc   3540
tgttcatggg ttggcagaat caacatagtg aagatggcaa tacttcctaa agtgatatat   3600
cgctttaacg ccatcccaat taaactgcct atgaccttct ttacggagct cgagaaaaca   3660
acccttaaat ttatatggaa tcaaaagaga gcaagaatag cgaagtccat cttgagccag   3720
aagaataagg ccggtgggat tactttgcct gattttaagt tgtattataa agccacagta   3780
actaagacag cctggtattg gtatcagaat agagacatcg accagtggaa tcggaccgaa   3840
ccatcagaga taatgcccca catctataat taccttatat tcgataagcc agaaaagaat   3900
aaacagtggg gcaaagacag cctcttcaac aagtggtgtt gggagaattg gctggccata   3960
tgccggaaac tcaagctcga ccccttttctt acaccctaca ctaaaatcaa cagtaggtgg   4020
atcaaggact tgaatgtcaa gccaaagact ataaagacac tggaagagaa tcttgggatc   4080
acaatacaag atataggcgt cggcaaagat tttatgtcaa agacgcccaa ggccatggcc   4140
actaaggata agattgataa gtgggacctt attaagctca aaagcttctg tactgccaag   4200
gagaccacga tcagagttaa taggcagccc actacatggg aaaagatttt cgccacttat   4260
tcatcagata aggggttgat aagcagaata tataacgagc tgaagcagat ctacaagaag   4320
aaaacgaata atcccatcaa gaagtgggca aaagatatga acaggcattt tagcaaagag   4380
gatatctacg ccgcgaagaa gcatatgaag aagtgtagtt caagcttggc cattcgtgag   4440
atgcagatta agacgaccat gcgataccac cttaccccag tgaggatggc aattatcaag   4500
aaatctggca ataatagatg ttggcggggc tgtggcgaga ttggcaccct gctccattgc   4560
tggtgggatt gcaagctggt gcagccgctt tggaaatcag tctggcgctt tctgagggac   4620
ctcgagcttg agattccctt cgatcccgca attcccttgc tcggaatcta tcctaacgaa   4680
tacaagagct gttgttacaa ggatacgtgt acccggatgt tcatcgcggc cttgtttacg   4740
atagctaaga cgtggaatca gcctaagtgc cccacaatga tcgattggat caagaaaatg   4800
tggcatattt ataccatgga gtattacgca gcaattaaga atgacgaatt tatttccttc   4860
gttgggaccct ggatgaagct ggagactatt attctgagca agctgtctca ggagcaaaag   4920
acaaagcata gaatcttctc tctcattggt ggtaacgctt ctaactttac tcagttcgtt   4980
ctcgtcgaca atggcggaac tggcgacgtg actgtcgccc aagcaacttt cgctaacggg   5040
```

```
atcgctgaat ggatcagctc taactcgcgt tcacaggctt acaaagtaac ctgtagcgtt    5100
cgtcagagct ctgcgcagaa tcgcaaatac accatcaaag tcgaggtgcc taaaggcgcc    5160
tggcgttcgt acttaaatat ggaactaacc attccaattt tcgccacgaa ttccgactgc    5220
gagcttattg ttaaggcaat gcaaggtctc ctaaaagatg gaaacccgat tccctcagca    5280
atcgcagcaa actccggcat ctacgccatg ccagcaact tcacccagtt cgtgctggtg    5340
gacaacggcg caccggcga cgtgaccgtg gcccccagca acttcgccaa cggcatcgcc    5400
gagtggatca gcagcaacag cagaagccag gcctacaagg tgacctgcag cgtgagacag    5460
agcagcgccc agaacagaaa gtacaccatc aaggtggagg tgcccaaggg cgcctggaga    5520
agctacctga acatggagct gaccatcccc atcttcgcca ccaacagcga ctgcgagctg    5580
atcgtgaagg ccatgcaggg cctgctgaag gacggcaacc ccatccccag cgccatcgcc    5640
gccaacagcg gcatctacga ctacaaagac gatgacgaca agtaaagcaa cctacaaacg    5700
ggtggaggat cacccacccc gacacttcac aatcaagggg tacaatacac aagggtggag    5760
gaacacccca ccctccagac acattacaca gaaatccaat caaacagaag caccatcagg    5820
gcttctgcta ccaaatttat ctcaaaaaac tacaacaagg aatcaccatc agggattccc    5880
tgtgcaatat acgtcaaacg agggccacga cgggaggacg atcacgcctc ccgaatatcg    5940
gcatgtctgg ctttcgaatt cagtgcgtgg agcatcagcc cacgcagcca atcagagtcg    6000
aatacaagtc gactttcgcg aagagcatca gccttcgcgc cattcttaca caaccacac    6060 tctcccctac aggaacagca tcagcgttcc tgcccagtac ccaactcaag aaaatttatg    6120
tccccatgca gcatcagcgc atgggcccca agaatacatc cccaacaaaa tcacatccga    6180
gcaccaacag ggctcggagt gttgtttctt gtccaactgg acaaaccctc catggaccat    6240
caggccatgg actctcacca acaagacaaa aactactctt ctcgaagcag catcagcgct    6300
tcgaaacact cgagcataca ttgtgcctat tcttgggtg gacgatcacg ccacccatgc    6360
tctcacgaat ttcaaaacac ggacaaggac gagcaccacc agggctcgtc gttccacgtc    6420
caatacgatt acttaccttt cgggatcacg atcacggatc ccgcagctac atcacttcca    6480
ctcaggacat tcaagcatgc acgatacagg catgctccac aagtctcaac cacagaaact    6540
accaaatggg ttcagcacca gcgaacccac tcctacctca aacctcttcc cacaaaactg    6600
gcaagcagga tcaccgcttg cccattccaa cataccaaat caaaaacaat tactggtaca    6660
gcatcagcgt accagcccac atctctcact actatcaaaa accaaaccgt tcagcaacag    6720
cgaacggtac acacggaaaa atcaactggt ttacaaatac gaaagacgat cacgctttcg    6780
tccagcgcaa actattacga aaaacatccg acgggaagag caacagcctt cccgcggcgg    6840
aaaacctcac aaaaacacga caaacggatg cacgaacacg gcatccgccg acaacccaca    6900
aacttacaac caggcaaacg gtgcaggatc accgcaccgt acatcaaaca cctcagatct    6960
catgcttcta gaagttgtct cctcctgcac tgactgactg atacaatcga tttctggatc    7020
cgcaggccta atcaacctct ggattacaaa atttgtgaaa gattgactgg tattcttaac    7080
tatgttgctc cttttacgct atgtggatac gctgctttaa tgcctttgta tcatgctatt    7140
gcttcccgta tggctttcat tttctcctcc ttgtataaat cctggttgct gtctctttat    7200
gaggagttgt ggcccgttgt caggcaacgt ggcgtggtgt gcactgtgtt tgctgacgca    7260
acccccactg gttggggcat tgccaccacc tgtcagctcc tttccgggac tttcgctttc    7320
cccctcccta ttgccacggc ggaactcatc gccgcctgcc ttgcccgctg ctggacaggg    7380
gctcggctgt tgggcactga caattccgtg gtgttgtcgg ggaagctgac gtccttccca    7440
```

```
tggctgctcg cctgtgttgc cacctggatt ctgcgcggga cgtccttctg ctacgtccct    7500
tcggccctca atccagcgga ccttccttcc cgctgagaga cacaaaaaat tccaacacac    7560
tattgcaatg aaaataaatt tcctttatta gccagaagtc agatgctcaa ggggcttcat    7620
gatgtcccca taattttttgg cagagggaaa aagatctcag tggtatttgt gagccagggc    7680
attggccttc tgataggcag cctgcacctg aggagtgcgg ccgctttact tgtacagctc    7740
gtccatgccg agagtgatcc cggcggcggt cacgaactcc agcaggacca tgtgatcgcg    7800
cttctcgttg gggtctttgc tcagggcgga ctgggtgctc aggtagtggt tgtcgggcag    7860
cagcacgggg ccgtcgccga tgggggtgtt ctgctggtag tggtcggcga gctgcacgct    7920
gccgtcctcg atgttgtggc ggatcttgaa gttcaccttg atgccgttct tctgcttgtc    7980
ggccatgata tagacgttgt ggctgttgta gttgtactcc agcttgtgcc ccaggatgtt    8040
gccgtcctcc ttgaagtcga tgcccttcag ctcgatgcgg ttcaccaggg tgtcgccctc    8100
gaacttcacc tcggcgcggg tcttgtagtt gccgtcgtcc ttgaagaaga tggtgcgctc    8160
ctggacgtag ccttcgggca tggcggactt gaagaagtcg tgctgcttca tgtggtcggg    8220
gtagcggctg aagcactgca cgccgtaggt caggtggtc acgagggtgg gccagggcac    8280
gggcagcttg ccggtggtgc agatgaactt cagggtcagc ttgccgtagg tggcatcgcc    8340
ctcgccctcg ccgacacgc tgaacttgtg gccgtttacg tcgccgtcca gctcgaccag    8400
gatgggcacc accccggtga acagctcctc gcccttgctc accatggtgg cgggatctga    8460
cggttcacta aaccagctct gcttatatag acctcccacc gtacacgcct accgcccatt    8520
tgcgtcaatg gggcggagtt gttacgacat tttggaaagt cccgttgatt ttggtgccaa    8580
aacaaactcc cattgacgtc aatggggtgg agacttggaa atccccgtga gtcaaaccgc    8640
tatccacgcc cattgatgta ctgccaaaac cgcatcacca tggtaatagc gatgactaat    8700
acgtagatgt actgccaagt aggaaagtcc cataaggtca tgtactgggc ataatgccag    8760
gcgggccatt taccgtcatt gacgtcaata gggggcgtac ttggcatatg atacacttga    8820
tgtactgcca gtgggcagt ttaccgtaaa tactccaccc attgacgtca atggaaagtc    8880
cctattggcg ttactatggg aacatacgtc attattgacg tcaatgggcg ggggtcgttg    8940
ggcggtcagc caggcgggcc atttaccgta agttatgtaa cgggcctgct gccggctctg    9000
cggcctcttc cgcgtcttcg ccttcgccct cagacgagtc ggatctccct ttgggccgcc    9060
tccccgcctg tctagcttga ctgactgaga tacagcgtac cttcagctca cagacatgat    9120
aagatacatt gatgagtttg gacaaaccac aactagaatg cagtgaaaaa aatgctttat    9180
ttgtgaaatt tgtgatgcta ttgctttatt tgtaaccatt ataagctgca ataaacaagt    9240
t                                                                   9241
```

<210> SEQ ID NO 50
<211> LENGTH: 7309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
taatacgact cactataggg agaagtactg ccaccatggg caagaagcaa atcgcaaga      60 cggggaattc caagacacaa tccgctagcc caccacctaa agagcgttct agctcccctg    120
ctactgagca gtcctggatg gaaaacgact tcgatgaact ccgggaagag ggatttaggc    180
```

-continued

```
gatccaacta ttcagaactc cgcgaagata tccagacaaa ggggaaggaa gtcgagaatt    240
tcgagaagaa cctcgaggag tgcatcaccc gtatcacaaa cactgagaaa tgtctcaaag    300
aactcatgga acttaagaca aaagccaggg agcttcgaga ggagtgtcgg agtctgagat    360
ccaggtgtga ccagctcgag gagcgcgtga gcgcgatgga agacgagatg aacgagatga    420
aaagagaggg caaattcagg gagaagcgca ttaagaggaa cgaacagagt ctgcaggaga    480
tttgggatta cgtcaagagg cctaacctgc ggttgatcgg cgtccccgag agcgacgtag    540
aaaacgggac taaactggag aatacacttc aagacatcat tcaagaaaat tttccaaacc    600
tggctcggca agctaatgtg caaatccaag agatccaacg cacacccag cggtatagct     660 ctcggcgtgc caccccctagg catattatcg tgcgctttac taaggtggag atgaaagaga    720
agatgctgcg agccgctcgg gaaaagggaa gggtgacttt gaagggcaaa cctattcggc    780
tgacggttga ccttagcgcc gagacactcc aggcacgccg ggaatggggc cccatctta     840 atatcctgaa ggagaagaac ttccagccac gaatctctta ccctgcaaag ttgagtttta    900
tctccgaggg tgagattaag tatttcatcg ataaacagat gctgcgagac ttcgtgacaa    960
ctcgcccagc tctcaaggaa ctgctcaaag aggctcttaa tatggagcgc aataatagat   1020
atcaacccct gcagaaccac gcaaagatgt gagacagccg tcagaccatc aagactagga   1080
agaaactgca tcaactaatg agcaaaatca ccagctaaca tcatagtata catggtcata   1140
ggaacttaca tttcgattat taccttaaac gtgaatgggt taaatgcccc aaccaagaga   1200
catcggctgg ctgaatggat tcagaaacag gaccccctata tttgctgtct gcaggagacc   1260
cacttccgtc ctcgcgacac atacagactg aaagtgaggg gctggaaaaa gatcttccat   1320
gccaatggaa atcaaagaa agctggagtg gctattctca tctcagataa aattgacttc    1380
aaaataaaga atgttactcg agataaggag ggacactaca taatgatcca ggggtccatc   1440
caagaagagg atataactat tattaatatt tatgcaccca acattggcgc ccctcagtac   1500
atcaggcagc tgcttacagc tatcaaggag gaaatcgaca gtaacacgat tatcgtgggg   1560
gactttaaca ccagccttac tccgatggat agatcatcca aaatgaaaat aaataaggaa   1620
acagaggctc ttaatgacac cattgaccag atagatctga ttgatatata taggacattc   1680
catccaaaaa ctgccgatta cactttcttc agcagtgcgc atggaaccctt ctccaggata   1740 gatcacatct tgggtcacaa aagtagcctc agtaagttta agaaaattga atcattagc    1800 agcatctttt ctgaccataa cgctatgcgc ctggagatga atcacaggga gaagaacgta   1860
aagaagacaa acacctggag gctgaacaat acgctgctaa ataaccaaga gatcactgag   1920
gaaatcaaac aggaaataaa aaaatacttg gagacaaatg acaatgaaaa cacgaccacc   1980
cagaacttgt gggatgcagc taaagcggtt ctgagaggga agtttatagc tattcaagcc   2040
taccttaaga aacaggaaaa atctcaagtg aacaatttga ccttacacct aaagaaactg   2100
gagaaggagg agcagaccaa acccaaagtg agcaggagga agaaaatcat caagatcaga   2160
gccgaaatca atgaaataga aactaagaag acaattgcca agatcaataa aactaaatcc   2220
tggttctttg agaagatcaa caaaattgat aagccattag ccagactcat caagaaaaag   2280
agggagagga ctcagatcaa taagatcaga aatgagaaag gggaagttac aaccgacacc   2340
gcggagattc agaacatcct gagagactac tacaagcaac tttatgccaa taaaatggac   2400
aacctggaag aaatggacaa attcctggaa aggtataacc ttccccggct gaaccaggag   2460
gagactgaaa atatcaaccg cccaatcaca agtaatgaga ttgagactgt gattaagaat   2520
```

-continued

```
cttccaacta caaaaagtcc cggccccgat ggcttcacag gtgaattcta tcagaccttt    2580
cgggaggagt tgacacccat ccttctcaag ctcttccaaa aaattgcaga ggagggcaca    2640
ctcccgaact cattctatga ggccaccatc accctgatcc caaagcccga caaggacact    2700
acaaagaaag aaaattaccg accaatttcc ctgatgaata tcgatgccaa gatcctcaac    2760
aaaatcttgg caaacagaat ccagcagcac attaagagga tcatacacca cgatcaggtg    2820
ggctttatcc cggggatgca aggattcttc aatatccgca atcaatcaa tgtgatccac     2880
catattaaca agttgaagaa gaagaaccat atgatcatct ccatcgatgc agagaaagct    2940
tttgacaaaa ttcaacaccc atttatgatc aaaactctcc agaaggtggg catcgagggg    3000
acctacctca acataattaa ggccatctat gataagccca cagccaacat cattctcaat    3060
ggtgaaaagc tgaaggcatt tcctctgcgg tccggaacga gacagggatg tcctctctct    3120
cctcttctgt tcaacatcgt tctggaagtc ctagccaccg ctatccgcga ggaaaaggaa    3180
attaaaggca tacagattgg aaaggaagag gtaaaactgt ctctgtttgc ggatgatatg    3240
atactgtaca tagagaatcc taaaactgcc acccggaagc tgttggagct aattaatgag    3300
tatggtaagg tcgccggtta caagattaat gctcagaagt ctcttgcttt cctgtacact    3360
aatgatgaaa agtctgaacg ggaaattatg gagacactcc cctttaccat tgcaaccaaa    3420
cgtattaaat accttggcat taacctgcct aaggagacaa agacctgta  tgctgaaaac    3480
tataagacac tgatgaaaga gattaaagat gataccaacc ggtggcggga tatcccatgt    3540
tcttggattg gcagaatcaa cattgtgaag atgagcatcc tgcccaaggc catctacaga    3600
ttcaatgcca tccctatcaa attacctatg gcatttttta cggagctgga acagatcatc    3660
ttaaaatttg tgtggcgcca caagcggccc cgaatcgcca aagcggtctt gaggcagaag    3720
aatggcgctg ggggaatccg actccctgac ttcagattgt actacaaagc taccgtcatc    3780
aagacaatct ggtactggca caagaacaga acatcgatc agtggaacaa gatcgaaagc    3840
cctgagatta accccccgcac ctatggtcaa ctgatctatg acaaagggggg caaggatata   3900
caatggcgca aggacagcct cttcaataag tggtgctggg aaaactggac agccacctgc    3960
aagcgtatga agctggagta ctccctgaca ccatacacaa aaataaactc aaagtggatt    4020
cgagacctca atattcggct ggacactata aaactcctgg aggagaacat tgggcgtaca    4080
ctctttgaca ttaatcatag caagatcttt ttcgatcccc ctcctcgtgt aatgaaaata    4140
aaaacaaaaa taaacaagtg ggatctgatg aaacttcaga gcttttgcac cgcaaaggag    4200
accataaaca agacgaagcg ccaaccctca gaatgggaga aaatatttgc gaatgagtct    4260
acggacaaag gcttaatctc caaaatatat aagcagctca ttcagctcaa tatcaaggaa    4320
acaaacaccc cgatccaaaa gtgggcagag gacctaaatc ggcatttctc caaggaagac    4380
atccagacgg ccacgaagca catgaagcga tgctcaactt ccctgattat tcgcgaaatg    4440
cagatcaaga ctactatgcg ctatcacctc actcctgttc ggatgggcat catccggaaa    4500
tctacaaaca acaagtgctg gagagggtgt ggcgaaaagg gaaccctctt gcattgttgg    4560
tgggagtgta agttgatcca gccactatgg cggaccatat ggaggttcct taaaaaactg    4620
aagattgagc tgccatatga cccagcaatc ccactgctgg gcatataccc ggagaaaacc    4680
gtgattcaga aagacacttg caccccgaatg ttcattgcag cattgtttac aatagccagg    4740
tcatggaagc agcctaagtg cccctcgaca gacgagtgga tcaagaagat gtggtacatt    4800
tatactatgg aatattacag cgccatcaaa cgcaacgaaa ttgggtcttt tctgagacg     4860
tggatggatc tagagactgt catccagagt gaggtaagtc agaaagagaa gaacaaatat    4920
```

```
cgtattttaa cgcatatttg tggaacctgg aagaatggta cagatgagcc ggtctgccga   4980
accgagattg agacccagat ggactacaaa gacgatgacg acaagtgaag cgcttctaga   5040
agttgtctcc tcctgcactg actgactgat acaatcgatt tctggatccg caggcctaat   5100
caacctctgg attacaaaat ttgtgaaaga ttgactggta ttcttaacta tgttgctcct   5160
tttacgctat gtggatacgc tgctttaatg cctttgtatc atgctattgc ttcccgtatg   5220
gctttcattt tctcctcctt gtataaatcc tggttgctgt ctctttatga ggagttgtgg   5280
cccgttgtca ggcaacgtgg cgtggtgtgc actgtgtttg ctgacgcaac ccccactggt   5340
tggggcattg ccaccacctg tcagctcctt tccgggactt tcgctttccc cctccctatt   5400
gccacggcgg aactcatcgc cgcctgcctt gcccgctgct ggacaggggc tcggctgttg   5460
ggcactgaca attccgtggt gttgtcgggg aagctgacgt cctttccatg gctgctcgcc   5520
tgtgttgcca cctggattct gcgcgggacg tccttctgct acgtcccttc ggccctcaat   5580
ccagcggacc ttccttcccg ctgagagaca caaaaaattc caacacacta ttgcaatgaa   5640
aataaatttc ctttattagc cagaagtcag atgctcaagg gcttcatga tgtccccata   5700 attttggca gagggaaaaa gatctcagtg gtatttgtga gccagggcat ggccttctg   5760 ataggcagcc tgcacctgag gagtgcggcc gctttacttg tacagctcgt ccatgccgag   5820
agtgatcccg gcggcggtca cgaactccag caggaccatg tgatcgcgct tctcgttggg   5880
gtctttgctc agggcggact gggtgctcag gtagtggttg tcgggcagca gcacgggcc   5940 gtcgccgatg ggggtgttct gctggtagtg gtcggcgagc tgcacgctgc cgtcctcgat   6000
gttgtggcgg atcttgaagt tcaccttgat gccgttcttc tgcttgtcgg ccatgatata   6060
gacgttgtgg ctgttgtagt tgtactccag cttgtgcccc aggatgttgc cgtcctcctt   6120
gaagtcgatg cccttcagct cgatgcggtt caccagggtg tcgccctcga acttcacctc   6180
ggcgcgggtc ttgtagttgc cgtcgtcctt gaagaagatg gtgcgctcct ggacgtagcc   6240
ttcgggcatg gcggacttga agaagtcgtg ctgcttcatg tggtcggggt agcggctgaa   6300
gcactgcacg ccgtaggtca gggtggtcac gagggtgggc cagggcacgg gcagcttgcc   6360
ggtggtgcag atgaacttca gggtcagctt gccgtaggtg gcatcgccct cgccctcgcc   6420
ggacacgctg aacttgtggc cgtttacgtc gccgtccagc tcgaccagga tgggcaccac   6480
cccggtgaac agctcctcgc ccttgctcac catggtggcg gatctgacg gttcactaaa   6540 ccagctctgc ttatatagac ctcccaccgt acacgcctac cgcccatttg cgtcaatggg   6600
gcggagttgt tacgacattt tggaaagtcc cgttgatttt ggtgccaaaa caaactccca   6660
ttgacgtcaa tggggtggag acttggaaat ccccgtgagt caaaccgcta ccacgccca   6720 ttgatgtact gccaaaaccg catcaccatg gtaatagcga tgactaatac gtagatgtac   6780
tgccaagtag gaaagtccca taggtcatg tactgggcat aatgccaggc gggccattta   6840
ccgtcattga cgtcaatagg gggcgtactt ggcatatgat acacttgatg tactgccaag   6900
tgggcagttt accgtaaata ctccacccat tgacgtcaat ggaaagtccc tattggcgtt   6960
actatgggaa catacgtcat tattgacgtc aatgggcggg ggtcgttggg cggtcagcca   7020
ggcgggccat ttaccgtaag ttatgtaacg ggcctgctgc cggctctgcg gcctcttccg   7080
cgtcttcgcc ttcgccctca gacgagtcgg atctcccttt gggccgcctc cccgcctgtc   7140
tagcttgact gactgagata cagcgtacct tcagctcaca gacatgataa gatacattga   7200
tgagtttgga caaaccacaa ctagaatgca gtgaaaaaaa tgctttattt gtgaaatttg   7260
```

```
tgatgctatt gctttatttg taaccattat aagctgcaat aaacaagtt           7309
```

<210> SEQ ID NO 51
<211> LENGTH: 19
<212> TYPE: DNA
<213> ORGANISM: Unknown
<220> FEATURE:
<223> OTHER INFORMATION: Description of Unknown: transposon end
      sequence

<400> SEQUENCE: 51

```
agatgtgtat aagagacag                                            19
```

<210> SEQ ID NO 52
<211> LENGTH: 19
<212> TYPE: DNA
<213> ORGANISM: Unknown
<220> FEATURE:
<223> OTHER INFORMATION: Description of Unknown: transposon end
      sequence

<400> SEQUENCE: 52

```
ctgtctctta tacacatct                                            19
```

<210> SEQ ID NO 53
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Gly Lys Lys Gln Asn Arg Lys Thr Gly Asn Ser Lys Thr Gln Ser
1               5                   10                  15

Ala Ser Pro Pro Lys Glu Arg Ser Ser Pro Ala Thr Glu Gln
                20                  25                  30

Ser Trp Met Glu Asn Asp Phe Asp Glu Leu Arg Glu Glu Gly Phe Arg
        35                  40                  45

Arg Ser Asn Tyr Ser Glu Leu Arg Glu Asp Ile Gln Thr Lys Gly Lys
    50                  55                  60

Glu Val Glu Asn Phe Glu Lys Asn Leu Glu Glu Cys Ile Thr Arg Ile
65                  70                  75                  80

Thr Asn Thr Glu Lys Cys Leu Lys Glu Leu Met Glu Leu Lys Thr Lys
                85                  90                  95

Ala Arg Glu Leu Arg Glu Glu Cys Arg Ser Leu Arg Ser Arg Cys Asp
            100                 105                 110

Gln Leu Glu Glu Arg Val Ser Ala Met Glu Asp Glu Met Asn Glu Met
        115                 120                 125

Lys Arg Glu Gly Lys Phe Arg Glu Lys Arg Ile Lys Arg Asn Glu Gln
    130                 135                 140

Ser Leu Gln Glu Ile Trp Asp Tyr Val Lys Arg Pro Asn Leu Arg Leu
145                 150                 155                 160

Ile Gly Val Pro Glu Ser Asp Val Glu Asn Gly Thr Lys Leu Glu Asn
                165                 170                 175

Thr Leu Gln Asp Ile Ile Gln Glu Asn Phe Pro Asn Leu Ala Arg Gln
            180                 185                 190

Ala Asn Val Gln Ile Gln Glu Ile Gln Arg Thr Pro Gln Arg Tyr Ser
        195                 200                 205

Ser Arg Arg Ala Thr Pro Arg His Ile Ile Val Arg Phe Thr Lys Val

Glu Met Lys Glu Lys Met Leu Arg Ala Ala Arg Glu Lys Gly Arg Val
225                 230                 235                 240

Thr Leu Lys Gly Lys Pro Ile Arg Leu Thr Val Asp Leu Ser Ala Glu
            245                 250                 255

Thr Leu Gln Ala Arg Arg Glu Trp Gly Pro Ile Phe Asn Ile Leu Lys
                260                 265                 270

Glu Lys Asn Phe Gln Pro Arg Ile Ser Tyr Pro Ala Lys Leu Ser Phe
            275                 280                 285

Ile Ser Glu Gly Glu Ile Lys Tyr Phe Ile Asp Lys Gln Met Leu Arg
290                 295                 300

Asp Phe Val Thr Thr Arg Pro Ala Leu Lys Glu Leu Leu Lys Glu Ala
305                 310                 315                 320

Leu Asn Met Glu Arg Asn Asn Arg Tyr Gln Pro Leu Gln Asn His Ala
                325                 330                 335

Lys Met

<210> SEQ ID NO 54
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgggcaaga agcaaaatcg caagacgggg aattccaaga cacaatccgc tagcccacca      60
cctaaagagc gttctagctc ccctgctact gagcagtcct ggatggaaaa cgacttcgat     120
gaactccggg aagagggatt taggcgatcc aactattcag aactccgcga agatatccag     180
acaaagggga aggaagtcga gaatttcgag aagaacctcg aggagtgcat cacccgtatc     240
acaaacactg agaaatgtct caagaactc atggaactta agacaaaagc cagggagctt     300
cgagaggagt gtcggagtct gagatccagg tgtgaccagc tcgaggagcg cgtgagcgcg     360
atggaagacg agatgaacga gatgaaaaga gagggcaaat tcagggagaa gcgcattaag     420
aggaacgaac agagtctgca ggagatttgg gattacgtca gaggcctaa cctgcggttg     480 atcggcgtcc ccgagagcga cgtagaaaac gggactaaac tggagaatac acttcaagac     540
atcattcaag aaaattttcc aaacctggct cggcaagcta atgtgcaaat ccaagagatc     600
caacgcacac cccagcggta tagctctcgg cgtgccaccc ctaggcatat tatcgtgcgc     660
tttactaagg tggagatgaa agagaagatg ctgcgagccg ctcgggaaaa gggaagggtg     720
actttgaagg gcaaacctat tcggctgacg gttgacctta gcgccgagac actccaggca     780
cgccgggaat ggggccccat ctttaatatc ctgaaggaga gaacttcca gccacgaatc     840 tcttaccctg caaagttgag ttttatctcc gagggtgaga ttaagtattt catcgataaa     900
cagatgctgc gagacttcgt gacaactcgc ccagctctca ggaactgct caaagaggct     960 cttaatatgg agcgcaataa tagatatcaa cccttgcaga accacgcaaa gatgtga      1017

<210> SEQ ID NO 55
<211> LENGTH: 1275
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Thr Gly Ser Asn Ser His Ile Thr Ile Leu Thr Leu Asn Ile Asn
1               5                   10                  15

Gly Leu Asn Ser Ala Ile Lys Arg His Arg Leu Ala Ser Trp Ile Lys
            20                  25                  30

Ser Gln Asp Pro Ser Val Cys Cys Ile Gln Glu Thr His Leu Thr Cys
        35                  40                  45

Arg Asp Thr His Arg Leu Lys Ile Lys Gly Trp Arg Lys Ile Tyr Gln
    50                  55                  60

Ala Asn Gly Lys Gln Lys Ala Gly Val Ala Ile Leu Val Ser Asp
65                  70                  75                  80

Lys Thr Asp Phe Lys Pro Thr Lys Ile Lys Arg Asp Lys Glu Gly His
            85                  90                  95

Tyr Ile Met Val Lys Gly Ser Ile Gln Gln Glu Glu Leu Thr Ile Leu
            100                 105                 110

Asn Ile Tyr Ala Pro Asn Thr Gly Ala Pro Arg Phe Ile Lys Gln Val
        115                 120                 125

Leu Ser Asp Leu Gln Arg Asp Leu Asp Ser His Thr Leu Ile Met Gly
130                 135                 140

Asp Phe Asn Thr Pro Leu Ser Thr Leu Asp Arg Ser Thr Arg Gln Lys
145                 150                 155                 160

Val Asn Lys Asp Thr Gln Glu Leu Asn Ser Ala Leu His Gln Ala Asp
                165                 170                 175

Leu Ile Asp Ile Tyr Arg Thr Leu His Pro Lys Ser Thr Glu Tyr Thr
            180                 185                 190

Phe Phe Ser Ala Pro His His Thr Tyr Ser Lys Ile Asp His Ile Val
        195                 200                 205

Gly Ser Lys Ala Leu Leu Ser Lys Cys Lys Arg Thr Glu Ile Ile Thr
    210                 215                 220

Asn Tyr Leu Ser Asp His Ser Ala Ile Lys Leu Glu Leu Arg Ile Lys
225                 230                 235                 240

Asn Leu Thr Gln Ser Arg Ser Thr Thr Trp Lys Leu Asn Asn Leu Leu
                245                 250                 255

Leu Asn Asp Tyr Trp Val His Asn Glu Met Lys Ala Glu Ile Lys Met
            260                 265                 270

Phe Phe Glu Thr Asn Glu Asn Lys Asp Thr Thr Tyr Gln Asn Leu Trp
        275                 280                 285

Asp Ala Phe Lys Ala Val Cys Arg Gly Lys Phe Ile Ala Leu Asn Ala
    290                 295                 300

Tyr Lys Arg Lys Gln Glu Arg Ser Lys Ile Asp Thr Leu Thr Ser Gln
305                 310                 315                 320

Leu Lys Glu Leu Glu Lys Gln Glu Gln Thr His Ser Lys Ala Ser Arg
                325                 330                 335

Arg Gln Glu Ile Thr Lys Ile Arg Ala Glu Leu Lys Glu Ile Glu Thr
            340                 345                 350

Gln Lys Thr Leu Gln Lys Ile Asn Glu Ser Arg Ser Trp Phe Phe Glu
        355                 360                 365

Arg Ile Asn Lys Ile Asp Arg Pro Leu Ala Arg Leu Ile Lys Lys Lys
    370                 375                 380

Arg Glu Lys Asn Gln Ile Asp Thr Ile Lys Asn Asp Lys Gly Asp Ile
385                 390                 395                 400

Thr Thr Asp Pro Thr Glu Ile Gln Thr Thr Ile Arg Glu Tyr Tyr Lys
                405                 410                 415

-continued

```
His Leu Tyr Ala Asn Lys Leu Glu Asn Leu Glu Glu Met Asp Thr Phe
            420                 425                 430

Leu Asp Thr Tyr Thr Leu Pro Arg Leu Asn Gln Glu Glu Val Glu Ser
            435                 440                 445

Leu Asn Arg Pro Ile Thr Gly Ser Glu Ile Val Ala Ile Ile Asn Ser
450                 455                 460

Leu Pro Thr Lys Lys Ser Pro Gly Pro Asp Gly Phe Thr Ala Glu Phe
465                 470                 475                 480

Tyr Gln Arg Tyr Met Glu Leu Val Pro Phe Leu Leu Lys Leu Phe
                485                 490                 495

Gln Ser Ile Glu Lys Glu Gly Ile Leu Pro Asn Ser Phe Tyr Glu Ala
            500                 505                 510

Ser Ile Ile Leu Ile Pro Lys Pro Gly Arg Asp Thr Thr Lys Lys Glu
            515                 520                 525

Asn Phe Arg Pro Ile Ser Leu Met Asn Ile Asp Ala Lys Ile Leu Asn
            530                 535                 540

Lys Ile Leu Ala Asn Arg Ile Gln Gln His Ile Lys Lys Leu Ile His
545                 550                 555                 560

His Asp Gln Val Gly Phe Ile Pro Gly Met Gln Gly Trp Phe Asn Ile
                565                 570                 575

Arg Lys Ser Ile Asn Val Ile Gln His Ile Asn Arg Ala Lys Asp Lys
            580                 585                 590

Asn His Met Ile Ile Ser Ile Asp Ala Glu Lys Ala Phe Asp Lys Ile
            595                 600                 605

Gln Gln Pro Phe Met Leu Lys Thr Leu Asn Lys Leu Gly Ile Asp Gly
            610                 615                 620

Thr Tyr Phe Lys Ile Ile Arg Ala Ile Tyr Asp Lys Pro Thr Ala Asn
625                 630                 635                 640

Ile Ile Leu Asn Gly Gln Lys Leu Glu Ala Phe Pro Leu Lys Thr Gly
                645                 650                 655

Thr Arg Gln Gly Cys Pro Leu Ser Pro Leu Leu Phe Asn Ile Val Leu
            660                 665                 670

Glu Val Leu Ala Arg Ala Ile Arg Gln Glu Lys Glu Ile Lys Gly Ile
            675                 680                 685

Gln Leu Gly Lys Glu Glu Val Lys Leu Ser Leu Phe Ala Asp Asp Met
            690                 695                 700

Ile Val Tyr Leu Glu Asn Pro Ile Val Ser Ala Gln Asn Leu Leu Lys
705                 710                 715                 720

Leu Ile Ser Asn Phe Ser Lys Val Ser Gly Tyr Lys Ile Asn Val Gln
                725                 730                 735

Lys Ser Gln Ala Phe Leu Tyr Thr Asn Asn Arg Gln Thr Glu Ser Gln
            740                 745                 750

Ile Met Gly Glu Leu Pro Phe Val Ile Ala Ser Lys Arg Ile Lys Tyr
            755                 760                 765

Leu Gly Ile Gln Leu Thr Arg Asp Val Lys Asp Leu Phe Lys Glu Asn
            770                 775                 780

Tyr Lys Pro Leu Leu Lys Glu Ile Lys Glu Asp Thr Asn Lys Trp Lys
785                 790                 795                 800

Asn Ile Pro Cys Ser Trp Val Gly Arg Ile Asn Ile Val Lys Met Ala
                805                 810                 815

Ile Leu Pro Lys Val Ile Tyr Arg Phe Asn Ala Ile Pro Ile Lys Leu
            820                 825                 830
```

-continued

```
Pro Met Thr Phe Phe Thr Glu Leu Glu Lys Thr Thr Leu Lys Phe Ile
            835                 840                 845

Trp Asn Gln Lys Arg Ala Arg Ile Ala Lys Ser Ile Leu Ser Gln Lys
    850                 855                 860

Asn Lys Ala Gly Gly Ile Thr Leu Pro Asp Phe Lys Leu Tyr Tyr Lys
865                 870                 875                 880

Ala Thr Val Thr Lys Thr Ala Trp Tyr Trp Tyr Gln Asn Arg Asp Ile
                885                 890                 895

Asp Gln Trp Asn Arg Thr Glu Pro Ser Glu Ile Met Pro His Ile Tyr
            900                 905                 910

Asn Tyr Leu Ile Phe Asp Lys Pro Glu Lys Asn Lys Gln Trp Gly Lys
            915                 920                 925

Asp Ser Leu Phe Asn Lys Trp Cys Trp Glu Asn Trp Leu Ala Ile Cys
    930                 935                 940

Arg Lys Leu Lys Leu Asp Pro Phe Leu Thr Pro Tyr Thr Lys Ile Asn
945                 950                 955                 960

Ser Arg Trp Ile Lys Asp Leu Asn Val Lys Pro Lys Thr Ile Lys Thr
                965                 970                 975

Leu Glu Glu Asn Leu Gly Ile Thr Ile Gln Asp Ile Gly Val Gly Lys
            980                 985                 990

Asp Phe Met Ser Lys Thr Pro Lys Ala Met Ala Thr Lys Asp Lys Ile
            995                 1000                    1005

Asp Lys Trp Asp Leu Ile Lys Leu Lys Ser Phe Cys Thr Ala Lys
    1010                1015                1020

Glu Thr Thr Ile Arg Val Asn Arg Gln Pro Thr Thr Trp Glu Lys
    1025                1030                1035

Ile Phe Ala Thr Tyr Ser Ser Asp Lys Gly Leu Ile Ser Arg Ile
    1040                1045                1050

Tyr Asn Glu Leu Lys Gln Ile Tyr Lys Lys Lys Thr Asn Asn Pro
    1055                1060                1065

Ile Lys Lys Trp Ala Lys Asp Met Asn Arg His Phe Ser Lys Glu
    1070                1075                1080

Asp Ile Tyr Ala Ala Lys Lys His Met Lys Lys Cys Ser Ser Ser
    1085                1090                1095

Leu Ala Ile Arg Glu Met Gln Ile Lys Thr Thr Met Arg Tyr His
    1100                1105                1110

Leu Thr Pro Val Arg Met Ala Ile Ile Lys Lys Ser Gly Asn Asn
    1115                1120                1125

Arg Cys Trp Arg Gly Cys Gly Glu Ile Gly Thr Leu Leu His Cys
    1130                1135                1140

Trp Trp Asp Cys Lys Leu Val Gln Pro Leu Trp Lys Ser Val Trp
    1145                1150                1155

Arg Phe Leu Arg Asp Leu Glu Leu Glu Ile Pro Phe Asp Pro Ala
    1160                1165                1170

Ile Pro Leu Leu Gly Ile Tyr Pro Asn Glu Tyr Lys Ser Cys Cys
    1175                1180                1185

Tyr Lys Asp Thr Cys Thr Arg Met Phe Ile Ala Ala Leu Phe Thr
    1190                1195                1200

Ile Ala Lys Thr Trp Asn Gln Pro Lys Cys Pro Thr Met Ile Asp
    1205                1210                1215

Trp Ile Lys Lys Met Trp His Ile Tyr Thr Met Glu Tyr Tyr Ala
    1220                1225                1230

Ala Ile Lys Asn Asp Glu Phe Ile Ser Phe Val Gly Thr Trp Met
```

```
                    1235                1240                1245

Lys Leu Glu Thr Ile Ile Leu Ser Lys Leu Ser Gln Glu Gln Lys
        1250                1255                1260

Thr Lys His Arg Ile Phe Ser Leu Ile Gly Gly Asn
        1265                1270                1275

<210> SEQ ID NO 56
<211> LENGTH: 3828
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atgaccggct ctaactcaca tatcaccatc cttacactta acattaacgg cctcaactca     60
gctatcaagc gccatcggct ggccagctgg atcaaatcac aggatccaag cgtttgttgc    120
atccaagaga cccacctgac ctgtagagat actcaccgcc tcaagatcaa gggatggcga    180
aagatttatc aggcgaacgg taagcagaag aaagccggag tcgcaattct ggtctcagac    240
aagacggatt tcaagcccac caaaattaag cgtgataagg aaggtcacta tattatggtg    300
aaaggcagca tacagcagga gaacttacc atattgaaca tctacgcgcc aaacaccggc    360
gcacctcgct ttatcaaaca ggtcctgtcc gatctgcagc gagatctgga ttctcatacg    420
ttgattatgg gtgatttcaa taccattg agcaccctgg atcgcagcac caggcaaaag    480
gtaaataaag acacgcaaga gctcaatagc gcactgcatc aggcagatct cattgatatt    540
tatcgcactc ttcatcctaa gagtaccgag tacacattct tcagcgcccc acatcataca    600
tactcaaaga tcgatcatat cgtcggctca aaggctctgc tgtcaaagtg caagcgcaca    660
gagataatta caaattacct gtcagatcat agcgcgatca agctcgagct gagaatcaag    720
aacctgaccc agagccggag taccacttgg aagcttaata acctgctgct caacgattat    780
tgggtccaca atgagatgaa ggcagagatt aaaatgttct tcgaaacaaa tgagaataag    840
gatactacct atcaaaaacct tgggatgcc tttaaggccg tctgcagagg caagttcatc    900
gccctcaacg cctataaaag aaaacaagag agatctaaga tcgatactct cacctctcag    960
ctgaaggagt tggagaaaca ggaacagacc cactccaagg cgtcaagacg gcaggagatc   1020
acaaagattc gcgccgagtt gaaagagatc gaaacccaaa agactcttca gaaaattaac   1080
gagtctcgta gttggttctt cgagcggatt aataagatag acagacctct ggcacgactg   1140
attaagaaga gcgcgaaaaa gaaccagatt gataccatca gaacgacaa gggcgacatc   1200 actactgacc cgaccgagat ccagaccact attcgggagt attataagca tttgtatgct   1260
aacaagcttg agaacctgga agagatggac actttctgg ataccatatac ctgccacgg   1320 cttaatcaag aggaagtcga gtccctcaac cgcccaatta caggaagcga gattgtggcc   1380
ataattaact ccctgccgac aaagaaatct cctggtccgg acgggtttac agctgagttt   1440
tatcaacggt atatggaaga gcttgtaccg tttctgctca agctctttca gtctatagaa   1500
aaggaaggca tcttgcccaa ttccttctac gaagcttcta taatacttat tcccaaacca   1560
ggacgcgata ccacaaagaa ggaaaacttc cggcccatta gtctcatgaa tatcgacgct   1620
aaaatattga caagattct cgccaacaga atccaacaac atattaagaa attgatacat   1680
cacgaccagt ggggtttat acctggcatg cagggctggt ttaacatccg gaagagtatt   1740
aacgtcattc aacacattaa tagagctaag gataagaatc atatgatcat ctctatagac   1800
```

-continued

| | |
|---|---|
| gcggaaaagg cattcgataa gattcagcag ccatttatgc tcaagactct gaacaaactc | 1860 |
| ggcatcgacg gaacatattt taagattatt cgcgcaattt acgataagcc gactgctaac | 1920 |
| attatcctta acggccaaaa gctcgaggcc tttccgctca agactggaac ccgccaaggc | 1980 |
| tgtcccctct ccccgctttt gtttaatatt gtactcgagg tgctggctag gctattcgt | 2040 |
| caagagaaag agattaaagg gatacagctc gggaaggaag aggtcaagct ttccttgttc | 2100 |
| gccgatgata tgattgtgta cctggagaat cctattgtgt ctgctcagaa ccttcttaaa | 2160 |
| cttatttcta actttagcaa ggtcagcggc tataagatta acgtccagaa atctcaggcc | 2220 |
| tttctgtaca caaataatcg acagaccgaa tcccagataa tgggtgagct tccgtttgtc | 2280 |
| atagccagca aaggataaa gtatctcgga atccagctga cacgagacgt taaagatttg | 2340 |
| tttaaggaaa attacaagcc tctcctgaaa gagattaagg aagatactaa taagtggaag | 2400 |
| aatatcccct gttcatgggt tggcagaatc aacatagtga agatggcaat acttcctaaa | 2460 |
| gtgatatatc gctttaacgc catcccaatt aaactgccta tgaccttctt tacggagctc | 2520 |
| gagaaaacaa cccttaaatt tatatggaat caaaagagag caagaatagc gaagtccatc | 2580 |
| ttgagccaga agaataaggc cggtgggatt actttgcctg attttaagtt gtattataaa | 2640 |
| gccacagtaa ctaagacagc ctggtattgg tatcagaata gagacatcga ccagtggaat | 2700 |
| cggaccgaac catcagagat aatgccccac atctataatt accttatatt cgataagcca | 2760 |
| gaaaagaata acagtgggg caaagacagc ctcttcaaca gtggtgttg ggagaattgg | 2820 |
| ctggccatat gccggaaact caagctcgac cccttcttta caccctacac taaaatcaac | 2880 |
| agtaggtgga tcaaggactt gaatgtcaag ccaaagacta taagacact ggaagagaat | 2940 |
| cttgggatca caatacaaga tataggcgtc ggcaaagatt ttatgtcaaa gacgcccaag | 3000 |
| gccatggcca ctaaggataa gattgataag tgggacctta ttaagctcaa aagcttctgt | 3060 |
| actgccaagg agaccacgat cagagttaat aggcagccca ctacatggga aaagattttc | 3120 |
| gccacttatt catcagataa ggggttgata agcagaatat ataacgagct gaagcagatc | 3180 |
| tacaagaaga aaacgaataa tcccatcaag aagtgggcaa agatatgaa caggcatttt | 3240 |
| agcaaagagg atatctacgc cgcgaagaag catatgaaga agtgtagttc aagcttggcc | 3300 |
| attcgtgaga tgcagattaa gacgaccatg cgataccacc ttaccccagt gaggatggca | 3360 |
| attatcaaga aatctggcaa taatagatgt tggcggggct gtggcgagat tggcacctg | 3420 |
| ctccattgct ggtgggattg caagctggtg cagccgcttt ggaaatcagt ctggcgcttt | 3480 |
| ctgagggacc tcgagcttga gattcccttc gatcccgcaa ttcccttgct cggaatctat | 3540 |
| cctaacgaat acaagagctg ttgttacaag gatacgtgta cccggatgtt catcgcggcc | 3600 |
| ttgtttacga tagctaagac gtggaatcag cctaagtgcc ccacaatgat cgattggatc | 3660 |
| aagaaaatgt ggcatattta taccatggag tattacgcag caattaagaa tgacgaattt | 3720 |
| atttccttcg ttgggacctg gatgaagctg gagactatta ttctgagcaa gctgtctcag | 3780 |
| gagcaaaaga caaagcatag aatcttctct ctcattggtg gtaactaa | 3828 |

<210> SEQ ID NO 57
<211> LENGTH: 1290
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 57

-continued

```
Met Val Ile Gly Thr Tyr Ile Ser Ile Ile Thr Leu Asn Val Asn Gly
1               5                   10                  15

Leu Asn Ala Pro Thr Lys Arg His Arg Leu Ala Glu Trp Ile Gln Lys
            20                  25                  30

Gln Asp Pro Tyr Ile Cys Cys Leu Gln Glu Thr His Phe Arg Pro Arg
            35                  40                  45

Asp Thr Tyr Arg Leu Lys Val Arg Gly Trp Lys Lys Ile Phe His Ala
        50                  55                  60

Asn Gly Asn Gln Lys Lys Ala Gly Val Ala Ile Leu Ile Ser Asp Lys
65                  70                  75                  80

Ile Asp Phe Lys Ile Lys Asn Val Thr Arg Asp Lys Glu Gly His Tyr
                85                  90                  95

Ile Met Ile Gln Gly Ser Ile Gln Glu Glu Asp Ile Thr Ile Ile Asn
            100                 105                 110

Ile Tyr Ala Pro Asn Ile Gly Ala Pro Gln Tyr Ile Arg Gln Leu Leu
            115                 120                 125

Thr Ala Ile Lys Glu Glu Ile Asp Ser Asn Thr Ile Ile Val Gly Asp
        130                 135                 140

Phe Asn Thr Ser Leu Thr Pro Met Asp Arg Ser Ser Lys Met Lys Ile
145                 150                 155                 160

Asn Lys Glu Thr Glu Ala Leu Asn Asp Thr Ile Asp Gln Ile Asp Leu
                165                 170                 175

Ile Asp Ile Tyr Arg Thr Phe His Pro Lys Thr Ala Asp Tyr Thr Phe
            180                 185                 190

Phe Ser Ser Ala His Gly Thr Phe Ser Arg Ile Asp His Ile Leu Gly
        195                 200                 205

His Lys Ser Ser Leu Ser Lys Phe Lys Lys Ile Glu Ile Ile Ser Ser
    210                 215                 220

Ile Phe Ser Asp His Asn Ala Met Arg Leu Glu Met Asn His Arg Glu
225                 230                 235                 240

Lys Asn Val Lys Lys Thr Asn Thr Trp Arg Leu Asn Asn Thr Leu Leu
                245                 250                 255

Asn Asn Gln Glu Ile Thr Glu Glu Ile Lys Gln Glu Ile Lys Lys Tyr
            260                 265                 270

Leu Glu Thr Asn Asp Asn Glu Asn Thr Thr Thr Gln Asn Leu Trp Asp
        275                 280                 285

Ala Ala Lys Ala Val Leu Arg Gly Lys Phe Ile Ala Ile Gln Ala Tyr
    290                 295                 300

Leu Lys Lys Gln Glu Lys Ser Gln Val Asn Asn Leu Thr Leu His Leu
305                 310                 315                 320

Lys Lys Leu Glu Lys Glu Glu Gln Thr Lys Pro Lys Val Ser Arg Arg
                325                 330                 335

Lys Glu Ile Ile Lys Ile Arg Ala Glu Ile Asn Glu Ile Glu Thr Lys
            340                 345                 350

Lys Thr Ile Ala Lys Ile Asn Lys Thr Lys Ser Trp Phe Phe Glu Lys
        355                 360                 365

Ile Asn Lys Ile Asp Lys Pro Leu Ala Arg Leu Ile Lys Lys Lys Arg
    370                 375                 380

Glu Arg Thr Gln Ile Asn Lys Ile Arg Asn Lys Gly Glu Val Thr
385                 390                 395                 400

Thr Asp Thr Ala Glu Ile Gln Asn Ile Leu Arg Asp Tyr Tyr Lys Gln
                405                 410                 415

Leu Tyr Ala Asn Lys Met Asp Asn Leu Glu Glu Met Asp Lys Phe Leu
```

```
            420                 425                 430
Glu Arg Tyr Asn Leu Pro Arg Leu Asn Gln Glu Glu Thr Glu Asn Ile
        435                 440                 445

Asn Arg Pro Ile Thr Ser Asn Glu Ile Glu Thr Val Ile Lys Asn Leu
450                 455                 460

Pro Thr Asn Lys Ser Pro Gly Pro Asp Gly Phe Thr Gly Glu Phe Tyr
465                 470                 475                 480

Gln Thr Phe Arg Glu Glu Leu Thr Pro Ile Leu Leu Lys Leu Phe Gln
                485                 490                 495

Lys Ile Ala Glu Glu Gly Thr Leu Pro Asn Ser Phe Tyr Glu Ala Thr
            500                 505                 510

Ile Thr Leu Ile Pro Lys Pro Asp Lys Asp Thr Thr Lys Lys Glu Asn
        515                 520                 525

Tyr Arg Pro Ile Ser Leu Met Asn Ile Asp Ala Lys Ile Leu Asn Lys
    530                 535                 540

Ile Leu Ala Asn Arg Ile Gln Gln His Ile Lys Arg Ile Ile His His
545                 550                 555                 560

Asp Gln Val Gly Phe Ile Pro Gly Met Gln Gly Phe Phe Asn Ile Arg
                565                 570                 575

Lys Ser Ile Asn Val Ile His His Ile Asn Lys Leu Lys Lys Lys Asn
            580                 585                 590

His Met Ile Ile Ser Ile Asp Ala Glu Lys Ala Phe Asp Lys Ile Gln
        595                 600                 605

His Pro Phe Met Ile Lys Thr Leu Gln Lys Val Gly Ile Glu Gly Thr
    610                 615                 620

Tyr Leu Asn Ile Ile Lys Ala Ile Tyr Asp Lys Pro Thr Ala Asn Ile
625                 630                 635                 640

Ile Leu Asn Gly Glu Lys Leu Lys Ala Phe Pro Leu Arg Ser Gly Thr
                645                 650                 655

Arg Gln Gly Cys Pro Leu Ser Pro Leu Leu Phe Asn Ile Val Leu Glu
            660                 665                 670

Val Leu Ala Thr Ala Ile Arg Glu Glu Lys Glu Ile Lys Gly Ile Gln
        675                 680                 685

Ile Gly Lys Glu Glu Val Lys Leu Ser Leu Phe Ala Asp Asp Met Ile
    690                 695                 700

Leu Tyr Ile Glu Asn Pro Lys Thr Ala Thr Arg Lys Leu Leu Glu Leu
705                 710                 715                 720

Ile Asn Glu Tyr Gly Lys Val Ala Gly Tyr Lys Ile Asn Ala Gln Lys
                725                 730                 735

Ser Leu Ala Phe Leu Tyr Thr Asn Asp Glu Lys Ser Glu Arg Glu Ile
            740                 745                 750

Met Glu Thr Leu Pro Phe Thr Ile Ala Thr Lys Arg Ile Lys Tyr Leu
        755                 760                 765

Gly Ile Asn Leu Pro Lys Glu Thr Lys Asp Leu Tyr Ala Glu Asn Tyr
    770                 775                 780

Lys Thr Leu Met Lys Glu Ile Lys Asp Asp Thr Asn Arg Trp Arg Asp
785                 790                 795                 800

Ile Pro Cys Ser Trp Ile Gly Arg Ile Asn Ile Val Lys Met Ser Ile
                805                 810                 815

Leu Pro Lys Ala Ile Tyr Arg Phe Asn Ala Ile Pro Ile Lys Leu Pro
            820                 825                 830

Met Ala Phe Phe Thr Glu Leu Glu Gln Ile Ile Leu Lys Phe Val Trp
        835                 840                 845
```

```
Arg His Lys Arg Pro Arg Ile Ala Lys Ala Val Leu Arg Gln Lys Asn
850                 855                 860
Gly Ala Gly Gly Ile Arg Leu Pro Asp Phe Arg Leu Tyr Tyr Lys Ala
865                 870                 875                 880
Thr Val Ile Lys Thr Ile Trp Tyr Trp His Lys Asn Arg Asn Ile Asp
                885                 890                 895
Gln Trp Asn Lys Ile Glu Ser Pro Glu Ile Asn Pro Arg Thr Tyr Gly
                900                 905                 910
Gln Leu Ile Tyr Asp Lys Gly Lys Asp Ile Gln Trp Arg Lys Asp
            915                 920                 925
Ser Leu Phe Asn Lys Trp Cys Trp Glu Asn Trp Thr Ala Thr Cys Lys
930                 935                 940
Arg Met Lys Leu Glu Tyr Ser Leu Thr Pro Tyr Thr Lys Ile Asn Ser
945                 950                 955                 960
Lys Trp Ile Arg Asp Leu Asn Ile Arg Leu Asp Thr Ile Lys Leu Leu
                965                 970                 975
Glu Glu Asn Ile Gly Arg Thr Leu Phe Asp Ile Asn His Ser Lys Ile
                980                 985                 990
Phe Phe Asp Pro Pro Pro Arg Val Met Glu Ile Lys Thr Lys Ile Asn
            995                 1000                1005
Lys Trp Asp Leu Met Lys Leu Gln Ser Phe Cys Thr Ala Lys Glu
            1010                1015                1020
Thr Ile Asn Lys Thr Lys Arg Gln Pro Ser Glu Trp Glu Lys Ile
            1025                1030                1035
Phe Ala Asn Glu Ser Thr Asp Lys Gly Leu Ile Ser Lys Ile Tyr
            1040                1045                1050
Lys Gln Leu Ile Gln Leu Asn Ile Lys Glu Thr Asn Thr Pro Ile
            1055                1060                1065
Gln Lys Trp Ala Glu Asp Leu Asn Arg His Phe Ser Lys Glu Asp
            1070                1075                1080
Ile Gln Thr Ala Thr Lys His Met Lys Arg Cys Ser Thr Ser Leu
            1085                1090                1095
Ile Ile Arg Glu Met Gln Ile Lys Thr Thr Met Arg Tyr His Leu
            1100                1105                1110
Thr Pro Val Arg Met Gly Ile Ile Arg Lys Ser Thr Asn Asn Lys
            1115                1120                1125
Cys Trp Arg Gly Cys Gly Glu Lys Gly Thr Leu Leu His Cys Trp
            1130                1135                1140
Trp Glu Cys Lys Leu Ile Gln Pro Leu Trp Arg Thr Ile Trp Arg
            1145                1150                1155
Phe Leu Lys Lys Leu Lys Ile Glu Leu Pro Tyr Asp Pro Ala Ile
            1160                1165                1170
Pro Leu Leu Gly Ile Tyr Pro Glu Lys Thr Val Ile Gln Lys Asp
            1175                1180                1185
Thr Cys Thr Arg Met Phe Ile Ala Ala Leu Phe Thr Ile Ala Arg
            1190                1195                1200
Ser Trp Lys Gln Pro Lys Cys Pro Ser Thr Asp Glu Trp Ile Lys
            1205                1210                1215
Lys Met Trp Tyr Ile Tyr Thr Met Glu Tyr Tyr Ser Ala Ile Lys
            1220                1225                1230
Arg Asn Glu Ile Gly Ser Phe Leu Glu Thr Trp Met Asp Leu Glu
            1235                1240                1245
```

```
Thr Val Ile Gln Ser Glu Val Ser Gln Lys Glu Lys Asn Lys Tyr
    1250                1255                1260

Arg Ile Leu Thr His Ile Cys Gly Thr Trp Lys Asn Gly Thr Asp
1265                1270                1275

Glu Pro Val Cys Arg Thr Glu Ile Glu Thr Gln Met
    1280                1285                1290

<210> SEQ ID NO 58
<211> LENGTH: 3873
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atggtcatag aacatacat atcgataatt accttaaacg tgaatggatt aaatgcccca        60
accaaaagac atagactggc tgaatggata caaaaacaag acccatatat atgctgtcta     120
caagagaccc acttcagacc tagggacaca tacagactga aagtgagggg atggaaaaag     180
atattccatg caaatggaaa tcaaagaaa gctggagtag ctatactcat atcagataaa      240
atagacttta aaataagaa tgttacaaga dacaaggaag gacactacat aatgatccag      300
ggatcaatcc aagaagaaga tataacaatt ataaatatat atgcacccaa cataggagca     360
cctcaataca taaggcaact gctaacagct ataaagagg aaatcgacag taacacaata     420
atagtggggg actttaacac ctcacttaca ccaatggaca gatcatccaa aatgaaaata     480
aataaggaaa cagaagcttt aaatgacaca atagaccaga tagatttaat tgatatatat     540
aggacattcc atccaaaaac agcagattac acgttcttct caagtgcgca cggaacattc     600
tccaggatag atcacatctt gggtcacaaa tcaagcctca gtaaatttaa gaaaattgaa     660
atcatatcaa gcatcttttc tgaccacaac gctatgagat tagaaatgaa tcacagggaa     720
aaaaacgtaa aaagacaaa cacatggagg ctaaacaata cgttactaaa taaccaagag     780
atcactgaag aaatcaaaca ggaaataaaa aaatacctag agacaaatga caatgaaaac     840
acgacgaccc aaaacctatg ggatgcagca aaagcggttc taagagggaa gtttatagct     900
atacaagcct acctaaagaa acaagaaaaa tctcaagtaa acaatctaac cttacaccta     960
aagaaactag agaagaaga acaaacaaaa cccaaagtta gcagaaggaa agaaatcata    1020
aagatcagag cagaaataaa tgaaatagaa acaagaaaaa caatagcaaa gatcaataaa    1080
actaaaagtt ggttctttga aagataaac aaaattgata agccattagc cagactcatc    1140
aagaaaaaga gggagaggac tcaaatcaat aaaatcagaa atgaaaaagg agaagttaca    1200
acagacaccg cagaaataca aaacatccta agagactact acaagcaact ttatgccaat    1260
aaaatggaca acctggaaga aatggacaaa ttcttagaaa ggtataacct tccaagactg    1320
aaccaggaag aaacagaaaa tatcaacaga ccaatcacaa gtaatgaaat tgaactgtg     1380 attaaaaatc ttccaacaaa caaaagtcca ggaccagatg gcttcacagg tgaattctat    1440
caaacattta gagaagagct aacacccatc cttctcaaac tcttccaaaa aattgcagaa    1500
gaaggaacac tcccaaactc attctatgag gccaccatca ccctgatacc aaaaccagac    1560
aaagacacta caaaaaaaga aaattacaga ccaatatcac tgatgaatat agatgcaaaa    1620
atcctcaaca aaatactagc aaacagaatc caacaacaca ttaaaaggat catacaccac    1680
gatcaagtgg gatttatccc agggatgcaa ggattcttca atatacgcaa atcaatcaat    1740
gtgatacacc atattaacaa attgaagaag aaaaaccata tgatcatctc aatagatgca    1800
```

```
gaaaaagctt tgacaaaat tcaacaccca tttatgataa aaactctcca gaaagtgggc   1860
atagagggaa cctacctcaa cataataaag gccatatatg acaaacccac agcaaacatc   1920
attctcaatg gtgaaaaact gaaagcattt cctctaagat caggaacgag acaaggatgt   1980
ccactctcac cactattatt caacatagtt ctggaagtcc tagccacggc aatcagagaa   2040
gaaaagaaa taaaggaat acaaattgga aagaagaag taaaactgtc actgtttgcg   2100
gatgacatga tactatacat agagaatcct aaaactgcca ccagaaaact gctagagcta   2160
attaatgaat atggtaaagt tgcaggttac aaaattaatg cacagaaatc tcttgcattc   2220
ctatacacta atgatgaaaa atctgaaaga gaaattatgg aaacactccc atttaccatt   2280
gcaacaaaaa gaataaaata cctaggaata aacctaccta aggagacaaa agacctgtat   2340
gcagaaaact ataagacact gatgaaagaa attaaagatg ataccaacag atggagagat   2400
ataccatgtt cttggattgg aagaatcaac attgtgaaaa tgagtatact acccaaagca   2460
atctacagat tcaatgcaat ccctatcaaa ttaccaatgg cattttttac ggagctagaa   2520
caaatcatct taaaatttgt atggagacac aaaagacccc gaatagccaa agcagtcttg   2580
aggcaaaaaa atggagctgg aggaatcaga ctccctgact tcagactata ctacaaagct   2640
acagtaatca agacaatatg gtactggcac aaaaacagaa acatagatca atggaacaag   2700
atagaaagcc cagagattaa cccacgcacc tatggtcaac taatctatga caaggaggc    2760
aaagatatac aatggagaaa agacagtctc ttcaataagt ggtgctggga aaactggaca   2820
gccacatgta aaagaatgaa attagaatac tccctaacac catacacaaa aataaactca   2880
aaatggatta gagacctaaa tataagactg gacactataa aactcttaga ggaaaacata   2940
ggaagaacac tctttgacat aaatcacagc aagatctttt tcgatccacc tcctagagta   3000
atggaaataa aaacaaaaat aaacaagtgg gacctaatga aacttcaaag cttttgcaca   3060
gcaaaggaaa ccataaacaa gacgaaaaga caaccctcag aatgggagaa aatatttgca   3120
aatgaatcaa cggacaaagg attaatctcc aaaatatata aacagctcat tcagctcaat   3180
atcaaagaaa caaacacccc aatccaaaaa tgggcagaag acctaaatag acatttctcc   3240
aaagaagaca tacagacggc cacgaagcac atgaaaagat gctcaacatc actaattatt   3300
agagaaatgc aaatcaaaac tacaatgagg tatcacctca ctcctgttag aatgggcatc   3360
atcagaaaat ctacaaacaa caaatgctgg agagggtgtg gagaaaaggg aaccctcttg   3420
cactgttggt gggaatgtaa attgatacag ccactatgga gaacaatatg gaggttcctt   3480
aaaaaactaa aaatagaatt accatatgac ccagcaatcc cactactggg catataccca   3540
gagaaaccg taattcaaaa agacacatgc acccgaatgt tcattgcagc actatttaca   3600
atagccaggt catggaagca acctaaatgc ccatcgacag acgaatggat aaagaagatg   3660
tggtacatat atacaatgga atattactca gccataaaaa ggaacgaaat tgggtcattt   3720
ttagagacgt ggatggatct agagactgtc atacagagtg aagtaagtca gaaagagaaa   3780
aacaaatatc gtatattaac gcatatatgt ggaacctgga aaaatggtac agatgaaccg   3840
gtctgcagga cagaaattga gacacaaatg taa                              3873
```

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Pro Ala Ala Lys Arg Val Lys Leu Asp
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Tyr Lys Asp Asp Asp Asp Lys
1               5

<210> SEQ ID NO 61
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Ser Asn Phe Thr Gln Phe Val Leu Val Asp Asn Gly Gly Thr Gly
1               5                   10                  15

Asp Val Thr Val Ala Pro Ser Asn Phe Ala Asn Gly Ile Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Gly Ala Trp Arg Ser Tyr Leu Asn Met Glu Leu Thr Ile Pro
65                  70                  75                  80

Ile Phe Ala Thr Asn Ser Asp Cys Glu Leu Ile Val Lys Ala Met Gln
                85                  90                  95

Gly Leu Leu Lys Asp Gly Asn Pro Ile Pro Ser Ala Ile Ala Ala Asn
            100                 105                 110

Ser Gly Ile Tyr Ala Met Ala Ser Asn Phe Thr Gln Phe Val Leu Val
        115                 120                 125

Asp Asn Gly Gly Thr Gly Asp Val Thr Val Ala Pro Ser Asn Phe Ala
    130                 135                 140

Asn Gly Ile Ala Glu Trp Ile Ser Ser Asn Ser Arg Ser Gln Ala Tyr
145                 150                 155                 160

Lys Val Thr Cys Ser Val Arg Gln Ser Ser Ala Gln Asn Arg Lys Tyr
                165                 170                 175

Thr Ile Lys Val Glu Val Pro Lys Gly Ala Trp Arg Ser Tyr Leu Asn
            180                 185                 190

Met Glu Leu Thr Ile Pro Ile Phe Ala Thr Asn Ser Asp Cys Glu Leu
        195                 200                 205

Ile Val Lys Ala Met Gln Gly Leu Leu Lys Asp Gly Asn Pro Ile Pro
    210                 215                 220

Ser Ala Ile Ala Ala Asn Ser Gly Ile Tyr
225                 230

<210> SEQ ID NO 62
<211> LENGTH: 9

```
<212> TYPE: PRT
<213> ORGANISM: Unknown
<220> FEATURE:
<223> OTHER INFORMATION: Description of Unknown: "LAGLIDADG" family
      motif peptide

<400> SEQUENCE: 62

Leu Ala Gly Leu Ile Asp Ala Asp Gly
1               5

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
                100                 105                 110

Thr Val Thr Val
            115

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
                100                 105
```

```
<210> SEQ ID NO 65
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Tyr Cys Arg Arg Leu Lys Ile Gln Val Arg Lys Ala Ala Ile Thr
1               5                   10                  15

Ser Tyr Glu Lys Ser Asp Gly Val Tyr Thr Gly Leu Ser Thr Arg Asn
            20                  25                  30

Gln Glu Thr Tyr Glu Thr Leu Lys His Glu Lys Pro Pro
        35                  40                  45

<210> SEQ ID NO 66
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Tyr Glu Asp Met Arg Gly Ile Leu Tyr Ala Ala Pro Gln Leu Arg Ser
1               5                   10                  15

Ile Arg Gly Gln Pro Gly Pro Asn His Glu Glu Asp Ala Asp Ser Tyr
            20                  25                  30

Glu Asn Met
        35

<210> SEQ ID NO 67
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Lys Val Ala Lys Lys Pro Thr Asn Lys Ala Pro His Pro Lys Gln Glu
1               5                   10                  15

Pro Gln Glu Ile Asn Phe Pro Asp Asp Leu Pro Gly Ser Asn Thr Ala
            20                  25                  30

Ala Pro Val Gln Glu Thr Leu His Gly Cys Gln Pro Val Thr Gln Glu
        35                  40                  45

Asp Gly Lys Glu Ser Arg Ile Ser Val Gln Glu Arg Gln
    50                  55                  60

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 69
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp
    50                  55                  60

<210> SEQ ID NO 70
<211> LENGTH: 415
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190

Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240

```
Ser Gly Gly Gly Gly Ser Gly Ala Leu Ser Asn Ser Ile Met Tyr Phe
            245                 250                 255

Ser His Phe Val Pro Val Phe Leu Pro Ala Lys Pro Thr Thr Thr Pro
        260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Arg Leu
                325                 330                 335

Lys Ile Gln Val Arg Lys Ala Ala Ile Thr Ser Tyr Glu Lys Ser Asp
            340                 345                 350

Gly Val Tyr Thr Gly Leu Ser Thr Arg Asn Gln Glu Thr Tyr Glu Thr
        355                 360                 365

Leu Lys His Glu Lys Pro Pro Gln Gly Ser Gly Ser Tyr Glu Asp Met
    370                 375                 380

Arg Gly Ile Leu Tyr Ala Ala Pro Gln Leu Arg Ser Ile Arg Gly Gln
385                 390                 395                 400

Pro Gly Pro Asn His Glu Glu Asp Ala Asp Ser Tyr Glu Asn Met
                405                 410                 415

<210> SEQ ID NO 71
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Thr Gly Glu Pro Thr Tyr Ala Asp Ser Phe
    50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Ile Asn Ser Tyr Leu Ser Trp Phe Gln Gln Lys Pro Gly Lys Ala
                165                 170                 175

Pro Lys Thr Leu Ile Tyr Arg Ala Asn Arg Leu Glu Ser Gly Val Pro
            180                 185                 190
```

```
Ser Arg Phe Ser Gly Ser Gly Ser Gly Thr Asp Tyr Thr Leu Thr Ile
        195                 200                 205

Ser Ser Leu Gln Tyr Glu Asp Phe Gly Ile Tyr Tyr Cys Gln Gln Tyr
    210                 215                 220

Asp Glu Ser Pro Trp Thr Phe Gly Gly Gly Thr Lys Leu Glu Ile Lys
225                 230                 235                 240

Ser Gly Gly Gly Gly Ser Gly Ala Leu Ser Asn Ser Ile Met Tyr Phe
                245                 250                 255

Ser His Phe Val Pro Val Phe Leu Pro Ala Lys Pro Thr Thr Thr Pro
                260                 265                 270

Ala Pro Arg Pro Pro Thr Pro Ala Pro Thr Ile Ala Ser Gln Pro Leu
                275                 280                 285

Ser Leu Arg Pro Glu Ala Cys Arg Pro Ala Ala Gly Gly Ala Val His
                290                 295                 300

Thr Arg Gly Leu Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Leu Lys
                325                 330                 335

Ile Gln Val Arg Lys Ala Ala Ile Thr Ser Tyr Glu Lys Ser Asp Gly
                340                 345                 350

Val Tyr Thr Gly Leu Ser Thr Arg Asn Gln Glu Thr Tyr Glu Thr Leu
                355                 360                 365

Lys His Glu Lys Pro Pro Gln Lys Lys Val Ala Lys Lys Pro Thr Asn
                370                 375                 380

Lys Ala Pro His Pro Lys Gln Glu Pro Gln Ile Asn Phe Pro Asp Asp
385                 390                 395                 400

Asp Leu Pro Gly Ser Asn Thr Ala Ala Pro Val Gln Glu Thr Leu His
                405                 410                 415

Gly Cys Gln Pro Val Thr Gln Glu Asp Gly Lys Glu Ser Arg Ile Ser
                420                 425                 430

Val Gln Glu Arg Gln
                435
```

<210> SEQ ID NO 72
<211> LENGTH: 438
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

```
Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Met
            35                  40                  45

Gly Trp Ile Asn Thr His Thr Gly Glu Pro Thr Tyr Ala Asp Ser Phe
        50                  55                  60

Lys Gly Arg Phe Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Thr
```

```
            100                 105                 110
Thr Val Thr Val Ser Ser Gly Gly Gly Gly Gly Gly Gly Ser
            115                 120                 125
Gly Gly Gly Gly Ser Asp Ile Gln Met Thr Gln Ser Pro Ser Ser Leu
            130                 135                 140
Ser Ala Ser Val Gly Asp Arg Val Thr Ile Thr Cys Arg Ala Ser Gln
145                 150                 155                 160
Asp Ile Asn Ser Tyr Leu Ser Trp Phe Gln Gln Lys Pro Gly Lys Ala
                165                 170                 175
Pro Lys Thr Leu Ile Tyr Arg Ala Asn Arg Leu Glu Ser Gly Val Pro
            180                 185                 190
Ser Arg Phe Ser Gly Ser Gly Ser Gly Thr Asp Tyr Thr Leu Thr Ile
            195                 200                 205
Ser Ser Leu Gln Tyr Glu Asp Phe Gly Ile Tyr Tyr Cys Gln Gln Tyr
            210                 215                 220
Asp Glu Ser Pro Trp Thr Phe Gly Gly Gly Thr Lys Leu Glu Ile Lys
225                 230                 235                 240
Ser Gly Gly Gly Gly Ser Gly Ala Leu Ser Asn Ser Ile Met Tyr Phe
                245                 250                 255
Ser His Phe Val Pro Val Phe Leu Pro Ala Lys Pro Thr Thr Thr Pro
            260                 265                 270
Ala Pro Arg Pro Pro Thr Pro Ala Pro Thr Ile Ala Ser Gln Pro Leu
            275                 280                 285
Ser Leu Arg Pro Glu Ala Cys Arg Pro Ala Ala Gly Gly Ala Val His
            290                 295                 300
Thr Arg Gly Leu Asp Ile Tyr Ile Trp Ala Pro Leu Ala Gly Thr Cys
305                 310                 315                 320
Gly Val Leu Leu Leu Ser Leu Val Ile Thr Leu Tyr Cys Arg Arg Leu
                325                 330                 335
Lys Ile Gln Val Arg Lys Ala Ala Ile Thr Ser Tyr Glu Lys Ser Asp
            340                 345                 350
Gly Val Tyr Thr Gly Leu Ser Thr Arg Asn Gln Glu Thr Tyr Glu Thr
            355                 360                 365
Leu Lys His Glu Lys Pro Pro Gln Lys Lys Val Ala Lys Lys Pro Thr
            370                 375                 380
Asn Lys Ala Pro His Pro Lys Gln Glu Pro Gln Glu Ile Asn Phe Pro
385                 390                 395                 400
Asp Asp Leu Pro Gly Ser Asn Thr Ala Ala Pro Val Gln Glu Thr Leu
                405                 410                 415
His Gly Cys Gln Pro Val Thr Gln Glu Asp Gly Lys Glu Ser Arg Ile
            420                 425                 430
Ser Val Gln Glu Arg Gln
            435

<210> SEQ ID NO 73
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Arg Asn Lys Lys Ile Leu Lys Glu Asp Glu Leu Leu Ser Glu Thr
1               5                   10                  15
```

```
Gln Gln Ala Ala Phe His Gln Ile Ala Met Glu Pro Phe Glu Ile Asn
            20                  25                  30

Val Pro Lys Pro Lys Arg Arg Asn Gly Val Asn Phe
        35                  40
```

```
<210> SEQ ID NO 74
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Glu Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45

Phe Lys
    50
```

```
<210> SEQ ID NO 75
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gly Ala Ala Pro Ala Ala Ala Pro Ala Lys Gln Glu Ala Ala Ala Pro
1               5                   10                  15

Ala Pro Ala Ala Lys Ala Glu Ala Pro Ala Ala Ala Pro Ala Ala Lys
            20                  25                  30

Ala
```

```
<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units
<220> FEATURE:
<223> OTHER INFORMATION: See specification as filed for detailed
      description of substitutions and preferred embodiments

<400> SEQUENCE: 76

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 77
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 77

Gly Gly Gly Gly Gly Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Gly Gly Gly Gly Gly Gly
1               5

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Glu Ala Ala
      Ala Lys" repeating units
<220> FEATURE:
<223> OTHER INFORMATION: See specification as filed for detailed
      description of substitutions and preferred embodiments

<400> SEQUENCE: 79

Glu Ala Ala Ala Lys Glu Ala Ala Ala Lys Glu Ala Ala Ala Lys Glu
1               5                   10                  15

Ala Ala Ala Lys
            20

<210> SEQ ID NO 80
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cuaggaaucu ggaaguaccg aggaaacucg guacuuccug uguccuag                 48

<210> SEQ ID NO 81
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
auauggaaga uccugggggaa cugggaucuu ccuaagu                            37

<210> SEQ ID NO 82
<211> LENGTH: 76
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (16)..(17)
<223> OTHER INFORMATION: Dihydrouridine
<220> FEATURE:
<221> NAME/KEY: modified_base
<222> LOCATION: (37)..(37)
<223> OTHER INFORMATION: a, c, t, g or u
<220> FEATURE:
<221> NAME/KEY: modified_base
<222> LOCATION: (39)..(39)
<223> OTHER INFORMATION: Pseudouridine
<220> FEATURE:
<221> NAME/KEY: modified_base
<222> LOCATION: (55)..(55)
<223> OTHER INFORMATION: Pseudouridine

<400> SEQUENCE: 82
gcgcauuuag cucagnnggg agagcgccag acugaananc uggagcuccu gugtncgauc     60
cacagaauuc gcacca                                                    76

<210> SEQ ID NO 83
<211> LENGTH: 203
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (66)..(185)
<223> OTHER INFORMATION: a, c, u or g
<220> FEATURE:
<223> OTHER INFORMATION: See specification as filed for detailed
      description of substitutions and preferred embodiments

<400> SEQUENCE: 83
gcuggguuuu uccuuguucg caccggacac cuccagugac cagacggcaa gguuuuuauc     60
ccagunnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnaaaaa aaaaaaaaaa aaa                                           203

<210> SEQ ID NO 84
<211> LENGTH: 93
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gaagguuuuu cuuuccuga gaaacaaca cguauuguuu ucucagguuu ugcuuuugg        60 ccuuuuucua gcuuaaaaaa aaaaaaagca aaa                                 93

<210> SEQ ID NO 85
<211> LENGTH: 76
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 85
ggaagguuuu ucuuuuccug aggcgaaagu cucagguuuu gcuuuuuggc cuuucuuaaa    60
aaaaaaaaaa gcaaaa                                                   76
```

METHODS AND COMPOSITIONS FOR GENOMIC INTEGRATION

CROSS REFERENCE

This application is a continuation in part of and claims priority to International Application No. PCT/US2020/049240, filed Sep. 3, 2020, which claims priority to U.S. Provisional Application No. 62/895,441, filed on Sep. 3, 2019, U.S. Provisional Application No. 62/908,800, filed on Oct. 1, 2019, and U.S. Provisional Application No. 63/039,261, filed on Jun. 15, 2020, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Oct. 13, 2020, is named 56371701601_SL.txt and is 363,857 bytes in size.

BACKGROUND

Cell therapy is a rapidly developing field for addressing difficult to treat diseases, such as cancer, persistent infections and certain diseases that are refractory to other forms of treatment. Cell therapy often utilizes cells that are engineered ex vivo and administered to an organism to correct deficiencies within the body. An effective and reliable system for manipulation of a cell's genome is crucial, in the sense that when the engineered cell is administered into an organism, it functions optimally and with prolonged efficacy. Likewise, reliable mechanisms of genetic manipulation form the cornerstone in the success of gene therapy. However, severe deficiencies exist in methods for delivering nucleic acid cargo (e.g., large cargo) in a therapeutically safe and effective manner. Viral delivery mechanisms are frequently used to deliver large nucleic acid cargo in a cell but are tied to safety issues and cannot be used to express the cargo in some cell types. Additionally, subjecting a cell to repeated gene manipulation can affect cell health, induce alterations of cell cycle and render the cell unsuitable for therapeutic use. Advancements are continually sought in the area for efficacious delivery and stabilization of an exogenously introduced genetic material for therapeutic purposes.

SUMMARY

Provided herein are compositions and methods for stable, non-viral transfer and integration of genetic material into a cell. In one aspect, the genetic material is a self-integrating polynucleotide. The genetic material can be stably integrated in the genome of the cell. The cell may be a human cell. The method is designed for a safe and reliable integration of a genetic material into the genome of a cell.

Provided herein is pharmaceutical composition comprising a therapeutically effective amount of one or more polynucleic acids, or at least one vector encoding the one or more polynucleic acids, the one or more polynucleic acids comprising: (a) a mobile genetic element comprising a sequence encoding a polypeptide; and (b) an insert sequence, wherein the insert sequence comprises a sequence that is a reverse complement of a sequence encoding an exogenous therapeutic polypeptide, wherein the polypeptide encoded by the sequence of the mobile genetic element promotes integration of the insert sequence into a genome of a cell; and wherein the pharmaceutical composition is substantially non-immunogenic to a human subject.

In some embodiments, the polypeptide encoded by the sequence of the mobile genetic element comprises one or more long interspersed nuclear element (LINE) polypeptides, wherein the one or more LINE polypeptides comprises: (i) human ORF1p or a functional fragment thereof, and (ii) human ORF2p or a functional fragment thereof.

In some embodiments, the insert sequence stably integrates and/or is retrotransposed into the genome of a human cell.

In some embodiments, the human cell is an immune cell selected from the group consisting of a T cell, a B cell, a myeloid cell, a monocyte, a macrophage and a dendritic cell.

In some embodiments, the insert sequence is integrated into the genome (i) by cleavage of a DNA strand of a target site by an endonuclease encoded by the one or more polynucleic acids, (ii) via target-primed reverse transcription (TPRT) or (iii) via reverse splicing of the insert sequence into a DNA target site of the genome.

In some embodiments, the insert sequence is integrated into the genome at a poly T site using specificity of an endonuclease domain of the human ORF2p.

In some embodiments, the poly T site comprises the sequence TTTTTA.

In some embodiments, the one or more polynucleic acids comprises homology arms complementary to a target site in the genome.

In some embodiments, the insert sequence integrates into: (a) the genome at a locus that is not a ribosomal locus; (b) a gene or regulatory region of a gene of the genome, thereby disrupting the gene or downregulating expression of the gene; (c) a gene or regulatory region of a gene of the genome, thereby upregulating expression of the gene; or (d) the genome and replaces a gene of the genome.

In some embodiments, the pharmaceutical composition further comprises (i) one or more siRNAs and/or (ii) an RNA guide sequence or a polynucleic acid encoding the RNA guide sequence, and wherein the RNA guide sequence targets a DNA target site of the genome and the insert sequence is integrated into the genome at the DNA target site of the genome.

In some embodiments, the one or more polynucleic acids have a total length of from 3 kb to 20 kb.

In some embodiments, the one or more polynucleic acids comprises one or more polyribonucleic acids, one or more RNAs or one or more mRNAs.

In some embodiments, the exogenous therapeutic polypeptide is selected from the group consisting of a ligand, an antibody, a receptor, an enzyme, a transport protein, a structural protein, a hormone, a contractile protein, a storage protein and a transcription factor.

In some embodiments, the exogenous therapeutic polypeptide is a receptor selected from the group consisting of a chimeric antigen receptor (CAR) and a T cell receptor (TCR).

In some embodiments, the one or more polynucleic acids comprises a first expression cassette comprising a promoter sequence, a 5' UTR sequence, a 3' UTR sequence and a poly A sequence; wherein: (i) the promoter sequence is upstream of the 5' UTR sequence, (ii) the 5' UTR sequence is upstream of the sequence of the mobile genetic element encoding a polypeptide, (iii) the 3' UTR sequence is downstream of the insert sequence; an (iv) the 3' UTR is upstream of the poly A sequence; and wherein the 5' UTR sequence, the 3' UTR sequence or the poly A sequence comprises a binding site for a human ORF2p or a functional fragment thereof.

In some embodiments, the insert sequence comprises a second expression cassette comprising a sequence that is a reverse complement of a promoter sequence, a sequence that is a reverse complement of a 5' UTR sequence, a sequence that is a reverse complement of a 3' UTR sequence and a sequence that is a reverse complement of a poly A sequence; wherein: (i) the sequence that is a reverse complement of a promoter sequence is downstream of the sequence that is a reverse complement of a 5' UTR sequence, (ii) the sequence that is a reverse complement of a 5' UTR sequence is downstream of the sequence that is a reverse complement of a sequence encoding an exogenous therapeutic polypeptide (iii) the sequence that is a reverse complement of a 3' UTR sequence is upstream of the sequence that is a reverse complement of a sequence encoding an exogenous therapeutic polypeptide, and (iv) the sequence that is a reverse complement of a poly A sequence is upstream of the sequence that is a reverse complement of a 3' UTR sequence and downstream of the sequence of the mobile genetic encoding a polypeptide.

In some embodiments, the promoter sequence of the first expression cassette is different from the promoter sequence of the second expression cassette.

In some embodiments, the one or more LINE polypeptides comprises a first LINE polypeptide comprising the human ORF1p or functional fragment thereof and a second LINE polypeptide comprising the human ORF2p or functional fragment thereof, wherein the first LINE polypeptide and the second LINE polypeptide are translated from different open reading frames (ORFs).

In some embodiments, the one or more polynucleic acids comprises a first polynucleic acid molecule encoding the human ORF1p or functional fragment thereof and a second polynucleic acid molecule encoding the human ORF2p or functional fragment thereof.

In some embodiments, the one or more polynucleic acids comprises a 5' UTR sequence and a 3' UTR sequence, wherein (a) the 5' UTR comprises a 5' UTR from LINE-1 or a sequence with at least 80% sequence identity to

ACUCCUCCCCAUCCUCUCCCUCUGUCCCUCUGUCCCUCUGA

CCCUGCACUGUCCCAGCACC;

and/or (b) the 3' UTR comprises a 3' UTR from LINE-1 or a sequence with at least 80% sequence identity to

CAGGACACAGCCUUGGAUCAGGACAGAGACUUGGGGGCCAU

CCUGCCCCUCCAACCCGACAUGUGUACCUCAGCUUUUUCCC

UCACUUGCAUCAAUAAAGCUUCUGUGUUUGGAACAG.

In some embodiments, the sequence encoding the exogenous therapeutic polypeptide does not comprise introns.

In some embodiments, the polypeptide encoded by the sequence of the mobile genetic element comprises a C-terminal nuclear localization signal (NLS), an N-terminal NLS or both.

In some embodiments, the sequence encoding the exogenous polypeptide is not in frame with a sequence encoding the ORF1p or functional fragment thereof and/or is not in frame with a sequence encoding the ORF2p or functional fragment thereof.

In some embodiments, the one or more polynucleic acids comprises a sequence encoding a nuclease domain, a nuclease domain that is not derived from ORF2p, a megaTAL nuclease domain, a TALEN domain, a Cas9 domain, a Cas6 domain, a Cas7 domain, a Cas8 domain, a zinc finger binding domain from an R2 retroelement, or a DNA binding domain that binds to repeat sequences.

In some embodiments, the one or more polynucleic acids comprises a sequence encoding the nuclease domain, wherein the nuclease domain does not have nuclease activity or comprises a mutation that reduces activity of the nuclease domain compared to the nuclease domain without the mutation.

In some embodiments, the ORF2p or functional fragment thereof lacks endonuclease activity or comprises a mutation selected from the group consisting of S228P and Y1180A, and/or wherein the ORF1p or functional fragment comprises a K3R mutation.

In some embodiments, the insert sequence comprises a sequence that is a reverse complement of a sequence encoding two or more exogenous therapeutic polypeptides.

In some embodiments, the one or more polynucleic acids comprises one or more polyribonucleic acids, wherein the exogenous therapeutic polypeptide is a receptor selected from the group consisting of a chimeric antigen receptor (CAR) and a T cell receptor (TCR), and wherein the pharmaceutical composition is formulated for systemic administration to a human subject.

In some embodiments, the one or more polynucleic acids (i) are formulated in a nanoparticle selected from the group consisting of a lipid nanoparticle and a polymeric nanoparticle; and/or (ii) comprises one or more polynucleic acids selected from the group consisting of glycosylated RNAs, circular RNAs and self-replicating RNAs.

Also provided herein is a method of treating a disease or condition in a human subject in need thereof comprising administering a pharmaceutical composition described herein to the human subject.

Also provided herein is a method of modifying a population of human cells ex vivo comprising contacting a composition to a population of human cell ex vivo, thereby forming an ex vivo modified population of human cells, the composition comprising one or more polynucleic acids, or at least one vector encoding the one or more polynucleic acids, the one or more polynucleic acids comprising: (a) a mobile genetic element comprising a sequence encoding a polypeptide; and (b) an insert sequence, wherein the insert sequence is a reverse complement of a sequence encoding an exogenous therapeutic polypeptide, wherein the ex vivo modified population of human cells is substantially non-immunogenic to a human subject.

In one aspect, provided herein are compositions and methods that allow integration of genetic material into the genome of a cell, wherein the genetic material that can be integrated is not specifically restricted by size. In some aspects, the method described herein provides a one-step, single polynucleotide-mediated delivery and integration of genetic "cargo" in the genome of a cell. The genetic material may comprise a coding sequence, e.g., a sequence encoding a transgene, a peptide, a recombinant protein, or an antibody or fragments thereof, wherein the method and compositions ensure stable expression of the transcribed product encoded by the coding sequence. The genetic material may comprise a non-coding sequence, for example, a regulatory RNA sequences, e.g., a regulatory small inhibitory RNA (siRNA), microRNA (miRNA), long non-coding RNA (lncRNA), or one or more transcription regulators such as a promoter and/or an enhancer, and may also include, but not limited to structural biomolecules such as ribosomal RNA (rRNA), transfer RNA (tRNA) or a fragment thereof or a combination thereof.

In another aspect, provided herein are methods and compositions for site-specific integration of a genetic material that may not be specifically restricted by size, into the genome of a cell via a non-viral delivery that ensures both safety and efficacy of the transfer. Provided methods and compositions may be particularly useful in developing a therapeutic, such as a therapeutic comprising a polynucleotide comprising a genetic material and a machinery that allows transfer into a cell and stable integration into the genome of the cell into which the polynucleotide or an mRNA encoding the polynucleotide is transferred. In some embodiments, the therapeutic may be a cell that comprises a polynucleotide that has been stably integrated into the genome of the cell using the methods and compositions described herein.

In one aspect, the present disclosure provides compositions and methods for stable gene transfer into a cell. In some embodiments, the compositions and methods are for stable gene transfer into an immune cell. In some cases, the immune cell is a myeloid cell. In some cases, the methods described herein relate to development of myeloid cells for immunotherapy.

Provided herein is a method of treating a disease in a subject in need thereof, comprising: administering a pharmaceutical composition to the subject wherein the pharmaceutical composition comprises a polycistronic mRNA sequence encoding a gene or fragment thereof, operably linked to a sequence encoding an L1 retrotransposon; wherein the gene or the fragment thereof is at least 10.1 kb in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is at least 10.1 kb in length. In some embodiments, the gene or the fragment thereof (e.g., the payload) is at least about 10.2 kb, 10.3 kb, 10.4 kb, 10.5 kb, 10.6 kb, 10.7 kb, 10.8 kb, 10.9 kb, 11 kb, 12 kb, 13 kb, 14 kb, 15 kb, 16 kb, 17 kb, 18 kb, 19 kb, 20 kb or more in length.

Provided herein is a method for integrating a nucleic acid sequence into the genome of a cell, comprising contacting the cell with a composition comprising a polycistronic mRNA sequence encoding a gene or fragment thereof, operably linked to a sequence encoding an L1 retrotransposon; wherein the gene or the fragment thereof is selected from a group consisting of ABCA4, MY07A, CEP290, CDH23, EYS, USH2a, GPR98, ALMS1, GDE, OTOF, and F8.

Provided herein is a method of expressing a protein encoded by a recombinant nucleic acid in a cell, the method comprising integrating a nucleic acid sequence into the genome of a cell by contacting the cell with a composition comprising a polycistronic mRNA sequence encoding a gene or fragment thereof, operably linked to a sequence encoding an L1 retrotransposon; and expressing a protein encoded by the gene or fragment thereof, wherein expression of the protein is detectable more than 30 days after (a).

In one embodiment of a method described herein, the disease is a genetic disease.

Provided herein is a method of treating Stargardt disease, LCA10, USH1D, DFNB12, retinitis pigmentosa (RP) USH2A, USH2C, Alstrom syndrome, Glycogen storage disease III, Non-syndromic deafness, Hemophilia A, or Leber congenital aumaurosis in a subject, the method comprising: (i) introducing into the subject an mRNA encoding a suitable gene or a fragment thereof, operably linked to a human L1 transposon, or (ii) introducing to the subject a population of cells comprising an mRNA encoding a suitable gene or a fragment thereof, operably linked to a human L1 transposon.

In one embodiment of a method described herein, the method comprises treating Stargardt disease in a subject in need thereof, and wherein the mRNA encodes an ABCA4 gene, or a fragment thereof.

In one embodiment of a method described herein, the method comprises treating Usher Syndrome Type 1b (Usher 1b) disease in a subject in need thereof, and wherein the mRNA encodes an MY07A gene, or a fragment thereof.

In one embodiment of a method described herein, the method comprises treating Leber congenital amaurosis (LCA)10 disease in a subject in need thereof, and wherein the mRNA encodes a CEP290 gene, or a fragment thereof.

In one embodiment of a method described herein, the method comprises treating a User Syndrome Type 1D (USH1D) non-syndromic deafness or hearing loss USH1D, DFN12 disease in a subject in need thereof, and wherein the mRNA encodes a CDH23 gene, or a fragment thereof.

In one embodiment of a method described herein, the method comprises treating a retinitis pigmentose (RP) disease in a subject in need thereof, and wherein the mRNA encodes an EYS gene, or a fragment thereof.

In one embodiment of a method described herein, the method comprises treating a User Syndrome Type 2A (USH2A) and wherein the mRNA encodes an USH2a gene, or a fragment thereof.

In one embodiment of a method described herein, the method comprises treating a User Syndrome Type 2C (USH2C) and wherein the mRNA encodes a GPR98 gene, or a fragment thereof.

In one embodiment of a method described herein, the method comprises treating an Altrom Syndrome, and wherein the mRNA encodes an ALMS1 gene, or a fragment thereof.

In one embodiment of a method described herein, the method comprises treating a Glycogen Storage Disease III, and wherein the mRNA encodes a GDE gene, or a fragment thereof.

In one embodiment of a method described herein, the method comprises treating a non-syndromic deafness or hearing loss and wherein the mRNA encodes an OTOF gene, or a fragment thereof.

In one embodiment of a method described herein, the method comprises treating Hemophilia A, and the mRNA encodes an Factor VIII (F8) gene, or a fragment thereof.

Provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment of a method described herein, the nucleic acid sequence comprising the one or more mutations comprises a pathogenic variant of a cellular gene.

In one embodiment of a method described herein, the a nucleic acid sequence in (B) comprising the nucleic acid sequence that does not contain the one or more mutations is operably linked to the ORF2 sequence.

In one embodiment of a method described herein, the method further comprising introducing a sequence comprising a plurality of thymidine residues at the excision site.

In some embodiment, introducing the sequence comprises introducing at least four thymidine residues.

In one embodiment of a method described herein, the targeted excision machinery comprises a sequence guided site-specific excision endonuclease.

In one embodiment of a method described herein, the targeted excision machinery comprises a CRISPR-CAS system.

In some embodiments, the targeted excision machinery is a modified recombinant LINE 1 (L1) endonuclease.

In some embodiments, introducing the sequence comprising a plurality of thymidine residues comprises base extension by prime editing at the excision site.

In some embodiments, the mRNA sequence encoding an L1 retrotransposon ORF2 protein further comprises a sequence encoding the L1 retrotransposon ORF1 protein.

In some embodiments, the mRNA comprises a sequence for an inducible promoter.

In one embodiment of a method described herein, the excised sequence is greater than 1000 bases.

In one embodiment of a method described herein, the excised sequence is greater than 6 kb.

In one embodiment of a method described herein, the excised sequence is about 10 kb.

In some embodiments, the cell is a lymphocyte. In some embodiments, the cell is a myeloid cell. In some embodiments, the cell is an epithelial cell. In some embodiments, the cell is a cancer cell.

In some embodiments, the nucleic acid sequence encodes an ATP-binding cassette (ABC) transporter gene, (ABCA4) gene, or a fragment thereof.

In some embodiments, the nucleic acid sequence encodes an MY07A, CEP290, CDH23, EYS, USH2a, GPR98, ALMS1, GDE, OTOF or an F8 gene or a fragment thereof.

In some embodiments, introducing comprises introducing to the cell ex vivo. In some embodiments, introducing comprises electroporation. In some embodiments, introducing comprises introducing to the cell in vivo. In some embodiments, expression of the nucleic acid sequence comprising the sequence that does not contain the one or more mutations, is detectable at least 35 days after introducing to the cell. In some embodiments, introducing into the subject comprises direct administration of the mRNA systemically.

In some embodiments, introducing into the subject comprises local administration of the mRNA.

In some embodiments, the mRNA sequence comprises a cell targeting moiety.

In some embodiments, the cell targeting moiety is an aptamer.

In some embodiments, introducing into the subject comprises introducing the mRNA in the retina of the subject.

Provided herein is a method of integrating a nucleic acid sequence into a genome of a cell, the method comprising introducing a recombinant mRNA or a vector encoding an mRNA into the cell, wherein the mRNA comprises: (a) an insert sequence, wherein the insert sequence comprises (i) an exogenous sequence, or (ii) a sequence that is a reverse complement of the exogenous sequence; (b) a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises a binding site for human ORF2p.

Provided herein is a method for integrating a nucleic acid sequence into the genome of an immune cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the insert sequence is integrated into the genome of the immune cell, wherein the insert sequence is a gene selected from a group consisting of ABCA4, MY07A, CEP290, CDH23, EYS, USH2a, GPR98, ALMS1, GDE, OTOF, and F8.

Provided herein is a method for integrating a nucleic acid sequence into the genome of a cell, the method comprising introducing a recombinant mRNA or a vector encoding an mRNA, wherein the mRNA comprises: (a) an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell, wherein the insert sequence is a gene selected from a group consisting of ABCA4, MY07A, CEP290, CDH23, EYS, USH2a, GPR98, ALMS1, GDE, OTOF, and F8.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence.

In some embodiments, the sequence of a human retrotransposon is upstream of the 3' UTR sequence. In some embodiments, the sequence of a human retrotransposon encodes for two proteins that are translated from a single RNA containing two ORFs. In some embodiments, the two ORFs are non-overlapping ORFs.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase.

In some embodiments, the endonuclease and/or a reverse transcriptase is ORF2p.

In some embodiments, the reverse transcriptase is a group II intron reverse transcriptase domain.

In some embodiments, the endonuclease and/or a reverse transcriptase is a minke whale endonuclease and/or a reverse transcriptase.

In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA. In some embodiments, the retrotransposon comprises an ORF1p and/or the ORF2p fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences.

Provided herein is a composition comprising a recombinant mRNA or vector encoding an mRNA, wherein the mRNA comprises a human LINE-1 transposon sequence comprising: (i) a human LINE-1 transposon 5' UTR sequence, (ii) a sequence encoding ORF1p downstream of the human LINE-1 transposon 5' UTR sequence, (iii) an inter-ORF linker sequence downstream of the sequence encoding ORF1p, (iv) a sequence encoding ORF2p downstream of the inter-ORF linker sequence, and (v) a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element, wherein the insert sequence is a gene selected from a group consisting of ABCA4, MY07A, CEP290, CDH23, EYS, USH2a, GPR98, ALMS1, GDE, OTOF, and F8.

Provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic, wherein the insert sequence is a gene selected from a group consisting of ABCA4, MY07A, CEP290, CDH23, EYS, USH2a, GPR98, ALMS1, GDE, OTOF, and F8.

Immunotherapy using phagocytic cells involves making and using engineered myeloid cells, such as macrophages or other phagocytic cells that attack and kill diseased cells, such as cancer cells, or infected cells. Engineered myeloid cells, such as macrophages and other phagocytic cells are prepared by incorporating in them via recombinant nucleic acid technology, a synthetic, recombinant nucleic acid encoding an engineered protein, such as a chimeric antigen receptor, that comprises a targeted antigen binding extracellular domain that is designed to bind to specific antigens on the surface of a target, such as a target cell, such as a cancer cell. Binding of the engineered chimeric receptor to an antigen on a target, such as cancer antigen (or likewise, a disease target), initiates phagocytosis of the target. This triggers two fold action: one, phagocytic engulfment and lysis of the target destroys the target and eliminates it as a first line of immune defense; two, antigens from the target are digested in the phagolysosome of the myeloid cell, are presented on the surface of the myeloid cell, which then leads to activation of T cells and further activation of the immune response and development of immunological memory. Chimeric receptors are engineered for enhanced phagocytosis and immune activation of the myeloid cell in which it is incorporated and expressed. Chimeric antigen receptors of the disclosure are variously termed herein as a chimeric fusion protein, CFP, phagocytic receptor (PR) fusion protein (PFP), or chimeric antigen receptor for phagocytosis (CAR-P), while each term is directed to the concept of a recombinant chimeric and/or fusion receptor protein. In some embodiments, genes encoding non-receptor proteins are also co-expressed in the myeloid cells, typically for an augmentation of the chimeric antigen receptor function. In summary, contemplated herein are various engineered receptor and non-receptor recombinant proteins that are designed to augment phagocytosis and or immune response of a myeloid cell against a disease target, and methods and compositions for creating and incorporating recombinant nucleic acids that encode the engineered receptors or non-receptor recombinant protein, such that the methods and compositions are suitable for creating an engineered myeloid cell for immunotherapy.

In one aspect, the present disclosure provides compositions and methods for stable gene transfer into a cell, where the cell can be any somatic cell. In some embodiments the compositions and methods are designed for cell-specific or tissue-specific delivery. In some cases, the methods described herein relate to supplying a functional protein or a fragment thereof to compensate for an absent or defective (mutated) protein in vivo, e.g., for a protein replacement therapy.

Incorporation of a recombinant nucleic acid in a cell can be accomplished by one or more gene transfer techniques that are available in the state of the art. However, incorporation of exogenous genetic (e.g., nucleic acid) elements into the genome for therapeutic purposes still faces several challenges. Achieving stable integration in a safe and dependable manner, and efficient and prolonged expression are a few among them. Most of the successful gene transfer systems aimed at genomic integration of the cargo nucleic acid sequence rely on viral delivery mechanisms, which have some inherent safety and efficacy issues. Delivery and integration of long nucleic acid sequences cannot be achieved by current gene editing systems.

Little attention has so far been devoted to making and using engineered myeloid cells for stable long-term gene transfer and expression of the transgene. For example, gene transfer to differentiated mammalian cells ex vivo for cell therapy can be accomplished via viral gene transfer mechanisms. However, there are several strategic disadvantages associated with the use of viral gene-transfer vectors, including an undesired potential for transgene silencing over time, the preferential integration into transcriptionally active sites of the genome with associated undesired activation of other genes (e.g. oncogenes) and genotoxicity. In addition to the safety issues increased expense and cumbersome effort of manufacturing, storing and handling integrating viruses often stand in the way of large-scale use of viral vector mediated of gene-modified cells in therapeutic applications. These persistent concerns associated with viral vectors regarding safety, as well as cost and scale of vector production necessitates alternative methods for effective therapy.

Integration of a transgene into the genome of a cell to be used for an immunotherapy can be advantageous in the sense that it is stable and a lower number of cells is required for delivery during the therapy. On the other hand, integrating a transgene in a non-dividing cell can be challenging in both affecting the health and function of the cell as well as the ultimate lifespan of the cell in vivo, and therefore affects its overall utility as the therapeutic. In some embodiments, the methods described herein for generating a myeloid cell for immunotherapy can be a cumulative product of a number of steps and compositions involving but not limited to, for example, selecting a myeloid cell for modifying; method and compositions for incorporating a recombinant nucleic acid in a myeloid cell; methods and compositions for enhancing expression of the recombinant nucleic acid; methods and compositions for selecting and modifying vectors; methods of preparing a recombinant nucleic acid suitable for in vivo administration for uptake and incorporation of the recombinant nucleic acid by a myeloid cell in vivo and therefore generating a myeloid cell for therapy. In some aspects, one or more embodiments of the various inventions described herein are transferrable among each other, and one of skill in the art is expected to use them in alternatives, combinations or interchangeably without the necessity of undue experimentation. All such variations of the disclosed elements are contemplated and fully encompassed herein.

In one aspect, transposons, or transposable elements (TEs) are considered herein, for means of incorporating a heterologous, synthetic or recombinant nucleic acid encoding a transgene of interest in a myeloid cell. Transposon, or transposable elements are genetic elements that have the capability to transpose fragments of genetic material into the genome by use of an enzyme known as transposase. Mammalian genomes contain a high number of transposable element (TE)-derived sequences, and up to 70% of our genome represents TE-derived sequences (de Koning et al. 2011; Richardson et al. 2015). These elements could be exploited to introduce genetic material into the genome of a cell. The TE elements are capable of mobilization, often termed as "jumping" genetic material within the genome. TEs generally exist in eukaryotic genomes in a reversibly inactive, epigenetically silenced form. In the present disclosure methods and compositions for efficient and stable integration of transgenes into macrophages and other phagocytic cells. The method is based on use of a transposase and transposable elements mRNA-encoded transposase. In some embodiments, Long Interspersed Element-1(L1) RNAs are used for stable integration and/or retrotransposition of the transgene into a cell (e.g., a macrophage or phagocytic cell).

Contemplated herein are methods for retrotransposon mediated stable integration of an exogenous nucleic acid sequence into the genome of a cell. The method may take advantage of the random genomic integration machinery of the retrotransposon into the cell without creating an adverse effect. Methods described herein can be used for robust and versatile incorporation of an exogenous nucleic acid sequence into a cell, such that the exogenous nucleic acid is incorporated at a safe locus within the genome and is expressed without being silenced by the cell's inherent defense mechanism. The method described herein can be used to incorporate an exogenous nucleic acid that is about 1 kb, about 2 kb, about 3 kb, about 4 kb, about 5 kb, about 6 kb, about 7 kb about 8 kb, about 9 kb, about 10 kb, or more in size. In some embodiments, the exogenous nucleic acid is not incorporated within a ribosomal locus. In some embodiments, the exogenous nucleic acid is not incorporated within a ROSA26 locus, or another safe harbor locus. In some embodiments, the methods and compositions described herein can incorporate an exogenous nucleic acid sequence anywhere within the genome of the cell. Furthermore, contemplated herein is a retrotransposition system that is developed to incorporate an exogenous nucleic acid sequence into a specific predetermined site within the genome of a cell, without creating an adverse effect. The disclosed methods and compositions incorporate several mechanisms of engineering the retrotransposons for highly specific incorporation of the exogenous nucleic acid into a cell with high fidelity. Retrotransposons chosen for this purpose may be a human retrotransposon.

Methods and compositions described herein represent a salient breakthrough in the molecular systems and mechanisms for manipulating the genome of a cell. Shown here for the first time is a method that exploits a human retrotransposon system into non-virally delivering and stably integrating a large fragment of exogenous nucleic acid sequence (at least greater than 100 nucleobases, at least greater than 1 kb, at least greater than 2 kb, at least greater than 3 kb, etc.) into a non-conserved region of the genome that is not an rDNA or a ribosomal locus or a designated safe-harbor locus such as the ROSA 26 locus.

In some embodiments, a retrotransposable system is used to stably incorporate into the genome and express a non-endogenous nucleic acid, where the non-endogenous nucleic acid comprises retrotransposable elements within the nucleic acid sequence. In some embodiments, a cell's endogenous retrotransposable system (e.g., proteins and enzymes) is used to stably express a non-endogenous nucleic acid in the cell. In some embodiments, a cell's endogenous retrotransposable system (e.g., proteins and enzymes, such as a LINE-1 retrotransposition system) is used, but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for genomic integration and/or retrotransposition.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell. In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence. In some embodiments, the polynucleotide sequence that is desired to be transferred and incorporated into the genome of a cell (e.g., the insert) is inserted at a site 3' to the sequence encoding ORF1 in a recombinant nucleic acid construct. In some embodiments, the polynucleotide sequence that is desired to be transferred and incorporated into the genome of a cell is inserted at a site 3' to the sequence encoding ORF2 in a recombinant nucleic acid construct. In some embodiments the sequence that is desired to be transferred and incorporated into the genome of a cell is inserted within the 3'-UTR of ORF1 or ORF2, or both. In some embodiments, the polynucleotide sequence that is sequence that is desired to be transferred and incorporated into the genome of a cell is inserted upstream of the poly A tail of ORF2 in a recombinant nucleic acid construct.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, provided herein is a polynucleotide construct comprising an mRNA wherein the mRNA comprises a sequence encoding a human retrotransposon, wherein, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding proteins (e.g., PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell. In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence is integrated into the genome at a locus that is not a rDNA locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT). In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon. In some embodiments, provided herein is an mRNA comprising sequences encoding human LINE 1 retrotransposition elements, and a payload comprising a nucleic acid sequence which can be retrotransposed and integrated into a genome of a cell comprising the mRNA. In some embodiments, provided herein is an mRNA that can be delivered into a living cell, e.g., a human cell, wherein, the mRNA comprises sequences encoding human LINE 1 retrotransposition elements, and a payload comprising a nucleic acid sequence which can be retrotransposed and integrated into the genome of the cell. In some embodiments, the sequences encoding human LINE 1 retrotransposition elements comprise a L1 retrotransposon ORF1 sequence or a fragment thereof. In some embodiments, the sequences encoding human LINE 1 retrotransposition elements comprise a L1 retrotransposon ORF2 sequence or a fragment thereof. In some embodiments, the sequences encoding human LINE 1 retrotransposition elements comprise a L1 retrotransposon ORF1 sequence or a fragment thereof and a L1 retrotransposon ORF2 sequence or a fragment thereof, and a nucleic acid "payload" sequence which is a heterologous sequence which is integrated into the genome of cell by retrotransposition. (See, for example, FIG. 1B).

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a megaTAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p, a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex. In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining live subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

Accordingly, it is an object of the present invention to provide novel transposon-based vectors useful in providing gene therapy to an animal. It is an object of the present invention to provide novel transposon-based vectors for use in the preparation of a medicament useful in providing gene therapy to an animal or human. It is another object of the present invention to provide novel transposon-based vectors that encode for the production of desired proteins or peptides in cells. Yet another object of the present invention to provide novel transposon-based vectors that encode for the production of desired nucleic acids in cells. It is a further object of the present invention to provide methods for cell and tissue specific incorporation of transposon-based DNA or RNA constructs comprising targeting a selected gene to a specific cell or tissue of an animal. It is yet another object of the present invention to provide methods for cell and tissue specific expression of transposon-based DNA or RNA constructs comprising designing a DNA or RNA construct with cell specific promoters that enhance stable incorporation of the selected gene by the transposase and expressing the selected gene in the cell. It is an object of the present invention to provide gene therapy for generations through germ line administration of a transposon-based vector. Another object of the present invention is to provide gene therapy in animals through non germ line administration of a transposon-based vector. Another object of the present invention is to provide gene therapy in animals through administration of a transposon-based vector, wherein the animals produce desired proteins, peptides or nucleic acids. Yet another object of the present invention is to provide gene therapy in animals through administration of a transposon-based vector, wherein the animals produce desired proteins or peptides that are recognized by receptors on target cells. Still another object of the present invention is to provide gene therapy in animals through administration of a transposon-based vector, wherein the animals produce desired fusion proteins or fusion peptides, a portion of which are recognized by receptors on target cells, in order to deliver the other protein or peptide component of the fusion protein or fusion peptide to the cell to induce a biological response. Yet another object of the present invention is to provide a method for gene therapy of animals through administration of transposon-based vectors comprising tissue specific promoters and a gene of interest to facilitate tissue specific incorporation and expression of a gene of interest to produce a desired protein, peptide or nucleic acid. Another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid. Still another object of the present invention is to provide a method for gene therapy of animals through administration of transposon-based vectors comprising cell specific promoters and a gene of interest to facilitate cell specific incorporation and expression of a gene of interest to produce a desired protein, peptide or nucleic acid, wherein the desired protein, peptide or nucleic acid has a desired biological effect in the animal.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

FIG. 8A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding GFP, where the coding sequence of GFP is interrupted with an intron. The GFP is not expressed until the sequence is integrated in the genome and the intron is spliced.

FIG. 8B shows exemplary results showing successful integration of the mRNA transcript encoded by the plasmid shown in FIG. 8A and expression of GFP relative to mock-transfected cells (fold increase in mean fluorescence intensity of GFP positive cells is shown). Mock transfected cells were transfected by the vector lacking the GFP cargo sequence.

FIG. 8C shows exemplary flow cytometry results from the results shown in FIG. 8B.

FIG. 10A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.

FIG. 10B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown). Mock transfected cells were transfected by the vector lacking the ATAK cargo sequence. Expression of ATAK receptor protein was detected by binding with a labeled CD5 antibody.

FIG. 10C shows representative flow cytometry data from two separate experimental runs for expression of both GFP and CD5 binder (ATAK) using the experimental setup shown in FIG. 10A.

FIG. 10D shows representative flow cytometry data from two separate experimental runs for expression of both GFP and CD5 binder (ATAK) using the experimental setup shown in FIG. 10A.

FIG. 17A depicts an exemplary plasmid construct encoding a LINE-1 mRNA transcript comprising ORF1 and ORF2 protein encoding sequences on a single mRNA molecule with a GFP sequence (top panel) and an exemplary LINE-1 mRNA transcript comprising ORF1 and ORF2 protein encoding sequences on a single mRNA molecule with a GFP sequence.

FIG. 17B depicts exemplary data showing expression of GFP (fold increase in mean fluorescence intensity of GFP positive cells is shown) in Jurkat cells using the constructs depicted in FIG. 17A. The plasmid construct was transfected, and the mRNA construct was electroporated.

DETAILED DESCRIPTION

Figure 1A:
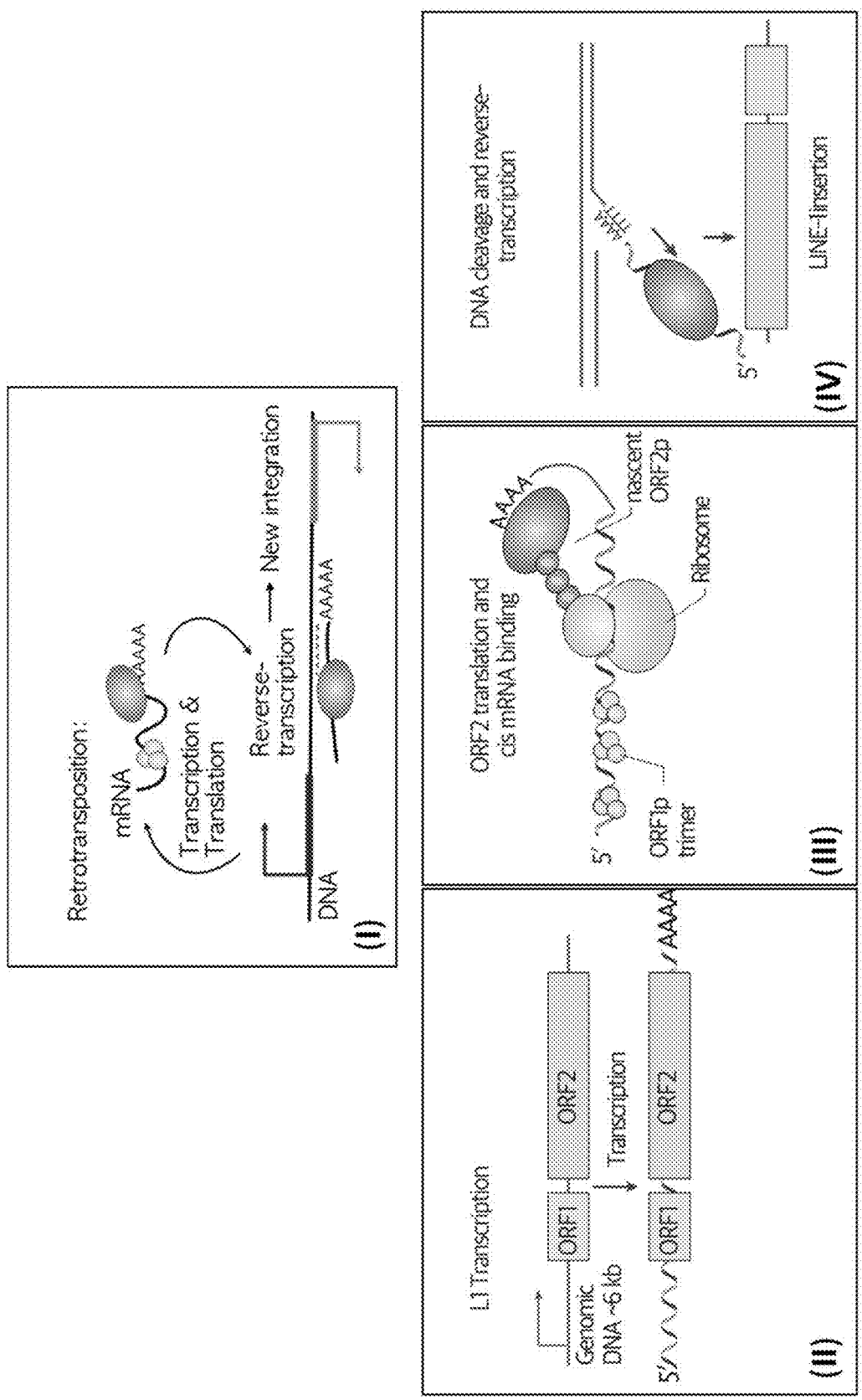
FIG. 1A illustrates a general mechanism of action of retrotransposons. (I) is a schematic representing the overall lifecycle of an autonomous retrotransposon. (II) LINE-1 retrotransposon comprises LINE-1 elements, which encode two proteins ORF1p and ORF2p that are expressed as mRNAs. The bicistronic mRNA is translated into the two proteins, and when ORF2p is translated by a read-through event by the ribosome, it binds the 3' end of its own mRNA through the poly A tail (III). ORF2p cleaves at a consensus sequence TAAAA, where the poly A at the 3' end of the mRNA hybridizes and primes the reverse transcriptase activity of the ORF2 protein. The protein reverse-transcribes the mRNA back into DNA leading to an insertion of the LINE-1 sequence back into a new location in the genome (IV).

The present invention arises in part from the exciting discovery that a polynucleotide could be designed and developed to accomplish transfer and integration of a genetic cargo (e.g., large genetic cargo) into the genome of a cell. In some embodiments, the polynucleotide comprises (i) a genetic material for stable expression, and (ii) a self-integrating genomic integration machinery that allows stable integration of the genetic material into a cell by non-viral means, that is both safe and efficacious. Moreover, the genetic material may be integrated at a locus other than a ribosomal locus; the genetic material may be integrated site-specifically; and/or the integrated genetic material appear to express without triggering a cell's natural silencing machinery.

Clustered Regularly-Interspaced Short Palindromic Repeats (CRISPR) revolutionized the molecular biology field and has developed into a potent gene editing too. It utilizes homology-directed repair (HDR) and can be directed to a genomic site. CRISPR/Cas9 is a naturally occurring RNA-guided endonuclease. While the CRISPR/Cas9 system has demonstrated great promise for site-specific gene editing and other applications, there are several factors that influence its efficacy which must be addressed, especially if it is to be used for in vivo human gene therapy. These factors include target DNA site selection, sgRNA design, off-target cutting, incidence/efficiency of HDR vs. NHEJ, Cas9 activity, and the method of delivery. Delivery remains the major obstacle for use of CRISPR for in vivo applications. Zinc finger nucleases ZFNs are a fusion protein of Cys2-His2 zinc finger proteins (ZFPs) and a non-specific DNA restriction enzyme derived from FokI endonucleases. Challenges with ZFPs include design and engineering of the ZFP for high-affinity binding of the desired sequence, which is non-trivial. Also, not all sequences are available for ZFP binding, so site selection is limited. Another significant challenge is off-target cutting. Transcription activator-like effector nucleases (TALENs) are a fusion protein comprised of a TALE and a FokI nuclease. While off-target cutting remains a concern, TALENs have been shown in one side-by-side comparison study to be more specific and less cytotoxic than ZFNs. However, TALENs are substantially larger, and the cDNA encoding TALEN only is 3 kb. This makes delivery of a pair of TALENs more challenging than a pair of ZFNs due to delivery vehicle cargo size limitations. Further, packaging and delivery of TALENs in some viral vectors may be problematic due to the high level of repetition in the TALENs sequence. A mutant Cas9 system, a fusion protein of inactive dCas9 and a FokI nuclease dimer increase specificity and reduce off-target cutting, the number of potential target sites is lower due to PAM and other sgRNA design constraints.

The present invention addresses the problems described above by providing new, effective and efficient compositions comprising transposon-based vectors for providing therapy, including gene therapy, to animals and humans. The present invention provides methods of using these compositions for providing therapy to animals and humans. These transposon-based vectors can be used in the preparation of a medicament useful for providing a desired effect to a recipient following administration. Gene therapy includes, but is not limited to, introduction of a gene, such as an exogenous gene, into an animal using a transposon-based vector. These genes may serve a variety of functions in the recipient such as coding for the production of nucleic acids, for example RNA, or coding for the production of proteins and peptides.

The present invention can facilitate efficient incorporation of the polynucleotide sequences, including the genes of interest, promoters, insertion sequences, poly A and any regulatory sequences. The invention is based on the finding that human LINE-1 elements are capable of retrotransposition in human cells as well as cells of other animal species and can be manipulated in a versatile manner to achieve efficient delivery and integration of a genetic cargo into the genome of a cell. Such LINE-1 elements have a variety of uses in human and animal genetics including, but not limited to, uses in diagnosis and treatment of genetic disorders and in cancer. The LINE-1 elements of the invention are also useful for the treatment of various phenotypic effects of various diseases. For example, LINE-1 elements may be used for transfer of DNA encoding anti-tumorigenic gene products into cancer cells. Other uses of the LINE-1 elements of the invention will become apparent to the skilled artisan upon a reading of the present specification.

In general, a human LINE-1 element comprises a 5' UTR with an internal promoter, two non-overlapping reading frames (ORF1 and ORF2), a 200 bp 3' UTR and a 3' poly A tail. The LINE-1 retrotransposon can also comprise an endonuclease domain at the LINE-1 ORF2 N-terminus. The finding that LINE-1 encodes an endonuclease demonstrates that the element is capable of autonomous retrotransposition. LINE-1 is a modular protein that contains non-overlapping functional domains which mediate its reverse transcription and integration. In some embodiments, the sequence specificity of the LINE-1 endonuclease itself can be altered or the LINE-1 endonuclease can be replaced with another site-specific endonuclease.

The LINE-1 retrotransposon may be manipulated using recombinant DNA technology to comprise and/or be contiguous with, other DNA elements which render the retrotransposon suitable for insertion of substantial lengths (up to 1 kb, or greater than 1 kb) of heterologous or homologous DNA into the genome of a cell. The LINE-1 retrotransposon may also be manipulated using the same type of technology such that insertion of the DNA into the genome of a cell is site-directed (site into which such DNA is inserted is known). Alternatively, the LINE-1 retrotransposon may be manipulated such that the insertion site of the DNA is random. The retrotransposon may also be manipulated to effect insertion of a desired DNA sequence into regions of DNA which are normally transcriptionally silent, wherein the DNA sequence is expressed in a manner such that it does not disrupt the normal expression of genes in the cell. In some embodiments, the integration or retrotransposition is in the trans orientation. In some embodiments, the integration or retrotransposition occurs in the cis orientation.

Since LINE-1 is native to human cells, when the constructs are placed into human cells, they should not be rejected by the immune system as foreign. In addition, the mechanism of LINE-1 retro-integration ensures that only one copy of the gene is integrated at any specific chromosomal location. Accordingly, there is a copy number control built into the system. In contrast, gene transfer procedures using ordinary plasmids offer little or no control regarding copy number and often result in complex arrays of DNA molecules tandemly integrated into the same genomic location.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, may be used interchangeably. These terms may convey that any combination is specifically contemplated. Solely for illustrative purposes, the following phrases "A, B, and/or C" or "A, B, C, or any combination thereof" may mean "A individually; B individually; C individually; A and B; B and C; A and C; and A, B, and C." The term "or" may be used conjunctively or disjunctively, unless the context specifically refers to a disjunctive use.

The term "about" or "approximately" may mean within an acceptable error range for the particular value as determined by one of ordinary skill in the art, which will depend in part on how the value is measured or determined, i.e., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Alternatively, particularly with respect to biological systems or processes, the term may mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification may be implemented with respect to any method or composition of the present disclosure, and vice versa. Furthermore, compositions of the present disclosure may be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

Applications of the present disclosure encompasses, but are not limited to methods and compositions related to expression of an exogenous nucleic acid in a cell. In some embodiments, the exogenous nucleic acid is configured for stable integration in the genome of a cell, such as a myeloid cell. In some embodiments, the stable integration of the exogenous nucleic acid may be at specific targets within the genome. In some embodiments, the exogenous nucleic acid comprises one or more coding sequences. In some embodiments, the exogenous nucleic acid may comprise one or more coding comprising a nucleic acid sequence encoding an immune receptor. In some embodiments, the present disclosure provides methods and compositions for a stable incorporation of a nucleic acid encoding a transmembrane receptor implicated in an immune response function (e.g. a phagocytic receptor or synthetic chimeric antigen receptor) into human macrophage or dendritic cell or a suitable myeloid cell or a myeloid precursor cell. An exogenous nucleic acid can refer to a nucleic acid that was not originally in a cell and is added from outside the cell, irrespective of whether it comprises a sequence that may already be present in the cell endogenously. An exogenous nucleic acid may be a DNA or an RNA molecule. An exogenous nucleic acid may comprise a sequence encoding a transgene. An exogenous nucleic acid may encode a recombinant protein, such as a recombinant receptor, or a chimeric antigen receptor (CAR). An exogenous nucleic acid may be referred to as a "genetic cargo" in the context of the exogenous nucleic acid being delivered inside a cell. The genetic cargo may be a DNA or an RNA. Genetic material can generally be delivered inside a cell ex vivo by a few different known techniques using either chemical ($CaCl_2$)-medicated transfection), or physical (electroporation), or biological (e.g. viral infection or transduction) means.

In one aspect, provided herein are methods and compositions for delivery inside a cell, for example a myeloid cell and stable incorporation of one or more nucleic acids, comprising nucleic acid sequences encoding one or more proteins, wherein the stable incorporation may be via non-viral mechanisms. In some embodiments, the delivery of a nucleic acid composition into a myeloid cell is via a non-viral mechanism. In some embodiments, the delivery of the nucleic acids may further bypass plasmid mediated delivery. A "plasmid," as used herein, refers to a non-viral expression vector, e.g., a nucleic acid molecule that encodes for genes and/or regulatory elements necessary for the expression of genes. A "viral vector," as used herein, refers to a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

In some embodiments, provided herein is a method of delivering a composition inside a cell, such as in a myeloid cell, the composition comprising one or more nucleic acid sequences encoding one or more proteins, wherein the one or more nucleic acid sequences is an RNA. In some embodiments, the RNA is mRNA. In some embodiments, one or more mRNA comprising one or more nucleic acid sequences are delivered. In some embodiments, the one or more mRNA may comprise at least one modified nucleotide. The term "nucleotide," as used herein, refers to a base-sugar-phosphate combination. A nucleotide may comprise a synthetic nucleotide. A nucleotide may comprise a synthetic nucleotide analog. Nucleotides may be monomeric units of a nucleic acid sequence (e.g. deoxyribonucleic acid (DNA) and ribonucleic acid (RNA)). The term nucleotide may include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, or derivatives thereof. Such derivatives may include, for example, [aS]dATP, 7-deaza-dGTP and 7-deaza-dATP, and nucleotide derivatives that confer nuclease resistance on the nucleic acid molecule containing them. The term nucleotide as used herein may refer to dideoxyribonucleoside triphosphates (ddNTPs) and their derivatives. Illustrative examples of dideoxyribonucleoside triphosphates may include, but are not limited to, ddATP, ddCTP, ddGTP, ddITP, and ddTTP. A nucleotide may be unlabeled or detectably labeled by well-known techniques. Labeling may also be carried out with quantum dots. Detectable labels may include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,NcN'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides may include [R6G]dUTP, [TAMRA]dUTP, [R110]dCTP, [R6G]dCTP, [TAMRA]dCTP, [JOE] ddATP, [R6G]ddATP, [FAM]ddCTP, R1101ddCTP, [TAN1RA] ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, TR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides may also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-cICTP, biotin-14-dCTP), and biotin-dUTP (e.g. biotin-11-dUTP, biotin-1.6-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide may be exogenous or endogenous to a cell. A polynucleotide may exist in a cell-free environment. A polynucleotide may be a gene or fragment thereof. A polynucleotide may be DNA. A polynucleotide may be RNA. A polynucleotide may have any three-dimensional structure, and may perform any function, known or unknown. A polynucleotide may comprise one or more analogs (e.g. altered backbone, sugar, or nucleobase). If present, modifications to the nucleotide structure may be imparted before or after assembly of the polymer. Some non-limiting examples of modified nucleotides or analogs include: pseudouridine, 5-bromouracil, 5-methylcytosine, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudouridine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides may be interrupted by non-nucleotide components.

In some embodiments, the nucleic acid composition may comprise one or more mRNA, comprising at least one mRNA encoding a transmembrane receptor implicated in an immune response function (e.g. a phagocytic receptor or synthetic chimeric antigen receptor) into human macrophage or dendritic cell or a suitable myeloid cell or a myeloid precursor cell. In some embodiments, the nucleic acid composition comprises one or more mRNA, and one or more lipids for delivery of the nucleic acid into a cell of hematopoietic origin, such as a myeloid cell or a myeloid cell precursor cell. In some embodiments, the one or more lipids may form a liposomal complex.

As used herein, the composition described herein may be used for delivery inside a cell. A cell may originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell may not be originating from a natural organism (e.g. a cell may be a synthetically made, sometimes termed an artificial cell). In some embodiments, the cell referred to herein is a mammalian cell. In some embodiments, the cell is a human cell. The methods and compositions described herein relates to incorporating a genetic material in a cell, more specifically a human cell, wherein the human cell can be any human cell. As used herein, a human cell may be of any origin, for example, a somatic cell, a neuron, a fibroblast, a muscle cell, an epithelial cell, a cardiac cell, or a hematopoietic cell. The methods and compositions described herein can also be applicable to and useful for incorporating exogenous nucleic acid in hard-to-transfect human cell. The methods are simple and universally applicable, once a suitable exogenous nucleic acid construct has been designed and developed. The methods and compositions described herein are applicable to incorporate an exogenous nucleic acid in a cell ex vivo. In some embodiments, the compositions may be applicable for systemic administration in an organism, where the nucleic acid material in the composition may be taken up by a cell in vivo, whereupon it is incorporated in cell in vivo.

In some embodiments, the methods and compositions described herein may be directed to incorporating an exogenous nucleic acid in a human hematopoietic cell, for example, a human cell of hematopoietic origin, such as a human myeloid cell or a myeloid cell precursor. However, the methods and compositions described herein can be used or made suitable for use in any biological cell with minimum modifications. Therefore, a cell as may refer to any cell that is a basic structural, functional and/or biological unit of a living organism.

In one aspect, provided herein are methods and compositions for utilizing transposable elements for stable incorporation of one or more nucleic acids into the genome of a cell, where the cell is a member of a hematopoietic cells, for example a myeloid cell. In some embodiments, the one or more nucleic acids comprise at least one nucleic acid sequence encoding a transmembrane receptor protein having a role in immune response. In some embodiments, the methods and compositions are directed to using a retrotransposable element for incorporating one or more nucleic acid sequences into a myeloid cell. The nucleic acid composition may comprise one or more nucleic sequences, such as a gene, where the gene is a transgene. The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and may include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene may refer to an "endogenous gene" or a native gene in its natural location in the genome of an organism. A gene may refer to an "exogenous gene" or a non-native gene. A non-native gene may refer to a gene not normally found in the host organism, but which is introduced into the host organism by gene transfer. A non-native gene may also refer to a gene not in its natural location in the genome of an organism. A non-native gene may also refer to a naturally occurring nucleic acid or polypeptide sequence that comprises mutations, insertions and/or deletions (e.g., non-native sequence).

The term "transgene" refers to any nucleic acid molecule that is introduced into a cell, that may be intermittently termed herein as a recipient cell. The resultant cell after receiving a transgene may be referred to a transgenic cell. A transgene may include a gene that is partly or entirely heterologous (i.e., foreign) to the transgenic organism or cell, or may represent a gene homologous to an endogenous gene of the organism or cell. In some cases, transgenes include any polynucleotide, such as a gene that encodes a polypeptide or protein, a polynucleotide that is transcribed into an inhibitory polynucleotide, or a polynucleotide that is not transcribed (e.g., lacks an expression control element, such as a promoter that drives transcription). Transcripts and encoded polypeptides may be collectively referred to as "gene product." If the polynucleotide is derived from genomic DNA, expression may include splicing of the mRNA in a eukaryotic cell. "Up-regulated," with reference to expression, refers to an increased expression level of a polynucleotide (e.g., RNA such as mRNA) and/or polypeptide sequence relative to its expression level in a wild-type state while "down-regulated" refers to a decreased expression level of a polynucleotide (e.g., RNA such as mRNA) and/or polypeptide sequence relative to its expression in a wild-type state. Expression of a transfected gene may occur transiently or stably in a cell. During "transient expression" the transfected gene is not transferred to the daughter cell during cell division. Since its expression is restricted to the transfected cell, expression of the gene is lost over time. In contrast, stable expression of a transfected gene may occur when the gene is co-transfected with another gene that confers a selection advantage to the transfected cell. Such a selection advantage may be a resistance towards a certain toxin that is presented to the cell. Where a transfected gene is required to be expressed, the application envisages the use of codon-optimized sequences. An example of a codon optimized sequence may be a sequence optimized for expression in a eukaryote, e.g., humans (i.e. being optimized for expression in humans), or for another eukaryote, animal or mammal Codon optimization for a host species other than human, or for codon optimization for specific organs is known. In some embodiments, the coding sequence encoding a protein may be codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. Codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell may generally reflect the codons used most frequently in peptide synthesis. Accordingly, genes may be tailored for optimal gene expression in a given organism based on codon optimization. Codon usage tables are readily available, for example, at the "Codon Usage Database" available at www.kazusa.orjp/codon/ and these tables may be adapted in a number of ways. Computer algorithms for codon optimizing a particular sequence for expression in a particular host cell are also available, such as Gene Forge (Aptagen; Jacobus, PA), are also available.

A "multicistronic transcript" as used herein refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5' end of a multicistronic mRNA molecule. A "5'-distal" coding region or cistron is one whose translation initiation codon (usually AUG) is not the closest initiation codon to the 5' end of the mRNA.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "promoter," as used herein, refers to a polynucleotide sequence capable of driving transcription of a coding sequence in a cell. Thus, promoters used in the polynucleotide constructs of the disclosure include cis-acting transcriptional control elements and regulatory sequences that are involved in regulating or modulating the timing and/or rate of transcription of a gene. For example, a promoter may be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions, developmental conditions, or drug or chemical conditions. Exemplary inducible promoter may be a doxycycline or a tetracycline inducible promoter. Tetracycline regulated promoters may be both tetracycline inducible or tetracycline repressible, called the tet-on and tet-off systems. The tet regulated systems rely on two components, i.e., a tetracycline-controlled regulator (also referred to as transactivator) (tTA or rtTA) and a tTA/rtTA-dependent promoter that controls expression of a downstream cDNA, in a tetracycline-dependent manner. tTA is a fusion protein containing the repressor of the Tn10 tetracycline-resistance operon of *Escherichia coli* and a carboxyl-terminal portion of protein 16 of herpes simplex virus (VP16). The tTA-dependent promoter consists of a minimal RNA polymerase II promoter fused to tet operator (tetO) sequences (an array of seven cognate operator sequences). This fusion converts the tet repressor into a strong transcriptional activator in eukaryotic cells. In the absence of tetracycline or its derivatives (such as doxycycline), tTA binds to the tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. In contrast, in the tet-ON system, a mutant form of tTA, termed rtTA, has been isolated using random mutagenesis. In contrast to tTA, rtTA is not functional in the absence of doxycycline but requires the presence of the ligand for transactivation. The term "exon" refers to a nucleic acid sequence found in genomic DNA that is bioinformatically predicted and/or experimentally confirmed to contribute contiguous sequence to a mature mRNA transcript. The term "intron" refers to a sequence present in genomic DNA that is bioinformatically predicted and/or experimentally confirmed to not encode part of or all of an expressed protein, and which, in endogenous conditions, is transcribed into RNA (e.g. pre-mRNA) molecules, but which is spliced out of the endogenous RNA (e.g. the pre-mRNA) before the RNA is translated into a protein.

The term "splice acceptor site" refers to a sequence present in genomic DNA that is bioinformatically predicted and/or experimentally confirmed to be the acceptor site during splicing of pre-mRNA, which may include identified and unidentified natural and artificially derived or derivable splice acceptor sites.

An "internal ribosome entry site" or "IRES" refers to a nucleotide sequence that allows for 5'-end/cap-independent initiation of translation and thereby raises the possibility to express 2 proteins from a single messenger RNA (mRNA) molecule. IRESs are commonly located in the 5' UTR of positive-stranded RNA viruses with uncapped genomes. Another means to express 2 proteins from a single mRNA molecule is by insertion of a 2A peptide(-like) sequence in between their coding sequence. 2A peptide(-like) sequences mediate self-processing of primary translation products by a process variously referred to as "ribosome skipping", "stop-go" translation and "stop carry-on" translation. 2A peptide (-like) sequences are present in various groups of positive- and double-stranded RNA viruses including Picornaviridae, Flaviviridae, Tetraviridae, Dicistroviridae, Reoviridae and Totiviridae.

The term "2A peptide" refers to a class of 18-22 amino-acid (AA)-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified. The mechanism of 2A-mediated "self-cleavage" is believed to be ribosome skipping the formation of a glycyl-prolyl peptide bond at the C-terminus of the 2A sequence. 2A peptide(-like) sequences mediate self-processing of primary translation products by a process variously referred to as "ribosome skipping", "stop-go" translation and "stop carry-on" translation. 2A peptide(-like) sequences are present in various groups of positive- and double-stranded RNA viruses including Picornaviridae, Flaviviridae, Tetraviridae, Dicistroviridae, Reoviridae and Totiviridae.

As used herein, the term "operably linked" refers to a functional relationship between two or more segments, such as nucleic acid segments or polypeptide segments. Typically, it refers to the functional relationship of a transcriptional regulatory sequence to a transcribed sequence.

The term "termination sequence" refers to a nucleic acid sequence which is recognized by the polymerase of a host cell and results in the termination of transcription. The termination sequence is a sequence of DNA that, at the 3' end of a natural or synthetic gene, provides for termination of mRNA transcription or both mRNA transcription and ribosomal translation of an upstream open reading frame. Prokaryotic termination sequences commonly comprise a GC-rich region that has a two-fold symmetry followed by an AT-rich sequence. A commonly used termination sequence is the T7 termination sequence. A variety of termination sequences are known in the art and may be employed in the nucleic acid constructs of the present invention, including the TINT3, TL13, TL2, TR1, TR2, and T6S termination signals derived from the bacteriophage lambda, and termination signals derived from bacterial genes, such as the trp gene of *E. coli*.

The terms "polyadenylation sequence" (also referred to as a "poly A site" or "poly A sequence") refers to a DNA sequence which directs both the termination and polyadenylation of the nascent RNA transcript. Efficient polyadenylation of the recombinant transcript is desirable, as transcripts lacking a poly A tail are typically unstable and rapidly degraded. The poly A signal utilized in an expression vector may be "heterologous" or "endogenous". An endogenous poly A signal is one that is found naturally at the 3' end of the coding region of a given gene in the genome. A heterologous poly A signal is one which is isolated from one gene and placed 3' of another gene, e.g., coding sequence for a protein. A commonly used heterologous poly A signal is the SV40 poly A signal. The SV40 poly A signal is contained on a 237 bp BamHI/BclI restriction fragment and directs both termination and polyadenylation; numerous vectors contain the SV40 poly A signal. Another commonly used heterologous poly A signal is derived from the bovine growth hormone (BGH) gene; the BGH poly A signal is also available on a number of commercially available vectors. The poly A signal from the Herpes simplex virus thymidine kinase (HSV tk) gene is also used as a poly A signal on a number of commercial expression vectors. The polyadenylation signal facilitates the transportation of the RNA from within the cell nucleus into the cytosol as well as increases cellular half-life of such an RNA. The polyadenylation signal is present at the 3'-end of an mRNA.

The terms "complement," "complements," "complementary," and "complementarity," as used herein, refer to a sequence that is complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/embossneedle/nucleotide.html), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.ukaools/psa/embosswater/nucleotide.html, optionally with default settings). Optimal alignment can be assessed using any suitable parameters of a chosen algorithm, including default parameters.

Complementarity may be perfect or substantial/sufficient. Perfect complementarity between two nucleic acids may mean that the two nucleic acids may form a duplex in which every base in the duplex is bonded to a complementary base by Watson-Crick pairing. Substantial or sufficient complementary may mean that, a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions may be predicted by using the sequences and standard mathematical calculations to predict the melting temperature ($T_m$) of hybridized strands, or by empirical determination of $T_m$ by using routine methods.

"Transposons" as used herein are segments within the chromosome that can translocate within the genome, also known as "jumping gene". There are two different classes of transposons: class 1, or retrotransposons, that mobilize via an RNA intermediate and a "copy-and-paste" mechanism, and class II, or DNA transposons, that mobilize via excision integration, or a "cut-and-paste" mechanism (Ivics Nat Methods 2009). Bacterial, lower eukaryotic (e.g. yeast) and invertebrate transposons appear to be largely species specific, and cannot be used for efficient transposition of DNA in vertebrate cells. "Sleeping Beauty" (Ivics Cell 1997), was the first active transposon that was artificially reconstructed by sequence shuffling of inactive TEs from fish. This made it possible to successfully achieve DNA integration by transposition into vertebrate cells, including human cells. Sleeping Beauty is a class II DNA transposon belonging to the Tcl/mariner family of transposons (Ni Genomics Proteomics 2008). In the meantime, additional functional transposons have been identified or reconstructed from different species, including *Drosophila*, frog and even human genomes, that all have been shown to allow DNA transposition into vertebrate and also human host cell genomes. Each of these transposons have advantages and disadvantages that are related to transposition efficiency, stability of expression, genetic payload capacity etc. Exemplary class II transposases that have been created include Sleeping Beauty, PiggyBac, Frog Prince, Himarl, Passport, Minos, hAT, To11, To12, AciDs, PIF, Harbinger, Harbinger3-DR, and Hsmarl.

"Heterologous" as used herein, includes molecules such as DNA and RNA which may not naturally be found in the cell into which it is inserted. For example, when mouse or bacterial DNA is inserted into the genome of a human cell, such DNA is referred to herein as heterologous DNA. In contrast, the term "homologous" as used herein, denotes molecules such as DNA and RNA that are found naturally in the cell into which it is inserted. For example, the insertion of mouse DNA into the genome of a mouse cell constitutes insertion of homologous DNA into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

A "transposase" is an enzyme that is capable of forming a functional complex with a transposon end-containing composition (e.g., transposons, transposon ends), and catalyze insertion or transposition of the transposon end-containing composition into double stranded DNA which is incubated with an in vitro transposon reaction. The term "transposon end" means a double-stranded DNA that contains the nucleotide sequences (the "transposon end sequences") necessary to form the complex with the transposase or integrase enzyme that is functional in an in vitro transposition reaction.

A transposon end forms a complex or a synaptic complex or a transposon complex or a transposon composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a transferred transposon end sequence or transferred strand and a non-transferred transposon end sequence, or non-transferred strand For example, one transposon end that forms a complex with a hyperactive Tn5 transposase that is active in an in vitro transposition reaction comprises a transferred strand that exhibits a transferred transposon end sequence as follows: 5' AGATGTGTATAAGAGACAG 3' (SEQ ID NO: 51), and a non-transferred strand that exhibits a "non-transferred transposon end sequence" as follows: 5' CTGTCTCTTATACACATCT 3 (SEQ ID NO: 52)'. The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure. As used herein an "cleavage domain" refers to a nucleic acid sequence that is susceptible to cleavage by an agent, e.g., an enzyme.

A "restriction site domain" means a tag domain that exhibits a sequence for the purpose of facilitating cleavage using a restriction endonuclease. For example, in some embodiments, the restriction site domain is used to generate di-tagged linear ssDNA fragments. In some embodiments, the restriction site domain is used to generate a compatible double-stranded 5'-end in the tag domain so that this end can be ligated to another DNA molecule using a template-dependent DNA ligase. In some embodiments, the restriction site domain in the tag exhibits the sequence of a restriction site that is present only rarely, if at all, in the target DNA (e.g., a restriction site for a rare-cutting restriction endonuclease such as NotI or AscI).

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. A recombinant nucleic acid may be synthesized in the laboratory. A recombinant nucleic acid can be prepared by using recombinant DNA technology by using enzymatic modification of DNA, such as enzymatic restriction digestion, ligation, and DNA cloning. A recombinant DNA may be transcribed in vitro, to generate a messenger RNA (mRNA), the recombinant mRNA may be isolated, purified and used to transfect a cell. A recombinant nucleic acid may encode a protein or a polypeptide. A recombinant nucleic acid, under suitable conditions, can be incorporated into a living cell, and can be expressed inside the living cell. As used herein, "expression" of a nucleic acid usually refers to transcription and/or translation of the nucleic acid. The product of a nucleic acid expression is usually a protein but can also be an mRNA. Detection of an mRNA encoded by a recombinant nucleic acid in a cell that has incorporated the recombinant nucleic acid, is considered positive proof that the nucleic acid is "expressed" in the cell. The process of inserting or incorporating a nucleic acid into a cell can be via transformation, transfection or transduction. Transformation is the process of uptake of foreign nucleic acid by a bacterial cell. This process is adapted for propagation of plasmid DNA, protein production, and other applications. Transformation introduces recombinant plasmid DNA into competent bacterial cells that take up extracellular DNA from the environment. Some bacterial species are naturally competent under certain environmental conditions, but competence is artificially induced in a laboratory setting. Transfection is the forced introduction of small molecules such as DNA, RNA, or antibodies into eukaryotic cells. Just to make life confusing, 'transfection' also refers to the introduction of bacteriophage into bacterial cells. 'Transduction' is mostly used to describe the introduction of recombinant viral vector particles into target cells, while 'infection' refers to natural infections of humans or animals with wild-type viruses.

A "stem-loop" sequence refers to a nucleic acid sequence (e.g., RNA sequence) with sufficient self-complementarity to hybridize and form a stem and the regions of non-complementarity that bulges into a loop. The stem may comprise mismatches or bulges.

The term "vector" refers to a nucleic acid molecule capable of transporting or mediating expression of a heterologous nucleic acid. A "vector sequence" as used herein, refers to a sequence of nucleic acid comprising at least one origin of replication and at least one selectable marker gene. Vectors capable of directing the expression of genes and/or nucleic acid sequence to which they are operatively linked are referred to herein as "expression vectors".

A plasmid is a species of the genus encompassed by the term "vector." In general, expression vectors of utility are often in the form of "plasmids" which refer to circular double stranded DNA molecules which, in their vector form are not bound to the chromosome, and typically comprise entities for stable or transient expression of the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked. A safe harbor locus is a region within the genome where additional exogenous or heterologous nucleic acid sequence can be inserted, and the host genome is able to accommodate the inserted genetic material. Exemplary safe harbor sites include but are not limited to: AAVS1 site, GGTA1 site, CMAH site, B4GALNT2 site, B2M site, ROSA26 site, COLA1 site, and TIGRE site. For example, the heterologous nucleic acid described in this disclosure may be integrated at one or more sites in the genome of the cell, wherein the one or more locations is selected from the group consisting of: AAVS1 site, GGTA1 site, CMAH site, B4GALNT2 site, B2M site, ROSA26 site, COLA1 site, and TIGRE site. In some embodiments, the nucleic acid cargo comprising the transgene may be delivered to a R2D locus.

In some embodiments, the nucleic acid cargo comprising the transgene may be delivered to the genome in an intergenic or intragenic region. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous active gene. In some embodiments the nucleic acid cargo comprising the transgene is integrated into the genome 5' or 3' within 0.1 kb, 0.25 kb, 0.5 kb, 0.75, kb, 1 kb, 2 kb, 3 kb, 4 kb, 5 kb, 7.5 kb, 10 kb, 15 kb, 20 kb, 25 kb, 50, 75 kb, or 100 kb of an endogenous promoter or enhancer. In some embodiments the nucleic acid cargo comprising the transgene is 50-50,000 base pairs, e.g., between 50-40,000 bp, between 500-30,000 bp between 500-20,000 bp, between 100-15,000 bp, between 500-10,000 bp, between 50-10,000 bp, between 50-5,000 bp. In some embodiments the nucleic acid cargo comprising the transgene is less than 1,000, 1,300, 1,500, 2,000, 3,000, 4,000, 5,000, or 7,500 nucleotides in length.

L1 and Non-L1 Retrotransposon Systems

Retrotransposons can contain transposable elements that are active participants in reorganizing their resident genomes. Broadly, retrotransposons can refer to DNA sequences that are transcribed into RNA and translated into protein and have the ability to reverse-transcribe themselves back into DNA. Approximately 45% of the human genome is comprised of sequences that result from transposition events. Retrotransposition occasionally generates target site deletions or adds non-retrotransposon DNA to the genome by processes termed 5'- and 3'-transduction. Recombination between non-homologous retrotransposons causes deletions, duplications or rearrangements of gene sequence. Ongoing retrotransposition can generate novel splice sites, polyadenylation signals and promoters, and so builds new transcription modules.

Generally, retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposons are structurally different and also retrotranspose using radically different mechanisms. Exemplary, non-limiting examples of LINE-encoded polypeptides are found in GenBank Accession Nos. AAC51261, AAC51262, AAC51263, AAC51264, AAC51265, AAC51266, AAC51267, AAC51268, AAC51269, AAC51270, AAC51271, AAC51272, AAC51273, AAC51274, AAC51275, AAC51276, AAC51277, AAC51278 and AAC51279.

The decision to focus on LINE-1 to develop into a system as described in the disclosure for a number of reasons at least some of which are exemplified below: (a) LINE-1 (or L1-) elements are autonomous as they encode all of the machinery alone to complete this reverse transcription and integration process; (b) L1 elements are abundant in the human genome, such that these elements may be considered as a naturalized element of the genome; (c) L1 retrotransposon retrotransposes its own mRNA with high degree of specificity, compared to other mRNAs floating around in the cells.

The L1 expresses a 6-kb bicistronic RNA that encodes the 40 kDa Open Reading Frame-1 RNA-binding protein (ORF1p) of essential but uncertain function, and a 150 kDa ORF2 protein with endonuclease and reverse transcriptase (RT) activities. L1 retrotransposition is a complex process involving transcription of the L1, transport of its RNA to the cytoplasm, translation of the bicistronic RNA, formation of a ribonucleoprotein (RNP) particle, its re-import to the nucleus and target-primed reverse transcription at the integration site. A few transcription factors that interact with L1s have been identified. Transcribed L1 RNA forms an RNP in cis with the proteins that are translated from the transcript. L1 integrates into genomic DNA by target-site primer reverse transcription (TPRT) by ORF2p cleavage at the 5'-TTTT-3' where a poly A sequence of L1 RNA anneals and primes reverse transcriptase (RT) activity to make L1 cDNA.

Other mobile elements of the genome can "hijack" the L1 ORF for retrotransposition. For example, Alu elements are such mobile DNA elements that belong to the class of short interspersed elements (SINEs) that are non-autonomous retrotransposons and acquire trans-factors to integrate. Alu elements and SINE-1 elements can associate with the L1 ribonucleoproteins in trans to be also retrotransposed by ORF1p and ORF2p. Somewhat similar to the L1 RNA, the Alu element ends with a long A-run, often referred to as the A-tail, and it also has a smaller A-rich region (indicated by AA) separating the two halves of a diverged dimer structure. Alu elements are likely to have the internal components of an RNA polymerase III promoter (such as, commonly designated as an A box and a B box promoters), but they do not encode a terminator for RNA polymerase III. They may utilize a stretch of T nucleotides at various distances downstream of the Alu element to terminate a transcription. A typical Alu transcript encompasses the entire Alu, including the A-tail, and has a 3' region that is unique for each locus. The Alu RNA folds into separate structures for each monomer unit. The RNA has been shown to bind the 7SL RNA SRP9 and 14 heterodimer, as well as poly A-binding protein (PABP). The poly A tail of Alu primes with T rich (TTTT) region of the genome and attracts ORF2p to bind to the primed region and cleaves at the T rich region via its endonuclease activity. The T-rich region primes reverse transcription by ORF2p on the 3' A-tail region of the Alu element. This creates a cDNA copy of the body of the Alu element. A nick occurs by an unknown mechanism on the second strand and second-strand synthesis is primed. The new Alu element is then flanked by short direct repeats that are duplicates of the DNA sequence between the first and second nicks. Alu elements are extremely prevalent within RNA molecules, owing to their preference for gene-rich regions. A full-length Alu (~300 bp) is derived from the signal recognition particle RNA 7SL and consists of two similar monomers with an A-rich linker in-between, A- and B-boxes present in the 5' monomer, and a poly-A tail lacking the preceding polyadenylation signal resulting in an elongated tail (up to 100 bp in length). Alus can be transcribed by RNA polymerase III using the internal promoters within the A- and B-boxes; however, Alus contain no ORFs and therefore do not encode for protein products.

Other non-L1 transposons include SVAs and HERV-Ks. A full-length SVA (SINE-VNTR-Alu) element (~2-3 kb) is a composite unit that contains a CCCTCT repeat, two Alu-like sequences, a VNTR, a SINE-R region with env (envelope) gene, the 3' LTR of HERV-K10, and a polyadenylation signal followed by a poly-A tail. It is most likely that SVAs are transcribed by RNA polymerase II, although it is unknown whether SVA elements carry an internal promoter.

A full-length HERV-K element (~9-10 kb) is comprised of ancient remnants of endogenous retroviral sequences and includes two flanking LTR regions surrounding three retroviral ORFs: (1) gag encoding the structural proteins of a retroviral capsid; (2) pol-pro encoding the enzymes: protease, RT, and integrase; and (3) env encoding proteins allowing for horizontal transfer. The LTR of HERV-K contains an internal, bidirectional promoter that appears to be under the transcriptional control of RNA polymerase II.

L1 retrotransposition and RNA binding can take place at or near poly-A tail. The 3'-UTR plays a role in the recognition of stringent-type LINE RNA of ORF1 protein (ORF1p). Stringent-type LINEs can contain a stem-loop structure located at the end of the 3'UTR. Branched molecules consisting of junctions between transposon 3'-end cDNA and the target DNA, as well as specific positioning of L1 RNA within ORF2 protein (ORF2p), were detected during initial stages of L1 retrotransposition in vitro. Secondary or tertiary RNA structure shared by L1 and Alu are likely to be responsible for recognition by and binding of ORF2, possibly along with a poly-A tail. In some embodiments, the stem-loop structure located downstream of the poly-A sequence correlates with cleavage intensity.

Mechanisms for restricting or resolving L1 integration have also evolved for the sake of maintaining genetic integrity and stability of the genome. Non-homologous end joining repair proteins, such as XRCC1, Ku70 and DNA-PK, have been implicated in resolution of the L1 integrate at the time of insertion. In addition, the cell has evolved a number of proteins that stand against unrestricted retrotransposition, including the APOBEC3 family of cytosine deaminases, adenosine deaminase ADAR1, chromatin-remodeling factors and members of the piRNA pathway for post-transcription gene silencing that functions in the male germ line.

I. Compositions Comprising Nucleic Acid Constructs and Methods Involved for Stable Expression of Encoded Protein Provided herein is a recombinant nucleic acid encoding one or more proteins for expression in a cell, such as a myeloid cell. In one embodiment, the recombinant nucleic acid is designed for stable expression of the one or more proteins or polypeptides encoded by the recombinant nucleic acid. In some embodiments, the stable expression is achieved by incorporation of recombinant nucleic acid within the genome of the cell.

It can be easily understood by one of skill in the art that the compositions and methods described herein can be utilized to design products in which the recombinant nucleic acid may comprise one or more sequences that do not translate as a protein or a polypeptide component, but may encode an oligonucleotide that can be a regulatory nucleic acid, such as an inhibitor oligonucleotide product, such as an activator oligonucleotide.

In one aspect, provided herein is a composition comprising a synthetic nucleic acid, comprising a nucleic acid sequence encoding a gene of interest and one or more retrotransposable elements to stably incorporate a non-endogenous nucleic acid into a cell. In some embodiments, the cell is a hematopoietic cell. In some embodiments, the cell is a myeloid cell. In some embodiments, the cell is a precursor cell. In some embodiments, the cell is undifferentiated. In some embodiments, the cell has further differentiation potential. In some embodiments, the cell is not a stem cell.

A. LINE/Alu Retrotransposon Construct

In some embodiments, the present disclosure may utilize a retrotransposable system to stably incorporate into the genome and express a non-endogenous nucleic acid, where the non-endogenous nucleic acid comprises retrotransposable elements within the nucleic acid sequence. In some embodiments, the present disclosure may utilize a cell's endogenous retrotransposable system (e.g., proteins and enzymes), to stably express a non-endogenous nucleic acid in the cell. In some embodiments, the present disclosure may utilize a cell's endogenous retrotransposable system (e.g., proteins and enzymes, such as a LINE1 retrotransposition system), but may further express one or more components of the retrotransposable system to stably express a non-endogenous nucleic acid in the cell.

In some embodiments, a synthetic nucleic acid is provided herein, the synthetic nucleic acid encoding a transgene, and encoding one or more components for retrotransposition. The synthetic nucleic acid described herein is interchangeably termed as a nucleic acid construct, transgene or the exogenous nucleic acid.

In one aspect, provided herein is a method of integrating a nucleic acid sequence into a genome of a cell, the method comprising introducing a recombinant mRNA or a vector encoding an mRNA into the cell, wherein the mRNA comprises: an insert sequence, wherein the insert sequence comprises an exogenous sequence, or a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein, and wherein the insert sequence is integrated into the genome of the cell.

In some embodiments, the 5' UTR sequence or the 3' UTR sequence comprises a binding site for human ORF2p.

In one aspect, provided herein is a method for integrating a nucleic acid sequence into the genome of an immune cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; 5' UTR sequence and a 3' UTR sequence downstream of the 5' UTR sequence, wherein the 5' UTR sequence or the 3' UTR sequence comprises an endonuclease binding site and/or a reverse transcriptase binding site, and wherein the transgene sequence is integrated into the genome of the immune cell.

In one aspect, provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and/or a reverse transcriptase binding site, and wherein the sequence of a human retrotransposon encodes for two proteins that are translated from a single RNA containing two ORFs, and wherein the insert sequence is integrated into the genome of the cell.

In some embodiments, the 5' UTR sequence or the 3' UTR sequence comprises an ORF2p binding site. In some embodiments, the ORF2p binding site is a poly A sequence in the 3' UTR sequence.

In some embodiments, the mRNA comprises a sequence of a human retrotransposon. In some embodiments, the sequence of a human retrotransposon is downstream of the 5' UTR sequence. In some embodiments, the sequence of a human retrotransposon is upstream of the 3' UTR sequence.

In some embodiments, the sequence of a human retrotransposon encodes for two proteins that are translated from a single RNA containing two ORFs. In some embodiments, the two ORFs are non-overlapping ORFs. In some embodiments, the two ORFs are ORF1 and ORF2. In some embodiments, the ORF1 encodes ORF1p and ORF2 encodes ORF2p.

In some embodiments, the sequence of a human retrotransposon comprises a sequence of a non-LTR retrotransposon. In some embodiments, the sequence of a human retrotransposon encodes comprises a LINE-1 retrotransposon. In some embodiments, the LINE-1 retrotransposon is a human LINE-1 retrotransposon. In some embodiments, the sequence of a human retrotransposon comprises a sequence encoding an endonuclease and/or a reverse transcriptase. In some embodiments, the endonuclease and/or a reverse transcriptase is ORF2p. In some embodiments, the reverse transcriptase is a group II intron reverse transcriptase domain. In some embodiments, the endonuclease and/or a reverse transcriptase is a minke whale endonuclease and/or a reverse transcriptase. In some embodiments, the sequence of a human retrotransposon comprises a sequence encoding ORF2p. In some embodiments, the insert sequence is integrated into the genome at a poly T site using specificity of an endonuclease domain of the ORF2p. In some embodiments, the poly T site comprises the sequence TTTTTA.

In some embodiments, (i) the sequence of a human retrotransposon comprises a sequence encoding ORF1p, (ii) the mRNA does not comprise a sequence encoding ORF1p, or (iii) the mRNA comprises a replacement of the sequence encoding ORF1p with a 5' UTR sequence from the complement gene. In some embodiments, the mRNA comprises a first mRNA molecule encoding ORF1p, and a second mRNA molecule encoding an endonuclease and/or a reverse transcriptase. In some embodiments, the mRNA is an mRNA molecule comprising a first sequence encoding ORF1p, and a second sequence encoding an endonuclease and/or a reverse transcriptase. In some embodiments, the first sequence encoding ORF1p and the second sequence encoding an endonuclease and/or a reverse transcriptase are separated by a linker sequence.

In some embodiments, the linker sequence comprises an internal ribosome entry sequence (IRES). In some embodiments, the IRES is an IRES from CVB3 or EV71. In some embodiments, the linker sequence encodes a self-cleaving peptide sequence. In some embodiments, the linker sequence encodes a T2A, a E2A or a P2A sequence In some embodiments, the sequence of a human retrotransposon comprises a sequence that encodes ORF1p fused to an additional protein sequence and/or a sequence that encodes ORF2p fused to an additional protein sequence. In some embodiments, the ORF1p and/or the ORF2p is fused to a nuclear retention sequence. In some embodiments, the nuclear retention sequence is an Alu sequence. In some embodiments, the ORF1p and/or the ORF2p is fused to an MS2 coat protein. In some embodiments, the 5' UTR sequence or the 3' UTR sequence comprises at least one, two, three or more MS2 hairpin sequences. In some embodiments, the 5' UTR sequence or the 3' UTR sequence comprises a sequence that promotes or enhances interaction of a poly A tail of the mRNA with the endonuclease and/or a reverse transcriptase. In some embodiments, the 5' UTR sequence or the 3' UTR sequence comprises a sequence that promotes or enhances interaction of a poly-A-binding protein (PABP) with the endonuclease and/or a reverse transcriptase. In some embodiments, the 5' UTR sequence or the 3' UTR sequence comprises a sequence that increases specificity of the endonuclease and/or a reverse transcriptase to the mRNA relative to another mRNA expressed by the cell.

In some embodiments, the 5' UTR sequence or the 3' UTR sequence comprises an Alu element sequence.

In some embodiments, the first sequence encoding ORF1p and the second sequence encoding an endonuclease and/or a reverse transcriptase have the same promoter. In some embodiments, the insert sequence has a promoter that is different from the promoter of the first sequence encoding ORF1p. In some embodiments, the insert sequence has a promoter that is different from the promoter of the second sequence encoding an endonuclease and/or a reverse transcriptase. In some embodiments, the first sequence encoding ORF1p and/or the second sequence encoding an endonuclease and/or a reverse transcriptase have a promoter or transcription initiation site selected from the group consisting of an inducible promoter, a CMV promoter or transcription initiation site, a T7 promoter or transcription initiation site, an EF1a promoter or transcription initiation site and combinations thereof. In some embodiments, the insert sequence has a promoter or transcription initiation site selected from the group consisting of an inducible promoter, a CMV promoter or transcription initiation site, a T7 promoter or transcription initiation site, an EF1a promoter or transcription initiation site and combinations thereof.

In some embodiments, the first sequence encoding ORF1p and the second sequence encoding an endonuclease and/or a reverse transcriptase are codon optimized for expression in a human cell.

In some embodiments, the mRNA comprises a WPRE element. In some embodiments, the mRNA comprises a selection marker. In some embodiments, the mRNA comprises a sequence encoding an affinity tag. In some embodiments, the affinity tag is linked to the sequence encoding an endonuclease and/or a reverse transcriptase.

In some embodiments, the 3' UTR comprises a poly A sequence or wherein a poly A sequence is added to the mRNA in vitro. In some embodiments, the poly A sequence is downstream of a sequence encoding an endonuclease and/or a reverse transcriptase. In some embodiments, the insert sequence is upstream of the poly A sequence.

In some embodiments, the 3' UTR sequence comprises the insert sequence. In some embodiments, the insert sequence comprises a sequence that is a reverse complement of the sequence encoding the exogenous polypeptide. In some embodiments, the insert sequence comprises a polyadenylation site. In some embodiments, the insert sequence comprises an SV40 polyadenylation site. In some embodiments, the insert sequence comprises a polyadenylation site upstream of the sequence that is a reverse complement of the sequence encoding the exogenous polypeptide. In some embodiments, the insert sequence is integrated into the genome at a locus that is not a ribosomal locus. In some embodiments, the insert sequence integrates into a gene or regulatory region of a gene, thereby disrupting the gene or downregulating expression of the gene. In some embodiments, the insert sequence integrates into a gene or regulatory region of a gene, thereby upregulating expression of the gene. In some embodiments, the insert sequence integrates into the genome and replaces a gene. In some embodiments, the insert sequence is stably integrated into the genome. In some embodiments, the insert sequence is retrotransposed into the genome. In some embodiments, the insert sequence is integrated into the genome by cleavage of a DNA strand of a target site by an endonuclease encoded by the mRNA. In some embodiments, the insert sequence is integrated into the genome via target-primed reverse transcription (TPRT).

In some embodiments, the insert sequence is integrated into the genome via reverse splicing of the mRNA into a DNA target site of the genome.

In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell.

In some embodiments, the mRNA is a self-integrating mRNA. In some embodiments, the method comprises introducing into the cell the mRNA. In some embodiments, the method comprises introducing into the cell the vector encoding the mRNA. In some embodiments, the method comprises introducing the mRNA or the vector encoding the mRNA into a cell ex vivo. In some embodiments, the method further comprises administering the cell to a human subject. In some embodiments, the method comprises administering the mRNA or the vector encoding the mRNA to a human subject. In some embodiments, an immune response is not elicited in the human subject. In some embodiments, the mRNA or the vector is substantially non-immunogenic.

In some embodiments, the vector is a plasmid or a viral vector. In some embodiments, the vector comprises a non-LTR retrotransposon. In some embodiments, the vector comprises a human L1 element. In some embodiments, the vector comprises a L1 retrotransposon ORF1 gene. In some embodiments, the vector comprises a L1 retrotransposon ORF2 gene. In some embodiments, the vector comprises a L1 retrotransposon.

In some embodiments, the mRNA is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases.

In some embodiments, the mRNA comprises a payload that is at least about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 kilobases. In some embodiments, the mRNA is a most about 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 kilobases. In some embodiments, the mRNA is at least about 5.1, 5.2, 5.3, 5.4, 5.5, 5.6, 5.7, 5.8, 5.9 or 6 kilobases. In some embodiments, the mRNA is at least about 6.1, 6.2, 6.3, 6.4, 6.5, 6.6, 6.7, 6.8, 6.9 or 7 kilobases. In some embodiments, the mRNA is at least about 7.1, 7.2, 7.3, 7.4, 7.5, 7.6, 7.7, 7.8, 7.9 or 8 kilobases. In some embodiments, the mRNA is at least about 8.1, 8.2, 8.3, 8.4, 8.5, 8.6, 8.7, 8.8, 8.9 or 9 kilobases. In some embodiments, the mRNA is at least about 9.1, 9.2, 9.3, 9.4, 9.5, 9.6, 9.7, 9.8, 9.9 or 10 kilobases. In some embodiments, the mRNA is at least about 10.1, 10.2, 10.3, 10.4, 10.5, 10.6, 10.7, 10.8, 10.9 or 11 kilobases. In some embodiments, the mRNA is at least about 11.1, 11.2, 11.3, 11.4, 11.5, 11.6, 11.7, 11.8, 11.9 or 12 kilobases. In some embodiments, the mRNA comprises a payload of about 6.8 kB, e.g., a sequence encoding a ABCA4 gene product. In some embodiments, the mRNA comprises a payload of about 6.7 kB, e.g., a sequence encoding a MY07A gene product. In some embodiments, the mRNA comprises a payload of about 7.5 kB, e.g., a sequence encoding a CEP290 gene product. In some embodiments, the mRNA comprises a payload of about 10.1 kB, e.g., a sequence encoding a CDH23 gene product. In some embodiments, the mRNA comprises a payload of about 9.4 kB, e.g., a sequence encoding a EYS gene product. In some embodiments, the mRNA comprises a payload of about 15.6 kB, e.g., a sequence encoding a USH2a gene product. In some embodiments, the mRNA comprises a payload of about 12.5 kB, e.g., a sequence encoding a ALMS1 gene product. In some embodiments, the mRNA comprises a payload of about 4.6 kB, e.g., a sequence encoding a GDE gene product. In some embodiments, the mRNA comprises a payload of about 6 kB, e.g., a sequence encoding the OTOF gene product. In some embodiments, the mRNA comprises a payload of about 7.1 kB, e.g., a sequence encoding a F8 gene product.

One of the advantages of using the method of integration of a nucleic acid into the genome using retrotransposition is that it can be designed as described herein to deliver a nucleic acid cargo that is much larger than that using any other existing methods. For example, lentiviral and adeno-associated viral (AAV) gene delivery method are not expected to deliver a nucleic acid cargo of greater than 4 kB. In addition, lentiviral delivery entails risk of insertional mutagenesis and other toxicities. AAV mediated delivery entails unresolved liver and CNS toxicity. On the other hand, retrotransposition mediated method (Retro-T) using mRNA as described herein is rapid, safer and less complex than these viral methods.

In some embodiments, the mRNA comprises a sequence that inhibits or prevents degradation of the mRNA. In some embodiments, the sequence that inhibits or prevents degradation of the mRNA inhibits or prevents degradation of the mRNA by an exonuclease or an RNAse. In some embodiments, the sequence that inhibits or prevents degradation of the mRNA is a G quadruplex, pseudoknot or triplex sequence. In some embodiments, the sequence the sequence that inhibits or prevents degradation of the mRNA is an exoribonuclease-resistant RNA structure from a flaviviral RNA or an ENE element from KSV. In some embodiments, the sequence that inhibits or prevents degradation of the mRNA inhibits or prevents degradation of the mRNA by a deadenylase. In some embodiments, the sequence that inhibits or prevents degradation of the mRNA comprises non-adenosine nucleotides within or at a terminus of a poly A tail of the mRNA. In some embodiments, the sequence that inhibits or prevents degradation of the mRNA increases stability of the mRNA. In some embodiments, the exogenous sequence comprises a sequence encoding an exogenous polypeptide. In some embodiments, the sequence encoding an exogenous polypeptide is not in frame with a sequence encoding an endonuclease and/or a reverse transcriptase. In some embodiments, the sequence encoding an exogenous polypeptide is not in frame with a sequence encoding an endonuclease and/or a reverse transcriptase. In some embodiments, the exogenous sequence does not comprise introns. In some embodiments, the exogenous sequence comprises a sequence encoding an exogenous polypeptide selected from the group consisting of an enzyme, a receptor, a transport protein, a structural protein, a hormone, an antibody, a contractile protein and a storage protein. In some embodiments, the exogenous sequence comprises a sequence encoding an exogenous polypeptide selected from the group consisting of a chimeric antigen receptor (CAR), a ligand, an antibody, a receptor, and an enzyme. In some embodiments, the exogenous sequence comprises a regulatory sequence. In some embodiments, the regulatory sequence comprises a cis-acting regulatory sequence. In some embodiments, the regulatory sequence comprises a cis-acting regulatory sequence selected from the group consisting of an enhancer, a silencer, a promoter or a response element. In some embodiments, the regulatory sequence comprises a trans-acting regulatory sequence. In some embodiments, the regulatory sequence comprises a trans-acting regulatory sequence that encodes a transcription factor.

In some embodiments, integration of the insert sequence does not adversely affect cell health. In some embodiments, the endonuclease, the reverse transcriptase or both are capable of site-specific integration of the insert sequence.

In some embodiments, the mRNA comprises a sequence encoding an additional nuclease domain or a nuclease domain that is not derived from ORF2. In some embodiments, the mRNA comprises a sequence encoding a megaTAL nuclease domain, a TALEN domain, a Cas9 domain, a zinc finger binding domain from an R2 retroelement, or a DNA binding domain that binds to repetitive sequences such as a Rep78 from AAV. In some embodiments, the endonuclease comprises a mutation that reduces activity of the endonuclease compared to the endonuclease without the mutation. In some embodiments, the endonuclease is an ORF2p endonuclease and the mutation is S228P. In some embodiments, the mRNA comprises a sequence encoding a domain that increases fidelity and/or processivity of the reverse transcriptase. In some embodiments, the reverse transcriptase is a reverse transcriptase from a retroelement other than ORF2 or reverse transcriptase that has higher fidelity and/or processivity compared to a reverse transcriptase of ORF2p. In some embodiments, the reverse transcriptase is a group II intron reverse transcriptase. In some embodiments, the group II intron reverse transcriptase is a group IIA intron reverse transcriptase, a group IIB intron reverse transcriptase, or a group IIC intron reverse transcriptase. In some embodiments, the group II intron reverse transcriptase is TGIRT-II or TGIRT-III.

In some embodiments, the mRNA comprises a sequence comprising an Alu element and/or a ribosome binding aptamer. In some embodiments, the mRNA comprises a sequence encoding a polypeptide comprising a DNA binding domain. In some embodiments, the 3' UTR sequence is derived from a viral 3' UTR or a beta-globin 3' UTR.

In one aspect, provided herein is a composition comprising a recombinant mRNA or vector encoding an mRNA, wherein the mRNA comprises a human LINE-1 transposon sequence comprising a human LINE-1 transposon 5' UTR sequence, a sequence encoding ORF1p downstream of the human LINE-1 transposon 5' UTR sequence, an inter-ORF linker sequence downstream of the sequence encoding ORF1p, a sequence encoding ORF2p downstream of the inter-ORF linker sequence, and a 3' UTR sequence derived from a human LINE-1 transposon downstream of the sequence encoding ORF2p; wherein the 3' UTR sequence comprises an insert sequence, wherein the insert sequence is a reverse complement of a sequence encoding an exogenous polypeptide or a reverse complement of a sequence encoding an exogenous regulatory element.

In some embodiments, the insert sequence integrates into the genome of a cell when introduced into the cell. In some embodiments, the insert sequence integrates into a gene associated a condition or disease, thereby disrupting the gene or downregulating expression of the gene. In some embodiments, the insert sequence integrates into a gene, thereby upregulating expression of the gene. In some embodiments, the recombinant mRNA or vector encoding the mRNA is isolated or purified.

In one aspect, provided herein is a composition comprising a nucleic acid comprising a nucleotide sequence encoding (a) a long interspersed nuclear element (LINE) polypeptide, wherein the LINE polypeptide includes human ORF1p and human ORF2p; and (b) an insert sequence, wherein the insert sequence is a reverse complement of a sequence encoding an exogenous polypeptide or a reverse complement of a sequence encoding an exogenous regulatory element, wherein the composition is substantially non-immunogenic.

In some embodiments, the composition comprises human ORF1p and human ORF2p proteins. In some embodiments, the composition comprises a ribonucleoprotein (RNP) comprising human ORF1p and human ORF2p complexed to the nucleic acid. In some embodiments, the nucleic acid is mRNA.

In one aspect, provided herein is a composition comprising a cell comprising a composition described herein. In some embodiments, the cell is an immune cell. In some embodiments, the immune cell is a T cell or a B cell. In some embodiments, the immune cell is a myeloid cell. In some embodiments, the immune cell is selected from a group consisting of a monocyte, a macrophage, a dendritic cell, a dendritic precursor cell, and a macrophage precursor cell. In some embodiments, the insert sequence is a reverse complement of a sequence encoding an exogenous polypeptide and the exogenous polypeptide is a chimeric antigen receptor (CAR).

In one aspect, provided herein is a pharmaceutical composition comprising a composition described herein, and a pharmaceutically acceptable excipient. In some embodiments, the pharmaceutical composition is for use in gene therapy. In some embodiments, the pharmaceutical composition is for use in the manufacture of a medicament for treating a disease or condition. In some embodiments, the pharmaceutical composition is for use in treating a disease or condition. In one aspect, provided herein is a method of treating a disease in a subject, comprising administering a pharmaceutical composition described herein to a subject with a disease or condition. In some embodiments, the method increases an amount or activity of a protein or functional RNA in the subject. In some embodiments, the subject has a deficient amount or activity of a protein or functional RNA. In some embodiments, the deficient amount or activity of a protein or functional RNA is associated with or causes the disease or condition.

In some embodiments, the method further comprising administering an agent that inhibits human silencing hub (HUSH) complex, an agent that inhibits FAM208A, or an agent that inhibits TRIM28. In some embodiments, the agent that inhibits human silencing hub (HUSH) complex is an agent that inhibits Periphilin, TASOR and/or MPP8. In some embodiments, the agent that inhibits human silencing hub (HUSH) complex inhibits assembly of the HUSH complex.

In some embodiments, the agent inhibits the fanconia anemia complex. In some embodiments, the agent inhibits FANCD2-FANC1 heterodimer monoubiquitination. In some embodiments, the agent inhibits FANCD2-FANC1 heterodimer formation. In some embodiments the agent inhibits the Fanconi Anemia (FA) core complex. FA core complex is a component of the fanconi anemia DNA damage repair pathway, e.g., in chemotherapy induced DNA inter-strand crosslinks. The FA core complex comprises two central dimers of the FANCB and FA-associated protein of 100 kDa (FAAP100) subunits, flanked by two copies of the RING finger subunit, FANCL. These two heterotrimers act as a scaffold to assemble the remaining five subunits, resulting in an extended asymmetric structure. Destabilization of the scaffold would disrupt the entire complex, resulting in a non-functional FA pathway. Examples of agents that can inhibit the FA core complex include Bortezomib and curcumin analogs EF24 and 4H-TTD.

In some embodiments, the sequences to be inserted may be placed under the control of tissue-specific elements, such that the entire inserted DNA is only functional in those cells in which the tissue-specific element is active.

In one aspect, provided herein are method and compositions for stable gene transfer to a cell by introducing to the cell a heterologous nucleic acid or gene of interest (e.g., a transgene, a regulatory sequence, for example, a sequence for an inhibitory nucleic acid, an siRNA, a miRNA), flanked by sequences that cause retrotransposition of the heterologous nucleic acid sequence into the genome of the cell. In some embodiments, the heterologous nucleic acid is termed insert for the purpose of the description in this document, where the insert is the nucleic acid sequence that will be reverse transcribed and inserted into the genome of the cell by the intended design of the constructs described herein. In some embodiments, the heterologous nucleic acid is also termed the cargo, or cargo sequence for the purpose of the description in this document. The cargo can comprise the sequence of the heterologous nucleic acid that that is inserted in the genome. In some embodiments, the cell may be a cell mammalian cell. The mammalian cell may be of epithelial, mesothelial or endothelial origin. In some embodiments, the cell may be a stem cell. In some embodiments, the cell may be a precursor cell. In some embodiments, the cell may be a cell that is terminally differentiated. In some embodiments, the cell may be a muscle cell, a cardiac cell, an epithelial cell, a hematopoietic cell, a mucous cell, an epidermal cell, a squamous cell, a cartilage cell, a bone cell, or any cell of mammalian origin. In some embodiments, the cell is of hematopoietic lineage. In some embodiments, he cell is of myeloid lineage, or a phagocytic cell, for example a monocyte, macrophage, a dendritic cell or a myeloid precursor cell. In some embodiments, the nucleic acid encoding the transgene is an mRNA.

In some embodiments, the retrotransposable elements may be derived from a non-LTR retrotransposon.

Provided herein is a method of integrating a nucleic acid sequence into a genome of a cell, the method comprising introducing a recombinant mRNA or a vector encoding an mRNA into the cell, wherein the mRNA comprises an insert sequence and wherein the insert sequence is integrated into the genome of the cell. In some embodiments, the insert sequence comprises (i) an exogenous sequence, or (ii) a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein. In some embodiments, the ORF protein is a human LINE 1 ORF2 protein. In some embodiments, the ORF protein is a non-human ORF protein. In some embodiments, the ORF protein is a chimeric protein, a recombinant protein or an engineered protein.

Provided herein is a method for integrating a nucleic acid sequence into the genome of an immune cell, the method comprising introducing a recombinant mRNA or a vector encoding an mRNA, wherein the mRNA comprises, (a) an insert sequence, wherein the insert sequence comprises (i) an exogenous sequence or (ii) a sequence that is a reverse complement of the exogenous sequence; (b) 5' UTR sequence and a 3' UTR sequence downstream of the 5' UTR sequence, wherein the 5' UTR sequence or the 3' UTR sequence comprises an endonuclease binding site and a reverse transcriptase binding site, and wherein the transgene sequence is integrated into the genome of the immune cell.

In some embodiments, the structural elements that mediate RNA integration or transposition may be encoded in a synthetic construct and are relied upon to deliver a heterologous gene of interest to the cell. In some embodiments, the synthetic construct may comprise a nucleic acid encoding the heterologous gene of interest and the structural elements that cause integration or retrotransposition of a heterologous gene of interest into the genome. In some embodiments, the structural elements that cause integration or retrotransposition may include a 5' L1 RNA region, and a 3'-L1 region, the latter comprising a poly A 3' region for priming. In some embodiments, the 5' L1 RNA region may comprise one or more stem loop regions. In some embodiments, the L1-3' region may comprise one or more stem loop regions. In some embodiments, the 5'- and 3' L1 regions are constructed as flanking the nucleic acid sequence encoding the heterologous gene of interest (the transgene). In some embodiments, the structural elements may include a region from an L1 or an Alu RNA comprising the hairpin loop structure that includes the A-Box and the B-Box elements that are ribosomal binding sites In some embodiments, the synthetic nucleic acid may comprise a L1-Ta promoter.

There may be two types of LINE RNA recognition by ORF2p— the stringent and the relaxed. In the stringent type RT recognizes its own 3'UTR tail, and in the relaxed type RT does not require any specific recognition except for the poly-A tail. Division into the stringent and the relaxed type came from the observation that some LINE/SINE pairs share the same 3'-end. For the stringent type, the experimental studies showed that a 3'UTR stem-loop promotes retrotransposition. The 5'-UTR of the LINE retrotransposition sequences have been shown to contain three conserved stem loop regions.

In some embodiments, the transgene, or transcript of interest may be flanked by transposable elements from a L1 or an Alu sequence at the 5' and the 3' end. In some embodiments, the 5' region of a retrotransposon comprises an Alu sequence. In some embodiments, the 3' region of a retrotransposon comprises an Alu sequence. In some embodiments, the 5' region of a retrotransposon comprises an L1 sequence. In some embodiments, the 3' region of a retrotransposon comprises an L1 sequence. In some embodiments, the transgene or transcript of interest is flanked by an SVA transposon sequence.

In some embodiments, the transcript of interest may comprise an L1 or an Alu sequence, encoding the binding regions for ORF2p and the 3'-poly A priming regions. In some embodiments, the heterologous nucleic acid encoding the transgene of interest may be flanked by an L1 or an Alu sequence, encoding the binding regions for ORF1p and the 3'-poly A priming regions. The 3'-region may comprise one or more stem loop structures. In some embodiments, the transcript of interest is structured for cis integration or retrotransposition. In some embodiments, the transcript of interest is structured for trans integration or retrotransposition.

In some embodiments, the retrotransposon is a human retrotransposon. The sequence of a human retrotransposon can comprise a sequence encoding an endonuclease and/or a reverse transcriptase. The sequence of a human retrotransposon can encode for two proteins that are translated from a single RNA containing two non-overlapping ORFs. In some embodiments, the two ORFs are ORF1 and ORF2.

Accordingly, provided herein is a method for stably integrating a heterologous nucleic acid encoding a transgene into the genome of a cell, such as a myeloid cell, the method comprising introducing to the cell a nucleic acid encoding: the transgene; one or more 5'nucleic acid sequences flanking the region encoding the transgene, comprising a 5' region of a retrotransposon; and one or more 3' nucleic acid sequence flanking the region encoding the transgene, comprising a 3' region of a retrotransposon, wherein the 3' region of the retrotransposon comprises a genomic DNA priming sequence and a LINE transposase binding sequence, having the respective endonuclease and reverse transcriptase (RT) activity.

Provided herein is a method for integrating a nucleic acid sequence into the genome of a cell, the method comprising introducing a recombinant mRNA or a vector encoding an mRNA, wherein the mRNA comprises an insert sequence, wherein the insert sequence comprises (i) an exogenous sequence or (ii) a sequence that is a reverse complement of the exogenous sequence; (b) a 5' UTR sequence, a sequence of a human retrotransposon downstream of the 5' UTR sequence, and a 3' UTR sequence downstream of the sequence of a human retrotransposon; wherein the 5' UTR sequence or the 3' UTR sequence comprises an endonuclease binding site and a reverse transcriptase binding site, and wherein the sequence of a human retrotransposon encodes for two proteins that are translated from a single RNA containing two ORFs, and wherein the insert sequence is integrated into the genome of the cell.

In some embodiments, the method comprising using a single nucleic acid molecule for delivering and integrating the insert sequence into the genome of a cell. The single nucleic acid molecule may be a plasmid vector. The single nucleic acid may be DNA or an RNA molecule. The single nucleic acid may be an mRNA.

In some embodiments, the method comprises introducing into a cell one or more polynucleotides comprising the human retrotransposon and a heterologous nucleic acid sequence. In some embodiments, the one or more polynucleotides comprises (i) a first nucleic acid molecule encoding an ORF1p; (ii) a second nucleic acid molecule encoding an ORF2p and a sequence encoding a cargo. In some embodiments, the first nucleic acid and the second nucleic acid are mRNA. In some embodiments, the first nucleic acid and the second nucleic acid are DNA, e.g., encoded in separate plasmid vectors.

Provided herein is a self-integrating polynucleotide that comprises a sequence which is inserted into the genome of a cell, and insert is stably integrated into the genome by the self-integrating naked polynucleotide. In some embodiments, the polynucleotide is an RNA. In some embodiments, the polynucleotide is an mRNA. In some embodiments, the polynucleotide is an mRNA that has modifications. In some embodiments, the modifications ensure protection against RNases in the intracellular milieu. In some embodiments, the modifications include substituted modified nucleotides, e.g., 5-methylcytidine, pseudouridine or 2-thiouridine.

In some embodiments, a single polynucleotide is used for delivery and genomic integration of the insert (or cargo) nucleic acid. In some embodiments, the single polynucleotide is bicistronic. In some embodiments, the single polynucleotide is tricistronic. In some embodiments, the single polynucleotide is multi-cistronic. In some embodiments, a two or more polynucleotide molecules are used for delivery and genomic integration of the insert (or cargo) nucleic acid.

In some embodiments, a retrotransposable genetic element may be generated, the retrotransposable genetic element comprising (i) a heterologous nucleic acid encoding a transgene or a non-coding sequence to be inserted into the genome of a cell (the insert); (ii) a nucleic acid sequence encoding one or more retrotransposon ORF-encoding sequences; (iii) one or more UTR regions of the ORF-coding sequences, such that the heterologous nucleic acid encoding a transgene or a non-coding sequence to be inserted is comprised within the UTR sequences; wherein the 3' region of the retrotransposon ORF-encoding sequences comprises a genomic DNA priming sequence.

In some embodiments, the retrotransposable genetic element may be introduced into a cell for stably integrating the transgene into the genomic DNA. In some embodiments, the retrotransposable genetic element comprises (a) a retrotransposon protein coding sequence, and a 3' UTR; and (b) a sequence comprising a heterologous nucleic acid that is to be inserted (e.g., integrated) within the genome of a cell. The retrotransposon protein coding sequence, and the 3' UTR may be a complete and sufficient unit for delivering the heterologous nucleic acid sequence within the genome of the cell, and comprise the retrotransposable elements, such as an endonuclease, a reverse transcriptase, a sequence in the 3' UTR for binding to and priming the genomic DNA at the region cleaved by the endonuclease to start reverse transcribing and incorporating the heterologous nucleic acid.

In some embodiments, the coding sequence of the insert is in forward orientation with respect to the coding sequence of the one or more ORFs. In some embodiments, the coding sequence of the insert is in reverse orientation with respect to the coding sequence of the one or more ORFs. The coding sequence of the insert and the coding sequence of the one or more ORFs may comprise distinct regulatory elements, including 5' UTR, 3' UTR, promoter, enhancer, etc. In some embodiments, the 3' UTR or the 5'-UTR of the insert may comprise the coding sequence of the one or more ORFs, and likewise, the coding sequence of the insert may be situated within in the 3' UTR of the coding sequence of the one or more ORFs.

In some embodiments, a retrotransposable genetic element may be generated, the retrotransposable genetic element comprising: (a) an insert sequence, comprising (i) an exogenous sequence, a sequence that is a reverse complement of the exogenous sequence; a 5' UTR sequence and a 3' UTR sequence downstream of the 5' UTR sequence; wherein the 5' UTR sequence or the 3' UTR sequence comprises a binding site for a human ORF protein.

In some embodiments, the retrotransposon may comprise a SINE or LINE element. In some embodiments, the retrotransposon comprises a SINE or LINE stem loop structure, such as an Alu element.

In some embodiments, the retrotransposon is a LINE-1 (L1) retrotransposon. In some embodiments, the retrotransposon is human LINE-1. Human LINE-1 sequences are abundant in the human genome. There are approximately 13,224 total human L1s, of which 480 are active, which make up about 3.6%. Therefore, human L1 proteins are well tolerated and non-immunogenic in humans. Moreover, a tight regulation of random transposition in human ensures that random transposase activity will not be triggered by introduction of the L1 system as described herein. In addition, the retrotransposable constructs designed herein may comprise targeted and specific incorporation of the insert sequence. In some embodiments, the retrotransposable genetic element may comprise designs intended to overcome the silencing machinery actively prevalent in human cells, while being careful that random integration resulting in genomic instability is not initiated.

Accordingly, the retrotransposable constructs may comprise a sequence encoding a human LINE-1 ORF1 protein; and a human LINE-1 ORF2 protein. In some embodiments, the construct comprises a nucleic acid sequence encoding an ORF1p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 53)
MGKKQNRKTGNSKTQSASPPPKERSSSPATEQSWMENDFDELREEGF

RRSNYSELREDIQTKGKEVENFEKNLEECITRITNTEKCLKELMELK

TKARELREECRSLRSRCDQLEERVSAMEDEMNEMKREGKFREKRIKR

NEQSLQEIWDYVKRPNLRLIGVPESDVENGTKLENTLQDIIQENFPN

LARQANVQIQEIQRTPQRYSSRRATPRHIIVRFTKVEMKEKMLRAAR

EKGRVTLKGKPIRLTVDLSAETLQARREWGPIFNILKEKNFQPRISY

PAKLSFISEGEIKYFIDKQMLRDFVTTRPALKELLKEALNMERNNRY

QPLQNHAKM.

In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 54)
atgggcaagaagcaaaatcgcaagacggggaattccaagacacaatc cgctagcccaccacctaaagagcgttctagctcccctgctactgagc agtcctggatggaaaacgacttcgatgaactccgggaagagggattt aggcgatccaactattcagaactccgcgaagatatccagacaaggg gaaggaagtcgagaatttcgagaagaacctcgaggagtgcatcaccc gtatcacaaacactgagaaatgtctcaaagaactcatggaacttaag acaaaagccagggagcttcgagaggagtgtcggagtctgagatccag gtgtgaccagctcgaggagcgcgtgagcgcgatggaagacgagatga acgagatgaaaagagagggcaaattcagggagaagcgcattaagagg aacgaacagagtctgcaggagatttgggattacgtcaagaggcctaa cctgcggttgatcggcgtccccgagagcgacgtagaaaacgggacta aactggagaatacacttcaagacatcattcaagaaaattttccaaac ctggctcggcaagctaatgtgcaaatccaagagatccaacgcacacc ccagcggtatagctctcggcgtgccacccctaggcatattatcgtgc gctttactaaggtggagatgaaagagaagatgctgcgagccgctcgg gaaaagggaagggtgactttgaagggcaaacctattcggctgacggt tgaccttagcgccgagacactccaggcacgccgggaatggggccca tctttaatatcctgaaggagaagaacttccagccacgaatctcttac cctgcaaagttgagttttatctccgagggtgagattaagtatttcat cgataaacagatgctgcgagacttcgtgacaactcgccagctctca aggaactgctcaaagaggctcttaatatggagcgcaataatagatat caacccttgcagaaccacgcaaagatgtga.

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 55)
MTGSNSHITILTLNINGLNSAIKRHRLASWIKSQDPSVCCIQETHLTC
RDTHRLKIKGWRKIYQANGKQKKAGVAILVSDKTDFKPTKIKRDKEGH
YIMVKGSIQQEELTILNIYAPNTGAPRFIKQVLSDLQRDLDSHTLIMG
DFNTPLSTLDRSTRQKVNKDTQELNSALHQADLIDIYRTLHPKSTEYT
FFSAPHHTYSKIDHIVGSKALLSKCKRTEIITNYLSDHSAIKLELRIK
NLTQSRSTTWKLNNLLLNDYWVHNEMKAEIKMFFETNENKDTTYQNLW
DAFKAVCRGKFIALNAYKRKQERSKIDTLTSQLKELEKQEQTHSKASR
RQEITKIRAELKEIETQKTLQKINESRSWFFERINKIDRPLARLIKKK
REKNQIDTIKNDKGDITTDPTEIQTTIREYYKHLYANKLENLEEMDTF
LDTYTLPRLNQEEVESLNRPITGSEIVAIINSLPTKKSPGPDGFTAEF
YQRYMEELVPFLLKLFQSIEKEGILPNSFYEASIILIPKPGRDTTKKE
NFRPISLMNIDAKILNKILANRIQQHIKKLIHHDQVGFIPGMQGWFNI
RKSINVIQHINRAKDKNHMIISIDAEKAFDKIQQPFMLKTLNKLGIDG
TYFKIIRAIYDKPTANIILNGQKLEAFPLKTGTRQGCPLSPLLFNIVL
EVLARAIRQEKEIKGIQLGKEEVKLSLFADDMIVYLENPIVSAQNLLK
LISNFSKVSGYKINVQKSQAFLYTNNRQTESQIMGELPFVIASKRIKY
LGIQLTRDVKDLFKENYKPLLKEIKEDTNKWKNIPCSWVGRINIVKMA
ILPKVIYRFNAIPIKLPMTFFTELEKTTLKFIWNQKRARIAKSILSQK
NKAGGITLPDFKLYYKATVTKTAWYWYQNRDIDQWNRTEPSEIMPHIY
NYLIFDKPEKNKQWGKDSLFNKWCWENWLAICRKLKLDPFLTPYTKIN
SRWIKDLNVKPKTIKTLEENLGITIQDIGVGKDFMSKTPKAMATKDKI
DKWDLIKLSFCTAKETTIRVNRQPTTWEKIFATYSSDKGLISRIYNE
LKQIYKKKTNNPIKKWAKDMNRHFSKEDIYAAKKHMKKCSSSLAIREM
QIKTTMRYHLTPVRMAIIKKSGNNRCWRGCGEIGTLLHCWWDCKLVQP
LWKSVWRFLRDLELEIPFDPAIPLLGIYPNEYKSCCYKDTCTRMFIAA
LFTIAKTWNQPKCPTMIDWIKKMWHIYTMEYYAAIKNDEFISFVGTWM
KLETIILSKLSQEQKTKHRIFSLIGGN In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 56)
atgaccggctctaactcacatatcaccatccttacacttaacattaacggcctcaactcagctatcaagcgccatcggctggccagctgga
tcaaatcacaggatccaagcgtttgttgcatccaagagacccacctgacctgtagagatactcaccgcctcaagatcaagggatggcgaaa
gatttatcaggcgaacggtaagcagaagaaagccggagtcgcaattctggtctcagacaagacggatttcaagcccaccaaaattaagcgt
gataaggaaggtcactatattatggtgaaaggcagcatacagcaggaagaacttaccatattgaacatctacgcgccaaacaccggcgcac
ctcgctttatcaaacaggtcctgtccgatctgcagcgagatctggattctcatacgttgattatgggtgatttcaatacaccattgagcac
cctggatcgcagcaccaggcaaaaggtaaataaagacacgcaagagctcaatagcgcactgcatcaggcagatctcattgatatttatcgc
actcttcatcctaagagtaccgagtacacattcttcagcgccccacatcatacactcaaagatcgatcatatcgtcggctcaaaggctc
tgctgtcaaagtgcaagcgcacagagataattacaaattacctgtcagatcatagcgcgatcaagctcgagctgagaatcaagaacctgac
ccagagccggagtaccacttggaagcttaataacctgctgctcaacgattattgggtccacaatgagatgaaggcagagattaaaatgttc
ttcgaaacaaatgagaataaggatactacctatcaaaaccctttgggatgcctttaaggccgtctgcagaggcaagttcatcgccctcaacg
cctataaaagaaaacaagagagatctaagatcgatactctcacctctcagctgaaggagttggagaaacaggaacagacccactccaaggc
gtcaagacggcaggagatcacaaagattcgcgccgagttgaaagagatcgaaacccaaaagactcttcagaaaattaacgagtctcgtagt
tggttcttcgagcggattaataagatagacagacctctggcacgactgattaagaagaagcgcgaaaagaaccagattgataccatcaaga
acgacaagggcgacatcactactgacccgaccgagatccagaccactattcgggagtattataagcatttgtatgctaacaagcttgagaa
cctggaagagatggacacttttctggatacctatactctgccacggcttaatcaagaggaagtcgagtccctcaaccgcccaattacagga
agcgagattgtggccataattaactccctgccgacaaagaaatcctcctggtccggacggggtttacagctgagttttatcaacggtatatgg
aagagcttgtaccgtttctgctcaagctctttcagtctatagaaaaggaaggcatcttgcccaattccttctacgaagcttctataatact
tattcccaaaccaggacgcgataccacaaagaaggaaaacttccggcccattagtctcatgaatatcgacgctaaaatattgaacaagatt
ctcgccaacagaatccaacaacatattaagaaattgatacatcacgaccaggtggggtttatacctggcatgcagggctggtttaacatcc
ggaagagtattaacgtcattcaacacattaatagagctaaggataagaatcatatgatcatctctatagacgcggaaaaggcattcgataa
gattcagcagccatttatgctcaagactctgaacaaactcggcatcgacggaacatatttttaagattattcgcgcaatttacgataagccg -continued

```
actgctaacattatccttaacggccaaaagctcgaggcctttccgctcaagactggaacccgccaaggctgtcccctctcccgcttttgt ttaatattgtactcgaggtgctggctagggctattcgtcaagagaaagagattaaagggatacagctcgggaaggaagaggtcaagctttc cttgttcgccgatgatatgattgtgtacctggagaatcctattgtgtctgctcagaaccttcttaaacttatttctaactttagcaaggtc agcggctataagattaacgtccagaaatctcaggcctttctgtacacaaataatcgacagaccgaatcccagataatgggtgagcttccgt ttgtcatagccagcaaaaggataaagtatctcggaatccagctgacacgagacgttaaagatttgtttaaggaaaattacaagcctctcct gaaagagattaaggaagatactaataagtggaagaatatcccctgttcatgggttggcagaatcaacatagtgaagatggcaatacttcct aaagtgatatatcgctttaacgccatcccaattaaactgcctatgaccttctttacggagctcgagaaaacaacccttaaatttatatgga atcaaaagagagcaagaatagcgaagtccatcttgagccagaagaataaggccgtgggattactttgcctgattttaagttgtattataa agccacagtaactaagacagcctggtattggtatcagaatagagacatcgaccagtggaatcggaccgaaccatcagagataatgccccac atctataattaccttatattcgataagccagaaaagaataaacagtggggcaaagacagcctcttcaacaagtggtgttgggagaattggc tggccatatgccggaaactcaagctcgaccccttcttacaccctacactaaaatcaacagtaggtggatcaaggacttgaatgtcaagcc aaagactataaagacactggaagagaatcttgggatcacaatacaagatataggcgtcggcaaagattttatgtcaaagacgcccaaggcc atggccactaaggataagattgataagtgggaccttattaagctcaaaagcttctgtactgccaaggagaccacgatcagagttaataggc agcccactacatgggaaagattttcgccacttattcatcagataaggggttgataagcagaatatataacgagctgaagcagatctacaa gaagaaaacgaataatcccatcaagaagtgggcaaaagatatgaacaggcattttagcaaagaggatatctacgccgcgaagaagcatatg aagaagtgtagttcaagcttggccattcgtgagatgcagattaagacgaccatgcgataccaccttaccccagtgaggatggcaattatca agaaatctggcaataatagatgttggcggggctgtggcgagattggcaccctgctccattgctggtgggattgcaagctggtgcagccgct ttggaaatcagtctggcgctttctgagggacctcgagcttgagattcccttcgatcccgcaattccttgctcggaatctatcctaacgaa tacaagagctgttgttacaaggatacgtgtacccggatgttcatcgcggcctgtttacgatagctaagacgtgaatcagcctaagtgcc ccacaatgatcgattggatcaagaaaatgtggcatatttataccatggagtattacgcagcaattaagaatgacgaatttatttccttcgt tgggacctggatgaagctggagactattattctgagcaagctgtctcaggagcaaaagacaaagcatagaatcttctctctcattggtggt aactaa.
```

In some embodiments, the construct comprises a nucleic acid sequence encoding an ORF2p protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to

```
                                           (SEQ ID NO: 57)
MVIGTYISIITLNVNGLNAPTKRHRLAEWIQKQDPYICCLQETHFRPRDTYRLKVRGW

KKIFHANGNQKKAGVAILISDKIDFKIKNVTRDKEGHYIMIQGSIQEEDITIINIYAP

NIGAPQYIRQLLTAIKEEIDSNTIIVGDFNTSLTPMDRSSKMKINKETEALNDTIDQI

DLIDIYRTFHPKTADYTFFSSAHGTFSRIDHILGHKSSLSKFKKIEIISSIFSDHNAM

RLEMNHREKNVKKTNTWRLNNTLLNNQEITEEIKQEIKKYLETNDNENTTTQNLWDAA

KAVLRGKFIAIQAYLKKQEKSQVNNLTLHLKKLEKEEQTKPKVSRRKEIIKIRAEINE

IETKKTIAKINKTKSWFFEKINKIDKPLARLIKKKRERTQINKIRNEKGEVTTDTAEI

QNILRDYYKQLYANKMDNLEEMDKFLERYNLPRLNQEETENINRPITSNEIETVIKNL

PTNKSPGPDGFTGEFYQTFREELTPILLKLFQKIAEEGTLPNSFYEATITLIPKPDKD

TTKKENYRPISLMNIDAKILNKILANRIQQHIKRIIHHDQVGFIPGMQGFFNIRKSIN

VIHHINKLKKKNHMIISIDAEKAFDKIQHPFMIKTLQKVGIEGTYLNIIKAIYDKPTA

NIILNGEKLKAFPLRSGTRQGCPLSPLLFNIVLEVLATAIREEKEIKGIQIGKEEVKL
```

-continued

```
SLFADDMILYIENPKTATRKLLELINEYGKVAGYKINAQKSLAFLYTNDEKSEREIME

TLPFTIATKRIKYLGINLPKETKDLYAENYKTLMKEIKDDTNRWRDIPCSWIGRINIV

KMSILPKAIYRFNAIPIKLPMAFFTELEQIILKFVWRHKRPRIAKAVLRQKNGAGGIR

LPDFRLYYKATVIKTIWYWHKNRNIDQWNKIESPEINPRTYGQLIYDKGGKDIQWRKD

SLFNKWCWENWTATCKRMKLEYSLTPYTKINSKWIRDLNIRLDTIKLLEENIGRTLFD

INHSKIFFDPPPRVMEIKTKINKWDLMKLQSFCTAKETINKTKRQPSEWEKIFANEST

DKGLISKIYKQLIQLNIKETNTPIQKWAEDLNRHFSKEDIQTATKHMKRCSTSLIIRE

MQIKTTMRYHLTPVRMGIIRKSTNNKCWRGCGEKGTLLHCWWECKLIQPLWRTIWRFL

KKLKIELPYDPAIPLLGIYPEKTVIQKDTCTRMFIAALFTIARSWKQPKCPSTDEWIK

KMWYIYTMEYYSAIKRNEIGSFLETWMDLETVIQSEVSQKEKNKYRILTHICGTWKNG

TDEPVCRTEIETQM
```

In some embodiments, the construct comprises a nucleic acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 58)

```
atggtcataggaacatacatatcgataattaccttaaacgtgaatggattaaatgccccaaccaaaagacatagactggctgaatgg atacaaaaacaagacccatatatgctgtctacaagagacccacttcagacctagggacacatacagactgaaagtgaggggatgg aaaaagatattccatgcaaatggaaatcaaaagaaagctggagtagctatactcatatcagataaaatagactttaaaataaagaat gttacaagagacaaggaaggacactacataatgatccagggatcaatccaagaagaagatataacaattataaatatatatgcaccc aacataggagcacctcaatacataaggcaactgctaacagctataaaagagggaaatcgacagtaacacaataatagtgggggacttt aacacctcacttacaccaatggacagatcatccaaaatgaaaataaataaggaaacagaagctttaaatgacacaatagaccagata gatttaattgatatatataggacattccatccaaaaacagcagattacacgttcttctcaagtgcgcacggaacattctccaggata gatcacatcttgggtcacaaatcaagcctcagtaaatttaagaaaattgaaatcatatcaagcatcttttctgaccacaacgctatg agattagaaatgaatcacagggaaaaaaacgtaaaaaagacaaacacatggaggctaaacaatacgttactaaataaccaagagatc actgaagaaatcaaacaggaaataaaaaaatacctagagacaaatgacaatgaaaacacgacgacccaaaacctatgggatgcagca aaagcggttctaagagggaagtttatagctatacaagcctacctaaagaaacaagaaaaatctcaagtaaacaatctaaccttacac ctaaagaaactagagaagaagaacaaacaaaacccaaagttagcagaaggaaagaaatcataaagatcagagcagaaataaatgaa atagaaacaaagaaaacaatagcaaagatcaataaaactaaaagttggttctttgagaagataaacaaaattgataagccattagcc agactcatcaagaaaagagggagaggactcaaatcaataaaatcagaaatgaaaaaggagaagttacaacagacaccgcagaaata caaaacatcctaagagactactacaagcaactttatgccaataaaatggacaacctggaagaaatggacaaattcttagaaaggtat aaccttccaagactgaaccaggaagaaacagaaaatatcaacagaccaatcacaagtaatgaaattgaactgtgattaaaaatctt ccaacaaacaaaagtccaggaccagatggcttcacaggtgaattctatcaaacatttagagaagagctaacacccatccttctcaaa ctcttccaaaaaattgcagaagaaggaacactcccaaactcattctatgaggccaccatcaccctgataccaaaaccagacaaagac actacaaaaaagaaaattacagaccaatatcactgatgaatatagatgcaaaaatcctcaacaaaatactagcaaacagaatccaa caacacattaaaaggatcatacaccacgatcaagtgggatttatcccagggatgcaaggattcttcaatatacgcaaatcaatcaat gtgatacaccatattaacaaattgaagaagaaaaaccatatgatcatctcaatagatgcagaaaaagcttttgacaaaattcaacac ccatttatgataaaaactctccagaaagtgggcatagagggaacctacctcaacataataaaggccatatatgacaaacccacagca aacatcattctcaatggtgaaaaactgaaagcatttcctctaagatcaggaacgagacaaggatgtccactctcaccactattattc
```

```
aacatagttctggaagtcctagccacggcaatcagagaagaaaaagaaataaaaggaatacaaattggaaaagaagaagtaaaactg tcactgtttgcggatgacatgatactatacatagagaatcctaaaactgccaccagaaaactgctagagctaattaatgaatatggt aaagttgcaggttacaaaattaatgcacagaaatctcttgcattcctatacactaatgatgaaaaatctgaaagagaaattatggaa acactcccatttaccattgcaacaaaaagaataaaatacctaggaataaaacctacctaaggagacaaaagacctgtatgcagaaaac tataagacactgatgaaagaaattaaagatgataccaacagtggagagatataccatgttcttggattggaagaatcaacattgtg aaaatgagtatactacccaaagcaatctacagattcaatgcaatccctatcaaattaccaatggcatttttacggagctagaacaa atcatcttaaaatttgtatggagacacaaaagaccccgaatagccaaagcagtcttgaggcaaaaaaatggagctggaggaatcaga ctccctgacttcagactatactacaaagctacagtaatcaagacaatatggtactggcacaaaaacagaaacatagatcaatggaac aagatagaaagcccagagattaacccacgcacctatggtcaactaatctatgacaaaggaggcaaagatataacaatggagaaaagac agtctcttcaataagtggtgctgggaaaactggacagccacatgtaaaagaatgaaattagaatactccctaacaccatacacaaaa ataaactcaaaatggattagagacctaaatataagactggacactataaaactcttagaggaaaacataggaagaacactctttgac ataaatcacagcaagatcttttttcgatccacctcctagagtaatggaaataaaaacaaaaataaacaagtgggacctaatgaaactt caaagcttttgcacagcaaaggaaaccataaacaagacgaaaagacaaccctcagaatgggagaaaatatttgcaaatgaatcaacg gacaaaggattaatctccaaaatatataaacagctcattcagctcaatatcaaagaaacaaacaccccaatccaaaaatgggcagaa gacctaaatagacatttctccaaagaagacatacagacggccacgaagcacatgaaaagatgctcaacatcactaattattagagaa atgcaaatcaaaactacaatgaggtatcacctcactcctgttagaatgggcatcatcagaaaatctacaaacaacaaatgctggaga gggtgtggagaaaagggaaccctcttgcactgttggtgggaatgtaaattgatacagccactatggagaacaatatggaggttcctt aaaaaactaaaaatagaattaccatatgacccagcaatcccactactgggcatatacccagagaaaaccgtaattcaaaaagacaca tgcacccgaatgttcattgcagcactatttacaatagccaggtcatggaagcaacctaaatgcccatcgacagacgaatggataaag aagatgtggtacatatatacaatggaatattactcagccataaaaaggaacgaaattgggtcattttagagacgtggatggatcta gagactgtcatacagagtgaagtaagtcagaaagagaaaaacaaatatcgtatattaacgcatatatgtggaacctggaaaaatggt acagatgaaccggtctgcaggacagaaattgagacacaaatgtaa.
```

In some embodiments, the construct comprises a nucleic acid sequence encoding a nuclear localization sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to PAAKRVKLD ((SEQ ID NO: 59). In some embodiments, the nuclear localization sequence is fused to the ORF2p sequence. In some embodiments, the construct comprises a nucleic acid sequence encoding a flag tag having the sequence DYKDDDDK (SEQ ID NO: 60). In some embodiments, the flag tag is fused to the ORF2p sequence. In some embodiments, the flag tag is fused to the nuclear localization sequence.

In some embodiments, the construct comprises a nucleic acid sequence encoding an MS2 coat protein with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to (SEQ ID NO: 61)
ASNFTQFVLVDNGGTGDVTVAPSNFANGIAEWISSNSRSQAYKVTCSV

RQSSAQNRKYTIKVEVPKGAWRSYLNMELTIPIFATNSDCELIVKAMQ

GLLKDGNPIPSAIAANSGIYAMASNFTQFVLVDNGGTGDVTVAPSNFA

-continued

NGIAEWISSNSRSQAYKVTCSVRQSSAQNRKYTIKVEVPKGAWRSYLN

MELTIPIFATNSDCELIVKAMQGLLKDGNPIPSAIAANSGIY.

In some embodiments, the MS2 coat protein sequence is fused to the ORF2p sequence.

In some embodiments, the transgene may comprise a flanking sequence which comprises an Alu ORF2p recognition sequence.

In some embodiments, additional elements may be introduced into the mRNA. In some embodiments, the additional elements may be an IRES element or a T2A element. In some embodiments, the mRNA transcript comprises one, two, three or more stop codons at the 3'-end.

In some embodiments, the one, two, three or more stop codons are designed to be in tandem. In some embodiments, the one, two, three or more stop codons are designed to be in all three reading frames. In some embodiments, the one, two, three or more stop codons may be designed to be both in multiple reading frames and in tandem.

In some embodiments, one or more target specific nucleotides may be added at the priming end of the L1 or the Alu RNA priming region.

In some embodiments, the 5' UTR sequence or the 3' UTR sequence in addition to be able to bind the ORF protein may also be capable of binding to one or more endogenous proteins that regulate gene retrotransposition and/or stable integration. In some embodiments, the flanking sequence is capable of binding to a PABP protein.

In some embodiments, the 5' region flanking the transcript may comprise a strong promoter. In some embodiments, the promoter is a CMV promoter.

In some embodiments, an additional nucleic encoding L1 ORF2p is introduced into the cell. In some embodiments, the sequence encoding L1 ORF1 is omitted, and only L1-ORF2 is included. In some embodiments, the nucleic acid encoding the transgene with the flanking elements is mRNA. In some embodiments, the endogenous L1-ORF1p function may be suppressed or inhibited.

In some embodiments, the nucleic acid encoding the transgene with the retrotransposition flanking elements comprise one or more nucleic acid modifications. In some embodiments, the nucleic acid encoding the transgene with the retrotransposition flanking elements comprises one or more nucleic acid modifications in the transgene. In some embodiments, the modifications comprise codon optimization of the transgene sequence. In some embodiments, the codon optimization is for more efficient recognition by the human translational machinery, leading to more efficient expression in a human cell. In some embodiments, the one or more nucleic acid modification is performed in the 5'-flanking sequence or the 3'-flanking sequence including one or more stem-loop regions. the nucleic acid encoding the transgene with the retrotransposition flanking elements comprise one, two, three, four, five, six, seven eight, nine, ten or more nucleic acid modifications.

In some embodiments, the retrotransposed transgene is stably expressed for the life of the cell. In some embodiments, the cell is a myeloid cell. In some embodiments, the myeloid cell is a monocyte precursor cell. In some embodiments, the myeloid cell is an immature monocyte. In some embodiments, the monocyte is an undifferentiated monocyte. In some embodiments, the myeloid cell is a CD14+ cell. In some embodiments, the myeloid cell does not express CD16 marker. In some embodiments, the myeloid cell is capable of remaining functionally active for a desired period of greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 14 days or more under suitable conditions. A suitable condition may denote an in vitro condition, or an in vivo condition or a combination of both.

In some embodiments, the retrotransposed transgene may be stably expressed in the cell for about 2 days, about 3 days, about 4 days, about 5 days, about 6 days, about 7 days, about 8 days, about 9 days or about 10 days. In some embodiments, the retrotransposed transgene is stably expressed in the cell for more than 10 days. In some embodiments, the retrotransposed transgene is stably expressed in the cell for more than 2 weeks. In some embodiments, the retrotransposed transgene is stably expressed in the cell for about 1 month.

In some embodiments, the retrotransposed transgene may be modified for stable expression. In some embodiments, the retrotransposed transgene may be modified for resistant to in vivo silencing.

In some embodiments, the expression of the retrotransposed transgene may be controlled by a strong promoter. In some embodiments, the expression of the retrotransposed transgene may be controlled by a moderately strong promoter. In some embodiments, the expression of the retrotransposed transgene may be controlled by a strong promoter that can be regulated in an in vivo environment. In some embodiments, the promoter is a CMV promoter. In some embodiments, the promoter is a L1-Ta promoter.

In some embodiments, the ORF1p may be overexpressed. In some embodiments, the ORF2 may be overexpressed. In some embodiments, the ORF1p or ORF2p or both are overexpressed. In some embodiments, upon overexpression of an ORF1, ORF1p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF1.

In some embodiments, upon overexpression of an ORF2 sequence, ORF2p is at least 1.1 fold, 1.5 fold, 2 fold, 3 fold, 4 fold, 5 fold, 6 fold, 7 fold, 8 fold, 9 fold, 10 fold, 12 fold, 14 fold, 16 fold, 18 fold, 20 fold, 30 fold, 40 fold, 50 fold, 60 fold, 70 fold, 80 fold, 90 fold, or at least 100 fold higher than a cell not overexpressing and ORF2p.

Retrotransposition Fidelity and Target Specificity

The LINE-1 elements can bind to their own mRNA poly A tail to initiate retrotransposition. LINE-1 elements preferably retrotranspose their own mRNA over random mRNAs (Dewannieux et al., 2013, 3,000-fold higher LINE-1 retrotransposition as compared to random mRNAs). In addition, LINE-1 elements can also integrate non-specific poly-A sequences within a genome.

In one aspect, provided herein are retrotransposition compositions and methods of using the same with increased retrotransposition specificity. For example, retrotransposition compositions with high specificity may be used for highly specific and efficient reverse transcription and subsequently, integration into genome of a target cell, e.g., a myeloid cell. In some embodiments, a retrotransposition composition provided herein comprises a retrotransposition cassette that comprises one or more additional components that increases integration or retrotransposing specificity. For example, the retrotransposon cassette may encode one or more additional elements that allows for high affinity RNA-protein interaction to out compete non-specific binding between poly-A sequences and ORF2.

Accordingly, several measures are disclosed herein for enhancing integration or retrotransposition efficiency.

One exemplary measure for enhancing integration or retrotransposition efficiency is external manipulation of the cells. The endonuclease function of the retrotransposition machinery delivered in a cell may likely be subject to inhibition by the cell's transposition silencing machinery, such as DNA repair pathways. For example, small molecules can be used to modulate or inhibit DNA repair pathways in the cells prior to introducing the nucleic acid. For example, cell sorting and/or synchronization can be used prior to introducing the nucleic acid, such as by electroporation, as cell cycle synchronized cell populations were shown to increase gene transfer to the cells. Cell sorting may be utilized to synchronize or homogenize the cell types and increase uniform transfer and expression of the exogenous nucleic acid. Uniformity may be achieved sorting stem cells from non-stem cells. Another exemplary measure for enhancing integration or retrotransposition efficiency is to enhance biochemical activity. For example, this may be achieved by increasing reverse-transcriptase processivity or DNA cleavage (endonuclease) activity. Another exemplary measure for enhancing integration or retrotransposition efficiency is to subvert endogenous silencing mechanisms. For example, this may be achieved by replacing entire LINE-1 sequence with a different organisms' LINE-1. Another exemplary measure for enhancing integration or retrotransposition efficiency is to enhance translation and ribosome binding. For example, this may be achieved by increasing expression of LINE-1 proteins, increasing LINE protein binding LINE-1 mRNA, or increasing LINE-1 complex binding to ribosomes. Another exemplary measure for enhancing integration or retrotransposition efficiency is to increase nuclear import or retention. For example, this may be achieved by fusing the LINE-1 sequence to a nuclear retention signal sequence. Another exemplary measure for enhancing integration or retrotransposition efficiency is to enhance sequence-specific insertion. For example, this may be achieved by fusing a targeting domain to ORF2 to increase sequence specific retrotransposition.

In one embodiment, the method encompasses enhancing the retrotransposon for increasing specificity and robustness of expression of the cargo by modifying the UTR sequence of the LINE-1 ORFs. In some embodiments, the 5'UTR upstream of ORF1 or ORF2 encoding sequence may be further modified to comprise a sequence that is complementary to the sequence of a target region within the genome that helps in homologous recombination at the specific site where the ORF nuclease can act and the retrotransposition can take place. In some embodiments, the sequence that can bind to a target sequence by homology is between 2-15 nucleotides long. In some embodiments, the sequence having homology to a genomic target that is included in the 5'UTR of an ORF1 mRNA may be about 3 nucleotides, about 4 nucleotides, about 5 nucleotides, about 6 nucleotides, about 7 nucleotides, about 8 nucleotides, about 9 nucleotides or about 10 nucleotides long. In some embodiments, the sequence having homology to a genomic target is about 12 or about 15 nucleotides long. In some embodiments, the sequence having homology to a genomic target is at least about 10, 15, 20, 25, 30, 35, 40, 45, 50, 55, 60, 65, 70, 75, 80, 85, 90, 95, 100, 105, 110, 115, 1120 or 125 nucleotides in length. In some embodiments, the sequence having homology to a genomic target comprises about 2-5, about 2-6, about 2-8 or about 2-10, or about 2-12 contiguous nucleotides that share complementarity with the respective target region within the genome. In some embodiments, the sequence having homology to a genomic target is at least about or about 10, 15, 20, 25, 30, 35, 40, 45, 50, 55, 60, 65, 70, 75, 80, 85, 90, 95, 100, 105, 110, 115, 1120 or 125 contiguous nucleotides that share complementarity with the respective target region within the genome.

In some embodiments, an ORF2 is associated with or fused to an additional protein domain that comprises RNA binding activity. In some embodiments, the retrotransposon cassette comprises a cognate RNA sequence that comprises affinity with the additional protein domain associated with or fused to the ORF2. In some embodiments, the ORF2 is associated with or fused to a MS2-MCP coat protein. In some embodiments, the retrotransposon cassette further comprises a MS2 hairpin RNA sequence in the 3' or 5' UTR sequence that interacts with the MS2-MCP coat protein. In some embodiments, the ORF2 is associated with or fused to a PP7 coat protein. In some embodiments, the retrotransposon cassette further comprises a PP7 hairpin RNA sequence in the 3' or 5' UTR sequence that interacts with the MS2-MCP coat protein. In some embodiments, the one or more additional elements increases retrotransposition specificity by at least 1.5 fold, at least 2 fold, at least 3 fold, at least 4 fold, at least 5 fold, at least 10 fold, at least 20 fold, at least 30 fold, at least 50 fold, at least 100 fold, at least 200 fold, at least 300 fold, at least 500 fold, at least 1000 fold, at least 1500 fold, at least 2000 fold, at least 3000 fold, at least 5000 fold or more as compared to a retrotransposon cassette without the one or more additional elements.

The DNA endonuclease domain appears to have specificity for a series of purines 3' of the target site followed by a series of pyrimidines $(Py)_n \downarrow (Pu)_n$. An exemplary sequence may be $(Adenosine)_n \downarrow (Thymidine)_n$.

In one aspect, provided herein are methods of using retrotransposition having high target specificity. Consequently, provided herein is a method and compositions for stable incorporation of a transgene into the genome of a myeloid cell, such as a monocyte or macrophage, wherein the method comprises incorporating the transgene using a non-LTR retrotransposon system, wherein the retrotransposition occurs at a specific genomic locus with a target specificity, high precision and fidelity. Therefore, in some embodiments, the method comprises administration to the cell a composition comprising a system having at least one transgene, flanked with one or more retrotransposable elements, and one or more nucleic acids encoding one or more proteins for increasing the transposition specificity, and/or further comprising modifying one or more genes associated with the retrotransposition.

The nucleic acid comprising the transgene, situated in 3' UTR region of the retrotransposable elements is often referred to as a retrotransposition cassette. Accordingly, in some embodiments, the retrotransposition cassette comprises the nucleic acid encoding the transgene and flanking Alu transposable elements. The retrotransposable elements comprise a sequence for binding the retrotransposons, for example, L1-transposons, such as L1-ORF proteins, ORF1p and ORF2p. ORF proteins are known to bind to their own mRNA sequence for retrotransposition. Therefore, the retrotransposition cassette comprises the nucleic acid encoding the transgene; a flanking L1-ORF2p binding sequence, and/or a L1-ORF1p binding sequence, comprising a sequence encoding a L1-ORF1p encoding sequence and a L1-ORF2p encoding sequence outside the transgene sequence. In some embodiments, the L1-ORF1 and L1-ORF2 are interspersed by a spacer region, also termed as an ORF1-ORF2 inter-region. In some embodiments, the L1-ORF1 and L1-ORF2 coding sequences are in an opposite orientation with respect to the coding region of the transgene. The retrotransposition cassette can comprise a poly A region downstream of the L1-ORF2-coding sequence and the transgene sequence is placed downstream of the poly A sequence. The L1-ORF2 comprises a nucleic acid sequence that encodes an endonuclease (EN) and a reverse transcriptase (RT) followed by the poly A sequence. In some embodiments, the L1-ORF2 sequence in the retrotransposition cassette described herein is a complete (intact) sequence, that is, encodes the full length native (WT) L1-ORF2 sequence. In some embodiments, the L1-ORF2 sequence in the retrotransposition cassette described herein comprises a partial or modified sequence.

The system described herein can comprise a promoter for expressing the L1-ORF1p and L1-ORF2p. In some embodiments, the transgene expression is driven by a separate promoter. In some embodiments, the transgene and the ORFs are in tandem orientation. In some embodiments, the transgene and the ORFs are in opposite orientation.

In some embodiments, the method comprises incorporating one or more elements in addition to the retrotransposon cassette. In some embodiments, the one or more additional elements comprise a nucleic acid sequence encoding one or more domains of a heterologous protein. The heterologous protein may be a sequence specific nucleic acid binding protein, for example, a sequence specific DNA binding protein domain (DBD). In some embodiments, the heterologous protein is a nuclease or a fragment thereof. In some embodiments, the additional elements comprise a nucleic acid sequence encoding one or more nuclease domains or fragments thereof from a heterologous protein. In some embodiments, the heterologous nuclease domain has reduced nuclease activity. In some embodiments, the heterologous nuclease domain is rendered inactive. In some embodiments, the ORF2 nuclease is rendered inactive; whereas one or more nuclease domains from the heterologous protein is configured to render specificity to the retrotransposition. In some embodiments, one or more nuclease domains or fragments thereof from the heterologous protein targets a specific desired polynucleotide within the genome where retrotransposition and incorporation of the polynucleotide of interest is to be incorporated. In some embodiments, the one or more nuclease domains from the heterologous protein comprise a mega-TAL nuclease domain, TALENs, or a zinc finger nuclease domain, for example, a mega-TAL, a TALE, or a zinc finger domain fused to or associated with a nuclease domain, e.g., a FokI nuclease domain. In some embodiments, the one or more nuclease domains from the heterologous protein comprise a CRISPR-Cas protein domain loaded with a specific guide nucleic acid, e.g., a guide RNA (gRNA) for a specific target locus. In some embodiments, the CRISPR-Cas protein is a Cas9, a Cas12a, a Cas12b, a Cas13, a CasX, or a CasY protein domain. In some embodiments, the one or more nuclease domains from the heterologous protein has target specificity.

In some embodiments, the additional nuclease domain may be incorporated into the ORF2 domain. In some embodiments, the additional nuclease may be fused with the ORF2p domain. In some embodiments, the additional nuclease domain may be fused to an ORF2p, wherein the ORF2p includes a mutation in the ORF2p endonuclease domain. In some embodiments, the mutation inactivates the ORF2p endonuclease domain. In some embodiments, the mutation is a point mutation. In some embodiments, the mutation is a deletion. In some embodiments, the mutation is an insertion. In some embodiments, the mutation abrogates the ORF2 endonuclease (nickase) activity. In some embodiments, a mutation inactivates the DNA target recognition of ORF2p endonuclease. In some embodiments, the mutation covers a region associated with ORF2p nuclease-DNA recognition. In some embodiments, a mutation reduces the DNA target recognition of ORF2p endonuclease. In some embodiments, the ORF2p endonuclease domain mutation is in the N-terminal region of the protein. In some embodiments, the ORF2p endonuclease domain mutation is in a conserved region of the protein. In some embodiments, the ORF2p endonuclease domain mutation is in the conserved N-terminal region of the protein. In some embodiments, the mutation comprises the N14 amino acid within L1 endonuclease domain. In some embodiments, the mutation comprises 2, 3, 4, 5, 6, 7, 8, 9, 10, 11, 12, 13, 14, 15, 16, 17, 18, 19, 20 or more consecutive amino acids including the N14 amino acid within L1 endonuclease domain. In some embodiments, the mutation comprises the comprises the E43 amino acid within L1 endonuclease. In some embodiments, the mutation comprises 2, 3, 4, 5, 6, 7, 8, 9, 10, 11, 12, 13, 14, 15, 16, 17, 18, 19, 20 or more consecutive amino acids including the E43 amino acid within L1 endonuclease domain. In some embodiments, the mutation comprises 2 or more amino acids in the L1 endonuclease domain including N14, or E43 or a combination thereof. In some embodiments, the mutation comprises D145 of the L1 endonuclease domain. In some embodiments, the mutation may be D145A. In some embodiments, the may be a comprise D205 of the L1 endonuclease domain. In some embodiments, the mutation may be D205G. In some embodiments, the mutation may comprise H230 of L1 endonuclease domain. In some embodiments, the may be a comprise S228 of the L1 endonuclease domain. In some embodiments, the mutation may be S228P.

In some embodiments, a mutation reduces the DNA target recognition of ORF2p endonuclease by at least 50%. In some embodiments, a mutation reduces the DNA target recognition of ORF2p endonuclease by at least 60%. In some embodiments, a mutation reduces the DNA target recognition of ORF2p endonuclease by at least 70%. In some embodiments, a mutation reduces the DNA target recognition of ORF2p endonuclease 80%. In some embodiments, a mutation reduces the DNA target recognition of ORF2p endonuclease 90%. In some embodiments, a mutation reduces the DNA target recognition of ORF2p by 95%. In some embodiments, a mutation reduces the DNA target recognition of ORF2p by 100%.

In some embodiments, the mutation is a deletion. In some embodiments, the deletion is complete, i.e., 100% of the L1 endonuclease domain is deleted. In some embodiments, the deletion is partial. In some embodiments, the about 98%, about 95%, about 94%, about 93%, about 92% about 91%, about 90%, about 85%, about 80%, about 75%, about 70%, about 65%, about 60%, or about 50% of the ORF2 endonuclease domain is deleted.

In some embodiments, an additional nuclease domain is inserted into the ORF2 protein sequence. In some embodiments, ORF2 endonuclease domain is deleted, and is replaced with an endonuclease domain from a heterologous protein. In some embodiments, the ORF2 endonuclease is partially deleted and replaced with an endonuclease domain from a heterologous protein. The endonuclease domain from a heterologous protein may be a mega-TAL nuclease domain. The endonuclease domain from a heterologous protein may be a TALENs. The endonuclease domain from a heterologous protein may be a Cas9 loaded with a specific gRNA for a locus.

In some embodiments, the endonuclease is an endonuclease that has (i) a specific target on the genome and (ii) it creates a 5'-P and a 3'-OH terminus at the cleavage site.

In some embodiments, the additional endonuclease domain from a heterologous protein is an endonuclease domain from a related retrotransposon.

In some embodiments, the endonuclease domain from a heterologous protein may comprise a bacterial endonuclease engineered for targeting a specific site. In some embodiments, the endonuclease domain from a heterologous protein may comprise a domain of a homing endonuclease or a fragment thereof. In some embodiments, the endonuclease is a homing endonuclease. In some embodiments, the homing endonuclease is an engineered LAGLIDADG (SEQ ID NO: 62) homing endonucleases (LHEs) or a fragment thereof. In some embodiments, additional endonucleases may be a restriction endonuclease, Cre, Cas TAL or fragments thereof. In some embodiments, the endonuclease may comprise a Group II intron encoded protein (ribozyme) or a fragment thereof.

An engineered or modified L1-ORF2p as discussed in the preceding paragraphs, that is endowed with specific DNA targeting capability due to the additional/heterologous endonuclease is expected to be highly advantageous in driving targeted stable integration of a transgene into the genome. The engineered L1-ORF2p can generate much reduced off-target effects when expressed in a cell than using a native, non-engineered L1-ORF2p. In some embodiments, the engineered L1-ORF2p generates no off-target effect.

In some embodiments, the engineered or modified L1-ORF2p targets a recognition site that is other than the usual (Py)$_n$↓(Pu)$_n$ site. In some embodiments, engineered L1-ORF2p targets a recognition site that comprises the (Py)$_n$↓(Pu)$_n$ site, for example, TTTT/AA site, such as a hybrid target site. In some embodiments, the engineered L1-ORF2p targets a recognition site having at least one nucleotide in addition to the conventional L1-ORF2 (Py)$_n$↓(Pu)$_n$ site, for example TTTT/AAG, or TTTT/AAC, or TTTT/AAT, TTTT/AAA, GTTTT/AA, CTTTT/AA, ATTTT/AA, or TTTTT/AA. In some embodiments, the engineered L1-ORF2p targets a recognition site that is in addition to the conventional L1-ORF2p (Py)$_n$↓(Pu)$_n$ site. In some embodiments, the engineered L1-ORF2p targets a recognition site that is other than to the conventional L1-ORF2p (Py)$_n$↓(Pu)$_n$ site. In some embodiments, the engineered L1-ORF2p targets a recognition site that is 4, 5, 6, 7, 8, 9, 10 or more nucleotides long. In some embodiments, the engineered or modified L1-ORF2p recognition site may be 11, 12, 13, 14, 15, 16, 17, 18, 19, 20 or more nucleotides.

The engineered L1-ORF2p can be engineered to retain its ability to bind to its own mRNA after translation and reverse transcribe with high efficiency. In some embodiments, the engineered L1-ORF2p has enhanced efficiency of reverse transcription compared to a native (WT) L1-ORF2p.

In some embodiments, the system comprising a retrotransposable element further comprises a gene modification that reduces non-specific retrotransposition. In some embodiments, the gene modification may comprise a sequence encoding the L1-ORF2p. In some embodiments, the modification may comprise mutation of one or more amino acids that are essential for binding to a protein that helps ORF2p binding to the target genomic DNA. A protein that helps ORF2p binding to the target genomic DNA may be part of the chromatin-ORF interactome. In some embodiments, the modification may comprise one or more amino acids that are essential for binding to a protein that helps ORF2p DNA endonuclease activity. In some embodiments, the modification may comprise one or more amino acids that are essential for binding to a protein that helps ORF2p RT activity. In some embodiments, the modification may comprise at a protein binding site on ORF2p such that the association of a protein with ORF2p is altered, wherein binding of the protein to ORF2p is required for binding to chromatin. In some embodiments, the modification may comprise at a protein binding site on ORF2p such that the association of the protein with ORF2p is more stringent and/or specific than in absence of the modification. In some embodiments, as a consequence of altered association of ORF2p with the protein owing to the modification of ORF2p coding sequence at the protein binding site, the binding of ORF2p to the target DNA has increased specificity. In some embodiments, the modification may reduce binding of ORF2 to one or more proteins that are part of the ORF2p chromatin interactome.

In some embodiments, the gene modification may be in the PIP domain of ORF2p.

In some embodiments, the gene modification may be in one or more genes encoding a protein that binds to an ORF2p and helps in the recognition, binding, endonuclease or RT activity of ORF2p. In some embodiments, the gene modification may be in one or more genes encoding PCNA, PARP1, PABP, MCM, TOP1, RPA, *PURA*, PURB, RUVBL2, NAP1, ZCCHC3, UPF1 or MOV10 proteins at an ORF2p interacting site for each protein or at a site that affects the protein's interaction with ORF2p or the interaction of ORF2p with target DNA. In some embodiments, the modification may be on an ORF2p binding domain of PCNA at an ORF2p interacting site or at a site that affects the protein's interaction with ORF2p or the interaction of ORF2p with target DNA. In some embodiments, the modification may be on an ORF2p binding domain of TOP1. In some embodiments, the modification may be on an ORF2p binding domain of RPA. In some embodiments, the modification may be on an ORF2p binding domain of PARP1 at an ORF2p interacting site or at a site that affects the protein's interaction with ORF2p or the interaction of ORF2p with target DNA. In some embodiments, the modification may be on an ORF2p binding domain of PABP (e.g., PABPC1) at an ORF2p interacting site or at a site that affects the protein's interaction with ORF2p or the interaction of ORF2p with target DNA. In some embodiments, the gene modification may be on an MCM gene. In some embodiments, the gene modification may be on a gene encoding MCM3 protein at an ORF2p interacting site or at a site that affects the protein's interaction with ORF2p or the interaction of ORF2p with target DNA. In some embodiments, the gene modification may be on a gene encoding MCM5 protein at an ORF2p interacting site or at a site that affects the protein's interaction with ORF2p or the interaction of ORF2p with target DNA. In some embodiments, the gene modification may be on a gene encoding MCM6 protein at an ORF2p interacting site or at a site that affects the protein's interaction with ORF2p or the interaction of ORF2p with target DNA. In some embodiments, the gene modification may be on a gene encoding MEPCE protein at an ORF2p interacting site or at a site that affects the protein's interaction with ORF2p or the interaction of ORF2p with target DNA. In some embodiments, the gene modification may be on a gene encoding on a gene encoding RUVBL1 or RUVBL2 protein at an ORF2p interacting site or at a site that affects the protein's interaction with ORF2p or the interaction of ORF2p with target DNA. In some embodiments, the gene modification may be on a gene encoding on a gene encoding TROVE protein at an ORF2p interacting site or at a site that affects the protein's interaction with ORF2p or the interaction of ORF2p with target DNA.

In some embodiments, the retrotransposition system disclosed herein comprises one or more elements that increase the fidelity of reverse transcription.

In some embodiments, the L1-ORF2 RT domain is modified. In some embodiments, the modification includes one or more of: increasing fidelity, increasing processivity, increasing DNA-RNA substrate affinity; or inactivating RNase H activity.

In some embodiments, the modification comprises introducing one or more mutations in the RT domain of the L1-ORF2, such that the fidelity of the RT is increased. In some embodiments, the mutation comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modification may comprise inclusion of an additional RT domain or fragment thereof from a second protein. In some embodiments, the second protein is a viral reverse transcriptase. In some embodiments, the second protein is a non-viral reverse transcriptase. In some embodiments, the second protein is a retrotransposable element. In some embodiments, the second protein is a non-LTR retrotransposable element. In some embodiments, the second protein is a group II intron protein. In some embodiments, the group II intron is as TGIRTII. In some embodiments, the second protein is a Cas nickase, wherein the retrotransposable system further comprises introducing a guide RNA. In some embodiments, the second protein is a Cas9 endonuclease, wherein the retrotransposable system further comprises introducing a guide RNA. In some embodiments, the second protein or fragment thereof is fused to the N-terminus of the L1-ORF2 RT domain or the modified L1-ORF2 RT domain. In some embodiments, the second protein or fragment thereof is fused to the C-terminus of the L1-ORF2 RT domain or the modified L1-ORF2 RT domain.

In some embodiments, the additional RT domain or fragment thereof from the second protein is incorporated in the retrotransposition system in addition to the full-length WT L1-ORF2p RT domain. In some embodiments, the additional RT domain or fragment thereof from the second protein is incorporated in presence of a modified (engineered) L1-ORF2p RT domain or a fragment thereof, where the modification (or engineering) may comprise a mutation for enhancement of the L1-ORF2p RT processivity, stability and/or fidelity of the modified L1-ORF2p RT compared to the native or WT ORF2p.

In some embodiments, the reverse transcriptase domain could be replaced with other more highly processive and high-fidelity RT domains from other retroelements or group II introns, such as TGIRTII.

In some embodiments, the modification may comprise a fusion with an additional RT domain or fragment thereof from a second protein. In some embodiments, the second protein may comprise a retroelement. The additional RT domain or fragment thereof from a second protein is configured to increase the fidelity of reverse transcription of the fused L1-ORF2p RT domain. In some embodiments, the nucleic acid encoding the additional RT domain or fragment thereof is fused to a native or WT L1-ORF2 encoding sequence. In some embodiments, the nucleic acid encoding the additional RT domain or fragment thereof from a second protein is fused to a modified L1-ORF2 encoding sequence. In some embodiments, the modification comprises introducing one or more mutations in the RT domain of the L1-ORF2 or fragment thereof, such that the fidelity of the fused RT is increased. In some embodiments, the mutation in the RT domain of the L1-ORF2 or fragment thereof comprises a point mutation. In some embodiments, the mutation comprises alteration, such as substitution of one, two three, four, five, six or more amino acids in the L1-ORF2p RT domain. In some embodiments, the mutation comprises deletion of one or more amino acids, for example, one, two, three, four, five, six, seven, eight, nine, ten or more amino acids in the L1-ORF2p RT domain. In some embodiments, the mutation may comprise an in-del mutation. In some embodiments, the mutation may comprise a frame-shift mutation.

In some embodiments, the modified L1-ORF2p RT domain has increased processivity than the WT L1-ORF2p RT domain.

In some embodiments, the modified L1-ORF2p RT domain has at least 10% higher processivity and/or fidelity over the WT L1-ORF2p RT domain. In some embodiments, the modified L1-ORF2p RT domain has at least 20%, 30%, 40%, 50%, 60%, 70%, 80%, 90%, 100%, 110%, 120%, 150%, 200%, 300%, 400%, 500%, 1000% or higher processivity and/or fidelity over the WT L1-ORF2p RT domain. In some embodiments, the modified RT can process greater than 6 kb nucleic acid stretch. In some embodiments, the modified RT can process greater than 7 kb nucleic acid stretch. In some embodiments, the modified RT can process greater than 8 kb nucleic acid stretch. In some embodiments, the modified RT can process greater than 9 kb nucleic acid stretch. In some embodiments, the modified RT can process greater than 10 kb nucleic acid stretch.

B. Group II Introns and Ribozymes

Group II enzymes are mobile ribozymes that self-splice precursor RNAs, yielding excised intron lariat RNAs. The introns encode a reverse transcriptase. The reverse transcriptase may stabilize the RNA for forward and reverse splicing, and later in converting the integrated intron RNA to DNA.

Group II RNAs are characterized by a conserved secondary structure spanning 400-800 nucleotides. The secondary structure is formed by six domains DI-VI, and is organized in a structure resembling a wheel, where the domains radiate from a central point. The domains interact to form a conserved tertiary structure that brings together distant sequences to form an active site. The active site binds the splice sites and branch point residue nucleotide and in association of Mg2+ cations, activate catalysis of splicing. The DV domain is within the active site, which has the conserved catalytic AGC and an AY bulge and both these regions bind Mg2+ ions necessary for the catalysis. DI is the largest domain with upper and lower halves separated by kappa and zeta motifs. The lower half contains the ε' motif, which is associated with an active site. The upper half contains sequence elements that bind to the 5' and 3' exons at the active sites. DIV encodes the intron-encoded protein (IEP) with subdomain IVa near the 5'-end containing the high affinity binding site for IEP. Group II introns have conserved 5'- and 3'-end sequences, GUGYG and AY respectively.

Group II RNA introns can be utilized to retrotranspose a sequence of interest into DNA via target primed reverse transcription. This process of transposition by Group II RNA introns is often referred to as retrohoming. Group II introns recognize DNA target sites by base pairing of the intron RNA to the DNA target sequence, they can be modified to retarget a specific sequence carried within the intron to a desired DNA site.

In some embodiments, the method and compositions for retrotransposition described herein may comprise a Group II intron sequence, a modified Group II intron sequence or a fragment thereof. Exemplary Group II IEPs (maturase) include but are not limited to bacterial, fungal, yeast IEPs, that are functional in human cells. In particular, the nuclease leaves a 3'-OH at the cleavage site of the DNA which can be utilized by another RT for priming and reverse transcription. An exemplary Group II maturase may be TGIRT (thermally stable group II intron maturase).

In one or more embodiments of several aspects described herein, the nucleic acid construct comprises an RNA. In one or more embodiments of several aspects of the disclosure, the nucleic acid construct is an RNA. In one or more embodiments of several aspects of the disclosure, the nucleic acid construct is an mRNA. In one aspect, the mRNA comprises a sequence of a heterologous gene or portion thereof, wherein the heterologous gene or portion thereof encodes a polypeptide or protein. In some embodiments, the mRNA comprises a sequence encoding a fusion protein. In some embodiments, the mRNA comprises a sequence encoding a recombinant protein. In some embodiments, the mRNA comprises a sequence encoding a synthetic protein. In some embodiments, the nucleic acid comprises one or more sequences, wherein the one or more sequences encode on or more heterologous proteins, one or more recombinant proteins, or one or more synthetic proteins or a combination thereof. In some embodiments, the nucleic acid comprises one or more sequences, wherein the one or more sequences encode on or more heterologous proteins comprising a synthetic protein or a recombinant protein. In some embodiments, the synthetic or recombinant protein is a recombinant fusion protein.

In one or more of embodiments of several aspects of the disclosure, the nucleic acid construct is developed for expressing in a eukaryotic cell. In some embodiments, the nucleic acid construct is developed for expressing in a human cell. In some embodiments, the nucleic acid construct is developed for expressing in a hematopoietic cell. In some embodiments, the nucleic acid construct is developed for expressing in a myeloid cell. In some embodiments, the myeloid cell is a human cell.

II. Modifications in Nucleic Acid Constructs for Methods of Enhancement of Expression of Encoded Protein In some aspects of the disclosure, the recombinant nucleic acid is modified for enhanced expression of the protein encoded by a sequence of the nucleic acid Enhanced expression of the protein encoded therein can be a function of the nucleic acid stability, translation efficiency and the stability of the translated protein. A number of modifications are contemplated herein for incorporation in the design of the nucleic acid construct that can confer nucleic acid stability, such as stability of the messenger RNA encoding the exogenous or heterologous protein, which may be a synthetic recombinant protein or a fragment thereof.

In some embodiments, the nucleic acid is mRNA, comprising one or more sequences, wherein the one or more sequences encode one or more heterologous proteins comprising a synthetic or a recombinant fusion protein.

In some embodiments, one or more modifications are made in the mRNA comprising a sequence encoding a recombinant or fusion protein to increase the mRNA half-life.

Structural elements to block 5'- and 3'-degradations by exonucleases: 5'-Cap and 3' UTR modifications A proper 5'-cap structure is important in the synthesis of functional messenger RNA. In some embodiments, the 5'-cap comprises a guanosine triphosphate arranged as GpppG at the 5'terminus of the nucleic acid. In some embodiments, the mRNA comprises a 5' 7-methylguanosine cap, m7-GpppG. A 5' 7-methylguanosine cap increases mRNA translational efficiency and prevents degradation of mRNA 5'-3'exonucleases. In some embodiments, the mRNA comprises "anti-reverse" cap analog (ARCA, ° GpppG). Translational efficiency, however, can be markedly increased by usage of the ARCA. In some embodiments, the guanosine cap is a Cap 0 structure. In some embodiments, the guanosine cap is a Cap 1 structure. In addition to its essential role of cap-dependent initiation of protein synthesis, the mRNA cap also functions as a protective group from 5' to 3' exonuclease cleavage and a unique identifier for recruiting protein factors for pre-mRNA splicing, polyadenylation and nuclear export. It acts as the anchor for the recruitment of initiation factors that initiate protein synthesis and the 5' to 3' looping of mRNA during translation. Three enzymatic activities are required to generate the Cap 0 structure, namely, RNA triphosphatase (TPase), RNA guanylyltransferase (GTase) and guanine-N7 methyltransferase (guanine-N7 MTase). Each of these enzyme activities carries out an essential step in the conversion of the 5' triphosphate of nascent RNA to the Cap 0 structure. RNA TPase removes the γ-phosphate from the 5' triphosphate to generate 5' diphosphate RNA. GTase transfers a GMP group from GTP to the 5' diphosphate via a lysine-GMP covalent intermediate. The guanine-N7 MTase then adds a methyl group to the N7 amine of the guanine cap to form the cap 0 structure. For Cap 1 structure, m7G-specific 2'O methyltransferase (2'O MTase) methylates the +1 ribonucleotide at the 2'O position of the ribose to generate the cap 1 structure. The nuclear RNA capping enzyme interacts with the polymerase subunit of RNA polymerase II complex at phosphorylated Ser5 of the C-terminal heptad repeats. RNA guanine-N7 methyltransferase also interacts with the RNA polymerase II phosphorylated heptad repeats. In some embodiments, the cap is a G-quadruplex cap.

In some embodiments, the mRNA is synthesized by in vitro transcription (IVT). In some embodiments, mRNA synthesis and capping may be performed in one step. Capping may occur in the same reaction mixture as IVT. In some embodiments, mRNA synthesis and capping may be performed in separate steps. mRNA thus formed by IVT is purified and then capped.

In some embodiments, the nucleic acid construct, e.g., the mRNA construct, comprises one or more sequences encoding a protein or a polypeptide of interest can be designed to comprise elements that protect, prevent, inhibit or reduce degradation of the mRNA by endogenous 5'-3' exoribonucleases, for example, Xrn1. Xrn1 is a cellular enzyme in the normal RNA decay pathways that degrades 5' monophosphorylated RNAs. However, some viral RNA structural elements are found to be particularly resistant to such RNases, for example, the Xrn1-resistant structure in flaviviral sfRNAs, called the 'xrRNA'. For example, the mosquito-borne flaviviruses (MBFV) genomes contain discrete RNA structures in their 3'-untranslated region (UTR) that block the progression of Xrn1. These RNA elements are sufficient to block Xrn1 without the use of accessory proteins. xrRNAs halt the enzyme at a defined location such that the viral RNA located downstream of the xrRNAs is protected from degradation. The xrRNAs from Zika virus or Murray Valley encephalitis virus, for example, comprise three-way junction and multiple pseudoknot interactions that create an unusual and complex fold that requires a set of nucleotides conserved across the MBFVs structure. xrRNAs halt the enzyme at a defined location such that the viral RNA located downstream of the xrRNAs is protected from degradation. The 5'-end of the RNA passes through a ring-like structure of the fold and is believed to remain protected from the Xrn1-like exonuclease.

In some embodiments, the nucleic acid construct comprising the one or more sequences that encode a protein of interest may comprise one or more xrRNA structures incorporated therein. In some embodiments, the xrRNA is a stretch of nucleotides having the conserved regions of the 3' UTR of one or more viral xrRNA sequences. In some embodiments, 1, 2, 3, 4, 5, 6, 7, 8, 9, 10 or more xrRNA elements are incorporated within the nucleic acid construct. In some embodiments, 2 or more xrRNA elements are incorporated in tandem within the nucleic acid construct. In some embodiments, the xrRNA comprise one or more regions comprising conserved sequences or fragments thereof or modifications thereof. In some embodiments, the xrRNA is placed at the 3'UTR of a retrotransposon element. In some embodiments, the xrRNA is placed at upstream of the sequences encoding the one or more proteins or polypeptides. In some embodiments, the xrRNA is placed in the 3'UTR of a retrotransposon element, such as an ORF2 sequence, and upstream of the sequences encoding the one or more proteins or polypeptides.

Figure 3A:
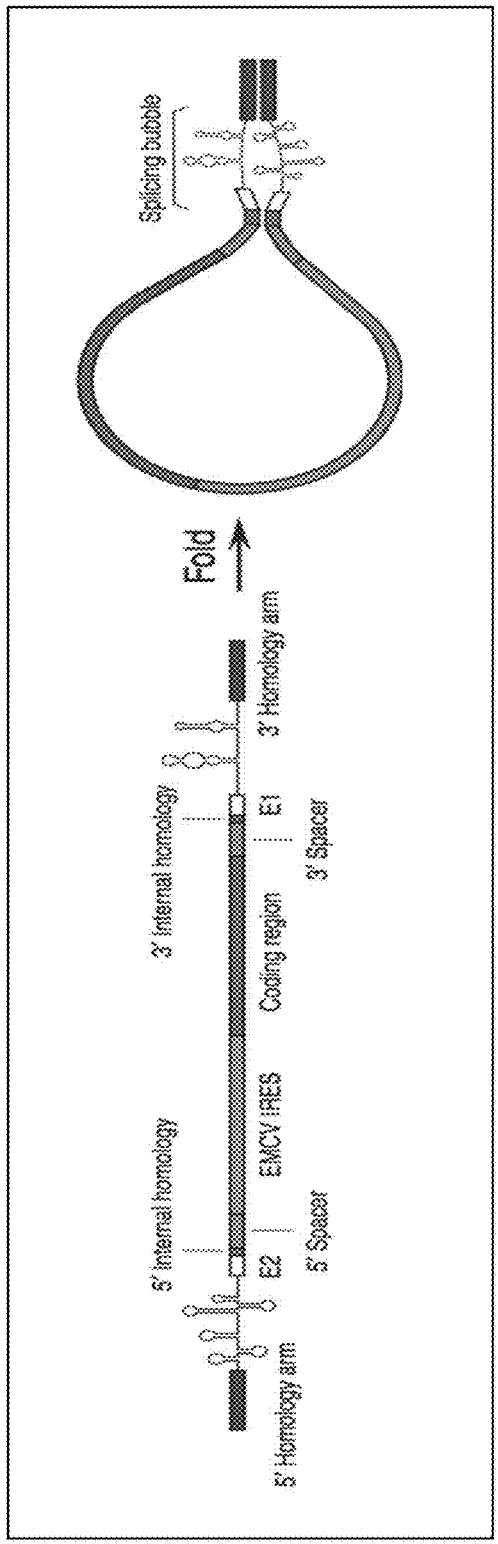
FIG. 3A illustrates an exemplary diagram of conventional circRNA structure and formation.

In some embodiments, the xrRNA structure comprises a MBFV xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a tick-borne flaviviruses (TBFVs) xrRNA sequence, or a sequence that is at least 90% identical thereof. In some embodiments, the xrRNA structure comprises a xrRNA sequence from a member of no known arthropod vector flaviviruses (NKVFVs), or a sequence that is at least 90% identical thereof. In some embodiments, the xrRNA structure comprises a xrRNA sequence from a member of insect-specific flaviviruses (ISFVs), or a sequence that is at least 90% identical thereof. In some embodiments, the xrRNA structure comprises a Zikavirus xrRNA sequence, or a sequence that is at least 90% identical thereof. It is hereby contemplated that any known xrRNA structural elements or conceivable non-obvious variations thereof may be used for the purpose described herein.

Several messenger RNAs from different organisms exhibit one or more pseudoknot structures that exhibits resistance from 5'-3' exonuclease. A pseudoknot is a RNA structure that is minimally composed of two helical segments connected by single-stranded regions or loops. Although several distinct folding topologies of pseudoknots exist.

Poly a Tail Modifications

The poly A structure in the 3'UTR of an mRNA is an important regulator of mRNA half-life. Deadenylation of the 3' end of the poly A tail is the first step of the intracellular mRNA degradation. In some embodiments, the length of the poly A tail of the mRNA construct is taken into critical consideration and designed for maximizing the expression of the protein encoded by the mRNA coding region, and the mRNA stability. In some embodiments, the nucleic acid construct comprises one or more poly A sequences. In some embodiments, the poly A sequence at the 3'UTR of the sequences encoding the one or more proteins or polypeptides comprise 20-200 adenosine nucleobases. In some embodiments, the poly A sequence comprises 30-200 adenosine nucleobases. In some embodiments, the poly A sequence comprises 50-200 adenosine nucleobases. In some embodiments, the poly A sequence comprises 80-200 adenosine nucleobases. In some embodiments, the mRNA segment comprising the sequences that encode one or more proteins or polypeptides comprises a 3'-UTR having a poly-A tail comprising about 180 adenosine nucleobases, or about 140 adenosine nucleobases, or about 120 adenosine nucleobases. In some embodiments, the poly A tail comprises about 122 adenosine nucleobases. In some embodiments, the poly A sequence comprises 50 adenosine nucleobases. In some embodiments, the poly A sequence comprises 30 adenosine nucleobases. In some embodiments, the adenosine nucleobases in the poly A tail are placed in tandem, with or without intervening non-adenosine bases. In some embodiments, one or more non-adenosine nucleobases are incorporated in the poly A tail, which confer further resistance to certain exonucleases.

In some embodiments, the stretch of adenosines in poly A tail of the construct comprises one or more non-adenosine (A) nucleobase. In some embodiments, the non-A nucleobase is present at −3, −2, −1, and/or +1 position at the poly A 3'-terminal region. In some embodiments, the non-A bases comprise a guanosine (G) or a cytosine (C) or an uracil base (U). In some embodiments, the non-A base is a G. In some embodiments, the non-A base more than one, in tandem, for example, GG. In some embodiments, the modification at the 3' end of the poly A tail with one or more non-A base is directed at disrupting the A base stacking at the poly A tail. The poly A base stacking promotes deadenylation by various deadenylating enzymes, and therefore 3' end of poly A tail ending in -AAAG, -AAAGA, or -AAAGGA are effective in conferring stability against deadenylation. In some organisms, a GC sequence intervening a poly A sequence is shown to effectively show down 3'-5' exonuclease mediated decay. A modification contemplated herein comprises an intervening non-A residue, or a non-A residue duplex intervening a poly A stretch at the 3' end.

In some embodiments, a triplex structure is introduced in the 3' UTR which effectively stalls or slows down exonuclease activity involving the 3' end.

In some embodiments, the mRNA with the modifications described above has an extended half-life and demonstrates stable expression over a longer period than the unmodified mRNA. In some embodiments, the mRNA stably expresses for greater than 2 days, 3 days, 4 days, 5 days, 6 days, 7 days, 8 days 9 days or 10 days or more, and the mRNA or its protein product is detectable in vivo. In some embodiments, the mRNA is detected up to 3 days, 4 days, 5 days, 6 days, 7 days, 8 days, 9 days, 10 days, 11 days, 12 days, 13 days, 14 days or 15 days in vivo. In some embodiments, a protein product of the mRNA is detected up to 3 days, 4 days, 5 days, 6 days, 7 days, 8 days, 9 days, 10 days, 11 days, 12 days, 13 days, 14 days, 15 days, 16 days, 17 days, 18 days, 20 days, 25 days or 30 days in vivo.

CircRNA and tectoRNA

Circular RNA is useful in the design and production of stable form of RNA used as a messenger RNA to direct synthesis protein chains, such as long, multiply repeating protein chains. There are few methods to make circular RNA (circRNA). They include protein-mediated ligation of RNA ends using RNA ligase and using a split self-splicing intron, such that if the two halves of the intron are located and the ends of a transcribed mRNA, the intron will splice itself out and leave a ligated product (FIG. 3A). Another technique relies on the ability of T4 DNA ligase to act as an RNA ligase when the RNA ends to be ligated are held together by an oligonucleotide. Both these techniques suffer from inefficiency and require a large amount of enzyme. A third technique uses the cyclization or circularization activity of group I introns where most of the intron sequences that carry out the reaction must remain a part of the circle. Group I introns share a complex set of secondary and tertiary structures containing a series of conserved RNA stem loops which form the catalytic core. Many of these introns are self-splicing in vitro and can splice and form two ligated exons as RNA with no accessory protein factors. The products created by the group I autocatalytic reaction are (1) an upstream exon ligated at the 5' splice site to the 3' splice site of a downstream exon and (2) a linear intron that can undergo further reversible auto-catalysis to form a circular intron. The presence of such a large highly structured nucleic acid sequence severely limits the types of RNA sequences that can be made circular by that technique. In addition, the catalytic activity of the intron may remain and interfere with structure and function of the circular RNA.

It is useful to increase the rate of the reaction, and thus the overall efficiency, by bringing the ends of the RNA in closer proximity. Previous work has achieved this by including complementary RNA sequences 3' and 5' to the ends of the mRNA such that upon hybridization of these sequences, the ends of the mRNA are in closer proximity such that it can undergo the ligation or self-splicing reaction with an overall faster rate compared to without the complementary sequences. These are called homology arms (FIG. 3A) of the self-splicing version of the circularization reaction. A major issue with such hybridization strategy is that if there are complementary sequences within the coding region to either of the homology arms, hybridization would actually inhibit the splicing reaction and the arms would need to be optimized for each new coding region. An alternative to this strategy described herein is the use of RNA sequences that fold a three-dimensional structure to form a stable binding interaction that is independent of sequence.

Non-Watson-Crick RNA tertiary interactions can be exploited to construct 'tectoRNA' molecular units, defined as RNA molecules capable of self-assembly. The use of such type of tertiary interactions allows one to control and modulate the assembly process by manipulating cation concentration (e.g. $Mg^{2+}$), and/or suitable temperature and employing modularly designed 'selector' RNA molecules. For the self-assembly of one-dimensional arrays, a basic modular unit was designed that comprises a 4-way junction with an interacting module on each helical arm. In some embodiments, the interacting module is a GAAA loop or a specific GAAA loop receptor. Each tectoRNA can interact with two other tectoRNAs via the formation of four loop-receptor interactions, two with each partner molecule.

In some embodiments, the tectoRNA structures are suitably selected, and integrated in the RNA comprising the exon and intron to form a circRNA. In some embodiments, the integration is done by well-known molecular biology techniques such as ligation. In some embodiments, the tectoRNA forms a stable structure at high temperatures. The tectoRNA structure do not compete with internal RNA sequences, thereby creating high efficiency circularization and splicing.

The circRNA can comprise a coding sequence described in any of the preceding sections. For example, it can comprise a sequence encoding fusion protein comprising a tethering or a receptor molecule. The receptor can be a phagocytic receptor fusion protein.

In some embodiments, the intron is a self-splicing intron.

In some embodiments, the terminal regions having the tertiary structures, also termed scaffolding regions for the circRNA, are about 30 nucleotides to about 100 nucleotides long. In some embodiments, the tertiary structure motif is about 45 nucleotides, about 50 nucleotides, about 55 nucleotides, about 60 nucleotides, about 65 nucleotides, about 70 nucleotides or about 75 nucleotides long. In some embodiments, the tertiary motifs are formed at high temperatures. In some embodiments, the tertiary motifs are stable.

In some embodiments, the nucleic acid construct having the one or more modifications as described herein and comprising one or more sequences encoding one or more proteins or polypeptides, is stable when administered in vivo. In some embodiments, the nucleic acid is an mRNA. In some embodiments, the mRNA comprising one or more sequences encoding one or more proteins or polypeptides is stable in vivo for more than 2 days, for more than 3 days, more than 4 days, more than 5 days, more than 6 days, more than 7 days, more than 8 days, more than 9 days, more than 10 days, more than 11 days, more than 12 days, more than 13 days, more than 14 days, more than 15 days, more than 16 days, more than 17 days, more than 18 days, more than 19 days, or more than 20 days. In some embodiments, the protein encoded by the sequences in the mRNA can be detected in vivo at greater than 3 days, 4 days, 5 days, 6 days, 7 days, 8 days, 9 days, 10 days, 11 days, 12 days, 13 days, 14 days, 15 days, 16 days, 17 days, 18 days, 19 days, or 20 days. In some embodiments, the protein encoded by the sequences in the mRNA can be detected in vivo for about 7 days after the mRNA is administered. In some embodiments, the protein encoded by the sequences in the mRNA can be detected in vivo for about 14 days after the mRNA is administered. In some embodiments, the protein encoded by the sequences in the mRNA can be detected in vivo for about 21 days after the mRNA is administered. In some embodiments, the protein encoded by the sequences in the mRNA can be detected in vivo for about 30 days after the mRNA is administered. In some embodiments, the protein encoded by the sequences in the mRNA can be detected in vivo for more than about 30 days after the mRNA is administered.

In some aspects, enhancing nucleic acid uptake or incorporation within the cell is contemplated for enhancing expression of the retrotransposition. One of the methods include obtaining a homogenous population of cells to initiate incorporation of the nucleic acid, e.g. via transfection, in case of plasmid vector constructs, or via electroporation or any other means that may be used suitably to deliver a nucleic acid molecule into the cell. In some embodiments, cell cycle synchronization may be sought. Cell cycle synchronization may be accomplished by sorting cells for a certain common phenotype. In some embodiments, the cell population may be subjected to a treatment with a reagent that can stall cell cycle progression of all cells at a certain stage. Exemplary reagents can be found in commercial databases, such as www.tocris.com/cell-biology/cell-cycle-inhibitors, or www.scbt.com/browse/chemicals-Other-Chemicals-cell-cycle-arresting-compounds. For example, itraconazole or nocodazole inhibits cell cycle at G1 phase, or reagents that arrest cell cycle at G0/G1 phase, for example, 5-[(4-Ethylphenyl)methylene]-2-thioxo-4-thiazolidinone (compound 10058-F4) (Tocris Bioscience); or a G2M cell cycle blocker, such as AZD 5438 (chemical name, 4-[2-Methyl-1-(1-methylethyl)-1H-imidazol-5-yl]-N-[4-(methylsulfonyl)phenyl]-2-pyrimidinamine) which blocks cell cycle at G2M, G1 or S phases, to name a few. Cyclosporin, hydroxyurea, thymidine, are well known reagents that can cause cell cycle arrests. Some reagents may irreversibly alter a cell state or may be toxic for the cells. Serum deprivation of cells for about 2-16 hours prior to electroporation or transfection, depending on the cell type, may also be an easy and reversible strategy for cell synchronization.

In some embodiments, retrotransposition efficiency may be increased by encouraging generation of DNA double stranded breaks to a cell that has been transfected with or electroporated with the retrotransposition constructs as described herein and/or modulating the DNA repair machinery. Application of these techniques may be limited depending on end uses of the cell that would undergo the genetic manipulation ex vivo for stable incorporation of a nucleic acid sequence by this method. In some cases, use of such techniques may be contemplated where robust expression of the protein or transcript encoded by the incorporated nucleic acid is expected as an outcome for a determined period of time. Method of introducing double stranded breaks in a cell include subjecting the cell to controlled ionizing radiation of about 0.1 Gy or less for a short period.

In some embodiments, efficiency of LINE-1 mediated retrotransposition may be increased by treating the cell with small molecule inhibitors of DNA repair proteins to increase the window for the reverse transcriptase to act. Exemplary small molecule inhibitors of DNA repair proteins may be Benzamide (CAS 55-21-0), Olaparib (Lynparza) (CAS 763113-22-0), Rucaparib (Clovis-AG014699, PF-01367338 Pfizer), Niraparib (MK-827 Tesaro) CAS 1038915-60-4); Veliparib (ABT-888 Abbvie) (CAS 912444-00-9); Camptothecin (CPT) (CAS 7689-03-4); Irinotecan (CAS 100286-90-6); Topotecan (Hycamtin® GlaxoSmithKline) (CAS 123948-87-8); NSC 19630 (CAS 72835-26-8); NSC 617145 (CAS 203115-63-3); ML216 (CAS 1430213-30-1); 6-hydroxyDL-dopa (CAS 21373-30-8); D-103; D-G23; DIDS (CAS 67483-13-0); B02 (CAS 1290541-46-6); RI-1 (CAS 415713-60-9); RI-2 (CAS 1417162-36-7); Streptonigrin (SN) (CAS 3930-19-6).

III. Nucleic Acid Cargo:

A. Transgene

In one aspect the transgene or noncoding sequence that is the heterologous nucleic acid sequence to be inserted within the genome of a cell is delivered as an mRNA. The mRNA may comprise greater than about 100, 200, 300, 400, 500, 600, 700, 800, 900, 1000, 1100, 1200, 1300, 1400, 1500, 1600, 1700, 1800, 1900, 2000, 3000, 4000, 5000, 6000, 7000, 8000, 9000, 10,000 bases. In some embodiments, the mRNA may be more than 10,000 bases long. In some embodiments, the mRNA may be about 11,000 bases long. In some embodiments, the mRNA may be about 12,000 bases long. In some embodiments, the mRNA comprises a transgene sequence that encodes a fusion protein. In some embodiments, the nucleic acid is delivered as a plasmid.

In some embodiments, the nucleic acid is delivered in the cell by transfection. In some embodiments, the nucleic acid is delivered in the cell by electroporation. In some embodiments, the transfection or electroporation is repeated more than once to enhance incorporation of the nucleic acid into the cell.

Contemplated herein are retrotransposon mediated stable integration of a recombinant nucleic acid encoding a phagocytic or tethering receptor (PR) fusion protein (CFP). In some embodiments, the CFPs comprise: a PR subunit comprising: a transmembrane domain, and an intracellular domain comprising an intracellular signaling domain; and an extracellular domain comprising an antigen binding domain specific to an antigen of a target cell; wherein the transmembrane domain and the extracellular domain are operatively linked.

In some embodiments, the nucleic acid comprises a sequence encoding a chimeric fusion protein (CFP), the CFP comprising an extracellular domain comprising a CD5 binding domain, and a transmembrane domain operatively linked to the extracellular domain. In some embodiments, the CD5 binding domain is a CD5 binding protein, such as an antigen binding fragment of an antibody, a Fab fragment, an scFv domain or an sdAb domain. In some embodiments, wherein the CD5 binding domain comprises an scFv comprising (i) a variable heavy chain (VH) sequence with at least 90% sequence identity to (SEQ ID NO: 63)
EIQLVQSGGGLVKPGGSVRISCAASGYTFTNYGMNWVRQAPGKGLEW

MGWINTHTGEPTYADSFKGRFTFSLDDSKNTAYLQINSLRAEDTAVY

FCTRRGYDWYFDVWGQGTTVTV;

and (ii) a variable light chain (VL) sequence with at least 90% sequence identity to (SEQ ID NO: 64)
DIQMTQSPSSLSASVGDRVTITCRASQDINSYLSWFQQKPG

KAPKTLIYRANRLESGVPSRFSGSGSGTDYTLTISSLQYED

FGIYYCQQYDESPWTFGGGTKLEIK

In some embodiments, the CFP further comprises an intracellular domain, wherein the intracellular domain comprises one or more intracellular signaling domains, and wherein a wild-type protein comprising the intracellular domain does not comprise the extracellular domain. In some embodiments, the one or more intracellular signaling domains comprises a phagocytic signaling domain. In some embodiments, the phagocytosis signaling domain comprises an intracellular signaling domain derived from a receptor other than Megf10, MerTk, FcαR, and Bai1. In some embodiments, the phagocytosis signaling domain comprises an intracellular signaling domain derived from FcγR, FcαR or FcεR. In some embodiments, the phagocytosis signaling domain comprises an intracellular signaling domain with at least 90% sequence identity to (SEQ ID NO: 65)
LYCRRLKIQVRKAAITSYEKSDGVYTGLSTRNQETYETLKHEKPP In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence with at least 90% sequence identity to (SEQ ID NO: 66)
YEDMRGILYAAPQLRSIRGQPGPNHEEDADSYENM In some embodiments, the proinflammatory signaling domain is derived from an intracellular signaling domain of CD40. In some embodiments, the proinflammatory signaling domain comprises a sequence with at least 90% sequence identity to (SEQ ID NO: 67)
KVAKKPTNKAPHPKQEPQEINFPDDLPGSNT

AAPVQETLHGCQPVTQEDGKESRISVQERQ.

In some embodiments, the transmembrane domain comprises a CD8 transmembrane domain. In some embodiments, the transmembrane domain comprises a sequence with at least 90% sequence identity to (SEQ ID NO: 68)
IYIWAPLAGTCGVLLLSLVIT In some embodiments, the extracellular domain further comprises a hinge domain derived from CD8, wherein the hinge domain is operatively linked to the transmembrane domain and the CD5 binding domain. In some embodiments, the extracellular domain comprises a sequence with at least 90% sequence identity to

```
                                          (SEQ ID NO: 69)
ALSNSIMYFSHFVPVFLPAKPTTTPAPRPPTPAPTIASQPLSL

RPEACRPAAGGAVHTRGLD.
```

In some embodiments, the CFP comprises an extracellular domain comprising a scFv that specifically binds CD5, and a hinge domain derived from CD8; a hinge domain derived from CD28 or at least a portion of an extracellular domain from CD68; a CD8 transmembrane domain, a CD28 transmembrane domain or a CD68 transmembrane domain; and an intracellular domain comprising at least two intracellular signaling domains, wherein the at least two intracellular signaling domains comprise: a first intracellular signaling domain derived from FcγR or FcεR, and a second intracellular signaling domain comprising a PI3K recruitment domain, or derived from CD40. In some embodiments, the recombinant polynucleic acid is an mRNA or circRNA. In some embodiments, the nucleic acid is delivered into a myeloid cell. In some embodiments, the nucleic acid is delivered into a CD14+ cell, a CD14+CD16-cell, an M0 macrophage, an M2 macrophage, an M1 macrophage or a mosaic myeloid cell/macrophage. In some embodiments, the fusion protein comprises a sequence with at least 90% sequence identity to

```
                                          (SEQ ID NO: 70)
EIQLVQSGGGLVKPGGSVRISCAASGYTFTNYGMNWVRQAPG

KGLEWMGWINTHTGEPTYADSFKGRFTFSLDDSKNTAYLQIN

SLRAEDTAVYFCTRRGYDWYFDVWGQGTTVTVSSGGGGSGGG

GSGGGGSDIQMTQSPSSLSASVGDRVTITCRASQDINSYLSW

FQQKPGKAPKTLIYRANRLESGVPSRFSGSGSGTDYTLTISS

LQYEDFGIYYCQQYDESPWTFGGGTKLEIKSGGGGSGALSNS

IMYFSHFVPVFLPAKPTTTPAPRPPTPAPTIASQPLSLRPEA

CRPAAGGAVHTRGLDIYIWAPLAGTCGVLLLSLVITLYCRRL

KIQVRKAAITSYEKSDGVYTGLSTRNQETYETLKHEKPPQGS

GSYEDMRGILYAAPQLRSIRGQPGPNHEEDADSYENM
```

In some embodiments, the fusion protein comprises a sequence with at least 90% sequence identity to

```
                                          (SEQ ID NO: 71)
EIQLVQSGGGLVKPGGSVRISCAASGYTFTNYGMNWVRQAPGKGLEWMGWINTHTGEPT

YADSFKGRFTFSLDDSKNTAYLQINSLRAEDTAVYFCTRRGYDWYFDVWGQGTTVTVSS

GGGGSGGGGSGGGGSDIQMTQSPSSLSASVGDRVTITCRASQDINSYLSWFQQKPGKAP

KTLIYRANRLESGVPSRFSGSGSGTDYTLTISSLQYEDFGIYYCQQYDESPWTFGGGTK

LEIKSGGGGSGALSNSIMYFSHFVPVFLPAKPTTTPAPRPPTPAPTIASQPLSLRPEAC

RPAAGGAVHTRGLDIYIWAPLAGTCGVLLLSLVITLYCRLKIQVRKAAITSYEKSDGVY

TGLSTRNQETYETLKHEKPPQKKVAKKPTNKAPHPKQEPQEINFPDDLPGSNTAAPVQE

TLHGCQPVTQEDGKESRISVQERQ
or
                                          (SEQ ID NO: 72)
EIQLVQSGGGLVKPGGSVRISCAASGYTFTNYGMNWVRQAPGKGLEWMGWINTHTGEPT

YADSFKGRFTFSLDDSKNTAYLQINSLRAEDTAVYFCTRRGYDWYFDVWGQGTTVTVSS

GGGGSGGGGSGGGGSDIQMTQSPSSLSASVGDRVTITCRASQDINSYLSWFQQKPGKAP

KTLIYRANRLESGVPSRFSGSGSGTDYTLTISSLQYEDFGIYYCQQYDESPWTFGGGTK

LEIKSGGGGSGALSNSIMYFSHFVPVFLPAKPTTTPAPRPPTPAPTIASQPLSLRPEAC

RPAAGGAVHTRGLDIYIWAPLAGTCGVLLLSLVITLYCRRLKIQVRKAAITSYEKSDGV

YTGLSTRNQETYETLKHEKPPQKKVAKKPTNKAPHPKQEPQEINFPDDLPGSNTAAPVQ

ETLHGCQPVTQEDGKESRISVQERQ.
```

In some embodiments, the fusion protein is a transmembrane protein, an intracellular protein or an intracellular protein. In one embodiment the fusion protein is directed to enhancing the function of an immune cell, e.g., a myeloid cell, selected from monocyte, macrophages dendritic cells or precursors thereof. In one embodiment the fusion protein augments a cellular function of an immune cell, such as phagocytosis. The disclosure is not limited by the transgenes that can be expressed using the methods and compositions described. The transgenes indicated in this section are exemplary.

Provided herein are exemplary transgene candidates, for stable integration into the genome of a phagocytic cell. In one embodiment the transgene is a recombinant nucleic acid encoding a phagocytic receptor (PR) fusion protein (CFP). The recombinant nucleic acid has a PR subunit comprising: (i) a transmembrane domain, and (ii) an intracellular domain comprising a phagocytic receptor intracellular signaling domain; and an extracellular antigen binding domain specific to an antigen of a target cell; wherein the transmembrane domain and the extracellular antigen binding domain are operatively linked such that antigen binding to the target by the extracellular antigen binding domain of the fused receptor activated in the intracellular signaling domain of the phagocytic receptor. In some embodiments, the recombinant nucleic acid encodes a chimeric antigen receptor. In some embodiments, the chimeric antigen receptor is a chimeric antigen receptor (phagocytosis) (CAR-P). In some embodiments, the fusion protein is a recombinant protein for locking anti-phagocytic signals. In some embodiments, the fusion protein is a phagocytosis enhancing chimeric protein. In some embodiments, the chimeric protein has intracellular domains comprising active phagocytosis signal transduction domains. In some embodiments, the chimeric protein enhances the phagocytic potential by enhancing the inflammatory potential of the phagocytic cell in which it expresses. In some embodiments, the transgene is designed to express a chimeric protein which is activated by contact with an antigen in a target cell, whereupon the phagocytic cell phagocytoses the target cell and kills the target cell.

The terms "spacer" or "linker" as used in reference to a fusion protein refers to a peptide sequence that joins the protein domains of a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence.

The various exemplary proteins encoded by a transgene that can be expressed for enhancing the immune potential of a phagocytic cell are described below. This is not an exhaustive list but serves as an exemplary list for transgene design within the scope of the present disclosure.

In some embodiments, the PSP subunit comprises a transmembrane (TM) domain of a phagocytic receptor.

In some embodiments, the PSP subunit comprises an ICD domain of a phagocytic receptor.

In some embodiments, the ICD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSCSD, CD205, CD207, CD209, RAGE, CD14, CD64, F4/80, CCR2, CX3CR1, CSF1R, Tie2, HuCRIg(L), and CD169 receptor.

In some embodiments, the ICD comprises the signaling domain derived from any one or more of: lectin, dectin 1, mannose receptor (CD206), scavenger receptor A1 (SRA1), MARCO (Macrophage Receptor with Collagenous Structure, aliases: SRA6, SCARA2), CD36 (Thrombospondin receptor, aliases: Scavenger Receptor class B, member 3), CD163 (Scavenger receptor, cysteine rich-type 1), MSR1, SCARA3, COLEC12 (aliases: Scavenger Receptor With C-Type Lectin, SCARA4, or Collectin 12), SCARA5, SCARB1, SCARB2, CD68 (SCARD, microsialin), OLR1 (Oxidized Low Density Lipoprotein Receptor 1, LOX1, or C-Type Lectin Domain Family 8 Member A), SCARF1, SCARF2, SRCRB4D, SSCSD, and CD169 (aliases, Sialoadhesin receptor, SIGLEC1).

In some embodiments, the recombinant nucleic acid encodes, for example, an intracellular domain of human MARCO. The PSR subunit comprises an intracellular domain having a 44 amino acid ICD of human MARCO having an amino acid sequence:

```
                                    (SEQ ID NO: 73)
MRNKKILKEDELLSETQQAAFHQIAMEPFEINVPKPKRRN
GVNF
```

In some embodiments, the PSR subunit comprises a variant which is at least 70%, 75%, 80%, 85%, 90% or 95% identical to the intracellular domain of MARCO.

In some embodiments, for example, the PSR (phagocytic scavenger receptor) comprises a transmembrane region of human MARCO.

In some embodiments, the recombinant nucleic acid encodes an intracellular domain of human SRA1. The PSR subunit comprises an intracellular domain having a 50 amino acid ICD of human SRA1 having an amino acid sequence:

```
                                    (SEQ ID NO: 74)
MEQWDHFHNQQEDTDSCSESVKFDARSMTALLPPNPKNSPSLQEKL
KSFK
```

In some embodiments, the PSR subunit comprises a variant which is at least 70%, 75%, 80%, 85%, 90% or 95% identical to the intracellular domain of human SRA1. The intracellular region of SRA has a phosphorylation site.

In some embodiments, the PSR comprises a transmembrane region of human SRA1.

In some embodiments, for example, the recombinant nucleic acid comprises an intracellular domain of CD36. In some embodiments, the recombinant nucleic acid comprises a TM domain of CD36. Naturally occurring full length CD36 has two TM domains and two short intracellular domains, and an extracellular domain of CD36 binds to oxidized LDL. Both of the intracellular domains contain pairs of cysteines that are fatty acid acylated. It lacks known signaling domains (e.g. kinase, phosphatase, g-protein binding, or scaffolding domains). N-terminal cytoplasmic domain is extremely short (5-7 amino acid residues) and is closely associated with the internal leaflet of the plasma membrane. The carboxy-terminal domain contains 13 amino acids, containing a CXCXSK motif homologous to a region in the intracellular domain of CD4 and CD8 that is known to interact with signaling molecules. The intracellular domain of CD36 is capable of assembling a signaling complex that activates lyn kinases, MAP kinases and Focal Adhesion Kinases (FAK), and inactivation of src homology 2-containing phosphotyrosine phosphatase (SHP-2). Members of the guanine nucleotide exchange factors (GEFs) have been identified as potential key signaling intermediates.

In some embodiments, the recombinant nucleic acid encodes for example, an intracellular domain of human SCARA3. In some embodiments, the PSR subunit comprises a variant which is at least 70%, 75%, 80%, 85%, 90% or 95% identical to the intracellular domain of human SCARA3. In some embodiments, the PSR comprises the TM domain of SCARA3. In some embodiments, the TM domains are about 20-30 amino acids long.

Scavenger receptors may occur as homo or hetero dimers. MARCO, for example occurs as a homo trimer.

In some embodiments, the TM domain or the ICD domain of the PSP is not derived from FcR, Megf10, Bai1 or MerTK. In some embodiments, the ICD of the PSR does not comprise a CD3 zeta intracellular domain.

In some embodiments, the intracellular domain and transmembrane domains are derived from FcR beta.

In one aspect the recombinant nucleic acid encodes a chimeric antigenic receptor for enhanced phagocytosis (CAR-P), which is a phagocytic scavenger receptor (PSR) fusion protein (CFP) comprising: (a) an extracellular domain comprising an extracellular antigen binding domain specific to an antigen of a target cell, (b) a transmembrane domain, and (c) a recombinant PSR intracellular signaling domain, wherein the recombinant PSR intracellular signaling domain comprises a first portion derived from a phagocytic and a second portion derived from non-phagocytic receptor.

In some embodiments, the second portion is not a PI3K recruitment domain. In some embodiments, the second portion is a PI3K recruitment domain.

The second portion derived from non-phagocytic receptor may comprise an intracellular signaling domain that enhances phagocytosis, and/or inflammatory potential of the engineered phagocytic cells expressing the recombinant nucleic acid. In some embodiments, the second portion derived from non-phagocytic receptor comprises more than one intracellular domain (ICD). In some embodiments, the second portion derived from non-phagocytic receptor comprises a second ICD. In some embodiments, the second portion derived from non-phagocytic receptor comprises a second and a third ICD. In some embodiments, the second portion derived from non-phagocytic receptor comprises a second, a third and a fourth ICD, wherein the second portion is encoded by the recombinant nucleic acid. The respective second portions comprising a second, or third or fourth ICD derived from non-phagocytic receptor are described as follows.

Chimeric Antigen Receptors for Enhancing Intracellular Signaling and Inflammation Activation In one aspect, the recombinant nucleic acid encodes a second intracellular domain in addition to the phagocytic ICD, which confers capability of potent pro-inflammatory immune activation, such as when macrophages engage in fighting infection. The second intracellular domain (second ICD) is fused to the cytoplasmic terminus of the first phagocytic ICD. The second intracellular domain provides a second signal is necessary to trigger inflammasomes and pro-inflammatory signals. Nod-like receptors (NLRs) are a subset of receptors that are activated in innate immune response, and oligomerize to form multi-protein complexes that serve as platforms to recruit proinflammatory caspases and induce their cleavage and activation. This leads to direct activation of ROS, and often result in a violent cell death known as pyroptosis. There are four inflammasome complexes, NLRP1m, NLRP3, IPAF and AIM2.

The tumor microenvironment (TME) constitutes an immunosuppressive environment. Influence of IL-10, glucocorticoid hormones, apoptotic cells, and immune complexes can interfere with innate immune cell function. Immune cells, including phagocytic cells settle into a tolerogenic phenotype. In macrophages, this phenotype, commonly known as the M2 phenotype is distinct from the M1 phenotype, where the macrophages are potent and capable of killing pathogens. Macrophages exposed to LPS or IFN-gamma, for example, can polarize towards an M1 phenotype, whereas macrophages exposed to IL-4 or IL-13 will polarize towards an M2 phenotype. LPS or IFN-gamma can interact with Toll-like receptor 4 (TLR4) on the surface of macrophages inducing the Trif and MyD88 pathways, inducing the activation of transcription factors IRF3, AP-1, and NFKB and thus activating TNFs genes, interferon genes, CXCL10, NOS2, IL-12, etc., which are necessary in a pro-inflammatory M1 macrophage response. Similarly, IL-4 and IL-13 bind to IL-4R, activation the Jak/Stat6 pathway, which regulates the expression of CCL17, ARG1, IRF4, IL-10, SOCS3, etc., which are genes associated with an anti-inflammatory response (M2 response). Expression of CD14, CD80, D206 and low expression of CD163 are indicators of macrophage polarization towards the M1 phenotype.

In some embodiments, the recombinant nucleic acid encodes one or more additional intracellular domains, comprising a cytoplasmic domain for inflammatory response. In some embodiments, expression of the recombinant nucleic acid encoding the phagocytic receptor (PR) fusion protein (CFP) comprising the cytoplasmic domain for inflammatory response in the engineered macrophages confers potent pro-inflammatory response similar to the M1 phenotype.

In some embodiments, the cytoplasmic domain for inflammatory response can be the signal transducing domains or regions of TLR3, 4, 9, MYD88, TRIF, RIG-1, MDAS, CD40, IFN receptor, NLRP-1-14, NOD1, NOD2, Pyrin, AIM2, NLRC4, CD40.

In some embodiments, the expression of the recombinant nucleic acid encoding the phagocytic scavenger receptor (PSR) fusion protein (CFP) comprises a pro-inflammatory cytoplasmic domain for activation of IL-1 signaling cascade.

In some embodiments, the cytoplasmic portion of the chimeric receptor (for example, phagocytic receptor (PR) fusion protein (CFP)) comprises a cytoplasmic domain from a toll-like receptor, such as the intracellular signaling domains of toll-like receptor 3 (TLR3), toll-like receptor 4 (TLR4), toll-like receptor 7 (TLR7), toll-like receptor 8 (TLR8), toll-like receptor 9 (TLR9). In some embodiments, the cytoplasmic portion of the chimeric receptor comprises a suitable region from interleukin-1 receptor-associated kinase 1 (IRAK1). In some embodiments, the cytoplasmic portion of the chimeric receptor comprises a suitable region from differentiation primary response protein (MYD88). In some embodiments, the cytoplasmic portion of the chimeric receptor comprises a suitable region from myelin and lymphocyte protein (MAL). In some embodiments, the cytoplasmic portion of the chimeric receptor comprises a suitable region from retinoic acid inducible gene (RIG-1).

In some embodiments, the transmembrane domain of the PSR comprises the transmembrane domain of any one of MYD88, TLR3, TLR4, TLR7, TLR8, TLR9, MAL, IRAK1, proteins.

In some embodiments, the recombinant PSR intracellular signaling domain comprises a first portion derived from a phagocytic and a second portion derived from non-phagocytic receptor wherein the second portion derived from non-phagocytic receptor comprises a phosphorylation site. In some embodiments, the phosphorylation site comprises amino acid sequences suitable for an autophosphorylation site. In some embodiments, the phosphorylation site comprises amino acid sequences suitable phosphorylation by Src family kinases. In some embodiments, the phosphorylation site comprises amino acid sequences, which upon phosphorylation are capable of binding to SH2 domains in a kinase. In some embodiments, a receptor tyrosine kinase domain is fused at the cytoplasmic end of the CFP in addition to the first cytoplasmic portion. In some embodiments, the phosphorylation is a tyrosine phosphorylation.

In some embodiments, the second intracellular domain is an Immune receptor Tyrosine Activation Motif (ITAM). The ITAM motif is present in mammalian α and β immunoglobulin proteins, TCR γ receptors, FCR γ receptors subunits, CD3 chains receptors and NFAT activation molecule.

In some embodiments, the CFP intracellular domain comprises one ITAM motif. In some embodiments, the CFP intracellular domain comprises more than one ITAM motifs. In some embodiments, the CFP intracellular domain comprises two or more ITAM motifs. In some embodiments, the CFP intracellular domain comprises three or more ITAM motifs. In some embodiments, the CFP intracellular domain comprises four or more ITAM motifs. In some embodiments, the CFP intracellular domain comprises five or more ITAM motifs. In some embodiments, the CFP intracellular domain comprises six or more ITAM motifs. In some embodiments, the CFP intracellular domain comprises seven or more ITAM motifs. In some embodiments, the CFP intracellular domain comprises eight or more ITAM motifs. In some embodiments, the CFP intracellular domain comprises nine or more ITAM motifs. In some embodiments, the CFP intracellular domain comprises ten or more ITAM motifs.

In some embodiments, one or more domains in the first phagocytic ICD comprises a mutation.

In some embodiments, one or more domains in the second ICD comprises a mutation to enhance a kinase binding domain, to generate a phosphorylation site, to generate an SH2 docking site or a combination thereof.

Co-expression of an Inflammatory Gene

In one aspect, the recombinant nucleic acid comprises a coding sequence for a pro-inflammatory gene, which is co-expressed with the CFP in the engineered cell. In some embodiments, the pro-inflammatory gene is a cytokine. Examples include but not limited to TNF-α, IL-1α, IL-1β, IL-6, CSF, GMCSF, or IL-12 or interferons.

The recombinant nucleic acid encoding the proinflammatory gene can be monocistronic, wherein the two coding sequences for (a) the PSP and (b) the proinflammatory gene are post-transcriptionally or post-translationally cleaved for independent expression.

In some embodiments, the two coding sequences comprise a self-cleavage domain, encoding a P2A sequence, for example.

In some embodiments, the two coding regions are separated by an IRES site.

In some embodiments, the two coding sequences are encoded by a bicistronic genetic element. The coding regions for (a) the PSP and (b) the proinflammatory gene can be unidirectional, where each is under a separate regulatory control. In some embodiments, the coding regions for both are bidirectional and drive in opposite directions. Each coding sequence is under a separate regulatory control.

Co-expression of the proinflammatory gene is designed to confer strong inflammatory stimulation of the macrophage and activate the surrounding tissue for inflammation.

Integrin Activation Domains

Cell-cell and cell-substratum adhesion is mediated by the binding of integrin extracellular domains to diverse protein ligands; however, cellular control of these adhesive interactions and their translation into dynamic cellular responses, such as cell spreading or migration, requires the integrin cytoplasmic tails. These short tails bind to intracellular ligands that connect the receptors to signaling pathways and cytoskeletal networks (Calderwood DA, 2004, Integrin Activation, Journal of Cell Science 117, 657-666). Integrins are heterodimeric adhesion receptors formed by the non-covalent association of α and β subunits. Each subunit is a type I transmembrane glycoprotein that has relatively large extracellular domains and, with the exception of the β4 subunit, a short cytoplasmic tail. Individual integrin family members have the ability to recognize multiple ligands. Integrins can bind to a large number of extracellular matrix proteins (bone matrix proteins, collagens, fibronectins, fibrinogen, laminins, thrombospondins, vitronectin, and von Willebrand factor), reflecting the primary function of integrins in cell adhesion to extracellular matrices. Many "counter-receptors" are ligands, reflecting the role of integrins in mediating cell-cell interactions. Integrins undergo conformational changes to increase ligand affinity.

The Integrin β2 subfamily consists of four different integrin receptors, $\alpha_M\beta_2$ (CD11b/CD18, Mac-1, CR3, Mo-1), $\alpha_L\beta_2$ (CD11a/CD18, LFA-1), $\alpha_X\beta_2$ (CD11c/CD18), and $\alpha_D\beta_2$ (CD11d/CD18). These leukocyte integrins are involved in virtually every aspect of leukocyte function, including the immune response, adhesion to and transmigration through the endothelium, phagocytosis of pathogens, and leukocyte activation.

The α subunits of all $\beta_2$ integrins contain an inserted region of ~200 amino acids, termed the I or A domain. Highly conserved I domains are found in several other integrin a subunits and other proteins, such as certain coagulation and complement proteins. I domains mediate protein-protein interactions, and in integrins, they are integrally involved in the binding of protein ligands. Although the I domains dominate the ligand binding functions of their integrins, other regions of the a subunits do influence ligand recognition. As examples, in $\alpha_M\beta_2$ a mAb (OKM1) recognizing an epitope outside the I domain but in the am subunit inhibits ligand binding; and the EF-hand regions in $\alpha_L\beta_2$ and $\alpha_2\beta_1$, integrins with I domains in their a subunits, contribute to ligand recognition. The $\alpha_M$ subunit, and perhaps other a subunits, contains a lectin-like domain, which is involved in engagement of non-protein ligands, and occupancy may modulate the function of the I domain.

As integrins lack enzymatic activity, signaling is instead induced by the assembly of signaling complexes on the cytoplasmic face of the plasma membrane. Formation of these complexes is achieved in two ways; first, by receptor clustering, which increases the avidity of molecular interactions thereby increasing the on-rate of binding of effector molecules, and second, by induction of conformational changes in receptors that creates or exposes effector binding sites. Within the ECM, integrins have the ability to bind fibronectin, laminins, collagens, tenascin, vitronectin and thrombospondin. Clusters of integrin/ECM interactions form focal adhesions, concentrating cytoskeletal components and signaling molecules within the cell. The cytoplasmic tail of integrins serve as a binding site for α-actinin and talin which then recruit vinculin, a protein involved in anchoring F-actin to the membrane. Talin is activated by kinases such as protein kinase C (PKCα).

Integrins are activated by selectins. Leucocytes express L-selectin, activated platelets express P-selectin, and activated endothelial cells express E- and P-selectin. P-selectin-mediated adhesion enables chemokine- or platelet-activating factor-triggered activation of β2 integrins, which stabilizes adhesion. It also facilitates release of chemokines from adherent leucocytes. The cytoplasmic domain of P-selectin glycoprotein ligand 1 formed a constitutive complex with Nef-associated factor 1. After binding of P-selectin, Src kinases phosphorylated Nef-associated factor 1, which recruit the phosphoinositide-3-OH kinase p85-p110δ heterodimer and result in activation of leukocyte integrins. E-selectin ligands transduce signals that also affect β2 integrin function. Selectins trigger activation of Src family kinases. SFKs activated by selectin engagement phosphorylate the immunoreceptor tyrosine-based activation motifs (ITAMs) in the cytoplasmic domains of DAP12 and FcRγ. In some respects, CD44 is sufficient to transduce signals from E-selectin. CD44 triggers the inside-out signaling of integrins. A final common step in integrin activation is binding of talin to the cytoplasmic tail of the β subunit. Kindlins, another group of cytoplasmic adaptors, bind to a different region of integrin 13 tails. Kindlins increase the clustering of talin-activated integrins. Kindlins are responsive to selectin signaling, however, kindlins are found mostly in hematopoietic cells, such as neutrophils. Selectin signaling as well as signaling upon integrin activation by chemokines components have shared components, including SFKs, Syk, and SLP-76.

In some embodiments, the intracellular domain of the recombinant PSR fusion protein comprises an integrin activation domain. The integrin activation domain comprises an intracellular domain of a selectin, for example, a P-selectin, L-selectin or E-selectin.

In some embodiments, the intracellular domain of the recombinant PSR fusion protein comprises an integrin activation domain of laminin.

In some embodiments, the intracellular domain of the recombinant PSR fusion protein comprises an integrin activation domain for activation of Talin.

In some embodiments, the intracellular domain of the recombinant PSR fusion protein comprises an integrin activation domain fused to the cytoplasmic end of the phagocytic receptor ICD domain.

Chimeric Receptor for Enhancing Antigen Cross Presentation

In some embodiments, the recombinant nucleic acid encodes a domain capable of enabling cross presentation of antigens. In general, MHC class I molecules present self- or pathogen-derived antigens that are synthesized within the cell, whereas exogenous antigens derived via endocytic uptake are loaded onto MHC class II molecules for presentation to CD4+ T cells. MHC I-restricted presentation of endogenous antigens, in which peptides are generated by the proteasome. However, in some cases, DC can process exogenous antigens into the MHC-I pathway for presentation to CD8+ T cells. This is referred to as cross presentation of antigens. Soluble or exogenous antigenic components may get degraded by lysosomal proteases in the vacuoles and cross presented by DCs, instead of following the endocytotic pathway. In some instances, chaperones, such as heat shock protein 90 (Hsp90) have shown to help cross present antigens by certain APCs. HSP-peptide complexes are known to be internalized by a distinct group of receptors compared to free polypeptides. These receptors are from the scavenger receptor families and included LOX-1, SREC-I/SCARF-I, and FEEL1/Stabilin-1. Both SREC-I and LOX-1 have been shown to mediate the cross presentation of molecular chaperone bound antigens and lead to activation of CD8+ T lymphocytes.

SREC-1 (scavenger receptor expressed by endothelial cells) has no significant homology to other types of scavenger receptors but has unique domain structures. It contains 10 repeats of EGF-like cysteine-rich motifs in the extracellular domain. Recently, the structure of SREC-I was shown to be similar to that of a transmembrane protein with 16 EGF-like repeats encoded by the *Caenorhabditis elegans* gene ced-I, which functions as a cell surface phagocytic receptor that recognizes apoptotic cells.

Cross presentation of cancer antigens through the Class-I MHC pathway results in enhanced CD8+ T cell response, which is associated with cytotoxicity and therefore beneficial in tumor regression. In some embodiments, the intracellular domain of the CFP comprises a SREC1 intracellular domain. In some embodiments, the intracellular domain of the CFP comprises a SRECII intracellular domain.

In some embodiments, the PSR subunit comprises: an intracellular domain comprising a PSR intracellular signaling domain from SREC1 or SRECII.

In some embodiments, the PSR subunit comprises: (i) a transmembrane domain, and (ii) an intracellular domain comprising a PSR intracellular signaling domain from SREC1 or SRECII.

In some embodiments, the PSR subunit comprises: (i) a transmembrane domain, (ii) an intracellular domain comprising a PSR intracellular signaling domain, and (iii) an extracellular domain from SREC1 or SRECII.

Transmembrane Domain of a CFP Fusion Protein

In some embodiments, the TM encoded by the recombinant nucleic acid comprises a domain of a scavenger receptor (SR). In some embodiments, the TM can be the TM domain of or derived from any one or more of: lectin, dectin 1, mannose receptor (CD206), SRA1, MARCO, CD36, CD163, MSR1, SCARA3, COLEC12, SCARA5, SCARB1, SCARB2, CD68, OLR1, SCARF1, SCARF2, SRCRB4D, SSCSD, and CD 169.

In some embodiments, the TM domains are about 20-30 amino acids long. TM domains of SRs are about 20-30 amino acids long.

The TM domain or the ICD domain of the PSP is not derived from Megf10, Bai1 or MerTK. The ICD of the PSR does not comprise a CD3 zeta intracellular domain.

In some embodiments, the TM is derived from the same phagocytic receptor as the ICD.

In some embodiments, the TM region is derived from a plasma membrane protein. The TM can be selected from an Fc receptor (FcR). In some embodiments, nucleic acid sequence encoding domains from specific FcRs are used for cell-specific expression of a recombinant construct. An FCR-alpha region comprising the TM domain may be used for macrophage specific expression of the construct. FcRβ recombinant protein expresses in mast cells.

In some embodiments, the CFP comprises the TM of an FCR-beta (FcRβ).

In some embodiments, the CFP comprises both the FcRβ TM and ICD domains.

In some embodiments, the TM domain is derived from CD8.

In some embodiments, the TM is derived from CD2.

In some embodiments, the TM is derived from FCR alpha.

Extracellular Domain of a CFP Fusion Protein

The extracellular domain comprises an antigen binding domain that binds to one or more target antigens on a target cell. The target binding domain is specific for the target. The extracellular domain can include an antibody or an antigen-binding domain selected from intrabodies, peptibodies, nanobodies, single domain antibodies. SMIPs, and multi-specific antibodies.

In some embodiments, the extracellular domain includes a Fab binding domain. In yet other such embodiments, the extracellular domain includes a scFv.

In some embodiments, the chimeric antigen receptor comprises an extracellular antigen binding domain is derived from the group consisting of an antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof. In some embodiments, the antigen-binding fragment (Fab), a single-chain variable fragment (scFv), a nanobody, a VH domain, a VL domain, a single domain antibody (sdAb), a VNAR domain, and a VHH domain, a bispecific antibody, a diabody, or a functional fragment of any thereof specifically bind to one or more antigens.

In some embodiments, the antigens are cancer antigens, and the target cell is a target cancer cell. In some embodiments, the antigen for a target cancer cell is selected from the group consisting of CD3, CD4, CD5, CD7, CD19, CCR2, CCR4, CD30, CD37, TCRB1/2, TCR □□, TCR □□, CD22, HER2 (ERBB2/neu), Mesothelin, PSCA, CD123, CD30, CD171, CD138, CS-1, CLECL1, CD33, CD79b, EGFRvIII, GD2, GD3, BCMA, PSMA, ROR1, FLT3, TAG72, CD38, CD44v6, CEA, EPCAM, B7H3 (CD276), KIT (CD 117), CD213A2, IL-1 IRa, PRSS21, VEGFR2, CD24, MUC-16, PDGFR-beta, SSEA-4, CD20, MUC1, EGFR, NCAM, Prostase, PAP, ELF2M, Ephrin B2, FAP, EphA2, GM3, TEM1/CD248, TEM7R, CLDN6, TSHR, GPRCSD, CD97, CD179a, ALK, and IGLL1.

Various cancer antigen targets can be selected from cancer antigens known to one of skill in the art. Depending on the cancer and the cell type involved cancer antigens are mutated native proteins. The antigen binding domains are screened for specificity towards mutated/cancer antigens and not the native antigens.

In some embodiments, for example, the cancer antigen for a target cancer cell can be one or more of the mutated/cancer antigens: MUC16, CCAT2, CTAG1A, CTAG1B, MAGE A1, MAGEA2, MAGEA3, MAGE A4, MAGEA6, PRAME, PCA3, MAGE C1, MAGEC2, MAGED2, AFP, MAGEA8, MAGE9, MAGEA11, MAGEA12, IL13RA2, PLAC1, SDCCAG8, LSP1, CT45A1, CT45A2, CT45A3, CT45A5, CT45A6, CT45A8, CT45A10, CT47A1, CT47A2, CT47A3, CT47A4, CT47A5, CT47A6, CT47A8, CT47A9, CT47A10, CT47A11, CT47A12, CT47B1, SAGE1, and CT55.

In some embodiments, for example, the cancer antigen for a target cancer cell can be one or more of the mutated/cancer antigens: CD2, CD3, CD4, CD5, CD7, CD8, CD20, CD30, CD45, CD56, where the cancer is a T cell lymphoma.

In some embodiments, for example, the cancer antigen for a target cancer cell can be one or more of the mutated/cancer antigens: IDH1, ATRX, PRL3, or ETBR, where the cancer is a glioblastoma.

In some embodiments, for example, the cancer antigen for a target cancer cell can be one or more of the mutated/cancer antigens: CA125, beta-hCG, urinary gonadotropin fragment, AFP, CEA, SCC, inhibin or extradiol, where the cancer is ovarian cancer.

In some embodiments, the cancer antigen for a target cancer cell may be HER2.

In some embodiments, the cancer antigen for a target cancer cell may be EGFR Variant III.

In some embodiments, the cancer antigen for a target cancer cell may be CD19.

In some embodiments, the SR subunit region comprises an extracellular domain (ECD) of the scavenger receptor. In some embodiments, the ECD of the scavenger receptor comprises an ECD domain of the SR comprising the ICD and the TM domains. In some embodiments, the SR-ECD contributes to the binding of the phagocyte to the target cell, and in turn is activated, and activates the phagocytosis of the target cell.

In some embodiments, the PSR domain optionally comprises the ECD domain or portion thereof of the respective scavenger receptor the ICD and TM domains of which is incorporated in the PSR. Therefore, in some embodiments, In some embodiments, the ECD encoded by the recombinant nucleic acid comprises a domain selected from the group consisting of lectin, dectin 1, mannose receptor (CD206), scavenger receptor A1 (SRA1), MARCO, CD36, CD163, MSR1, SCARA3, COLEC12, SCARA5, SCARB1, SCARB2, CD68, OLR1, SCARF1, SCARF2, CXCL16, STAB1, STAB2, SRCRB4D, SSCSD, CD205, CD207, CD209, RAGE, CD14, CD64, F4/80, CCR2, CX3CR1, CSF1R, Tie2, HuCRIg(L), and CD169 receptor. The extracellular domains of most macrophage scavenger receptors contain scavenger receptors with a broad binding specificity that may be used to discriminate between self and non-self in the nonspecific antibody-independent recognition of foreign substances. The type I and II class A scavenger receptors (SR-AI1 and SR-AII) are trimeric membrane glycoproteins with a small NH2-terminal intracellular domain, and an extracellular portion containing a short spacer domain, an a-helical coiled-coil domain, and a triple-helical collagenous domain. The type I receptor additionally contains a cysteine-rich COOH-terminal (SRCR) domain. These receptors are present in macrophages in diverse tissues throughout the body and exhibit an unusually broad ligand binding specificity. They bind a wide variety of polyanions, including chemically modified proteins, such as modified LDL, and they have been implicated in cholesterol deposition during atherogenesis. They may also play a role in cell adhesion processes in macrophage-associated host defense and inflammatory conditions.

In some embodiments, the SR ECD is designed to bind to pro-apoptotic cells. In some embodiments, the scavenger receptor ECD comprises a binding domain for a cell surface molecule of a cancer cell or an infected cell.

In some embodiments, the extracellular domain of the PR subunit is linked by a linker to a target cell binding domain, such as an antibody or part thereof, specific for a cancer antigen.

In some embodiments, the extracellular antigen binding domain comprises one antigen binding domain. In some embodiments, the extracellular antigen binding domain comprises more than one binding domain. In some embodiments, the binding domain is an scFv. In some embodiments, the binding domain is an single domain antibody (sdAb). In some embodiments, the binding domain is fused to the recombinant PR at the extracellular domain. In some embodiments, the binding domain (e.g., scFv) and the extracellular domain of the PR are linked via a linker.

In some embodiments, the ECD antigen binding domain can bind to an intracellular antigen. In some embodiments, the intracellular antigen is a cancer antigen.

In some embodiments, the extracellular antigen binding domain binds to the target ligand with an affinity of less than 1000 nM. In some embodiments, the extracellular antigen binding domain binds to the target ligand with an affinity of less than 500 nM. In some embodiments, the extracellular antigen binding domain binds to the target ligand with an affinity of less than 450 nM. In some embodiments, the extracellular antigen binding domain binds to the target ligand with an affinity of less than 400 nM. In some embodiments, the extracellular antigen binding domain binds to the target ligand with an affinity of less than 350 nM. In some embodiments, the extracellular antigen binding domain binds to the target ligand with an affinity of less than 250 nM. In some embodiments, the extracellular antigen binding domain binds to the target ligand with an affinity of less than 200 nM. In some embodiments, the extracellular antigen binding domain binds to the target ligand with an affinity of less than 100 nM. In some embodiments, the extracellular antigen binding domain binds to the target ligand with an affinity ranging between than 200 nM to 1000 nM. In some embodiments, the extracellular antigen binding domain binds to the target ligand with an affinity ranging between than 300 nM to 1.5 mM. In some embodiments, the antigen binding domain binds to the target ligand with an affinity >200 nM, >300 nM or >500 nM.

Peptide Linker

In some embodiments, the extracellular antigen binding domains, scfvs are linked to the TM domain or other extracellular domains by a linker. In some embodiments, where there are more than one scfv at the extracellular antigen binding domain the more than scfvs are linked with each other by linkers.

In some embodiments, the linkers are flexible. In some embodiments, the linkers comprise a hinge region. Linkers are usually short peptide sequences. In some embodiments, the linkers are stretches of Glycine and one or more Serine residues. Other amino acids preferred for short peptide linkers include but are not limited to threonine (Thr), serine (Ser), proline (Pro), glycine (Gly), aspartic acid (Asp), lysine (Lys), glutamine (Gln), asparagine (Asn), and alanine (Ala) arginine (Arg), phenylalanine (Phe), glutamic acid (Glu). Of these Pro, Thr, and Gln are frequently used amino acids for natural linkers. Pro is a unique amino acid with a cyclic side chain which causes a very restricted conformation. Pro-rich sequences are used as interdomain linkers, including the linker between the lipoyl and E3 binding domain in pyruvate dehydrogenase (GA$_2$PA$_3$PAKQEA$_3$PAPA$_2$KAEAPA$_3$PA$_2$KA) (SEQ ID NO: 75). For the purpose of the disclosure, the empirical linkers may be flexible linkers, rigid linkers, and cleavable linkers. Sequences such as (G4S)x (SEQ ID NO: 76) (where x is multiple copies of the moiety, designated as 1, 2, 3, 4, and so on) comprise a flexible linker sequence. Other flexible sequences used herein include several repeats of glycine, e.g., (Gly)6(SEQ ID NO: 77) or (Gly)8 (SEQ ID NO: 78). On the other hand, a rigid linker may be used, for example, a linker (EAAAK)x (SEQ ID NO: 79), where x is an integer, 1, 2, 3, 4 etc. gives rise to a rigid linker.

In some embodiments, the linker comprises at least 2, or at least 3 amino acids. In some embodiments, the linker comprises 4 amino acids. In some embodiments, the linker comprises 5 amino acids. In some embodiments, the linker comprises 6 amino acids. In some embodiments, the linker comprises 7 amino acids. In some embodiments, the linker comprises 8 amino acids. In some embodiments, the linker comprises 9 amino acids. In some embodiments, the linker comprises 8 amino acids. In some embodiments, the linker comprises 10 amino acids. In some embodiments, the linker comprises 11 amino acids. In some embodiments, the linker comprises 12 amino acids. In some embodiments, the linker comprises 13 amino acids. In some embodiments, the linker comprises 14 amino acids. In some embodiments, the linker comprises 15 amino acids. In some embodiments, the linker comprises 16 amino acids. In some embodiments, the linker comprises 17 amino acids. In some embodiments, the linker comprises 18 amino acids. In some embodiments, the linker comprises 19 amino acids. In some embodiments, the linker comprises 20 amino acids.

As contemplated herein, any suitable ECD, TM or ICD domain can be cloned interchangeably in the suitable portion of any one of the CARP receptors described in the disclosure to obtain a protein with enhanced phagocytosis compared to an endogenous receptor.

Characteristics of the Fusion Proteins:

The CFP can structurally incorporate into the cell membrane of the cell in which it is expressed. Specific leader sequences in the nucleic acid construct, such as the signal peptide can be used to direct plasma membrane expression of the encoded protein. The transmembrane domain encoded by the construct can incorporate the expressed protein in the plasma membrane of the cell.

In some embodiments, the transmembrane domain comprises a TM domain of an FcRalpha receptor, which dimerizes with endogenous FcR-gamma receptors in the macrophages, ensuring macrophage specific expression.

The CFP can render the cell that expresses it as potently phagocytic. When the recombinant nucleic acid encoding the CFP is expressed in a cell, the cell can exhibit an increased phagocytosis of a target cell having the antigen of a target cell, compared to a cell not expressing the recombinant nucleic acid. When the recombinant nucleic acid is expressed in a cell, the cell can exhibit an increased phagocytosis of a target cell having the antigen of a target cell, compared to a cell not expressing the recombinant nucleic acid. In some embodiments, the recombinant nucleic acid when expressed in a cell, the cell exhibits at least 2-fold increased phagocytosis of a target cell having the antigen of a target cell, compared to a cell not expressing the recombinant nucleic acid. In some embodiments, the recombinant nucleic acid when expressed in a cell, the cell exhibits at least 3-fold, 4-fold, 5-fold, 6-fold, 7-fold, 8-fold, 9-fold, 10-fold, 20-fold 30-fold or at least 5-fold increased phagocytosis of a target cell having the antigen of a target cell, compared to a cell not expressing the recombinant nucleic acid.

In some embodiments, expression of SIRP-ΔICD enhances phagocytosis of the cell expressing it by 1.1 fold or more, 1.2 fold or more, 1.3 fold or more, q.4 fold or more, 1.5 fold or more, by 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing SIRP-ΔICD.

In some embodiments, the cells co-expressing SIRP-ΔICD and a CFP encoding a phagocytic receptor as described herein exhibits an augmented phagocytosis compared to a cell that does not express either of the proteins. In some embodiments, co-expressing SIRP-ΔICD and a CFP encoding a phagocytic receptor as described herein exhibits more than 2-fold, more than 3-fold, more than 4-fold, more than 5-fold, more than 6-fold, more than 7-fold, more than 8-fold, more than 9-fold, more than 10-fold, more than 20-fold, more than 30-fold, more than 40-fold, more than 50-fold, more than 60-fold, more than 70-fold, more than 80-fold, more than 90-fold, more than 100-fold, or more than 150-fold or more than 200-fold increase in phagocytic potential (measured in fold change of phagocytic index) compared to a cell that does not express either the SIRP-ΔICD or the CFP encoding a phagocytic receptor.

In some embodiments, expression of the any one of a CFP expressing a CD47 blocking extracellular domain of SIRPα and an intracellular domain of a phagocytic receptor augments phagocytic activity of a cell expressing it by at least 1.5 fold or more, 1.6 fold or more, 1.7 fold or more, 1.8 fold or more, 1.9 fold or more, 2 fold or more, 3 fold or more, 4 fold or more, 5 fold or more, 8 fold or more, 10 fold or more, 15 fold or more, 20 fold or more, 30 fold or more, 40 fold or more, 50 fold or more, 60 fold or more, 70 fold or more 80 fold or more, 90 fold or more, 100 fold or more, compared to a cell not expressing the CFP, or compared to a cell expressing SIRP-ΔICD.

In some embodiments, the enhancement in phagocytosis of target cells by a cell expressing either SIRP-ΔICD is highly increased compared to a phagocytic cell not expressing SIRP-ΔICD.

In some embodiments, the enhancement in phagocytosis of target cells by a cell expressing a CFP comprising a CD47 blocking extracellular domain of SIRPα and an intracellular domain of a phagocytic receptor is highly increased compared to a control phagocytic cell not expressing the fusion protein or a control phagocytic cell expressing the SIRP-ΔICD.

In some embodiments, when the recombinant nucleic acid described herein is expressed in a cell, the cell exhibits an increased cytokine production. The cytokine can comprise any one of: IL-1, IL-6, IL-12, IL-23, TNF, CXCL9, CXCL10, CXCL11, IL-18, IL-23, IL-27 and interferons.

In some embodiments, when the recombinant nucleic acid described herein is expressed in a cell, the cell exhibits an increased cell migration.

In some embodiments, when the recombinant nucleic acid described herein is expressed in a cell, the cell exhibits an increased immune activity. In some embodiments, when the recombinant nucleic acid is expressed in a cell, the cell exhibits an increased expression of MHC II. In some embodiments, when the recombinant nucleic acid is expressed in a cell, the cell exhibits an increased expression of CD80. In some embodiments, when the recombinant nucleic acid is expressed in a cell, the cell exhibits an increased expression of CD86. In some embodiments, when the recombinant nucleic acid is expressed in a cell, the cell exhibits an increased iNOS production.

In some embodiments, when the recombinant nucleic acid is expressed in a cell, the cell exhibits decreased trogocytosis of a target cell expressing the antigen of a target cell compared to a cell not expressing the recombinant nucleic acid.

In embodiments, the chimeric receptors may be glycosylated, pegylated, and/or otherwise post-translationally modified. In further embodiments, glycosylation, pegylation, and/or other posttranslational modifications may occur in vivo or in vitro and/or may be performed using chemical techniques. In additional embodiments, any glycosylation, pegylation and/or other posttranslational modifications may be N-linked or O-linked. In embodiments any one of the chimeric receptors may be enzymatically or functionally active such that, when the extracellular domain is bound by a ligand, a signal is transduced to polarize a macrophage.

In some embodiments, the chimeric fusion protein (CFP) comprises an extracellular domain (ECD) targeted to bind to CD5 (CD5 binding domain), for example, comprising a heavy chain variable region (VH) having an amino acid sequence as set forth in SEQ ID NO: 1. In some embodiments, the chimeric CFP comprises a CD5 binding heavy chain variable domain comprising an amino acid sequence that has at least 80%, 85%, 90%, 95%, 96%, 97%, 98%, 99% sequence identity to SEQ ID NO: 1. In some embodiments, the extracellular domain (ECD) targeted to bind to CD5 (CD5 binding domain) comprises a light chain variable domain (VL) having an amino acid sequence as set forth in SEQ ID NO: 2. In some embodiments, the chimeric CFP comprises a CD5 binding light chain variable domain comprising an amino acid sequence that has at least 80%, 85%, 90%, 95%, 96%, 97%, 98%, 99% sequence identity to SEQ ID NO: 2.

In some embodiments, the CFP comprises an extracellular domain targeted to bind to HER2 (HER2 binding domain) having for example a heavy chain variable domain amino acid sequence as set forth in SEQ ID NO: 8 and a light chain variable domain amino acid sequence as set forth in SEQ ID NO: 9. In some embodiments, the CFP comprises a HER2 binding heavy chain variable domain comprising an amino acid sequence that has at least 80%, 85%, 90%, 95%, 96%, 97%, 98%, 99% sequence identity to SEQ ID NO: 8. In some embodiments, the CFP comprises a HER2 binding light chain variable domain comprising an amino acid sequence that has at least 80%, 85%, 90%, 95%, 96%, 97%, 98%, 99% sequence identity to SEQ ID NO: 9.

In some embodiments, the CFP comprises a hinge connecting the ECD to the transmembrane (TM). In some embodiments the hinge comprises the amino acid sequence of the hinge region of a CD8 receptor. In some embodiments, the CFP may comprise a hinge having the amino acid sequence set forth in SEQ ID NO: 7 (CD8a chain hinge domain). In some embodiments, the PFP hinge region comprises an amino acid sequence that is at least 80%, 85%, 90%, 95%, 96%, 97%, 98%, 99% sequence identity to SEQ ID NO: 7.

In some embodiments, the CFP comprises a CD8 transmembrane region, for example having an amino acid sequence set forth in SEQ ID NO: 6. In some embodiments, the CFP TM region comprises an amino acid sequence that is at least 80%, 85%, 90%, 95%, 96%, 97%, 98%, 99% sequence identity to SEQ ID NO: 6.

In some embodiments, the CFP comprises an intracellular domain having an FcR domain. In some embodiments, the CFP comprises an FcR domain intracellular domain comprises an amino acid sequence set forth in SEQ ID NO: 3, or at least a sequence having 80%, 85%, 90%, 95%, 96%, 97%, 98%, 99% sequence identity to SEQ ID NO: 3.

In some embodiments, the CFP comprises an intracellular domain having a PI3K recruitment domain. In some embodiments the PI3K recruitment domain comprises an amino sequence set forth in SEQ ID NO: 4. In some embodiments the PI3K recruitment domain comprises an amino acid sequence that has at least 80%, 85%, 90%, 95%, 96%, 97%, 98%, 99% sequence identity to SEQ ID NO: 4.

In some embodiments, the CFP comprises an intracellular domain having a CD40 intracellular domain. In some embodiments the CD40 ICD comprises an amino sequence set forth in SEQ ID NO: 5. In some embodiments the CD40 ICD comprises an amino acid sequence that has at least 80%, 85%, 90%, 95%, 96%, 97%, 98%, 99% sequence identity to SEQ ID NO: 5.

In some embodiments, the CD5 binding domain comprises an scFv comprising: (i) a variable heavy chain (VH) sequence of SEQ ID NO: 1 or with at least 90% sequence identity to SEQ ID NO: 1; and (ii) a variable light chain (VL) sequence of SEQ ID NO: 2 or with at least 70%, 75%, 80%, 85%, 90%, 91%, 92%, 93%, 94%, 95%, 96%, 97%, 98% or 99% sequence identity to SEQ ID NO: 2. In some embodiments, the CD5 binding domain comprises an scFv comprising SEQ ID NO: 33 or with at least 70%, 75%, 80%, 85%, 90%, 91%, 92%, 93%, 94%, 95%, 96%, 97%, 98% or 99% sequence identity to SEQ ID NO: 33. In some embodiments, the HER2 binding domain comprises an scFv comprising: (i) a variable heavy chain (VH) sequence of SEQ ID NO: 8 or with at least 70%, 75%, 80%, 85%, 90%, 91%, 92%, 93%, 94%, 95%, 96%, 97%, 98% or 99% sequence identity to SEQ ID NO: 8; and (ii) a variable light chain (VL) sequence of SEQ ID NO: 9 or with at least 70%, 75%, 80%, 85%, 90%, 91%, 92%, 93%, 94%, 95%, 96%, 97%, 98% or 99% sequence identity to SEQ ID NO: 9. In some embodiments, the CD5 binding domain comprises an scFv comprising SEQ ID NO: 32 or with at least 70%, 75%, 80%, 85%, 90%, 91%, 92%, 93%, 94%, 95%, 96%, 97%, 98% or 99% sequence identity to SEQ ID NO: 32. In some embodiments, the CFP further comprises an intracellular domain, wherein the intracellular domain comprises one or more intracellular signaling domains, and wherein a wild-type protein comprising the intracellular domain does not comprise the extracellular domain.

In some embodiments, the extracellular domain further comprises a hinge domain derived from CD8, wherein the hinge domain is operatively linked to the transmembrane domain and the anti-CD5 binding domain. In some embodiments, the extracellular hinge domain comprises a sequence of SEQ ID NO: 7 or with at least 70%, 75%, 80%, 85%, 90%, 91%, 92%, 93%, 94%, 95%, 96%, 97%, 98% or 99% sequence identity to SEQ ID NO: 7.

In some embodiments, the CFP comprises an extracellular domain fused to a transmembrane domain of SEQ ID NO: 30 or with at least 70%, 75%, 80%, 85%, 90%, 91%, 92%, 93%, 94%, 95%, 96%, 97%, 98% or 99% sequence identity to SEQ ID NO: 30. In some embodiments, the CFP comprises an extracellular domain fused to a transmembrane domain of SEQ ID NO: 31 or with at least 70%, 75%, 80%, 85%, 90%, 91%, 92%, 93%, 94%, 95%, 96%, 97%, 98% or 99% sequence identity to SEQ ID NO: 31.

In some embodiments, the transmembrane domain comprises a CD8 transmembrane domain. In some embodiments, the transmembrane domain comprises a sequence of SEQ ID NO: 6 or 29 or with at least 70%, 75%, 80%, 85%, 90%, 91%, 92%, 93%, 94%, 95%, 96%, 97%, 98% or 99% sequence identity to SEQ ID NO: 6 or 29. In some embodiments, the transmembrane domain comprises a sequence of SEQ ID NO: 18 or with at least 70%, 75%, 80%, 85%, 90%, 91%, 92%, 93%, 94%, 95%, 96%, 97%, 98% or 99% sequence identity to SEQ ID NO: 18. In some embodiments, the transmembrane domain comprises a sequence of SEQ ID NO: 34 or with at least 70%, 75%, 80%, 85%, 90%, 91%, 92%, 93%, 94%, 95%, 96%, 97%, 98% or 99% sequence identity to SEQ ID NO: 34. In some embodiments, the transmembrane domain comprises a sequence of SEQ ID NO: 19 or with at least 70%, 75%, 80%, 85%, 90%, 91%, 92%, 93%, 94%, 95%, 96%, 97%, 98% or 99% sequence identity to SEQ ID NO: 19.

In some embodiments, the CFP comprises one or more intracellular signaling domains that comprise a phagocytic signaling domain. In some embodiments, the phagocytosis signaling domain comprises an intracellular signaling domain derived from a receptor other than Megf10, MerTk, FcRα, and Bai1. In some embodiments, the phagocytosis signaling domain comprises an intracellular signaling domain derived from a receptor other than Megf10, MerTk, an FcR, and Bai1. In some embodiments, the phagocytosis signaling domain comprises an intracellular signaling domain derived from a receptor other than CD3. In some embodiments, the phagocytosis signaling domain comprises an intracellular signaling domain derived from FcRγ, FcRα or FcRε. In some embodiments, the phagocytosis signaling domain comprises an intracellular signaling domain derived from CDζ. In some embodiments, the CFP comprises an intracellular signaling domain of any one of SEQ ID NOs: 3, 20, 27 and 28 or with at least 70%, 75%, 80%, 85%, 90%, 91%, 92%, 93%, 94%, 95%, 96%, 97%, 98% or 99% sequence identity to any one of SEQ ID NOs: 3, 20, 27 and 28. In some embodiments, the one or more intracellular signaling domains further comprises a proinflammatory signaling domain. In some embodiments, the proinflammatory signaling domain comprises a PI3-kinase (PI3K) recruitment domain. In some embodiments, the proinflammatory signaling domain comprises a sequence of SEQ ID NO: 4 or with at least 70%, 75%, 80%, 85%, 90%, 91%, 92%, 93%, 94%, 95%, 96%, 97%, 98% or 99% sequence identity to SEQ ID NO: 4. In some embodiments, the proinflammatory signaling domain is derived from an intracellular signaling domain of CD40. In some embodiments, the proinflammatory signaling domain comprises a sequence of SEQ ID NO: 5 or with at least 70%, 75%, 80%, 85%, 90%, 91%, 92%, 93%, 94%, 95%, 96%, 97%, 98% or 99% sequence identity to SEQ ID NO: 5. In some embodiments, the CFP comprises an intracellular signaling domain of SEQ ID NO: 21 or with at least 70%, 75%, 80%, 85%, 90%, 91%, 92%, 93%, 94%, 95%, 96%, 97%, 98% or 99% sequence identity to SEQ ID NO: 21. In some embodiments, the CFP comprises an intracellular signaling domain of SEQ ID NO: 23 or with at least 70%, 75%, 80%, 85%, 90%, 91%, 92%, 93%, 94%, 95%, 96%, 97%, 98% or 99% sequence identity to SEQ ID NO: 23.

In some embodiments, the CFP comprises a sequence of SEQ ID NO: 14 or with at least 70%, 75%, 80%, 85%, 90%, 91%, 92%, 93%, 94%, 95%, 96%, 97%, 98% or 99% sequence identity to SEQ ID NO: 14. In some embodiments, the CFP comprises a sequence of SEQ ID NO: 15 or with at least 70%, 75%, 80%, 85%, 90%, 91%, 92%, 93%, 94%, 95%, 96%, 97%, 98% or 99% sequence identity to SEQ ID NO: 15. In some embodiments, the CFP comprises a sequence of SEQ ID NO: 16 or with at least 70%, 75%, 80%, 85%, 90%, 91%, 92%, 93%, 94%, 95%, 96%, 97%, 98% or 99% sequence identity to SEQ ID NO: 16. In some embodiments, the CFP comprises a sequence of SEQ ID NO: 24 or with at least 70%, 75%, 80%, 85%, 90%, 91%, 92%, 93%, 94%, 95%, 96%, 97%, 98% or 99% sequence identity to SEQ ID NO: 24. In some embodiments, the CFP comprises a sequence of SEQ ID NO:25 or with at least 70%, 75%, 80%, 85%, 70%, 75%, 80%, 85%, 90%, 91%, 92%, 93%, 94%, 95%, 96%, 97%, 98% or 99%, 91%, 92%, 93%, 94%, 95%, 96%, 97%, 98% or 99% sequence identity to SEQ ID NO: 25.

In some embodiments, the CFP comprises: (a) an extracellular domain comprising: (i) a scFv that specifically binds CD5, and (ii) a hinge domain derived from CD8; a hinge domain derived from CD28 or at least a portion of an extracellular domain from CD68; (b) a CD8 transmembrane domain, a CD28 transmembrane domain, a CD2 transmembrane domain or a CD68 transmembrane domain; and (c) an intracellular domain comprising at least two intracellular signaling domains, wherein the at least two intracellular signaling domains comprise: (i) a first intracellular signaling domain derived from FcRα, FcRγ or FcRε, and (ii) a second intracellular signaling domain: (A) comprising a PI3K recruitment domain, or (B) derived from CD40. In some embodiments, the CFP comprises as an alternative (c) to the above: an intracellular domain comprising at least two intracellular signaling domains, wherein the at least two intracellular signaling domains comprise: (i) a first intracellular signaling domain derived from a phagocytic receptor intracellular domain, and (ii) a second intracellular signaling domain derived from a scavenger receptor phagocytic receptor intracellular domain comprising: (A) comprising a PI3K recruitment domain, or (B) derived from CD40. Exemplary scavenger receptors from which an intracellular signaling domain may be derived may be found in Table 2. In some embodiments, the CFP comprises and intracellular signaling domain derived from an intracellular signaling domain of an innate immune receptor.

In some embodiments, the recombinant polynucleic acid is an mRNA. In some embodiments, the recombinant polynucleic acid is a circRNA. In some embodiments, the recombinant polynucleic acid is a viral vector. In some embodiments, the recombinant polynucleic acid is delivered via a viral vector.

In some embodiments, the myeloid cell is a CD14+ cell, a CD14+/CD16− cell, a CD14+/CD16+ cell, a CD14−/CD16+ cell, CD14−/CD16− cell, a dendritic cell, an M0 macrophage, an M2 macrophage, an M1 macrophage or a mosaic myeloid cell/macrophage/dendritic cell.

In one aspect, provided herein is a method of treating cancer in a human subject in need thereof comprising administering a pharmaceutical composition to the human subject, the pharmaceutical composition comprising: (a) a myeloid cell comprising a recombinant polynucleic acid sequence, wherein the polynucleic acid sequence comprises a sequence encoding a chimeric fusion protein (CFP), the CFP comprising: (i) an extracellular domain comprising an anti-CD5 binding domain, and (ii) a transmembrane domain operatively linked to the extracellular domain; and (b) a pharmaceutically acceptable carrier; wherein the myeloid cell expresses the CFP.

In some embodiments, upon binding of the CFP to CD5 expressed by a target cancer cell of the subject killing or phagocytosis activity of the myeloid cell is increased by greater than 20% compared to a myeloid cell not expressing the CFP. In some embodiments, growth of a tumor is inhibited in the human subject.

In some embodiments, the cancer is a CD5+ cancer. In some embodiments, the cancer is leukemia, T cell lymphoma, or B cell lymphoma. In some embodiments, the CFP comprises one or more sequences shown in Table A and/or Table B below.

TABLE A

Exemplary sequences of CFPs and domains thereof

| SEQ ID NO | PFP/Domain | Sequence |
|---|---|---|
| 1 | Anti-CD5 heavy chain variable domain | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV |
| 2 | Anti-CD5 light chain variable domain | DIQMTQSPSSLSASVGDRVTITCRASQDINSYLSWFQQKPG KAPKTLIYRANRLESGVPSRFSGSGSGTDYTLTISSLQYEDF GIYYCQQYDESPWTFGGGTKLEIK |
| 33 | Anti-CD5 scFv | EIQLVQSGGGLVKPGGSVRISCAASGYTFTNYGMNWVRQA PGKGLEWMGWINTHTGEPTYADSFKGRFTFSLDDSKNTAY LQINSLRAEDTAVYFCTRRGYDWYFDVWGQGTTVTV*SSGG GGSGGGGSGGGGS*DIQMTQSPSSLSASVGDRVTITCRASQDI NSYLSWFQQKPGKAPKTLIYRANRLESGVPSRFSGSGSGTD YTLTISSLQYEDFGIYYCQQYDESPWTFGGGTKLEIK |
| 3 | FcRγ-chain intracellular signaling domain | LYCRRLKIQVRKAAITSYEKSDGVYTGLSTRNQETYETLKH EKPPQ |
| 20 | FcRγ-chain intracellular signaling domain | LYCRLKIQVRKAAITSYEKSDGVYTGLSTRNQETYETLKHE KPPQ |
| 27 | FcRγ-chain intracellular signaling domain | RLKIQVRKAAITSYEKSDGVYTGLSTRNQETYETLKHEKPP Q |
| 28 | FcRγ-chain intracellular signaling domain | RLKIQVRKAAITSYEKSDGVYTGLSTRNQETYETLKHEKPP Q |
| 4 | PI3K recruitment domain | YEDMRGILYAAPQLRSIRGQPGPNHEEDADSYENM |

TABLE A-continued

Exemplary sequences of CFPs and domains thereof

| SEQ ID NO | PFP/Domain | Sequence |
|---|---|---|
| 5 | CD40 intracellular domain | KKVAKKPTNKAPHPKQEPQEINFPDDLPGSNTAAPVQETLH GCQPVTQEDGKESRISVQERQ |
| 6 | CD8α chain transmembrane domain | IYIWAPLAGTCGVLLLSLVIT |
| 29 | CD8α chain transmembrane domain | IYIWAPLAGTCGVLLLSLVITLYC |
| 7 | CD8α chain hinge domain | ALSNSIMYFSHFVPVFLPAKPTTTPAPRPPTPAPTIASQPLSL RPEACRPAAGGAVHTRGLD |
| 8 | Anti-HER2 heavy chain variable domain | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE |
| 9 | Anti-HER2 light chain variable domain | LVQPGGSLRLSCAASGFNIKDTYIHWVRQAPGKGLEWVAR IYPTNGYTRYADSVKGRFTISADTSKNTAYLQMNSLRAEDT AVYYCSRWGGDGFYAMDVWGQGTLVTV |
| 32 | Anti-HER2 scFv | DIQMTQSPSSLSASVGDRVTITCRASQDVNTAVAWYQQKP GKAPKLLIYSASFLYSGVPSRFSGSRSGTDFTLTISSLQPEDF ATYYCQQHYTTPPTFGQGTKVEIKRTGSTSGSGKPGSGEGS EVQLVE*SSGGGGSGGGGSGGGGS*LVQPGGSLRLSCAASGFN IKDTYIHWVRQAPGKGLEWVARIYPTNGYTRYADSVKGRF TISADTSKNTAYLQMNSLRAEDTAVYYCSRWGGDGFYAM DVWGQGTLVTV |
| 17 | GMCSF Signal peptide | MWLQSLLLLGTVACSIS |
| 18 | CD28 transmembrane domain | FWVLVVVGGVLACYSLLVTVAFIIFWV |
| 34 | CD2 Transmembrane domain | IYLIIGICGGGSLLMVFVALLVFYIT |
| 19 | CD68 transmembrane domain | ILLPLIIGLILLGLLALVLIAFCII |
| 21 | TNFR1 intracellular domain | QRWKSKLYSIVCGKSTPEKEGELEGTTTKPLAPNPSFSPTPG FTPTLGFSPVPSSTFTSSSTYTPGDCPNFAAPRREVAPPYQG ADPILATALASDPIPNPLQKWEDSAHKPQSLDTDDPATLYA VVENVPPLRWKEFVRRLGLSDHEIDRLELQNGRCLREAQY SMLATWRRRTPRREATLELLGRVLRDMDLLGCLEDIEEAL CGPAALPPAPSLLR |
| 22 | TNFR2 intracellular domain | PLCLQREAKVPHLPADKARGTQGPEQQHLLITAPSSSSSSLE SSASALDRRAPTRNQPQAPGVEASGAGEARASTGSSDSSPG GHGTQVNVTCIVNVCSSSDHSSQCSSQASSTMGDTDSSPSE SPKDEQVPFSKEECAFRSQLETPETLLGSTEEKPLPLGVPDA GMKPS |
| 23 | MDA5 intracellular domain | MSNGYSTDENFRYLISCFRARVKMYIQVEPVLDYLTFLPAE VKEQIQRTVATSGNMQAVELLLSTLEKGVWHLGWTREFVE ALRRTGSPLAARYMNPELTDLPSPSFENAHDEYLQLLNLLQ PTLVDKLLVRDVLDKCMEEELLTIEDRNRIAAAENNGNESG VRELLKRIVQKENWFSAFLNVLRQTGNNELVQELTGSDCSE SNAEIEN |
| 30 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVITL YC |
| 31 | CD8α chain hinge domain + transmembrane domain | ALSNSIMYFSHFVPVFLPAKPTTTPAPRPPTPAPTIASQPLSL RPEACRPAAGGAVHTRGLDIYIWAPLAGTCGVLLLSLVIT |

TABLE A-continued

Exemplary sequences of CFPs and domains thereof

| SEQ ID NO | PFP/Domain | Sequence |
|---|---|---|
| 14 | CD5-FcRγ-PI3K | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV*SSGGGGSGGGGSGGGGS*DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK*SGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRRLKIQVRKAAITSYEKSDGVYTGLSTRNQETYETLKHEKPPQ*GSGS*YEDMRGILYAAPQLRSIRGQPGPNHEEDADSYENM |
| 15 | HER2-FcRγ-PI3K | MWLQSLLLLGTVACSISDIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTGSTSGSGKPGSGEGSEVQLVE*SGGGL*VQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDVWGQGTLVTV*SSSGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRRLKIQVRKAAITSYEKSDGVYTGLSTRNQETYETLKHEKPPQ*GSGS*YEDMRGILYAAPQLRSIRGQPGPNHEEDADSYENM |
| 16 | CD5-FcRγ-CD40 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTV*SSGGGGSGGGGSGGGGS*DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK*SGGGGS*GALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQKKVAKKPTNKAPHPKQEPQEINFPDDLPGSNTAAPVQETLHGCQPVTQEDGKESRISVQERQ |
| 24 | CD5-FcRγ-MDA5 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIKSGGGGSGALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQGSGSMSNGYSTDENFRYLISCFRARVKMYIQVEPVLDYLTFLPAEVKEQIQRTVATSGNMQAVELLLSTLEKGVWHLGWTREFVEALRRTGSPLAARYMNPELTDLPSPSFENAHDEYLQLLNLLQPTLVDKLLVRDVLDKCMEEELLTIEDRNRIAAAENNGNESGVRELLKRIVQKENWFSAFLNVLRQTGNNELVQELTGSDCSESNAEIEN |
| 25 | CD5-FcRγ-TNFR1 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIKSGGGGSGALSNSIMYFSHFVPVFLPAKPTTTPAPRPPTPAPTIASQPLSLRPEACRPAAGGAVHTRGLDIYIWAPLAGTCGVLLLSLVITLYCRLKIQVRKAAITSYEKSDGVYTGLSTRNQETYETLKHEKPPQGSGSQRWKSKLYSIVCGKSTPEKEGELEGTTTKPLAPNPSFSPTPGFTPTLGFSPVPSSTFTSSSTYTPGDCPNFAAPRREVAPPYQGADPILATALASDPIPNPLQKWEDSAHKPQSLDTDDPATLYAVVENVPPLRWKEFVRRLGLSDHEIDRLELQNGRCLREAQYSMLATWRRRTPRREATLELLGRVLRDMDLLGCLEDIEEALCGPAALPPAPSLLR |
| 26 | CD5-FcRγ-TNFR2 | MWLQSLLLLGTVACSISEIQLVQSGGGLVKPGGSVRISCAASGYTFTNYGMNWVRQAPGKGLEWMGWINTHTGEPTYADSFKGRFTFSLDDSKNTAYLQINSLRAEDTAVYFCTRRGYDWYFDVWGQGTTVTVSSGGGGSGGGGSGGGGSDIQMTQSPSSLSASVGDRVTITCRASQDINSYLSWFQQKPGKAPKTLIYRA |

TABLE A-continued

Exemplary sequences of CFPs and domains thereof

| SEQ ID NO | PFP/Domain | Sequence |
|---|---|---|
| | | NRLESGVPSRFSGSGSGTDYTLTISSLQYEDFGIYYCQQYDE SPWTFGGGTKLEIKSGGGGSGALSNSIMYFSHFVPVFLPAKP TTTPAPRPPTPAPTIASQPLSLRPEACRPAAGGAVHTRGLDI YIWAPLAGTCGVLLLSLVITLYCRLKIQVRKAAITSYEKSDG VYTGLSTRNQETYETLKHEKPPQGSGSPLCLQREAKVPHLP ADKARGTQGPEQQHLLITAPSSSSSSLESSASALDRRAPTRN QPQAPGVEASGAGEARASTGSSDSSPGGHGTQVNVTCIVN VCSSSDHSSQCSSQASSTMGDTDSSPSESPKDEQVPFSKEEC AFRSQLETPETLLGSTEEKPLPLGVPDAGMKPS |

TABLE B

Linker sequences

| SEQ ID | Sequence |
|---|---|
| 10 | SSGGGGSGGGGSGGGS |
| 11 | SGGGGSG |
| 12 | SGGG |
| 13 | GSGS |

IV. Noncoding Exogenous Sequence for Delivery and Incorporation into the Genome of a Cell A noncoding sequence may be delivered into the cell and designed to be incorporated in the genome of the cell. The noncoding sequence as used herein, is a sequence that does not result in a translated protein product, but may have regulatory elements, such as transcribed products, such as inhibitory RNA. In some embodiments, such a sequence may be a miRNA sequence. In some embodiments, the sequence may be a sequence for siRNA generation. In some embodiments, the sequence may comprise an intronic sequence, or a binding site created, such that one or more DNA binding proteins can dock on the site and influence the nature and behavior of the adjoining regions. In some embodiments, the sequence may be a transcription factor binding site. In some embodiments, the sequence may comprise an enhancer binding site. In some embodiments, the sequence may comprise a binding site for topoisomerase, gyrase, reverse transcriptase, polymerase, poly A binding protein, guanylyl cyclase, ligase, restriction enzymes, DNA methylase, HDAC enzymes, and many others. In some embodiments, the noncoding sequence may be directed to manipulating heterochromatin. A noncoding insert sequence, as it may also be referred to here, may be a few nucleotides to 5 kB in length.

V. Plasmid Design and Recombinant Nucleic Acid Design Comprising an Insert Sequence The nucleic acid construct comprising one or more sequences encoding one or more proteins or polypeptides is incorporated in a plasmid for transcription and generating an mRNA. mRNA can be transcribed in an in vitro system using synthetic system of cell extracts. Alternatively, mRNA can be generated in a cell and harvested. The cell can be a prokaryotic cell, such as a bacterial cell. In some embodiments, the cell is a eukaryotic cell. In some embodiments, the transcription occurs in a synthetic system. Provided herein are exemplary plasmid design.

In some embodiments, of the various aspects of the disclosure, a plasmid is designed for expression of the mRNA molecule comprising a heterologous sequence of interest that encodes a protein or a polypeptide. The plasmid comprises, inter alia: the sequences for genomic integration elements for integration of the heterologous sequence of interest that encodes a protein or a polypeptide; the sequence comprising the transgene or fragment thereof, operably linked to its separate promoter and regulatory elements that are required for its expression in the host following integration in the host genome, (such as, the subject who is administered the mRNA); one or more regulatory elements for transcription and generation of the mRNA including a promoter for expression of the mRNA, e.g. in a bacterial cell or cell extract, and 3' stabilizing elements; sequences for one or more detection marker and/or selection markers.

As is known to one of skill in the art, a plasmid backbone can be an available vector, such as an in-house or commercially developed vector, that can be improved in various ways for best expression of the transcribed sequences, for example, (but not limited to), by introducing one or more desirable restriction digestion sites in the MCS (multiple cloning site), introducing a desired promoter for overall mRNA transcription, such as the T7 promoter, exchanging an existing sequence within the plasmid vector for one or more desired sequences, or introducing one or more desired segments, such as a selection marker sequence.

The plasmid comprises transcription regulatory elements, such as a promoter at the 5' region, and a 3'-stabilizing element. In some embodiments, the promoter is chosen for enhanced mRNA transcription in the desired cell, such as an *E. coli* bacterial cell. In some embodiments, the promoter for transcription of the plasmid is selected from a T7 promoter, a Sp6 promoter, pL (lambda) promoter, T3 promoter, trp promoter, araBad promoter, lac promoter or a Ptac promoter. In some embodiments, the promoter is a T7 promoter. T7 or Sp6 promoters are constitutive promoters and are useful for high level transcription or in vitro transcription. In some embodiments, the 3' stabilizing element is a sequence from BGH 3' element, WPRE 3' element, SV40 element, hGH element and other elements. The 3' element comprises the necessary poly A and transcription termination sequences.

Exemplary selection markers include antibiotic selection marker and/or expression detection marker. Antibiotic selection markers include but are not limited to ampicillin resistance gene sequence (beta lactamase gene or fragment thereof) conferring resistance to ampicillin, for example G418 selection marker, tetracycline resistance gene sequence conferring resistance to tetracycline, kanamycin resistance gene sequence conferring resistance to kanamycin, erythromycin resistance gene sequence conferring resistance to erythromycin, chloramphenicol resistance gene sequence conferring resistance to chloramphenicol, neomycin resistant gene sequence conferring resistance to neomycin, and others. Exemplary expression detection marker include FLAG, HA, GFP and others.

In some embodiments, the and other tags that can be fused to one or more coding sequences to function as a surrogate for the expression of the desired protein or peptide to which it is fused.

In some embodiments, the plasmid is less than 20 kb in length. In some embodiments, the plasmid is less than 19 kb in length. In some embodiments, the plasmid is less than 20 kb in length. In some embodiments, the plasmid is less than 18 kb in length. In some embodiments, the plasmid is less than 20 kb in length. In some embodiments, the plasmid is less than 17 kb in length. In some embodiments, the plasmid is less than 20 kb in length. In some embodiments, the plasmid is less than 16 kb in length. In some embodiments, the plasmid is less than 15 kb in length. In some embodiments, the plasmid is less than 14 kb in length. In some embodiments, the plasmid is less than 13 kb in length. In some embodiments, the plasmid is less than 12 kb in length. In some embodiments, the plasmid is about 15 kb, about 14 kb, about 13 kb, about 12 kb or about 10 kb in length.

In some embodiments, the codon is optimized for maximized transcription suitable for the transcription system.

VI. Features Related to the Expression of the Transgene In Vivo

Transcription Regulatory Elements in the Recombinant Nucleic Acid Construct (Transgene)

In some embodiments, the recombinant nucleic comprises one or more regulatory elements within the noncoding regions that can be manipulated for desired expression profiles of the encoded proteins. In some embodiments, the noncoding region may comprise suitable enhancer. In some embodiments, the enhancer comprises a binding region for a regulator protein or peptide may be added to the cell or the system comprising the cell, for commencement of expression of the protein encoded under the influence of the enhancer. Conversely, a regulatory element may comprise a protein binding domain that remains bound with the cognate protein and continue to inhibit transcription and/or translation of recombinant protein until an extracellular signal is provided for the protein to decouple from the bound position to allow commencement of the protein synthesis. Examples include but are not limited to Tetracycline-inducible (Tet-Inducible or Tet-on) and Tetracycline repressible (Tet-off) systems known to one of skill in the art.

Construct comprising metabolic switch: In some embodiments, the 5' and 3' untranslated regions flanking the coding regions of the construct may be manipulated for regulation of expression of the recombinant protein encoded by the nucleic acid constructs described above. For instance, the 3'UTR may comprise one or more elements that are inserted for stabilizing the mRNA. In some embodiments, AU-Rich Elements (ARE) sequences are inserted in the 3' UTR that result in binding of RNA binding proteins that stabilize or destabilize the mRNA, allowing control of the mRNA half-life.

In some embodiments, the 3'UTR may comprise a conserved region for RNA binding proteins (e.g. GAPDH) binding to mature mRNA strand preventing translation. In some embodiments, glycolysis results in the uncoupling of the RNA binding proteins (e.g. GAPDH) allowing for mRNA strand translation. The principle of the metabolic switch is to trigger expression of target genes when a cell enters a certain metabolic state. In resting cells, for example, GAPDH is an RNA binding protein (RBP). It binds to ARE sequences in the 3 'UTR, preventing translation of mRNA. When the cell enters glycolysis, GAPDH is required to convert glucose into ATP, coming off the mRNA allowing for translation of the protein to occur. In some embodiments, the environment in which the cell comprising the recombinant nucleic acid is present, provides the metabolic switch to the gene expression. For example, hypoxic condition can trigger the metabolic switch inducing the disengaging of GAPDH from the mRNA. The expression of the mRNA therefore can be induced only when the macrophage leaves the circulation and enters into a tumor environment, which is hypoxic. This allows for systemic administration of the nucleic acid or a cell comprising the nucleic acid, but ensures a local expression, specifically targeting the tumor environment.

In some embodiments, the nucleic acid construct can be a split construct, for example, allowing a portion of the construct to be expressed under the control of a constitutive expression system whereas another portion of the nucleic acid is expressed under control of a metabolic switch, as described above. In some embodiments, the nucleic acid may be under bicistronic control. In some embodiments, the bicistronic vector comprises a first coding sequence under a first regulatory control, comprising the coding sequence of a target recognition moiety which may be under constitutive control; and a second coding sequence encoding an inflammatory gene expression which may be under the metabolic switch. In some embodiments, the bicistronic vector may be unidirectional. In some embodiments, the bicistronic vector may be bidirectional.

In some embodiments, the ARE sequences comprise protein binding motifs for binding ARE sequence that bind to ADK, ALDH18A1, ALDH6A1, ALDOA, ASS1, CCBL2, CS, DUT, ENO1, FASN, FDPS, GOT2, HADHB, HK2, HSD17B10, MDH2, NME1, NQO1, PKM2, PPP1CC, SUCLG1, TP11, GAPDH, or LDH.

Pharmaceutical Compositions and Immunotherapy

In one aspect provided herein is a pharmaceutical composition comprising (i) the nucleic acid encoding the transgene is incorporated in a transpositioning or retrotranspositioning system comprising the transgene, the 5'- and 3'-flanking transposition or retrotranspositioning elements, the expression regulation elements, such as promoters, introns; and a nucleic acid encoding the transposase or retrotransposase, (ii) a nucleic acid delivery vehicle and a pharmaceutically acceptable salt or excipient.

In some embodiments, the pharmaceutical composition comprises cells comprising the nucleic acid encoding the transgene that is stably integrated in the genome of the cell and a pharmaceutically acceptable excipient. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995), using viral vectors (Monahan, et al, Gene Therapy 4:40-49, 1997; Onodera, et al, Blood 91:30-36, 1998), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 pl).

In some embodiments, the nucleic acid comprising the transgene and the transposable elements is introduced or incorporated in the cell by known methods of nucleic acid transfer inside a cell, such as using lipofectamine, or calcium phosphate, or via physical means such as electroporation or nucleofection. In some embodiments, the nucleic acid is encapsulated in liposomes or lipid nanoparticles. LNPs are 100-300 nm in diameter provide efficient means of mRNA delivery to various cell types, including macrophages. In some embodiments, the nucleic acid is transferred by other nanoparticles. In some embodiments, the vector for expression of the CFP is of a viral origin, namely a lentiviral vector or an adenoviral vector. In some embodiments, the nucleic acid encoding the recombinant nucleic acid is encoded by a lentiviral vector. In some embodiments, the lentiviral vector is prepared in-house and manufactured in large scale for the purpose. In some embodiments, commercially available lentiviral vectors are utilized, as is known to one of skill in the art.

In some embodiments, the viral vector is an Adeno-Associated Virus (AAV) vector.

The methods find use in a variety of applications in which it is desired to introduce an exogenous nucleic acid into a target cell and are particularly of interest where it is desired to express a protein encoded by an expression cassette in a target cell, where the target cell or cells are part of a multicellular organism. The transposase system may be administered to the organism or host in a manner such that the targeting construct is able to enter the target cell(s), e.g., via an in vivo or ex vivo protocol. Such cells or organs are typically returned to a living body.

In some embodiments, the transgene encoding a fusion protein related to immune function is stably integrated in a living cell of a subject ex vivo, following which the cell comprising the transgene is returned to the subject. Of exemplary importance, the CFP transgene (phagocytic receptor fusion protein) is intended for expression in an immune cell, such as a myeloid cell, a phagocytic cell, a macrophage, a monocyte or a cell of dendritic cell lineage is contacted ex vivo with the recombinant nucleic acids for stable transfer of the transgene and re-introduced in the same subject for combating a disease of the subject. The diseases contemplated comprises infectious diseases, cancer and autoimmune diseases. The nucleic acid encoding the PSR subunit comprising fusion protein (CFP) described herein is used to generate engineered phagocytic cells for treating cancer.

Cancers include, but are not limited to T cell lymphoma, cutaneous lymphoma, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

In general, cellular immunotherapy comprises providing the patient a medicament comprising live cells, which should be HLA matched for compatibility with the subject, and such that the cells do not lead to graft versus Host Disease, GVHD. A subject arriving at the clinic for personalized medicine and immunotherapy as described above, is routinely HLA typed for determining the HLA antigens expressed by the subject.

Therapeutic Advantages of mRNA Driven Delivery

In one embodiment, provided herein is a method of introducing a nucleic acid sequence into a cell for sustained gene expression in the cell without adverse effects. In some embodiments, the cell is within a living system, e.g., a host organism such as a human. The nucleic acid sequence is an mRNA.

In particular, delivery via retrotransposon poses to be a highly lucrative mode. mRNA driven delivery simplifies gene delivery. While other technologies require expensive and sophisticated design and manufacturing, and a solution for delivery of the nucleic acid into the cell, and gene editing technologies to assist in integration, retrotransposon mediated delivery itself encodes for the editing machinery, encodes for new genes to be delivered. In addition, a single mRNA may be sufficient for gene delivery and editing.

In one embodiment, mRNA delivery is advantageous in that it can ensure introduction of a nucleic acid cargo without size restraint.

Table 9 summarizes some of the advantages over the other existing methods of nucleic acid deliveries.

TABLE 9

Advantages of retrotransposon mediated gene delivery

| | Lentiviral delivery | AAV-delivery | Retrotransposon delivery |
|---|---|---|---|
| Payload | ~4 kb | ~4 kb | >10 kb |
| Toxicity | Insertional mutagenesis | Unresolved liver & CNS toxicity | Unknown, pending clinical development |
| Manufacturing | Complex, expensive | Complex, expensive | Inexpensive, rapid |

Retrotransposons are advantageous for applications across multiple modalities. Gene manipulation using this method is easily attained both in vivo and ex vivo. In one embodiment, the application of retrotransposon may be in vivo, a piece of genetic material encoded in an mRNA can be directly introduced into a patient by systemic or local introduction. In contrast, cells can be taken out from a subject, and manipulated ex vivo and then introduced either to the same subject (autologous) or to another human (heterologous).

In one embodiment, retrotransposons and the related methods described herein may be instrumental in gene therapy. With the advantage of capacity to introduce large payloads, large sections of DNA carrying a gene encoding an entire protein may be introduced in one shot without requiring multiple introductions and multiple editing events. In one embodiment, for example, a gene that encodes a defective protein may be excised, the correct gene may be introduced in the correct site in one integration event using a retrotransposon mediated delivery. In one example, CRISPR editing may be used to excise a gene from precise locus and retrotransposition may be used to replace the correct genes. In some embodiments, a preferred retrotransposon integration site may be introduced at the excision site.

In one embodiment, retrotransposons and the related methods described herein may be instrumental in gene editing.

In one embodiment, retrotransposons and the related methods described herein may be instrumental in transcriptional regulation.

In one embodiment, retrotransposons and the related methods described herein may be instrumental in genome engineering.

In one embodiment, retrotransposons and the related methods described herein may be instrumental in developing cell therapy, for example chimeric antigen receptor (CAR)T cells, in NK cell therapy or in myeloid cell therapy. In one embodiment, retrotransposons and the related methods described herein may be instrumental in delivery of genes into neurons, which are difficult to access by existing technologies.

In one aspect, provided herein is a method for targeted replacement of a genomic nucleic acid sequence of a cell, the method comprising: (A) introducing to the cell a polynucleotide sequence encoding a first protein complex comprising a targeted excision machinery for excising from the genome of the cell a nucleic acid sequence comprising one or more mutations; and (B) a recombinant mRNA encoding a second protein complex, wherein the recombinant mRNA comprises: (i) a nucleic acid sequence comprising the excised nucleic acid sequence in (A) that does not contain the one or more mutations, and (ii) a sequence encoding an L1 retrotransposon ORF2 protein under the influence of an independent promoter.

In one embodiment, the first protein complex may be an endonuclease complex independent of the second protein complex. In one embodiment, the first protein complex comprises a CRISPR-CAS system that uses sequence guided genomic DNA excision. In one embodiment, the methods described herein couples a CRISPR CAS system or any other gene editing system with a Lil transposon machinery (e.g., the second protein complex) that delivers a replacement gene with a payload capacity of greater than 4 kb, or 5 kb, or 6 kb, or 7 kb, or 8 kb or 9 kb or 10 kb. This coupling can be utilized in precisely excising a large fragment (a mutated gene causing a disease) from the genomic locus and integrating a large fragment of a gene or an entire gene that encodes a correct, non-mutated sequence.

A large number of genetic diseases may require delivery of gene delivery of large payloads, often exceeding the functional capacity of existing methods. Contemplated herein are methods and compositions disclosed herein that can be instrumental in further designing therapy for such diseases using retrotransposons. An exemplary list of genetic diseases include but are not limited to the ones listed in Table 10.

TABLE 10

List of potential gene therapy applications

| Disease | Gene | CDS | Expression | Prevalence |
|---|---|---|---|---|
| Stargardt | ABCA4 | 6.8 kb | Rod and Cone PRs | 1:8000 |
| Usher 1B | MY07A | 6.7 kb | RPE and PRs | 3.2:100,000 |
| LCA10 | CEP290 | 7.4 kb | PR (pan retinal) | 1:50,000 |
| USH1D, DFNB12 | CDH23 | 10.1 kb | PR | 3:100,000 |
| RP | EYS | 9.4 kb | PRECM | 1:50,000 |
| USH2A | USH2a | 15.6 kb | Rod and Cone PRs | 4:100,000 |
| USH2C | GPR98 | 18.0 kb | Mainly PRs | 1:100,000 |
| Alstrom syndrome | ALMS1 | 12.5 kb | Rod and Cone PRs | 1:1,000,000 |
| Glycogen storage disease III | GDE | 4.6 kb | Muscle, Liver | 1:8000 |
| Non-syndromic deafness | OTOF | 6.0 kb | Ear | 14:100,000 |
| Hemophilia A | F8 | 7.1 kb | Liver | 1:10,000 |
| Leber congenital aumaurosis | CEP290 | 7.5 kb | Retina | 5:100,000 |

Provided herein is a method for targeted replacement of a genomic nucleic acid sequence in a cell. In one embodiment, the method comprises: (A) excising from the genome of the cell a nucleic acid sequence comprising one or more mutations and (B) introducing into the cell a recombinant mRNA encoding: (i) a nucleic acid sequence comprising a wild type sequence relative to the sequence excised in (A) that does not contain the one or more mutation, (ii) a sequence encoding an L1 retrotransposon ORF2 protein under the influence of an independent promoter. In one embodiment, Step (A) further comprises introducing a short sequence comprising at least a plurality of adenylate residues at the excision site. In one embodiment, the In one embodiment, the nucleic acid sequence comprising a wild type sequence is operably linked with the ORF2 encoding sequence in a way such that the ORF2 reverse transcriptase integrates the sequence comprising the wild type non-mutated sequence into the genome.

In one embodiment, the cell is a lymphocyte.

In one embodiment, the cell is an epithelial cell. In some embodiments the cell is a retinal pigmented epithelial cell (RPE).

In one embodiment, the cell is a neuron.

In one embodiment, the cell is a myeloid cell.

In one embodiment, the cell is a stem cell.

In one embodiment, the cell is a cancer cell.

In one embodiment, the gene is selected from a group consisting of ABCA4, MY07A, CEP290, CDH23, EYS, USH2a, GPR98, ALMS1, GDE, OTOF and F8.

In one embodiment, the mRNA comprises a sequence for an inducible promoter.

In one embodiment, the expression of the nucleic acid sequence comprising a non-mutated sequence is detectable at least 20, 21, 22, 23, 24, 25, 26, 27, 28, 29, 30, 31, 32, 33, 34 or 35 days post infection.

In one embodiment, the method comprises introducing into the cell a recombinant mRNA in vivo.

In one embodiment, the method comprises introducing into the cell a recombinant mRNA ex vivo.

Provided herein is a method of treating a genetic disease in a subject in need thereof, comprising: introducing into the subject a composition comprising a polycistronic mRNA encoding a gene or fragment thereof, operably linked to a sequence encoding an L1 retrotransposon; wherein the gene or the fragment thereof is at least 10.1 kb in length.

In one embodiment, the method comprises directly introducing the mRNA systemically.

In one embodiment, the method comprises directly introducing the mRNA locally.

In one embodiment, the genetic disease is a retinal disease. For example, the disease is macular dystrophy. In one embodiment, the disease is stargardt disease, also known as juvenile macular degeneration, or fundus flavimaculatus. The disease causes progressive degeneration and damage of the macula. The condition has a genetic basis due to mutation in the ATP-binding cassette (ABC) transporter gene. (ABCA4) gene, and arises from the deposition of lipofuscin-like substance in the retinal pigmented epithelium (RPE) with secondary photoreceptor cell death. In some embodiments, the method comprises direct delivery of the mRNA to the retina.

In one embodiment, the method comprises treating a nonsyndromic autosomal recessive deafness (DFNB12) and deafness associated with retinitis pigmentosa and vestibular dysfunction (USH1D). In one embodiment, provided herein is a method of treating non-syndromic deafness (DFNB12) or Usher syndrome (USH1D), the method comprises introducing an mRNA comprising a copy of CDH23 or a fragment thereof operably linked to a sequence encoding an L1 retrotransposon.

EXAMPLES

It should be appreciated that the invention should not be construed to be limited to the examples which are now described; rather, the invention should be construed to include any and all applications provided herein and all equivalent variations within the skill of the ordinary artisan.

Example 1. Exemplary Retrotransposon Designs Constructs

Figure 1B:
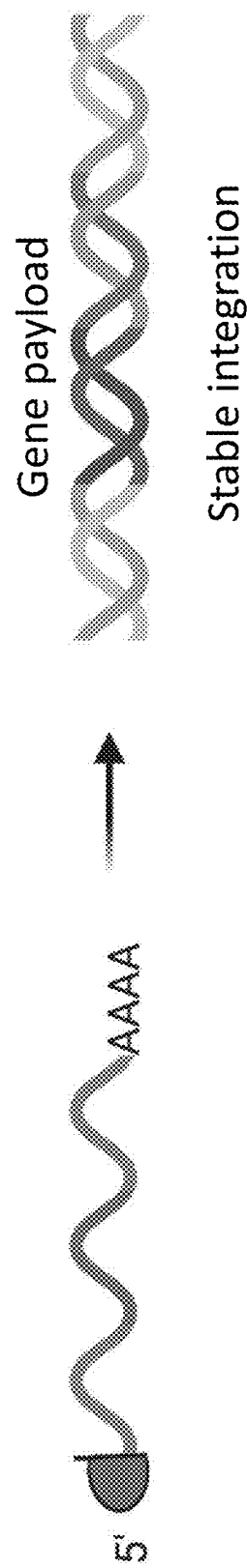
FIG. 1B is an illustration of a schematic diagram of an mRNA construct that comprises a genetic payload (left) that can be designed for integration into the genome (right).
Figure 1C:
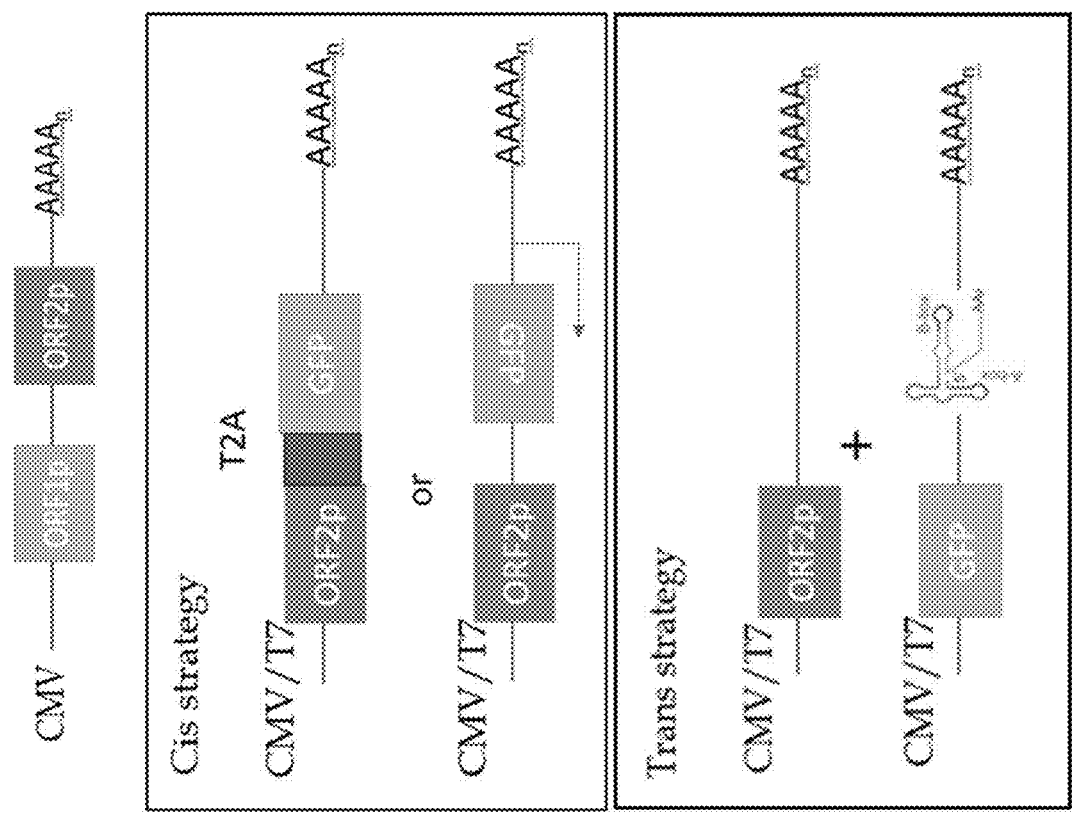
FIG. 1C illustrates various exemplary designs for integrating an mRNA encoding a transgene into the genome of a cell. GFP shown here in a box is an exemplary transgene.
Figure 1D:
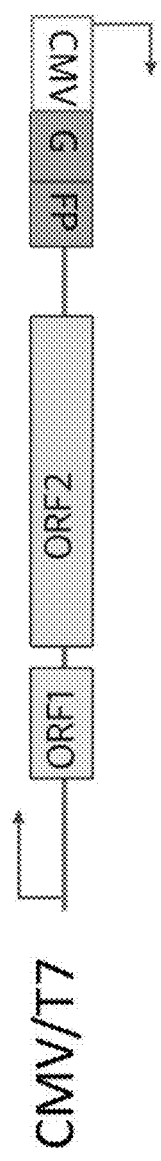
FIG. 1D illustrates various exemplary designs for integrating an mRNA encoding a transgene into the genome of a cell. GFP shown here in a box is an exemplary transgene.
Figure 1D:
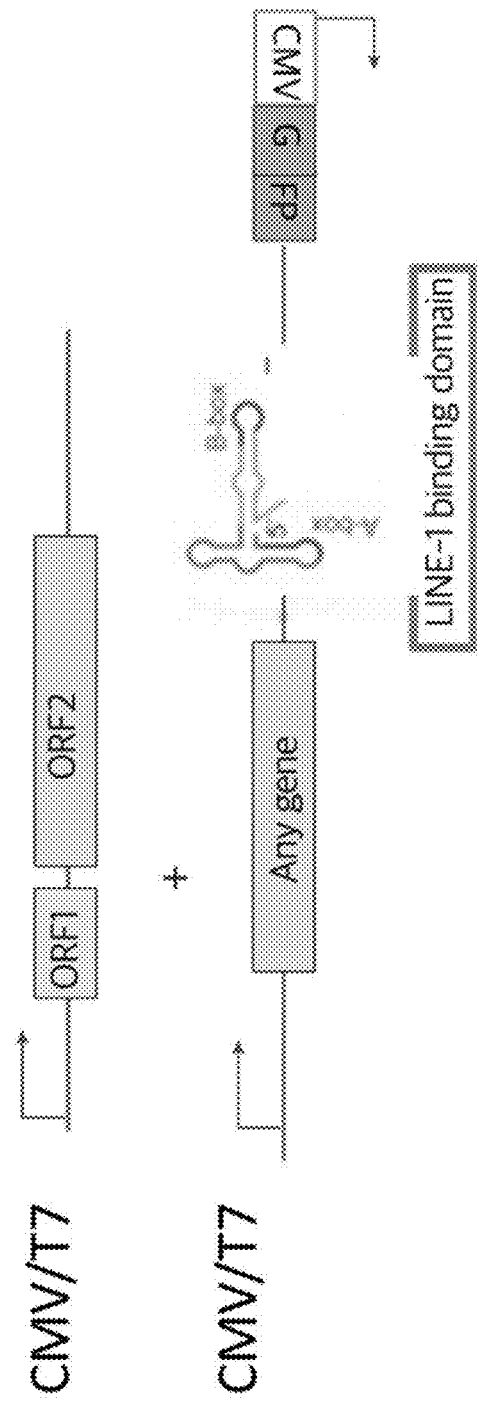
Figure 1E:
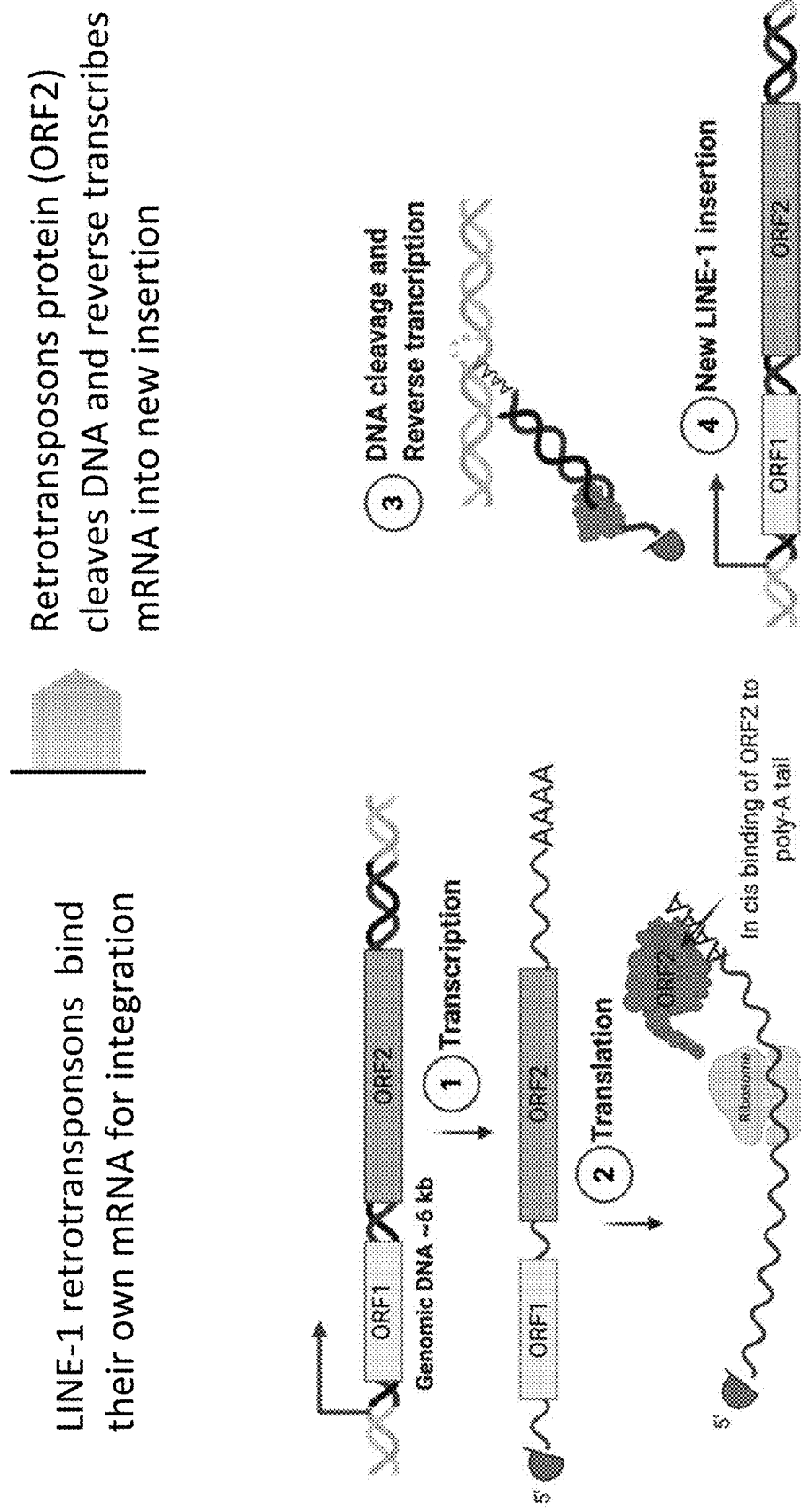
FIG. 1E is an illustration a schematic of the LINE-1 retrotransposition cycle showing the mechanism of action of the LINE transposons and introduction of a transgene cargo into a retrotransposon cite. LINE-1 retrotransposons are genomic sequences that encode for two proteins, ORF1 and ORF2. These elements are transcribed and translated into proteins that form an RNA-protein complex with the LINE-1 mRNA, ORF1 trimers, and ORF2, a reverse-transcriptase endonuclease. This complex translocates back into the nuclease where it cleaves DNA at a 5'-TTTT N-3' motif and is primed for reverse-transcription of the LINE-1 RNA by the ORF2 protein by making an RNA-DNA hybrid with the poly A tail of the mRNA and the resected cleaved DNA. Reverse-transcription of the LINE-1 into cDNA leads to a new LINE-1 integration event.

Provided here are exemplary strategies of designing retrotransposon constructs for incorporating into the genome of a cell and expressing an exemplary transgene. FIG. 1B and FIG. 1C illustrates various strategic designs for integrating an mRNA encoding transgene into the genome of a cell. GFP shown here in a box is an exemplary transgene. The mRNA encoding the transgene (e.g., GFP) can be co-expressed with a nucleic acid sequence encoding an ORF2p protein, in either sense or antisense orientation; the respective coding sequences may be in a monocistronic or bicistronic construct shown under exemplary Cis-strategies (FIG. 1B and FIG. 1C). CMV/T7 are promoters.

Figure 2A:
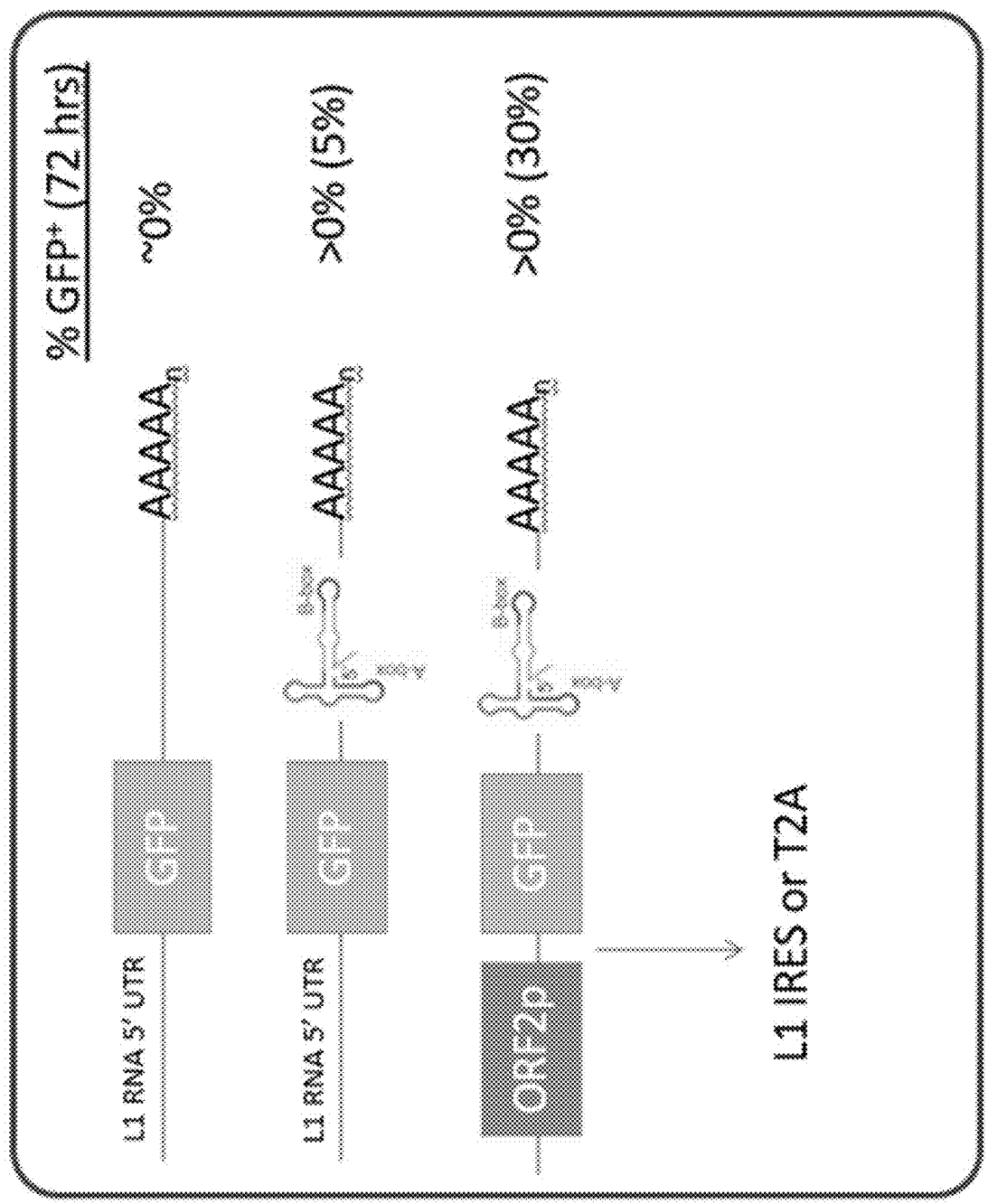
FIG. 2A illustrates three exemplary designs for expressing an exemplary transgene GFP by stably incorporating the sequence encoding GFP using the constructs. Expected GFP expression levels at 72 hours are shown on the right side.
Figure 2B:
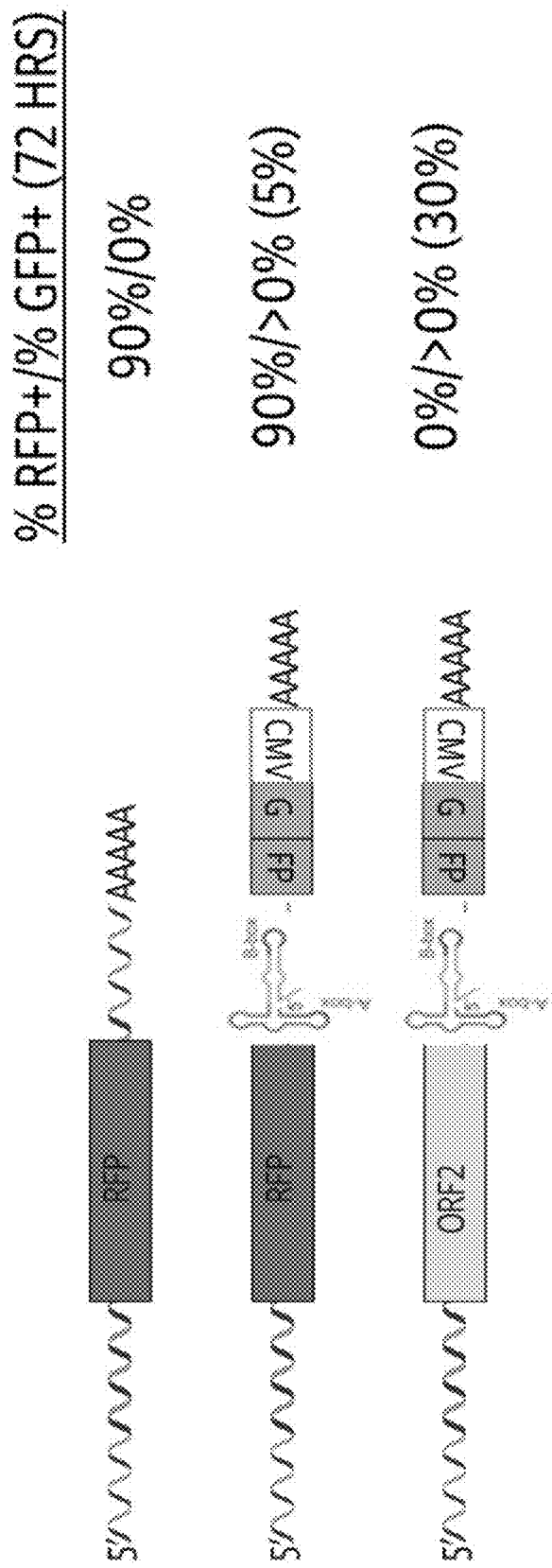
FIG. 2B illustrates three exemplary designs for expressing an exemplary transgene GFP by stably incorporating the sequence encoding RFP, RFP and GFP or ORF2p and GFP using the constructs. Expected GFP and RFP expression levels at 72 hours are shown on the right side.

On the other hand, the same could be directed to be expressed in a trans manner. The trans-strategy can include a sequence encoding an ORF2p protein or both ORF1p and ORF2p proteins from a bicistronic sequence and an mRNA encoding a GFP in a sense or antisense direction in the 3'UTR of any gene. The transgene is flanked by a retrotransposing sequence comprising transposase binding sequences, an A-box and B-box, and a poly A tail. FIG. 2A illustrates three exemplary designs for expressing an exemplary transgene GFP by stably incorporating the sequence encoding GFP using the constructs. The first construct comprises a sequence encoding GFP, flanked by L1 5'-UTR; and a poly A sequence at the 3' UTR, in absence of any transposase binding elements. The second and the third constructs comprise a sequence encoding GFP, a 3'UTR an A Box and a B-box, and a poly A sequence at the 3' UTR. The third construct comprises an additional sequence encoding ORF2p. Expected GFP expression levels at 72 hours are shown on the right side. FIG. 2B illustrates three exemplary designs for expressing an exemplary transgene GFP in an mRNA that either encodes RFP or ORF2p by stably incorporating the sequence encoding GFP using the constructs. The first construct comprises a sequence encoding RFP, and a poly A sequence at the 3' UTR, in absence of any L1 elements. The second and the third constructs comprise a 3'UTR comprising an A Box and a B-box, and a poly A sequence at the 3' UTR. The second construct comprises a sequence encoding RFP and the third construct comprises a sequence encoding ORF2p. Expected RFP and GFP expression levels at 72 hours are shown on the right side.

Example 2. Exemplary circRNA Designs Constructs

In this example, modular designs for circRNA are demonstrated, which incorporate a stretch of about 50 nucleotide long RNA having naturally occurring tertiary structures in order to prepare a circRNA. Use of the tertiary-structure forming RNA makes the circRNA formation process independent of sequence mediated hybridization for circularization. These RNA motifs having tertiary structures can be incorporated in the desired RNA having an exon and an intron in place of the 5' and 3' homology arms, thereby forming the terminal RNA scaffolds for circularization.

Figure 3C:
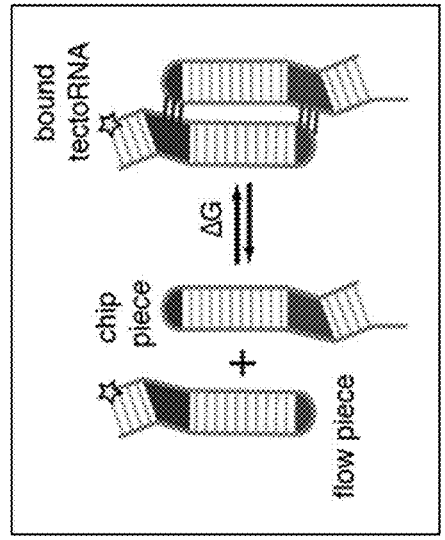
FIG. 3C illustrates exemplary structures of chip-flow piece RNAs as platforms for testing potential tectoRNA.
Figure 3B:
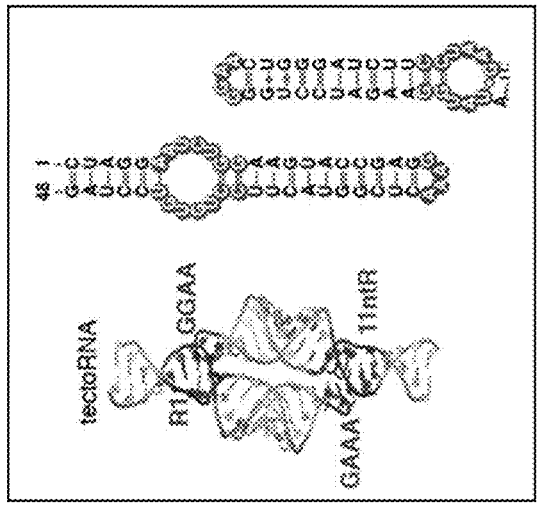
FIG. 3B illustrates two views of an exemplary RL-GAAA tectoRNA motif designs.

TectoRNA: RNA-RNA binding interfaces are constructed by combining pairs of GNRA loop/loop-receptor interaction motifs, yielding high affinity, high specificity tertiary structures. (FIG. 3B). Pairs of GNRA loop/loop-receptor interaction motifs are fused using the four-way junction from the hairpin ribozyme to create divalent, self-assembling scaffolding units ('tectoRNA') which help form a closed cooperatively assembling ring-shaped complexes. Using two orthogonal loop/loop-receptor interaction motifs, RNA monomers are designed that are capable of directional assembly in either the parallel ('up-up') or anti-parallel ('up-down') assembly modes. In anti-parallel assembly of interacting molecules, each incorporated monomer switches the directionality of the growing chain and thus compensates for its intrinsic bending, producing long, relatively straight multi-unit chains. For selecting a tectoRNA scaffolds having minimum occurrences of alternative secondary structures, sequences are checked by submitting them to the RNA folding program Mfold (bioinfo.math.rpi.edu/~zukerm/rna/mfold) which predicts the thermodynamically favored secondary structure of a given RNA sequence. A thermodynamically favored structure is selected for scaffolding that has minimum alternative secondary structures (typically but not exclusively, no other secondary structure is closer than 15% in energy to the lowest energy structure). RNA molecule is prepared by conventional methods, such as in vitro run-off transcription using T7 RNA polymerase. FIG. 3B shows a RL-GAAA loop structure. In order to profile tectoRNA heterodimers a fluorescence-based chip-flow piece testing method is utilized. In this method, a library of potential variants of the structured RNA (chip piece) is synthesized as DNA templates and amplified to include sequencing adapters and regions for RNAP initiation. Each DNA variant is transcribed in situ into RNA, enabling display of sequence-identified clusters of RNA on the surface of the sequencing chip. The fluorescently-labeled tectoRNA binding partner, the "flow piece", is introduced to the sequencing chip flow cell at increasing concentrations, allowing quantification of bound fluorescence to each cluster of RNA after equilibration. These fluorescence values are used to derive the affinity of the flow piece to each chip piece variant (FIG. 3C), in terms of the dissociation constant ($K_d$) and binding free energy, ($\Delta G = RT \log(K_d)$).

The selected terminal RNA scaffold segments comprising the tertiary structures are incorporated using T7 transcription or ligated at the 5' and 3' ends of the desired RNA to be circularized; or are incorporated in the desired RNA by any known molecular biology techniques.

Example 3: Exemplary Retrotransposon Designs with Enhanced Specificity

In this example, designs for a nucleic acid construct for L1-mediated retrotransposon for enhanced target specificity is demonstrated. An mRNA is designed comprising ORF2 encoding sequence and a sequence encoding a gene of interest, to incorporate the gene of interest into the genome of a cell using ORF2. In one exemplary design, the construct comprises an ORF2 that is further modified.

Figure 4A:
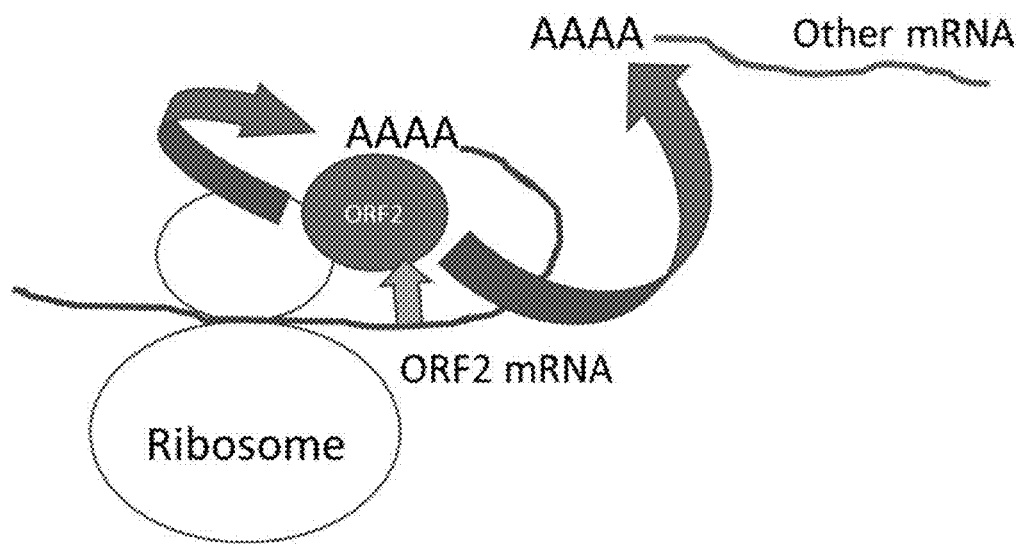
FIG. 4A illustrates an exemplary schematic showing ORF2p binding to an ORF2 poly A region.

As shown in FIG. 4A, ORF2 protein initiates retrotransposition by binding to its own poly A sequence. However, because poly A is abundantly present in mRNAs, a non-specific binding and integration becomes a possibility. To increase the specificity, a recombinant ORF2 is designed comprising an mRNA-binding domain of a heterologous protein, and the cognate mRNA sequence for the heterologous mRNA-binding domain is inserted near the poly A sequence in the 3'-UTR and the ORF2 poly A binding site.

Figure 4B:
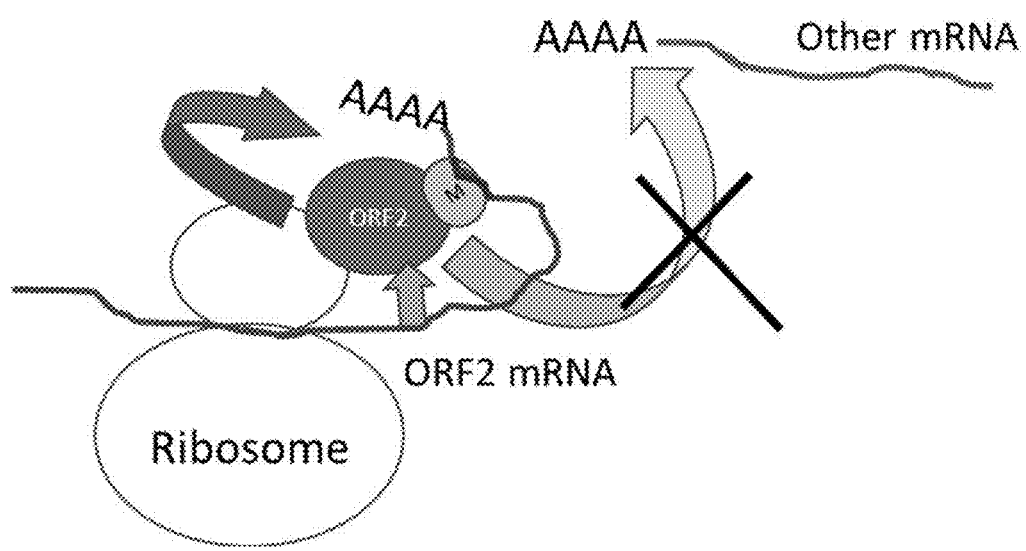
FIG. 4B illustrates an exemplary schematic showing how a fusion of ORF2p with an MS2 RNA binding domain binds to an MS2 binding RNA sequence in the 3'UTR of an mRNA encoding the ORF2 an increase specificity.

A chimeric ORF2 is thereby generated as shown in (FIG. 4B), in which a high affinity RNA-binding domain of a heterologous protein encoding sequence is incorporated or fused to the ORF2 sequence and cognate RNA sequences corresponding to the high affinity RNA-binding protein is incorporated in the 3'UTR region of the mRNA, proximal to the poly A region. In this example the heterologous high affinity RNA-binding domain is derived from MCP coat protein MS2 (shown as M in the figure), is incorporated within the ORF2 sequence and the cognate sequence, the MS2 hairpin, is included in the 3' UTR sequence of the mRNA (FIG. 4B). The MS2 binds to the cognate sequence, increasing the specificity of the chimeric ORF2 to its own mRNA for reverse transcribing and incorporating the respective sequence associated with the ORF2 mRNA in the mammalian cell genome (FIG. 4B).

Figure 4C:
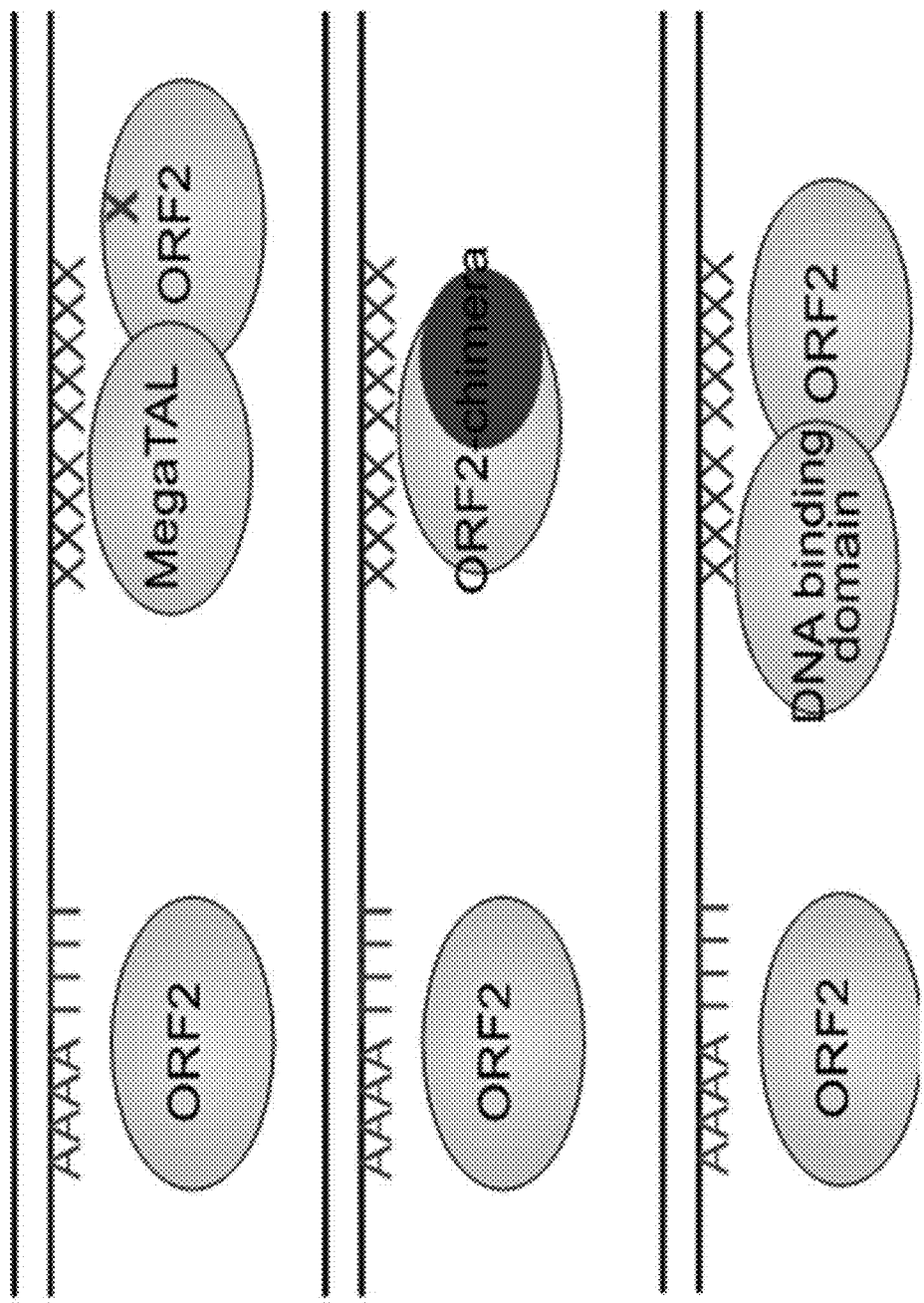
FIG. 4C illustrates exemplary designs of retrotransposon systems for stably integrating a nucleic acid into the genome of a cell at specific sites. The upper panel shows a design using an ORFp2-MegaTAL DNA binding domain fusion where the DNA binding and endonuclease activity of ORF2p is mutated to be inactive. The middle panel shows a chimeric ORF2p where the endonuclease domain has been replaced with a high specificity and high-fidelity nuclease domain of another protein. The lower panel shows a fusion of a DNA binding domain of a heterologous protein with ORF2p such that the fusion protein binds to ORF2 binding site as well additional DNA sequences in the vicinity of the ORF2 site.

In other exemplary designs, attempts to increase specificity of integration of the transgene by the ORF2 within the genome of a target cell is undertaken. In one exemplary design, Mega TAL encoding sequence fused to an ORF2 as shown in FIG. 4C (upper panel). Along with that, the ORF2 is mutated to remove its ability to recognize and bind to RNA sequence that has less specificity. The fused protein is directed to the TAL binding sequence incorporated within the 3'UTR and perform endonuclease function. The Mega TAL DNA binding sequence is targeted by the fusion protein. Likewise, other chimera (FIG. 4C (middle panel)) and fusion protein with a specific DNA binding domain FIG. 4C (lower panel) are designed.

Example 4. Exemplary Plasmid Design and Developments for LINE-1 Mediated Retrotransposition of an Exogenous Nucleic Acid Sequence In this example plasmid vectors are generated for delivery and incorporation of a recombinant LINE-1 construct comprising an ORF2 transposon element operably linked to a transgene transposable into a mammalian cell, and regulatory elements for mRNA transcription and stabilization. The mRNA can be transcribed in a bacterial host cell, which can be further processed and/or purified for introduction into a mammalian cell in vitro or administration in an organism, such as a mammal, a rodent, sheep, pig or a human.

Any suitable vector backbone is used for incorporating the recombinant nucleic acid sequence as insert and transcribing in a bacterial system for mRNA generation; or in vitro transcription system may be utilized to generate an mRNA comprising the recombinant nucleic acid sequence. Several features are added to the plasmid. Upon successful scalable mRNA production, and purification, the mRNA may be introduced in a mammalian cell of interest, such as a myeloid cell.

Plasmids traditionally used in the field of study for retrotransposition lack designer genes, gene blocks, and Gibson assembly methods were used regularly to insert different features. A new vector that takes features from the old vectors but has flexibility to insert new features can be beneficial both for the study and optimization of LINE-1 elements as a gene delivery system. Below is an outline of base features and additional features that can increase retrotransposition frequency, both using the plasmid alone or the mRNA transcribed from the plasmid. In an exemplary plasmid design shown graphically in FIG. 5(I), which contains the natural LINE-1 sequence with the original 5'UTR, 3'UTR and interORF sequence with no restriction sites to swap out any of these features. New optimized plasmid:
  Removed Dox inducible promoter, replaced with CMV or EIF1a or EF1a promoter
  Added a T7 site to make mRNA
  Codon optimized ORF1 and ORF2
  Added a WPRE element to stabilize mRNA
  Added FLAG tag to ORF2 to help with protein detection
  Decreased size from 18 kb to 14 kb
  Added blunt restriction sites (dotted lines with blunt arrows) at each feature to facilitate insertions
  Includes a G418 selection marker
  The plasmid is shown in FIG. 5 (II).

Figure 5:
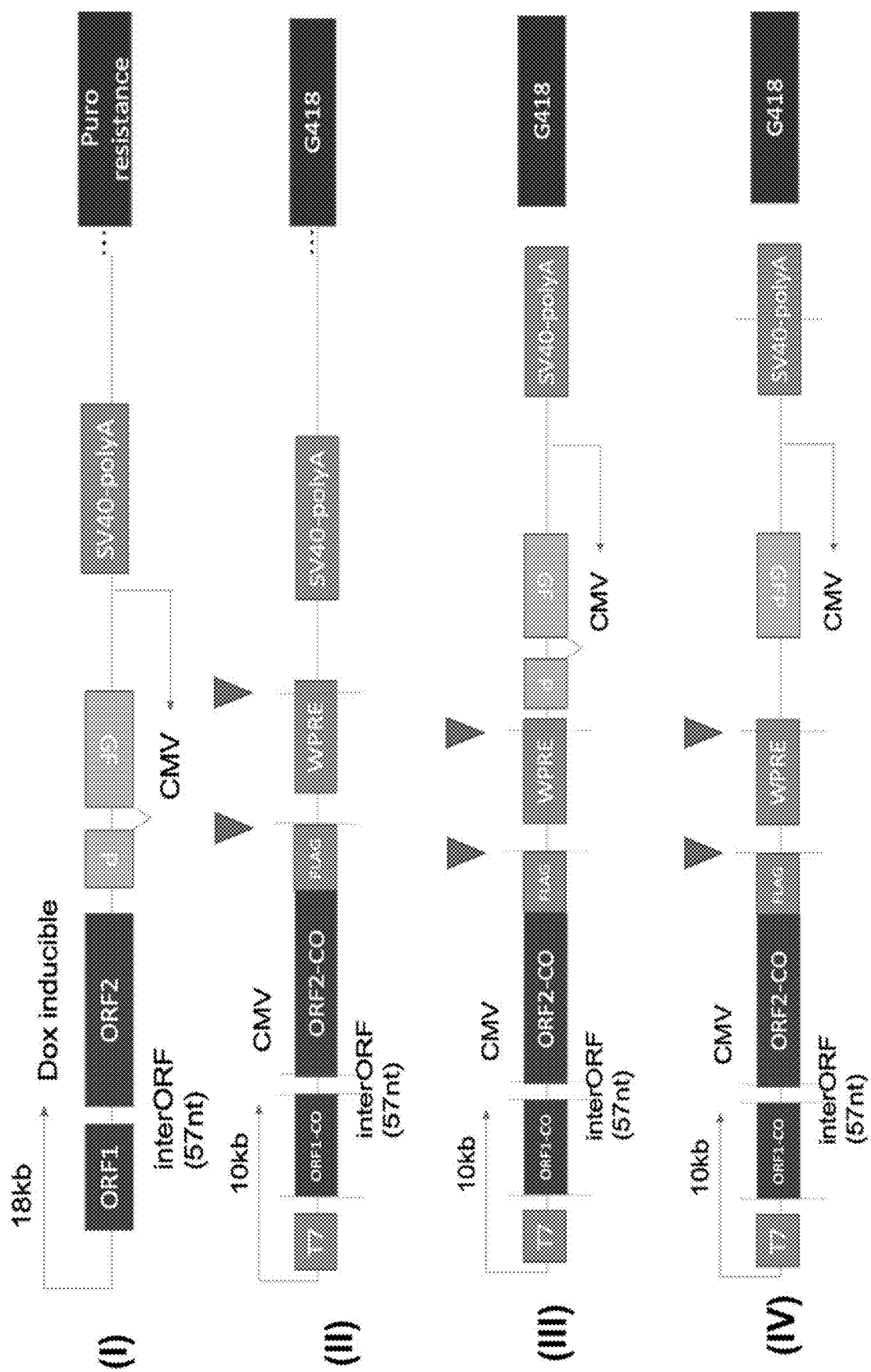
FIG. 5 illustrates exemplary constructs (I)-(X) for integrating an mRNA encoding a transgene into the genome of a cell.
Figure 5:
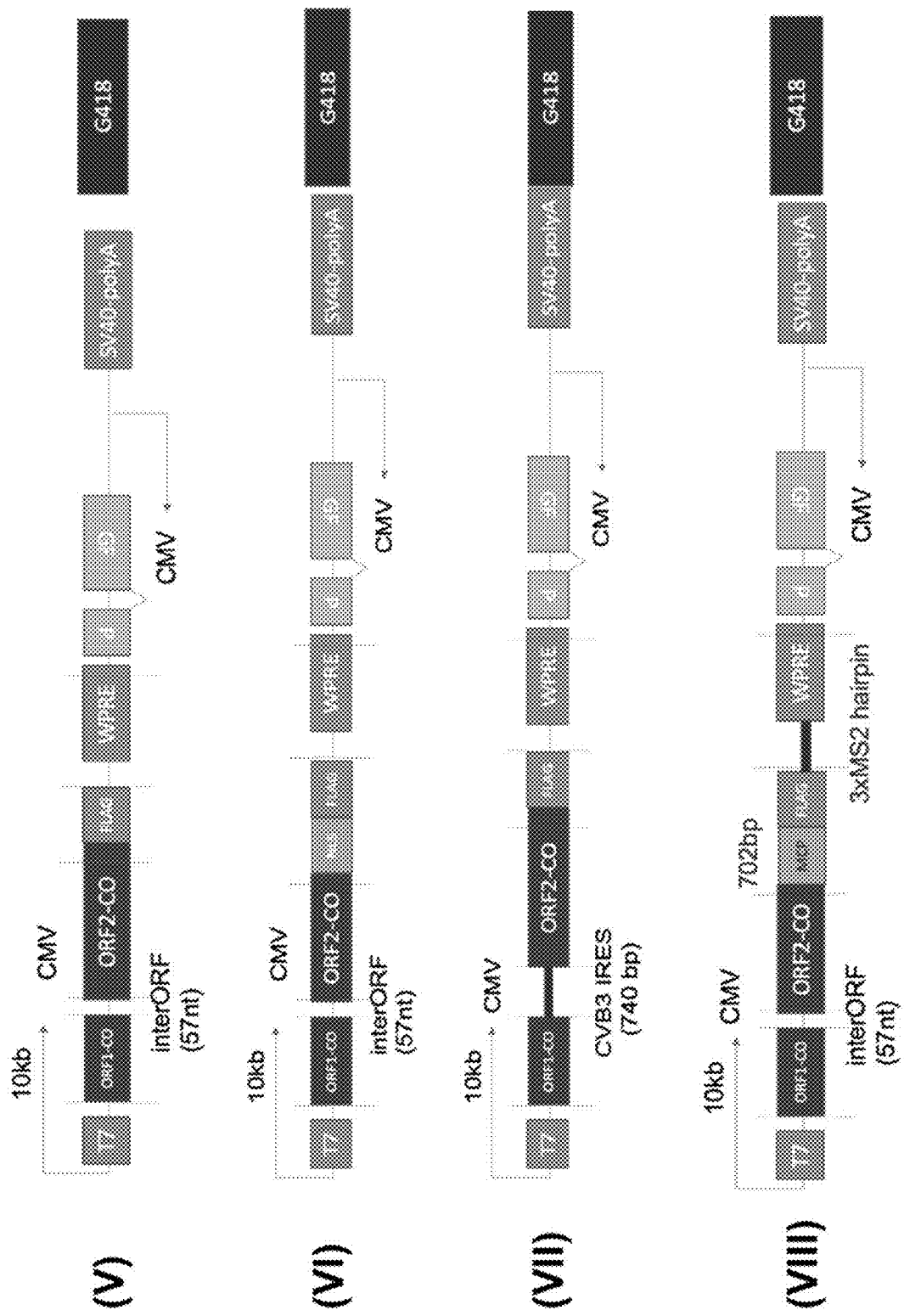
Figure 5:
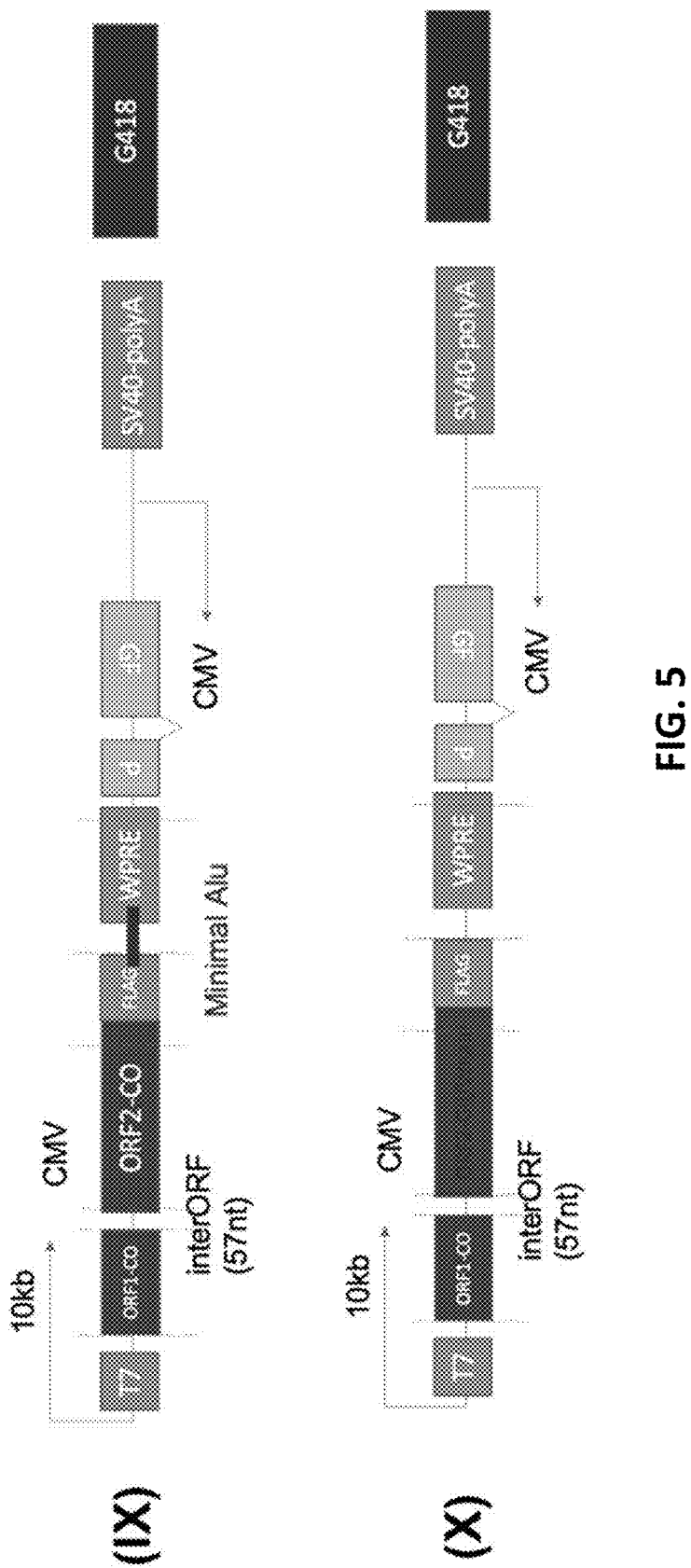

With Gibson a reverse split GFP is inserted for plasmid reporter gene as shown in FIG. 5 (III). A complete reverse GFP for the mRNA reporter is inserted as in FIG. 5 (IV).

Using the plasmid construct in FIG. 5(V) as parent, a nuclear localization sequence (NLS) is inserted at the N terminus of ORF2 to help with nuclear import (FIG. 5 (VI)). An IRES or another termination/promoter sequence is inserted to increase expression of ORF2 (FIG. 5 (VII)). To facilitate stronger interactions between ORF2 and the mRNA, MS2 hairpins are inserted in the 3'UTR and a MS2 coat protein sequence in the N terminus of the ORF2 protein (FIG. 5 (VIII)). A corresponding exemplary ORF2 with enhanced specificity and its mechanism of action is disclosed in the preceding example and in FIG. 4B. To facilitate stronger interactions of the mRNA with the translating ribosome and to stall translation so that nascent ORF2 will more likely bind the mRNA, an Alu element is inserted in the 3'UTR of the mRNA (FIG. 5 (IX)). To potentially use a more active ORF2 protein, the ORF2's RT domain is replaced with the Group II intron's reverse transcriptase domain (FIG. 5(X)). Additionally, the minke whale genome has the highest number and percentage of active LINE elements (~5,000 with 60% active compared to humans that have 480 with 3.6% active). The two sequences are 67% identical and the whale sequence has the active endonuclease and reverse-transcriptase residues. The respective minke whale domains can be used to replace native ORF2 endonuclease and/or RT domains or design a chimera domain.

Figure 6A:
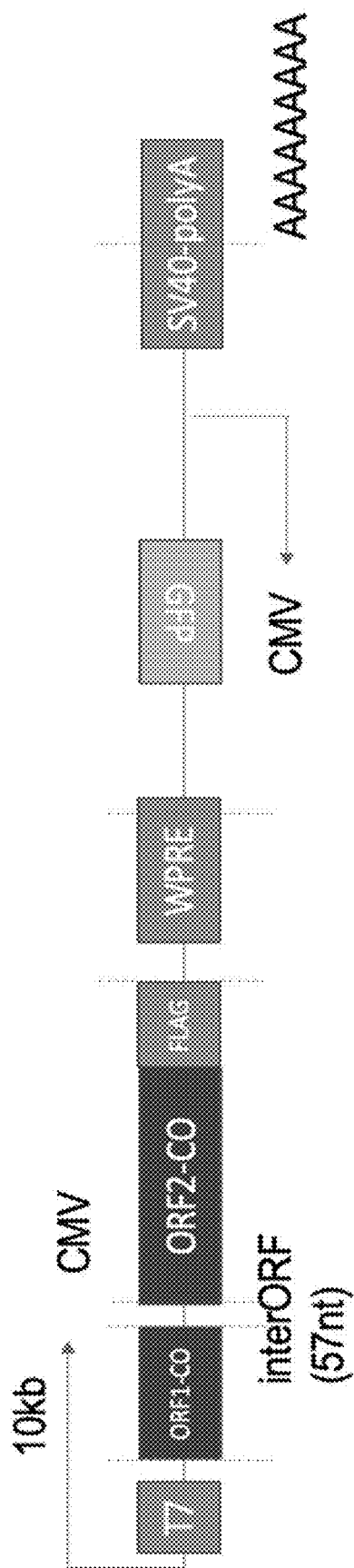
FIG. 6A illustrates an exemplary construct with a sequence encoding ORF1p for integrating an mRNA encoding a transgene into the genome of a cell.
Figure 6B:
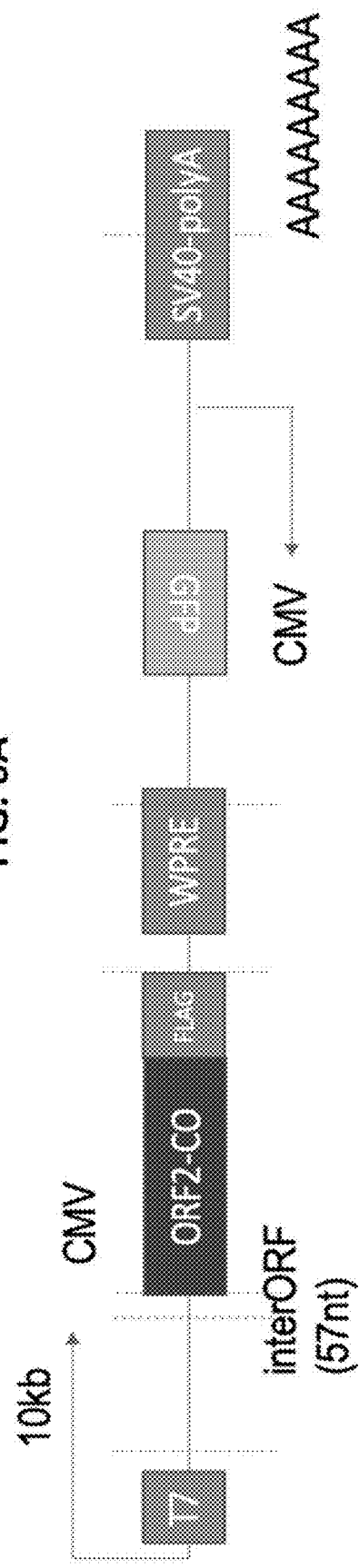
FIG. 6B illustrates an exemplary construct without a sequence encoding ORF1p for integrating an mRNA encoding a transgene into the genome of a cell.

Example 5. mRNA Design Synthetic mRNA Generation mRNA can be strategically designed for synthetic production by oligosynthesis and or ligation of oligonucleotides. Additionally, such designs are useful for in vitro transcription (IVT) mediated mRNA generation. The mRNA strategy can include the same variants as the plasmid strategy discussed in the previous example. The main differences are that the reporter GFP sequence does not include an intron (FIG. 6A) and that the constructs can be delivered without the ORF1 coding region (FIG. 6B).

Example 6. Structural Features for Increased mRNA Half-Life

In this example, structural features are introduced in the mRNA comprising the retrotransposition elements and/or the transgene for increasing the mRNA half-life. The goal is to increase the duration of protein expression from the mRNA in primary monocytes from three days to at least 5 days with an ultimate goal of 10 days.

Figure 7A:
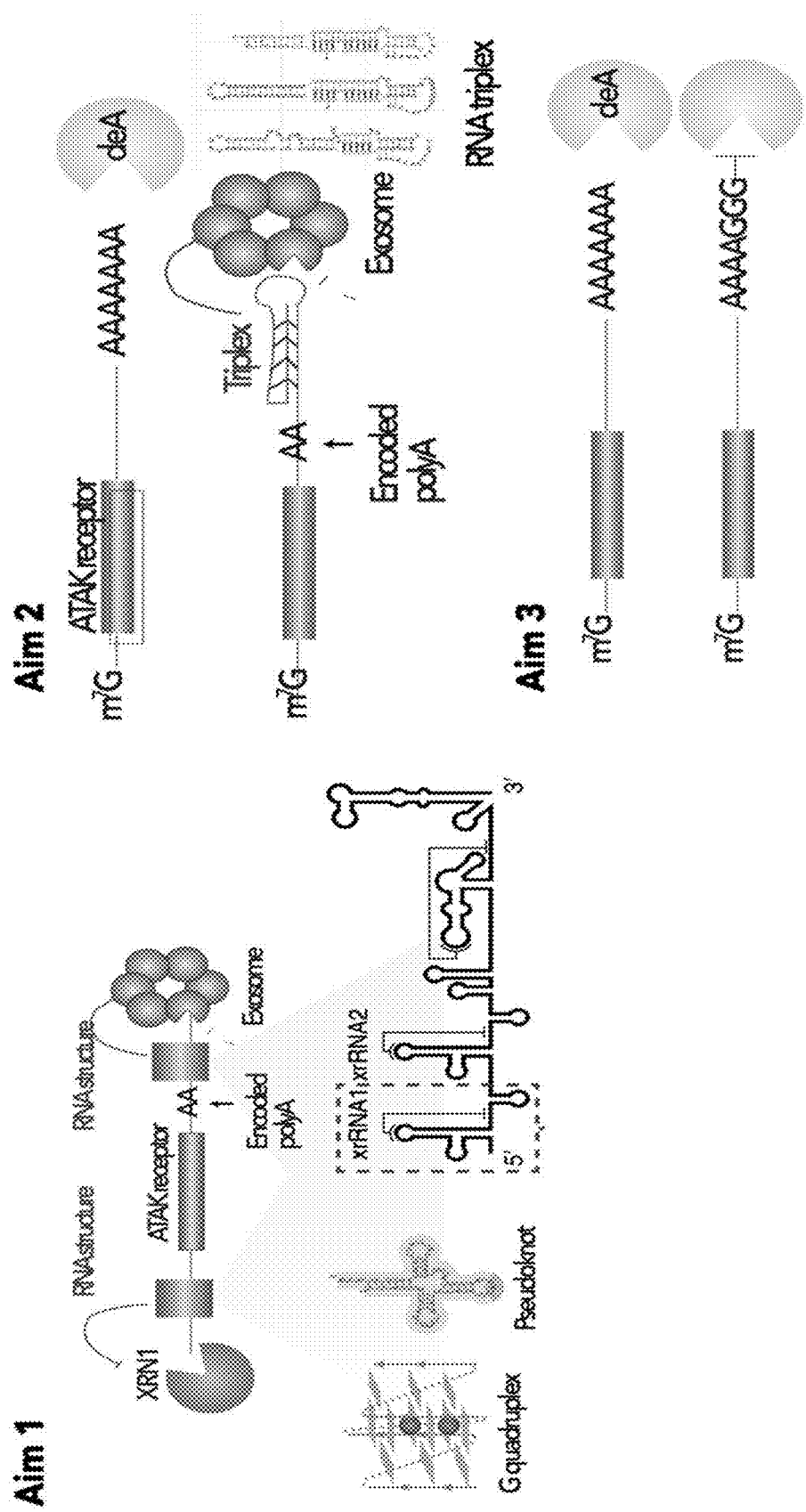
FIG. 7A illustrates exemplary methods of improving mRNA half-life by inhibiting degradation by 5'-3' exonucleases, such as XRN1, or 3'-5' exosomal degradation, by introducing structures corresponding to a G-quadruplex, or, a pseudoknot (SEQ ID NO: 82) in the 5'UTR; and/or xrRNAs, a triplex motifs (SEQ ID NOS. 83-85 in order of appearance) and/or a non-A nucleotide residues in the 3'UTR.
Figure 7C:
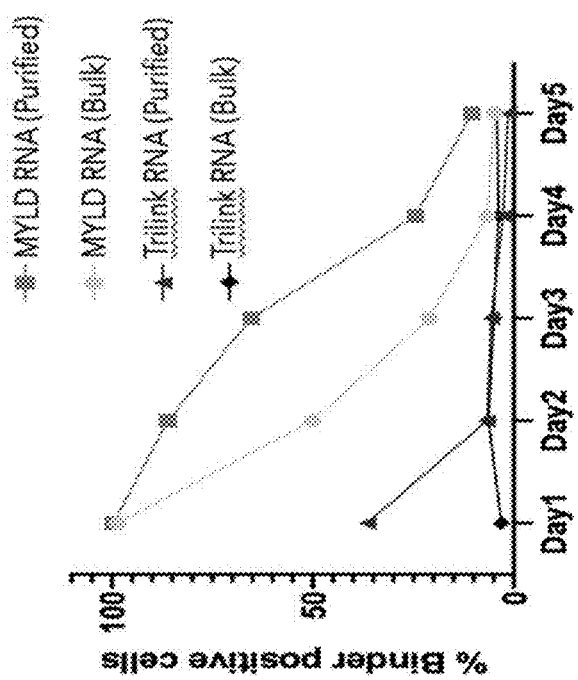
FIG. 7C shows expected results of introducing bulk or purified RNA encoding a chimeric receptor that binds a cancer cell as described in FIG. 7B on increased and prolonged expression of the chimeric receptors.
Figure 7B:
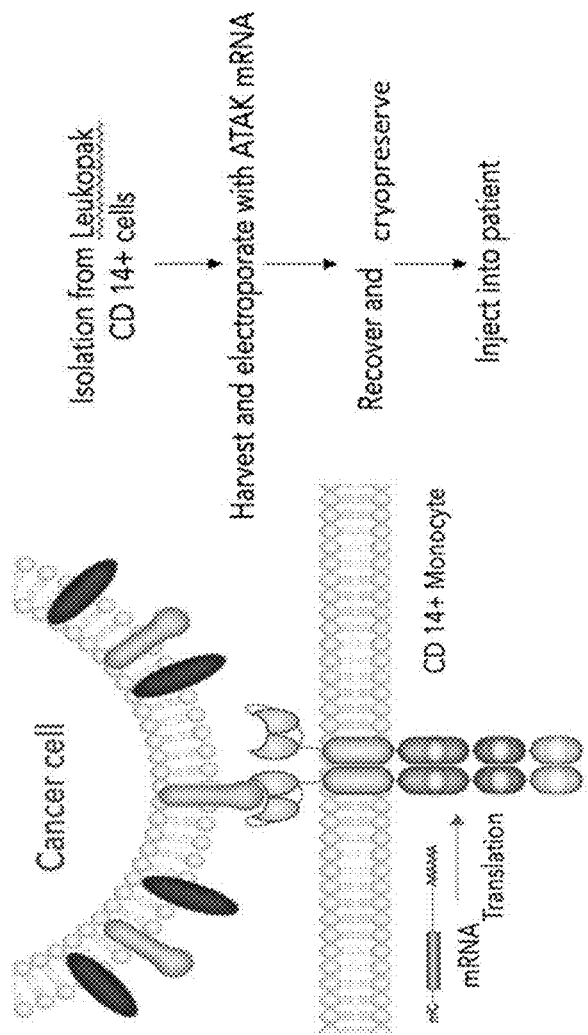
FIG. 7B illustrates an exemplary schematic of a myeloid cell expressing a transgene encoding a chimeric receptor that binds a cancer cell and induces anti-cancer activity.

As shown in FIG. 7B (left), the mRNA comprising a sequence encoding the transgene when introduced into a CD14+ myeloid cell (monocyte), is translated and expresses a chimeric receptor (an ATAK construct) capable of binding to an antigen on a cancer cell.

A number of mRNA designs are generated by synthesizing various gene blocks comprising singly, or combinations of one or more of: (i) a G-quadruplex, (ii) a viral pseudoknot structure in the 5' UTR; and/or (iii) one or (iv) more xrRNA loop structures in the 3' UTR (v) a triplex RNA structure as shown in FIG. 7A; and cloned into the transcription vector at the respective UTRs adjoining the coding sequence of the transgene. These constructs are individually prepared by an off-site vendor and tested in-house for determining stability of the mRNA, as measured by the expression of the chimeric receptor (An exemplary receptor and its function is depicted graphically in FIG. 7B (left). The process flow chart is shown on FIG. 7B (right). In short, constructs are cloned into plasmids, with encoded or modified poly A tails. The mRNA was transcribed and purified. Meanwhile, frozen monocytes was thawed and harvested. Harvested cells were electroporated with the purified mRNA (5-10 ug), and cultured for 1, 2, 3, 5 days. Cells positive for the chimeric receptor (binder positive cells), are detected by means of their ability to bind to a target cell or a substrate coated with the target antigen. The expected results are shown in FIG. 7C. Bulk or purified mRNA expressing one or more of the structural features outlined in (i)-(v) (data denoted by solid squares) or a combination thereof outperforms the commercially available counterparts that do not contain any of the features outlined in (i)-(v) (data denoted by triangles).

Example 7. LINE-1 Retrotransposon Plasmid Mediated Delivery of GFP Gene

In this test run, genomic integration of a GFP cargo and expression the GFP protein using a LINE-1 retrotransposon system was verified. The LINE-1-GFP construct (LINE-1 plasmid GFP) is exemplified in FIG. 8A: A plasmid construct having a LINE-1 sequence encoding ORF1p (ORF1), a sequence encoding ORF2p (ORF2), and a CMV promoter driven split GFP gene situated in the 3'UTR of the LINE-1 in reverse orientation with respect to the ORFs. The split GFP is designed to have an intronic sequence inserted in between a splice donor and acceptor sites, which ensures that the GFP is expressed only after integration and splicing mediated removal of the noncoding sequence in the middle of the coding sequence. In this case the cargo is 2.1 kb. HEK293T cells were transfected with the plasmid using Fugene reagent, and plasmid positive cells were selected by puromycin. The mRNA generated from a genome integrated GFP successfully translates and is measured by flow cytometry, as indicated as change in mean fluorescence intensity (MFI) (FIG. 8B) and fraction of cells with GFP fluorescence intensity compared to mock transfected cells (FIG. 8C). Mock transfected cells received the plasmid that lack the GFP sequence.

Figure 9A:
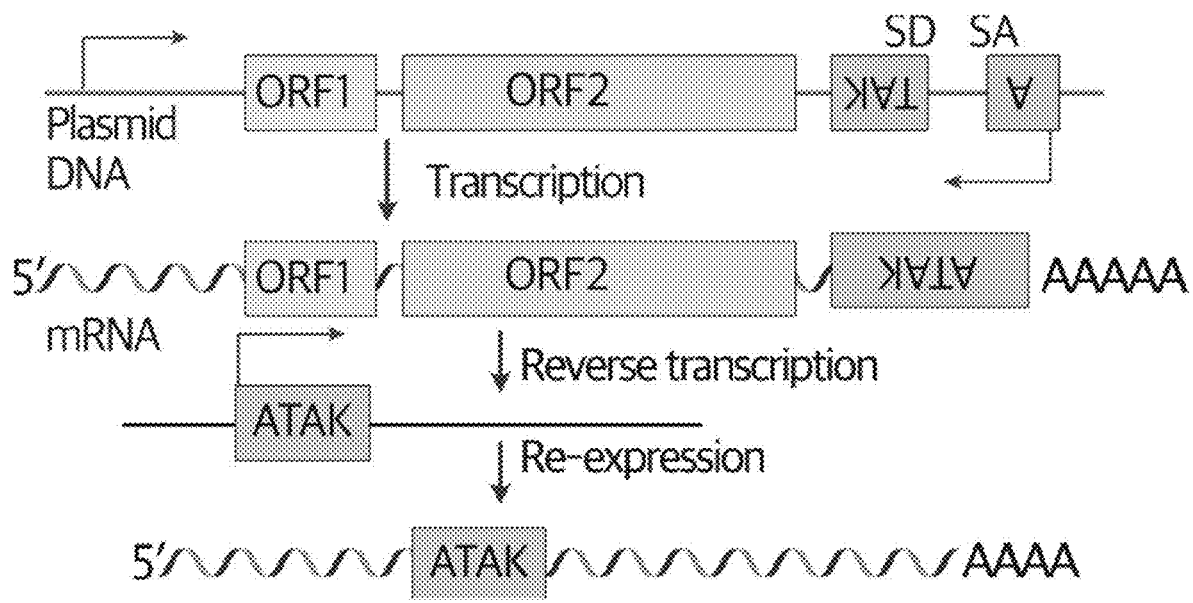
FIG. 9A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) that has extracellular region capable of binding to CD5 and an intracellular region comprising an FCR intracellular domain and a PI3 kinase recruitment domain. The coding sequence of the ATAK receptor is interrupted with an intron.
Figure 9B:
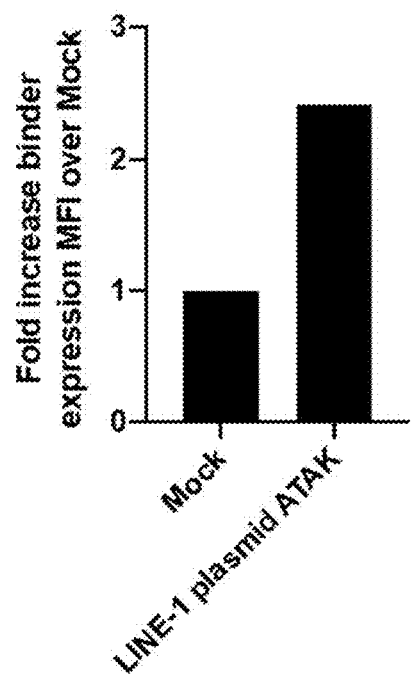
FIG. 9B shows exemplary results showing successful integration of the mRNA transcript encoded by the plasmid shown in FIG. 9A and expression of ATAK relative to mock-transfected cells (fold increase in mean fluorescence intensity of ATAK positive cells is shown). Mock transfected cells were transfected by the vector lacking the ATAK cargo sequence. Expression of ATAK receptor protein was detected by binding with a labeled CD5 antibody.
Figure 9C:
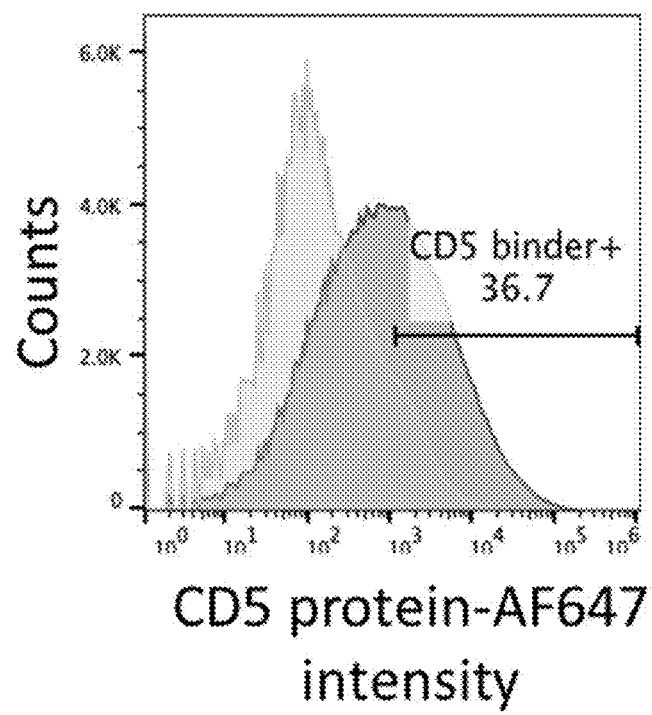
FIG. 9C shows exemplary flow cytometry results from the results shown in FIG. 9B.

Example 8. LINE-1 Retrotransposon Plasmid Mediated Delivery of a Chimeric Receptor Gene This example demonstrates that a recombinant gene can be successfully expressed using the LINE-1 sequence in a cell. HEK 293 cells were transfected with a plasmid having the LINE-1 elements, with a 3 kb cargo sequence encoding recombinant receptor protein CD5-intron-fcr-PI3K (ATAK) that is interrupted by an intron sequence in the CD5 binding domain. The cargo is a chimeric receptor that has a CD5 binding extracellular domain, a FCRγ transmembrane domain, and an intracellular domain having a PI3-kinase recruitment domain. The schematic representation of the retrotransposon plasmid is shown in FIG. 9A. As in the design of the experiment above, the ATAK receptor cannot express unless it is integrated in the genome and the intron is spliced off. Following transfection in HEK293T cells, the receptor expression is detected using labeled CD5 as bait for the CD5 binding extracellular domain. Results shown in FIGS. 9B and 9C show successful integration and expression of the receptor. 36.5% cells were ATAK (CD5 binder) positive (FIG. 9C).

In a further modification, a LINE-1 construct (LINE-1plasmid-cd5_fcr-pi3k_t2a_GFPintron) with a longer 3.7 kb cargo sequence encoding a non-interrupted recombinant receptor protein CD5-intron-fcr-PI3K and an interrupted GFP sequence with a T2A sequence between receptor and the GFP sequences (FIG. 10A). Normalized against mock-transfected cells, there was a greater than 10-fold increase of the ATAK receptor and GFP double-positive cells was noted (FIG. 10B). Exemplary fluorescence identification of GFP and fluorescent tagged CD5 binding and gating quantitation for experimental runs are shown in FIG. 10C and FIG. 10D.

Example 9. mRNA Encoding LINE-1 Retrotransposon for Delivery of a Cargo Gene

Figure 11A:
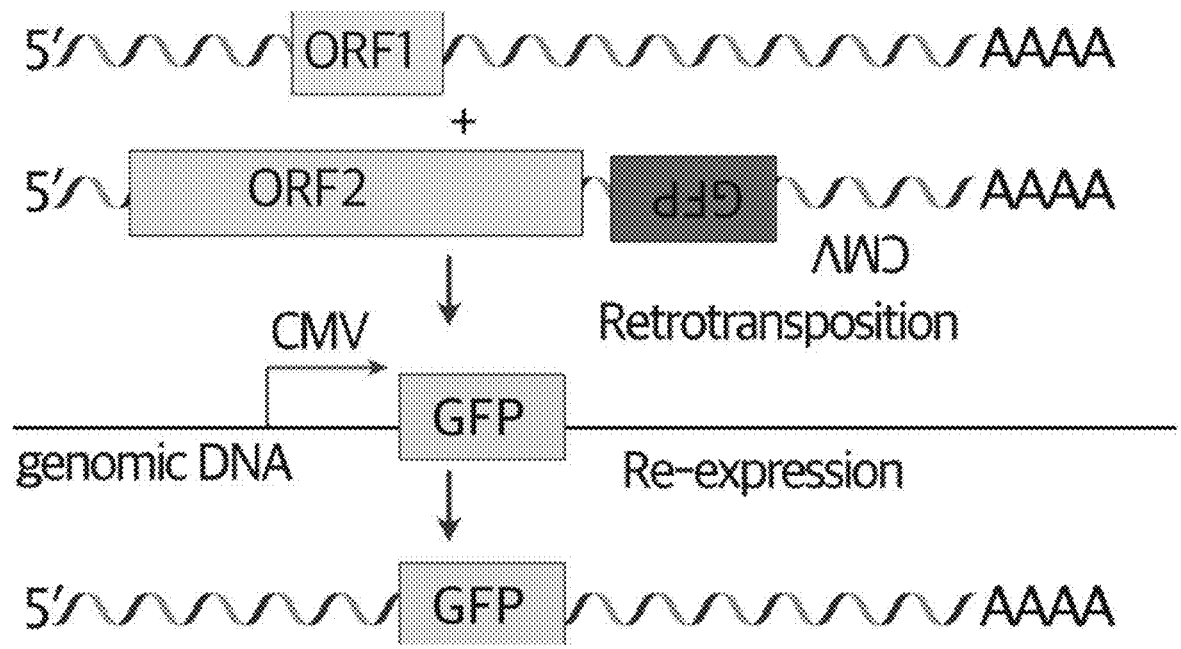
FIG. 11A shows exemplary mRNA constructs for retrotransposition-based gene delivery. The ORF1 and ORF2 sequences are in two difference mRNA molecules. The ORF2p (ORF2) coding mRNA comprises and inverted GFP coding sequence.
Figure 11B:
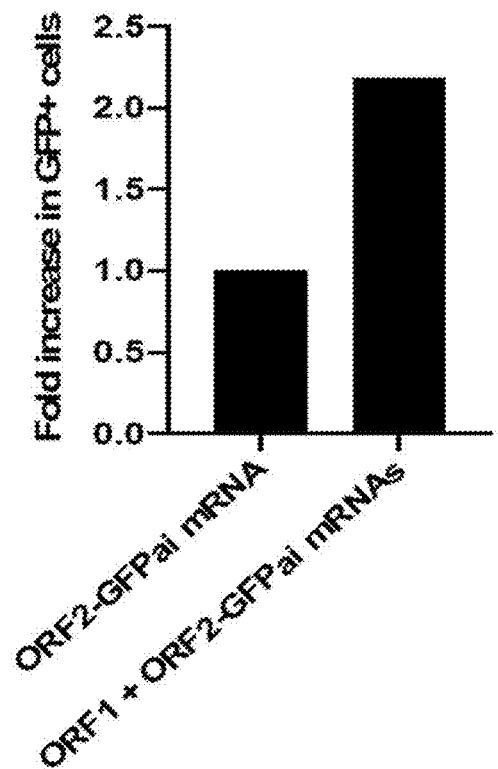
FIG. 11B depicts exemplary data showing expression of GFP (fold increase in mean fluorescence intensity of GFP positive cells is shown) upon electroporating both ORF1-mRNA and ORF2-FLAG-GFPai mRNA normalized to electroporation of ORF2-FLAG-GFPai mRNA only.

In this assay, capability of delivering and expressing a LINE-1 retrotransposable gene sequence as an mRNA was tested. An mRNA encoding an ORF1 (ORF1-FLAG-mRNA), and an mRNA encoding ORF2 and GFP in the antisense direction with a CMV promoter sequence (ORF2-FLAG-GFPai) are designed as shown in FIG. 11A. The cargo size in this assay was 2.4 kb, and GFP is in antisense orientation with respect to ORF2 sequence. The mRNAs were electroporated in 293T cells and the reporter genes expression was demonstrated as shown in FIG. 11B. This experimental set up demonstrated that no ORF1-read-through is necessary for the expression of the ORF2p, and expression of ORF2p from a different mRNA molecule can allow higher expression of ORF2p and GFP. With these results, a successful delivery of the LINE-1 and cargo in the form of mRNA was achieved.

Figure 12A:
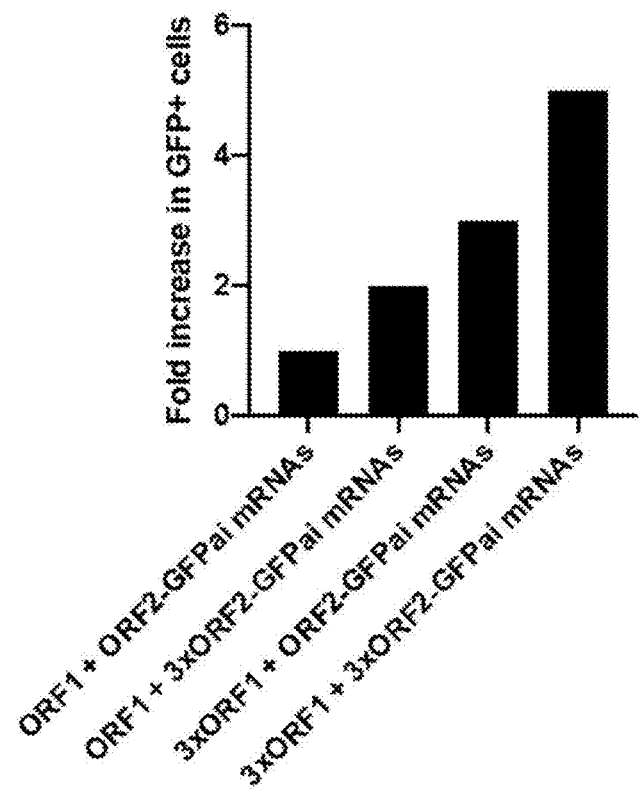
FIG. 12A depicts exemplary data showing expression of GFP (fold increase in mean fluorescence intensity of GFP positive cells is shown) upon electroporating ORF1-mRNA and ORF2-FLAG-GFPai mRNA at different amounts. Fold increase is relative to 1× ORF2-GFPao and 1× ORF1 mRNA.
Figure 12B:
FIG. 12B shows an exemplary fluorescent microscopy image of GFP+ cells following electroporation of the mRNA depicted in FIG. 11A.

In order to determine whether the relative levels of ORF1 and ORF2 mRNA affected GFP expression an experiment was set up to test the varying amounts of ORF1 and ORF2 mRNAs (FIG. 11A). 3× the amount of each and together is tested for increases in GFP+ cells and results are shown in FIG. 12A. Fold increase is relative to 1×ORF2-GFP and 1×ORF1 mRNA. GFP expression was higher when 3×ORF1 was used with 1×ORF2, but not the reverse; whereas having both 3×ORF1 and 3×ORF2 showed the maximum level of GFP expression in the sets compared. The cargo size here is 2.4 kb. FIG. 12B shows fluorescent microscopy image of GFP+ cells following retrotransposon mRNA electroporation.

Figure 13B:
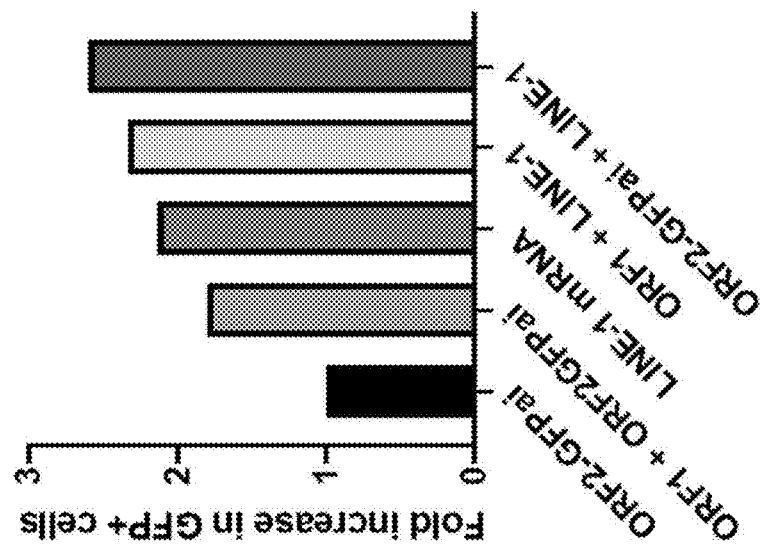
FIG. 13B depicts exemplary data showing expression of GFP (fold increase in mean fluorescence intensity of GFP positive cells is shown) upon electroporating the constructs depicted in FIG. 13A.
Figure 13A:
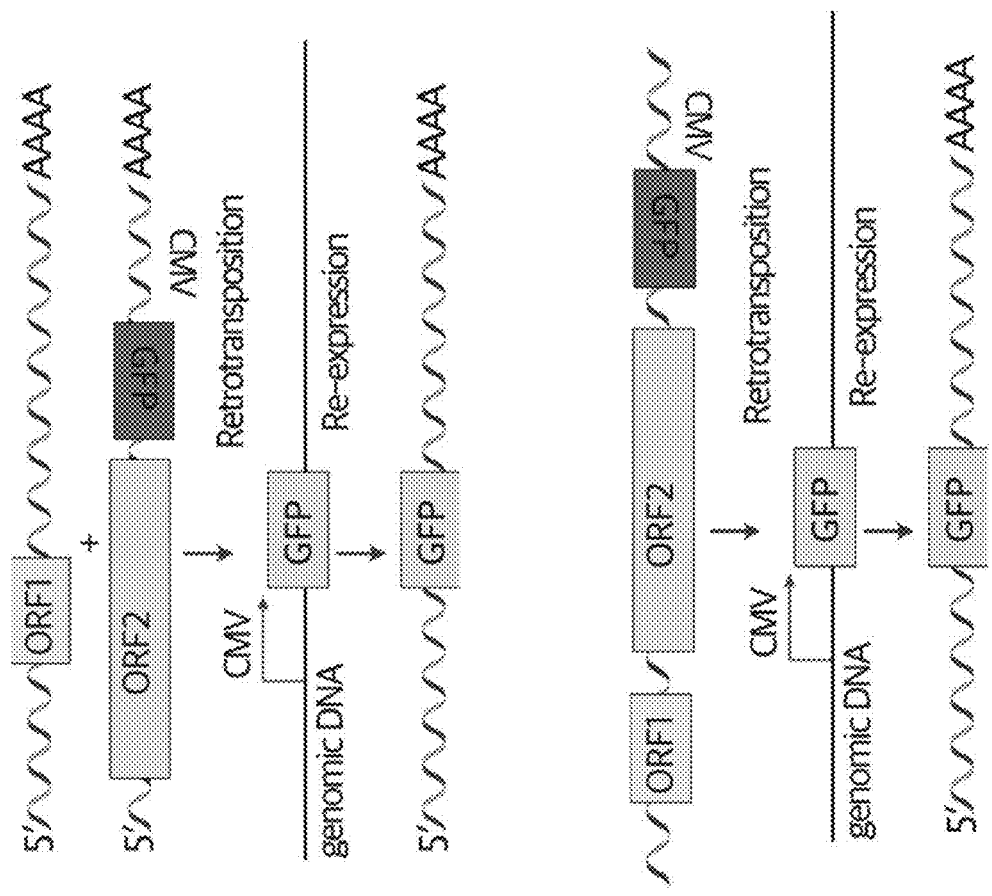
FIG. 13A shows exemplary mRNA constructs where the ORF1 and ORF2 sequences are in two difference mRNA molecules (top panel) and a LINE-1 mRNA transcript comprising ORF1 and ORF2 protein encoding sequences on a single mRNA molecule (bottom panel) for gene delivery. mRNA contains the bicistronic ORF1 and ORF2 sequence with a CMV-GFP sequence in the 3'UTR going from 3'-5'. Upon retrotransposition of the delivered ORF2-cmv-GFP antisense (LINE-1 mRNA), cells are expected to express GFP.

A complete LINE-1 mRNA encoding both ORF1 and ORF2 and GFP transgene in antisense orientation in a single mRNA molecule (LINE 1-GFP mRNA construct) was tested for delivery and genomic integration in a cell. mRNA contains the bicistronic ORF1 and ORF2 sequence with a CMV-GFP sequence in the 3'UTR going from 3'-5' (FIG. 13A). In this study the cargo size is 2.4 kb. As shown in FIG. 13B, upon retrotransposition of the delivered ORF2-cmv-GFP antisense (LINE-1 mRNA), third bar from left, cells expressed higher GFP compared to ORF1 and ORF2 being on separate mRNA molecules (graph bar 1, 2). Inclusion of ORF1 in a separate mRNA in addition to LINE-1 complete mRNA increased GFP expression over LINE-1 alone. Inclusion of ORF2+GFP expectantly showed higher GFP which could be the contribution of the additional ORF2 with the GFP cargo encoding mRNA.

Figure 14B:
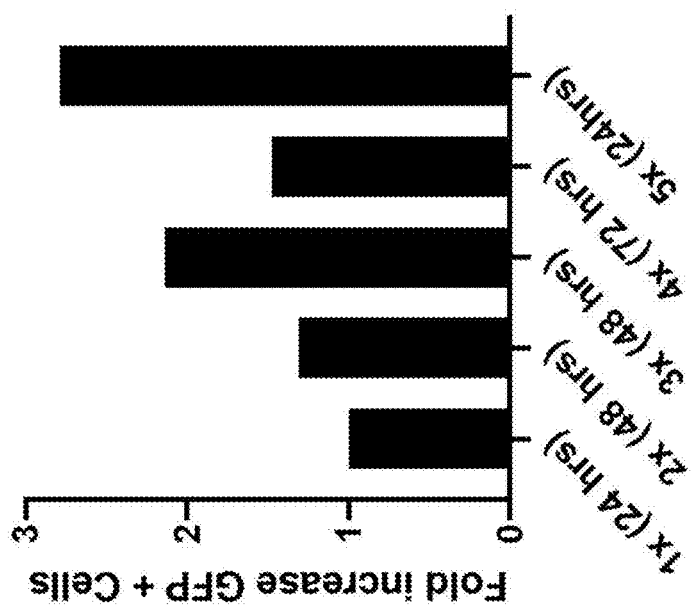
FIG. 14B depicts exemplary data showing expression of GFP at the indicated times (fold increase in mean fluorescence intensity of GFP positive cells is shown) upon electroporating 1-5 times according to FIG. 14A.
Figure 14A:
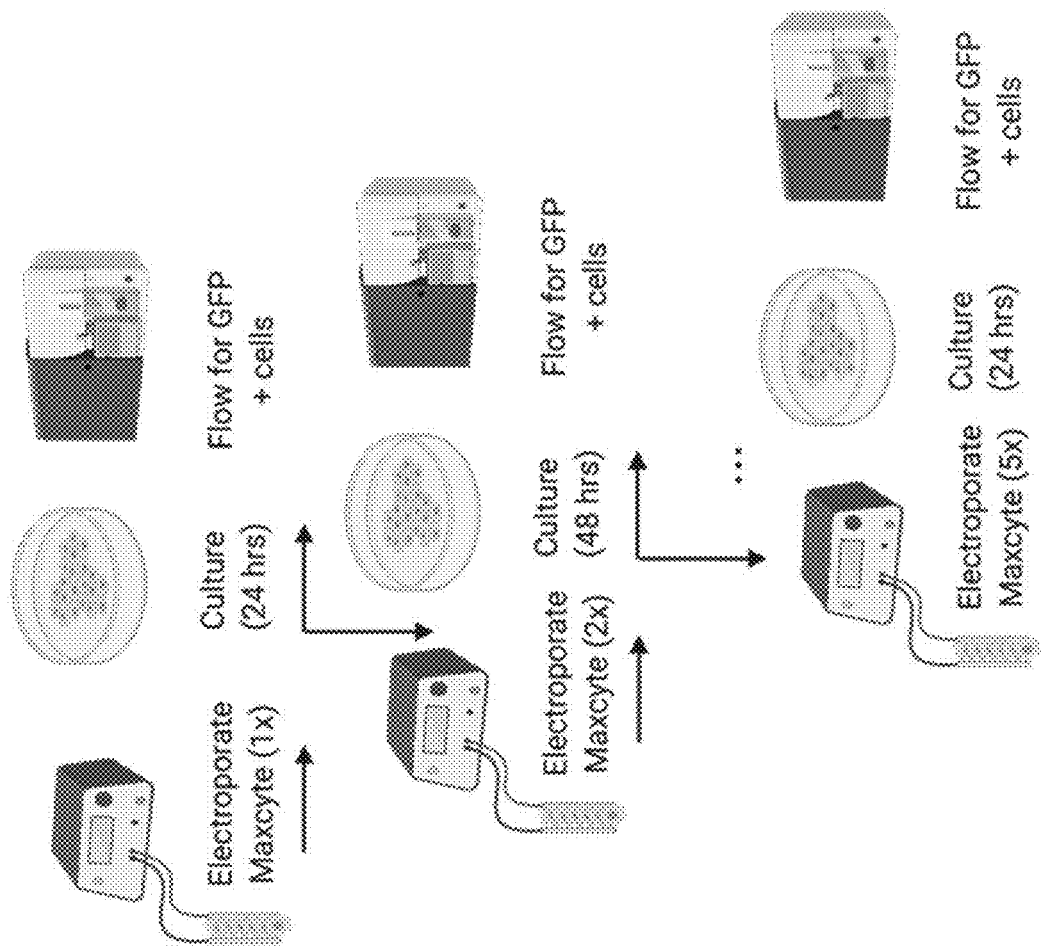
FIG. 14A shows an exemplary experimental design for testing whether multiple electroporations increases retrotransposition efficiency. HEK293T cells were electroporated every 48 hours with the Maxcyte system and assessed for GFP positive cells using flow after culturing for 24-72 hrs.

To test whether subsequent electroporation increases retrotransposition efficiency, cells were electroporation every 48 hours. GFP positive cells were assessed using flow after culturing for 24-72 hrs. The fluorescence data were normalized to the values in the set with a single electroporation event. As shown in FIGS. 14A and 14B, multiple electroporation led to an upward trend in the expression of the transposed gene, but the changes were modest.

Figure 15A:
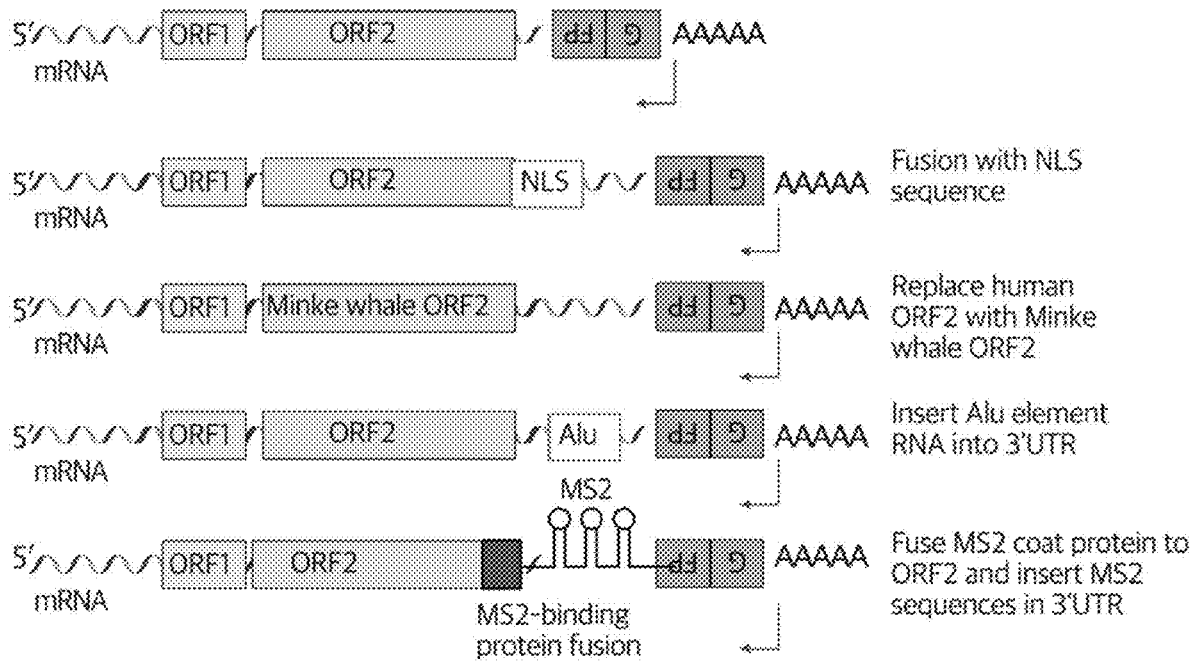
FIG. 15A depicts exemplary constructs to enhance retrotransposition via mRNA delivery. In one construct a nuclear localization signal (NLS) sequence is fused to the C terminus of the ORF2 sequence (ORF2-NLS fusion). In one construct a Minke whale ORF2 sequence was used in place of the human ORF2. In one construct a minimal sequence of the Alu element (AJL-H33delta) is inserted in the 3'UTR of the LINE-1 sequence. In one construct MS2 hairpins are inserted in the 3'UTR of the LINE-1 sequence and an MS2 hairpin binding protein (MCP) sequence is fused to the ORF2 sequence.

Example 10. Modifications to the ORF2 Protein Sequence to Enhance Retrotransposition by mRNA Modification of the LINE-1 sequence to enhance retrotransposition via mRNA delivery were tested using GFP reporter as readout. The experiment was performed as follows. All modifications were in the context of the bicistronic ORF1 and ORF2 sequence. (i) ORF2-NLS fusion was created by inserting C-terminal NLS sequence to the ORF2 sequence. (ii) Human ORF2 was replaced with Minke whale ORF2; (Ivancevic et al., 2016). (iii) Incorporation of an Alu element in the 3'UTR: Using a minimal sequence of the Alu element (AJL-H33Δ; Ahl et al., 2015) in the 3'UTR of the LINE-1. (iv) MS2-hairpin in the 3'UTR+ORF2-MCP fusion: MS2 hairpins in the 3'UTR of the LINE-1 sequence and a MS2 hairpin binding protein (MCP) fused to the ORF2 sequence (FIG. 15A). The mock construct had the wild-type human ORF2 sequence.

Figure 15B:
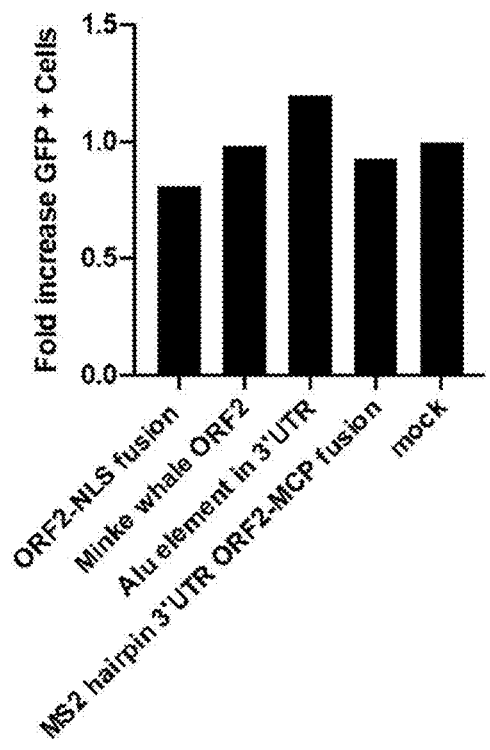
FIG. 15B depicts exemplary data showing expression of GFP (fold increase in mean fluorescence intensity of GFP positive cells is shown) using the constructs depicted in FIG. 15A.

Quantification of the fold increase in the fraction of GFP positive cells relative to mock construct electroporated cells are shown in FIG. 15B.

Example 11. Retrotransposition in an Immune Cell

Figure 16B:
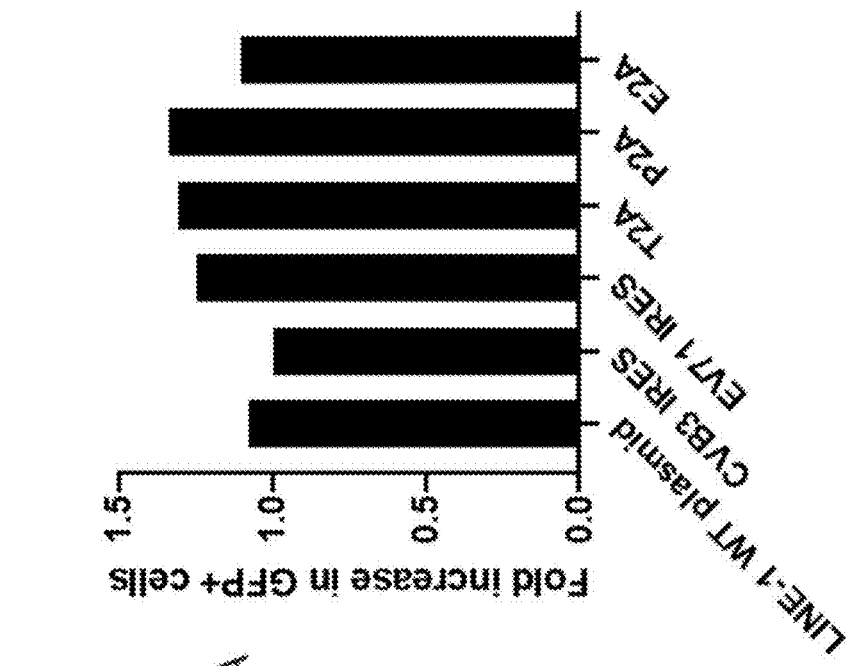
FIG. 16B depicts exemplary data showing expression of GFP (fold increase in mean fluorescence intensity of GFP positive cells is shown) using the constructs depicted in FIG. 16A.
Figure 16A:
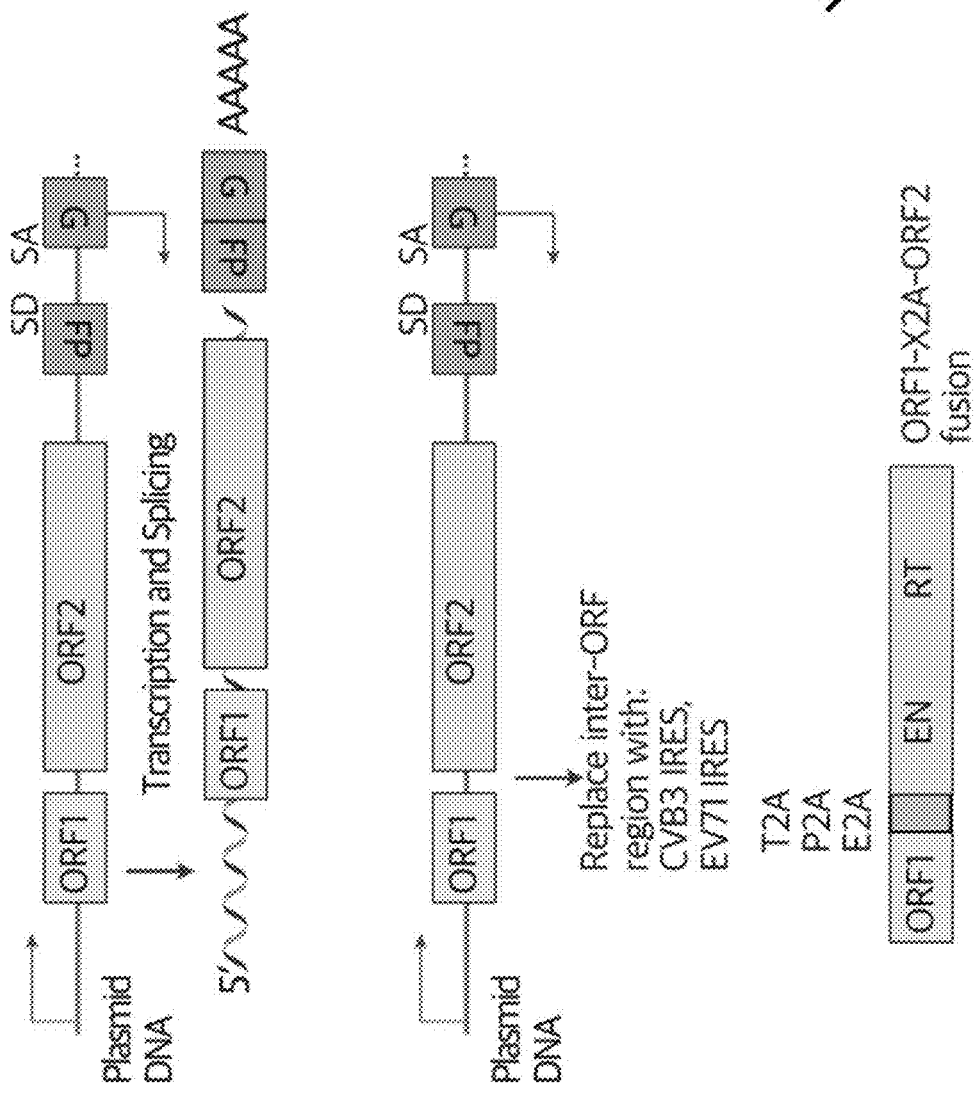
FIG. 16A shows exemplary plasmid constructs where the ORF1 and ORF2 sequences are in two difference plasmid molecules (top panel) and a plasmid encoding a LINE-1 mRNA transcript comprising ORF1 and ORF2 protein encoding sequences on a single mRNA molecule with various replacements of the inter-ORF sequence between ORF1 and ORF2 (bottom panel) for gene delivery.

In this experiment, the inter-ORF region is further manipulated to determine if any of the changes improve GFP expression after transfection of the HEK cells. Taking LINE-1plasmid GFP, the inter-ORF region is manipulated as follows: (a) In one construct the inter-ORF region is replaced with an IRES from CVB3; (b) In another construct, the inter-ORF region is replaced with an IRES from EV71; (c) In three separate constructs, an E2A or P2A or T2A self-cleavage sequence is intercalated in the inter-ORF region. Result are as shown in FIG. 16. Compared to the LINE-1 plasmid GFP (LINE-1 wild type plasmid) led to only modest changes in the GFP readout, especially with T2A sequence insertion. Insertion of EV71 IRES sequence improved GFP expression, while CVB3 IRES did not show any improvement.

Example 12. Retrotransposition in an Immune Cell

To test retrotransposition in immune cells, LINE-1 plasmid and mRNA were tested with the CMV-GFP antisense reporter cargo by electroporating into Jurkat cells, which is a T cell lymphoma line (FIG. 17A-FIG. 17B). Mock set were electroporated with a plasmid with no GFP sequence. GFP expression in the transfected cells was assessed, representative data at 4 days post electroporation is shown in FIG. 17B. Fold increase is reported relative to mock transfected cells. Both plasmid and mRNA delivery modes resulted in successful GFP expression.

Figure 18A:
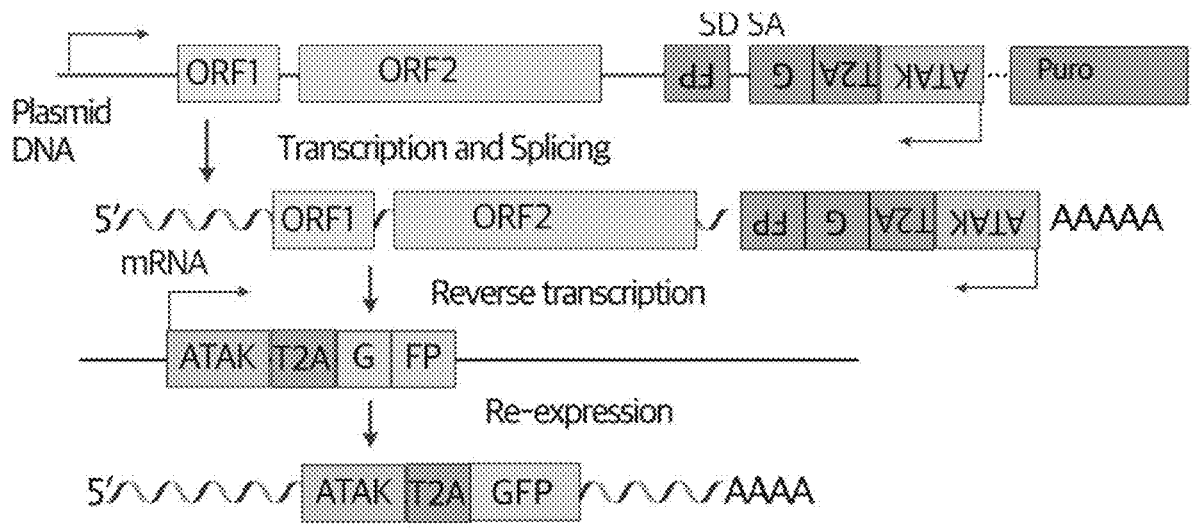
FIG. 18A shows an exemplary plasmid design and expected LINE-1 mRNA transcript with a cargo nucleic acid sequence. The plasmid has a LINE-1 sequence (comprising ORF1 and ORF2 protein encoding sequences) and a cargo sequence which is a nucleic acid sequence encoding a recombinant chimeric fusion receptor protein (ATAK receptor) followed by a T2A self-cleavage sequence followed by a split GFP sequence (all in a reverse orientation relative to the LINE-1 sequence). The coding sequence of the GFP is interrupted with an intron. Expected mRNA after reverse transcription and integration of the cargo are depicted.
Figure 18B:
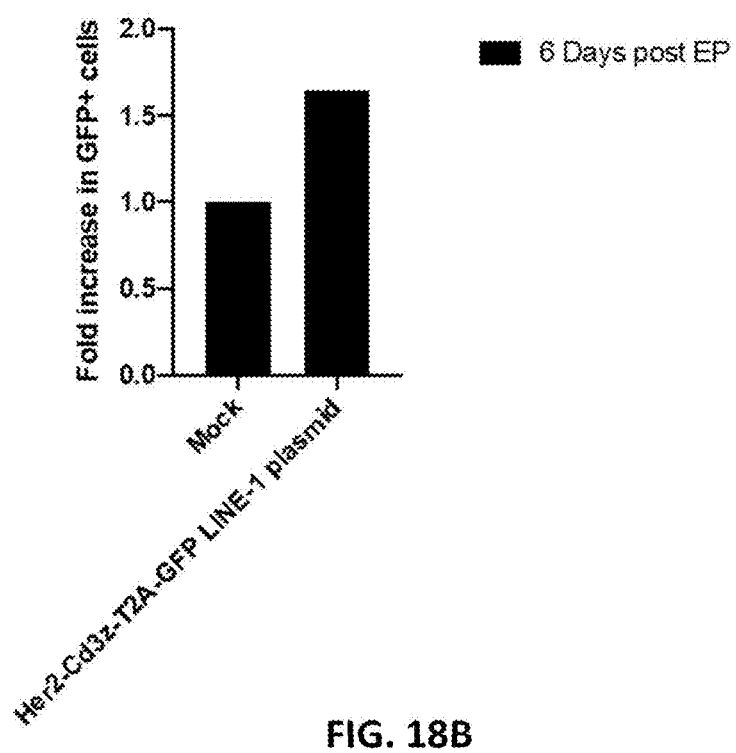
FIG. 18B shows exemplary results showing successful integration of the mRNA transcript encoded by the plasmid shown in FIG. 10A and expression of ATAK-T2A-GFP relative to mock-transfected cells (fold change in GFP and ATAK double positive cells is shown) in a myeloid cell line (THP-1). Data represents expression at 6 days post transfection, normalized over mock plasmid transfected cells wherein the mock plasmid does not have GFP coding sequence.

Next, THP-1 cells (a myeloid, monocytic cell line) were electroporated with a plasmid having LINE-1 sequences and a 3.7 kb cargo encoding a chimeric HER-2 binding receptor, and a split GFP (LINE-1 plasmid Her2-Cd3z-T2A-GFPintron) (FIG. 18A). The cargo is a chimeric receptor that comprises a HER2 binding extracellular domain, a CD3z transmembrane domain, and split GFP reporter. The plasmid was successfully integrated into the genome and showed prolonged expression, as demonstrated in FIG. 18B. Representative expression at day 6 post transfection is shown in the figure. From these studies, it was demonstrated that LINE-1 mediated gene delivery can result in successful stable genomic integration in various cell types, including epithelial cell types (HEK-293T cells); T cells (e.g., Jurkat cells); and cells of myeloid lineage (e.g., THP-1 cells) and results in prolonged expression. Moreover, unlike CRISPR dependent technologies such as Prime editing, retrotransposition can result in integration of large genetic cargo, and, these can be delivered as a single nucleic acid construct.

Example 13. External Methods for Further Enhancing Efficiency of LINE-1 Mediated Retrotransposition of the Cargo Sequences In this section, methods for further enhancing the efficiency of retrotransposition of cargo sequences into the genome of cells are detailed.

Figure 19:
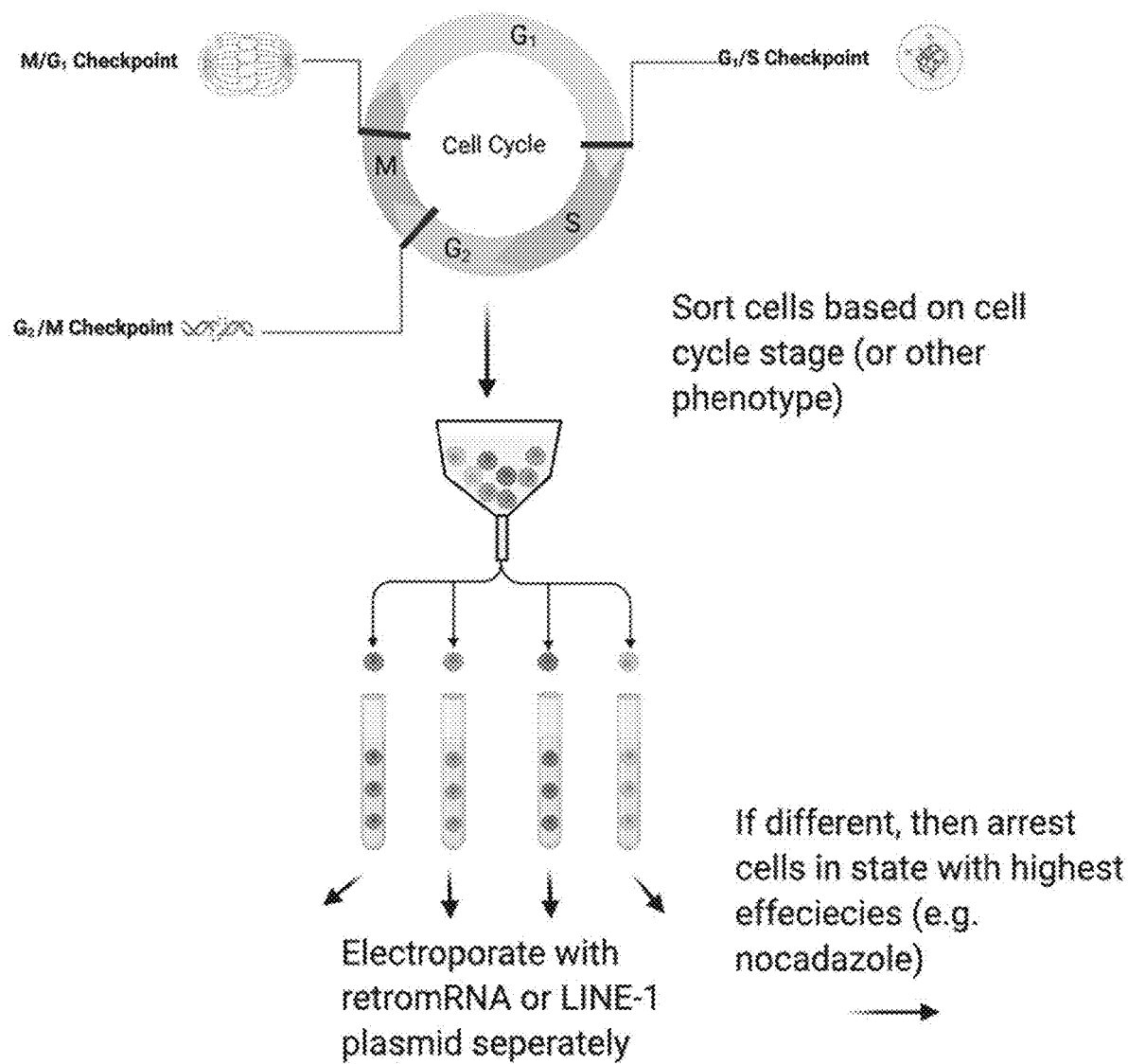
FIG. 19 illustrates an exemplary experimental set up for cell synchronization. A heterogenous cell population is sorted based on cell cycle stage, prior to delivery of an exogenous nucleic acid. Cell cycle synchronization is expected to result in higher expression and stabilization of the exogenous nucleic acid delivered. If cells are not homogeneous after cell sorting, then cells can be further incubated with a suitable agent that arrests cell cycle at a stage.

Cell cycle synchronization by selection of cells in a population that are in a certain stage of cell cycle or G1 arrest by a suitable agent can lead to higher nucleic acid uptake efficiency, e.g., plasmid vector transfection efficiency or electroporation efficiency. In this assay, cells are pre-sorted and each group is separately electroporated to ensure uniform electroporation. The efficiencies of electroporation are compared between these groups and a cell cycle stage that results in highest efficiency as determined by the expression of the GFP test plasmid or mRNA is selected (FIG. 19).

In another variation of this experiment, cells are synchronized with or without sorting by treating the cells, with a cell cycle arrest reagent for a few hours prior to electroporation. An exemplary list of cell cycle arrest reagents is provided in Table 1. The list is non-exhaustive, and is inclusive of reagents that can be proapoptotic, and hence careful selection suitable for the purpose and dose and time of incubation is optimized for use in the particular context.

is monitored. The intensity and time of irradiation is optimized for obtaining the maximum benefit, as indicated by higher GFP expression.

In another example, cells transfected with LINE-1 plasmid GFP were divided into experimental sets that are treated as follows (i) irradiation in order to induce DSB (as described above); (ii) treat cells in this set with a small molecule, such as SCR7, that blocks DNA ligase and therefore inhibits the DNA damage repair machinery. Preventing protective repair mechanism from inhibiting the progress of the retrotransposition is expected to enhance GFP expression: (iii) irradiate the cells then treat the cells with SCR7, combination of the two is expected to show a more robust effect. GFP expression is monitored over a period of 6 days, and the set that shows maximum GFP fluorescence over the longest period indicates a condition that is adopted in further studies.

Example 14. Enhancing Efficiency of LINE-1 Mediated Retrotransposition of the Cargo Sequences by Further Modification of the Construct I. Enhancing non-coding regions of the construct to offer stability and higher expression. In this example a LINE-1 plasmid-GFP is further modified to test for increased GFP expression as follows: (a) In one construct, the 5'UTR is replaced with an UTR of a complement gene; (b) In another construct, the 3' UTR is replaced with the UTR sequence of

TABLE 1

Exemplary non-exhaustive list of small molecule reagents that are used for inhibiting cell cycle

| Agent | Cell cycle | Mechanism |
| --- | --- | --- |
| 5-[(4-Ethylphenyl)methylene]-2-thioxo-4-thiazolidinone | Arrests cell cycle at G0-G1 | Inhibits c-Myc-Max dimerization |
| Itraconazole | Inhibits cell cycle at G1 | SMO antagonist |
| ABT 751 (Tocris Bioscience, cat #4138) | Blocks cell cycle at G2M | Inhibits microtubule proliferation |
| Artesunate | Arrests cell cycle at G2M | Suppresses ROS-induced NLRP3 |
| AZD 5438 | Blocks cell cycle at G2M, M, S and G1 phases | Inhibits Cdk |
| Baicalein | Arrests cell cycle at G1 and G2 phases | Inhibits lipoxygenases |
| CPI 203 (alternative name: TEN 101) | Arrests cell cycle at G1 phase | BET bromodomain inhibitor |
| Diadzein | Arrests cell cycle at G1 | Estrogen receptor agonist |
| DIM | Blocks cell cycle at G2M | Induces EGFR activation |
| Epothilone B | Arrests cell cycle at G2M | Inhibits tubulin proliferation |
| Indirubin-3'-oxime | Antiproliferative | Inhibits GSK3b |
| MPC 6827 hydrochloride | Cell cycle arrest | Inhibits microtubule proliferation |
| Pladienolide | Inhibits G1 and G2/M | Decreases mRNA splicing |
| Plumbagin | Induces G2/M arrest | Inhibits TOR signaling and others |
| Temsirolimus | Induces G1/S | mTOR inhibitor |
| Toceranib | Cell cycle arrest | Inhibits PDGFR and VEGFR |
| WYE 687 dihydrochloride | Induces G1 arrest | mTOR inhibitor |
| YC1 | Induces G1 arrest | Guanylyl cyclase activator |

Figure 20:
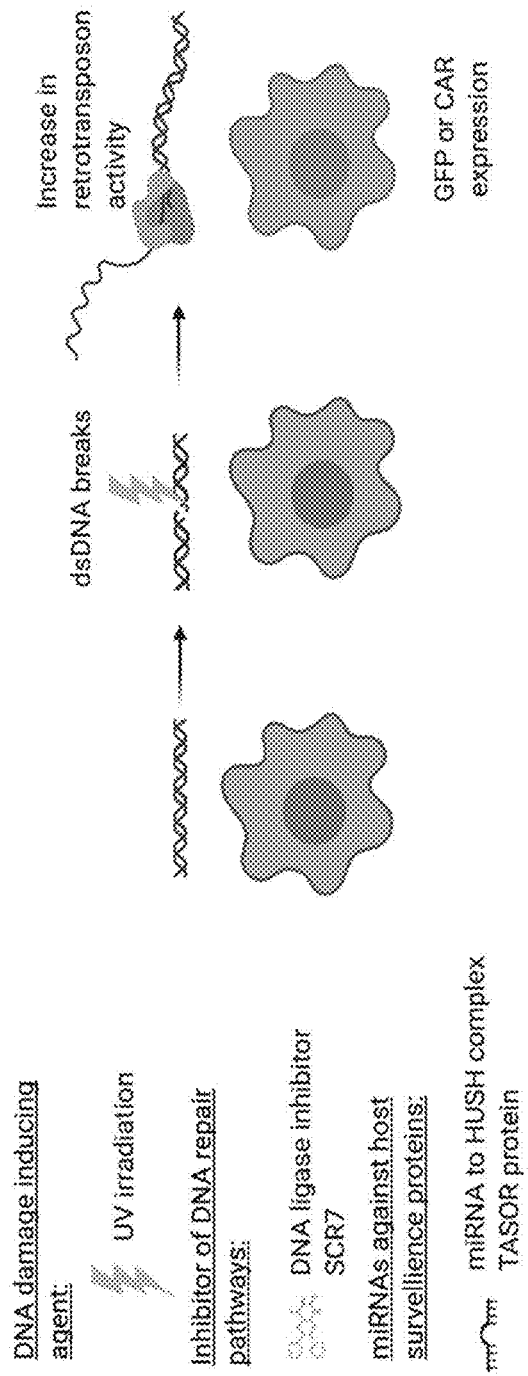
FIG. 20 illustrates an exemplary method for increasing retrotransposon efficiency by inducing DNA double stranded breaks, with or without inhibiting DNA repair pathways, such as by inducing DNA ligase inhibitor SCR7 or inhibiting host surveillance proteins, for example, using miRNA to HUSH complex TASOR protein.
Figure 21:
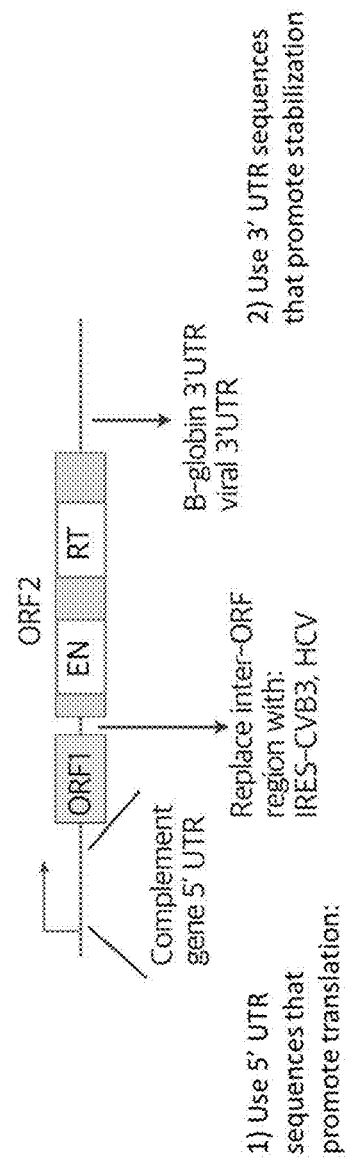
FIG. 21 illustrates exemplary constructs for integrating an mRNA encoding a transgene into the genome of a cell.

For certain ex vivo usages, retrotransposition is enhanced by inducing DNA double stranded breaks (DSB) in a cell that expresses a retrotransposition machinery as described in any of the examples above by controlled irradiation, which create opportunities for the homologous recombination and priming for the reverse transcriptase (FIG. 20). In another example, cells transfected with LINE-1 plasmid GFP construct and subjected to an irradiation pulse. GFP expression B-globin gene for increased stability; (c) In another construct the inter-ORF region is replaced with an IRES from CVB3; (d) In another construct, the inter-ORF region is replaced with an IRES from EV71 (e) In three separate constructs, an E2A or P2A or T2A self-cleavage sequence is intercalated in the inter-ORF region as shown in a diagrammatic representation in FIG. 21. In addition to the above, various combinations of (a)-(e) and additional combinations listed in Table 2 are tested using the same set-up as above.

GFP expressions are monitored after transfection of the constructs in parallel test sets into HEK293T cells to see if any of these constructs increased GFP expression compared to the LINE-1 plasmid GFP alone. The combinations that show improvement are adopted.

TABLE 2

Exemplary combinations of 5' and 3' UTR and inter-ORF insertion elements for inclusion in the LINE-1 construct for increase in retrotransposition efficiency.

| 5'-UTR sequences selected from sequences | 3'-UTR sequences | Inter-ORF sequences |
|---|---|---|
| Complement 5'UTR | WPRE | T2A, E2A, P2A |
| Covid-19 5' leader sequence | B-globin 3'UTR | CVB3 IRES |
| CYBA 5'UTR | RSV RSE | EV71 IRES |
| CYP2E1 5'UTR | AREs | EMCV IRES |
|  | RNA zipcodes for the ER mtRNRl-AES | PV IRES |
|  |  | CSFV IRES |
|  |  | HRV2 IRES |
|  |  | AAA (tri alanine fusion or any fusion-linker sequence) |

Figure 22:
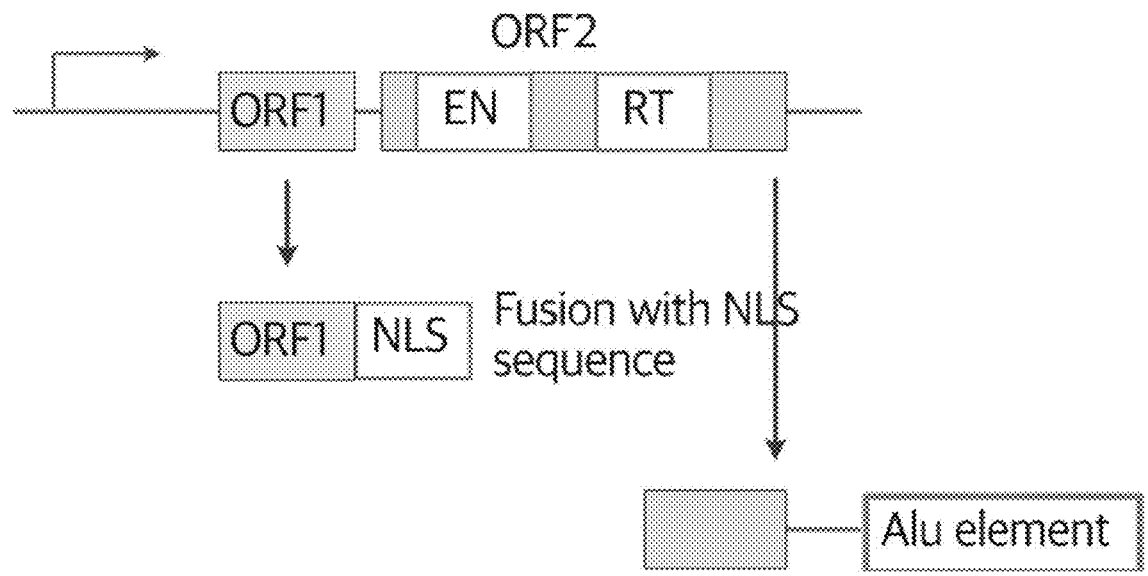
FIG. 22 illustrates exemplary constructs for integrating an mRNA encoding a transgene into the genome of a cell.

II. Enhancing localization and retention of the ORFs in the nucleus. In this example, LINE-1 plasmid-GFP is further modified to test for increased GFP expression as follows: (a) the ORF2 encoding sequence is fused with a nuclear localization sequence (NLS) (graphically represented in FIG. 15A second construct from top). (b) the ORF1 encoding sequence is fused with a nuclear localization sequence (NLS), graphically represented in FIG. 22; and (c) An Alu binding sequence is inserted 3' of the sequence encoding ORF2 reverse transcriptase (graphically represented in FIG. 15A, fourth construct from the top; (d) Both (a) and (c) together (not shown); (e) Both (b) and (c) together, the NLS sequence is fused to the ORF1 N-terminus, and an Alu binding sequence is inserted 3' of the sequence encoding ORF2 reverse transcriptase (FIG. 22) and (f) Integrating a SINE-derived nuclear RNA LOcalizatIoN (SIRLOIN) sequence in LINE-1 3' UTR. HEK-293T cells were transfected with constructs (a)-(f) and the LINE-plasmid GFP construct in parallel. GFP expression is monitored after transfection into HEK293T cells. The set that shows maximum GFP fluorescence over the longest period is adopted.

Figure 23:
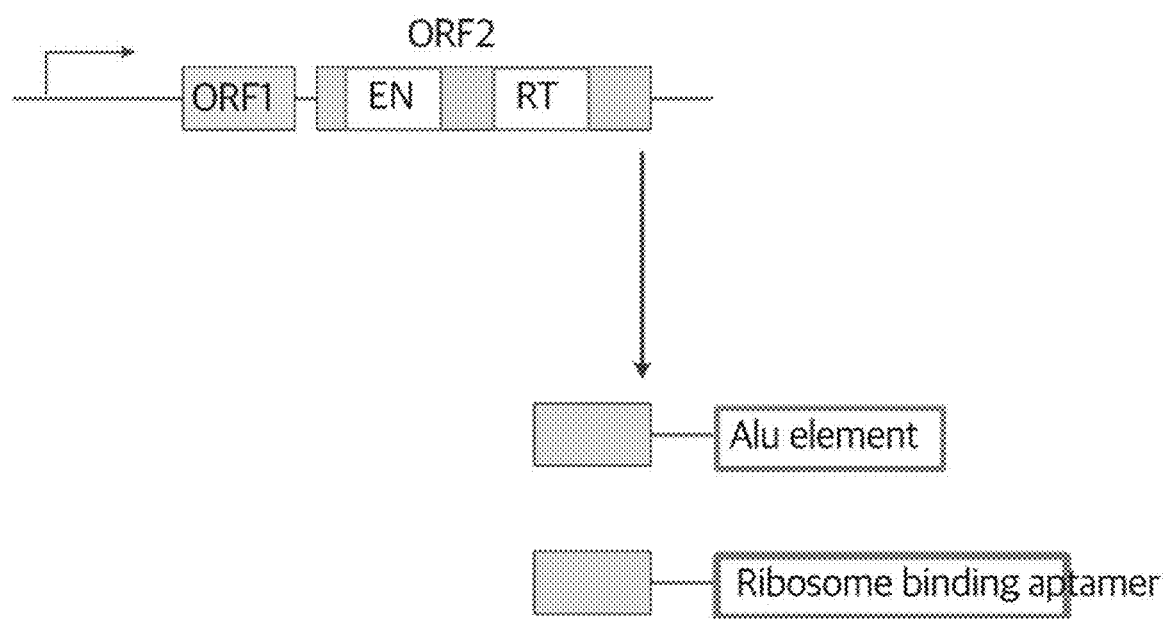
FIG. 23 illustrates exemplary constructs for integrating an mRNA encoding a transgene into the genome of a cell.

III. Modifying construct to increase LINE-1 protein-RNA complex binding to the ribosome. In this example, an additional sequence is inserted in the 3'UTR of the LINE-1 construct to increase association of the LINE-1 protein RNA construct to the ribosomes, the sequence is an Alu element, or a ribosome binding aptamer (FIG. 23).

For enhancing LINE-1 protein-RNA complex binding to the ribosome, insertion of the following elements in the 3' UTR of the mRNA is done and tested similar to the experiments above. Insertion of Alu elements is described above. In separate constructs, Alu element truncations, Ribosome binding aptamers (109.2-3) and Ribosome expansion segments (ES9S) binding sequence are inserted and each tested for increase in GFP expression.

Figure 24:
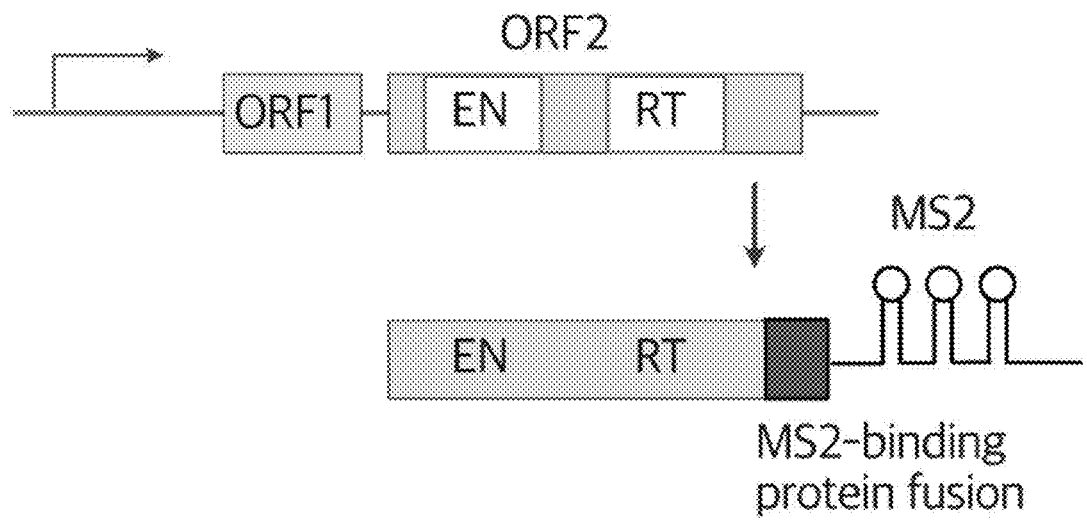
FIG. 24 illustrates exemplary constructs for integrating an mRNA encoding a transgene into the genome of a cell.

IV. Enhancing binding of ORF2 to its own mRNA for retrotransposition. In this example, a sequence containing MS2 binding loop structure is introduced into the 3 ' UTR of the LINE-1, and a sequence encoding MS2 RNA binding domain is fused to the RNA binding domain of the ORF2p-RT (graphically represented in FIGS. 4A and 4B, and FIG. 24, construct SEQ ID NO: 15). The fused protein will specifically attach to the MS2-binding structural motif in the 3' UTR, and therefore any non-specific binding and retrotransposition is minimized (FIG. 24). GFP expression is monitored after transfection into HEK293T cells. Following a similar design, the ORF is fused with the protein binding sequences shown in left column of Table 3 below, combined with a cognate sequence inserted in the 3'UTR region of the ORF2 shown in the corresponding right column in the same row.

TABLE 3

Exemplary list of elements to enhance translation efficiency and stability of the LINE-1 proteins and increased expression of LINE-1 proteins.

| Elements to be fused with the LINE-1 ORF2 | 3' UTR sequence recognizable by the element |
|---|---|
| PP7 coat protein | PP7 |
| Streptavidin | S1m aptamer |
| Tobramycin | Tobramycin aptamer |

Figure 25:
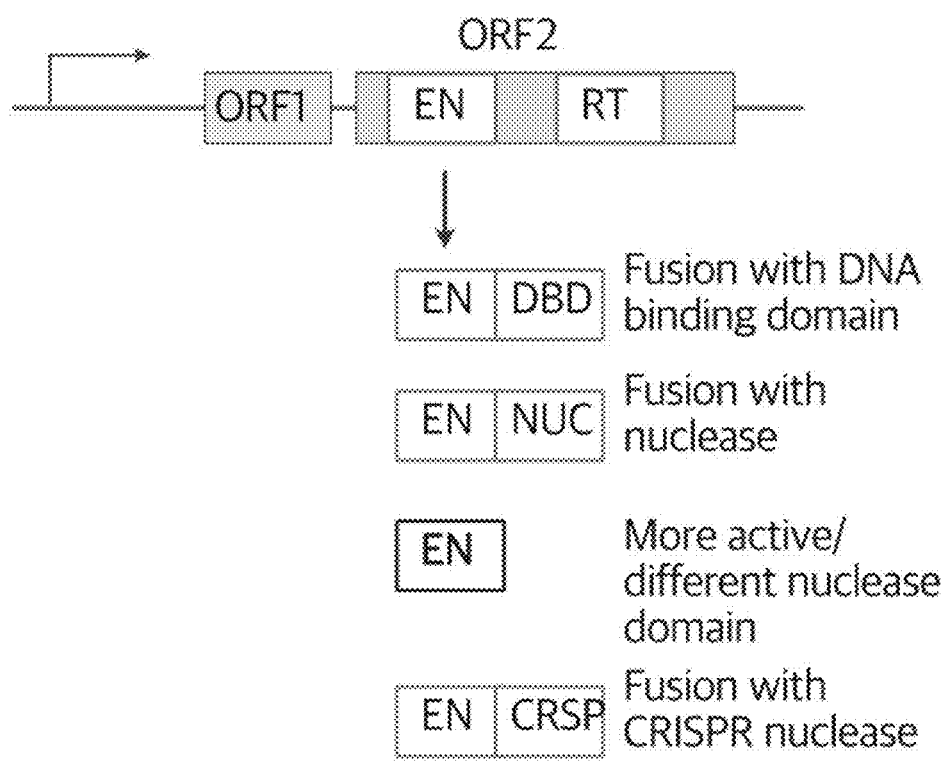
FIG. 25 illustrates exemplary constructs for integrating an mRNA encoding a transgene into the genome of a cell.

V. Modifying the endonuclease function of the retrotransposon. In this example, the constructs are modified to test increase in GFP expression as follows. In a first experimental set, the LINE-1 plasmid GFP is cut at the 3'end of the endonuclease coding sequence of ORF2, and a sequence encoding the DNA binding domain (DBD) of a heterologous zinc finger protein (ZFP) is inserted. In another experimental set, the endonuclease domain is fused with a CRISPR nuclease. A variety of nucleases can be tested by modifying the LINE-1 plasmid GFP ORF by creating a fusion protein using DNA binding domains and cleavage domain as shown in a non-exhaustive list in Table 4, In addition, two ORF-2 domains are encoded in one set to facilitate dimerization. The construct that has higher GFP expression than the ORF2 endonuclease can be further selected. The plasmid designs are graphically represented in FIG. 25. GFP expression is monitored after transfection of the plasmids into HEK293T cells, and the set that yielded best.

TABLE 4

Exemplary non-exhaustive list of additional DNA cleavage domains/enzymes that can be fused to or inserted in place of LINE-1 endonuclease.

| Gene /Enzyme | Description |
|---|---|
| FokI | Class II endonuclease from Flavobacterium okeanokoites, recognition and cleavage sequence are separated by a few nucleotides; recognizes DNA sequence 5-GGATG-3' |
| Restriction enzymes, | e.g., HindII, EcoR1, BamH1 |
| LAGLIDADG family nuclease A | Intron encoded homing proteins found in various genera including bacteria |
| GIY-YIG | This domain is found in the amino terminal region of excinuclease abc subunit c (uvrC), bacteriophage T4, endonuclease segA, segB, seg C, seg D, and seg E and group I introns of fungi and phage. |

TABLE 4-continued

Exemplary non-exhaustive list of additional DNA cleavage domains/enzymes that can be fused to or inserted in place of LINE-1 endonuclease.

| Gene /Enzyme | Description |
| --- | --- |
| His-Cys box | Homing endonucleases containing two clusters of conserved histidine and cysteine residues over a 100 amino acid region. |
| H-N-H | Widely present nuclease in phage DNA. Crucial component of the terminase packaging reaction of E. coli phage HK97. |
| PD-(D/E)xK | Phosphodiesterases, present in a large number of proteins, e.g., DUF4420, DUF3883, DUF4263, COG5482, COG1395, Tsp45I HacII, Eco47II. SeaI, HpaII. |
| Vsr-like/EDxHD | C-terminal nuclease domain that displays recognizable homology to bacterial Very short repair (Vsr) endonucleases |

Figure 26:
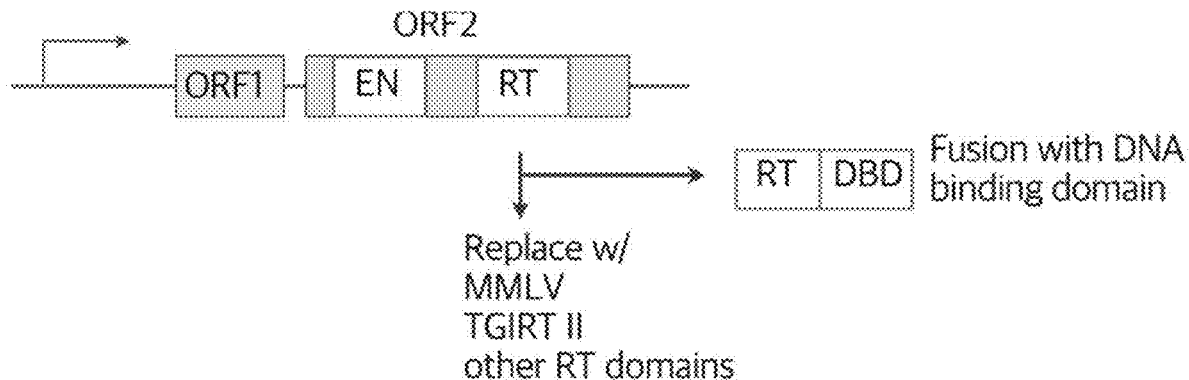
FIG. 26 illustrates exemplary constructs for integrating an mRNA encoding a transgene into the genome of a cell.

VI. Modifying the reverse transcriptase function of the retrotransposon. In this example, the reverse transcriptase domain of ORF2 is modified for increasing its efficiency. In one experimental set, the sequence encoding the human ORF2 in LINE-1plasmid GFP is excised and replaced with a sequence encoding MMLV or TGIRTII. In another experimental set, the ORF2 reverse transcriptase domain is fused with a DNA binding domain of a heterologous protein. The reverse transcriptase domains and/or the DNA binding domains can be selected from a non-exhaustive list provided in Table 5A-Table 5B. The constructs are graphically exemplified in FIG. 26. GFP expression is monitored after transfection into HEK293T cells.

TABLE 5A

Selected non-exhaustive list of reverse transcriptase for replacing the LINE-1 RT for higher efficiency

| Reverse Transcriptase | Description |
| --- | --- |
| M-MLV-RT | Murine leukemia virus |
| TGIRT-II | Thermostable group II intron reverse transcriptase with high fidelity and processivity |
| AMV-RT | Avian Myeloblastosis Virus reverse transcriptase |
| Group II intron maturase RT | Derived from *Eubacterium rectale* |
| HIV-RT | Efficient RT derived from HIV |
| TERT | Catalyzes the RNA-dependent extension of 3'-chromosomal termini with the 6-nucleotide telomeric repeat unit, 5'-TTAGGG-3'. |

TABLE 5B

Selected non-exhaustive list of DNA-binding domains for fusing to a RT for higher efficiency
DNA binding domains (DBD)

Zinc finger domains
Leucine zipper (bZip)
Helix-turn-helix domain
HMG-box
R2 retroelement DBD
Sso7d
Protein A (ssDNA)
OB-fold (ssDNA)

Figure 27:
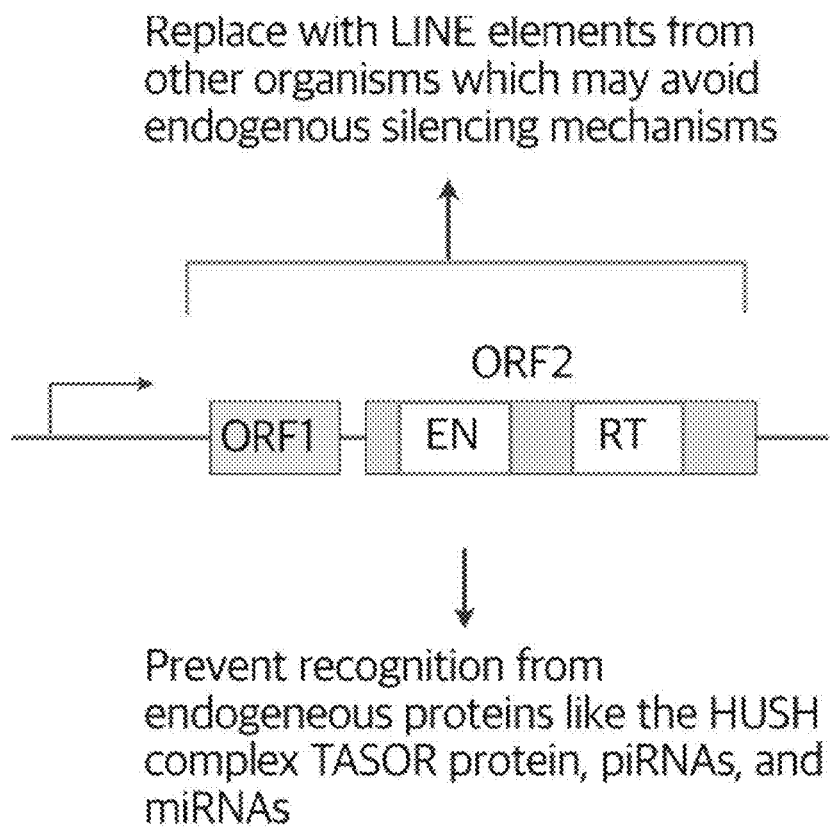
FIG. 27 illustrates exemplary constructs for integrating an mRNA encoding a transgene into the genome of a cell.

VII. Replacing human LINE-1 with LINE-1 from other organisms. In this example, the sequence encoding human LINE-1 is replaced by a LINE-1 from a different organism. In one example, the human LINE-1 construct is compared with a construct where the human LINE-1 is replaced by a minke whale LINE-1 sequence (FIG. 27). Using the same experimental framework, a number of ORFs are tested. An exemplary non-exhaustive list is provided in Table 6 below. A further comprehensive list is available in Ivancevic A. et al., Genome Biol Evol 8(11):3301-3322.

TABLE 6

Exemplary LINE-1 elements from organism for use in replacement of the human LINE-1

| Species Name | No of total LINE-1/ No active/percent active |
| --- | --- |
| *Balaenoptera acutorostrata scammoni* | 8,012/5,006/62.4% |
| *Rhinopithecus roxellana* | 11,115/2,954/26.5% |
| *Mus musculus* | 18,280/4,143/22.66% |
| *Aedes aegypti* | 519/184/35.4% |
| *Zea mays* | 744/165/22.17% |
| *Brassica napus* | 1,929/565/29.2% |
| *Brassica rapa* | 543/228/41.9% |
| *Danio rerio* | 590/268/45.4% |

In another set, human LINE-1 is retained as in the GFP plasmid, but an inhibitor of human LINE-1 silencer is utilized to prevent recognition by endogenous proteins like HUSH complex TASOR protein. In this case, the TASOR inhibitor is an inhibitory RNA, such as a miRNA.

Figure 28:
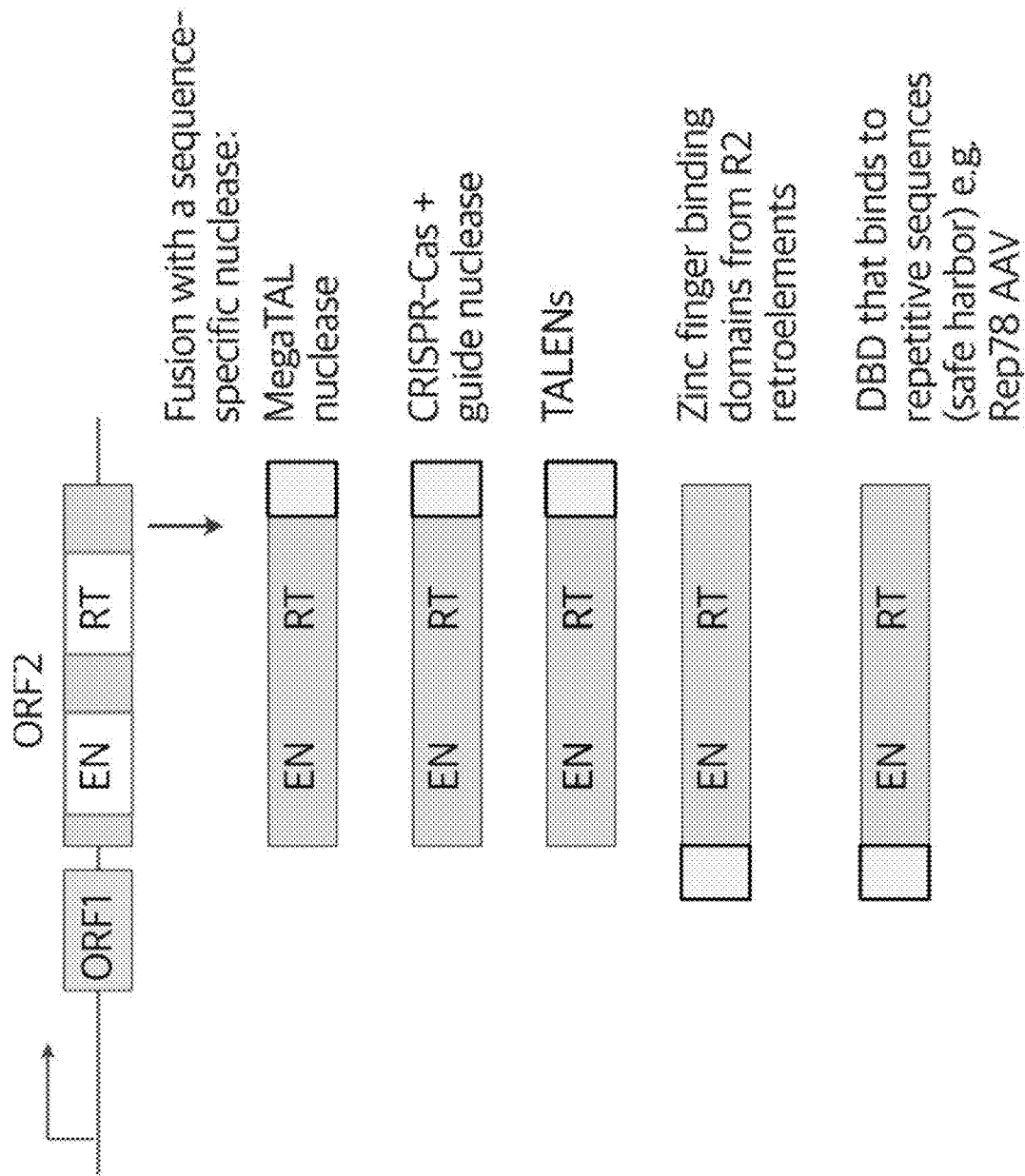
FIG. 28 illustrates exemplary constructs for integrating an mRNA encoding a transgene into the genome of a cell.

VIII. LINE-1 fusion proteins for target specificity. In this example, the LINE-1 plasmid GFP ORF2 is fused with a domain of a MegaTAL nuclease, a CRISPR-CAS nuclease, a TALEN, R2 retroelement binding zinc finger binding domain, or a DNA binding domain that can bind to repetitive elements such as Rep78 AAV. FIG. 28 exemplifies the deigns. Table 7 provides a list of the different elements that can be fused to increase sequence specific retrotransposition.

TABLE 7

Exemplary proteins with DNA binding domains to be fused to ORF2 for increasing retrotransposition specificity
Elements Transcription Factors
MegaTAL nucleases
TALENs
Zinc finger binding domains
from other retroelements
Safe harbor binding proteins
Cfpl Each plasmid is transfected into HEK293 cells and GFP expression is monitored.

The modifications described in this section under (I)-(VIII) are designed to test for increase in retrotransposition efficiency, using GFP as readout. Following this, a number of useful modifications from (I) —(VIII) are incorporated into a single retrotransposition construct, tested with GFP as insert for the outcome, and the GFP sequence is replaced by the desired insert sequence.

Example 15. Delivering a Large Payload for Prolonged Expression Using Retrotransposon Technology Provided here are exemplary demonstrations of retrotransposon constructs are versatile for incorporating nucleic acid payloads into the genome of a cell and expressing an exemplary transgene. Retrotransposon constructs were designed as elaborated elsewhere in the disclosure.

Figure 29:
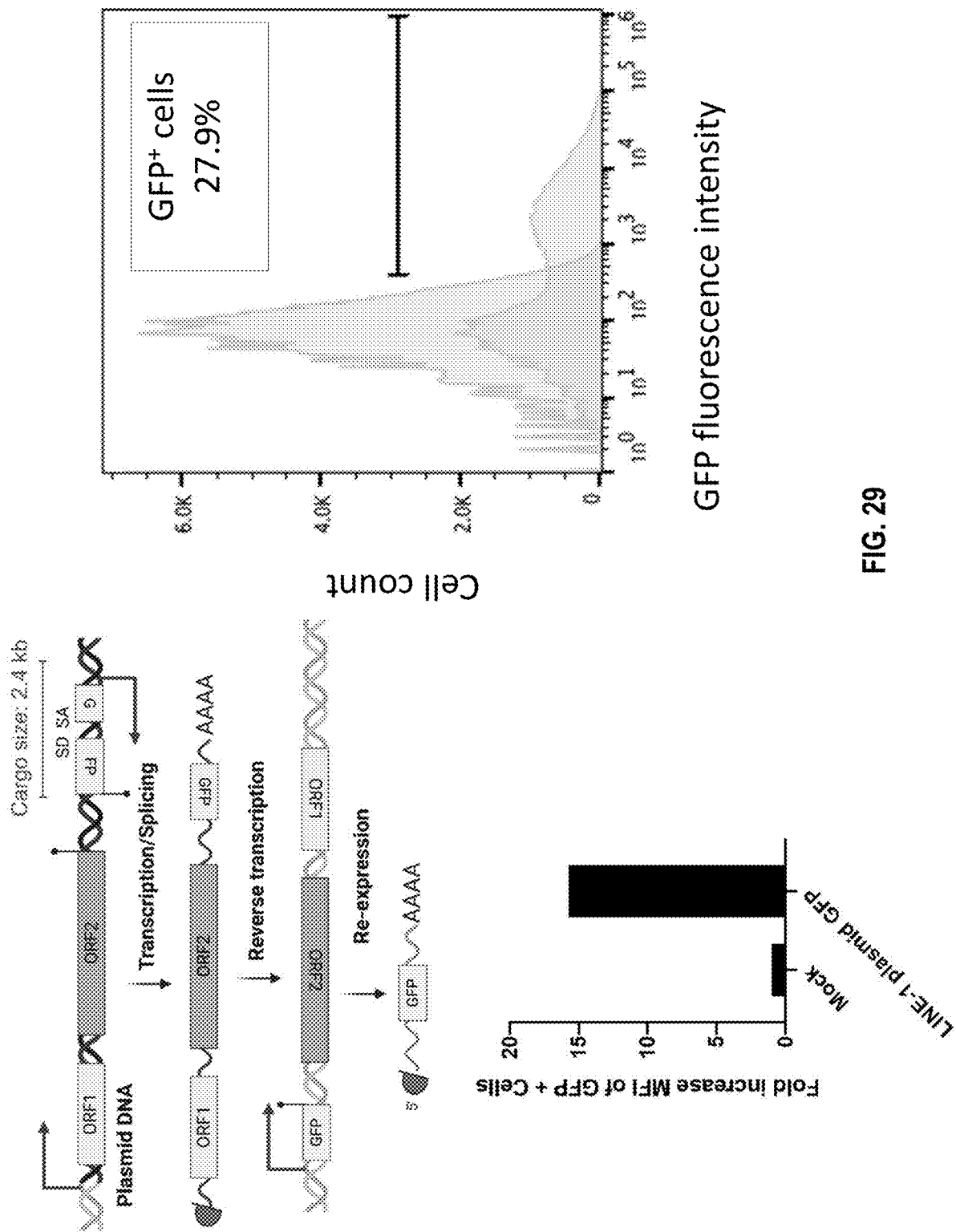
FIG. 29 illustrates exemplary retrotransposon constructs (left) with a 2.4 kb cargo with a general mechanism of action of the retrotransposon, and a representative data (right) for expression of a fluorescent GFP marker encoded by the cargo from a nucleic acid sequence integrated into the genome in HEK293 cells. Placement of an antisense GFP gene split with an intron in the sense direction and a promoter sequence in the 3'UTR of the LINE-1 leads to reconstitution and retrotransposition of the GFP cargo. GFP expression in 293T cells transfected with the construct shown on the left, as measured by flow cytometry (right) and quantitated bar graphs (bottom left). Data collected 35 days after doxycycline induction of the ORF.

Briefly, in one set of validation experiments, GFP encoding payloads were constructed as follows: an antisense promoter sequence under doxycycline inducible control followed by antisense GFP gene split with an intron in the sense direction was placed downstream of the LINE-1 ORFs (FIG. 29). Splicing donor (SD) and splicing acceptor (SA) sequences are recognized and spliced out only when the mRNA is produced from the promoter in the top strand, therefore only the GFP gene integrated into genome from spliced mRNA generates fluorescent signal. As shown in the representative flow cytometry data in FIG. 2, the GFP expression was measured 35 days post doxycycline induction of the ORF expression using flow cytometry (green histogram) compared to a negative control plasmid (grey histogram). In this case, the cargo size was 2.4 kb.

Figure 30:
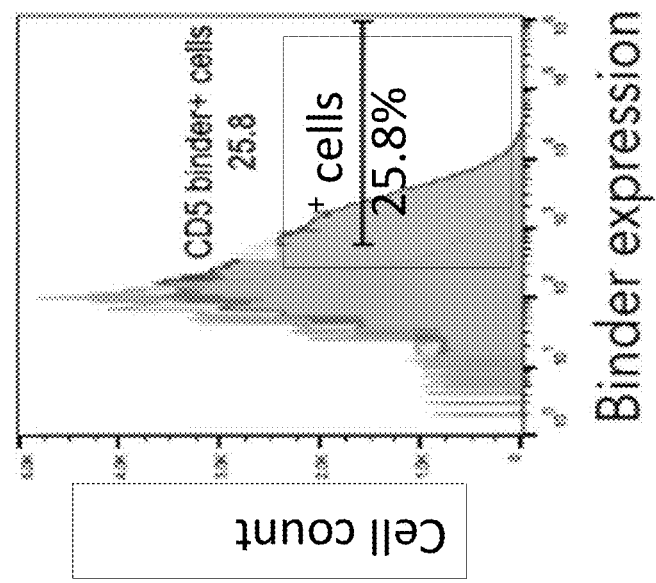
FIG. 30 illustrates exemplary retrotransposon constructs (left) with a 3.0 kb cargo comprising a membrane protein (CD5 binder chimeric antigen receptor, CD5-CAR), and a representative flow cytometry data for expression of the CD5 binder (right) from the nucleic acid sequence integrated into the genome in HEK293 cells. % of CD5 binder positive (+) cells is indicated in the inset.
Figure 30:
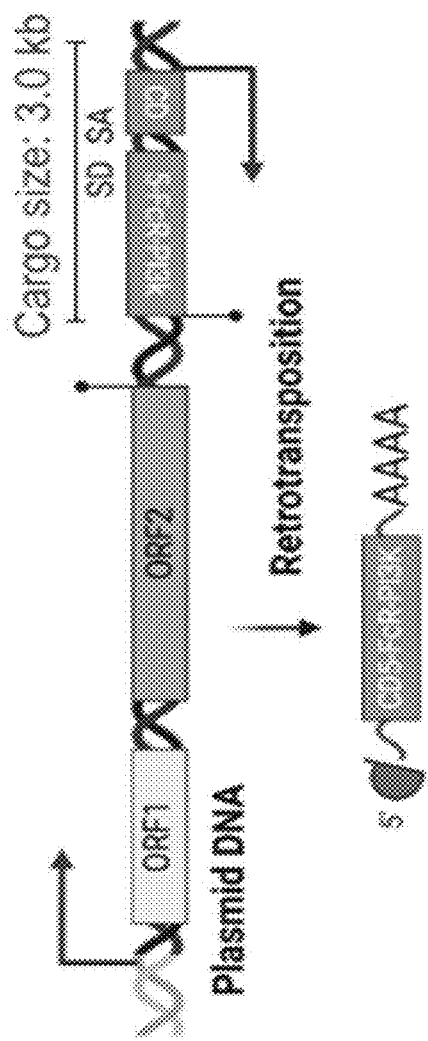

The cargo GFP gene in the previous construct was replaced with intron interrupted CD5-FcR-PI3K CAR-M sequence (Morrissey et al., 2018). The CD5 binder expression was measured by flow cytometry using a Alexa647-conjugated CD5 protein such that retrotransposed cells are CD5-AF647 positive (red histogram) compared with a plasmid transfected negative control cell population (grey histogram) (FIG. 30). Successful expression of the 3.0 kb construct was demonstrated as shown in the figure.

Figure 31:
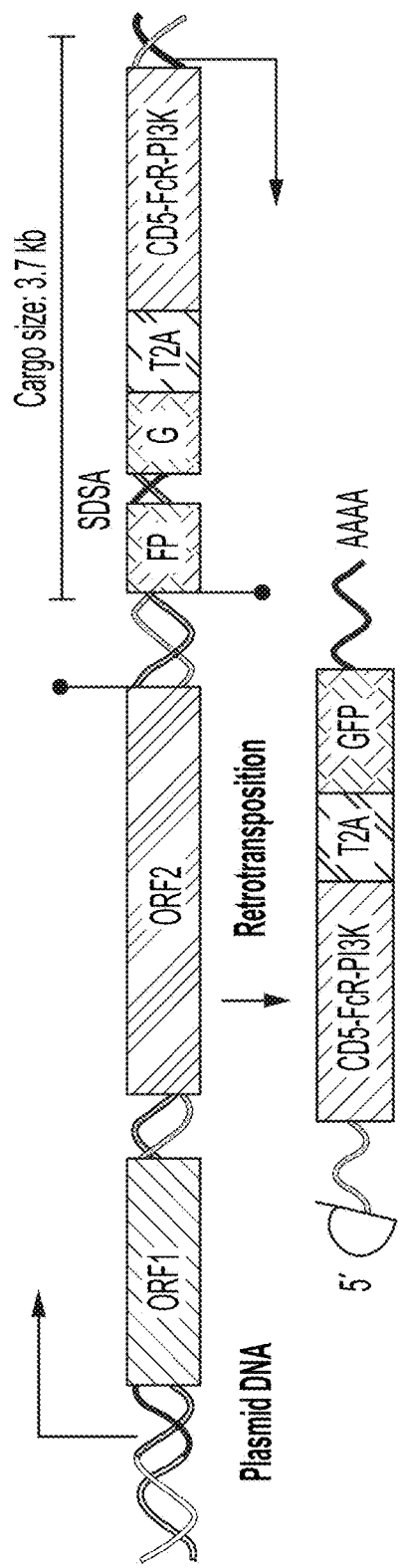
FIG. 31 illustrates an exemplary retrotransposon construct (top) with a 3.7 kb cargo comprising a membrane protein (CD5 binder chimeric antigen receptor, CD5-CAR and a GFP separated by an auto-cleavable T2A element), and a representative flow cytometry data (bottom) demonstrating the expression of the CD5 binder and GFP.
Figure 31:
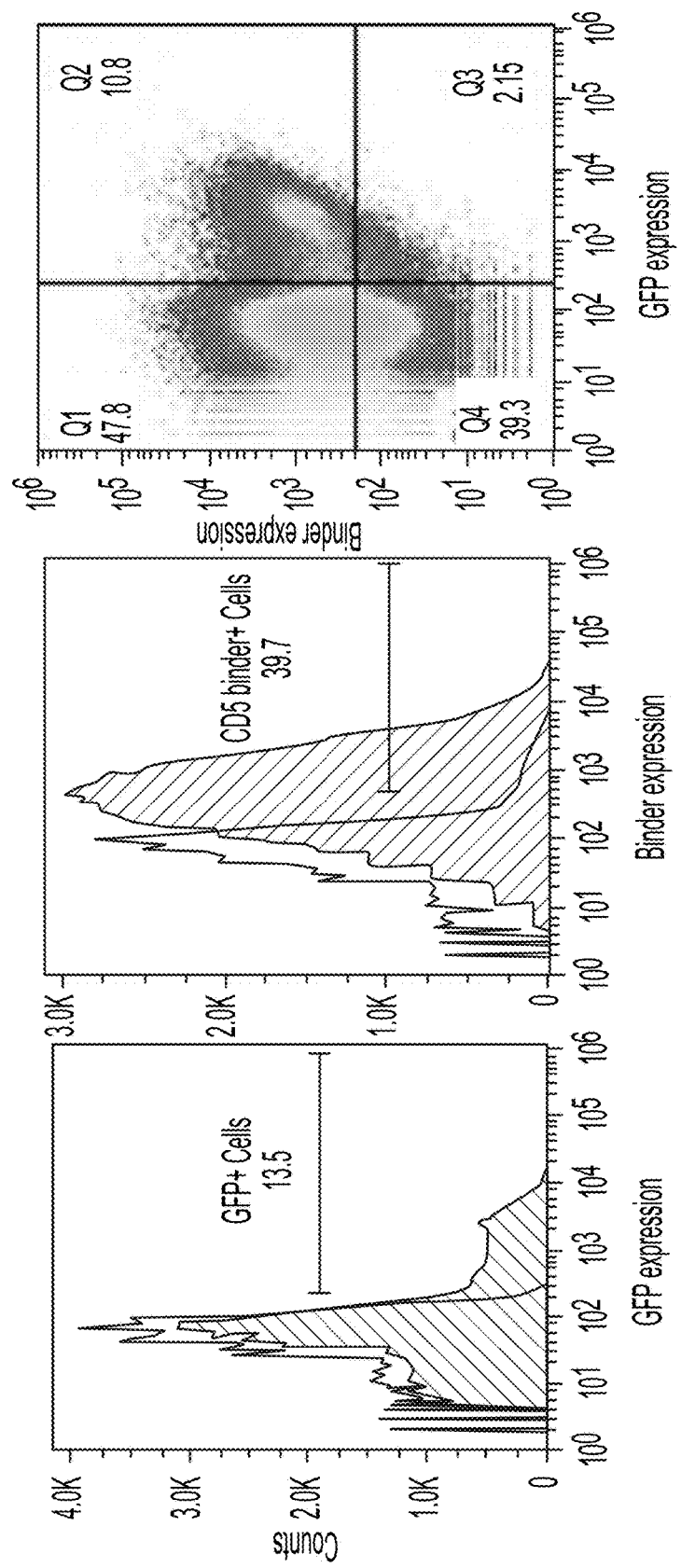

The cargo gene length was extended by adding the intron-interrupted GFP gene after the T2A sequence downstream of the CD5-FcR-PI3K CAR-M sequence (FIG. 31). The CD5 binder expression was measured by flow cytometry using a Alexa647-conjugated CD5 protein. The CD5 binder positive cells shown by red histogram, in comparison with a negative control (grey histogram). The GFP expression is measured using flow cytometry (green histogram) compared to a negative control plasmid transfected cells (grey histogram). The flow cytometry signal in the Q2 showed that 10.8% cells express both CAR-M and GFP proteins.

Figure 32:
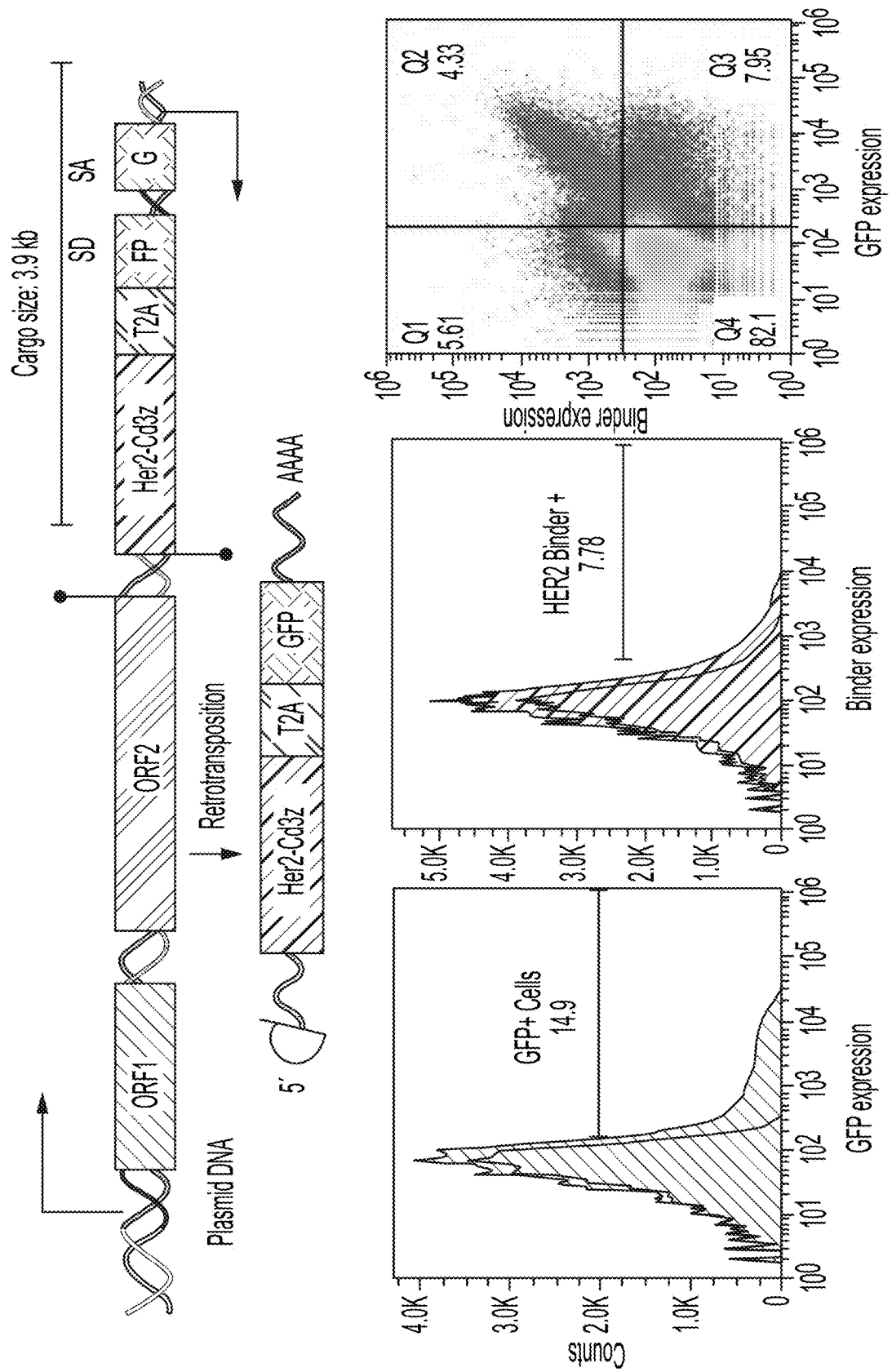
FIG. 32 illustrates an exemplary retrotransposon construct (top) with a 3.9 kb cargo comprising a membrane protein (HER2 binder chimeric antigen receptor, and a GFP separated by an auto-cleavable T2A element), and a representative flow cytometry data (bottom) demonstrating the expression of the HER2 binder and GFP.
Figure 33A:
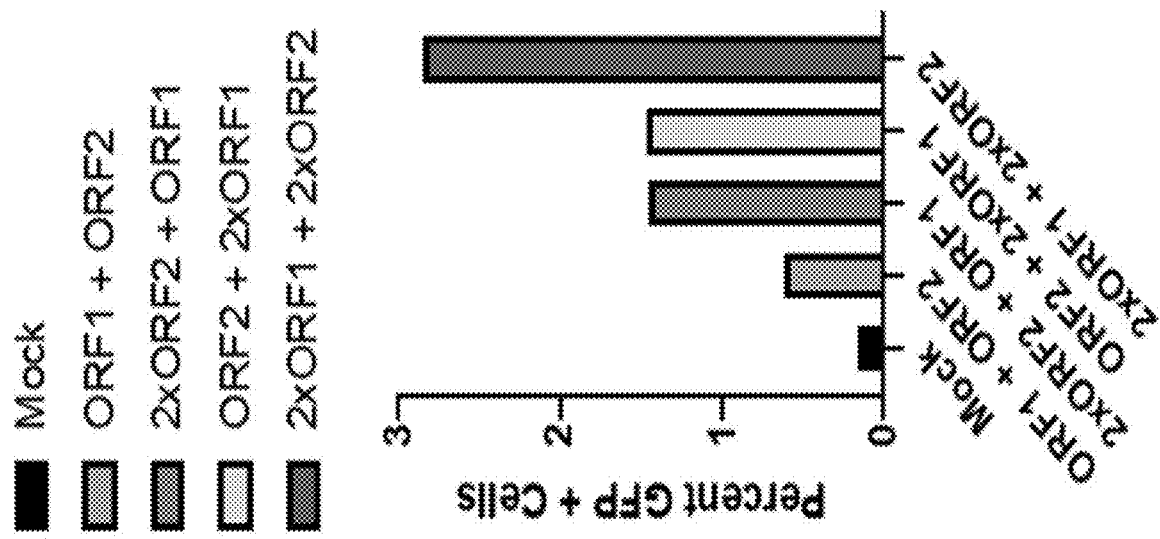
FIG. 33A shows exemplary data for delivery of retrotransposon elements delivered as mRNA.
Figure 33A:
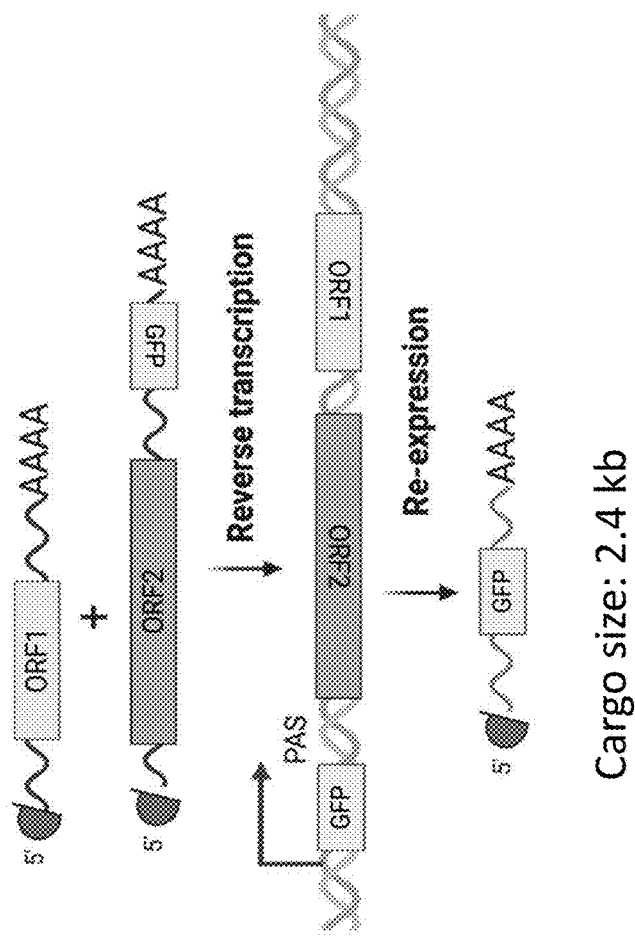
Figure 33B:
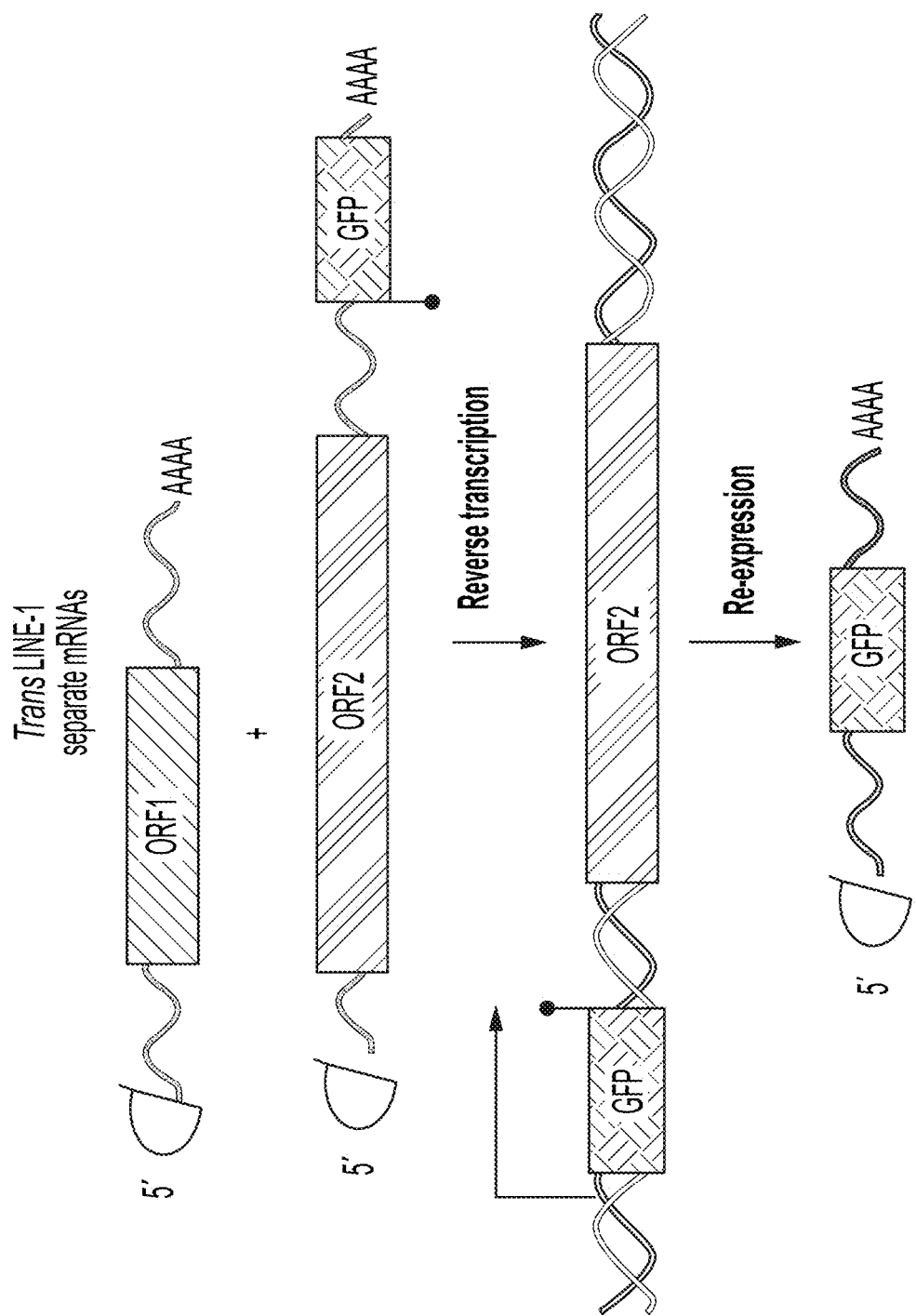
FIG. 33B shows schematic diagram showing a trans and a cis mRNA design for delivery of LINE 1 mRNA with GFP cargo (top panel). Representative results of electroporation of 293T cells with trans mRNAs with separate ORF1 and ORF2 mRNAs. 293T cells were electroporated with 100 ug/mL of mRNA either with ORF2 alone, ORF1+ORF2 mRNAs, each at 100 ug/mL, or a GFP-encoding mRNA with the same 5' and 3'UTRs as the ORF1 mRNA (left panel of data plots). Retrotransposition events result in GFP-positive cells. Cells were assayed for GFP fluorescence by flow cytometry 4 days and 10 days post-electroporation. Mock electroporated cells serve as the negative control population for gating. Bar graph on the right shows results from a representative experiment indicating titration of trans mRNAs and cis ORF1 and ORF2 containing mRNA concentration during electroporation. Trans mRNAs solid bars and cis mRNA stripes. 20X is 2000 ug/mL in the electroporation reaction.
Figure 33B:
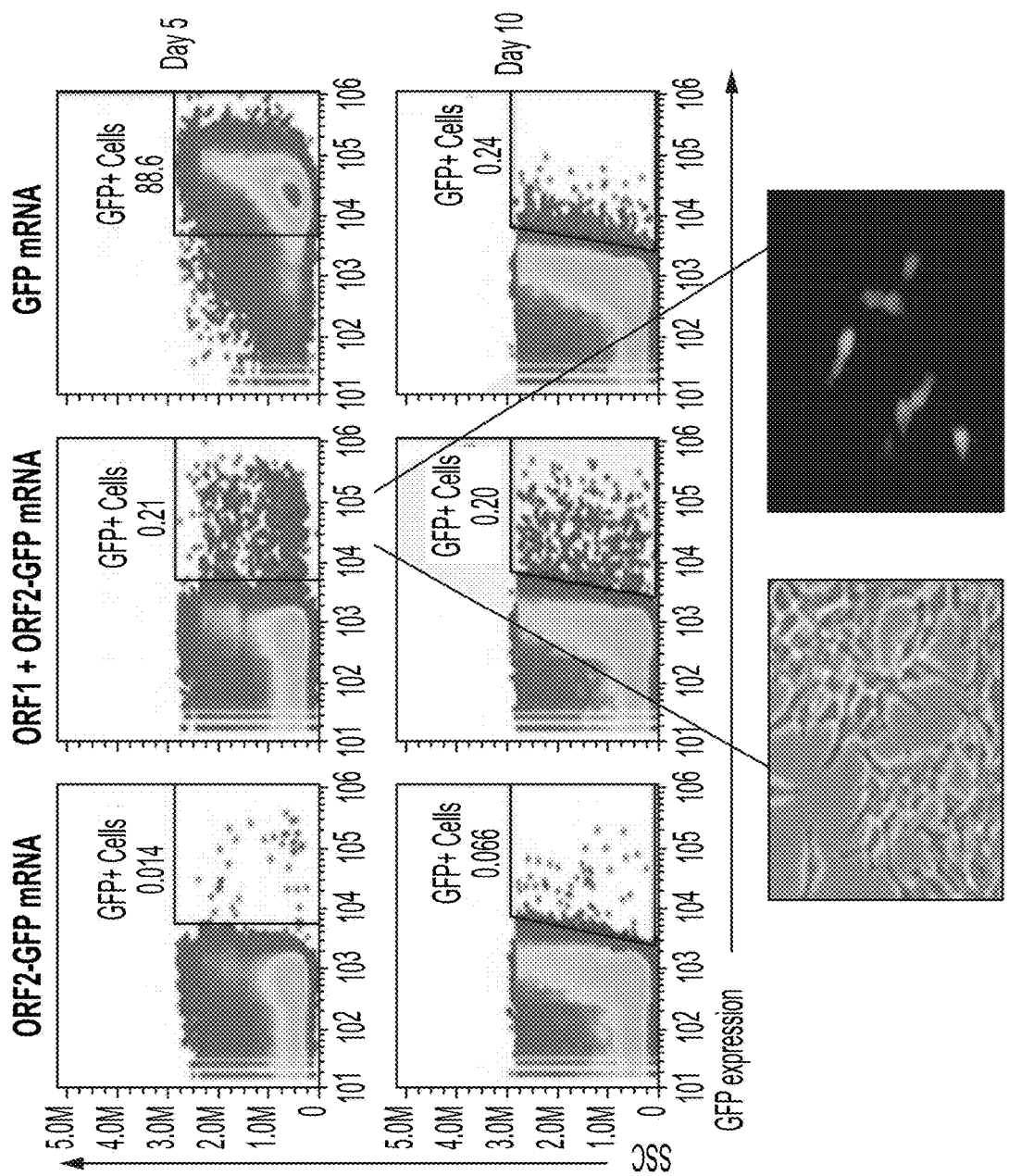
Figure 33B:
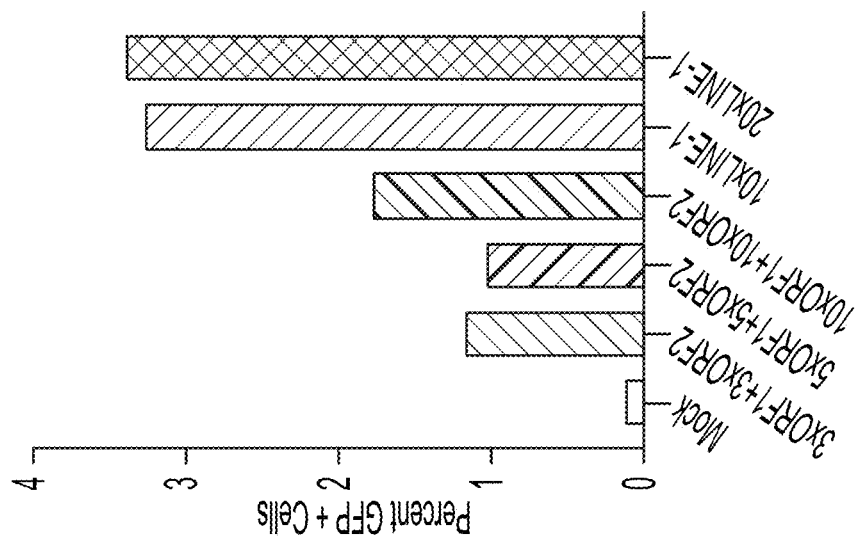
Figure 33B:
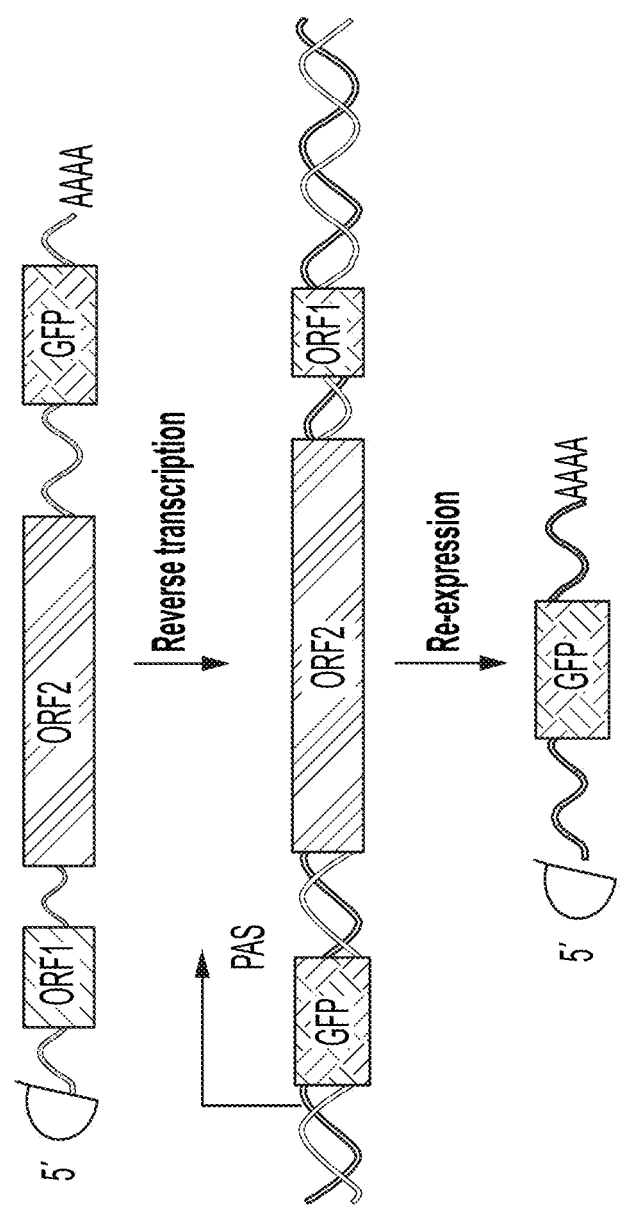
Figure 33C:
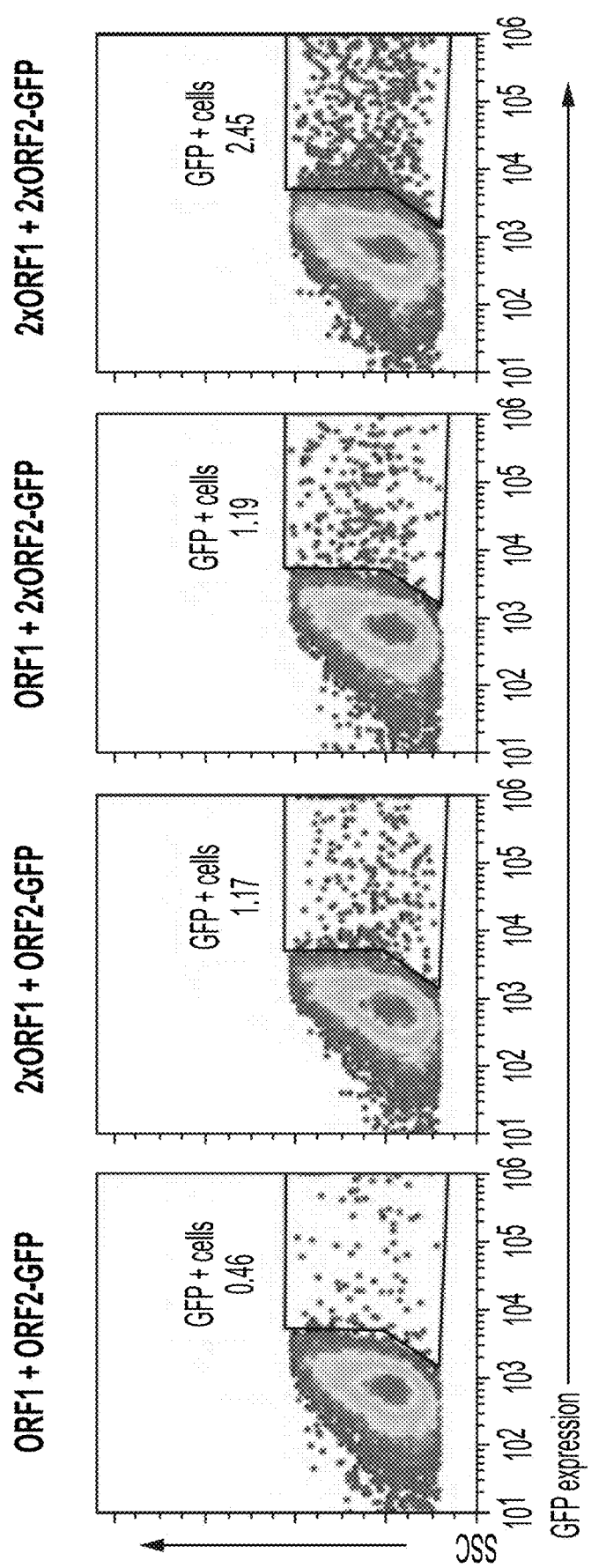
FIG. 33C shows titration of the ORF1 and ORF2-GFPai trans mRNAs. Increasing the concentration separately and together during the electroporation to 200 ug/mL increases retrotransposition of the GFP gene cargo.
Figure 33D:
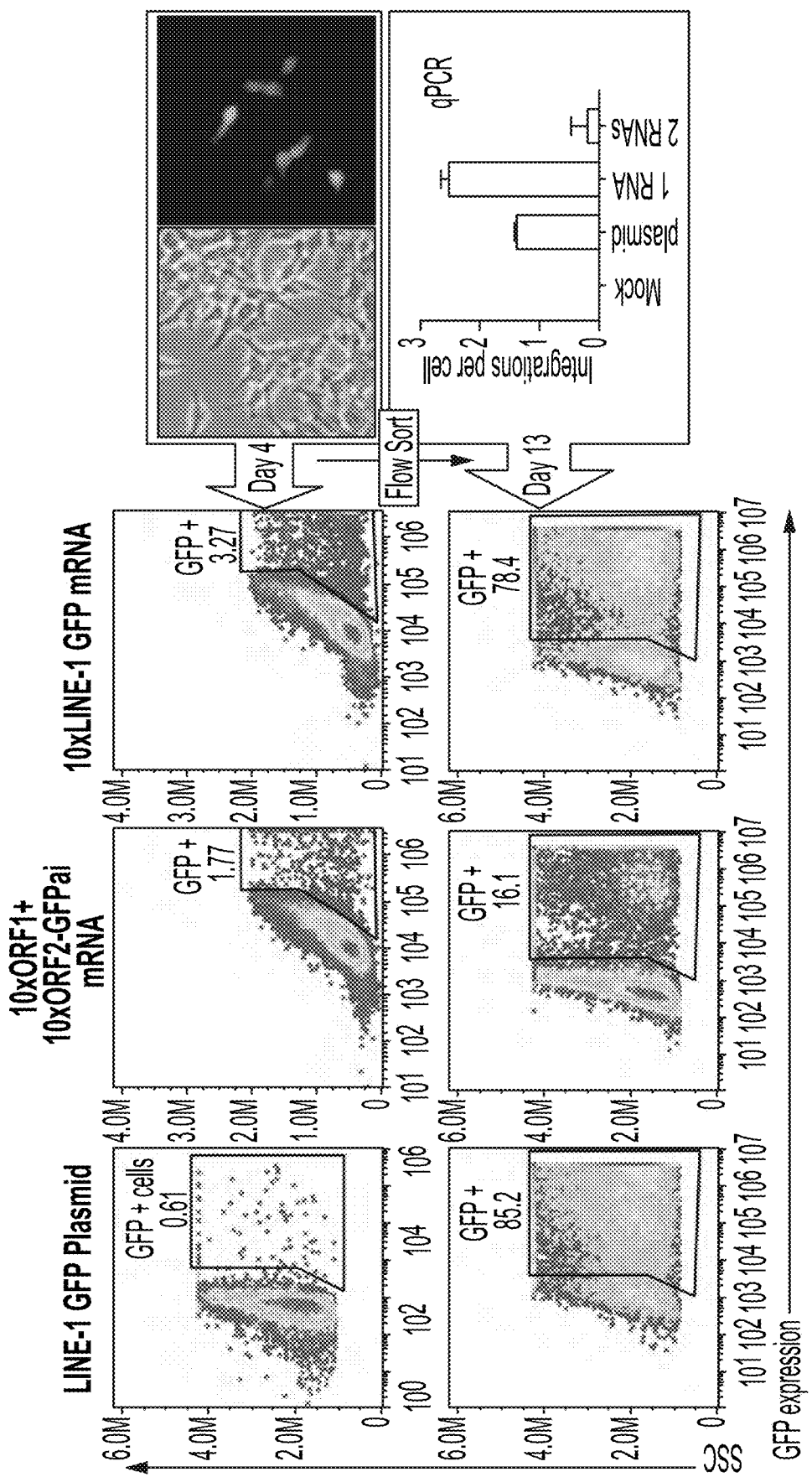
FIG. 33D illustrates an exemplary data for the different constructs indicated above each flow cytometry data plot in the figure, the top panel on day 4, and the bottom panel on day 13. Right hand figures illustrate light and fluorescent microscopic images of a the GFP expressing cells in culture. Copies of integrated cargo per construct is demonstrated in the bottom right at day 13. qPCR assay for genomic DNA integration from different LINE-1 plasmid transfected, LINE-1 mRNA (retro-mRNA), and ORF1 and ORF2-GFP mRNA electroporated cells is shown. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA, and normalizing for the two copies of RPS30 per 293T cell. Error bard denote standard deviation of three technical replicate measurements.
Figure 34:
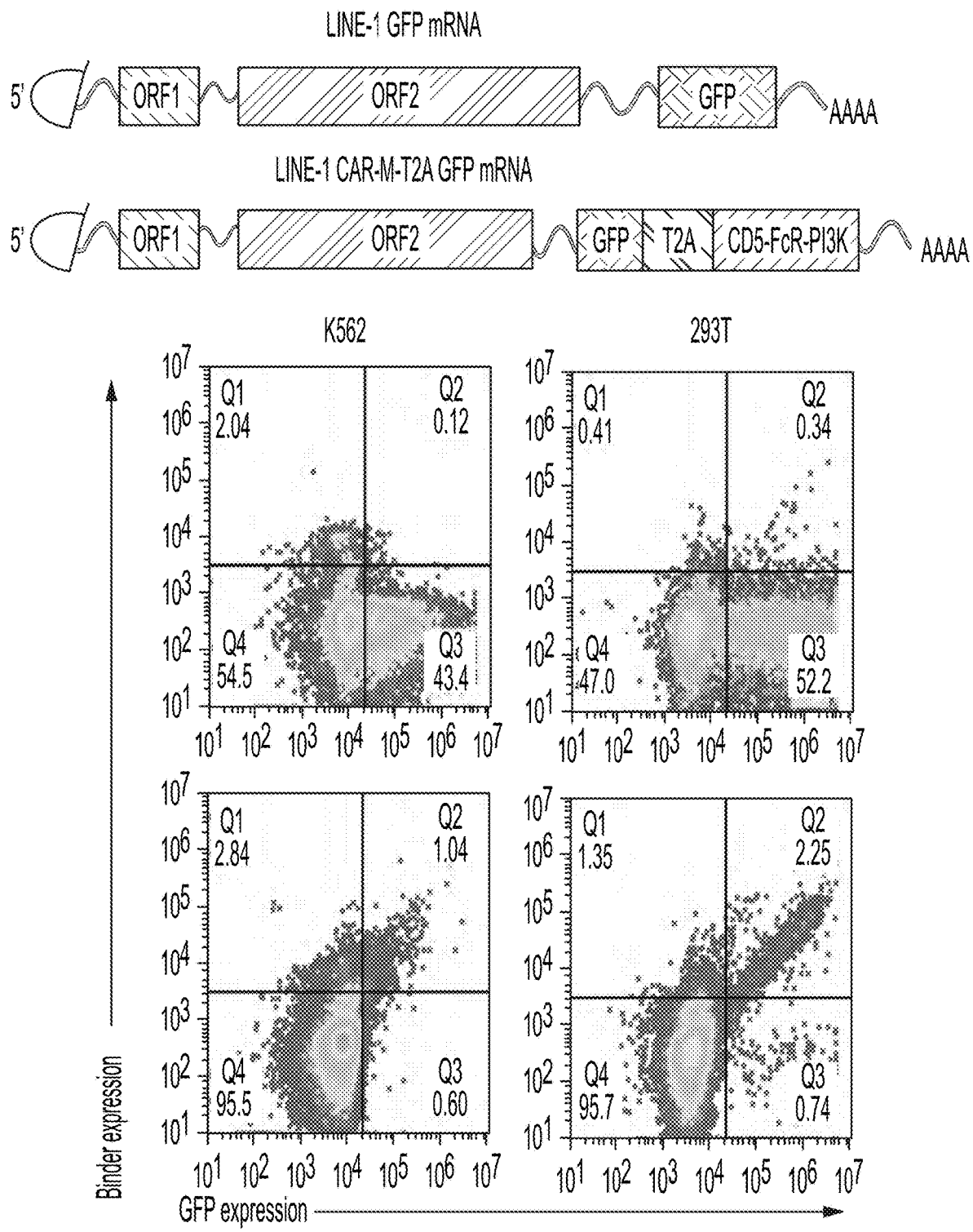
FIG. 34 illustrates exemplary retrotransposon construct (left) and expression data (right) in the indicated cell lines.
Figure 35:
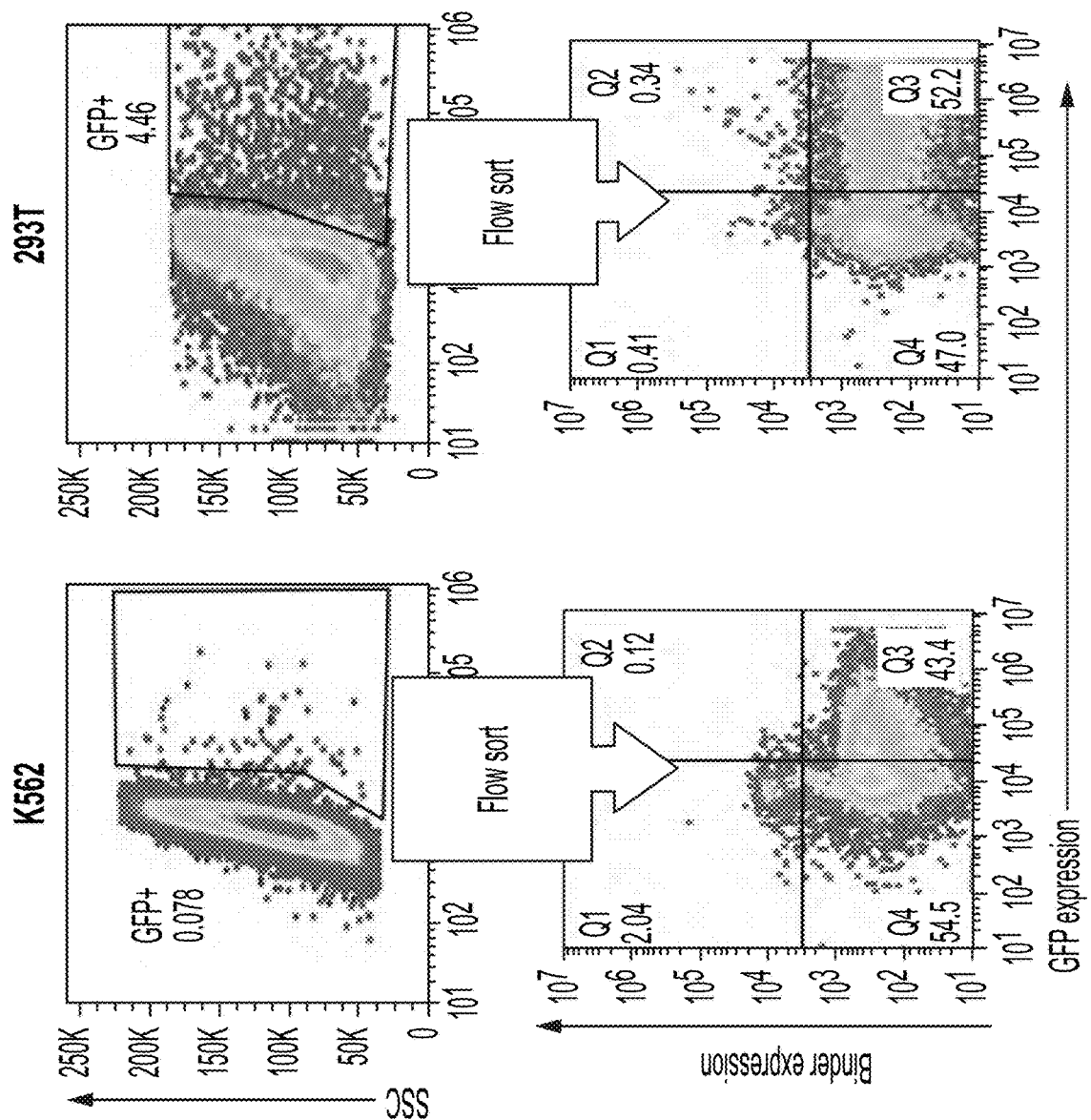
FIG. 35 illustrates flow cytometry data showing expression of LINE 1 GFP constructs in K562, 293T and THP1 cells (upper panel); and number of integrations of LINE-2-GFP mRNA per cell in K562 and THP-1 cell lines (lower panel).
Figure 35:
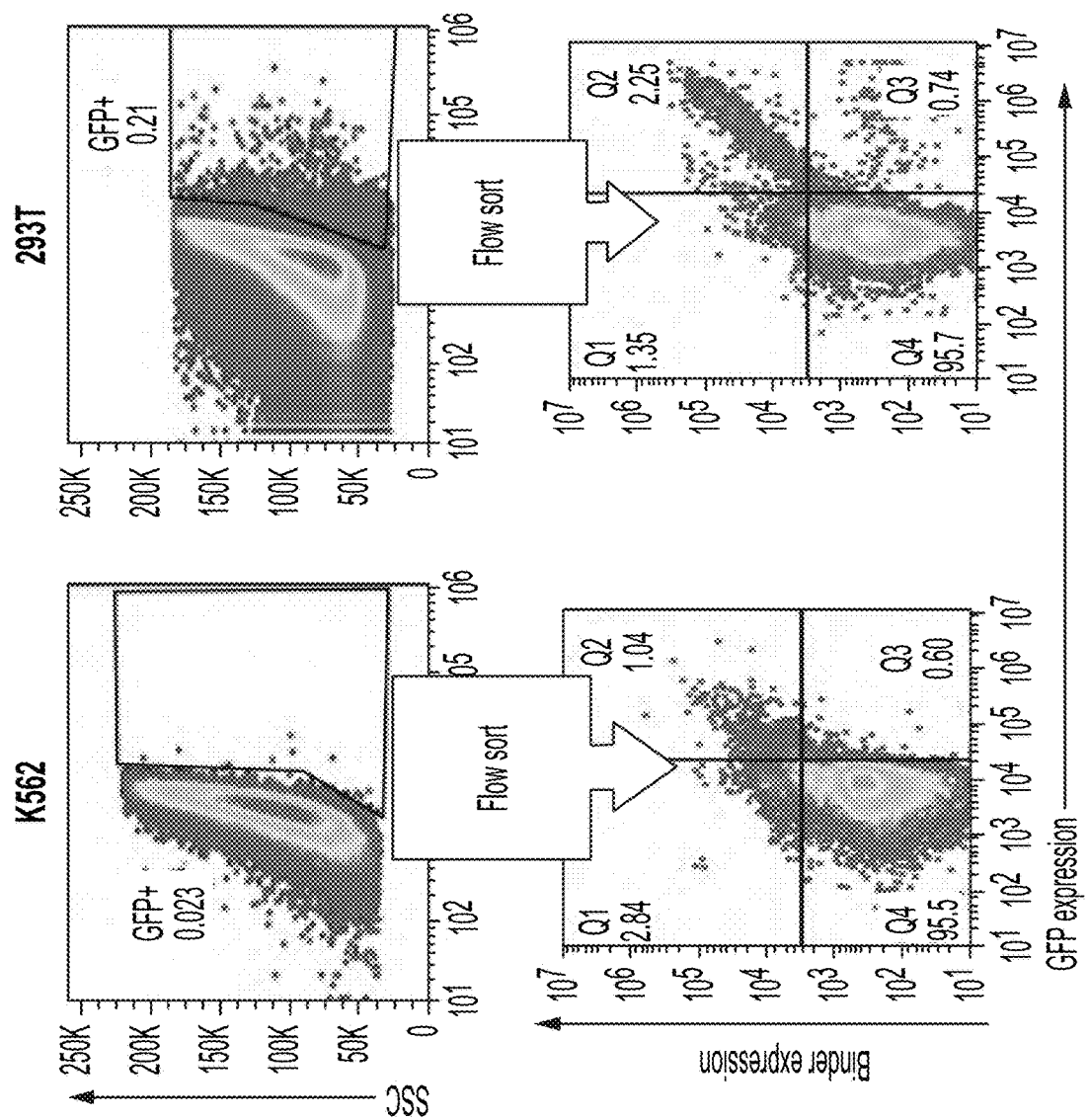
Figure 35:
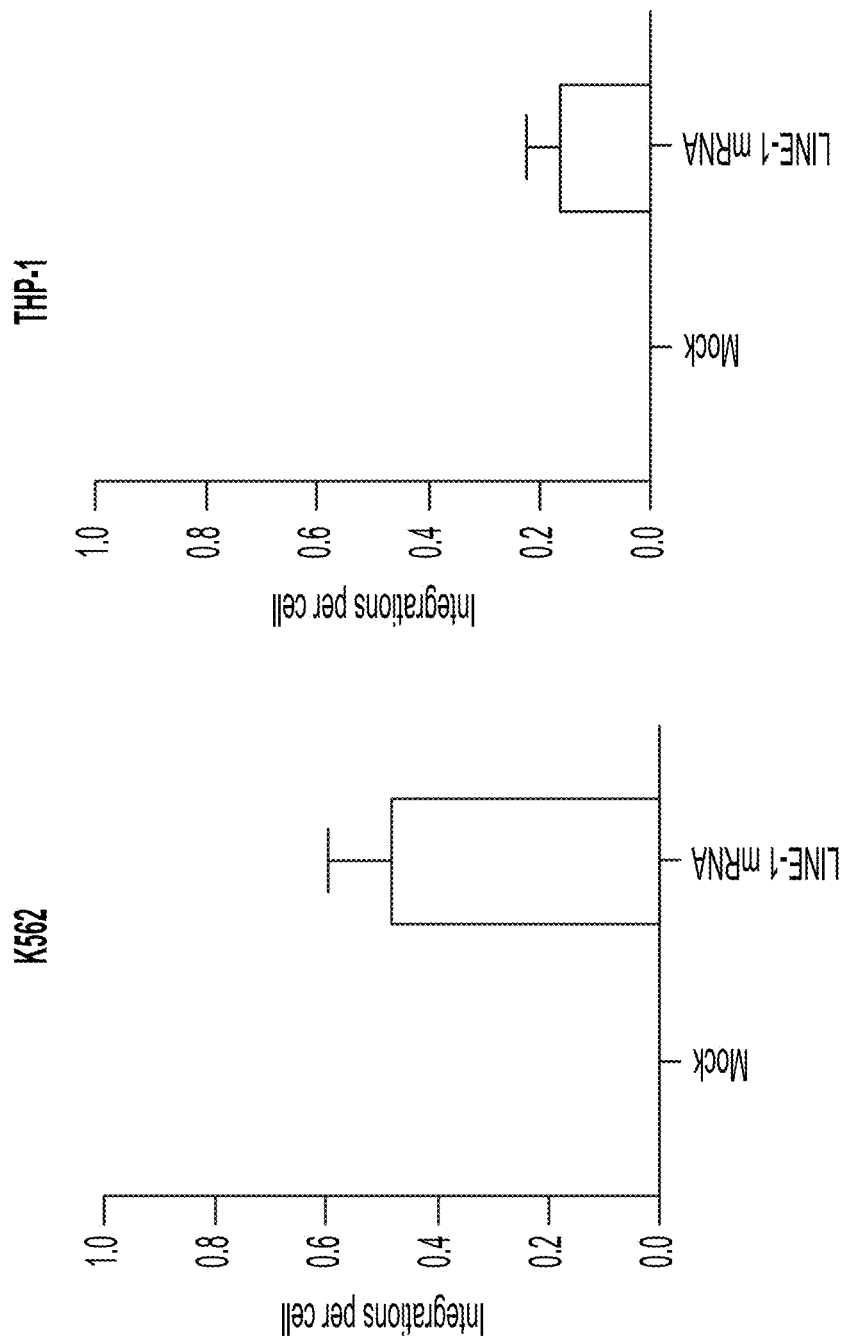

As shown in FIG. 32, the payload size limit has not been reached with retrotransposon delivery and integration (Retro-T delivery) with a 3.9 kb payload. The delivery mechanism described here was successful for expression of the first generation CART construct and GFP (separated by T2A site). In this example, different constructs were tested for retrotransposition efficiency of the insert sequence. FIG. 33A shows gene delivery as mRNA results in successful integration. This data is the first to show that Retro T can be delivered as mRNA. A trans strategy of using separate mRNAs encoding for ORF1 and ORF2 with antisense promoter and GFP cargo (ORF2-GFPai) in the 3' UTR for gene delivery was explored, as exemplified graphically in FIG. 33B (top panel). FIGS. 33B-33D demonstrate experimental results from multiple representative assays. Separate mRNAs that expression the LINE-1 proteins could reconstitute the RNA-protein complex required for retrotransposition. The cis strategy uses a single bicistronic LINE-1 mRNA with the antisense promoter and GFP gene cargo in the 3'UTR. Constructs comprising variable amounts and proportions of ORF2 and ORF1 were compared as shown in FIG. 33B and FIG. 33C with GFP encoding sequence as payload. FIG. 33D shows that introducing a single mRNA yields higher number of integrations per cell. Sorting of 293T GFP cells to enrich for retrotransposed cells for biochemical and integration assays. Cells are the same as in FIG. 33B and show GFP expression 4 days post-sort in bottom panels. The graph shows qPCR assay for genomic DNA integration from different LINE-1 plasmid transfected, LINE-1 mRNA (retro-mRNA), and ORF1 and ORF2-GFP mRNA electroporated cells. Two qPCR primer-probe sets were used, one for the housekeeping gene RPS30 and the other for the GFP gene. Plasmid-transfected cells use a plasmid that does not contain and SV40 maintenance sequence. Integration per cell is calculated from determining copy numbers per samples through interpolation of a standard curve of plasmid and genomic DNA and normalizing for the two copies of RPS30 per 293T cell. Error bar denote standard deviation of three technical replicate measurements.

Example 16. Delivery to Diverse Cell Types

Figure 36:
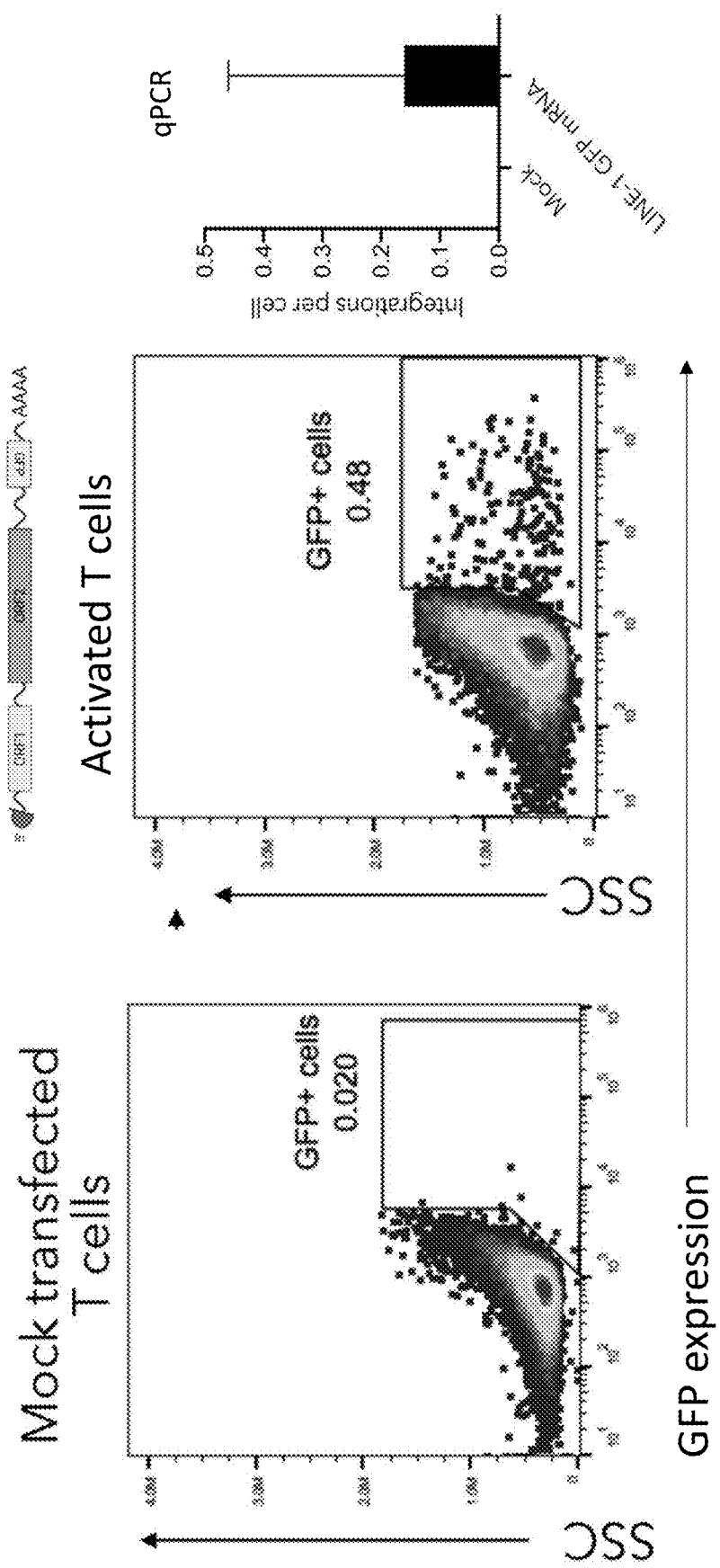
FIG. 36 illustrates flow cytometry data showing expression of LINE 1 GFP constructs in primary T cells (left). Integrations per cell are indicated in the graph on the right. Data was collected on day 6 after electroporation.
Figure 37A:
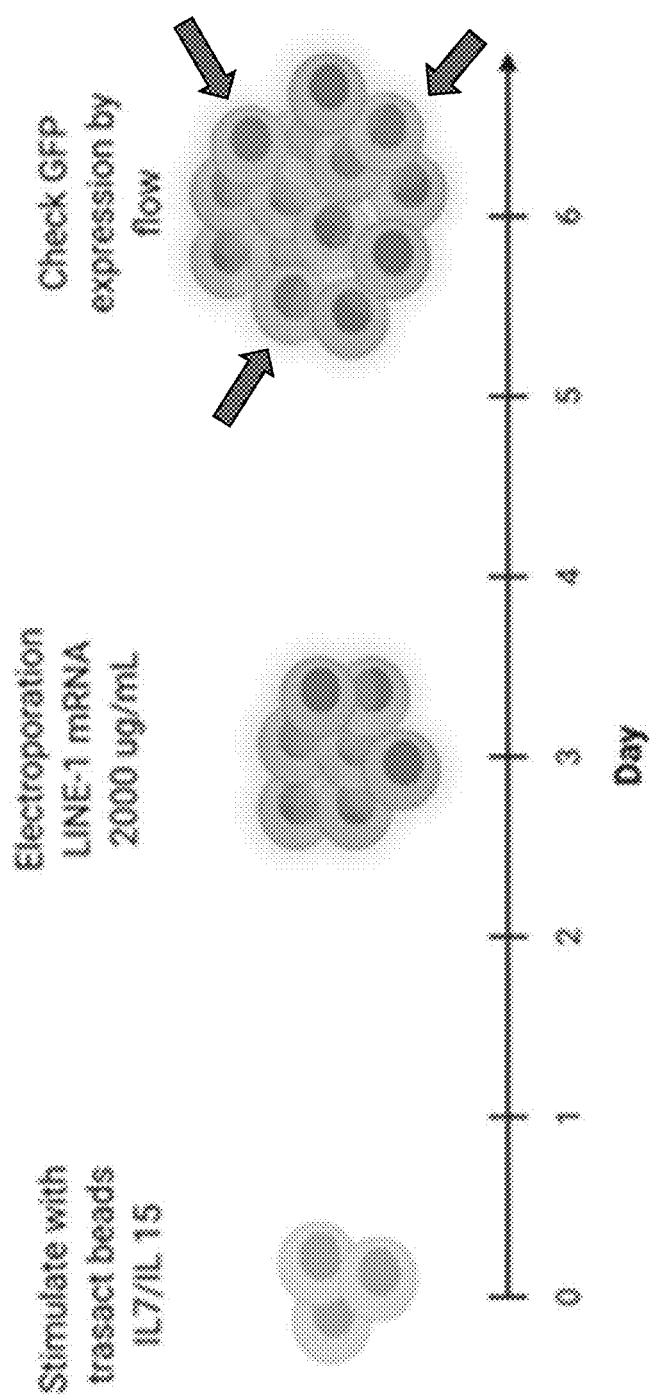
FIG. 37A shows a schematic of activation, culture times, electroporation, and GFP expression assay of isolated primary T cells.
Figure 37B:
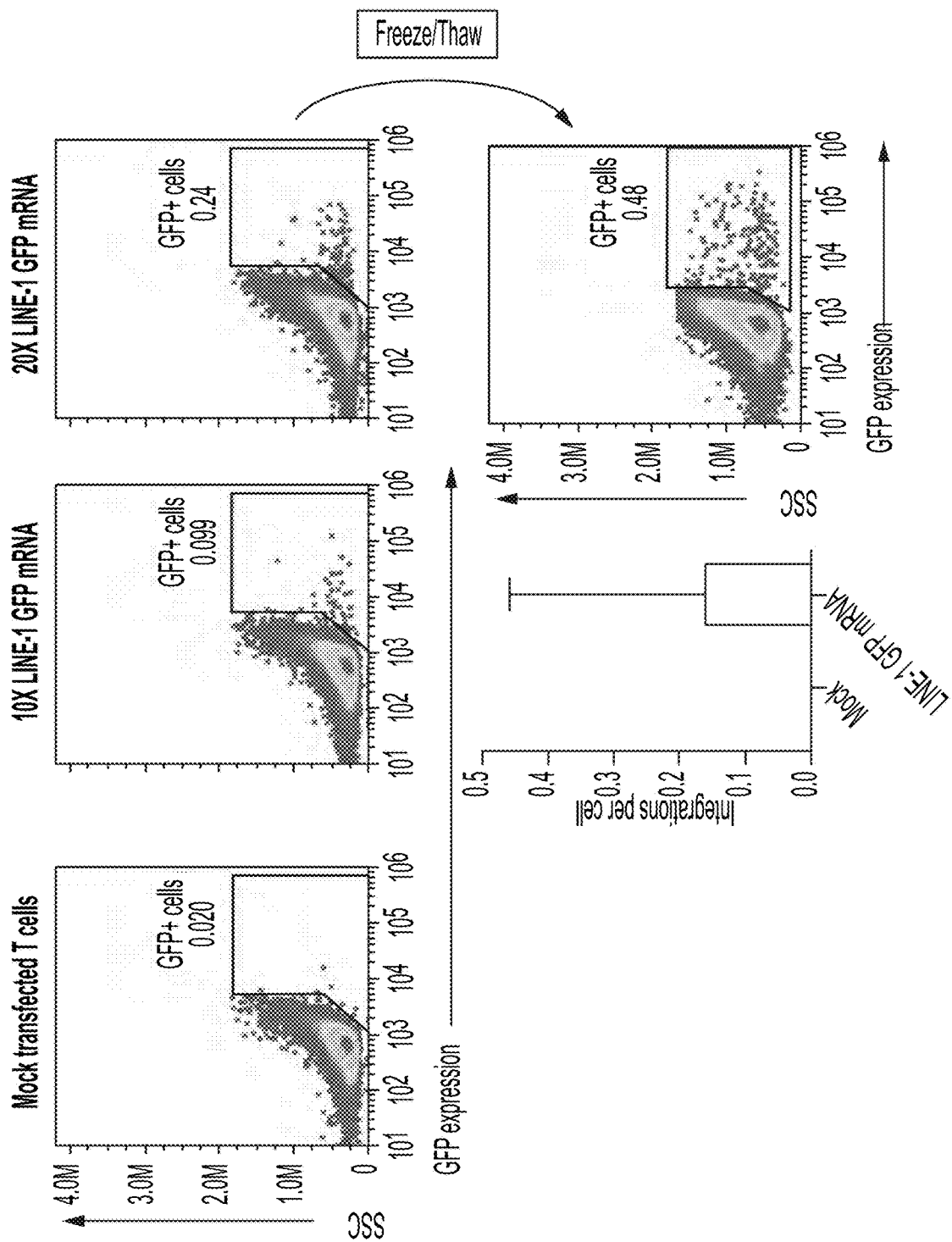
FIG. 37B illustrates flow cytometry data showing expression of LINE 1 GFP mRNA constructs in primary T cells at the indicated concentrations and before and after freeze-thaw as indicated in the figure. Integrations per cell is shown in the bar diagram. GFP expression using a retro-mRNA electroporation with a GFP cargo. GFP expression was assayed 4 days post electroporation and 15 days of culturing post electroporation. Primary T cells were cryo-preserved and thawed during this time. qPCR integration assay for GFP integration. Genomic DNA from the 20X sample was isolated and assayed for copies of GFP.
Figure 38:
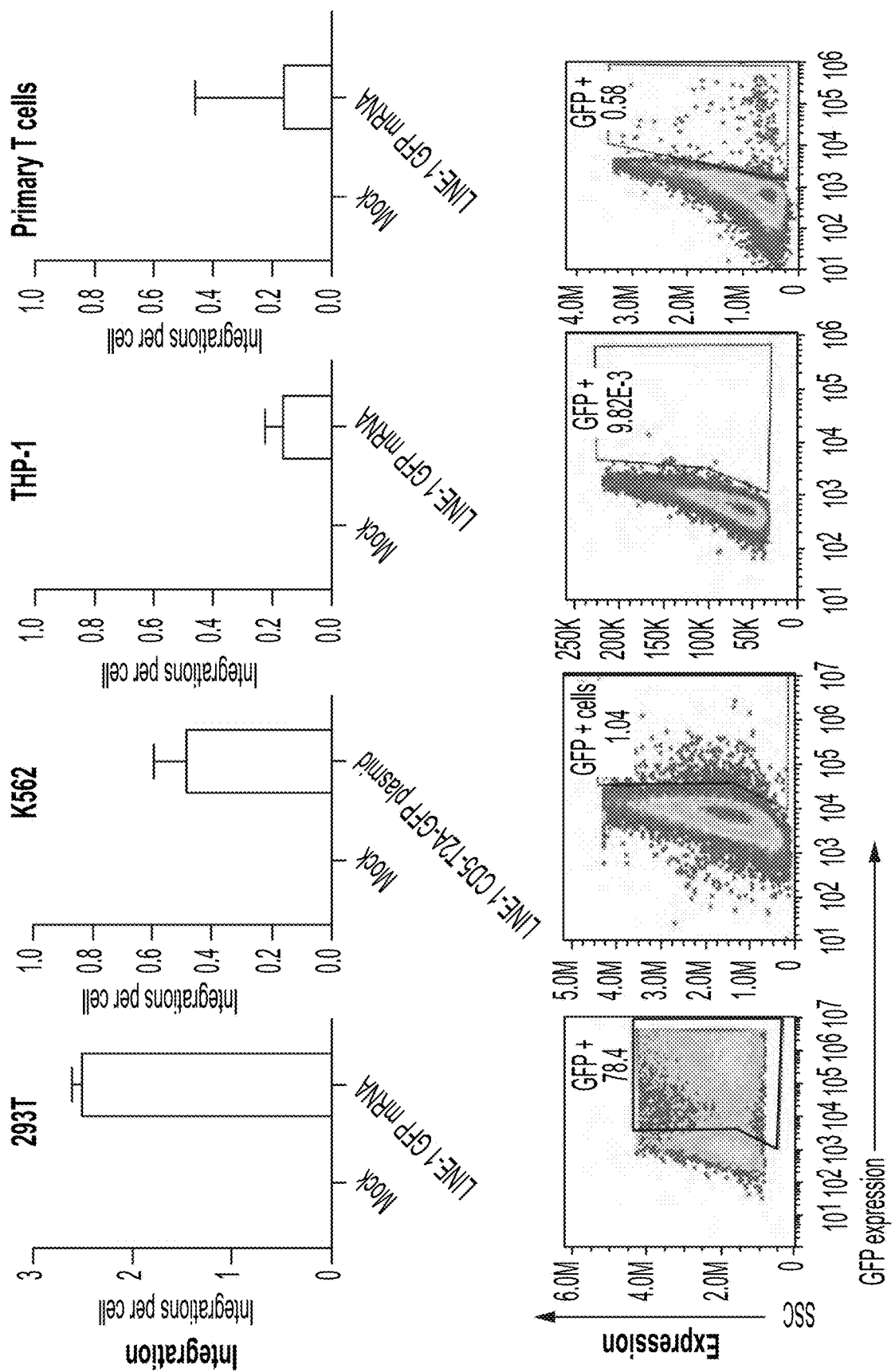
FIG. 38 demonstrates a summary of results of retrotransposon integration and expression across cell types.
Figure 39:
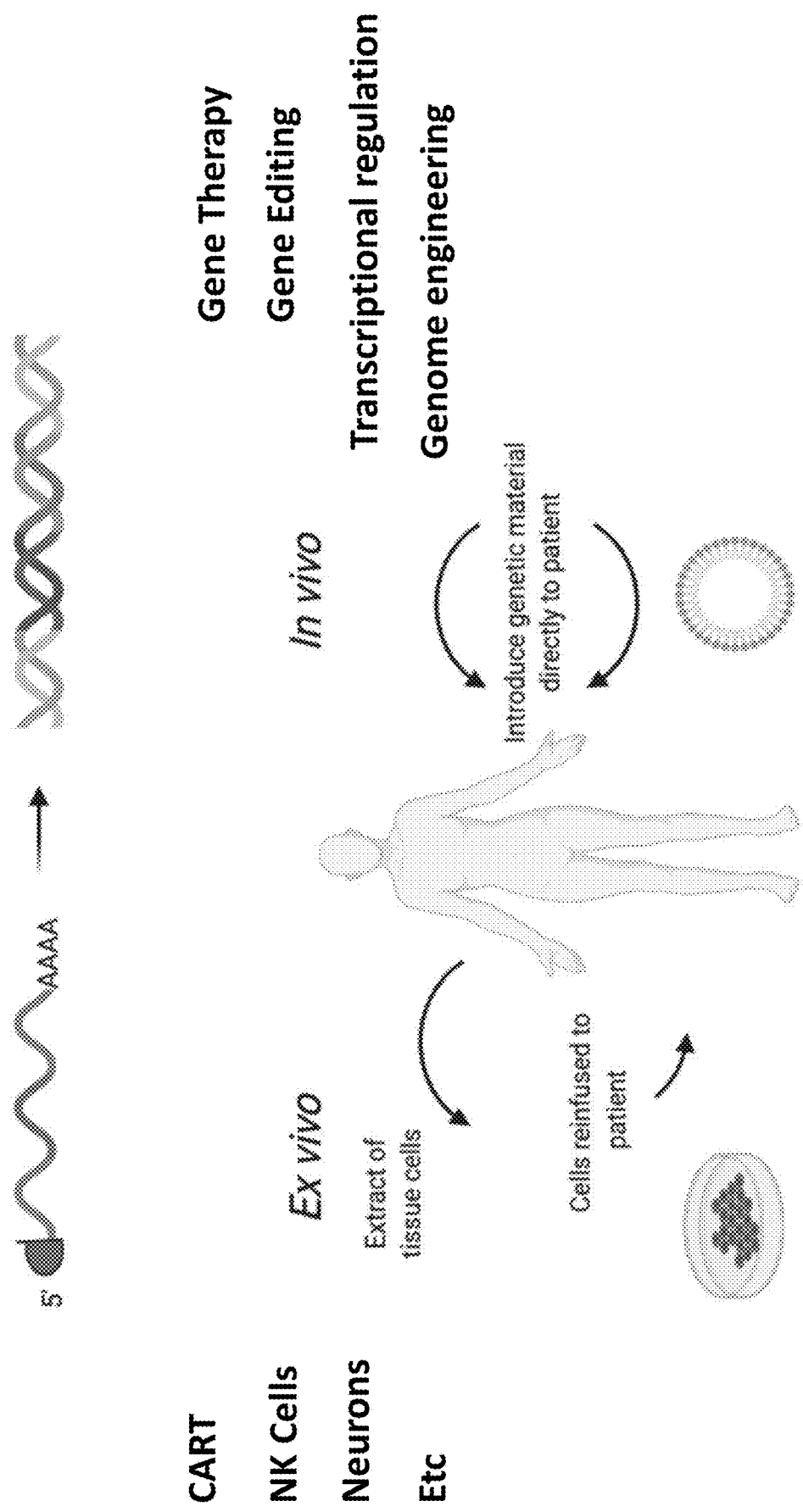
FIG. 39 shows various applications of the technology described herein, including but not limited to use of CART cells, NK cells, neurons and other cells for cell therapy, and use of in vivo applications in including but not limited to gene therapy, gene editing, transcription regulation, and genome engineering.

As shown in FIGS. 34-38, the mRNA constructs comprising a gene of interest, e.g. encoding a CAR protein, or for example, a GFP protein can be efficiently expressed in diverse cell types, such as epithelial cells (e.g., HEK 293 cells), monocytic cells lines (e.g., THP-1 cells), lymphoblastic cell lines (e.g., K562 cells), and primary lymphocytes (T cells). Activated primary T cells were also successfully transfected with mRNA with genomic integration and expression of GFP (FIG. 36). Primary T cells were isolated and expanded using IL7/IL15; and a $1^{st}$ Gen CAR construct was delivered on day 2 post activation. Cells sorted and frozen. GFP expression was detectable after a freeze-thaw cycle (FIG. 37A-B). This indicates the versatile nature of mRNA mediated delivery and L1-transposon mediated integration. FIG. 38 shows a representative assay of GFP mRNA integration and expression in 293T cells, K562 cells, THP-1 cells and Primary T cells.

EXEMPLARY SEQUENCES

Following are exemplary sequences of the constructs used in the examples. These sequences are for reference exemplary purposes and sequence variations and optimizations that are conceivable by one of skill in the art without undue experimentation are contemplated and encompassed by the disclosure. Where mRNA sequences are referred in the sequence title, the construct recites nucleotides of a DNA template and one of skill in the art can easily derive the corresponding mRNA sequence.

TABLE 8

Plasmid and mRNA construct sequences

```
ORF1-FLAG- mRNA (Codon Optimized human ORF1 coding sequence-FLAG)
(SEQ ID NO: 35):
    1  TAATACGACT CACTATAGGG AGAAAGACGC CACCATGGGC AAGAAGCAAA ATCGCAAGAC
   61  GGGGAATTCC AAGACACAAT CCGCTAGCCC ACCACCTAAA GAGCGTTCTA GCTCCCCTGC
  121  TACTGAGCAG TCCTGGATGG AAAACGACTT CGATGAACTC CGGGAAGAGG GATTTAGGCG
```

TABLE 8-continued

Plasmid and mRNA construct sequences

```
 181 ATCCAACTAT TCAGAACTCC GCGAAGATAT CCAGACAAAG GGGAAGGAAG TCGAGAATTT
 241 CGAGAAGAAC CTCGAGGAGT GCATCACCCG TATCACAAAC ACTGAGAAAT GTCTCAAAGA
 301 ACTCATGGAA CTTAAGACAA AAGCCAGGGA GCTTCGAGAG GAGTGTCGGA GTCTGAGATC
 361 CAGGTGTGAC CAGCTCGAGG AGCGCGTGAG CGCGATGGAA GACGAGATGA ACGAGATGAA
 421 AAGAGAGGGC AAATTCAGGG AGAAGCGCAT TAAGAGGAAC GAACAGAGTC TGCAGGAGAT
 481 TTGGGATTAC GTCAAGAGGC CTAACCTGCG GTTGATCGGC GTCCCCGAGA GCGACGTAGA
 541 AAACGGGACT AAACTGGAGA ATACACTTCA AGACATCATT CAAGAAAATT TTCCAAACCT
 601 GGCTCGGCAA GCTAATGTGC AAATCCAAGA GATCCAACGC ACACCCCAGC GGTATAGCTC
 661 TCGGCGTGCC ACCCCTAGGC ATATTATCGT GCGCTTTACT AAGGTGGAGA TGAAAGAGAA
 721 GATGCTGCGA GCCGCTCGGG AAAAGGGAAG GGTGACTTTG AAGGGCAAAC CTATTCGGCT
 781 GACGGTTGAC CTTAGCGCCG AGACACTCCA GGCACGCCGG GAATGGGGCC CCATCTTTAA
 841 TATCCTGAAG GAGAAGAACT TCCAGCCACG AATCTCTTAC CCTGCAAAGT TGAGTTTTAT
 901 CTCCGAGGGT GAGATTAAGT ATTTCATCGA TAAACAGATG CTGCGAGACT TCGTGACAAC
 961 TCGCCCAGCT CTCAAGGAAC TGCTCAAAGA GGCTCTTAAT ATGGAGCGCA ATAATAGATA
1021 TCAACCCTTG CAGAACCACG CAAAGATGGA TTATAAGGAT GACGATGATA AATGA
     (SEQ ID NO: 35)
```

ORF2-FLAG-GFPai mRNA (Codon Optimized human ORF2 coding sequence)
(SEQ ID NO: 36)

```
   1 TAATACGACT CACTATAGGG AGAAAGACGC CACCATGACA GGTTCAAATA GTCACATTAC
  61 GATTCTCACT CTGAATATAA ATGGGCTGAA TTCTGCAATT AAACGGCACA GGCTTGCTTC
 121 CTGGATAAAG TCTCAAGACC CCTCAGTGTG CTGTATTCAG GAAACGCATC TCACGTGCAG
 181 GGACACCCAT CGGCTGAAAA TAAAAGGCTG GCGGAAGATC TACCAAGCCA ATGGAAAACA
 241 AAAGAAGGCT GGGGTGGCGA TACTTGTAAG CGATAAAACA GACTTTAAAC CAACTAAGAT
 301 CAAACGGGAC AAAGAGGGCC ATTACATCAT GGTAAAGGGT AGTATTCAAC AAGAGGAGCT
 361 GACTATCCTG AATATTTATG CACCTAATAC TGGAGCCCCC AGATTCATAA AGCAAGTGTT
 421 GAGTGACCTT CAACGCGACC TCGACTCCCA CACTCTGATC ATGGGAGACT TTAACACCCC
 481 GCTGTCCACT CTCGACAGAT CTACTAGACA GAAAGTCAAC AAGGATACAC AGGAACTGAA
 541 CAGTGCTCTC CACCAAGCGG ACCTTATCGA CATCTACAGA ACACTCCACC CCAAAAGCAC
 601 AGAATATACC TTCTTTTCAG CCCCTCACCA CACCTATTCC AAAATTGACC ACATTGTGGG
 661 GAGTAAAGCC CTTCTCTCCA AATGTAAACG GACCGAAATT ATCACTAACT ATCTCTCCGA
 721 CCACAGTGCA ATAAAACTTG AATTGCGAAT TAAGAATCTC ACTCAAAGTA GATCCACGAC
 781 ATGGAAACTG AACAATCTCC TCTTGAATGA CTACTGGGTG CATAACGAAA TGAAGGCTGA
 841 AATAAAGATG TTCTTTGAGA CCAACGAAAA CAAAGACACC ACGTACCAGA ATCTCTGGGA
 901 CGCTTTCAAA GCAGTGTGTC GAGGAAAATT TATTGCACTG AATGCTTACA AGCGGAAGCA
 961 GGAAAGATCC AAAATAGACA CCCTGACTAG CCAACTTAAA GAACTGGAAA GCCAAGAGCA
1021 AACTCATAGC AAAGCTAGCC GTCGCCAAGA AATTACGAAA ATCAGAGCTG AACTGAAGGA
1081 AATTGAGACA CAGAAAACCC TGCAAAAGAT AAATGAAAGC CGCAGCTGGT TCTTTGAACG
1141 CATCAACAAA ATCGATAGGC CACTTGCTCG CCTTATCAAG AAGAAAGGG AGAAGAATCA
1201 AATCGACACT ATAAAGAATG ATAAAGGCGA TATAACCACC GATCCCACAG AAATTCAAAC
1261 AACCATACGC GAATACTACA AACACCTCTA CGCCAATAAA CTCGAAAATC TCGAGGAAAT
1321 GGATACATTC CTCGACACGT ACACCCTTCC CAGGCTGAAC CAGGAAGAAG TTGAATCACT
1381 GAATCGGCCT ATCACGGGGA GTGAAATAGT AGCTATCATC AATTCACTCC CTACCAAGAA
1441 GTCACCCGGA CCTGATGGAT TCACCGCCGA ATTCTACCAG AGATACATGG AAGAACTGAT
1501 GCCCTTCTTG CTGAAACTTT TCCAAAGTAT TGAGAAAGAG GGAATACTTC CAAACTCATT
1561 TTATGAGGCA TCCATCATTC TGATCCCGAA GCCCGGCAGG GACACGACCA AGAAAGAGAA
1621 TTTTCGACCA ATCTCATTGA TGAACATTGA TGCAAAGATC CTCAATAAAA TACTGGCAAA
1681 TCGGATTCAG CAGCACATAA AGAAGCTGAT CCACCATGAT CAAGTAGGCT TCATCCCCGG
1741 TATGCAAGGT TGGTTCAATA TACGAAAATC AATCAATGTT ATCCAGCATA TAAACCGGGC
1801 CAAAGACAAG AACCACATGA TTATTAGTAT CGATGCTGAG AAAGCCTTTG ACAAAATACA
1861 ACAACCCTTC ATGCTGAAAA CATTGAATAA GCTGGGAATT GATGGCACCT ACTTCAAAAT
1921 CATCAGAGCC ATATATGACA AACCAACAGC AAATATCATC TGAATGGTC AGAAATTGAA
1981 AGCATTCCCC TTGAAAACCG GCACACGGCA GGGTTGCCCT CTGTCACCAC TCCTCTTCAA
2041 CATCGTGTTG GAAGTTCTTG CCCGCGCAAT CCGGCAGGAA AAGGAAATCA AGGGCATTCA
2101 ACTGGGCAAA GAGGAAGTTA AATTGAGCCT GTTTGCAGAC GACATGATCG TCTATTTGGA
2161 AAACCCCATA GTTAGTGCAC AAAATCTGCT GAAGTTGATC AGTAATTTCT CCAAAGTGAG
2221 TGGGTACAAA ATCAATGTGC AAAAGAGCCA AGCTTTCTTG TACACCAACA ACAGGCAAAC
2281 TGAGTCTCAA ATCATGGGCG AACTCCCCTT CGTGATTGCA TCCAAGCGGA TCAAATACCT
2341 GGGGATTCAA TTGACTCGTG ATGTGAAGGA CCTCTTCAAG GAGAACTACA AACCCCTGCT
2401 CAAGGAAATC AAAGAGGACA CAAACAAATG GAAGAACATT CCATGCTCTT GGGTGGGAAG
2461 GATCAATATC GTCAAAATGG CCATCCTGCC CAAGGTAATT TACAGGTTCA ATGCTATACC
2521 CATCAAGCTC CCCATGACAT TCTTCACAGA ACTTGAAAAG ACGACGCTGA AGTTCATTTG
2581 GAACCAGAAA CGTGCCAGGA TTGCTAAATC TATTCTCTCC CAAAAGAACA AAGCTGGCGG
2641 AATCACACTC CCAGACTTCA AACTTTACTA CAAGGCGACC GTGACGAAAA CGGCTTGGTA
2701 CTGGTACCAA AACAGGGATA TAGATCAATG GAACCGAACG GAGCCCAGCG AAATTATGCC
2761 TCATATATAC AACTATCTGA TCTTTGACAA ACCGGAGAAG AACAAGCAAT GGGGAAAGGA
2821 TAGTCTGTTT AATAAATGGT GCTGGGAAAA CTGGCTCGCA ATCTGTAGGA AGCTGAAACT
2881 GGATCCATTC TTGACGCCTT ATACAAAGAT AAATTCCCGA TGGATTAAAG ATCTCAACGT
2941 GAAACCCAAA ACAATTAAAA CCCTCGAGGA AAACCTGGGT ATTACGATTC AGGACATTGG
3001 GGTGGGAAAG GACTTCATGT CCAAAACCCC AAAAGCGATG GCAACCAAAG ACAAAATCGA
3061 CAAATGGGAT CTCATAAAAC TTAAGTCATT TGCACAGCT AAAGAAACGA CAATTAGGGT
3121 GAACCGACAA CCGACCACTT GGGAGAAAAT CTTCGCAACA TACGTTCTG ACAAAGGCCT
3181 GATTTCCAGG ATCTACAATG AATTGAAACA AATTGAAACA AAGAAGACGA ACACCCTAT
3241 AAAGAAATGG GCCAAGGACA TGAACAGACA CTTCTCTAAG GAAGACATTT ATGCAGCCAA
3301 GAAACACATG AAGAAATGCA GCTCTTCACT GGCAATCAGG GAAATGCAAA TCAAAACAAC
3361 AATGAGATAT CATCTCACAC CCGTCAGAAT GGCCATCATT AAGAAGAGCG AAACAACCG
3421 GTGCTGGCGT GGTTGCGGAG AAATCGGTAC TCTCCTTCAC TGTTGGTGGG ACTGTAAACT
3481 CGTTCAACCA CTGTGGAAGT CTGTGTGGCG GTTCCTCAGA GATCTGGAAC TCGAAATCCC
```

TABLE 8-continued

Plasmid and mRNA construct sequences

```
3541 ATTTGACCCA GCCATCCCTC TCCTGGGTAT ATACCCGAAT GAGTATAAAT CCTGCTGCTA
3601 TAAAGACACC TGCACAAGGA TGTTTATTGC AGCTCTCTTC ACAATCGCGA AGACGTGGAA
3661 CCAACCCAAA TGTCCGACTA TGATTGACTG GATTAAGAAG ATGTGGCACA TATACACTAT
3721 GGAATACTAT GCTGCGATCA AGAACGATGA GTTCATATCA TTTGTGGGCA CATGGATGAA
3781 ACTCGAAACC ATCATACTCT CTAAATTGAG TCAAGAACAG AAAACTAAAC ACCGTATATT
3841 TTCCCTGATC GGTGGGAATT AGCTACAAAG ACGATGACGA CAAGGACCAT GGAGACGGTG
3901 AGAGACACAA AAAATTCCAA CACACTATTG CAATGAAAAT AAATTTCCTT TATTAGCCAG
3961 AAGTCAGATG CTCAAGGGGC TTCATGATGT CCCCATAATT TTTGGCAGAG GGAAAAAGAT
4021 CTCAGTGGTA TTTGTGAGCC AGGGCATTGG CCTTCTGATA GGCAGCCTGC ACCTGAGGAG
4081 TGCGGCCGCT TTACTTGTAC AGCTCGTCCA TGCCGAGAGT GATCCCGGCG GCGGTCACGA
4141 ACTCCAGCAG GACCATGTGA TCGCGCTTCT CGTTGGGGTC TTTGCTCAGG GCGGACTGGG
4201 TGCTCAGGTA GTGGTTGTCG GGCAGCAGCA CGGGGCCGTC GCCGATGGGG GTGTTCTGCT
4261 GGTAGTGGTC GGCGAGCTGC ACGCTGCCGT CCTCGATGTT GTGGCGGATC TTGAAGTTCA
4321 CCTTGATGCC GTTCTTCTGC TTGTCGGCCA TGATATAGAC GTTGTGGCTG TTGTAGTTGT
4381 ACTCCAGCTT GTGCCCCAGG ATGTTGCCGT CCTCCTTGAA GTCGATGCCC TTCAGCTCGA
4441 TGCGGTTCAC CAGGGTGTCG CCCTCGAACT TCACCTCGGC GCGGGTCTTG TAGTTGCCGT
4501 CGTCCTTGAA GAAGATGGTG CGCTCCTGGA CGTAGCCTTC GGGCATGGCG GACTTGAAGA
4561 AGTCGTGCTG CTTCATGTGG TCGGGGTAGC GGCTGAAGCA CTGCACGCCG TAGGTCAGGG
4621 TGGTCACGAG GGTGGGCCAG GGCACGGGCA GCTTGCCGGT GGTGCAGATG AACTTCAGGG
4681 TCAGCTTGCC GTAGGTGGCA TCGCCCTCGC CCTCGCCGGA CACGCTGAAC TTGTGGCCGT
4741 TTACGTCGCC GTCCAGCTCG ACCAGGATGG GCACCACCCC GGTGAACAGC TCCTCGCCCT
4801 TGCTCACCAT GGTGGCGGGA TCTGACGGTT CACTAAACCA GCTCTGCTTA TATAGACCTC
4861 CCACCGTACA CGCCTACCGC CCATTTGCGT CAATGGGGCG GAGTTGTTAC GACATTTTGG
4921 AAAGTCCCGT TGATTTTGGT GCCAAAACAA ACTCCCATTG ACGTCAATGG GGTGGAGACT
4981 TGGAAATCCC CGTGAGTCAA ACCGCTATCC ACGCCCATTG ATGTACTGCC AAAACCGCAT
5041 CACCATGGTA ATAGCGATGA CTAATACGTA GATGTACTGC CAAGTAGGAA AGTCCCATAA
5101 GGTCATGTAC TGGGCATAAT GCCAGGCGGG CCATTTACCG TCATTGACGT CAATAGGGGG
5161 CGTACTTGGC ATATGATACA CTTGATGTAC TGCCAAGTGG GCAGTTTACC GTAAATACTC
5221 CACCCATTGA CGTCAATGGA AAGTCCCTAT TGGCGTTACT ATGGGAACAT ACGTCATTAT
5281 TGACGTCAAT GGGCGGGGGT CGTTGGGCGG TCAGCCAGGC GGGCCATTTA CCGTAAGTTA
5341 TGTAACGACG TCTCAGCTGA CAATGAGATC ACATGGACAC AGGAAGGGGA ATATCACACT
5401 CTGGGGACTG TGGTGGGGTC GGGGGAGGGG GGAGGGATAG CATTGGGAGA TATACCTAAT
5461 GCTAGATGAC ACATTAGTGG GTGCAGCGCA CCAGCATGGC ACATGTATAC ATATGTAACT
5521 AACCTGCACA ATGTGCACAT GTACCCTAAA ACTTAGAGTA TAATGGATCC GCAGGCCTCT
5581 GCTAGCTTGA CTGACTGAGA TACAGCGTAC CTTCAGCTCA CAGACATGAT AAGATACATT
5641 GATGAGTTTG GACAAACCAC AACTAGAATG CAGTGAAAAA AATGCTTTAT TTGTGAAATT
5701 TGTGATGCTA TTGCTTTATT TGTAACCATT ATAAGCTGCA ATAAACAAGT T
     (SEQ ID NO: 36)

LINE-1 plasmid GFP (SEQ ID NO: 37)
   1 CGGCCGCGGG GGGAGGAGCC AAGATGGCCG AATAGGAACA GCTCCGGTCT ACAGCTCCCA
  61 GCGTGAGCGA CGCAGAAGAC GGTGATTTCT GCATTTCCAT CTGAGGTACC GGGTTCATCT
 121 CACTAGGGAG TGCCAGACAG TGGGCGCAGG CCAGTGTGTG TGCGCACCGT GCGCGAGCCG
 181 AAGCAGGGCG AGGCATTGCC TCACCTGGGA AGCGCAAGGG GTCAGGGAGT TCCCTTTCCG
 241 AGTCAAAGAA AGGGGTGACG GACGCACCTG GAAAATCGGG TCACTCCCAC CCGAATATTG
 301 CGCTTTTCAG ACCGGCTTAA GAAACGGCGC ACCACGAGAC TATATCCCAC ACCTGGCTCG
 361 GAGGGTCCTA CGCCCACGGA ATCTCGCTGA TTGCTAGCAC AGCAGTCTGA GATCAAACTG
 421 CAAGGCGGCA ACGAGGCTGG GGGAGGGGCG CCCGCCATTG CCCAGGCTTG CTTAGGTAAA
 481 CAAAGCAGCA GGGAAGCTCG AACTGGGTGG AGCCCACCAC AGCTCAAGGA GGCCTGCCTG
 541 CCTCTGTAGG CTCCACCTCT GGGGGCAGGG CACAGACAAA CAAAAGACA GCAGTAACCT
 601 CTGCAGACTT AAGTGTCCCT GTCTGACAGC TTTGAAGAGA GCAGTGGTTC TCCCAGCACG
 661 CAGCTGGAGA TCTGAGAACG GCAGACTGC CTCCTCAAGT GGGTCCCTGA CCCCTGACCC
 721 CCGAGCAGCC TAACTGGGAG GCACCCCCCA GCAGGGGCAC ACTGACACCT CACACGGCAG
 781 GGTATTCCAA CAGACCTGCA GCTGAGGGTC CTGTCTGTTA GAAGGAAAAC TAACAACCAG
 841 AAAGGACATC TACACCGAAA ACCCATCTGT ACATCACCAT CATCAAAGAC CAAAAGTAGA
 901 TAAAACCACA AAGATGGGGA AAAAACAGAA CAGAAAAACT GGAAACTCTA AAACGCAGAG
 961 CGCCTCTCCT CCTCCAAAGG AACGCAGTTC CTCACCAGCA ACAGAACAAA GCTGGATGGA
1021 GAATGATTTT GATGAGCTGA GAAGAAGAAGG CTTCAGACGA TCAAATTACT CTGAGCTACG
1081 GGAGGACATT CAAACCAAAG GCAAAGAAGT TGAAAACTTT GAAAAAAATT TAGAAGAATG
1141 TATAACTAGA ATAACCAATA CAGAGAAGTG CTTAAAGGAG CTGATGGAGC TGAAAACCAA
1201 GGCTCGAGAA CTACGTGAAG AATGCAGAAG CCTCAGGAGC CGATGCGATC AACTGGAAGA
1261 AAGGGTATCA GCAATGGAAG ATGAAATGAA TGAAATGAAG CGAGAAGGGA AGTTTAGAGA
1321 AAAAAGAATA AAAAGAAATG AGCAAAGCCT CCAAGAAATA TGGGACTATG TGAAAAGACC
1381 AAATCTACGT CTGATTGGTA TACCTGAAAG TGATGTGGAG AATGGAACCA AGTTGGAAAA
1441 CACTCTGCAG GATATTATCC AGGAGAACTT CCCCAATCTA GCCAGGCAGG CCAACGTTCA
1501 GATTCAGGAA ATACAGAGAA CGCCACAAAG ATACTCCTCG AGAAGAGCAA CTCCAAGACA
1561 CATAATTGTC AGATTCACCA AAGTTGAAAT GAAGGAAAAA ATGTTAAGGG CAGCCAGAGA
1621 GAAAGGTCGG GTTACCCTCA AAGGAAAGCC CATCAGACTA ACAGCGGATC TCTCGGCAGA
1681 AACCCTACAA GCCAGAAGAG AGTGGGGGCC AATATTCAAC ATTCTTAAAG AAAAGAATTT
1741 TCAACCCAGA ATTTCATATC CAGCCAAACT AAGCTTCATA AGTGAAGGAG AAATAAAATA
1801 CTTTATAGAC AAGCAAATGT TGAGAGATTT TGTCACCACC AGGCCTGCCC TAAAAGAGCT
1861 CCTGAAGGAA GCGCTAAACA TGGAAAGGAA CAACCGGTAC CAGCCGCTGC AAAATCATGC
1921 CAAAATGTAA AGACCATCAA GACTAGGAAG AAACTGCATC AACTAATGAG CAAAATCACC
1981 AGCTAACATC ATAATGACAG GATCAACTTC ACACATAACA ATATTAACTT TAAATATAAA
2041 TGGACTAAAT TCTGCAATTA AAAGACACAG ACTGGCAAGT TGGATAAAGA GTCAAGACCC
2101 ATCAGTGTGC TGTATTCAGG AAACCCATCT CACGTGCAGA GACACACATA GGCTCAAAAT
2161 AAAAGGATGG AGGAAGATCT ACCAAGCCAA TGGAAAACAA AAAAGGCAG GGGTTGCAAT
2221 CCTAGTCTCT GATAAAACAG ACTTTAAACC AACAAAGATC AAAAGAGACA AAGAAGGCCA
```

TABLE 8-continued

| Plasmid and mRNA construct sequences |
|---|

```
2281 TTACATAATG GTAAAGGGAT CAATTCAACA AGAGGAGCTA ACTATCCTAA ATATTTATGC
2341 ACCCAATACA GGAGCACCCA GATTCATAAA GCAAGTCCTC AGTGACCTAC AAAGAGACTT
2401 AGACTCCCAC ACATTAATAA TGGGAGACTT TAACACCCCA CTGTCAACAT TAGACAGATC
2461 AACGAGACAG AAAGTCAACA AGGATACCCA GGAATTGAAC TCAGCTCTGC ACCAAGCAGA
2521 CCTAATAGAC ATCTACAGAA CTCTCCACCC CAAATCAACA GAATATACAT TTTTTTCAGC
2581 ACCACACCAC ACCTATTCCA AAATTGACCA CATAGTTGGA AGTAAAGCTC TCCTCAGCAA
2641 ATGTAAAAGA ACAGAAATTA TAACAAACTA TCTCTCAGAC CACAGTGCAA TCAAACTAGA
2701 ACTCAGGATT AAGAATCTCA CTCAAAGCCG CTCAACTACA TGGAAACTGA ACAACCTGCT
2761 CCTGAATGAC TACTGGGTAC ATAACGAAAT GAAGGCAGAA ATAAAGATGT TCTTTGAAAC
2821 CAACGAGAAC AAAGACACCA CATACCAGAA TCTCTGGGAC GCATTCAAAG CAGTGTGTAG
2881 AGGGAAATTT ATAGCACTAA ATGCCTACAA GAGAAAGCAG GAAAGATCCA AAATTGACAC
2941 CCTAACATCA CAATTAAAAG AACTAGAAAA GCAAGAGCAA ACACATTCAA AAGCTAGCAG
3001 AAGGCAAGAA ATAACTAAAA TCAGAGCAGA ACTGAAGGAA ATAGAGACAC AAAAAACCCT
3061 TCAAAAAATC AATGAATCCA GGAGCTGGTT TTTTGAAAGG ATCAACAAAA TTGATAGACC
3121 GCTAGCAAGA CTAATAAAGA AAAAAAGAGA GAAGAATCAA ATAGACACAA TAAAAAATGA
3181 TAAAGGGGAT ATCACCACCG ATCCCACAGA AATACAAACT ACCATCAGAG AATACTACAA
3241 ACACCTCTAC GCAAATAAAC TAGAAAATCT AGAAGAAATG GATACATTCC TCGACACATA
3301 CACTCTCCCA AGACTAAACC AGGAAGAAGT TGAATCTCTG AATCGACCAA TAACAGGCTC
3361 TGAAATTGTG GCAATAATCA ATAGTTTACC AACCAAAAAG AGTCCAGGAC CAGATGGATT
3421 CACAGCCGAA TTCTACCAGA GGTACAAGGA GGAACTGGTA CCATTCCTTC TGAAACTATT
3481 CCAATCAATA GAAAAAGAGG GAATCCTCCC TAACTCATTT TATGAGGCCA GCATCATTCT
3541 GATACCAAAG CCGGGCAGAG ACACAACCAA AAAAGAGAAT TTTAGACCAA TATCCTTGAT
3601 GAACATTGAT GCAAAAATCC TCAATAAAAT ACTGGCAAC CGAATCCAGC AGCACATCAA
3661 AAAGCTTATC CACCATGATC AAGTGGGCTT CATCCCTGGG ATGCAAGGCT GGTTCAATAT
3721 ACGCAAATCA ATAAATGTAA TCCAGCATAT AAACAGAGCC AAAGACAAAA ACCACATGAT
3781 TATCTCAATA GATGCAGAAA AAGCCTTTGA CAAAATTCAA CAACCCTTCA TGCTAAAAAC
3841 TCTCAATAAA TTAGGTATTG ATGGGACGTA TTTCAAATA TAAGAGCTA TCTATGACAA
3901 ACCCACAGCC AATATCATAC TGAATGGGCA AAAACTGGAA GCATTCCCTT TGAAAACCGG
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA AACCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA ACCACTGCTC AAGGAAATAA AAGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA CAAGCAATG GGAAAGGAT TCCCTATTTA ATAAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAAACGTT AAACCTAAAA CCATAAAAAC
4921 CCTAGAAGAA AACCTAGGCA TTACCATTCA GGACATAGGC GTGGGCAAGG ACTTCATGTC
4981 CAAACACCA AAAGCAATGG CAACAAAAGA CAAAATTGAC AAATGGGATC TAATTAAACT
5041 AAAGAGCTTC TGCACAGCAA AGAAACTAC CATCAGAGTG AACAGGCAAC CTACAACATG
5101 GGAGAAAATT TTTGCAACCT ACTCATCTGA CAAAGGGCTA ATATCCAGAA TCTACAATGA
5161 ACTCAAACAA ATTTACAAGA AAAAAACAAA CAACCCCATC AAAAAGTGGG CGAAGGACAT
5221 GAACAGACAC TTCTCAAAAG AAGACATTTA TGCAGCCAAA AACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATGCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCCT TTGTAGGGAC ATGGATGAAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGGAGG GGGGAGGGAT AGCATTGGGA GATATACCTA ATGCTAGATG ACACATTAGT
5941 GGGTGCAGCG CACCAGCATG GCACATGTAT ACGGATCCGA ATTCTGACG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AAGCACGAGG AAGCGGTCAG CCCATTCGCC GCCAAGCTCT TCAGCAATAT CACGGGTAGC
6181 CAACGCTATG TCCTGATAGC GGTCGGCCGC TTTACTTGTA CAGCTCGTCC ATGCCGAGAG
6241 TGATCCCGGC GGCGGTCACG AACTCCAGCA GGACCATGTG ATCGCGCTTC TCGTTGGGGT
6301 CTTTGCTCAG GCGGACTGG GTGCTCAGGT AGTGGTTGTC GGGCAGCAGC ACGGGGCCGT
6361 CGCCGATGGG GGTGTTCTGC TGGTAGTGGT CGGCCAGGTG AGTCCAGGAG ATGTTTCAGC
6421 ACTGTTGCCT TTAGTCTCGA GGCAACTTAG ACAACTGAGT ATTGATCTGA GCACAGCAGG
6481 GTGTGAGCTG TTTGAAGATA CTGGGGTTGG GGTGAAGAA ACTGCAGAGG ACTAACTGGG
6541 CTGAGACCCA GTGGCAATGT TTTAGGGCCT AAGGAATGCC TCTGAAAATC TAGATGGACA
6601 ACTTTGACTT TGAGAAAAGA GAGGTGGAAA TGAGGAAAT GACTTTCTT TATTAGATTT
6661 CGGTAGAAAG AACTTTCATC TTTCCCCTAT TTTTGTTATT CGTTTTAAAA CATCTATCTG
6721 GAGGCAGGAC AAGTATGGTC ATTAAAAGA TGCAGGCAGA AGGCATATAT TGGCTCAGTC
6781 AAAGTGGGGA ACTTTGGTGG CCAAACATAC ATTGCTAAGG CTATTCCTAT ATCAGCTGGA
6841 CACATATAAA ATGCTGCTAA TGCTTCATTA CAAACTTATA TCCTTTAATT CCAGATGGGG
6901 GCAAAGTATG TCCAGGGGTG AGGAACAATT GAAACATTTG GCTGGAGTA GATTTTGAAA
```

TABLE 8-continued

Plasmid and mRNA construct sequences

```
 6961 GTCAGCTCTG TGTGTGTGTG TGTGTGTGTG TGTGTGAGAG CGTGTGTTTC TTTTAACGTT
 7021 TTCAGCCTAC AGCATACAGG GTTCATGGTG GCAAGAAGAT AACAAGATTT AAATTATGGC
 7081 CAGTGACTAG TGCTGCAAGA AGAACAACTA CCTGCATTTA ATGGGAAAGC AAAATCTCAG
 7141 GCTTTGAGGG AAGTTAACAT AGGCTTGATT CTGGGTGGAA GCTGGGTGTG TAGTTATCTG
 7201 GAGGCCAGGC TGGAGCTCTC AGCTCACTAT GGGTTCATCT TTATTGTCTC CTTTCATCTC
 7261 AACAGCTGCA CGCTGCCGTC CTCGATGTTG TGGCGGATCT TGAAGTTCAC GTCGATGCCG
 7321 TTCTTCTGCT TGTCGGCCAT GATATAGACG TTGTGGCTGT TGTAGTTGTA CTCCAGCTTG
 7381 TGCCCCAGGA TGTTGCCGTC CTCCTTGAAG TCGATGCCCT TCAGCTCGAT GCGGTTCACC
 7441 AGGGTGTCGC CCTCGAACTT CACCTCGGCG CGGGTCTTGT AGTTGCCGTC GTCCTTGAAG
 7501 AAGATGGTGC GCTCCTGGAC GTAGCCTTCG GGCATGGCGG ACTTGAAGAA GTCGTGCTGC
 7561 TTCATGTGGT CGGGGTAGCG GCTGAAGCAC TGCACGCCGT AGGTCAGGGT GGTCACGAGG
 7621 GTGGGCCAGG GCACGGGCAG CTTGCCGGTG GTGCAGATGA ACTTCAGGGT CAGCTTGCCG
 7681 TAGGTGGCAT CGCCCTCGCC CTCGCCGGAC ACGCTGAACT TGTGGCCGTT TACGTCGCCG
 7741 TCCAGCTCGA CCAGGATGGG CACCACCCCG GTGAACAGCT CCTCGCCCTT GCTCACCATG
 7801 GTGGCGAATT CGAAGCTTGA GCTCGAGATC TGAGTCCGGT AGCGCTAGCG GATCTGACGG
 7861 TTCACTAAAC CAGCTCTGCT TATATAGACC TCCCACCGTA CACGCCTACC GCCCATTTGC
 7921 GTCAATGGGG CGGAGTTGTT ACGACATTTT GGAAAGTCCC GTTGATTTTG GTGCCAAAAC
 7981 AAACTCCCAT TGACGTCAAT GGGGTGGAGA CTTGGAAATC CCCGTGAGTC AAACCGCTAT
 8041 CCACGCCCAT TGATGTACTG CCAAAACCGC ATCACCATGG TAATAGCGAT GACTAATACG
 8101 TAGATGTACT GCCAAGTAGG AAAGTCCCAT AAGGTCATGT ACTGGGCATA ATGCCAGGCG
 8161 GGCCATTTAC CGTCATTGAC GTCAATAGGG GCGTACTTG GCATATGATA CACTTGATGT
 8221 ACTGCCAAGT GGGCAGTTTA CCGTAAATAC TCCACCCATT GACGTCAATG GAAAGTCCCT
 8281 ATTGGCGTTA CTATGGGAAC ATACGTCATT ATTGACGTCA ATGGGCGGGG GTCGTTGGGC
 8341 GGTCAGCCAG GCGGGCCATT TACCGTAAGT TATGTAACGC GGAACTCCAT ATATGGGCTA
 8401 TGAACTAATG ACCCCGTAAT TGATTACTAT TAGCCCGGGG GATCCAGACA TGATAAGATA
 8461 CATTGATGAG TTTGGACAAA CCACAACTAG AATGCAGTGA AAAAAATGCT TTATTTGTGA
 8521 AATTTGTGAT GCTATTGCTT TATTTGTAAC CATTATAAGC TGCAATAAAC AAGTTAACAA
 8581 CAACAATTGC ATTCATTTTA TGTTTCAGGT TCAGGGGGAG GTGTGGGAGG TTTTTTAAAG
 8641 CAAGTAAAAC CTCTACAAAT GTGGTATGGC TGATTATGAT CCGGCTGCCT CGCGCGTTTC
 8701 GGTGATGACG GTGAAAACCT CTGACACATG CAGCTCCCGG AGACGGTCAC AGCTTGTCTG
 8761 TAAGCGGATG CCGGGAGCAG ACAAGCCCGT CAGGGCGCGT CAGCGGGTGT TGGCGGGTGT
 8821 CGGGGCGCAG CCATGAGGTC GATCGACTCT AGAGGATCGA TCCCCGCCCC GGACGAACTA
 8881 AACCTGACTA CGACATCTCT GCCCCTTCTT CGCGGGGCAG TGCATGTAAT CCCTTCAGTT
 8941 GGTTGGTACA ACTTGCCAAC TGGGCCCTGT TCCACATGTG ACACGGGGGG GGACCAAACA
 9001 CAAAGGGGTT CTCTGACTGT AGTTGACATC CTTATAAATG GATGTGCACA TTTGCCAACA
 9061 CTGAGTGGCT TTCATCCTGG AGCAGACTTT GCAGTCTGTG GACTGCAACA CAACATTGCC
 9121 TTTATGTGTA ACTCTTGGCT GAAGCTCTTA CACCAATGCT GGGGGACATG TACCTCCCAG
 9181 GGGCCCAGGA AGACTACGGG AGGCTACACC AACGTCAATC AGAGGGGCCT GTGTAGCTAC
 9241 CGATAAGCGG ACCCTCAAGA GGGCATTAGC AATAGTGTTT ATAAGGCCCC CTTGTTAACC
 9301 CTAAACGGGT AGCATATGCT TCCCGGGTAG TAGTATATAT TATCCAGACT AACCCTAATT
 9361 CAATAGCATA TGTTACCCAA CGGGAAGCAT ATGCTATCGA ATTAGGGTTA GTAAAAGGGT
 9421 CCTAAGGAAC AGCGATATCT CCCACCCCAT GAGCTGTCAC GGTTTTATTT ACATGGGGTC
 9481 AGGATTCCAC GAGGGTAGTG AACCATTTTA GTCACAAGGG CAGTGGCTGA AGATCAAGGA
 9541 GCGGGCAGTG AACTCTCCTG AATCTTCGCC TGCTTCTTCA TTCTCCTTCG TTTAGCTAAT
 9601 AGAATAACTG CTGAGTTGTG AACAGTAAGG TGTATGTGAG GTGCTCGAAA ACAAGGTTTC
 9661 AGGTGACGCC CCAGAATAA AATTTGGACG GGGGGTTCAG TGGTGGCATT GTGCTATGAC
 9721 ACCAATATAA CCCTCACAAA CCCCTTGGGC AATAAATACT AGTGTAGGAA TGAAACATTC
 9781 TGAATATCTT TAACAATAGA AATCCATGGG GTGGGGACAA GCCGTAAAGA CTGGATGTCC
 9841 ATCTCACACG AATTTATGGC TATGGGCAAC ACATAATCCT AGTGCAATAT GATACTGGGG
 9901 TTATTAAGAT GTGTCCCAGG CAGGGACCAA GACAGGTGAA CCATGTTGTT ACACTCTATT
 9961 TGTAACAAGG GGAAAGAGAG TGGACGCCGA CAGCAGCGGA CTCCACTGGT TGTCTCTAAC
10021 ACCCCCGAAA ATTAAACGGG GCTCCACGCC AATGGGCCCC ATAAACAAAG ACAAGTGGCC
10081 ACTCTTTTTT TTGAAATTGT GGAGTGGGGG CACGCGTCAG CCCCCACACG CCGCCCTGCG
10141 GTTTTGGACT GTAAAATAAG GGTGTAATAA CTTGCTGAT TGTAACCCCG CTAACCACTG
10201 CGGTCAAACC ACTTGCCCAC AAAACCACTA ATGGCACCCC GGGGAATACC TGCATAAGTA
10261 GGTGGGCGGG CCAAGATAGG GGCGCGATTG CTGCGATCTG GAGGACAAAT TACACACACT
10321 TGCGCCTGAG CGCCAAGCAC AGGGTTGTTG GTCCTCTATT TCACGAGGTC GCTGAGAGCA
10381 CGGTGGGCTA ATGTTGCCAT GGGTAGCATA TACTACCCAA ATATCTGGAT AGCATATGCT
10441 ATCCTAATCT ATATCTGGGT AGCATAGGCT ATCCTAATCT ATATCTGGGT AGCATATGCT
10501 ATCCTAATCT ATATCTGGGT AGTATATGCT ATCCTAATTT ATATCTGGGT AGCATAGGCT
10561 ATCCTAATCT ATATCTGGGT AGCATATGCT ATCCTAATCT ATATCTGGGT AGTATATGCT
10621 ATCCTAATCT GTATCCGGGT AGCATATGCT ATCCTAATAG AGATTAGGGT AGTATATGCT
10681 ATCCTAATTT ATATCTGGGT AGCATATACT ACCCAAATAT CTGGATAGCA TATGCTATCC
10741 TAATCTATAT CTGGGTAGCA TATGCTATCC TAATCTATAT CTGGGTAGCA TAGGCTATCC
10801 TAATCTATAT CTGGGTAGCA TATGCTATCC TAATCTATAT CTGGGTAGTA TATGCTATCC
10861 TAATTTATAT CTGGGTAGCA TAGGCTATCC TAATCTATAT CTGGGTAGCA TATGCTATCC
10921 TAATCTATAT CTGGGTAGTA TATGCTATCC TAATCTGTAT CCGGGTAGCA TATGCTATCC
10981 TCATGCATAT ACAGTCAGCA TATGATACCC AGTAGTAGAG TGGGAGTGCT ATCCTTTGCA
11041 TATGCCGCCA CCTCCCAAGG GGGCGTGAAT TTTCGCTGCT TGTCCTTTTC CTGCATGCTG
11101 GTTGCTCCCA TTCTTAGGTG AATTTAAGGA GGCCAGGCTA AAGCCGTCGC ATGTCTGATT
11161 GCTCACCAGG TAAATGTCGC TAATGTTTTC CAACGCGAGA AGGTCGTTGAG CGCGGAGCTG
11221 AGTGACGTGA CAACATGGGT ATGCCCAATT GCCCCATGTT GGGAGGACGA AAATGGTGAC
11281 AAGACAGATG GCCAGAAATA CACCAACAGC TCTACTGGGA ATTTATTCTT
11341 TAGTGCGGGG GAATACACGG CTTTTAATAC GATTGAGGGC GTCCTAACC AAGTTACATC
11401 ACTCCTGCCC TTCCTCACCC TCATCTCCAT CACCTCCTTC ATCTCCGTCA TCTCCGTCAT
11461 CACCCTCCGC GGCAGCCCCT TCCACCATAG GTGGAAACCA GGGAGGCAAA TCTACTCCAT
11521 CGTCAAAGCT GCACACAGTC ACCCTGATAT TGCAGGTAGG AGCGGGCTTT GTCATAACAA
11581 GGTCCTTAAT CGCATCCTTC AAAACCTCAG CAAATATATG AGTTTGTAAA AAGACCATGA
```

TABLE 8-continued

Plasmid and mRNA construct sequences

```
11641 AATAACAGAC AATGGACTCC CTTAGCGGGC CAGGTTGTGG GCCGGGTCCA GGGGCCATTC
11701 CAAGGGGAG ACGACTCAAT GGTGTAAGAC ACATTGTGG AATAGCAAGG GCAGTTCCTC
11761 GCCTTAGGTT GTAAAGGGAG GTCTTACTAC CTCCATATAC GAACACACCG GCGACCCAAG
11821 TTCCTTCGTC GGTAGTCCTT TCTACGTGAC TCCTAGCCAG GAGAGCTCTT AAACCTTCTG
11881 CAATGTTCTC AAATTTCGGG TTGGAACCTC CTTGACCACG ATGCTTTCCA AACCACCCTC
11941 CTTTTTTGCG CCTGCCTCCA TCACCCTGAC CCCGGGGTCC AGTGCTTGGG CCTTCTCCTG
12001 GGTCATCTGC GGGGCCCTGC TCTATCGCTC CCGGGGGCAC GTCAGGCTCA CCATCTGGC
12061 CACCTTCTTG GTGGTATTCA AAATAATCGG CTTCCCCTAC AGGGTGGAAA AATGGCCTTC
12121 TACCTGGAGG GGGCCTGCGC GGTGGAGACC CGGATGATGA TGACTGACTA CTGGGACTCC
12181 TGGGCCTCTT TTCTCCACGT CCACGACCTC TCCCCCTGGC TCTTTCACGA CTTCCCCCCC
12241 TGGCTCTTTC ACGTCCTCTA CCCCGGCGGC CTCCACTACC TCCTCGACCC CGGCCTCCAC
12301 TACCTCCTCG ACCCCGGCCT CCACTGCCTC CTCGACCCCG GCCTCCACCT CCTGCTCCTG
12361 CCCCTCCTGC TCCTGCCCCT CCTCCTGCTC CTGCCCCTCC TGCCCCTCCT GCTCCTGCCC
12421 CTCCTGCCCC TCCTGCTCCT GCCCCTCCTG CCCTCCTGC TCCTGCCCCT CCTGCCCCTC
12481 CTCCTGCTCC TGCCCCTCCT GCCCCTCCTC CTGCTCCTGC CCCTCCTGCC CCTCCTGCCC
12541 CTGCCCCTCC TGCCCCTCCT GCTCCTGCCC CTCCTGCCCC TCCTGCTCCT GCCCCTCCTG
12601 CTCCTGCCCC TCCTGCTCCT GCCCCTCCTG CTCCTGCCCC TCCTGCCCCT CCTGCCCCTC
12661 CTCCTGCTCC TGCCCCTCCT GCTCCTGCCC CTCCTGCCCC TCCTGCCCCT CCTGCTCCTG
12721 CCCCTCCTGC TCCTCCTGCC CCTCCTGCCC CTCCTGCCCC TCCTCCTGCC CCTCCCCCTC
12781 CTGCCCCTCC TCCTGCTCCT GCCCCTCCTC CTGCTCCTGC CCCTCCTGCC CCTCCTGCCC
12841 CTCCTCCTGC TCCTGCCCCT CCTGCCCCTC CTCCTGCTCC TGCCCCTCCT CCTGCTCCTG
12901 CCCCTCCTGC CCCTCCTGCC CCTCCTCCTG CTCCTGCCCC TCCTCCTGCT CCTGCCCCTC
12961 CTGCCCCTCC TGCCCCTCCT GCCCCTCCTC CCTCCTGCT CCTCCTCCT GCTCCTGCCC
13021 CTCCTGCTCC TGCCCCTCCC GCTCCTGCTC CTGCTCCTGT TCCACCGTGG GTCCCTTTGC
13081 AGCCAATGCA ACTTGGACGT TTTTGGGGTC TCCGACACC ATCTCTATGT CTTGGCCCTG
13141 ATCCTGAGCC GCCCGGGGCT CCTGGTCTTC CGCCTCCTCG TCCTCGTCCT CTTCCCCGTC
13201 CTCGTCCATG GTTATCACCC CCTCTTCTTT GAGGTCCACT GCCGCCGGAG CCTTCTGGTC
13261 CAGATGTGTC TCCCTTCTCT CCTAGGCCAT TTCCAGGTCC TGTACCTGGC CCCTCGTCAG
13321 ACATGATTCA CACTAAAAGA GATCAATAGA CATCTTTATT AGACGACGCT CAGTGAATAC
13381 AGGGAGTGCA GACTCCTGCC CCCTCCAACA GCCCCCCAC CCTCATCCCC TTCATGGTCG
13441 CTGTCAGACA GATCCAGGTC TGAAAATTCC CCATCCTCCG AACCATCCTC GTCCTCATCA
13501 CCAATTACTC GCAGCCCGGA AAACTCCCGC TGAACATCCT CAAGATTTGC GTCCTGAGCC
13561 TCAAGCCAGG CCTCAAATTC CTCGTCCCCC TTTTTGCTGG ACGGTAGGGA TGGGGATTCT
13621 CGGGACCCCT CCTCTTCCTC TTCAAGGTCA CCAGACAGAG ATGCTACTGG GGCAACGGAA
13681 GAAAAGCTGG GTGCGGCCTG TGAGGATCAG CTTATCGATG ATAAGCTGTC AAACATGAGA
13741 ATTCTTGAAG ACGAAAGGGC CTCGTGATAC GCCTATTTTT ATAGGTTAAT GTCATGATAA
13801 TAATGGTTTC TTAGACGTCA GGTGGCACTT TTCGGGGAAA TGTGCGCGGA ACCCCTATTT
13861 GTTTATTTTT CTAAATACAT TCAAATATGT ATCCGCTCAT GAGACAATAA CCCTGATAAA
13921 TGCTTCAATA ATATTGAAAA AGGAAGAGTA TGAGTATTCA ACATTTCCGT GTCGCCCTTA
13981 TTCCCTTTTT TGCGGCATTT TGCCTTCCTG TTTTTGCTCA CCCAGAAACG CTGGTGAAAG
14041 TAAAAGATGC TGAAGATCAG TTGGGTGCAC GAGTGGGTTA CATCGAACTG GATCTCAACA
14101 GCGGTAAGAT CCTTGAGAGT TTTCGCCCCG AAGAACGTTT TCCAATGATG AGCACTTTTA
14161 AAGTTCTGCT ATGTGGCGCG GTATTATCCC GTGTTGACGC CGGGCAAGAG CAACTCGGTC
14221 GCCGCATACA CTATTCTCAG AATGACTTGG TTGAGTACTC ACCAGTCACA GAAAAGCATC
14281 TTACGGATGG CATGACAGTA AGAGAATTAT GCAGTGCTGC CATAACCATG AGTGATAACA
14341 CTGCGGCCAA CTTACTTCTG ACAACGATCG GAGGACCGAA GGAGCTAACC GCTTTTTTGC
14401 ACAACATGGG GGATCATGTA ACTCGCCTTG ATCGTTGGGA ACCGGAGCTG AATGAAGCCA
14461 TACCAAACGA CGAGCGTGAC ACCACGATGC CTGCAGCAAT GGCAACAACG TTGCGCAAAC
14521 TATTAACTGG CGAACTACTT ACTCTAGCTT CCCGGCAACA ATTAATAGAC TGGATGGAGG
14581 CGGATAAAGT TGCAGGACCA CTTCTGCGCT CGGCCCTTCC GGCTGGCTGG TTTATTGCTG
14641 ATAAATCTGG AGCCGGTGAG CGTGGGTCTC GCGGTATCAT TGCAGCACTG GGGCCAGATG
14701 GTAAGCCCTC CCGTATCGTA GTTATCTACA CGACGGGGAG TCAGGCAACT ATGATGAAC
14761 GAAATAGACA GATCGCTGAG ATAGGTGCCT CACTGATTAA GCATTGGTAA CTGTCAGACC
14821 AAGTTTACTC ATATATACTT TAGATTGATT TAAAACTTCA TTTTTAATTT AAAAGGATCT
14881 AGGTGAAGAT CCTTTTTGAT AATCTCATGA CCAAAATCCC TTAACGTGAG TTTTCGTTCC
14941 ACTGAGCGTC AGACCCCGTA GAAAAGATCA AAGGATCTTC TTGAGATCCT TTTTTTCTGC
15001 GCGTAATCTG CTGCTTGCAA ACAAAAAAAC CACCGCTACC AGCGGTGGTT TGTTTGCCGG
15061 ATCAAGAGCT ACCAACTCTT TTTCCGAAGG TAACTGGCTT CAGCAGAGCG CAGATACCAA
15121 ATACTGTCCT TCTAGTGTAG CCGTAGTTAG GCCACCACTT CAAGAACTCT GTAGCACCGC
15181 CTACATACCT CGCTCTGCTA ATCCTGTTAC CAGTGGCTGC TGCCAGTGGC GATAAGTCGT
15241 GTCTTACCGG GTTGGACTCA AGACGATAGT TACCGGATAA GGCGCAGCGG TCGGGCTGAA
15301 CGGGGGGTTC GTGCACACAG CCCAGCTTGG AGCGAACGAC CTACACCGAA CTGAGATACC
15361 TACAGCGTGA GCTATGAGAA AGCGCCACGC TTCCCGAAGG GAGAAAGGCG GACAGGTATC
15421 CGGTAAGCGG CAGGGTCGGA ACAGGAGAGC GCACGAGGGA GCTTCCAGGG GGAAACGCCT
15481 GGTATCTTTA TAGTCCTGTC GGGTTTCGCC ACCTCTGACT TGAGCGTCGA TTTTTGTGAT
15541 GCTCGTCAGG GGGCGGAGC CTATGGAAAA ACGCCAGCAA CGCGGCCTTT TTACGGTTCC
15601 TGGCCTTTTG CTGGCCTTTT GCTCACATGT TCTTTCCTGC GTTATCCCCT GATTCTGTGG
15661 ATAACCGTAT TACCGCCTTT GAGTGAGCTG ATACCGCTCG CCGCAGCCGA ACGACCGAGC
15721 GCAGCGAGTC AGTGAGCGAG GAAGCGGAAG AGCGCCTGAT GCGGTATTTT CTCCTTACGC
15781 ATCTGTGCGG TATTTCACAC CGCATATGGT GCACTCTCAG TACAATCTGC TCTGATGCCG
15841 CATAGTTAAG CCAGCTGTGG AATGTGTGTC AGTTAGGGTG TGGAAAGTCC CCAGGCTCCC
15901 CAGCAGGCAG AAGTATGCAA AGCATGCATC TCAATTAGTC AGCAACCAGG TGTGGAAAGT
15961 CCCCAGGCTC CCCAGCAGGC AGAAGTATGC AAAGCATGCA TCTCAATTAG TCAGCAACCA
16021 TAGTCCCGCC CCTAACTCCG CCCATCCCGC CCTAACTCCG CCCAGTTCCG CCCATTCTC
16081 CGCCCCATGG CTGACTAATT TTTTTTATTT ATGCAGAGGC CGAGGCCGCC TCGGCCTCTG
16141 AGCTATTCCA GAAGTAGTGA GGAGGCTTTT TTGGAGGCCT AGGCTTTTGC AAAAAGCTTG
16201 CATGCCTGCA GGTCGGCCGC CACGACCGGT GCCGCCACCA TCCCCTGACC CACGCCCCTG
16261 ACCCCTCACA AGGAGACGAC CTTCCATGAC CGAGTACAAG CCCACGGTGC GCCTCGCCAC
```

TABLE 8-continued

Plasmid and mRNA construct sequences

```
16321 CCGCGACGAC GTCCCCCGGG CCGTACGCAC CCTCGCCGCC GCGTTCGCCG ACTACCCCGC
16381 CACGCGCCAC ACCGTCGACC CGGACCGCCA CATCGAGCGG GTCACCGAGC TGCAAGAACT
16441 CTTCCTCACG CGCGTCGGGC TCGACATCGG CAAGGTGTGG GTCGCGGACG ACGGCGCCGC
16501 GGTGGCGGTC TGGACCACGC CGGAGAGCGT CGAAGCGGGG GCGGTGTTCG CCGAGATCGG
16561 CCCGCGCATG GCCGAGTTGA GCGGTTCCCG GCTGGCCGCG CAGCAACAGA TGGAAGGCCT
16621 CCTGGCGCCG CACCGGCCCA AGGAGCCCGC GTGGTTCCTG GCCACCGTCG GCGTCTCGCC
16681 CGACCACCAG GGCAAGGGTC TGGGCAGCGC CGTCGTGCTC CCCGGAGTGG AGGCGGCCGA
16741 GCGCGCCGGG GTGCCCGCCT TCCTGGAGAC CTCCGCGCCC CGCAACCTCC CCTTCTACGA
16801 GCGGCTCGGC TTCACCGTCA CCGCCGACGT CGAGGTGCCC GAAGGACCGC GCACCTGGTG
16861 CATGACCCGC AAGCCCGGTG CCTGACGCCC GCCCCACGAC CCGCAGCGCC CGACCGAAAG
16921 GAGCGCACGA CCCCATGGCT CCGACCGAAG CCGACCCGGG CGGCCCCGCC GACCCCGCAC
16981 CCGCCCCCGA GGCCCACCGA CTCTAGAGGA TCATAATCAG CCATACCACA TTTGTAGAGG
17041 TTTTACTTGC TTTAAAAAAC CTCCCACACC TCCCCCTGAA CCTGAAACAT AAAATGAATG
17101 CAATTGTTGT TGTTAACTTG TTTATTGCAG CTTATAATGG TTACAAATAA AGCAATAGCA
17161 TCACAAATTT CACAAATAAA GCATTTTTTT CACTGCATTC TAGTTGTGGT TTGTCCAAAC
17221 TCATCAATGT ATCTTATCAT GTCTGGATCA CTCGCCGATA GTGGAAACCG ACGCCCCAGC
17281 ACTCGTCCGA GGGCAAAGGA ATAGGGGAGA TGGGGGAGGC TAACTGAAAC ACGGAAGGAG
17341 ACAATACCGG AAGGAACCCG CGCTATGACG GCAATAAAAA GACAGAATAA AACGCACGGG
17401 TGTTGGGTCG TTTGTTCATA AACGCGGGGT TCGGTCCCAG GGCTGGCACT CTGTCGATAC
17461 CCCACCGAGA CCCCATTGGG GCCAATACGC CCGCGTTTCT TCCTTTTCCC CACCCCACCC
17521 CCCAAGTTCG GGTGAAGGCC CAGGGCTCGC AGCCAACGTC GGGGCGGCAG GCCCTGCCAT
17581 AGCCACTGGC CCCGTGGGTT AGGGACGGGG TCCCCCATGG GAATGGTTT ATGGTTCGTG
17641 GGGGTTATTA TTTTGGGCGT TGCGTGGGGT CTGGTCCACG ACTGGACTGA GCAGACAGAC
17701 CCATGGTTTT TGGATGGCCT GGGCATGGAC CGCATGTACT GGCGCGACAC GAACACCGGG
17761 CGTCTGTGGC TGCCAAACAC CCCCGACCCC CAAAAACCAC CGCGCGGATT TCTGGCGTGC
17821 CAAGCTAGTC GACCAATTCT CATGTTTGAC AGCTTATCAT CGCAGATCCG GCAACGTTTG
17881 TTGCATTGCT GCAGGCGCAG AACTGGTAGG TATGGAAGAT CTCTAGAAGC TGGGTACCAG
17941 CTGCTAGCAA GCTTGCTAGC GGCCGGCTCG AGTTTACTCC CTATCAGTGA TAGAGAACGT
18001 ATGTCGAGTT TACTCCCTAT CAGTGATAGA GAACGATGTC GAGTTTACTC CCTATCAGTG
18061 ATAGAGAACG TATGTCGAGT TTACTCCCTA TCAGTGATAG AGAACGTATG TCGAGTTTAC
18121 TCCCTATCAG TGATAGAGAA CGTATGTCGA GTTTATCCCT ATCAGTGATA GAGAACGTAT
18181 GTCGAGTTTA CTCCCTATCA GTGATAGAGA ACGTATGTCG AGGTAGGCGT GTACGGTGGG
18241 AGGCCTATAT AAGCAGAGCT CGTTTAGTGA ACCGTCAGAT CGCCG (SEQ ID NO: 37)

LINE 1-GFP mRNA (SEQ ID NO: 38)
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
  481 TTTGGGATTA CGTCAAGAGG CCTAACCTGC GGTTGATCGG CGTCCCCGAG GGCGACGTAG
  541 AAAACGGGAC TAAACTGGAG AATACACTTC AAGACATCAT TCAAGAAAAT TTTCCAAACC
  601 TGGCTCGCA AGCTAATGTG CAAATCCAAG AGATCCAACG CACACCCCAG CGGTATAGCT
  661 CTCGGCGTGC CACCCCTAGG CATATTATCG TGCGCTTTAC TAAGGTGGAG ATGAAAGAGA
  721 AGATGCTGCG AGCCGCTCGG GAAAAGGGAA GGGTGACTTT GAAGGGCAAA CCTATTCGGC
  781 TGACGGTTGA CCTTAGCGCC GAGACACTCC AGGCACGCCG GAATGGGGC CCCATCTTTA
  841 ATATCCTGAA GGAGAAGAAC TTCCAGCCAC GAATCTCTTA CCCTGCAAAG TTGAGTTTTA
  901 TCTCCGAGGG TGAGATTAAG TATTTCATCG ATAAACAGAT GCTGCGAGAC TTCGTGACAA
  961 CTCGCCCAGC TCTCAAGGAA CTGCTCAAAG AGGCTCTTAA TATGGAGCGC AATAATAGAT
 1021 ATCAACCCTT GCAGAACCAC GCAAAGATGT GAGACAGCCG TCAGACCATC AAGACTAGGA
 1081 AGAAACTGCA TCAACTAATG AGCAAAATCA CCAGCTAACA TCATAGTATA CATGACCGGC
 1141 TCTAACTCAC ATATCACCAT CCTTACACTT AACATTAACG GCCTCAACTC AGCTATCAAG
 1201 CGCCATCGGC TGGCCAGCTG GATCAAATCA CAGGATCCAA GCGTTTGTTG CATCCAAGAG
 1261 ACCCACCTGA CCTGTAGAGA TACTCACCGC CTCAAGATCA AGGGATGGCG AAAGATTTAT
 1321 CAGGCGAACG GTAAGCAGAA GAAAGCCGGA GTCGCAATTC TGGTCTCAGA CAAGACGGAT
 1381 TTCAAGCCCA CCAAAATTAA GCGTGATAAG GAAGGTCACT ATATTATGGT GAAAGGCAGC
 1441 ATACAGCAGG AAGAACTTAC CATATTGAAC ATCTACGCGC CAAACAGCGG CGCACCTCGC
 1501 TTTATCAAAC AGGTCCTGTC CGATCTGCAG CGAGATCTGG ATTCTCATAC GTTGATTATG
 1561 GGTGATTTCA ATACACCATT GAGCACCCTG GATCGCAGCA CCAGGCAAAA GGTAAATAAA
 1621 GACACGCAAG AGCTCAATAG CGCACTGCAT CAGGCAGATC TCATTGATAT TTATCGCACT
 1681 CTTCATCCTA AGAGTACCGA GTACACATTC TTCAGCGCCC ACATCTACAC ATACTCAAAG
 1741 ATCGATCATA TCGTCGGCTC AAAGGCTCTG CTGTCAAAGT GCAAGCGCAC AGAGATAATT
 1801 ACAAATTACC TGTCAGATCA TAGCGCGATC AAGCTCGAGC TGAATCAA GAACCTGACC
 1861 CAGAGCCGGA GTACCACTTG GAAGCTTAAT AACCTGCTGC TCAACGATTA TTGGGTCCAC
 1921 AATGAGATGA AGGCAGAGAT TAAAATGTTC TTCGAAACAA ATGAGAATAA GGATACTACC
 1981 TATCAAAACC TTTGGGATGC CTTTAAGGCC GTCTGCAGG GCAAGTTCAT CGCCCTCAAC
 2041 GCCTATAAAA GAAAACAAGA GAGATCTAAG ATCGATACTC TCACCTCTCA GCTGAAGGAG
 2101 TTGGAGAAAC AGGAACAGAC CCACTCCAAG GCGTCAAGAC GGCAGGAGAT CACAAAGATT
 2161 CGCGCCGAGT TGAAAGAGAT CGAAACCCAA AAGACTCTTC AGAAAATTAA CGAGTCTCGT
 2221 AGTTGGTTCT TCGAGCGGAT TAATAAGATA GACCACCCTC TGGCACGACT GATTAAGAAG
 2281 AAGCGCGAAA AGAACCAGAT TGATACCATC AAGAACGACA AGGGCGACAT CACTACTGAC
 2341 CCGACCGAGA TCCAGACCAC TATTCGGGAG TATTATAAGC ATTTGTATGC TAACAAGCTT
 2401 GAGAACCTGG AAGAGATGGA CACTTTTCTG GATACCTATA CTCTGCCACG GCTTAATCAA
 2461 GAGGAAGTCG AGTCCCTCAA CCGCCCAATT ACAGGAAGCG AGATTGTGGC CATAATTAAC
 2521 TCCCTGCCGA CAAAGAAATC TCCTGGTCCG GACGGGTTTA CAGCTGAGTT TTATCAACGG
```

TABLE 8-continued

Plasmid and mRNA construct sequences

```
2581 TATATGGAAG AGCTTGTACC GTTTCTGCTC AAGCTCTTTC AGTCTATAGA AAAGGAAGGC
2641 ATCTTGCCCA ATTCCTTCTA CGAAGCTTCT ATAATACTTA TTCCCAAACC AGGACGCGAT
2701 ACCACAAAGA AGGAAAACTT CCGGCCCATT AGTCTCATGA ATATCGACGC TAAAATATTG
2761 AACAAGATTC TCGCCAACAG AATCCAACAA CATATTAAGA AATTCGATACA TCACGACCAG
2821 GTGGGGTTTA TACCTGGCAT GCAGGGCTGG TTTAACATCC GGAAGAGTAT TAACGTCATT
2881 CAACACATTA ATAGAGCTAA GGATAAGAAT CATATGATCA TCTCTATAGA CGCGGAAAAG
2941 GCATTCGATA AGATTCAGCA GCCATTTATG CTCAAGACTC TGAACAAACT CGGCATCGAC
3001 GGAACATATT TTAAGATTAT TCGCGCAATT TACGATAAGC CGACTGCTAA CATTATCCTT
3061 AACGGCCAAA AGCTCGAGGC CTTTCCGCTC AAGACTGGAA CCCGCCAAGG CTGTCCCCTC
3121 TCCCCGCTTT TGTTTAATAT TGTACTCGAG GTGCTGGCTA GGGCTATTCG TCAAGAGAAA
3181 GAGATTAAAG GGATACAGCT CGGGAAGGAA GAGGTCAAGC TTTCCTTGTT CGCCGATGAT
3241 ATGATTGTGT ACCTGGAGAA TCCTATTGTG TCTGCTCAGA ACCTTCTTAA ACTTATTTCT
3301 AACTTTAGCA AGGTCAGCGG CTATAAGATT AACGTCCAGA ATCTCAGGC CTTTCTGTAC
3361 ACAAATAATC GACAGACCGA ATCCCAGATA ATGGGTGAGC TTCCGTTTGT CATAGCCAGC
3421 AAAAGGATAA AGTATCTCGG AATCCAGCTG ACACGAGACG TTAAAGATTT GTTTAAGGAA
3481 AATTACAAGC CTCTCCTGAA AGAGATTAAG GAAGATACTA ATAAGTGGAA GAATATCCCC
3541 TGTTCATGGG TTGGCAGAAT CAACATAGTG AAGATGGCAA TACTTCCTAA AGTGATATAT
3601 CGCTTTAACG CCATCCCAAT TAAACTGCCT ATGACCTTCT TTACGGAGCT CGAGAAAACA
3661 ACCCTTAAAT TTATATGGAA TCAAAAGAGA GCAAGAATAG CGAAGTCCAT CTTGAGCCAG
3721 AAGAATAAGG CCGGTGGGAT TACTTTGCCT GATTTTAAGT TGTATTATAA AGCCACAGTA
3781 ACTAAGACAG CCTGGTATTG GTATCAGAAT AGAGACATCG ACCAGTGGAA TCGGACCGAA
3841 CCATCAGAGA TAATGCCCCA CATCTATAAT TACCTTATAT TCGATAAGCC AGAAAAGAAT
3901 AAACAGTGGG GCAAAGACAG CCTCTTCAAC AAGTGGTGTT GGGAGAATTG GCTGGCCATA
3961 TGCCGGAAAC TCAAGCTCGA CCCCTTTCTT ACACCCTACA CTAAAATCAA CAGTAGGTGG
4021 ATCAAGGACT TGAATGTCAA GCCAAAGACT ATAAAGACAC TGGAAGAGAA TCTTGGGATC
4081 ACAATACAAG ATATAGGCGT CGGCAAAGAT TTTATGTCAA AGACGCCCAA GGCCATGGCC
4141 ACTAAGGATA AGATTGATAA GTGGGACCTT ATTAAGCTCA AAAGCTTCTG TACTGCCAAG
4201 GAGACCACGA TCAGAGTTAA TAGGCAGCCC ACTACATGGG AAAAGATTTT CGCCACTTAT
4261 TCATCAGATA AGGGGTTGAT AAGCAGAATA TATAACGAGC TGAAGCAGAT CTACAAGAAG
4321 AAAACGAATA ATCCCATCAA GAAGTGGGCA AAAGATATGA ACAGGCATTT TAGCAAAGAG
4381 GATATCTACG CCGCGAAGAA GCATATGAAG AAGTGTAGTT CAAGCTTGGC CATTCGTGAG
4441 ATGCAGATTA AGACGACCAT GCGATACCAC CTTACCCCAG TGAGGATGGC AATTATCAAG
4501 AAATCTGCCA ATAATAGATG TTGGCGGGGC TGTGGCGAGA TTGGCACCCT GCTCCATTGC
4561 TGGTGGGATT GCAAGCTGGT GCAGCCGCTT TGGAAATCAG TCTGGCGCTT TCTGAGGGAC
4621 CTCGAGCTTG AGATTCCCTT CGATCCCGCA ATTCCCTTGC TCGGAATCTA TCCTAACGAA
4681 TACAAGAGCT GTTGTTACAA GGATACGTGT ACCCGGATGT TCATCGCGGC CTTGTTTACG
4741 ATAGCTAAGA CGTGGAATCA GCCTAAGTGC CCCACAATGA TCGATTGGAT CAAGAAAATG
4801 TGGCATATTT ATACCATGGA GTATTACGCA GCAATTAAGA ATGACGAATT TATTTCCTTC
4861 GTTGGGACCT GGATGAAGCT GGAGACTATT ATTCTGAGCA AGCTGTCTCA GGAGCAAAAG
4921 ACAAAGCATA GAATCTTCTC TCTCATTGGT GGTAACGACT ACAAAGACGA TGACGACAAG
4981 TAAAGCGCTT CTAGAAGTTG TCTCCTCCTG CACTGACTGA CTGATACAAT CGATTTCTGG
5041 ATCCGCAGGC CTAATCAACC TCTGGATTAC AAAATTTGTG AAAGATTGAC TGGTATTCTT
5101 AACTATGTTG CTCCTTTTAC GCTATGTGGA TACGCTGCTT TAATGCCTTT GTATCATGCT
5161 ATTGCTTCCC GTATGGCTTT CATTTTCTCC TCCTTGTATA AATCCTGGTT GCTGTCTCTT
5221 TATGAGGAGT TGTGGCCCGT TGTCAGGCAA CGTGGCGTGG TGTGCACTGT GTTTGCTGAC
5281 GCAACCCCCA CTGGTTGGGG CATTGCCACC ACCTGTCAGC TCCTTTCCGG GACTTTCGCT
5341 TTCCCCCTCC CTATTGCCAC GGCGGAACTC ATCGCCGCCT GCCTTGCCCG CTGCTGGACA
5401 GGGGCTCGGC TGTTGGGCAC TGACAATTCC GTGGTGTTGT CGGGGAAGCT GACGTCCTTT
5461 CCATGGCTGC TCGCCTGTGT TGCCACCTGG ATTCTGCGCG GACGTCCTT CTGCTACGTC
5521 CCTTCGGCCC TCAATCCAGC GGACCTTCCT TCCCGCTGAG ACACACAAAA AATTCCAACA
5581 CACTATTGCA ATGAAAATAA ATTTCCTTTA TTAGCCAGAA GTCAGATGCT CAAGGGGCTT
5641 CATGATGTCC CCATAATTTT TGGCAGAGGG AAAAAGATCT CAGTGGTATT TGTGAGCCAG
5701 GGCATTGGCC TTCTGATAGG CACCCTGCAC CTGAGGAGTG CGGCCGCTTT ACTTGTACAG
5761 CTCGTCCATG CCGAGAGTGA TCCCGGCGGC GGTCACGAAC TCCAGCAGGA CCATGTGATC
5821 GCGCTTCTCG TTGGGGTCTT TGCTCAGGGC GGACTGGGTG CTCAGGTAGT GGTTGTCGGG
5881 CAGCAGCACG GGCCGTCGC CGATGGGGGT GTTCTGCTGG TAGTGGTCGG CGAGCTGCAC
5941 GCTGCCGTCC TCGATGTGGT GGCGGATCTT GAAGTTCACC TTGATGCCGT TCTTCTGCTT
6001 GTCGGCCATG ATATAGACGT TGTGGCTGTT GTAGTTGTAC TCCAGCTTGT GCCCCAGGAT
6061 GTTGCCGTCC TCCTTGAAGT CGATGCCCTT CAGCTCGATG CGGTTCACCA GGGTGTCGCC
6121 CTCGAACTTC ACCTCGGCGC GGGTCTTGTA GTTGCCGTCG TCCTTGAAGA AGATGGTGCG
6181 CTCCTGGACG TAGCCTTCGG GCATGGCGGA CTTGAAGAAG TCGTGCTGCT TCATGTGGTC
6241 GGGGTAGCGG CTGAAGCACT GCACGCCGTA GGTCAGGGTG GTCACGAGGG TGGGCCAGGG
6301 CACGGGCAGC TTGCCGGTGG TGCAGATGAA CTTCAGGGTC AGCTTGCCGT AGGTGGCATC
6361 GCCCTCGCCC TCGCCGGACA CGCTGAACTT GTGGCCGTTT ACGTCGCCGT CCAGCTCGAC
6421 CAGGATGGGC ACCACCCCGG TGAACAGCTC CTCGCCCTTG CTCACCATGG TGGCGGGATC
6481 TGACGGTTCA CTAAACCAGC TCTGCTTATA TAGACCTCCC ACCGTACACG CCTACCGCCC
6541 ATTTGCGTCA ATGGGGCGGA GTTGTTACGA CATTTTGGAA AGTCCCGTTG ATTTTGGTGC
6601 CAAAACAAAC TCCCATTGAC GTCAATGGGG TGGAGACTTG GAAATCCCCG TGAGTCAAAC
6661 CGCTATCCAC GCCCATTGAT GTACTGCCAA AACCGCATCA CCATGGTAAT AGCGATGACT
6721 AATACGTAGA TGTACTGCCA AGTAGGAAAG TCCCATAAGG TCATGTACTG GGCATAATGC
6781 CAGGCGGGCC ATTTACCGTC ATTGACGTCA ATAGGGGGCG TACTTGGCAT ATGATACACT
6841 TGATGTACTG CCAAGTGGGC AGTTTACCGT AAATACTCCA CCCATTGACG TCAATGGAAA
6901 GTCCCTATTG GCGTTACTAT GGGAACATAC GTCATTATTG ACGTCAATGG GCGGGGGTCG
6961 TTGGGCGGTC AGCCAGGCGG GCCATTTACC GTAAGTTATG TAACGGGCCT GCTGCCGGCT
```

TABLE 8-continued

Plasmid and mRNA construct sequences

```
7021 CTGCGGCCTC TTCCGCGTCT TCGCCTTCGC CCTCAGACGA GTCGGATCTC CCTTTGGGCC
7081 GCCTCCCCGC CTGTCTAGCT TGACTGACTG AGATACAGCG TACCTTCAGC TCACAGACAT
7141 GATAAGATAC ATTGATGAGT TTGGACAAAC CACAACTAGA ATGCAGTGAA AAAAATGCTT
7201 TATTTGTGAA ATTTGTGATG CTATTGCTTT ATTTGTAACC ATTATAAGCT GCAATAAACA
7261 AGTT (SEQ ID NO: 38)
```

LINE-1-plasmid_CD5-intron-FCR-PI3K (SEQ ID NO: 39)
```
   1 CGGCCGCGGG GGGAGGAGCC AAGATGGCCG AATAGGAACA GCTCCGGTCT ACAGCTCCCA
  61 GCGTGAGCGA CGCAGAAGAC GGTGATTTCT GCATTTCCAT CTGAGGTACC GGGTTCATCT
 121 CACTAGGGAG TGCCAGACAG TGGGCGCAGG CCAGTGTGTG TGCGCACCGT GCGCGAGCCG
 181 AAGCAGGGCG AGGCATTGCC TCACCTGGGA AGCGCAAGGG GTCAGGGAGT TCCCTTTCCG
 241 AGTCAAAGAA AGGGGTGACG GACGCACCTG GAAAATCGGG TCACTCCCAC CCGAATATTG
 301 CGCTTTTCAG ACCGGCTTAA GAAACGGCGC ACCACGAGAC TATATCCCAC ACCTGGCTCG
 361 GAGGGTCCTA CGCCCACGGA ATCTCGCTGA TTGCTAGCAC AGCAGTCTGA GATCAAACTG
 421 CAAGGCGGCA ACGAGGCTGG GGGAGGGGCG CCCGCCATTG CCCAGGCTTG CTTAGGTAAA
 481 CAAAGCAGCA GGGAAGCTCG AACTGGGTGG AGCCCACCAC AGCTCAAGGA GGCCTGCCTG
 541 CCTCTGTAGG CTCCACCTCT GGGGGCAGGG CACAGACAAA CAAAAGACA GCAGTAACCT
 601 CTGCAGACTT AAGTGTCCCT GTCTGACAGC TTTGAAGAGA GCAGTGGTTC TCCCAGCACG
 661 CAGCTGGAGA TCTGAGAACG GGCAGACTGC CTCCTCAAGT GGGTCCCTGA CCCCTGACCC
 721 CCGAGCAGCC TAACTGGGAG GCACCCCCCA GCAGGGGCAC ACTGACACCT CACACGGCAG
 781 GGTATTCCAA CAGACCTGCA GCTGAGGGTC CTGTCTGTTA GAAGGAAAAC TAACAACCAG
 841 AAAGGACATC TACACCGAAA ACCCATCTGT ACATCACCAT CATCAAAGAC CAAAGTAGA
 901 TAAAACCACA AAGATGGGGA AAAAACAGAA CAGAAAAACT GGAAACTCTA AAACGCAGAG
 961 CGCCTCTCCT CCTCCAAAGG AACGCAGTTC CTCACCAGCA ACAGAACAAA GCTGGATGGA
1021 GAATGATTTT GATGAGCTGA GAGAAGAAGG CTTCAGACGA TCAAATTACT CTGAGCTACG
1081 GGAGGACATT CAAACCAAAG GCAAAGAAGT TGAAAACTTT GAAAAAAATT TAGAAGAATG
1141 TATAACTAGA ATAACCAATA CAGAGAAGTG CTTAAAGGAA CTGATGGAGC TGAAAACCAA
1201 GGCTCGAGAA CTACGTGAAG AATGCAGAAG CCTCAGGAGC CGATGCGATC AACTGGAAGA
1261 AAGGGTATCA GCAATGGAAG ATGAAATGAA TGAAATGAAG CGAGAAGGGA AGTTTAGAGA
1321 AAAAAGAATA AAAAGAAATG AGCAAAGCCT CCAAGAAATA TGGGACTATG TGAAAAGACC
1381 AAATCTACGT CTGATTGGTG TACCTGAAAG TGATGTGGAA AATGGAACCA AGTTGGAAAA
1441 CACTCTGCAG GATATTATCC AGGAGAACTT CCCCAATCTA GCAAGGCAGG CCAACGTTCA
1501 GATTCAGGAA ATACAGAGAA CGCCACAAAG ATACTCCTCG AGAAGAGCAA CTCCAAGACA
1561 CATAATTGTC AGATTCACCA AAGTTGAAAT GAAGGAAAAA ATGTTAAGGG CAGCCAGAGA
1621 GAAAGGTCGG GTTACCCTCA AAGGAAAGCC CATCAGACTA ACAGCGGATC TCTCGGCAGA
1681 AACCCTACAA GCCAGAAGAG AGTGGGGGCC AATATTCAAC ATTCTTAAAG AAAAGAATTT
1741 TCAACCCAGA ATTTCATATC CAGCCAAACT AAGCTTCATA AGTGAAGGAG AAATAAAATA
1801 CTTTATAGAC AAGCAAATGT TGAGAGATTT TGTCACCACC AGGCCTGCCC TAAAAGAGCT
1861 CCTGAAGGAA GCGCTAAACA TGGAAAGGAA CAACCGGTAC CAGCCGCTGC AAAATCATGC
1921 CAAAATGTAA AGACCATCAA GACTAGGAAG AAACTGCATC AACTAATGAG CAAAATCACC
1981 AGCTAACATC ATAATGACAG GATCAACTTC ACACATAACA ATATTAACTT TAAATATAAA
2041 TGGACTAAAT TCTGCAATTA AAAGACACAG ACTGGCAAGT TGGATAAAGA GTCAAGACCC
2101 ATCAGTGTGC TGTATTCAGG AAACCCATCT CACGTGCAGA GACACACATA GGCTCAAAAT
2161 AAAAGGATGG AGGAAGATCT ACCAAGCCAA TGGAAAACAA AAAAGGCAG GGGTTGCAAT
2221 CCTAGTCTCT GATAAAACAG ACTTTAAACC AACAAAGATC AAAAGAGACA AAGAAGGCCA
2281 TTACATAATG GTAAAGGGAT CAATTCAACA AGAGGAGCTA ACTATCCTAA ATATTTATGC
2341 ACCCAATACA GGAGCACCCA GATTCATAAA GCAAGTCCTC AGTGACCTAC AAAGAGACTT
2401 AGACTCCCAC ACATTAATAA TGGGAGACTT TAACACCCCA CTGTCAACAT TAGACAGATC
2461 AACGAGACAG AAAGTCAACA AGGATACCCA GGAATTGAAC TCAGCTCTGC ACCAAGCAGA
2521 CCTAATAGAC ATCTACAGAA CTCTCCACCC CAAATCAACA GAATATACAT TTTTTTCAGC
2581 ACCACACCAC ACCTATTCCA AAATTGACCA CATAGTTGGA AGTAAAGCTC TCCTCAGCAA
2641 ATGTAAAAGA ACAGAAATTA TAACAAACTA TCTCTCAGAC CACAGTGCAA TCAAACTAGA
2701 ACTCAGGATT AAGAATCTCA CTCAAAGCCG CTCAACTACA TGGAAACTGA ACAACCTGCT
2761 CCTGAATGAC TACTGGGTAC ATAACGAAAT GAAGGCAGAA ATAAAGATGT TCTTTGAAAC
2821 CAACGAGAAC AAAGACACCA CATACCAGAA TCTCTGGGAC GCATTCAAAG CAGTGTGTAG
2881 AGGGAAATTT ATAGCACTAA ATGCCTACAA GAGAAAGCAA GAAAGATCCA AAATTGACAC
2941 CCTAACATCA CAATTAAAAG AACTAGAAAA GCAAGAGCAA ACACATTCAA AAGCTAGCAG
3001 AAGGCAAGAA ATAACTAAAA TCAGAGCAGA ACTGAAGGAA ATAGAGACAC AAAAAACCCT
3061 TCAAAAAATC AATGAATCCA GGAGCTGGTT TTTTGAAAGG ATCAACAAAA TTGATAGACC
3121 GCTAGCAAGA CTAATAAAGA AAAAAAGAGA GAAGAATCAA ATAGACACAA TAAAAAATGA
3181 TAAAGGGGAT ATCACCACCG ATCCCACAGA AATACAAACT ACCATCAGAG AATACTACAA
3241 ACACCTCTAC GCAAATAAAC TAGAAAATCT AGAAGAAATG GATACATTCC TCGACACATA
3301 CACTCTCCCA AGACTAAACC AGGAAGAAGT TGAATCTCTG AATCGACCAA TAACAGGCTC
3361 TGAAATTGTG GCAATAATCA ATAGTTTACC AACCAAAAAG AGTCCAGGAC CAGATGGATT
3421 CACAGCCGAA TTCTACCAGA GGTACAAGGA GGAACTGGTA CCATTCCTTC TGAAACTATT
3481 CCAATCAATA GAAAAAGAGG GAATCCTCCC TAACTCATTT TATGAGGCCA GCATCATTCT
3541 GATACCAAAG CCGGGCAGAG ACACAACCAA AAAAGAGAAT TTTAGACCAA TATCCTTGAT
3601 GAACATTGAT GCAAAAATCC TCAATAAAAT ACTGGCAAAC CGAATCCAGC AGCACATCAA
3661 AAAGCTTATC CACCATGATC AAGTGGGCTT CATCCCTGGG ATGCAAGGCT GGTTCAATAT
3721 ACGCAAATCA ATAAATGTAA TCCAGCATAT AAACAGAGCC AAAGACAAAA ACCACATGAT
3781 TATCTCAATA GATGCAGAAA AAGCCTTTGA CAAAATTCAA CAACCCTTCA TGCTAAAAAC
3841 TCTCAATAAA TTAGGTATTG ATGGGACGTA TTTCAAAATA ATAAGAGCTA TCTATGACAA
3901 ACCCACAGCC AATATCATAC TGAATGGGCA AAAACTGGAA GCATTCCCTT TGAAACCGG
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA ACCCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
```

TABLE 8-continued

Plasmid and mRNA construct sequences

```
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA CCACTGCTC AAGGAAATAA AAGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA ACAAGCAATG GGGAAAGGAT TCCCTATTTA ATAAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAAACGTT AAACCTAAAA CCATAAAAAC
4921 CCTAGAAGAA AACCTAGGCA TTACCATTCA GGACATAGGC GTGGGCAAGG ACTTCATGTC
4981 CAAAACACCA AAAGCAATGG CAACAAAAGA CAAAATTGAC AAATGGGATC TAATTAAACT
5041 AAAGAGCTTC TGCACAGCAA AAGAAACTAC CATCAGAGTG AACAGGCAAC CTACAACATG
5101 GGAGAAAATT TTTGCAACCT ACTCATCTGA CAAAGGGTCA ATATCCAGAA TCTACAATGA
5161 ACTCAAACAA ATTTACAAGA AAAAAACAAA CAACCCCATC AAAAAGTGGG CGAAGGACAT
5221 GAACAGACAC TTCTCAAAAG AAGACATTTA TGCAGCCAAA AACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATGCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCCT TTGTAGGGAC ATGGATGAAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGAGG GGGAGGGAT AGCATTGGGA GATATACCTA ATGCTAGATG ACACATTAGT
5941 GGGTGCAGCG CACCAGCATG GCACATGTAT ACGGATCCGA ATTCTGACG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AGCACGAGG AAGCGGTCAG CCCATTCGCC GCCAAGCTCT TCAGCAATAT CACGGGTAGC
6181 CAACGCTATG TCCTGATAGC GGTCGGCCGC TCATGTTCTC GTAGGAGTCG GCGTCCTCTT
6241 CGTGGTTAGG TCCAGGTTGG CCTCTGATAG ACCGCAGCTG AGGAGCGGCG TACAGAATGC
6301 CTCTCATGTC CTCATAGCTG CCGCTGCCTT GTGGAGGCTT CTCGTGCTTC AGTGTCTCGT
6361 ATGTCTCTTG ATTCCGGGTG CTCAGGCCGG TGTACACGCC ATCAGATTTC TCGTAGCTGG
6421 TGATGGCGGC CTTCCGCACT TGGATCTTCA GCCGTCTGCA GTACAGGGTG ATGACCAGAG
6481 ACAGCAGCAG GACACCACAT GTGCCAGCCA GAGGGGCCCA AATGTAGATA TCCAGGCCTC
6541 TGGTATGCAC AGCTCCGCCT GCAGCAGGTC TACAGGCTTC AGGTCTGAGA GACAGAGGCT
6601 GGCTGGCGAT TGTAGGAGCT GGTGTAGGTG GTCTAGGAGC GGGTGTTGTT GTAGGCTTGG
6661 CGGGCAGAAA CACGGGCACG AAGTGGCTGA AGTACATGAT GCTATTGCTC AGGGCTCCGC
6721 TTCCTCCGCC GCCTGATTTG ATTTCCAGCT TGGTGCCTCC GCCAAATGTC CAAGGGCTCT
6781 CGTCGTACTG CTGGCAGTAG TAGATGCCGA AGTCCTCGTA CTGCAGGCTG CTGATTGTCA
6841 GGGTGTAGTC GGTGCCAGAG CCGCTGCCAG AAAATCTGCT TGGCACGCCG CTTTCCAGTC
6901 TGTTGGCCCG GTAGATCAGT GTCTTAGGGG CCTTGCCAGG CTTCTGCTGG AACCAGCTCA
6961 GGTAGCTGTT GATGTCCTGG CTGGCTCTAC AGGTGATGGT CACTCTATCG CCCACAGAGG
7021 CAGACAGGCT GCTAGGGCTC TGTGTCATCT GGATATCAGA GCCACCACCG CCAGATCCAC
7081 CGCCACCTGA TCCTCCGCCT CCGCTAGAAA CTGTCACTGT GGTGCCCTGG CCCCACACAT
7141 CGAAGTACCA GTCGTAGCCT CTTCTGGTGC AGAAGTACAC GGCGGTATCC TCGGCTCTCA
7201 GGCTGTTGAT CTGCAGGTAG GCGGTGTTCT TGCTGTCGTC CAGGCTGAAG GTGAATCTGC
7261 CCTTAAAGCT ATCGGCTAG GTTGGCTCGC CGGTGTGGGT ATTGATCCAG CCCATCCACT
7321 CAAGGCCAGG TGAGTCCAGG AGATGTTTCA GCACTGTTGC CTTTAGTCTC GGAGCAACTT
7381 AGACAACTGA GTATTGATCT GAGCACAGCA GGGTGTGAGC TGTTTGAAGA TACTGGGGTT
7441 GGGGGTGAAG AAACTGCAGA GGACTAACTG GCTGAGACC CAGTGGCAAT GTTTTAGGGC
7501 CTAAGGAATG CCTCTGAAAA TCTAGATGGA CAACTTTGAC TTTGAGAAAA GAGAGGTGGA
7561 AATGAGGAAA ATGACTTTTC TTTATTAGAT TTCGGTAGAA AGAACTTTCA TCTTTCCCCT
7621 ATTTTTGTTA TTCGTTTTAA AACATCTATC TGGAGGCAGG ACAAGTATGG TCATTAAAAA
7681 GATGCAGGCA GAAGGCATAT ATTGGCTCAG TCAAAGTGGG AACTTTGGT GGCCAAACAT
7741 ACATTGCTAA GGCTATTCCT ATATCAGCTG GACACATATA AAATGCTGCT AATGCTTCAT
7801 TACAAACTTA TATCCTTTAA TTCCAGATGG GGGCAAAGTA TGTCCAGGGG TGAGGAACAA
7861 TTGAAACATT TGGGCTGGAG TAGATTTTGA AAGTCAGCTC TGTGTGTGTG TGTGTGTGTG
7921 TGTGTGTGAG AGCGTGTGTT TCTTTTAACG TTTTCAGCCT ACAGCATACA GGGTTCATGG
7981 TGGCAAGAAG ATAACAAGAT TTAAATTATG GCCAGTGACT AGTGCTGCAA GAAGAACAAC
8041 TACCTGCATT TAATGGGAAA GCAAATCTC AGGCTTTGAG GAAGTTAAC ATAGGCTTGA
8101 TTCTGGGTGG AAGCTGGGTG TGTAGTTATC TGGAGGCCAG GCTGGAGCTC TCAGCTCACT
8161 ATGGGTTCAT CTTTATTGTC TCCTTTTTCC AGGGGCCTGT CGGACCCAGT TCATGCCGTA
8221 GTTGGTGAAG GTGTAGCCGC TGGCGGCACA GCTGATTCTG ACAGATCCGC CAGGTTTCAC
8281 AAGTCCGCCG CCAGACTGAA CCAGCTGGAT CTCAGAGATG CTACAGGCCA CTGTTCCCAG
8341 CAGCAGCAGA GACTGCAGCA ACATCTGGTG GCGAATTCGA AGCTTGAGCT CGAGATCTGA
8401 GTCCGGTAGC GCTAGCGGAT CTGACGGTTC ACTAAACCAG CTCTGCTTAT ATAGACCTCC
8461 CACCGTACAC GCCTACCGCC CATTTGCGTC AATGGGGCGG AGTTGTTACG ACATTTTGGA
8521 AAGTCCCGTT GATTTTGGTG CCAAAACAAA CTCCCATTGA CGTCAATGGG GTGGAGACTT
8581 GGAAATCCCC GTGAGTCAAA CCGCTATCCA CGCCCATTGA TGTACTGCCA AAACCGCATC
8641 ACCATGGTAA TAGCGATGAC TAATACGTAG ATGTACTGCC AAGTAGGAAA GTCCCATAAG
8701 GTCATGTACT GGGCATAATG CCAGGCGGGC CATTTACCGT CATTGACGTC AATAGGGGGC
8761 GTACTTGGCA TATGATACAC TTGATGTACT GCCAAGTGGG CAGTTTACCG TAAATACTCC
8821 ACCCATTGAC GTCAATGAA AGTCCCTATT GGCGTTACTA TGGGAACATA CGTCATTATT
8881 GACGTCAATG GGCGGGGGTC GTTGGGCGGT CAGCCAGGCG GGCCATTTAC CGTAAGTTAT
```

TABLE 8-continued

Plasmid and mRNA construct sequences

```
 8941 GTAACGCGGA ACTCCATATA TGGGCTATGA ACTAATGACC CCGTAATTGA TTACTATTAG
 9001 CCCGGGGAT CCAGACATGA TAAGATACAT TGATGAGTTT GGACAAACCA CAACTAGAAT
 9061 GCAGTGAAAA AAATGCTTTA TTTGTGAAAT TTGTGATGCT ATTGCTTTAT TTGTAACCAT
 9121 TATAAGCTGC AATAAACAAG TTAACAACAA CAATTGCATT CATTTTATGT TTCAGGTTCA
 9181 GGGGGAGGTG TGGGAGGTTT TTTAAAGCAA GTAAAACCTC TACAAATGTG GTATGGCTGA
 9241 TTATGATCCG GCTGCCTCGC GCGTTTCGGT GATGACGGTG AAAACCTCTG ACACATGCAG
 9301 CTCCCGGAGA CGGTCACAGC TTGTCTGTAA GCGGATGCCG GGAGCAGACA AGCCCGTCAG
 9361 GGCGCGTCAG CGGGTGTTGG CGGGTGTCGG GGCGCAGCCA TGAGGTCGAT CGACTCTAGA
 9421 GGATCGATCC CCGCCCCGGA CGAACTAAAC CTGACTACGA CATCTCTGCC CCTTCTTCGC
 9481 GGGGCAGTGC ATGTAATCCC TTCAGTTGGT TGGTACAACT TGCCAACTGG GCCCTGTTCC
 9541 ACATGTGACA CGGGGGGGGA CCAAACACAA AGGGGTTCTC TGACTGTAGT TGACATCCTT
 9601 ATAAATGGAT GTGCACATTT GCCAACACTG AGTGGCTTTC ATCCTGGAGC AGACTTTGCA
 9661 GTCTGTGGAC TGCAACACAA CATTGCCTTT ATGTGTAACT CTTGGCTGAA GCTCTTACAC
 9721 CAATGCTGGG GGACATGTAC CTCCCAGGGG CCCAGGAAGA CTACGGGAGG CTACACCAAC
 9781 GTCAATCAGA GGGGCCTGTG TAGCTACCGA TAAGCGGACC CTCAAGAGGG CATTAGCAAT
 9841 AGTGTTTATA AGGCCCCCTT GTTAACCCTA AACGGGTAGC ATATGCTTCC CGGGTAGTAG
 9901 TATATACTAT CCAGACTAAC CCTAATTCAA TAGCATATGT TACCCAACGG GAAGCATATG
 9961 CTATCGAATT AGGGTTAGTA AAAGGGTCCT AAGGAACAGC GATATCTCCC ACCCCATGAG
10021 CTGTCACGGT TTTATTTACA TGGGGTCAGG ATTCCACGAG GGTAGTGAAC CATTTTAGTC
10081 ACAAGGGCAG TGGCTGAAGA TCAAGGAGCG GGCAGTGAAC TCTCCTGAAT CTTCGCCTGC
10141 TTCTTCATTC TCCTTCGTTT AGCTAATAGA ATAACTGCTG AGTTGTGAAC AGTAAGGTGT
10201 ATGTGAGGTG CTCGAAAACA AGGTTTCAGG TGACGCCCC AGAATAAAAT TTGGACGGGG
10261 GGTTCAGTGG TGGCATTGTG CTATGACACC AATATAACCC TCACAAACCC CTTGGGCAAT
10321 AAATACTAGT GTAGGAATGA AACATTCTGA ATATCTTTAA CAATAGAAAT CCATGGGGTG
10381 GGGACAAGCC GTAAAGACTG GATGTCCATC TCACACGAAT TTATGCTAT GGGCAACACA
10441 TAATCCTAGT GCAATATGAT ACTGGGGTTA TTAAGATGTG TCCCAGGCAG GGACCAAGAC
10501 AGGTGAACCA TGTTGTTACA CTCTATTTGT AACAAGGGGA AAGAGAGTGG ACGCCGACAG
10561 CAGCGGACTC CACTGGTTGT CTCTAACACC CCGAAAATT AAACGGGGCT CCACGCCAAT
10621 GGGGCCCATA AACAAAGACA AGTGGCCACT CTTTTTTTTG AAATTGTGGA GTGGGGGCAC
10681 GCGTCAGCCC CCACACGCCG CCCTGCGGTT TTGGACTGTA AAATAAGGGT GTAATAACTT
10741 GGCTGATTGT AACCCCGCTA ACCACTGCGG TCAAACCACT TGCCCACAAA ACCACTAATG
10801 GCACCCCGGG GAATACCTGC ATAAGTAGGG GGGCGGGCCA AGATAGGGGC GCGATTGCTG
10861 CGATCTGGAG GACAAATTAC ACACACTTGC GCCTGAGCGC CAAGCACAGG GTTGTTGGTC
10921 CTCATATTCA CGAGGTCGCT GAGAGCACGG TGGGCTAATG TTGCCATGGG TAGCATATAC
10981 TACCCAAATA TCTGGATAGC ATATGCTATC CTAATCTATA TCTGGGTAGC ATAGGCTATC
11041 CTAATCTATA TCTGGGTAGC ATATGCTATC CTAATCTATA TCTGGGTAGT ATATGCTATC
11101 CTAATTTATA TCTGGGTAGC ATAGGCTATC CTAATCTATA TCTGGGTAGC ATATGCTATC
11161 CTAATCTATA TCTGGGTAGT ATATGCTATC CTAATCTGTA TCCGGGTAGC ATATGCTATC
11221 CTAATAGAGA TTAGGGTAGT ATATGCTATC CTAATTTATA TCTGGGTAGC ATATACTACC
11281 CAAATATCTG GATAGCATAT GCTATCCTAA TCTATATCTG GGTAGCATAT GCTATCCTAA
11341 TCTATATCTG GGTAGCATAG GCTATCCTAA TCTATATCTG GGTAGCATAT GCTATCCTAA
11401 TCTATATCTG GGTAGTATAT GCTATCCTAA TTTATATCTG GGTAGCATAG GCTATCCTAA
11461 TCTATATCTG GGTAGCATAT GCTATCCTAA TCTATATCTG GGTAGTATAT GCTATCCTAA
11521 TCTGTATCCG GGTAGCATAT GCTATCCTCA TGCATATACA GTCAGCATAT GATACCCAGT
11581 AGTAGAGTGG GAGTGCTATC CTTTGCATAT GCCGCCACCT CCCAAGGGGG CGTGAATTTT
11641 CGCTGCTTGT CCTTTTCCTG CATGCTGGTT GCTCCCATTC TTAGGTGAAT TTAAGGAGGC
11701 CAGGCTAAAG CCGTCGCATG TCTGATTGCT CACCAGGTAA ATGTCGCTAA TGTTTTCCAA
11761 CGCGAGAAGG TGTTGAGCGC GGAGCTGAGT GACGTGACAA CATGGGTATG CCCAATTGCC
11821 CCATGTTGGG AGGACGAAAA TGGTGACAAG ACAGATGGCC AGAAATACAC CAACAGCACG
11881 CATGATGTCT ACTGGGGATT TATTCTTTAG TGCGGGGAA TACACGGCTT TTAATACGAT
11941 TGAGGGCGTC TCCTAACAAG TTACATCACT CCTGCCCTTC CTCACCCTCA TCTCCATCAC
12001 CTCCTTCATC TCCGTCATCT CCGTCATCAC CCTCCGCGGC AGCCCCTTCC ACCATAGGTG
12061 GAAACCAGGG AGGCAAATCT ACTCCATCGT CAAAGCTGCA CACAGTCACC CTGATATTGC
12121 AGGTAGGAGC GGGCTTTGTC ATAACAAGGT CCTTAATCGC ATCCTTCAAA ACCTCAGCAA
12181 ATATATGAGT TTGTAAAAAG ACCATGAAAT AACAGACAAT GGACTCCCTT AGCGGGCCAG
12241 GTTGTGGGCC GGGTCCAGGG GCCATTCCAA AGGGGAGACG ACTCAATGGT GTAAGACGAC
12301 ATTGTGGAAT AGCAAGGGCA GTTCCTCGCC TTAGGTTGTA AAGGGAGGTC TTACTACCTC
12361 CATATACGAA CACACCGGCG ACCCAAGTTC CTTCGTCGGT AGTCCTTTCT ACGTGACTCC
12421 TAGCCAGGAG AGCTCTTAAA CCTTCTGCAA TGTTCTCAAA TTTCGGTTG GAACCTCCTT
12481 GACCACGATG CTTTCCAAAC CACCCTCCTT TTTTGCGCCT GCCTCCATCA CCCTGACCCC
12541 GGGGTCCAGT GCTTGGGCCT TCTCCTGGGT CATCTGCGGG GCCCTGCTCT ATCGCTCCCG
12601 GGGGCACGTC AGGCTCACCA TCTGGGCCAC CTTCTTGGTG GTATTCAAAA TAATCGGCTT
12661 CCCCTACAGG GTGGAAAAAT GGCCTTCTAC CTGGAGGGGG CCTGCGCGGT GGAGACCCGG
12721 ATGATGATGA CTGACTACTG GGACTCCTGG GCCTCTTTTC TCCACGTCCA CGACCTCTCC
12781 CCCTGGCTCT TTCACGACTT CCCCCCCTGG CTCTTTCACG TCCTCTACCC CGGCGGCCTC
12841 CACTACCTCC TCGACCCCGG CCTCCACTAC CTCCTCGACC CCGGCCTCCA CTGCCTCCTC
12901 GACCCCGGCC TCCACCTCCT GCTCCTGCCC CTCCTGCTCC TGCCCCTCCT CCTGCTCCTG
12961 CCCCTCCTGC CCCTCCTGCT CCTGCCCCTC CTGCCCCTCC TGCTCCTGCC CCTCCTGCCC
13021 CTCCTGCTCC TGCCCCTCCT CCTGCTCCTG CCCCTCCTGC CCTCCTCCTG
13081 CTCCTGCCCC TCCTGCCCCT CCTGCTCCTG CCCCTCCTGC CCTCCTGCT CCTGCCCCTC
13141 CTGCCCCTCC TGCTCCTGCC CCTCCTGCTC CTGCCCCTCC TGCTCCTGCC CCTCCTGCTC
13201 CTGCCCCTCC TGCCCCTCCT GCCCCTCCTC CTGCTCCTGC CCTCCTGCT CCTGCCCCTC
13261 CTGCCCCTCC TGCCCCTCCT GCTCCTGCCC CTCCTGCTCC TGCTCCCTCT CCTGCCCCTC
13321 CTGCCCCTCC TCCTGCTCCT GCCCCTCCTG CCCCTCCTCC TGCTCCTGCC CCTCCTCCTG
13381 CTCCTGCCCC TCCTGCCCCT CCTGCCCCTC CTGCTCCTGC TGCCCCTCCT GCCCCTCCTC
13441 CTGCTCCTGC CCTCCTCCT GCTCCTGCCC CTCCTGCCCC TCCTGCCCCT CCTCCTGCTC
13501 CTGCCCCTCC TCCTGCTCCT GCCCCTCCTG CCCCTCCTGC CCTCCTGCC CCTCCTCCTG
13561 CTCCTGCCCC TCCTCCTGCT CCTGCCCCTC CTGCTCCTGC CCCTCCCGCT CCTGCTCCTG
```

TABLE 8-continued

Plasmid and mRNA construct sequences

```
13621 CTCCTGTTCC ACCGTGGGTC CCTTTGCAGC CAATGCAACT TGGACGTTTT TGGGGTCTCC
13681 GGACACCATC TCTATGTCTT GGCCCTGATC CTGAGCCGCC CGGGGCTCCT GGTCTTCCGC
13741 CTCCTCGTCC TCGTCCTCTT CCCCGTCCTC GTCCATGGTT ATCACCCCCT CTTCTTTGAG
13801 GTCCACTGCC GCCGGAGCCT TCTGGTCCAG ATGTGTCTCC CTTCTCTCCT AGGCCATTTC
13861 CAGGTCCTGT ACCTGGCCCC TCGTCAGACA TGATTCACAC TAAAAGAGAT CAATAGACAT
13921 CTTTATTAGA CGACGCTCAG TGAATACAGG GAGTGCAGAC TCCTGCCCCC TCCAACAGCC
13981 CCCCCACCCT CATCCCCTTC ATGGTCGCTG TCAGACAGAT CCAGGTCTGA AAATTCCCCA
14041 TCCTCCGAAC CATCCTCGTC CTCATCACCA ATTACTCGCA GCCCGGAAAA CTCCCGCTGA
14101 ACATCCTCAA GATTTGCGTC CTGAGCCTCA AGCCAGGCCT CAAATTCCTC GTCCCCCTTT
14161 TTGCTGGACG GTAGGGATGG GGATTCTCGG GACCCCTCCT CTTCCTCTTC AAGGTCACCA
14221 GACAGAGATG CTACTGGGGC AACGGAAGAA AAGCTGGGTG CGGCCTGTGA GGATCAGCTT
14281 ATCGATGATA AGCTGTCAAA CATGAGAATT CTTGAAGACG AAAGGGCCTC GTGATACGCC
14341 TATTTTTATA GGTTAATGTC ATGATAATAA TGGTTTCTTA GACGTCAGGT GGCACTTTTC
14401 GGGGAAATGT GCGCGGAACC CCTATTTGTT TATTTTTCTA AATACATTCA AATATGTATC
14461 CGCTCATGAG ACAATAACCC TGATAAATGC TTCAATAATA TTGAAAAAGG AAGAGTATGA
14521 GTATTCAACA TTTCCGTGTC GCCCTTATTC CCTTTTTTGC GGCATTTTGC CTTCCTGTTT
14581 TTGCTCACCC AGAAACGCTG GTGAAAGTAA AAGATGCTGA AGATCAGTTG GGTGCACGAG
14641 TGGGTTACAT CGAACTGGAT CTCAACAGCG GTAAGATCCT TGAGAGTTTT CGCCCCGAAG
14701 AACGTTTTCC AATGATGAGC ACTTTTAAAG TTCTGCTATG TGGCGCGGTA TTATCCCGTG
14761 TTGACGCCGG GCAAGAGCAA CTCGGTCGCC GCATACACTA TTCTCAGAAT GACTTGGTTG
14821 AGTACTCACC AGTCACAGAA AAGCATCTTA CGGATGGCAT GACAGTAAGA GAATTATGCA
14881 GTGCTGCCAT AACCATGAGT GATAACACTG CGGCCAACTT ACTTCTGACA ACGATCGGAG
14941 GACCGAAGGA GCTAACCGCT TTTTTGCACA ACATGGGGGA TCATGTAACT CGCCTTGATC
15001 GTTGGGAACC GGAGCTGAAT GAAGCCATAC CAAACGACGA GCGTGACACC ACGATGCCTG
15061 CAGCAATGGC AACAACGTTG CGCAAACTAT TAACTGGCGA ACTACTTACT CTAGCTTCCC
15121 GGCAACAATT AATAGACTGG ATGGAGGCGG ATAAAGTTGC AGGACCACTT CTGCGCTCGG
15181 CCCTTCCGGC TGGCTGGTTT ATTGCTGATA AATCTGGAGC CGGTGAGCGT GGGTCTCGCG
15241 GTATCATTGC AGCACTGGGG CCAGATGGTA AGCCCTCCCG TATCGTAGTT ATCTACACGA
15301 CGGGGAGTCA GGCAACTATG GATGAACGAA ATAGACAGAT CGCTGAGATA GGTGCCTCAC
15361 TGATTAAGCA TTGGTAACTG TCAGACCAAG TTTACTCATA TATACTTTAG ATTGATTTAA
15421 AACTTCATTT TTAATTTAAA AGGATCTAGG TGAAGATCCT TTTTGATAAT CTCATGACCA
15481 AAATCCCTTA ACGTGAGTTT TCGTTCCACT GAGCGTCAGA CCCCGTAGAA AAGATCAAAG
15541 GATCTTCTTG AGATCCTTTT TTTCTGCGCG TAATCTGCTG CTTGCAAACA AAAAAACCAC
15601 CGCTACCAGC GGTGGTTTGT TTGCCGGATC AAGAGCTACC AACTCTTTTT CCGAAGGTAA
15661 CTGGCTTCAG CAGAGCGCAG ATACCAAATA CTGTCCTTCT AGTGTAGCCG TAGTTAGGCC
15721 ACCACTTCAA GAACTCTGTA GCACCGCCTA CATACCTCGC TCTGCTAATC CTGTTACCAG
15781 TGGCTGCTGC CAGTGGCGAT AAGTCGTGTC TTACCGGGTT GGACTCAAGA CGATAGTTAC
15841 CGGATAAGGC GCAGCGGTCG GGCTGAACGG GGGGTTCGTG CACACAGCCC AGCTTGGAGC
15901 GAACGACCTA CACCGAACTG AGATACCTAC AGCGTGAGCT ATGAGAAAGC GCCACGCTTC
15961 CCGAAGGGAG AAAGGCGGAC AGGTATCCGG TAAGCGGCAG GGTCGGAACA GGAGAGCGCA
16021 CGAGGGAGCT TCCAGGGGGA AACGCCTGGT ATCTTTATAG TCCTGTCGGG TTTCGCCACC
16081 TCTGACTTGA GCGTCGATTT TTGTGATGCT CGTCAGGGGG GCGGAGCCTA TGGAAAAACG
16141 CCAGCAACGC GGCCTTTTTA CGGTTCCTGG CCTTTTGCTG GCCTTTTGCT CACATGTTCT
16201 TTCCTGCGTT ATCCCCTGAT TCTGTGGATA ACCGTATTAC CGCCTTTGAG TGAGCTGATA
16261 CCGCTCGCCG CAGCCGAACG ACCGAGCGCA GCGAGTCAGT GAGCGAGGAA GCGGAAGAGC
16321 GCCTGATGCG GTATTTTCTC CTTACGCATC TGTGCGGTAT TTCACACCGC ATATGGTGCA
16381 CTCTCAGTAC AATCTGCTCT GATGCCGCAT AGTTAAGCCA GCTGTGGAAT GTGTGTCAGT
16441 TAGGGTGTGG AAAGTCCCCA GGCTCCCCAG CAGGCAGAAG TATGCAAAGC ATGCATCTCA
16501 ATTAGTCAGC AACCAGGTGT GGAAAGTCCC CAGGCTCCCC AGCAGGCAGA AGTATGCAAA
16561 GCATGCATCT CAATTAGTCA GCAACCATAG TCCCGCCCCT AACTCCGCCC ATCCCGCCCC
16621 TAACTCCGCC CAGTTCCGCC CATTCTCCGC CCCATGGCTG ACTAATTTTT TTTATTTATG
16681 CAGAGGCCGA GGCCGCCTCG GCCTCTGAGC TATTCCAGAA GTAGTGAGGA GGCTTTTTTG
16741 GAGGCCTAGG CTTTTGCAAA AAGCTTGCAT GCCTGCAGGT CGGCCGCCAC GACCGGTGCC
16801 GCCACCATCC CCTGACCCAC GCCCCTGACC CCTCACAAGG AGACGACCTT CCATGACCGA
16861 GTACAAGCCC ACGGTGCGCC TCGCCACCCG CGACGACGTC CCCCGGGCCG TACGCACCCT
16921 CGCCGCCGCG TTCGCCGACT ACCCCGCCAC GCGCCACCAG GTCGACCCGG ACCGCCACAT
16981 CGAGCGGGTC ACCGAGCTGC AAGAACTCTT CCTCACGCGC GTCGGGCTCG ACATCGGCAA
17041 GGTGTGGGTC GCGGACGACG GCGCCGCGGT GGCGGTCTGG ACCACGCCGG AGAGCGTCGA
17101 AGCGGGGGCG GTGTTCGCCG AGATCGGCCC GCGCATGGCC GAGTTGAGCG GTTCCCGGCT
17161 GGCCGCGCAG CAACAGATGG AAGGCCTCCT GGCGCCGCAC CGGCCCAAGG AGCCCGCGTG
17221 GTTCCTGGCC ACCGTCGGCG TCTCGCCCGA CCACCAGGGC AAGGGTCTGG GCAGCGCCGT
17281 CGTGCTCCCC GGAGTGGAGG CGGCCGAGCG CGCCGGGGTG CCCGCCTTCC TGGAGACCTC
17341 CGCGCCCCGC AACCTCCCCT TCTACGAGCG GCTCGGCTTC ACCGTCACCG CCGACGTCGA
17401 GGTGCCCGAA GGACCGCGCA CCTGGTGCAT GACCCGCAAG CCCGGTGCCT GACGCCCGCC
17461 CCACGACCCG CAGCGCCCGA CCGAAAGGAG CGCACGACCC CATGGCTCCG ACCGAAGCCG
17521 ACCCGGGCGG CCCCGCCGAC CCCGCACCCG CCCCGAGGCC CCACCGACTC TAGAGGATCA
17581 TAATCAGCCA TACCACATTT GTAGAGGTTT TACTTGCTTT AAAAAACCTC CCACACCTCC
17641 CCCTGAACCT GAAACATAAA ATGAATGCAA TTGTTGTTGT TAACTTGTTT ATTGCAGCTT
17701 ATAATGGTTA CAAATAAAGC AATAGCATCA CAAATTTCAC AAATAAAGCA TTTTTTTCAC
17761 TGCATTCTAG TTGTGGTTTG TCCAAACTCA TCAATGTATC TTATCATGTC TGGATCACTC
17821 GCCGATAGTG GAAACCGACG CCCCAGCACT CGTCCGAGGG CAAAGGAATA GGGGAGATGG
17881 GGGAGGCTAA CTGAAACACG GAAGGAGACA ATACCGGAAG GAACCCGCGC TATGACGGCA
17941 ATAAAAAGAC AGAATAAAAC GCACGGGTGT TGGGTCGTTT GTTCATAAAC GCGGGGTTCG
18001 GTCCCAGGGC TGGCACTCTG TCGATACCCC ACCGAGACCC CATTGGGGCC AATACGCCCG
18061 CGTTTCTTCC TTTTCCCCAC CCCACCCCCC AAGTTCGGGT GAAGGCCCAG GGCTCGCAGC
18121 CAACGTCGGG GCGGCAGGCC CTGCCATAGC CACTGGCCCC GTGGGTTAGG GACGGGGTCC
18181 CCCATGGGGA ATGGTTTATG GTTCGTGGGG GTTATTATTT TGGGCGTTGC GTGGGGTCTG
18241 GTCCACGACT GGACTGAGCA GACAGACCCA TGGTTTTTGG ATGGCCTGGG CATGGACCGC
```

TABLE 8-continued

Plasmid and mRNA construct sequences

```
18301 ATGTACTGGC GCGACACGAA CACCGGGCGT CTGTGGCTGC CAAACACCCC CGACCCCCAA
18361 AAACCACCGC GCGGATTTCT GGCGTGCCAA GCTAGTCGAC CAATTCTCAT GTTTGACAGC
18421 TTATCATCGC AGATCCGGGC AACGTTGTTG CATTGCTGCA GGCGCAGAAC TGGTAGGTAT
18481 GGAAGATCTC TAGAAGCTGG GTACCAGCTG CTAGCAAGCT TGCTAGCGGC CGGCTCGAGT
18541 TTACTCCCTA TCAGTGATAG AGAACGTATG TCGAGTTTAC TCCCTATCAG TGATAGAGAA
18601 CGATGTCGAG TTTACTCCCT ATCAGTGATA GAGAACGTAT GTCGAGTTTA CTCCCTATCA
18661 GTGATAGAGA ACGTATGTCG AGTTTACTCC CTATCAGTGA TAGAGAACGT ATGTCGAGTT
18721 TATCCCTATC AGTGATAGAG AACGTATGTC GAGTTTACTC CCTATCAGTG ATAGAGAACG
18781 TATGTCGAGG TAGGCGTGTA CGGTGGGAGG CCTATATAAG CAGAGCTCGT TTAGTGAACC
18841 GTCAGATCGC CG (SEQ ID NO: 39)

LINE-1 plasmid-CD5_FCR-PI3K_T2A-GFPintron (SEQ ID NO: 40)
   1 CGGCCGCGGG GGGAGGAGCC AAGATGGCCG AATAGGAACA GCTCCGGTCT ACAGCTCCCA
  61 GCGTGAGCGA CGCAGAAGAC GGTGATTTCT GCATTTCCAT CTGAGGTACC GGGTTCATCT
 121 CACTAGGGAG TGCCAGACAG TGGGCGCAGG CCAGTGTGTG TGCGCACCGT GCGCGAGCCG
 181 AAGCAGGGCG AGGCATTGCC TCACCTGGGA AGCGCAAGGG GTCAGGGAGT TCCCTTTCCG
 241 AGTCAAAGAA AGGGGTGACG GACGCACCTG GAAAATCGGG TCACTCCCAC CCGAATATTG
 301 CGCTTTTCAG ACCGGCTTAA GAAACGGCGC ACCACGAGAC TATATCCCAC ACCTGGCTCG
 361 GAGGGTCCTA CGCCCACGGA ATCTCGCTGA TTGCTAGCAC AGCAGTCTGA GATCAAACTG
 421 CAAGGCGGCA ACGAGGCTGG GGGAGGGGCG CCCGCCATTG CCCAGGCTTG CTTAGGTAAA
 481 CAAAGCAGCA GGGAAGCTCG AACTGGGTGG AGCCCACCAC AGCTCAAGGA GGCCTGCCTG
 541 CCTCTGTAGG CTCCACCTCT GGGGGCAGGG CACAGACAAA CAAAAGACA GCAGTAACCT
 601 CTGCAGACTT AAGTGTCCCT GTCTGACAGC TTTGAAGAGA GCAGTGGTTC TCCCAGCACG
 661 CAGCTGGAGA TCTGAGAACG GCAGACTGC CTCCTCAAGT GGGTCCCTGA CCCCTGACCC
 721 CCGAGCAGCC TAACTGGGAG GCACCCCCCA GCAGGGGCAC ACTGACACCT CACACGGCAG
 781 GGTATTCCAA CAGACCTGCA GCTGAGGGTC CTGTCTGTTA GAAGGAAAAC TAACAACCAG
 841 AAAGGACATC TACACCGAAA ACCCATCTGT ACATCACCAT CACAAAGAC CAAAAGTAGA
 901 TAAAACCACA AAGATGGGGA AAAAACAGAA CAGAAAAACT GGAAACTCTA AAACGCAGAG
 961 CGCCTCTCCT CCTCCAAAGG AACGCAGTTC CTCACCAGCA ACAGAACAAA GCTGGATGGA
1021 GAATGATTTT GATGAGCTGA GAGAAGAAGG CTTCAGACGA TCAAATTACT CTGAGCTACG
1081 GGAGGACATT CAAACCAAAG GCAAAGAAGT TGAAAACTTT GAAAAAAATT TAGAAGAATG
1141 TATAACTAGA ATAACCAATA CAGAGAAGTG CTTAAAGGAG CTGATGGAGC TGAAAACCAA
1201 GGCTCGAGAA CTACGTGAAG AATGCAGAAG CCTCAGGAGC CGATGCGATC AACTGGAAGA
1261 AAGGGTATCA GCAATGGAAG ATGAAATGAA TGAAATGAAG CGAGAAGGGA AGTTTAGAGA
1321 AAAAAGAATA AAAAGAAATG AGCAAAGCCT CCAAGAAATA TGGGACTATG TGAAAAGACC
1381 AAATCTACGT CTGATTGGTG TACCTGAAAG TGATGTGGAG AATGGAACCA AGTTGGAAAA
1441 CACTCTGCAG GATATTATCC AGGAGAACTT CCCCAATCTA GCAAGGCAGG CCAACGTTCA
1501 GATTCAGGAA ATACAGAGAA CGCCACAAAG ATACTCCTCG AGAAGAGCAA CTCCAAGACA
1561 CATAATTGTC AGATTCACCA AAGTTGAAAT GAAGGAAAAA ATGTTAAGGG CAGCCAGAGA
1621 GAAAGGTCGG GTTACCCTCA AAGGAAAGCC CATCAGACTA ACAGCGGATC TCTCGGCAGA
1681 AACCCTACAA GCCAGAAGAG AGTGGGGGCC AATATTCAAC ATTCTTAAAG AAAAGAATTT
1741 TCAACCCAGA ATTTCATATC CAGCCAAACT AAGCTTCATA AGTGAAGGAG AAATAAAATA
1801 CTTTATAGAC AAGCAAATGT TGAGAGATTT TGTCACCACC AGGCCTGCCC TAAAAGAGCT
1861 CCTGAAGGAA GCGCTAAACA TGGAAAGGAA CAACCGGTAC CAGCCGCTGC AAAATCATGC
1921 CAAAATGTAA AGACCATCAA GACTAGGAAG AAACTGCATC AACTAATGAG CAAAATCACC
1981 AGCTAACATC ATAATGACAG GATCAACTTC ACACATAACA ATATTAACTT TAAATATAAA
2041 TGGACTAAAT TCTGCAATTA AAAGACACAG ACTGGCAAGT TGGATAAAGA GTCAAGACCC
2101 ATCAGTGTGC TGTATTCAGG AAACCCATCT CACGTGCAGA GACACATAAA GGCTCAAAAT
2161 AAAAGGATGG AGGAAGATCT ACCAAGCCAA TGGAAAACAA AAAAAGGCAG GGGTTGCAAT
2221 CCTAGTCTCT GATAAAACAG ACTTTAAACC AACAAAGATC AAAAGAGACA AAGAAGGCCA
2281 TTACATAATG GTAAAGGGAT CAATTCAACA AGAGGAGCTA ACTATCCTAA ATATTTATGC
2341 ACCCAATACA GGAGCACCCA GATTCATAAA GCAAGTCCTC AGTGACCTAC AAAGAGACTT
2401 AGACTCCCAC ACATTAATAA TGGGAGACTT TAACACCCCA CTGTCAACAT TAGACAGATC
2461 AACGAGACAG AAAGTCAACA AGGATACCCA GGAATTGAAC TCAGCTCTGC ACCAAGCAGA
2521 CCTAATAGAC ATCTACAGAA CTCTCCACCC CAAATCAACA GAATATACAT TTTTTTCAGC
2581 ACCACACCAC ACCTATTCCA AAATTGACCA CATAGTTGGA AGTAAAGCTC TCCTCAGCAA
2641 ATGTAAAAGA ACAGAAATTA TAACAAACTA TCTCTCAGAC CACAGTGCAA TCAAACTAGA
2701 ACTCAGGATT AAGAATCTCA CTCAAAGCCG CTCAACTACA TGGAAACTGA ACAACCTGCT
2761 CCTGAATGAC TACTGGGTAC ATAACGAAAT GAAGGCAGAA ATAAAGATGT TCTTTGAAAC
2821 CAACGAGAAC AAAGACACCA CATACCAGAA TCTCTGGGAC GCATTCAAAG CAGTGTGTAG
2881 AGGGAAATTT ATAGCACTAA ATGCCTACAA GAGAAAGCAG GAAAGATCCA AAATTGACAC
2941 CCTAACATCA CAATTAAAAG AACTAGAAAA GCAAGAGCAA ACACATTCAA AAGCTAGCAG
3001 AAGGCAAGAA ATAACTAAAA TCAGAGCAGA ACTGAAGGAA ATAGAGACAC AAAAAACCCT
3061 TCAAAAAATC AATGAATCCA GGAGCTGGTT TTTTGAAAGG ATCAACAAAA TTGATAGACC
3121 GCTAGCAAGA CTAATAAAGA AAAAAAGAGA GAAGAATCAA TAAAAAATGA
3181 TAAAGGGGAT ATCACCACCG ATCCCACAGA AATACAAACT ACCATCAGAG AATACTACAA
3241 ACACCTCTAC GCAAATAAAC TAGAAAATCT AGAAGAAATG GATACATTCC TCGACACATA
3301 CACTCTCCCA AGACTAAACC AGGAAGAAGT TGAATCTCTG AATCGACCAA TAACAGGCTC
3361 TGAAATTGTG GCAATAATCA ATAGTTTACC AACCAAAAGG AGTCCAGGAC CAGATGGATT
3421 CACAGCCGAA TTCTACCAGA GGTACAAGGA GGAACTGGTA CCATTCCTTC TGAAACTATT
3481 CCAATCAATA GAAAAAGAGG GAATCCTCCC TAACTCATTT TATGAGGCCA GCATCATTCT
3541 GATACCAAAG CCGGGCAGAG ACACAACCAA AAAAGAGAAT TTTAGACCAA TATCCTTGAT
3601 GAACATTGAT GCAAAAATCC TCAATAAAAT ACTGGCAAAC CGAATCCAGC AGCACATCAA
3661 AAAGCTTATC CACCATGATC AAGTGGGCTT CATCCCTGGG ATGCAAGGCT GGTTCAATAT
3721 ACGCAAATCA ATAAATGTAA TCCAGCATAT AAACAGAGCC AAAGACAAAA ACCACATGAT
3781 TATCTCAATA GATGCAGAAA AAGCCTTTGA CAAAATTCAA CAACCCTTCA TGCTAAAAAC
3841 TCTCAATAAA TTAGGTATTG ATGGGACGTA TTTCAAAATA ATAAGAGCTA TCTATGACAA
3901 ACCCACAGCC AATATCATAC TGAATGGGCA AAAACTGGAA GCATTCCCTT TGAAAACCGG
```

TABLE 8-continued

Plasmid and mRNA construct sequences

```
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA AACCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA ACCACTGCTC AAGGAAATAA AAGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA CAAGCAATG GGAAAGGAT TCCCTATTTA ATAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAACGTT AAACCTAAAA CCATAAAAAC
4921 CCTAGAAGAA AACCTAGGCA TTACCATTCA GGACATAGGC GTGGGCAAGG ACTTCATGTC
4981 CAAAACACCA AAAGCAATGG CAACAAAAGA CAAAATTGAC AAATGGGATC TAATTAAACT
5041 AAAGAGCTTC TGCACAGCAA AAGAAACTAC CATCAGAGTG AACAGGCAAC CTACAACATG
5101 GGAGAAAATT TTTGCAACCT ACTCATCTGA CAAAGGGCTA ATATCCAGAA TCTACAATGA
5161 ACTCAAACAA ATTTACAAGA AAAAAACAAA CAACCCCATC AAAAGTGGG CGAAGGACAT
5221 GAACAGACAC TTCTCAAAAG AAGACATTTA TGCAGCCAAA AAACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCCT TTGTAGGGAC ATGGATGAAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGGAGG GGGGAGGGAT AGCATTGGGA GATATACCTA ATGCTAGATG ACACATTAGT
5941 GGGTGCAGCG CACCAGCATG GCACATGTAT ACGGATCCGA ATTCTGACG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AAGCACGAGG AAGCGGTCAG CCCATTCGCC GCCAAGCTCT TCAGCAATAT CACGGGTAGC
6181 CAACGCTATG TCCTGATAGC GGTCGGCCGC TTTACTTGTA CAGCTCGTCC ATGCCGAGAG
6241 TGATCCCGGC GGCGGTCACG AACTCCAGCA GGACCATGTG ATCGCGCTTC TCGTTGGGGT
6301 CTTTGCTCAG GGCGGACTGG GTGCTCAGGT AGTGGTTGTC GGGCAGCAGC ACGGGGCCGT
6361 CGCCGATGGG GGTGTTCTGC TGGTAGTGGT CGGCCAGGTG AGTCCAGGAG ATGTTTCAGC
6421 ACTGTTGCCT TTAGTCTCGA GGCAACTTAG ACAACTGAGT ATTGATCTGA GCACAGCAGG
6481 GTGTGAGCTG TTTGAAGATA CTGGGGTTGG GGGTGAAGAA ACTGCAGAGG ACTAACTGGG
6541 CTGAGACCCA GTGGCAATGT TTTAGGGCCT AAGGAATGCC TCTGAAAATC TAGATGGACA
6601 ACTTTGACTT TGAGAAAAGA GAGGTGGAAA TGAGGAAAAT GACTTTTCTT TATTAGATTT
6661 CGGTAGAAAG AACTTTCATC TTTTCCCTAT TTTTGTTATT CGTTTTAAAA CATCTATCTG
6721 GAGGCAGGAC AAGTATGGTC ATTAAAAAGA TGCAGGCAGA AGGCATATAT TGGCTCAGTC
6781 AAAGTGGGGA ACTTTGGTGG CCAAACATAC ATTGCTAAGG CTATTCCTAT ATCAGCTGGA
6841 CACATATAAA ATGCTGCTAA TGCTTCATTA CAAACTTATA TCCTTTAATT CCAGATGGGG
6901 GCAAAGTATG TCCAGGGGTG AGGAACAATT GAAACATTTG GCTGGAGTA GATTTTGAAA
6961 GTCAGCTCTG TGTGTGTGTG TGTGTGTGTG TGTGTGAGAG CGTGTGTTTC TTTTAACGTT
7021 TTCAGCCTAC AGCATACAGG GTTCATGGTG CAAGAAGAT AACAAGATTT AAATTATGGC
7081 CAGTGACTAG TGCTGCAAGA AGAACAACTA CCTGCATTTA ATGGGAAAGC AAAATCTCAG
7141 GCTTTGAGGG AAGTTAACAT AGGCTTGATT CTGGGTGGAA GCTGGGTGTG TAGTTATCTG
7201 GAGGCCAGGC TGGAGCTCTC AGCTCACTAT GGGTTCATCT TTATTGTCTC CTTTCATCTC
7261 AACAGCTGCA CGCTGCCGTC CTCGATGTTG TGGCGGATCT TGAAGTTCAC CTTGATGCCG
7321 TTCTTCTGCT TGTCGGCCAT GATATAGACG TTGTGGCTGT TGTAGTTGTA CTCCAGCTTG
7381 TGCCCCAGGA TGTTGCCGTC CTCCTTGAAG TCGATGCCCT TCAGCTCGAT GCGGTTCACC
7441 AGGGTGTCGC CCTCGAACTT CACCTCGGCG CGGGTCTTGT AGTTGCCGTC GTCCTTGAAG
7501 AAGATGGTGC GCTCCTGGAC GTAGCCTTCG GGCATGGCGG ACTTGAAGAA GTCGTGCTGC
7561 TTCATGTGGT CGGGGTAGCG GCTGAAGCAC TGCACGCCGT AGGTCAGGGT GGTCACGAGG
7621 GTGGGCCAGG GCACGGGCAG CTTGCCGGTG GTGCAGATGA ACTTCAGGGT CAGCTTGCCG
7681 TAGGTGGCAT CGCCCTCGCC CTCGCCGGAC ACGCTGAACT TGTGGCCGTT TACGTCGCCG
7741 TCCAGCTCGA CCAGGATGGG CACCACCCCG GTGAACAGCT CCTCGCCCTT GCTCACCATA
7801 GGGCCGGGAT TCTCCTCCAC GTCACCGCAT GTTAGAAGAC TTCCTCTGCC CTCCATGTTG
7861 TCGTAGGAGT CGGCGTCCTC TTCGTGGTTA GGTCCAGGTT GGCCTCTGAT AGACCGCAGC
7921 TGAGGAGCGG CGTACAGAAT GCCTCTCATG TCCTCATAGC TGCCGCTGCC TTGTGGAGGC
7981 TTCTCGTGCT TCAGTGTCTC GTATGTCTCT TGATTCCGGG TGCTCAGGCC GGTGTACACG
8041 CCATCAGATT TCTCGTAGCT GGTGATGGCG CCCTTCCGCA CTTGGATCTT CAGCCGTCTA
8101 CAGTACAGGG TGATGACCAG AGACAGCAGC AGGACACCAC ATGTGCCAGC CAGAGGGGCC
8161 CAAATGTAGA TATCCAGGCC TCTGGTATGC ACAGCTCCGC CTGCAGCAGG TCTACAGGCT
8221 TCAGGTCTGA GAGACAGAGG CTGGCTGGCG ATTGTAGGAG CTGGTGTAGG TGGTCTAGGA
8281 GCGGGTGTTG TTGTAGGCTT GGCGGGCAGA AACACGGGCA CGAAGTAGCT GAAGTACATG
8341 ATGCTATTGC TCAGGGCTCC GCTTCCTCCG CCGCCTGATT TGATTTCCAG CTTGGTGCCT
8401 CCGCCAAATG TCCAAGGGCT CTCGTCGTAC TGCTGGCAGT AGTAGATGCC GAAGTCCTCG
8461 TACTGCAGGC TGCTGATTGT CAGGGTGTAG TCGGTGCCAG AGCCGCTGCC AGAAAATCTG
8521 CTTGGCACGC CGCTTTCCAG TCTGTTGGCC CGGTAGATCA GTGTCTTAGG GGCCTTGCCA
8581 GGCTTCTGCT GGAACCAGCT CAGGTAGCTG TTGATGTCCT GGCTGGCTCT ACAGGTGATG
```

TABLE 8-continued

Plasmid and mRNA construct sequences

```
 8641 GTCACTCTAT CGCCCACAGA GGCAGACAGG CTGCTAGGGC TCTGTGTCAT CTGGATATCA
 8701 GAGCCACCAC CGCCAGATCC ACCGCCACCT GATCCTCCGC CTCCGCTAGA AACTGTCACT
 8761 GTGGTGCCCT GGCCCCACAC ATCGAAGTAC CAGTCGTAGC CTCTTCTGGT GCAGAAGTAC
 8821 ACGGCGGTAT CCTCGGCTCT CAGGCTGTTG ATCTGCAGGT AGGCGGTGTT CTTGCTGTCG
 8881 TCCAGGCTGA AGGTGAATCT GCCCTTAAAG CTATCGGCGT AGGTTGGCTC GCCGGTGTGG
 8941 GTATTGATCC AGCCCATCCA CTCAAGGCCT TTTCCAGGGG CCTGTCGGAC CCAGTTCATG
 9001 CCGTAGTTGG TGAAGGTGTA GCCGCTGGCG CACAGCTGA TTCTGACAGA TCCGCCAGGT
 9061 TTCACAAGTC CGCCGCCAGA CTGAACCAGC TGGATCTCAG AGATGCTACA GGCCACTGTT
 9121 CCCAGCAGCA GCAGAGACTG CAGCCACATT CGAAGCTTGA GCTCGAGATC TGAGTCCGGT
 9181 AGCGCTAGCG GATCTGACGG TTCACTAAAC CAGCTCTGCT TATATAGACC TCCCACCGTA
 9241 CACGCCTACC GCCCATTTGC GTCAATGGGG CGGAGTTGTT ACGACATTTT GGAAAGTCCC
 9301 GTTGATTTTG GTGCCAAAAC AAACTCCCAT TGACGTCAAT GGGGTGGAGA CTTGGAAATC
 9361 CCCGTGAGTC AAACCGCTAT CCACGCCCAT TGATGTACTG CCAAAACCGC ATCACCATGG
 9421 TAATAGCGAT GACTAATACG TAGATGTACT GCCAAGTAGG AAAGTCCCAT AAGGTCATGT
 9481 ACTGGGCATA ATGCCAGGCG GGCCATTTAC CGTCATTGAC GTCAATAGGG GGCGTACTTG
 9541 GCATATGATA CACTTGATGT ACTGCCAAGT GGGCAGTTTA CCGTAAATAC TCCACCCATT
 9601 GACGTCAATG GAAAGTCCCT ATTGGCGTTA CTATGGGAAC ATACGTCATT ATTGACGTCA
 9661 ATGGGCGGGG GTCGTTGGGC GGTCAGCCAG GCGGGCCATT TACCGTAAGT TATGTAACGC
 9721 GGAACTCCAT ATATGGGCTA TGAACTAATG ACCCCGTAAT TGATTACTAT TAGCCCGGGG
 9781 GATCCAGACA TGATAAGATA CATTGATGAG TTTGGACAAA CCACAACTAG AATGCAGTGA
 9841 AAAAAATGCT TTATTTGTGA AATTTGTGAT GCTATTGCTT TATTTGTAAC CATTATAAGC
 9901 TGCAATAAAC AAGTTAACAA CAACAATTGC ATTCATTTTA TGTTTCAGGT TCAGGGGGAG
 9961 GTGTGGGAGG TTTTTTAAAG CAAGTAAAAC TCTACAAAT GTGGTATGGC TGATTATGAT
10021 CCGGCTGCCT CGCGCGTTTC GGTGATGACG GTGAAAACCT CTGACACATG CAGCTCCCGG
10081 AGACGGTCAC AGCTTGTCTG TAAGCGGATG CCGGGAGCAG ACAAGCCCGT CAGGGCGCGT
10141 CAGCGGGTGT TGGCGGGTGT CGGGGCGCAG CCATGAGGTC GATCGACTCT AGAGGATCGA
10201 TCCCCGCCCC GGACGAACTA AACCTGACTA CGACATCTCT GCCCCTTCTT CGCGGGGCAG
10261 TGCATGTAAT CCCTTCAGTT GGTTGGTACA ACTTGCCAAC TGGGCCCTGT TCCACATGTG
10321 ACACGGGGGG GGACCAAACA CAAAGGGGTT CTCTGACTGT AGTTGACATC CTTATAAATG
10381 GATGTGCACA TTTGCCAACA CTGAGTGGCT TTCATCCTGG AGCAGACTTT GCAGTCTGTG
10441 GACTGCAACA CAACATTGCC TTTATGTGTA ACTCTTGGCT GAAGCTCTTA CACCAATGCT
10501 GGGGGACATG TACCTCCCAG GGGCCCAGGA AGACTACGGG AGGCTACACC AACGTCAATC
10561 AGAGGGGCCT GTGTAGCTAC CGATAAGCGG ACCCTCAAGA GGGCATTAGC AATAGTGTTT
10621 ATAAGGCCCC CTTGTTAACC CTAAACGGGT AGCATATGCT TCCCGGGTAG TAGTATATAC
10681 TATCCAGACT AACCCTAATT CAATAGCATA TGTTACCCAA CGGGAAGCAT ATGCTATCGA
10741 ATTAGGGTTA GTAAAAGGGT CCTAAGGAAC AGCGATATCT CCCACCCCAT GAGCTGTCAC
10801 GGTTTTATTT ACATGGGGTC AGGATTCCAC GAGGGTAGTG AACCATTTTA GTCACAAGGG
10861 CAGTGGCTGA AGATCAAGGA GCGGGCAGTG AACTCTCCTG AATCTTCGCC TGCTTCTTCA
10921 TTCTCCTTCG TTTAGCTAAT AGAATAACTG CTGAGTTGTG AACAGTAAGG TGTATGTGAG
10981 GTGCTCGAAA ACAAGGTTTC AGGTGACGCC CCAGAATAA AATTTGGACG GGGGTTGTGG
11041 TGGTGGCATT GTGCTATGAC ACCAATATAA CCCTCACAAA CCCCTTGGGC AATAAATACT
11101 AGTGTAGGAA TGAAACATTC TGAATATCTT TAACAATAGA AATCCATGGG GTGGGGACAA
11161 GCCGTAAAGA CTGGATGTCC ATCTCACACG AATTTATGGC TATGGGCAAC ACATAATCCT
11221 AGTGCAATAT GATACTGGGG TTATTAAGAT GTGTCCCAGG CAGGGACCAA GACAGGTGAA
11281 CCATGTTGTT ACACTCTATT TGTAACAAGG GGAAAGAGAG TGGACGCCGA CAGCAGCGGA
11341 CTCCACTGGT TGTCTCTAAC ACCCCCGAAA ATTAAACGGG GCTCCACGCC AATGGGGCCC
11401 ATAAACAAAG ACAAGTGGCC ACTCTTTTTT TTGAAATTGT GGAGTGGGGG CACGCGTCAG
11461 CCCCCACACG CCGCCCTGCG GTTTTGGACT GTAAAATAAG GGTGTAATAA CTTGGCTGAT
11521 TGTAACCCCG CTAACCACTG CGGTCAAACC ACTTGCCCAC AAAACCACTA ATGGCACCCC
11581 GGGGAATACC TGCATAAGTA GGTGGGCGGG CCAAGATAGG GGCGCGATTG CTGCGATCTG
11641 GAGGACAAAT TACACACACT TGCGCCTGAG CGCCAAGCAC AGGGTTGTTG GTCCTCATAT
11701 TCACGAGGTC GCTGAGAGCA CGGTGGGCTA ATGTTGCCAT GGGTAGCATA TACTACCCAA
11761 ATATCTGGAT AGCATATGCT ATCCTAATCT ATATCTGGGT AGCATAGGCT ATCCTAATCT
11821 ATATCTGGGT AGCATATGCT ATCCTAATCT ATATCTGGGT AGTATATGCT ATCCTAATTT
11881 ATATCTGGGT AGCATAGGCT ATCCTAATCT ATATCTGGGT AGCATATGCT ATCCTAATCT
11941 ATATCTGGGT AGTATATGCT ATCCTAATCT GTATCCGGGT AGCATATGCT ATCCTAATAG
12001 AGATTAGGGT AGTATATGCT ATCCTAATTT ATATCTGGGT AGCATATACT ACCCAAATAT
12061 CTGGATAGCA TATGCTATCC TAATCTATAT CTGGGTAGCA TATGCTATCC TAATCTATAT
12121 CTGGGTAGCA TAGGCTATCC TAATCTATAT CTGGGTAGCA TATGCTATCC TAATCTATAT
12181 CTGGGTAGTA TATGCTATCC TAATTTATAT CTGGGTAGCA TAGGCTATCC TAATCTATAT
12241 CTGGGTAGCA TATGCTATCC TAATCTATAT CTGGGTAGTA TATGCTATCC TAATCTGTAT
12301 CCGGGTAGCA TATGCTATCC TCATGCATAT ACAGTCAGCA TATGATACCC AGTAGTAGAG
12361 TGGGAGTGCT ATCCTTTGCA TATGCCGCCA CCTCCCAAGG GGGCGTGAAT TTTCGCTGCT
12421 TGTCCTTTTC CTGCATGCTG GTTGCTCCCA TTCTTAGGTG AATTTAAGGA GGCCAGGCTA
12481 AAGCCGTCGC ATGTCTGATT GCTCACCAGG TAAATGTTTC TAATGTTTTC CAACGCAAGA
12541 AGGTGTTGAG CGCGGAGCTG AGTGACGTGA AACATGGGT ATGCCCAATT GCCCCATGTT
12601 GGGAGGACGA AAATGGTGAC AAGACAGATG CCAGAAATA CACCAACAGC ACGCATGATG
12661 TCTACTGGGG ATTTATTCTT TAGTGCGGGG GAATACACGG CTTTTAATAC GATTGAGGGC
12721 GTCTCCTAAC AAGTTACATC ACTCCTGCCC TTCCTACCC TCATCTCCAT CACCTCCTTC
12781 ATCTCCGTCA TCTCCGTCAT CACCCTCCGC GGCAGCCCCT TCCACCATAG GTGGAAACCA
12841 GGGAGGCAAA TCTACTCCAT CGTCAAAGCT GCACACAGTC ACCCTGATAT TGCAGGTAGG
12901 AGCGGGCTTT GTCATAACAA GGTCCTTAAT CGCATCCTTC AAAACCTCAG CAAATATATG
12961 AGTTTGTAAA AATGACCATGA AATAACAGAC AATGCTATCC CTTAGCGGAC GGGGTTGTGG
13021 GCCGGGTCCA GGGGCCATTC CAAAGGGGAG ACGACTCAAT GGTGTAAGAC GACATTGTGG
13081 AATAGCAAGG GCAGTTCCTC GCCTTAGGTT GTAAAGGGAG GTCTTACTAC CTCCATATAC
13141 GAACACACCG GCGACCCAAG TTCCTTCGTC GGTAGTCCTT TCTACGTGAC TCCTAGCCAG
13201 GAGAGCTCTT AAACCTTCTG CAATGTTCTC AAATTTCGGG TTGGAACCTC CTTGACCACG
13261 ATGCTTTCCA AACCACCCTC CTTTTTTGCG CCTGCCTCCA TCACCCTGAC CCCGGGGTCC
```

TABLE 8-continued

Plasmid and mRNA construct sequences

```
13321 AGTGCTTGGG CCTTCTCCTG GGTCATCTGC GGGGCCCTGC TCTATCGCTC CCGGGGGCAC
13381 GTCAGGCTCA CCATCTGGGC CACCTTCTTG GTGGTATTCA AAATAATCGG CTTCCCCTAC
13441 AGGGTGGAAA AATGGCCTTC TACCTGGAGG GGGCCTGCGC GGTGGAGACC CGGATGATGA
13501 TGACTGACTA CTGGGACTCC TGGGCCTCTT TTCTCCACGT CCACGACCTC TCCCCCTGGC
13561 TCTTTCACGA CTTCCCCCCC TGGCTCTTTC ACGTCCTCTA CCCCGGCGGC CTCCACTACC
13621 TCCTCGACCC CGGCCTCCAC TACCTCCTCG ACCCCGGCCT CCACTGCCTC CTCGACCCCG
13681 GCCTCCACCT CCTGCTCCTG CCCCTCCTGC TCCTGCCCCT CCTCCTGCTC CTGCCCCTCC
13741 TGCCCCTCCT GCTCCTGCCC CTCCTGCCCC TCCTGCTCCT GCCCCTCCTG CCCCTCCTGC
13801 TCCTGCCCCT CCTGCCCCTC CTCCTGCTCC TGCCCCTCCT GCCCCTCCTC CTGCTCCTGC
13861 CCCTCCTGCC CCTCCTGCTC CTGCCCCTCC TGCCCCTCCT GCTCCTGCCC CTCCTGCCCC
13921 TCCTGCTCCT GCCCCTCCTG CTCCTGCCCC TCCTGCTCCT GCCCCTCCTG CTCCTGCCCC
13981 TCCTGCCCCT CCTGCCCCTC CTCCTGCTCC TGCCCCTCCT GCTCCTGCCC CTCCTGCCCC
14041 TCCTGCCCCT CCTGCTCCTG CCCCTCCTCC TGCTCCTGCC CCTCCTGCCC CTCCTGCCCC
14101 TCCTCCTGCT CCTGCCCCTC CTGCCCCTCC TCCTGCTCCT GCCCCTCCTC CTGCTCCTGC
14161 CCCTCCTGCC CCTCCTGCCC CTCCTCCTGC TCCTGCCCCT CCTGCCCCTC CTCCTGCTCC
14221 TGCCCCTCCT CCTGCTCCTG CCCCTCCTGC CCCTCCTGCC CCTCCTCCTG TCCTGCCCCC
14281 TCCTCCTGCT CCTGCCCCTC CTGCCCCTCC TGCCCCTCCT GCCCCTCCTC CTGCTCCTGC
14341 CCCTCCTCCT GCTCCTGCCC CTCCTGCTCC TGCCCCTCCC GCTCCTGCTC CTGCTCCTGT
14401 TCCACCGTGG GTCCCTTTGC AGCCAATGCA ACTTGACGT TTTTGGGGTC TCCGGACACC
14461 ATCTCTATGT CTTGGCCCTG ATCCTGAGCC GCCCGGGGCT CCTGGTCTTC CGCCTCCTCG
14521 TCCTCGTCCT CTTCCCCGTC CTCGTCCATG GTTATCACCC CCTCTTCTTT GAGGTCCACT
14581 GCCGCCGGAG CCTTCTGGTC CAGATGTGTC TCCCTTCTCT CCTAGGCCAT TTCCAGGTCC
14641 TGTACCTGGC CCCTCGTCAG ACATGATTCA CACTAAAAGA GATCAATAGA CATCTTTATT
14701 AGACGACGCT CAGTGAATAC AGGGAGTGCA GACTCCTGCC CCCTCCAACA GCCCCCCCAC
14761 CCTCATCCCC TTCATGGTCG CTGTCAGACA GATCCAGGTC TGAAAATTCC CCATCCTCCG
14821 AACCATCCTC GTCCTCATCA CCAATTACTC GCAGCCCGGA AAACTCCCGC TGAACATCCT
14881 CAAGATTTGC GTCCTGAGCC TCAAGCCAGG CCTCAAATTC CTCGTCCCCC TTTTTGCTGG
14941 ACGGTAGGGA TGGGGATTCT CGGGACCCCT CCTCTTCCTC TTCAAGGTCA CCAGACAGAG
15001 ATGCTACTGG GGCAACGGAA GAAAGCTGG GTGCGGCCTG TGAGGATCAG CTTATCGATG
15061 ATAAGCTGTC AAACATGAGA ATTCTTGAAG ACGAAAGGGC CTCGTGATAC GCCTATTTTT
15121 ATAGGTTAAT GTCATGATAA TAATGGTTTC TTAGACGTCA GGTGGCACTT TTCGGGGAAA
15181 TGTGCGCGGA ACCCCTATTT GTTTATTTTT CTAAATACAT TCAAATATGT ATCCGCTCAT
15241 GAGACAATAA CCCTGATAAA TGCTTCAATA ATATTGAAAA AGGAAGAGTA TGAGTATTCA
15301 ACATTTCCGT GTCGCCCTTA TTCCCTTTTT TGCGGCATTT TGCCTTCCTG TTTTTGCTCA
15361 CCCAGAAACG CTGGTGAAAG TAAAAGATGC TGAAGATCAG TTGGGTGCAC GAGTGGGTTA
15421 CATCGAACTG GATCTCAACA GCGGTAAGAT CCTTGAGAGT TTTCGCCCCG AAGAACGTTT
15481 TCCAATGATG AGCACTTTTA AAGTTCTGCT ATGTGGCGCG GTATTATCCC GTGTTGACGC
15541 CGGGCAAGAG CAACTCGGTC GCCGCATACA CTATTCTCAG AATGACTTGG TTGAGTACTC
15601 ACCAGTCACA GAAAAGCATC TTACGGATGG CATGACAGTA AGAGAATTAT GCAGTGCTGC
15661 CATAACCATG AGTGATAACA CTGCGGCCAA CTTACTTCTG ACAACGATCG GAGGACCGAA
15721 GGAGCTAACC GCTTTTTTGC ACAACATGGG GGATCATGTA ACTCGCCTTG ATCGTTGGGA
15781 ACCGGAGCTG AATGAAGCCA TACCAAACGA CGAGCGTGAC ACCACGATGC CTGCAGCAAT
15841 GGCAACAACG TTGCGCAAAC TATTAACTGG CGAACTACTT ACTCTAGCTT CCCGGCAACA
15901 ATTAATAGAC TGGATGGAGG CGGATAAAGT TGCAGGACCA CTTCTGCGCT CGGCCCTTCC
15961 GGCTGGCTGG TTTATTGCTG ATAAATCTGG AGCCGGTGAG CGTGGGTCTC GCGGTATCAT
16021 TGCAGCACTG GGGCCAGATG GTAAGCCCTC CCGTATCGTA GTTATCTACA CGACGGGGAG
16081 TCAGGCAACT ATGGATGAAC GAAATAGACA GATCGCTGAG ATAGGTGCCT CACTGATTAA
16141 GCATTGGTAA CTGTCAGACC AAGTTTACTC ATATATACTT TAGATTGATT TAAAACTTCA
16201 TTTTTAATTT AAAAGGATCT AGGTGAAGAT CCTTTTTGAT AATCTCATGA CCAAAATCCC
16261 TTAACGTGAG TTTTCGTTCC ACTGAGCGTC AGACCCCGTA GAAAAGATCA AAGGATCTTC
16321 TTGAGATCCT TTTTTTCTGC GCGTAATCTG CTGCTTGCAA ACAAAAAAAC CACCGCTACC
16381 AGCGGTGGTT TGTTTGCCGG ATCAAGAGCT ACCAACTCTT TTTCCGAAGG TAACTGGCTT
16441 CAGCAGAGCG CAGATACCAA ATACTGTCCT TCTAGTGTAG CCGTAGTTAG GCCACCACTT
16501 CAAGAACTCT GTAGCACCGC CTACATACCT CGCTCTGCTA ATCCTGTTAC CAGTGGCTGC
16561 TGCCAGTGGC GATAAGTCGT GTCTTACCGG GTTGGACTCA AGACGATAGT TACCGGATAA
16621 GGCGCAGCGG TCGGGCTGAA CGGGGGGTTC GTGCACACAG CCCAGCTTGG AGCGAACGAC
16681 CTACACCGAA CTGAGATACC TACAGCGTGA GCTATGAGAA AGCGCCACGC TTCCCGAAGG
16741 GAGAAAGGCG GACAGGTATC CGGTAAGCGG CAGGGTCGGA ACAGGAGAGC GCACGAGGGA
16801 GCTTCCAGGG GGAAACGCCT GGTATCTTTA TAGTCCTGTC GGGTTTCGCC ACCTCTGACT
16861 TGAGCGTCGA TTTTTGTGAT GCTCGTCAGG GGGCGGAGC CTATGGAAAA ACGCCAGCAA
16921 CGCGGCCTTT TTACGGTTCC TGGCCTTTTG CTGGCCTTTT GCTCACATGT TCTTTCCTGC
16981 GTTATCCCCT GATTCTGTGG ATAACCGTAT TACCGCCTTT GAGTGAGCTG ATACCGCTCG
17041 CCGCAGCCGA ACGACCGAGC GCAGCGAGTC AGTGAGCGAG GAAGCGGAAG AGCGCCTGAT
17101 GCGGTATTTT CTCCTTACGC ATCTGTGCGG TATTTCACAC CGCATATGGT GCACTCTCAG
17161 TACAATCTGC TCTGATGCCG CATAGTTAAG CCAGCTGTGA AATGTGTGTC AGTTAGGGTG
17221 TGGAAAGTCC CCAGGCTCCC CAGCAGGCAG AAGTATGCAA AGCATGCATC TCAATTAGTC
17281 AGCAACCAGG TGTGGAAAGT CCCCAGGCTC CCCAGCAGGC AGAAGTATGC AAAGCATGCA
17341 TCTCAATTAG TCAGCAACCA TAGTCCCGCC CCTAACTCCG CCCATCCCGC CCCTAACTCC
17401 CGAGGCCGCC TCGGCCTCTG AGCTATTCCA GAAGTAGTGA GGAGGCTTTT TTGGAGGCCT
17461 GCCTCCGGTG GGCGGCGCAT GCGCCCATGG CTGACTAATT TTTTTTATTT ATGCAGAGGC
17521 AGGCTTTTGC AAAAAGCTTG CATGCCTGCA GGTCGGCCGC CACGACCGGT GCCGCCACCA
17581 TCCCCTGACC CACGCCCCTG ACCCCTCACA AGGAGACGAC CTTCCATGAC CGAGTACAAG
17641 CCCACGGTGC GCCTCGCCAC CCGCGACGAC GTCCCCCGGG CCGTACGCAC CCTCGCCGCC
17701 GCGTTCGCCG ACTACCCCGC CACGCGCCAC ACCGTCGACC CGGACCGCCA CATCGAGCGG
17761 GTCACCGAGC TGCAAGAACT CTTCCTCACG CGCGTCGGGC TCGACATCGG CAAGGTGTGG
17821 GTCGCGGACG ACGGCGCCGC GGTGGCGGTC TGGACCACGC CGGAGAGCGT CGAAGCGGGG
17881 GCGGTGTTCG CCGAGATCGG CCCGCGCATG GCCGAGTTGA GCGGTTCCCG GCTGGCCGCG
17941 CAGCAACAGA TGGAAGGCCT CCTGGCGCCG CACCGGCCCA AGGAGCCCGC GTGGTTCCTG
```

TABLE 8-continued

Plasmid and mRNA construct sequences

```
18001 GCCACCGTCG GCGTCTCGCC CGACCACCAG GGCAAGGGTC TGGGCAGCGC CGTCGTGCTC
18061 CCCGGAGTGG AGGCGGCCGA GCGCGCCGGG GTGCCCGCCT TCCTGGAGAC TCCCGCCGCC
18121 CGCAACCTCC CCTTCTACGA GCGGCTCGGC TTCACCGTCA CCGCCGACGT CGAGGTGCCC
18181 GAAGGACCGC GCACCTGGTG CATGACCCGC AAGCCCGGTG CCTGACGCCC GCCCCACGAC
18241 CCGCAGCGCC CGACCGAAAG GAGCGCACGA CCCCATGGCT CCGACCGAAG CCGACCCGGG
18301 CGGCCCCGCC GACCCCGCAC CCGCCCCCGA GGCCACCGA CTCTAGAGGA TCATAATCAG
18361 CCATACCACA TTTGTAGAGG TTTTACTTGC TTTAAAAAAC CTCCCACACC TCCCCCTGAA
18421 CCTGAAACAT AAAATGAATG CAATTGTTGT TGTTAACTTG TTTATTGCAG CTTATAATGG
18481 TTACAAATAA AGCAATAGCA TCACAAATTT CACAAATAAA GCATTTTTTT CACTGCATTC
18541 TAGTTGTGGT TTGTCCAAAC TCATCAATGT ATCTTATCAT GTCTGGATCA CTCGCCGATA
18601 GTGGAAACCG ACGCCCCAGC ACTCGTCCGA GGGCAAAGGA ATAGGGGAGA TGGGGGAGGC
18661 TAACTGAAAC ACGGAAGGAG ACAATACCGG AAGGAACCCG CGCTATGACG GCAATAAAAA
18721 GACAGAATAA AACGCACGGG TGTTGGGTCG TTTGTTCATA AACGCGGGGT TCGGTCCCAG
18781 GGCTGGCACT CTGTCGATAC CCCACCGAGA CCCCATTGGG GCCAATACGC CCGCGTTTCT
18841 TCCTTTTCCC CACCCCACCC CCCAAGTTCG GGTGAAGGCC CAGGGCTCGC AGCCAACGTC
18901 GGGGCGGCAG GCCCTGCCAT AGCCACTGGC CCCGTGGGTT AGGGACGGGG TCCCCCATGG
18961 GGAATGGTTT ATGGTTCGTG GGGGTTATTA TTTTGGGCGT TGCGTGGGGT CTGGTCCACG
19021 ACTGGACTGA GCAGACAGAC CCATGGTTTT TGGATGGCCT GGGCATGGAC CGCATGTACT
19081 GGCGCGACAC GAACACCGGG CGTCTGTGGC TGCCAAACAC CCCCGACCCC CAAAAACCAC
19141 CGCGCGGATT TCTGGCGTGC CAAGCTAGTC GACCAATTCT CATGTTTGAC AGCTTATCAT
19201 CGCAGATCCG GCAACGTTG TTGCATTGCT GCAGGCGCAG AACTGGTAGG TATGGAAGAT
19261 CTCTAGAAGC TGGGTACCAG CTGCTAGCAA GCTTGCTAGC GGCCGGCTCG AGTTTACTCC
19321 CTATCAGTGA TAGAGAACGT ATGTCGAGTT TACTCCCTAT CAGTGATAGA GAACGATGTC
19381 GAGTTTACTC CCTATCAGTG ATAGAGAACG TATGTCGAGT TTACTCCCTA TCAGTGATAG
19441 AGAACGTATG TCGAGTTTAC TCCCTATCAG TGATAGAGAA CGTATGTCGA GTTTATCCCT
19501 ATCAGTGATA GAGAACGTAT GTCGAGTTTA CTCCCTATCA GTGATAGAGA ACGTATGTCG
19561 AGGTAGGCGT GTACGGTGGG AGGCCTATAT AAGCAGAGCT CGTTTAGTGA ACCGTCAGAT
19621 CGCCG (SEQ ID NO: 40)
```

LINE-1 plasmid Her2-Cd3z-T2A GFPintron (SEQ ID NO: 41)

```
   1 CGGCCGCGGG GGGAGGAGCC AAGATGGCCG AATAGGAACA GCTCCGGTCT ACAGCTCCCA
  61 GCGTGAGCGA CGCAGAAGAC GGTGATTTCT GCATTTCCAT CTGAGGTACC GGGTTCATCT
 121 CACTAGGGAG TGCCAGACAG TGGGCGCAGG CCAGTGTGTG TGCGCACCGT GCGCGAGCCG
 181 AAGCAGGGCG AGGCATTGCC TCACCTGGGA AGCGCAAGGG GTCAGGGAGT TCCCTTTCCG
 241 AGTCAAAGAA AGGGGTGACG GACGCACCTG GAAAATCGGG TCACTCCCAC CCGAATATTG
 301 CGCTTTTCAG ACCGGCTTAA GAAACGGCGC ACCACGAGAC TATATCCCAC ACTGGCTCG
 361 GAGGGTCCTA CGCCCACGGA ATCTCGCTGA TTGCTAGCAC AGCAGTCTGA GATCAAACTG
 421 CAAGGCGGCA ACGAGGCTGG GGGAGGGGCG CCCGCCATTG CCCAGGCTTG CTTAGGTAAA
 481 CAAAGCAGCA GGGAAGCTCG AACTGGGTGG AGCCCACCAC AGCTCAAGGA GGCCTGCCTG
 541 CCTCTGTAGG CTCCACCTCT GGGGGCAGGG CACGACAACA CAAAAGACA GCAGTAACCT
 601 CTGCAGACTT AAGTGTCCCT GTCTGACAGC TTTGAAGAGA GCAGTGGTTC TCCCAGCACG
 661 CAGCTGGAGA TCTGAGAACG GCAGACTGC CTCCTCAAGT GGGTCCCTGA CCCCTGACCC
 721 CCGAGCAGCC TAACTGGAG GCACCCCCCA GCAGGGGCAC ACTGACACCT CACACGGCAG
 781 GGTATTCCAA CAGACCTGCA GCTGAGGGTC CTGTCTGTTA GAAGGAAAAC TAACAACCAG
 841 AAAGGACATC TACACCGAAA ACCCATCTGT ACATCACCAT CATCAAAGAC CAAAAGTAGA
 901 TAAAACCACA AAGATGGGGA AAAAACAGAA CAGAAAAACT GGAAACTCTA AAACGCAGAG
 961 CGCCTCTCCT CCTCCAAAGG AACGCAGTTC CTCACCAGCA ACAGAACAAA GCTGGATGGA
1021 GAATGATTTT GATGAGCTGA GAGAAGAAGG CTTCAGACGA TCAAATTACT CTGAGCTACG
1081 GGAGGACATT CAAACCAAAG GCAAAGAAGT TGAAAACTTT GAAAAAAATT TAGAAGAATG
1141 TATAACTAGA ATAACCAATA CAGAGAAGTG CTTAAGGGAG CTGATGGAGC TGAAAACCAA
1201 GGCTCGAGAA CTACGTGAAG AATGCAGAAG CCTCAGGAGC CGATGCGATC AACTGGAAGA
1261 AAGGGTATCA GCAATGGAAG ATGAAATGAA TGAAATGAAC CAGAAGGGA AGTTTAGAGA
1321 AAAAAGAATA AAAAGAAATG AGCAAAGCCT CCAAGAAATA TGGGACTATG TGAAAAGACC
1381 AAATCTACGT CTGATTGGTG TACCTGAAAG TGATGTGGAG AATGGAACCA AGTTGGAAAA
1441 CACTCTGCAG GATATTATCC AGGAGAACTT CCCCAATCTA GCAAGGCAGG CCAACGTTCA
1501 GATTCAGGAA ATACAGAGAA CGCCACAAAG ATACTCCTCG AGAAGAGCAA CTCCAAGACA
1561 CATAATTGTC AGATTCACCA AAGTTGAAAT GAAGGAAAAA ATGTTAAGGG CAGCCAGAGA
1621 GAAAGGTCGG GTTACCCTCA AAGGAAAGCC CATCAGACTA ACAGCGGATC TCTCGGCAGA
1681 AACCCTACAA GCCAGAAGAG AGTGGGGGCC AATATTCAAC ATTCTTAAAG AAAAGAATTT
1741 TCAACCCAGA ATTTCATATC CAGCCAAACT AAGCTTCATA AGTGAAGGAG AAATAAAATA
1801 CTTTATAGAC AAGCAAATGT TGAGAGATTT TGTCACCACC AGGCCTGCCC TAAAAGAGCT
1861 CCTGAAGGAA GCGCTAAACA TGGAAAGGAA CAACCGGTAC CAGCCGCTGC AAAATCATGC
1921 CAAAATGTAA AGACCATCAA GACTAGGAAG AAACTGCATC AACTAATGAG CAAAATCACC
1981 AGCTAACATC ATAATGACAG GATCAACTTC ACACATAACA ATATTAACTT TAAATATAAA
2041 TGGACTAAAT TCTGCAATTA AAAGACACAG ACTGGCAAGT TGGATAAAGA GTCAAGACCC
2101 ATCAGTGTGC TGTATTCAGG AAACCCATCT CACGTGCAGA GACACACATA GGCTCAAAAT
2161 AAAAGGATGG AGGAAGATCT ACCAAGCCAA TGGAAAACAA AAAAGGCAG GGGTTGCAAT
2221 CCTAGTCTCT GATAAAACAG ACTTTAAACC AACAAAGATC AAAAGAGACA AGAAGGCCA
2281 TTACATAATG GTAAAGGGAT CAATTCAACA AGAGGAGCTA ACTATCCTAA ATATTTATGC
2341 ACCCAATACA GGAGCACCCA GATTCATAAA GCAAGTCCTC AGTGACCTAC AAAGAGACTT
2401 AGACTCCCAC ACATTAATAA TGGGAGACTT TAACACCCCA CTGTCAACAT TAGACAGATC
2461 AACGAGACAG AAAGTCAACA AGGATACCCA GGAATTGAAC TCAGCTCTGC ACCAAGCAGA
2521 CCTAATAGAC ATCTACAGAA CTCTCCACCC CAAATCAACA GAATATACAT TTTTTTCAGC
2581 ACCACACCAC ACCTATTCCA AAATTGACCA CATAGTTGGA AGTAAAGCTC TCCTCAGCAA
2641 ATGTAAAAGA ACAGAAATTA TAACAAACTA TCTCTCAGAC CACAGTGCAA TCAAACTAGA
2701 ACTCAGGATT AAGAATCTCA CTCAAAGCCG CTCAACTACA TGGAAACTGA ACAACCTGCT
2761 CCTGAATGAC TACTGGGTAC ATAACGAAAT GAAGGCAGAA ATAAAGATGT CTTTGAAAC
2821 CAACGAGAAC AAAGACACCA CATACCAGAA TCTCTGGGAC GCATTCAAAG CAGTGTGTAG
```

TABLE 8-continued

Plasmid and mRNA construct sequences

```
2881 AGGGAAATTT ATAGCACTAA ATGCCTACAA GAGAAAGCAG GAAAGATCCA AAATTGACAC
2941 CCTAACATCA CAATTAAAAG AACTAGAAAA GCAAGACAA ACACATTCAA AAGCTAGCAG
3001 AAGGCAAGAA ATAACTAAAA TCAGAGCAGA ACTGAAGGAA ATAGAGACAC AAAAAACCCT
3061 TCAAAAAATC AATGAATCCA GGAGCTGGTT TTTTGAAAGG ATCAACAAAA TTGATAGACC
3121 GCTAGCAAGA CTAATAAAGA AAAAAAGAGA GAAGAATCAA ATAGACACAA TAAAAAATGA
3181 TAAAGGGGAT ATCACCACCG ATCCCACAGA AATACAAACT ACCATCAGAG AATACTACAA
3241 ACACCTCTAC GCAAATAAAC TAGAAAATCT AGAAGAAATG GATACATTCC TCGACACATA
3301 CACTCTCCCA AGACTAAACC AGGAAGAAGT TGAATCTCTG AATCGACCAA TAACAGGCTC
3361 TGAAATTGTG GCAATAATCA ATAGTTTACC AACCAAAAAG AGTCCAGGAC CAGATGGATT
3421 CACAGCCGAA TTCTACCAGA GGTACAAGGA GGAACTGGTA CCATTCCTTC TGAAACTATT
3481 CCAATCAATA GAAAAAGAGG GAATCCTCCC TAACTCATTT TATGAGGCCA GCATCATTCT
3541 GATACCAAAG CCGGGCAGAG ACACAACCAA AAAAGAGAAT TTTAGACCAA TATCCTTGAT
3601 GAACATTGAT GCAAAAATCC TCAATAAAAT ACTGGCAAAC CGAATCCAGC AGCACATCAA
3661 AAAGCTTATC CACCATGATC AAGTGGGCTT CATCCCTGGG ATGCAAGGCT GGTTCAATAT
3721 ACGCAAATCA ATAAATGTAA TCCAGCATAT AAACAGAGCC AAAGACAAAA ACCACATGAT
3781 TATCTCAATA GATGCAGAAA AAGCCTTTGA CAAAATTCAA CAACCCTTCA TGCTAAAAAC
3841 TCTCAATAAA TTAGGTATTG ATGGGACGTA TTTCAAAATA ATAAGAGCTA TCTATGACAA
3901 ACCCACAGCC AATATCACAC TGAATGGGCA AAAACTGGAA GCATTCCCTT TGAAAACCGG
3961 CACAAGACAG GGATGCCCTC TCTCACCGCT CCTATTCAAC ATAGTGTTGG AAGTTCTGGC
4021 CAGGGCAATC AGGCAGGAGA AGGAAATAAA GGGTATTCAA TTAGGAAAAG AGGAAGTCAA
4081 ATTGTCCCTG TTTGCAGACG ACATGATTGT TTATCTAGAA AACCCCATCG TCTCAGCCCA
4141 AAATCTCCTT AAGCTGATAA GCAACTTCAG CAAAGTCTCA GGATACAAAA TCAATGTACA
4201 AAAATCACAA GCATTCTTAT ACACCAACAA CAGACAAACA GAGAGCCAAA TCATGGGTGA
4261 ACTCCCATTC ACAATTGCTT CAAAGAGAAT AAAATACCTA GGAATCCAAC TTACAAGGGA
4321 TGTGAAGGAC CTCTTCAAGG AGAACTACAA ACCACTGCTC AAGGAAATAA AGAGGAGAC
4381 AAACAAATGG AAGAACATTC CATGCTCATG GGTAGGAAGA ATCAATATCG TGAAAATGGC
4441 CATACTGCCC AAGGTAATTT ACAGATTCAA TGCCATCCCC ATCAAGCTAC CAATGACTTT
4501 CTTCACAGAA TTGGAAAAAA CTACTTTAAA GTTCATATGG AACCAAAAAA GAGCCCGCAT
4561 TGCCAAGTCA ATCCTAAGCC AAAAGAACAA AGCTGGAGGC ATCACACTAC CTGACTTCAA
4621 ACTATACTAC AAGGCTACAG TAACCAAAAC AGCATGGTAC TGGTACCAAA ACAGAGATAT
4681 AGATCAATGG AACAGAACAG AGCCCTCAGA AATAATGCCG CATATCTACA ACTATCTGAT
4741 CTTTGACAAA CCTGAGAAAA ACAAGCAATG GGGAAAGGAT TCCCTATTTA ATAAATGGTG
4801 CTGGGAAAAC TGGCTAGCCA TATGTAGAAA GCTGAAACTG GATCCCTTCC TTACACCTTA
4861 TACAAAAATC AATTCAAGAT GGATTAAAGA TTTAAACGTT AAACCTAAAA CCATAAAAAC
4921 CCTAGAAGAA AACCTAGGCA TTACCATTCA GGACATAGGC GTGGGCAAGG ACTTCATGTC
4981 CAAAACACCA AAAGCAATGG CAACAAAAGA CAAAATTGAC AAATGGGATC TAATTAAACT
5041 AAAGAGCTTC TGCACAGCAA AAGAAACTAC CATCAGAGTG AACAGGCAAC CTACAACATG
5101 GGAGAAAATT TTTGCAACCT ACTCATCTGA CAAAGGGCTA ATATCCAGAA TCTACAATGA
5161 ACTCAAACAA ATTTACAAGA AAAAAACAAA CAACCCCATC AAAAAGTGGG CGAAGGACAT
5221 GAACAGACAC TTCTCAAAAG AAGACATTTA TGCAGCCAAA AAACACATGA AGAAATGCTC
5281 ATCATCACTG GCCATCAGAG AAATGCAAAT CAAAACCACT ATGAGATATC ATCTCACACC
5341 AGTTAGAATG GCAATCATTA AAAAGTCAGG AAACAACAGG TGCTGGAGAG GATGCGGAGA
5401 AATAGGAACA CTTTTACACT GTTGGTGGGA CTGTAAACTA GTTCAACCAT TGTGGAAGTC
5461 AGTGTGGCGA TTCCTCAGGG ATCTAGAACT AGAAATACCA TTTGACCCAG CCATCCCATT
5521 ACTGGGTATA TACCCAAATG AGTATAAATC ATGCTGCTAT AAAGACACAT GCACACGTAT
5581 GTTTATTGCG GCACTATTCA CAATAGCAAA GACTTGGAAC CAACCCAAAT GTCCAACAAT
5641 GATAGACTGG ATTAAGAAAA TGTGGCACAT ATACACCATG GAATACTATG CAGCCATAAA
5701 AAATGATGAG TTCATATCTT TTGTAGGGAC ATGGATGGAA TTGGAAACCA TCATTCTCAG
5761 TAAACTATCG CAAGAACAAA AAACCAAACA CCGCATATTC TCACTCATAG GTGGGAATTG
5821 AACAATGAGA TCACATGGAC ACAGGAAGGG GAATATCACA CTCTGGGGAC TGTGGTGGGG
5881 TCGGGGGAGG GGGAGGGAT AGCATTGGGA GATATACCTA ATGCTAGATG ACACATTAGT
5941 GGGTGCAGCG CACCAGCATG GCACATGTAT ACGGATCCGA ATTCTGCAG GATCGATCCG
6001 AACAAACGAC CCAACACCCG TGCGTTTTAT TCTGTCTTTT TATTGCCGAT CCCCTCAGAA
6061 GAACTCGTCA AGAAGGCGAT AGAAGGCGAT GCGCTGCGAA TCGGGAGCGG CGATACCGTA
6121 AAGCACGAGG AAGCGGTCAG CCCATTCGCC GCCAAGCTCT TCAGCAATAT CACGGGTAGC
6181 CAACGCTATG TCCTGATAGC GGTCGGCCGC TTTACTTGTA CAGCTCGTCC ATGCCGAGAG
6241 TGATCCCGGC GGCGGTCACG AACTCCAGCA GGACCATGTG ATCGCGCTTC TCGTTGGGGT
6301 CTTTGCTCAG GGCGGACTGG GTGCTCAGGT AGTGGTTGTC GGGCAGCAGC ACGGGGCCGT
6361 CGCCGATGGG GGTGTTCTGC TGGTAGTGGT CGGCCAGGTG AGTCCAGGAG ATGTTTCAGC
6421 ACTGTTGCCT TTAGTCTCGA GGCAACTTAG ACAACTGAGT ATTGATCTGA GCACAGCAGG
6481 GTGTGAGCTG TTTGAAGATA CTGGGGTTGG GGGTGAAGAA ACTGCAGAGG ACTAACTGGG
6541 CTGAGACCCA GTGGCAATGT TTTAGGGCCT AAGGAATGCC TCTGAAAATC TAGATGGACA
6601 ACTTTGACTT TGAGAAAAGA GAGGTGGAAA TGAGGAAAAT GACTTTTCTT TATTAGATTT
6661 CGGTAGAAAG AACTTTCATC TTTCCCCTAT TTTTGTTATT CGTTTTAAAA CATCTATCTG
6721 GAGGCAGGAC AAGTATGGTC ATTAAAAAGA TGCAGGCAGA AGGCATATAT TGGCTCAGTT
6781 AAAGTGGGGA ACTTTGGTGG CCAAACATAC ATTGCTAAGG CTATTCCTAT ATCAGCTGGA
6841 CACATATAAA ATGCTGCTAA TGCTTCATTA CAAACTTATA TCCTTTAATT CCAGATGGGG
6901 GCAAAGTATG TCCAGGGGTG AGGAACAATT GAAACATTTG GCTGGAGTA GATTTGAAA
6961 GTCAGCTCTG TGTGTGTGTG TGTGTGTGTG TGTGAGGAC CGTGTGTTTC TTTTAACGTT
7021 TTCAGCCTAC AGCATACAGG GTTCATGGTG GCAAGAAGAT AACAAGATTT AAATTATGGC
7081 CAGTGACTAG TGCTGCAAGA AGAACAACTA CCTGCATTTA ATGGGAAAGC AAAATCTCAG
7141 GCTTTGAGGG AAGTTAACAT AGGCTTGATT CTGGGTGGAA GCTGGGTGTG TAGTTATCTG
7201 GAGGCAGGAC TGGAGCTCTC AGCTCACTAT GGTTCATCT TTATTGTCTC CTTTCATCTC
7261 AACAGCTGCA CGCTGCCGTC CTCGATGTTG TGGCGGATCT TGAAGTTCAC CTTGATGCCG
7321 TTCTTCTGCT TGTCGGCCAT GATATAGACG TTGTGGCTGT TGTAGTTGTA CTCCAGCTTG
7381 TGCCCCAGGA TGTTGCCGTC CTCCTTGAAG TCGATGCCCT TCAGCTCGAT GCGGTTCACC
7441 AGGGTGTCGC CCTCGAACTT CACCTCGGCG CGGGTCTTGT AGTTGCCGTC GTCCTTGAAG
7501 AAGATGGTGC GCTCCTGGAC GTAGCCTTCG GGCATGGCGG ACTTGAAGAA GTCGTGCTGC
```

TABLE 8-continued

| Plasmid and mRNA construct sequences |
|---|

```
7561 TTCATGTGGT CGGGGTAGCG GCTGAAGCAC TGCACGCCGT AGGTCAGGGT GGTCACGAGG
7621 GTGGGCCAGG GCACGGGCAG CTTGCCGGTG GTGCAGATGA ACTTCAGGGT CAGCTTGCCG
7681 TAGGTGGCAT CGCCCTCGCC CTCGCCGGAC ACGCTGAACT TGTGGCCGTT TACGTCGCCG
7741 TCCAGCTCGA CCAGGATGGG CACCACCCCG TGAACAGCT CCTCGCCCTT GCTCACCATA
7801 GGGCCGGGAT TCTCCTCCAC GTCACCGCAT GTTAGAAGAC TTCCTCTGCC CTCTCTTGGA
7861 GGCAGGGCCT GCATGTGCAG GGCATCGTAG GTATCCTTGG TGGCTGTGCT CAGTCCCTGG
7921 TACAGTCCAT CGTGGCCCTT GCCTCTTCTT CTCTCGCCCT TCATGCCGAT CTCGCTGTAG
7981 GCCTCGGCCA TCTTGTCTTT CTGCAGCTCA TTATACAGGC CCTCTTGAGG ATTCTTTCTC
8041 CGCTGGGGCT TGCCGCCCAT CTCAGGATCT CTGCCTCTCC GCTTATCCAG CACGTCGTAC
8101 TCTTCTCTTC TCCCCAGGTT CAGCTCGTTG TACAGCTGAT TCTGGCCCTG CTGGTAAGCA
8161 GGAGCGTCGG CGGATCTGCT GAACTTCACT CTGCAGTACA GGGTGATGAC CAGAGAGAGC
8221 AGCAGAACGC CACATGTGCC AGCCAGAGGG GCCCAAATGT AGATATCCAG GCCTCTGGTA
8281 TGCACAGCTC CGCCAGCTGC AGGTCTACAG GCTTCAGGTC TGAGAGACAG AGGCTGGCTG
8341 GCGATTGTAG GAGCTGGTGT AGGTGGTCTA GGAGCGGGTG TTGTTGTAGG CTTGGCGGGC
8401 AGAAACACGG GCACGAAGTG GCTGAAGTAC ATGATGCTAT TGCTCAGGGC TCCGCTTCCT
8461 CCGCCTCCGC TAGAAGAAAC TGTGACCAGG GTGCCCTGTC CCCAAACATC CATGGCGTAG
8521 AAGCCGTCGC CTCCCCATCT AGAACAGTAG TACACGGCGG TGTCCTCGGC TCTCAGGCTG
8581 TTCATCTGCA GGTAGGCGGT GTTCTTGCTG GTGTCGGCGC TGATGGTGAA TCTGCCCTTC
8641 ACGCTATCGG CGTATCTGGT GTAGCCGTTG GTGGGGTAGA TTCTGGCGAC CCATTCAAGT
8701 CCCTTTCCAG GGGCCTGTCG GACCCAGTGG ATGTAGGTGT CCTTGATGTT GAAGCCGCTG
8761 GCGGCACAAG ACAGTCTCAG AGAGCCGCCA GGCTGAACAA GTCCTCCGCC AGATTCAACC
8821 AGCTGCACCT CAGATCCTTC GCCAGATCCA GGCTTTCCAG AGCCGCTGGT GCTGCCTGTT
8881 CTCTTGATTT CCACCTTGGT GCCCTGGCCA AAGGTTGGAG GTGTGGTGTA GTGCTGCTGG
8941 CAGTAGTAGG TGGCGAAGTC CTCAGGCTGC AGGCTAGAGA TGGTCAGGGT GAAGTCGGTG
9001 CCAGATCTGC TGCCGCTGAA TCTGCTTGGC ACGCCGCTGT ACAGAAAGCT GGCGCTGTAG
9061 ATCAGCAGCT TAGGGGCTTT TCCAGGCTTC TGCTGATACC AGGCCACGGC GGTATTCACA
9121 TCCTGGCTGG CTCTACAGGT GATGGTCACT CTATCGCCCA CAGAGGCAGA CAGGCTGCTA
9181 GGGCTCTGTG TCATCTGGAT GTCGCTGATG CTGCAGGCCA CTGTTCCCAG CAGCAGCAGA
9241 GACTGCAGCC ACATTCGAAG CTTGAGCTCG AGATCTGAGT CCGGTAGCGC TAGCGGATCT
9301 GACGGTTCAC TAAACCAGCT CTGCTTATAT AGACCTCCCA CCGTACACGC CTACCGCCCA
9361 TTTGCGTCAA TGGGGCGGAG TTGTTACGAC ATTTTGGAAA GTCCCGTTGA TTTTGGTGCC
9421 AAAACAAACT CCCATTGACG TCAATGGGGT GGAGACTTGG AAATCCCCGT GAGTCAAACC
9481 GCTATCCACG CCCATTGATG TACTGCCAAA ACCGCATCAC CATGGTAATA GCGATGACTA
9541 ATACGTAGAT GTACTGCCAA GTAGGAAAGT CCCATAAGGT CATGTACTGG GCATAATGCC
9601 AGGCGGGCCA TTTACCGTCA TTGACGTCAA TAGGGGGCGT ACTTGGCATA TGATACACTT
9661 GATGTACTGC CAAGTGGGCA GTTTACCGTA AATACTCCAC CCATTGACGT CAATGGAAAG
9721 TCCCTATTGG CGTTACTATG GAACATACG TCATTATTGA CGTCAATGGG CGGGGGTCGT
9781 TGGGCGGTCA GCCAGGCGGG CCATTTACCG TAAGTTATGT AACGCGGAAC TCCATATATG
9841 GCTATGAAC TAATGACCCC GTAATTGATT ACTATTAGCC CGGGGGATCC AGACATGATA
9901 AGATACATTG ATGAGTTTGG ACAAACCACA ACTAGAATGC AGTGAAAAAA ATGCTTTATT
9961 TGTGAAATTT GTGATGCTAT TGCTTTATTT GTAACCATTA TAAGCTGCAA TAAACAAGTT
10021 AACAACAACA ATTGCATTCA TTTTATGTTT CAGGTTCAGG GGGAGGTGTG GGAGGTTTTT
10081 TAAAGCAAGT AAAACCTCTA CAAATGTGGT ATGGCTGATT ATGATCCGGC TGCCTCGCGC
10141 GTTTCGGTGA TGACGGTGAA AACCTCTGAC ACATGCAGCT CCCGGAGACG GTCACAGCTT
10201 GTCTGTAAGC GGATGCCGGG AGCAGACAAG CCCGTCAGGG CGCGTCAGCG GGTGTTGGCG
10261 GGTGTCGGGG CGCAGCCATG AGGTCGATCG ACTCTAGAGG ATCGATCCCC GCCCCGGACG
10321 AACTAAACCT GACTACGACA TCTCTGCCCC TTCTTCGCGG GGCAGTGCAT GTAATCCCTT
10381 CAGTTGGTTG GTACAACTTG CCAACTGGGC CCTGTTCCAC ATGTGACACG GGGGGGGACC
10441 AAACACAAAG GGGTTCTCTG ACTGTAGTTG ACATCCTTAT AAATGGATGT GCACATTTGC
10501 CAACACTGAG TGGCTTTCAT CCTGGAGCAG ACTTTGCAGT CTGTGGACTG CAACACAACA
10561 TTGCCTTTAT GTGTAACTCT TGGCTGAAGC TCTTACACCA ATGCTGGGG ACATGTACCT
10621 CCCAGGGGCC CAGGAAGACT ACGGGAGGCT ACACCAACGT CAATGAGGG GGCCTGTGTA
10681 GCTACCGATA AGCGGACCCT CAAGAGGGCA TTAGCAATAG TGTTTATAAG GCCCCCTTGT
10741 TAACCCTAAA CGGGTAGCAT ATGCTTCCCG GGTAGTAGTA TATACTATCC AGACTAACCC
10801 TAATTCAATA GCATATGTTA CCCAACGGGA AGCATATGCT ATCGAATTAG GGTTAGTAAA
10861 AGGGTCCTAA GGAACAGCGA TATCTCCCAC CCCATGAGCT GTCACGGTTT TATTTACATG
10921 GGGTCAGGAT TCCACGAGGG TAGTGAACCA TTTTAGTCAC AAGGGCAGTG GCTGAAGATC
10981 AAGGAGCGGG CAGTGAACTC TCCTGAATCT TCGCCTGCTT CTTCATTCTC CTTCGTTTAG
11041 CTAATAGAAT AACTGCTGAG TTGTGAACAG TAAGGTGTAT GTGAGGTGCT CGAAAACAAG
11101 GTTTCAGGTG ACGCCCCCAG AATAAAATTT GGACGGGGGA TTCAGTGGTG GCATTGTGCT
11161 ATGACACCAA TATAACCCTC ACAAACCCCT TGGGCAATAA ATACTAGTGT AGGAATGAAA
11221 CATTCTGAAT ATCTTTAACA ATAGAAATCC ATGGGGTGGG GACAAGCCGT AAAGACTGGA
11281 TGTCCATCTC ACACGAATTT ATGGCTATGG CAACACATA ATCCTAGTGC AATATGATAC
11341 TGGGGTTATT AAGATGTGTC CCAGGCAGGG ACCAAGACAG GTGAACCATG TTGTTACACT
11401 CTATTTGTAA CAAGGGGAAA GAGAGTGGAC GCCGACAGCA GCGGACTCCA CTGGTTGTCT
11461 CTAACACCCC CGAAAATTAA ACGGGCTCC AGCGCAATGG GGCCCATAAA CAAAGACAAG
11521 TGGCCACTCT TTTTTTTGAA ATTGTGGAGT GGGGGCACGC GTCAGCCCCC ACACGCCGCC
11581 CTGCGGTTTT GGACTGTAAA ATAAGGGTGT AATAACTTGG CTGATTGTAA CCCCGCTAAC
11641 CACTGCGGTC AAACCACTTG CCCACAAAAC ACCCCGGGAA ACCCTGCAT
11701 AAGTAGGTGG GCGGGCCAAG ATAGGGGCGC GATTGCTGCG ATCTGGAGGA CAAATTACAC
11761 ACACTTGCGC CTGAGCGCCA AGCACAGGGT TGTTGGTCCT CATATTCACG AGGTCGCTGA
11821 GAGCACGGTG GGCTAATGTT GCCATGGGTA GCATATACTA CCCAAATATC TGGATAGCAT
11881 ATGCTATCCT AATCTATATC TGGGTAGCAT AGGCTATCCT AATCTATATC TGGGTAGCAT
11941 ATGCTATCCT AATCTATATC TGGGTAGTAT ATGCTATCCT AATTTATATC TGGGTAGCAT
12001 AGGCTATCCT AATCTATATC TGGGTAGCAT ATGCTATCCT AATCTATATC TGGGTAGTAT
12061 ATGCTATCCT AATCTGTATC CGGGTAGCAT ATGCTATCCT AATAGAGATT AGGGTAGTAT
12121 ATGCTATCCT AATTTATATC TGGGTAGCAT ATACTACCCA AATATCTGGA TAGCATATGC
12181 TATCCTAATC TATATCTGGG TAGCATATGC TATCCTAATC TATATCTGGG TAGCATAGGC
```

TABLE 8-continued

Plasmid and mRNA construct sequences

```
12241 TATCCTAATC TATATCTGGG TAGCATATGC TATCCTAATC TATATCTGGG TAGTATATGC
12301 TATCCTAATT TATATCTGGG TAGCATAGGC TATCCTAATC TATATCTGGG TAGCATATGC
12361 TATCCTAATC TATATCTGGG TAGTATATGC TATCCTAATC TGTATCCGGG TAGCATATGC
12421 TATCCTCATG CATATACAGT CAGCATATGA TACCCAGTAG TAGAGTGGGA GTGCTATCCT
12481 TTGCATATGC CGCCACCTCC CAAGGGGGCG TGAATTTTCG CTGCTTGTCC TTTTCCTGCA
12541 TGCTGGTTGC TCCCATTCTT AGGTGAATTT AAGGAGGCCA GGCTAAAGCC GTCGCATGTC
12601 TGATTGCTCA CCAGGTAAAT GTCGCTAATG TTTTCCAACG CGAGAAGGTG TTGAGCGCGG
12661 AGCTGAGTGA CGTGACAACA TGGGTATGCC CAATTGCCCC ATGTTGGGAG GACGAAAATG
12721 GTGACAAGAC AGATGGCCAG AAATACACCA ACAGCACGCA TGATGTCTAC TGGGGATTTA
12781 TTCTTTAGTG CGGGGGAATA CACGGCTTTT AATACGATTG AGGGCGTCTC CTAACAAGTT
12841 ACATCACTCC TGCCCTTCCT CACCCTCATC TCCATCACCT CCTTCATCTC CGTCATCTCC
12901 GTCATCACCC TCCGCGGCAG CCCCTTCCAC CATAGGTGGA AACCAGGGAG GCAAATCTAC
12961 TCCATCGTCA AGCTGCACA CAGTCACCCT GATATTCAG GTAGGAGCGG GCTTTGTCAT
13021 AACAAGGTCC TTAATCGCAT CCTTCAAAAC CTCAGCAAAT ATATGAGTTT GTAAAAGAC
13081 CATGAAATAA CAGACAATGG ACTCCCTTAG CGGGCCAGGT TGTGGGCCGG GTCCAGGGGC
13141 CATTCCAAAG GGGAGACGAC TCAATGGTGT AAGACGACAT TGTGGAATAG CAAGGGCAGT
13201 TCCTCGCCTT AGGTTGTAAA GGGAGGTCTT ACTACCTCCA TATACGAACA CACCGGCGAC
13261 CCAAGTTCCT TCGTCGGTAG TCCTTTCTAC GTGACTCCTA GCCAGGAGAG CTCTTAAACC
13321 TTCTGCAATG TTCTCAAATT TCGGGTTGGA ACCTCCTTGA CCACGATGCT TTCCAAACCA
13381 CCCTCCTTTT TTGCGCCTGC CTCCATCACC CTGACCCCGG GGTCCAGTGC TTGGGCCTTC
13441 TCCTGGGTCA TCTGCGGGGC CCTGCTCTAT CGCTCCCGGG GGCACGTCAG GCTCACCATC
13501 TGGGCCACCT TCTTGGTGGT ATTCAAAATA ATCGGCTTCC CCTACAGGGT GGAAAAATGG
13561 CCTTCTACCT GGAGGGGGCC TGCGCGGTGG AGACCCGGAT GATGATGACT GACTACTGGG
13621 ACTCCTGGGC CTCTTTTCTC CACGTCCACG ACCTCTCCCC CTGGCTCTTT CACGACTTCC
13681 CCCCCTGGCT CTTTCACGTC CTCTACCCCG GCGGCCTCCA CTACCTCCTC GACCCCGGCC
13741 TCCACTACCT CCTCGACCCC GGCCTCCACT GCCTCCTCGA CCCCGGCCTC CACCTCCTGC
13801 TCCTGCCCCT CCTGCTCCTG CCCCTCCTCC TGCTCCTGCC CCTCCTGCCC CTCCTGCTGC
13861 TGCCCCTCCT GCCCCTCCTG CTCCTGCCCC TCCTGCCCCT CCTGCTCCTG CCCTCCTGC
13921 CCCTCCTCCT GCTCCTGCCC CTCCTGCCCC TCCTCCTGCT CCTGCCCCTC CTGCCCCTCC
13981 TGCTCCTGCC CCTCCTGCCC CTCCTGCTCC TGCCCCTCCT GCCCCTCCTG CTCCTGCCCC
14041 TCCTGCTCCT GCCCCTCCTG CTCCTGCCCC TCCTGCTCCT GCCCCTCCTG CCCCTCCTGC
14101 CCCTCCTCCT GCTCCTGCCC CTCCTGCTCC TGCCCCTCCT GCCCCTCCTG CCCCTCCTGC
14161 TCCTGCCCCT CCTCCTGCTC CTGCCCCTCC TGCCCCTCCT GCCCCTCCTC CTGCTCCTGC
14221 CCCTCCTGCC CCTCCTCCTG CTCCTGCCCC TCCTCCTGCT CCTGCCCCTC CTGCCCCTCC
14281 TGCCCCTCCT CCTGCTCCTG CCCCTCCTGC CCTCCTCCT GCTCCTGCCC CTCCTCCTGC
14341 TCCTGCCCCT CCTGCCCCTC CTGCCCCTCC TGCTCCTCCT GCCCCTCCTC CTGCTCCTGC
14401 CCCTCCTGCC CCTCCTGCCC CTCCTGCCCC TCCTCCTGCT CCTGCCCCTC CTCCTGCTCC
14461 TGCCCCTCCT GCTCCTGCCC CTCCCGCTCC TGCTCCTGCT CCTGTTCCAC CGTGGGTCCC
14521 TTTGCAGCCA ATGCAACTTG GACGTTTTTG GGGTCTCCGG ACACCATCTC TATGTCTTGG
14581 CCCTGATCCT GAGCCGCCCG GGGCTCCTGG TCTTCCGCCT CCTCGTCCTC GTCCTCTTCA
14641 CCGTCCTCGT CCATGGTTAT CACCCCCTCT TCTTTGAGGT CCACTGCCGC CGGAGCCTTC
14701 TGGTCCAGAT GTGTCTCCCT TCTCTCCTAG GCCATTTCCA GGTCCTGTAC CTGGCCCCTC
14761 GTCAGACATG ATTCACACTA AAAGAGATCA ATAGACATCT TTATTAGACG ACGCTCAGTG
14821 AATACAGGGA GTGCAGACTC CTGCCCCCTC CAACAGCCCC CCCACCCTCA TCCCCTTCCA
14881 GGTCGCTGTC AGACAGATCC AGGTCTGAAA ATTCCCCATC CTCCGAACCA TCCTCGTCCT
14941 CATCACCAAT TACTCGCAGC CCGGAAAACT CCCGCTGAAC ATCCTCAAGA TTTGCGTCCT
15001 GAGCCTCAAG CCAGGCCTCA AATTCCTCGT CCCCCTTTTT GCTGGACGGT AGGGATGGGG
15061 ATTCTCGGGA CCCTCCTCT TCCTCTTCAA GGTCACCAGA CAGAGATGCT ACTGGGGCAA
15121 CGGAAGAAAA GCTGGGTGCG GCCTGTGAGG ATCAGCTTAT CGATGATAAG CTGTCAAACA
15181 TGAGAATTCT TGAAGACGAA AGGGCCTCGT GATACGCCTA TTTTTATAGG TTAATGTCAT
15241 GATAATAATG GTTTCTTAGA CGTCAGGTGG CACTTTTCGG GGAAATGTGC GCGGAACCCC
15301 TATTTGTTTA TTTTTCTAAA TACATTCAAA TATGTATCCG CTCATGAGAC AATAACCCTG
15361 ATAAATGCTT CAATAATATT GAAAAAGGAA GAGTATGAGT ATTCAACATT TCCGTGTCGC
15421 CCTTATTCCC TTTTTTGCGG CATTTTGCCT TCCTGTTTTT GCTCACCCAG AAACGCTGGT
15481 GAAAGTAAAA GATGCTGAAG ATCAGTTGGG TGCACGAGTG GGTTACATCG AACTGGATCT
15541 CAACAGCGGT AAGATCCTTG AGAGTTTTCG CCCCGAAGAA CGTTTTCCAA TGATGAGCAC
15601 TTTTAAAGTT CTGCTATGTG GCGCGGTATT ATCCCGTGTT GACGCCGGGC AAGAGCAACT
15661 CGGTCGCCGC ATACACTATT CTCAGAATGA CTTGGTTGAG TACTCACCAG TCACAGAAAA
15721 GCATCTTACG GATGGCATGA CAGTAAGAGA ATTATGCAGT GCTGCCATAA CCATGAGTGA
15781 TAACACTGCG GCCAACTTAC TTCTGACAAC GATCGGAGGA CCGAAGGAGC TAACCGCTTT
15841 TTTGCACAAC ATGGGGGATC ATGTAACTCG CCTTGATCGT TGGGAACCGG AGCTGAATGA
15901 AGCCATACCA AACGACGAGC GTGACACCAC GATGCCTGCA GCAATGGCAA CAACGTTGCG
15961 CAAACTATTA ACTGGCGAAC TACTTACTCT AGCTTCCCGG CAACAATTAA TAGACTGGAT
16021 GGAGGCGGAT AAAGTTGCAG GACCACTTCT GCGCTCGGCC CTTCCGGCTG GCTGGTTTAT
16081 TGCTGATAAA TCTGGAGCCG GTGAGCGTGG GTCTCGCGGT ATCATTGCAG CACTGGGGCC
16141 AGATGGTAAG CCCTCCCGTA TCGTAGTTAT CTACACGACG GGGAGTCAGG CAACTATGGA
16201 TGAACGAAAT AGACAGATCG CTGAGATAGG TGCCTCACTG ATTAAGCATT GGTAACTGTC
16261 AGACCAAGTT TACTCATATA TACTTTAGAT TGATTTAAAA CTTCATTTTT AATTTAAAAG
16321 GATCTAGGTG AAGATCCTTT TTGATAATCT CATGACCAAA ATCCCTTAAC GTGAGTTTTC
16381 GTTCCACTGA GCGTCAGACC CCGTAGAAAA GATCAAAGGA TCTTCTTGAG ATCCTTTTTT
16441 TCTGCGCGTA ATCTGCTGCT TGCAAACAAA AAAACCACCG CTACCAGCGG TGGTTTGTTT
16501 GCCGGATCAA GAGCTACCAA CTCTTTTTCC GAAGGTAACT GGCTTCAGCA GAGCGCAGAT
16561 ACCAAATACT GTCCTTCTAG TGTAGCCGTA GTTAGGCCAC CACTTCAAGA ACTCTGTAGC
16621 ACCGCCTACA TACCTCGCTC TGCTAATCCT GTTACCAGTG GCTGCTGCCA GTGGCGATAA
16681 GTCGTGTCTT ACCGGGTTGG ACTCAAGACG ATAGTTACCG GATAAGGCGC AGCGGTCGGG
16741 CTGAACGGGG GGTTCGTGCA CACAGCCCAG CTTGGAGCGA ACGACCTACA CCGAACTGAG
16801 ATACCTACAG CGTGAGCTAT GAGAAAGCGC CACGCTTCCC GAAGGGAGAA AGGCGGACAG
16861 GTATCCGGTA AGCGGCAGGG TCGGAACAGG AGAGCGCACG AGGGAGCTTC CAGGGGGAAA
```

TABLE 8-continued

Plasmid and mRNA construct sequences

```
16921 CGCCTGGTAT CTTTATAGTC CTGTCGGGTT TCGCCACCTC TGACTTGAGC GTCGATTTTT
16981 GTGATGCTCG TCAGGGGGGC GGAGCCTATG GAAAAACGCC AGCAACGCGG CCTTTTTACG
17041 GTTCCTGGCC TTTTGCTGGC CTTTTGCTCA CATGTTCTTT CCTGCGTTAT CCCCTGATTC
17101 TGTGGATAAC CGTATTACCG CCTTTGAGTG AGCTGATACC GCTCGCCGCA GCCGAACGAC
17161 CGAGCGCAGC GAGTCAGTGA GCGAGGAAGC GGAAGAGCGC CTGATGCGGT ATTTTCTCCT
17221 TACGCATCTG TGCGGTATTT CACACCGCAT ATGGTGCACT CTCAGTACAA TCTGCTCTGA
17281 TGCCGCATAG TTAAGCCAGC TGTGGAATGT GTGTCAGTTA GGGTGTGGAA AGTCCCCAGG
17341 CTCCCCAGCA GGCAGAAGTA TGCAAAGCAT GCATCTCAAT TAGTCAGCAA CCAGGTGTGG
17401 AAAGTCCCCA GGCTCCCCAG CAGGCAGAAG TATGCAAAGC ATGCATCTCA ATTAGTCAGC
17461 AACCATAGTC CCGCCCCTAA CTCCGCCCAT CCCGCCCCTA ACTCCGCCCA GTTCCGCCCA
17521 TTCTCCGCCC CATGGCTGAC TAATTTTTTT TATTTATGCA GAGGCCGAGG CCGCCTCGGC
17581 CTCTGAGCTA TTCCAGAAGT AGTGAGGAGG CTTTTTTGGA GGCCTAGGCT TTTGCAAAAA
17641 GCTTGCATGC CTGCAGGTCG GCCGCCACGA CCGGTGCCGC CACCATCCCC TGACCCACGC
17701 CCCTGACCCC TCACAAGGAG ACGACCTTCC ATGACCGAGT ACAAGCCCAC GGTGCGCCTC
17761 GCCACCCGCG ACGACGTCCC CCGGGCCGTA CGCACCCTCG CCGCCGCGTT CGCCGACTAC
17821 CCCGCCACGC GCCACACCGT CGACCCGGAC CGCCACATCG AGCGGGTCAC CGAGCTGCAA
17881 GAACTCTTCC TCACGCGCGT CGGGCTCGAC ATCGGCAAGG TGTGGGTCGC GGACGACGGC
17941 GCCGCGGTGG CGGTCTGGAC CACGCCGGAG AGCGTCGAAG CGGGGGCGGT GTTCGCCGAG
18001 ATCGGCCCGC GCATGGCCGA GTTGAGCGGT TCCCGGCTGG CCGCGCAGCA ACAGATGGAA
18061 GGCCTCCTGG CGCCGCACCG GCCCAAGGAG CCCGCGTGGT TCCTGGCCAC CGTCGGCGTC
18121 TCGCCCGACC ACCAGGGCAA GGGTCTGGGC AGCGCCGTCG TGCTCCCCGG AGTGGAGGCG
18181 GCCGAGCGCG CCGGGGTGCC CGCCTTCCTG GAGACCTCCG CGCCCCGCAA CCTCCCCTTC
18241 TACGAGCGGC TCGGCTTCAC CGTCACCGCC GACGTCGAGG TGCCCGAAGG ACCGCGCACC
18301 TGGTGCATGA CCCGCAAGCC CGGTGCCTGA CGCCCGCCCC ACGACCCGCA GCGCCCGACC
18361 GAAAGGAGCG CACGACCCCA TGGCTCCGAC CGAAGCCGAC CCGGGCGGCC CCGCCGACCC
18421 CGCACCCGCC CCCGAGGCCC ACCGACTCTA GAGGATCATA ATCAGCCATA CCACATTTGT
18481 AGAGGTTTTA CTTGCTTTAA AAAACCTCCC ACACCTCCCC CTGAACCTGA AACATAAAAT
18541 GAATGCAATT GTTGTTGTTA ACTTGTTTAT TGCAGCTTAT AATGGTTACA AATAAAGCAA
18601 TAGCATCACA AATTTCACAA ATAAAGCATT TTTTTCACTG CATTCTAGTT GTGGTTTGTC
18661 CAAACTCATC AATGTATCTT ATCATGTCTG GATCACTGCC GATAGTGGA AACCGACGCC
18721 CCAGCACTCG TCCGAGGGCA AAGGAATAGG GGAGATGGGG GAGGCTAACT GAAACACGGA
18781 AGGAGACAAT ACCGGAAGGA ACCCGCGCTA TGACGGCAAT AAAAAGACAG AATAAAACGC
18841 ACGGGTGTTG GGTCGTTTGT TCATAAACGC GGGGTTCGGT CCCAGGGCTG GCACTCTGTC
18901 GATACCCCAC CGAGACCCCA TTGGGGCCAA TACGCCCGCG TTTCTTCCTT TTCCCCACCC
18961 CACCCCCCAA GTTCGGGTGA AGGCCCAGGG CTCGCAGCCA ACGTCGGGGC GGCAGGCCCT
19021 GCCATAGCCA CTGGCCCCGT GGGTTAGGGA CGGGGTCCCC CATGGGGAAT GGTTTATGGT
19081 TCGTGGGGGT TATTATTTTG GGCGTTGCGT GGGGTCTGGT CCACGACTGG ACTGAGCAGA
19141 CAGACCCATG GTTTTTGGAT GGCCTGGGCA TGGACCGCAT GTACTGGCGC GACACGAACA
19201 CCGGGCGTCT GTGGCTGCCA AACACCCCCG ACCCCCAAAA ACCACCGCGC GGATTTCTGG
19261 CGTGCCAAGC TAGTCGACCA ATTCTCATGT TTGACAGCTT ATCATCGCAG ATCGGGCAA
19321 CGTTGTTGCA TTGCTGCAGG CGCAGAACTG GTAGGTATGG AAGATCTCTA GAAGCTGGGT
19381 ACCAGCTGCT AGCAAGCTTG CTAGCGGCCG GCTCGAGTTT ACTCCCTATC AGTGATAGAG
19441 AACGTATGTC GAGTTTACTC CCTATCAGTG ATAGAGAACG ATGTCGAGTT TACTCCCTAT
19501 CAGTGATAGA GAACGTATGT CGAGTTTACT CCCTATCAGT GATAGAGAAC GTATGTCGAG
19561 TTTACTCCCT ATCAGTGATA GAGAACGTAT GTCGAGTTTA TCCCTATCAG TGATAGAGAA
19621 CGTATGTCGA GTTTACTCCC TATCAGTGAT AGAGAACGTA TGTCGAGGTA GGCGTGTACG
19681 GTGGGAGGCC TATATAAGCA GAGCTCGTTT AGTGAACCGT CAGATCGCCG
      (SEQ ID NO: 41)

LINE-1 ORF2-NLS mRNA (SEQ ID NO: 42)
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCAAGATA TCCGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGGAG GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
  481 TTTGGGATTA CGTCAAGAGG CCTAACCTGC GGTTGATCGG CGTCCCCGAG AGCGACGTAG
  541 AAAACGGGAC TAAACTGGAG AATACACTTC AAGACATCAT TCAAGAAAAT TTTCCAAACC
  601 TGGCTCGGCA AGCTAATGTG CAAATCCAAG AGATCCAACG CACACCCCAG CGGTATAGCT
  661 CTCGGCGTGC CACCCCTAGG CATATTATCG TGCGCTTTAC TAAGGTGGAG ATGAAAGAGC
  721 AGATGCTGCG AGCCGCTCGG GAAAAGGGAA GGGTGACTTT GAAGGGCAAA CCTATTCGGC
  781 TGACGGTTGA CCTTAGCGCC GAGACACTCC AGGCACGCCG GAATGGGGC CCCATCTTTA
  841 ATATCCTGAA GGAGAAGAAC TTCCAGCCAC GAATCTCTTA CCCTGCAAAG TTGAGTTTTA
  901 TCTCCGAGGG TGAGATTAAG TATTTCATCG ATAAACAGAT GCTGCGAGAC TTCGTGACAA
  961 CTCGCCCAGC TCTCAAGGAA CTGCTCAAAG AGGCTCTTAA TATGGAGCGC AATAATAGAT
 1021 ATCAACCCTT GCAGAACCAC GCAAAGATGT GAGACAGCCG TCAGACCATC AAGACTAGGA
 1081 AGAAACTGCA TCAACTAATG AGCAAAATCA CCAGCTAACA TCATAGTATA CATGACCGGC
 1141 TCTAACTCAC ATATCACCAT CCTTACACTT AACATTAACG GCCTCAACTC AGCTATCAAG
 1201 CGCCATCGGC TGGCCAGCTG GATCAAATCA CAGGATCCAA GCGTTTGTTG CATCCAAGAG
 1261 ACCCACCTGA CCTGTAGAGA TACTCACCGC CTCAAGATCA AGGGATGGCG AAAGATTTAT
 1321 CAGGCGAACG GTAAGCAGAA GAAAGCCGGA CGCAATTC TGGTCTCAGA CAGACGGAT
 1381 TTCAAGCCCA CCAAAATTAA GCGTGATAAG GAAGGTCACT ATATTATGGT GAAAGGCAGC
 1441 ATACAGCAGG AAGAACTTAC CATATTGAAC ATCTACGCGC CAAACACCGG CGCACCTCGC
 1501 TTTTATCAAAC AGGTCCTGTC CGATCTGCAG CGAGATCTGG ATTCTCATAC GTTGATTATG
 1561 GGTGATTTCA ATACACCATT GAGCACCCTG GATCGCAGCA CCAGGCAAAA GGTAAATAAA
 1621 GACACGCAAG AGCTCAATAG CGCACTGCAT CAGGCAGATC TCATTGATAT TTATCGCACT
```

TABLE 8-continued

Plasmid and mRNA construct sequences

```
1681 CTTCATCCTA AGAGTACCGA GTACACATTC TTCAGCGCCC CACATCATAC ATACTCAAAG
1741 ATCGATCATA TCGTCGGCTC AAAGGCTCTG CTGTCAAAGT GCAAGCGCAC AGAGATAATT
1801 ACAAATTACC TGTCAGATCA TAGCGCGATC AAGCTCGAGC TGAGAATCAA GAACCTGACC
1861 CAGAGCCGGA GTACCACTTG GAAGCTTAAT AACCTGCTGC TCAACGATTA TTGGGTCCAC
1921 AATGAGATGA AGGCAGAGAT TAAAATGTTC TTCGAAACAA ATGAGAATAA GGATACTACC
1981 TATCAAAACC TTTGGGATGC CTTTAAGGCC GTCTGCAGAG GCAAGTTCAT CGCCCTCAAC
2041 GCCTATAAAA GAAAACAAGA GAGATCTAAG ATCGATACTC TCACCTCTCA GCTGAAGGAG
2101 TTGGAGAAAC AGGAACAGAC CCACTCCAAG GCGTCAAGAC GGCAGGAGAT CACAAAGATT
2161 CGCGCCGAGT TGAAAGAGAT CGAAACCCAA AAGACTCTTC AGAAAATTAA CGAGTCTCGT
2221 AGTTGGTTCT TCGAGCGGAT TAATAAGATA GACAGACCTC TGGCACGACT GATTAAGAAG
2281 AAGCGCGAAA AGAACCAGAT TGATACCATC AAGAACGACA AGGGCGACAT CACTACTGAC
2341 CCGACCGAGA TCCAGACCAC TATTCGGGAG TATTATAAGC ATTTGTATGC TAACAAGCTT
2401 GAGAACCTGG AAGAGATGGA CACTTTTCTG GATACCTATA CTCTGCCACG GCTTAATCAA
2461 GAGGAAGTCG AGTCCCTCAA CCGCCCAATT ACAGGAAGCG AGATTGTGGC CATAATTAAC
2521 TCCCTGCCGA CAAAGAAATC TCCTGGTCCG GACGGGTTTA CAGCTGAGTT TTATCAACGG
2581 TATATGGAAG AGCTTGTACC GTTTCTGCTC AAGCTCTTTC AGTCTATAGA AAAGGAAGGC
2641 ATCTTGCCCA ATTCCTTCTA CGAAGCTTCT ATAATACTTA TTCCCAAACC AGGACGCGAT
2701 ACCACAAAGA AGGAAAACTT CCGGCCCATT AGTCTCATGA ATATCGACGC TAAAATATTG
2761 AACAAGATTC TCGCCAACAG AATCCAACAA CATATTAAGA AATTGATACA TCACGACCAG
2821 GTGGGGTTTA TACCTGGCAT GCAGGGCTGG TTTAACATCC GGAAGAGTAT TAACGTCATT
2881 CAACACATTA ATAGAGCTAA GGATAAGAAT CATATGATCA TCTCTATAGA CGCGGAAAAG
2941 GCATTCGATA AGATTCAGCA GCCATTTATG CTCAAGACTC TGAACAAACT CGGCATCGAC
3001 GGAACATATT TTAAGATTAT TCGCGCAATT TACGATAAGC TGACTGCTAA CATTATCCTT
3061 AACGCCAAA AGCTCGAGGC CTTTCCGCTC AAGACTGGAA CCCGCCAAGG CTGTCCCCTC
3121 TCCCCGCTTT TGTTTAATAT TGTACTCGAG GTGCTGGCTA GGGCTATTCG TCAAGAGAAA
3181 GAGATTAAAG GGATACAGCT CGGGAAGGAA GAGGTCAAGC TTTCCTTGTT CGCCGATGAT
3241 ATGATTGTGT ACCTGGAGAA TCCTATTGTG TCTGCTCAGA ACCTTCTTAA ACTTATTTCT
3301 AACTTTAGCA AGGTCAGCGG CTATAAGATT AACGTCCAGA AATCTCAGGC CTTTCTGTAC
3361 ACAAATAATC GACAGACCGA ATCCCAGATA ATGGGTGAGC TTCCGTTTGT CATAGCCAGC
3421 AAAAGGATAA AGTATCTCGG AATCCAGCTG ACACGAGACG TTAAAGATTT GTTTAAGGAA
3481 AATTACAAGC CTCTCCTGAA AGAGATTAAG GAAGATACTA ATAAGTGGAA GAATATCCCC
3541 TGTTCATGGG TTGGCAGAAT CAACATAGTG AAGATGGCAA TACTTCCTAA AGTGATATAT
3601 CGCTTTAACG CCATCCCAAT TAAACTGCCT ATGACCTTCT TTACGGAGCT CGAGAAAACA
3661 ACCCTTAAAT TTATATGGAA TCAAAAGAGA GCAAGAATAG CGAAGTCCAT CTTGAGCCAG
3721 AAGAATAAGG CCGGTGGGAT TACTTTGCCT GATTTTAAGT TGTATTATAA AGCCACAGTA
3781 ACTAAGACAG CCTGGTATTG GTATCAGAAT AGAGACATCG ACCAGTGGAA TCGGACCCAG
3841 CCATCAGAGA TAATGCCCCA CATCTATAAT TACCTTATAT TCGATAAGCC AGAAAAGAAT
3901 AAACAGTGGG GCAAAGACAG CCTCTTCAAC AAGTGGTGTT GGGAGAATTG GCTGGCCATA
3961 TGCCGGAAAC TCAAGCTCGA CCCCTTTCTT ACACCCTACA CTAAAATCAA CAGTAGGTGG
4021 ATCAAGGACT TGAATGTCAA GCCAAAGACT ATAAAGACAC TGGAAGAGAA TCTTGGGATC
4081 ACAATACAAG ATATAGGCGT CGGCAAAGAT TTTATGTCAA AGACGCCCAA GGCCATGGCC
4141 ACTAAGGATA AGATTGATAA GTGGGACCTT ATTAAGCTCA AAAGCTTCTG TACTGCCAAG
4201 GAGACCACGA TCAGAGTTAA TAGGCAGCCC ACTACATGGG AAAAGATTTT CGCCACTTAT
4261 TCATCAGATA AGGGGTTGAT AAGCAGAATA TATAACGAGC TGAAGCAGAT TATAACAGAG
4321 AAAACGAATA ATCCCATCAA GAAGTGGGCA AAAGATATGA ACAGGCATTT TAGCAAAGAG
4381 GATATCTACG CCGCGAAGAA GCATATGAAG AAGTGTAGTT CAAGCTTGGC CATTCGTGAG
4441 ATGCAGATTA AGACGACCAT GCGATACCAC CTTACCCCAG TGAGGATGGC AATTATCAAG
4501 AAATCTGCCA ATAATAGATG TTGGCGGGGC TGTGGCAGGA TTGGCACCCT GCTCCATTGC
4561 TGGTGGGATT GCAAGCTGGT GCAGCCGCTT TGGAAATCAG TCTGGCGCTT TCTGAGGGAC
4621 CTCGAGCTTG AGATTCCCTT CGATCCCGCA ATTCCCTTGC TCGGAATCTA TCCTAACGAA
4681 TACAAGAGCT GTTGTTACAA GGATACGTGT ACCCGGATGT TCATCGCGGC CTTGTTTACG
4741 ATAGCTAAGA CGTGGAATCA GCCTAAGTGC CCCACAATGA TCGATTGGAT CAAGAAAATG
4801 TGGCATATTT ATACCATGGA GTATTACGCA GCAATTAAGA ATGACGAATT TATTTCCTTC
4861 GTTGGGACCT GGATGAAGCT GGAGACTATT ATTCTGAGCA AGCTGTCTCA GGAGCAAAAG
4921 ACAAAGCATA GAATCTTCTC TCTCATTGGT GGTAACGACT ACAAAGACGA TGACGACAAG
4981 CCCGCCGCCA AGAGGGTGAA GCTGGACTAA AGCGCTTCTA GAAGTTGTCT CCTCCTGCAC
5041 TGACTGACTG ATACAATCGA TTTCTGGATC CGCAGGCCTA ATCAACCTCT GGATTACAAA
5101 ATTTGTGAAA GATTGACTGG TATTCTTAAC TATGTTGCTC CTTTTACGCT ATGTGGATAC
5161 GCTGCTTTAA TGCCTTTGTA TCATGCTATT GCTTCCCGTA TGGCTTTCAT TTTCTCCTCC
5221 TTGTATAAAT CCTGGTTGCT GTCTCTTTAT GAGGAGTTGT GGCCCGTTGT CAGGCAACGT
5281 GGCGTGGTGT GCACTGTGTT TGCTGACGCA ACCCCCACTG GTTGGGGCAT TGCCACCACC
5341 TGTCAGCTCC TTTCCGGGAC TTTCGCTTTC CCCCTCCCTA TTGCCACGGC GGAACTCATC
5401 GCCGCCTGCC TTGCCCGCTG CTGGACAGGG CTCGGCTGTT GGGCACTGA CAATTCCGTG
5461 GTGTTGTCGG GGAAGCTGAC GTCCTTTCCA TGGCTGCTCG CCTGTGTTGC CACCTGGATT
5521 CTGCGCGGGA CGTCCTTCTG CTACGTCCCT TCGGCCCTCA ATCCAGCGGA CCTTCCTTCC
5581 CGCTGAGAGA CACAAAAAAT TCCAACACAC TATTGCAATG AAAATAAATT TCCTTTATTA
5641 GCCAGAAGTC AGATGCTCAA GGGGCTTCAT GATGTCCCCA TAATTTTTGG CAGAGGGAAA
5701 AAGATCTCAG TGGTATTTGT GAGCCAGGGC ATTGGCCTTC TGATAGGCAG CCTGCACCTG
5761 AGGAGTGCGG CCGCTTTACT TGTACAGCTC GTCCATGCCG AGAGTGATCC CGGCGGCGGT
5821 CACGAACTCC AGCAGGACCA TGTGATCGCG CTTCTCGTTG GGGTCTTTGC TCAGGGCGGA
5881 CTGGGTGCTC AGGTAGTGGT TGTCGGGCAG CAGCACGGGG CCGTCGCCGA TGGGGGTGTT
5941 CTGCTGGTAG TGGTCGGCGA GCTGCACGCT GCCGTCCTCG ATGTTGTGGC GGATCTTGAA
6001 GTTCACCTTG ATGCCGTTCT TCTGCTTGTC GGCCATGATA TAGACGTTGT GGCTGTTGTA
6061 GTTGTACTCC AGCTTGTGCC CCAGGATGTT GCCGTCCTCC TTGAAGTCGA TGCCCTTCAG
6121 CTCGATGCGG TTCACCAGGG TGTCGCCCTC GAACTTCACC TCGGCGCGGG TCTTGTAGTT
6181 GCCGTCGTCC TTGAAGAAGA TGGTGCGCTC CTGGACGTAG CCTTCGGGCA TGGCGGACTT
6241 GAAGGAGTCG TGCTGCTTCA TGTGGTCGGG GTAGCGGCTG AAGCACTGCA CGCCGTAGGT
6301 CAGGGTGGTC ACGAGGGTGG GCCAGGGCAC GGGCAGCTTG CCGGTGGTGC AGATGAACTT
```

TABLE 8-continued

Plasmid and mRNA construct sequences

```
6361  CAGGGTCAGC TTGCCGTAGG TGGCATCGCC CTCGCCCTCG CCGGACACGC TGAACTTGTG
6421  GCCGTTTACG TCGCCGTCCA GCTCGACCAG GATGGGCACC ACCCCGGTGA ACAGCTCCTC
6481  GCCCTTGCTC ACCATGGTGG CGGGATCTGA CGGTTCACTA AACCAGCTCT GCTTATATAG
6541  ACCTCCCACC GTACACGCCT ACCGCCCATT TGCGTCAATG GGGCGGAGTT GTTACGACAT
6601  TTTGGAAAGT CCCGTTGATT TTGGTGCCAA AACAAACTCC CATTGACGTC AATGGGGTGG
6661  AGACTTGGAA ATCCCCGTGA GTCAAACCGC TATCCACGCC CATTGATGTA CTGCCAAAAC
6721  CGCATCACCA TGGTAATAGC GATGACTAAT ACGTAGATGT ACTGCCAAGT AGGAAAGTCC
6781  CATAAGGTCA TGTACTGGGC ATAATGCCAG GCGGGCCATT TACCGTCATT GACGTCAATA
6841  GGGGGCGTAC TTGGCATATG ATACACTTGA TGTACTGCCA AGTGGGCAGT TTACCGTAAA
6901  TACTCCACCC ATTGACGTCA ATGGAAAGTC CTATTGGCG TTACTATGGG AACATACGTC
6961  ATTATTGACG TCAATGGGCG GGGTCGTTG GGCGGTCAGC CAGGCGGGCC ATTTACCGTA
7021  AGTTATGTAA CGGGCCTGCT GCCGGCTCTG CGGCCTCTTC CGCGTCTTCG CCTTCGCCCT
7081  CAGACGAGTC GGATCTCCCT TTGGGCCGCC TCCCCGCCTG TCTAGCTTGA CTGACTGAGA
7141  TACAGCGTAC CTTCAGCTCA CAGACATGAT AAGATACATT GATGAGTTTG GACAAACCAC
7201  AACTAGAATG CAGTGAAAAA AATGCTTTAT TTGTGAAATT TGTGATGCTA TTGCTTTATT
7261  TGTAACCATT ATAAGCTGCA ATAAACAAGT T (SEQ ID NO: 42)
```

LINE-1 alu mRNA GFP (SEQ ID NO: 43)

```
   1  TAATACGACT CACTATAGGG AGAAGTACTG CCACCATGGG CAAGAAGCAA AATCGCAAGA
  61  CGGGGAATTC CAAGACACAA TCCGCTAGCC CACCACCTAA AGAGCGTTCT AGCTCCCCTG
 121  CTACTGAGCA GTCCTGGATG GAAACGACT TCGATGAACT CCGGGAAGAG GGATTTAGGC
 181  GATCCAACTA TTCAGAACTC CGCGAAGATA TCCAGACAAA GGGGAAGGAA GTCGAGAATT
 241  TCGAGAAGAA CCTCGAGGAG TGCATCACCC GTATCACAA CACTGAGAA TGTCTCAAAG
 301  AACTCATGGA ACTTAAGACA AAAGCCAGGG AGCTTCGAGA GGAGTGTCGG AGTCTGAGAT
 361  CCAGGTGTGA CCAGCTCGAG GAGCGCGTGA GCGCGATGGA AGACGAGATG AACGAGATGA
 421  AAAGAGAGGG CAAATTCAGG GAGAAGCGCA TTAAGAGGAA CGAACAGAGT CTGCAGGAGA
 481  TTTGGGATTA CGTCAAGAGG CCTAACCTGC GGTTGATCGG CGTCCCCGAG GCGGACGTAG
 541  AAAACGGGAC TAAACTGGAG AATACACTTC AAGACATCAT TCAAGAAAAT TTTCCAAACC
 601  TGGCTCGGCA AGCTAATGTG CAAATCCAAG AGATCCAACC CACACCCCAG CGGTATAGCT
 661  CTCGGCGTGC CACCCCTAGG CATATTATCG TGCGCTTTAC TAAGGTGGAG ATGAAAGAGA
 721  AGATGCTGCG AGCCGCTCGG GAAAAGGGAA GGGTGACTTT GAAGGGCAAA CCTATTCGGC
 781  TGACGGTTGA CCTTAGCGCC GAGACACTCC AGGCACGCCG GAATGGGGC CCCATCTTTA
 841  ATATCCTGAA GGAGAAGAAC TTCCAGCCAC GAATCTCTTA CCCTGCAAAG TTGAGTTTTA
 901  TCTCCGAGGG TGAGATTAAG TATTTCATCG ATAAACAGAT GCTGCGAGAC TTCGTGACAA
 961  CTCGCCCAGC TCTCAAGGAA CTGCTCAAAG AGGCTCTTAA TATGGAGCGC AATAATAGAT
1021  ATCAACCCTT GCAGAACCAC GCAAAGATGT GAGACAGCCG TCAGACCATC AAGACTAGGA
1081  AGAACTGCA TCAACTAATG AGCAAAATCA CCAGCTAACA TCATAGTATA CATGACCGGC
1141  TCTAACTCAC ATATCACCAT CCTTACACTT AACATTAACG GCCTCAACTC AGCTATCAAG
1201  CGCCATCGGC TGGCCAGCTG GATCAAATCA CAGGATCCAA GCGTTTGTTG CATCCAAGAG
1261  ACCCACCTGA CCTGTAGAGA TACTCACCGC CTCAAGATCA AGGGATGGCG AAAGATTTAT
1321  CAGGCGAACG GTAAGCAGAA GAAAGCCGGA GTCGCAATTC TGGTCTCAGA CAAGACGGAT
1381  TTCAAGCCCA CCAAAATTAA GCGTGATAAG GAAGGTCACT ATATTATGGT GAAAGGCAGC
1441  ATACAGCAGG AAGAACTTAC CATATTGAAC ATCTACGCGC AAACACCGG CGCACCTCGC
1501  TTTATCAAAC AGGTCCTGTC CGATCTGCAG CGGAGATTG ATTCTCATAC GTGATTATG
1561  GGTGATTTCA ATACACCATT GAGCACCCTG GATCGCAGCA CCAGGCAAAA GGTAAATAAA
1621  GACACGCAAG AGCTCAATAG CGCACTGCAT CAGGCAGATC TCATTGATAT TTATCGCACT
1681  CTTCATCCTA AGAGTACCGA GTACACATTC TTCAGCGCCC ACATCATAC ATACTCAAAG
1741  ATCGATCATA TCGTCGGCTC AAAGGCTCTG CTGTCAAAGT GCAAGCGCAC AGAGATAATT
1801  ACAAATTACC TGTCAGATCA TAGCGCGATC AAGCTCGAGC TGAAATCAA GAACCTGACC
1861  CAGAGCCGGA GTACCACTTG GAAGCTTAAT AACCTGCTGC TCAACGATTA TTGGGTCCAC
1921  AATGAGATGA AGGCAGAGAT TAAAATGTTC TTCGAAACAA ATGAGAATAA GGATACTACC
1981  TATCAAAACC TTTGGGATGC CTTTAAGGCC GTCTGCAGAG GCAAGTTCAT CGCCCTCAAC
2041  GCCTATAAAA GAAAACAAGA GAGATCTAAG ATCGATACTC TCACCTCTCA GCTGAAGGAG
2101  TTGGAGAAAC AGGAACAGAC CCACTCCAAG GCGTCAAGAC GGCAGGAGAT CACAAAGATT
2161  CGCGCCGAGT TGAAAGAGAT CGAAACCCAA AAGACTCTTC AGAAAATTAA CGAGTCTCGT
2221  AGTTGGTTCT TCGAGCGGAT TAATAAGATA GACAGACCTC TGGCACGACT GATTAAGAAG
2281  AAGCGCGAAA AGAACCAGAT TGATACCATC AAGAACGACA AGGGCGACAT CACTACTGAC
2341  CCGACCGAGA TCCAGACCAC TATTCGGGAG TATTATAAGC ATTTGTATGC TAACAAGCTT
2401  GAGAACCTGG AAGAGATGGA CACTTTTCTG GATACCTATA CTCTGCCACG GCTTAATCAA
2461  GAGGAAGTCG AGTCCCTCAA CCGCCCAATT ACAGGAAGCG AGATTGTGGC CATAATTAAC
2521  TCCCTGCCGA CAAAGAAATC TCCTGGTCCG GACGGGTTTA CAGCTGAGTT TTATCAACGG
2581  TATATGGAAG AGCTTGTACC GTTTCTGCTC AAGCTCTTTC AGTCTATAGA AAAGGAAGGC
2641  ATCTTGCCCA ATTCCTTCTA CGAAGCTTCT ATAATACTTA TTCCCAAACC AGGACGCGAT
2701  ACCACAAAGA AGGAAAACTT CCGGCCCATT AGTCTCATGA ATATCGACGC TAAAATATTG
2761  AACAAGATTC TCGCCAACAA AATCCAACAA CATATTAAGA AATTGATACA TCACGACCAG
2821  GTGGGGTTTA TACCTGGCAT GCAGGGCTGG TTTAACATCC GGAAGAGTAT TAACGTCATT
2881  CAACACATTA ATAGAGCTAA GGATAAGAAT CATATGATCA TCTCTATAGA CGCGGAAAAG
2941  GCATTCGATA AGATTCAGCA GCCATTTATG CTCAAGACTC TGAACAAACT CGGCATCGAC
3001  GGAACATATT TTAAGATTAT TCGCGCAATT TACGATAAGC CTACTGCTCA CATTATCCTT
3061  AACGCCAAA AGCTCGAGGC CTTTCCGCTC AAGACTGGAA CCCGCCAAGG CTGTCCCCTC
3121  TCCCCGCTTT TGTTTAATAT TGTACTCGAG GTGCTGGCTA GGGCTATTCG TCAAGAGAAA
3181  GAGATTAAAG GGATACAGCT CGGGAAGGAA GAGGTCAAGC TTTCCTTGTT CGCCGATGAT
3241  ATGATTGTGT ACCTGGAGAA TCCTATTGTG TCTGCTCAGA ACCTTCTTAA ACTTATTTCT
3301  AACTTTAGCA AGGTCAGCGG CTATAAGATT AACGTCCAGA AATCTCAGGC CTTTCTGTAC
3361  ACAAATAATC GACAGACCGA ATCCCAGATA TGGGTGAGC TTCGTTTGT CATAGCCAGC
3421  AAAGGATAA AGTATCCGG AATCCAGCTG ACACGAGACG TTAAAGATTT GTTTAAGGAA
3481  AATTACAAGC CTCTCCTGAA AGAGATTAAG GAAGATACTA ATAAGTGGAA GAATATCCCC
3541  TGTTCATGGG TTGGCAGAAT CAACATAGTG AAGATGGCAA TACTTCCTAA AGTGATATAT
```

TABLE 8-continued

Plasmid and mRNA construct sequences

```
3601 CGCTTTAACG CCATCCCAAT TAAACTGCCT ATGACCTTCT TTACGGAGCT CGAGAAAACA
3661 ACCCTTAAAT TTATATGGAA TCAAAAGAGA GCAAGAATAG CGAAGTCCAT CTTGAGCCAG
3721 AAGAATAAGG CCGGTGGGAT TACTTTGCCT GATTTTAAGT TGTATTATAA AGCCACAGTA
3781 ACTAAGACAG CCTGGTATTG GTATCAGAAT AGAGACATCG ACCAGTGGAA TCGGACCGAA
3841 CCATCAGAGA TAATGCCCCA CATCTATAAT TACCTTATAT TCGATAAGCC AGAAAAGAAT
3901 AAACAGTGGG GCAAAGACAG CCTCTTCAAC AAGTGGTGTT GGGAGAATTG GCTGGCCATA
3961 TGCCGGAAAC TCAAGCTCGA CCCCTTTCTT ACACCCTACA CTAAAATCAA CAGTAGGTGG
4021 ATCAAGGACT TGAATGTCAA GCCAAAGACT ATAAAGCACA TGGAAGAGAA TCTTGGGATC
4081 ACAATACAAG ATATAGGCGT CGGCAAAGAT TTTATGTCAA AGACGCCCAA GGCCATGGCC
4141 ACTAAGGATA AGATTGATAA GTGGGACCTT ATTAAGCTCA AAAGCTTCTG TACTGCCAAG
4201 GAGACCACGA TCAGAGTTAA TAGGCAGCCC ACTACATGGG AAAAGATTTT CGCCACTTAT
4261 TCATCAGATA AGGGGTTGAT AAGCAGAATA TATAACGAGC TGAAGCAGAT CTACAAGAAG
4321 AAAACGAATA ATCCCATCAA GAAGTGGGCA AAAGATATGA ACAGGCATTT TAGCAAAGAG
4381 GATATCTACG CCGCAAGAA GCATATGAAG AAGTGTAGTT CAAGCTTGGC CATTCGTGAG
4441 ATGCAGATTA AGACGACCAT GCGATACCAC CTTACCCCAG TGAGGATGGC AATTATCAAG
4501 AAATCTGGCA ATAATAGATG TTGGCGGGGC TGTGGCGAGA TTGGCACCCT GCTCCATTGC
4561 TGGTGGGATT GCAAGCTGGT GCAGCCGCTT TGGAAATCAG TCTGGCGCTT TCTGAGGGAC
4621 CTCGAGCTTG AGATTCCCTT CGATCCCGCA ATTCCCTTGC TCGGAATCTA TCCTAACGAA
4681 TACAAGAGCT GTTGTTACAA GGATACGTGT ACCCGGATGT TCATCGCGGC CTTGTTTACG
4741 ATAGCTAAGA CGTGGAATCA GCCTAAGTGC CCCACAATGA TCGATTGGAT CAAGAAAATG
4801 TGGCATATTT ATACCATGGA GTATTACGCA GCAATTAAGA ATGACGAATT TATTTCCTTC
4861 GTTGGGACCT GGATGAAGCT GGAGACTATT ATTCTGAGCA AGCTGTCTCA GGAGCAAAAG
4921 ACAAAGCATA GAATCTTCTC TCTCATTGGT GGTAACGACT ACAAAGACGA TGACGACAAG
4981 TAAAGCGGCC GGGCGCGGTG GCTCACGCCT GTAATCCCAG CACTTTGGGA GGCCGAGGCG
5041 GGAGGATCGC AGTTCGAGAC CAGCGCGAGA CCCCGTCTCT ACAAAAATAC AAAAATTAGC
5101 TTCTAGAAGT TGTCTCCTCC TGCACTGACT GACTGATACA ATCGATTTCT GGATCCGCAG
5161 GCCTAATCAA CCTCTGGATT ACAAAATTTG TGAAAGATTG ACTGGTATTC TTAACTATGT
5221 TGCTCCTTTT ACGCTATGTG GATACGCTGC TTTAATGCCT TTGTATCATG CTATTGCTTC
5281 CCGTATGCT TTCATTTTCT CCTCCTTGTA TAAATCCTGG TTGCTGTCTC TTTATGAGGA
5341 GTTGTGGCCC GTTGTCAGGC AACGTGGCGT GGTGTGCACT GTGTTTGCTG ACGCAACCCC
5401 CACTGGTTGG GGCATTGCCA CCACCTGTCA GCTCCTTTCC GGGACTTTCG CTTTCCCCCT
5461 CCCTATTGCC ACGGCGGAAC TCATCGCCGC CTGCCTTGCC CGCTGCTGGA CAGGGGCTCG
5521 GCTGTTGGGC ACTGACAATT CCGTGGTGTT GTCGGGGAAG CTGACGTCCT TTCCATGGCT
5581 GCTCGCCTGT GTTGCCACCT GGATTCTGCG CGGGACGTCC TTCTGCTACG TCCCTTCGGC
5641 CCTCAATCCA GCGGACCTTC CTTCCCGCTG AGAGACACAA AAAATTCCAA CACACTATTG
5701 CAATGAAAAT AAATTTCCTT TATTAGCCAG AAGTCAGATG CTCAAGGGGC TTCATGATGT
5761 CCCCATAATT TTTGGCAGAG GGAAAAGATT CTCAGTGGTA TTTGTGAGCC AGGGCATTGG
5821 CCTTCTGATA GGCAGCCTGC ACCTGAGGAG TGCGCCGCT TTACTTGTAC AGCTCGTCCA
5881 TGCCGAGAGT GATCCCGGCG GCGGTCACGA ACTCCAGCAG GACCATGTGA TCGCGCTTCT
5941 CGTTGGGGTC TTTGCTCAGG GCGGACTGGG TGCTCAGGTA GTGGTTGTCG GGCAGCAGCA
6001 CGGGGCCGTC GCCGATGGGG GTGTTCTGCT GGTAGTGGTC GGCGAGCTGC ACGCTGCCGT
6061 CCTCGATGTT GTGGCGGATC TTGAAGTTCA CCTTGATGCC GTTCTTCTGC TTGTCGGCCA
6121 TGATATAGAC GTTGTGGCTG TTGTAGTTGT ACTCCAGCTT GTGCCCCAGG ATGTTGCCGT
6181 CCTCCTTGAA GTCGATGCCC TTCAGCTCGA TGCGGTTCAC CAGGGTGTCG CCCTCGAACT
6241 TCACCTCGGC GCGGGTCTTG TAGTTGCCGT CGTCCTTGAA GAAGATGGTG CGCTCCTGGA
6301 CGTAGCCTTC GGGCATGGCG GACTTGAAGA AGTCGTGCTG CTTCATGTGG TCGGGGTAGC
6361 GGCTGAAGCA CTGCACGCCG TAGGTCAGGG TGGTCACGAG GGTGGGCCAG GGCACGGGCA
6421 GCTTGCCGGT GGTGCAGATG AACTTCAGGG TCAGCTTGCC GTAGGTGGCA TCGCCCTCGC
6481 CCTCGCCGGA CACGCTGAAC TTGTGGCCGT TTACGTCGCC GTCCAGCTCG ACCAGGATGG
6541 GCACCACCCC GGTGAACAGC TCCTCGCCCT TGCTCACCAT GGTGGCGGGA TCTGACGGTT
6601 CACTAAACCA GCTCTGCTTA TATAGACCTC CCACCGTACA CGCCTACCGC CCATTTGCGT
6661 CAATGGGGCG GAGTTGTTAC GACATTTTGG AAAGTCCCGT TGATTTTGGT GCCAAAACAA
6721 ACTCCCATTG ACGTCAATGG GGTGGAGACT TGGAAATCCC CGTGAGTCAA ACCGCTATCC
6781 ACGCCCATTG ATGTACTGCC AAAACCGCAT CACCATGGTA ATAGCGATGA CTAATACGTA
6841 GATGTACTGC CAAGTAGGAA AGTCCCATAA GGTCATGTAC TGGGCATAAT GCCAGGCGGG
6901 CCATTTACCG TCATTGACGT CAATAGGGGG CGTACTTGGC ATATGATACA CTTGATGTAC
6961 TGCCAAGTGG GCAGTTTACC GTAAATACTC CACCCATTGA CGTCAATGGA AAGTCCCTAT
7021 TGGCGTTACT ATGGGAACAT ACGTCATTAT TGACGTCAAT GGGCGGGGT CGTTGGGCGG
7081 TCAGCCAGGC GGGCCATTTA CCGTAAGTTA TGTAACGGGC TGCTGCCGG CTCTGCGGCC
7141 TCTTCCGCGT CTTCGCCTTC GCCCTCAGAC GAGTCGGATC TCCCTTTGGG CCGCCTCCCC
7201 GCCTGTCTAG CTTGACTGAC TGAGATACAG CGTACCTTCA GCTCACAGAC ATGATAAGAT
7261 ACATTGATGA GTTTGGACAA ACCACAACTA GAATGCAGTG AAAAAAATGC TTTATTTGTG
7321 AAATTTGTGA TGCTATTGCT TTATTTGTAA CCATTATAAG CTGCAATAAA CAAGTT
     (SEQ ID NO: 43)
```

LINE-1 plasmid CVBE IRES GFP (SEQ ID NO: 44)
```
  1 TAATACGACT CACTATAGGG AGAAGTACTG CCACCATGGG CAAGAAGCAA AATCGCAAGA
 61 CGGGGAATTC CAAGACACAA TCCGCTAGCC CACCACCTAA AGAGCGTTCT AGCTCCCCTG
121 CTACTGAGCA GTCCTGGATG GAAAACGACT TCGATGAACT CCGGGAAGAG GGATTTAGGC
181 GATCCAACTA TTCAGAACTC CGCGAAGATA TCCAGACAAA GGGGAAGGAA GTCGAGAATT
241 TCGAGAAGAA CCTCGAGGAG TGCATCACCC GTATCACAAA CACTGAGAAA TGTCTCAAAG
301 AACTCATGGA ACTTAAGACA AAAGCCAGGG AGCTTCGAGA GGAGTGTCGG AGTCTGAGAT
361 CCAGGTGTGA CCAGCTCGAG GAGCGCGTGA GCGCATGGAG AGACAGGTA AACGAGATGA
421 AAAGAGAGGG CAAATTCAGG GAGAAGCGCA TTAAGGAGAA CGAACAGAGT CTGCAGGAGA
481 TTTGGGATTA CGTCAAGAGG CCTAACCTGC GGTTGATCGG CGTCCCCGAG AGCGACGTAG
541 AAAACGGGAC TAAACTGGAG AATACACTTC AAGACATCAT TCAAGAAAAT TTTCCAAACC
601 TGGCTCGGCA AGCTAATGTG CAAATCCAAG AGATCCAACG CACACCCCAG CGGTATAGCT
661 CTCGGCGTGC CACCCCTAGG CATATTATCG TGCGCTTTAC TAAGGTGGAG ATGAAAGAGA
```

TABLE 8-continued

Plasmid and mRNA construct sequences

```
 721 AGATGCTGCG AGCCGCTCGG GAAAAGGGAA GGGTGACTTT GAAGGGCAAA CCTATTCGGC
 781 TGACGGTTGA CCTTAGCGCC GAGACACTCC AGGCACGCCG GGAATGGGGC CCCATCTTTA
 841 ATATCCTGAA GGAGAAGAAC TTCCAGCCAC GAATCTCTTA CCCTGCAAAG TTGAGTTTTA
 901 TCTCCGAGGG TGAGATTAAG TATTTCATCG ATAAACAGAT GCTGCGAGAC TTCGTGACAA
 961 CTCGCCCAGC TCTCAAGGAA CTGCTCAAAG AGGCTCTTAA TATGGAGCGC AATAATAGAT
1021 ATCAACCCTT GCAGAACCAC GCAAAGATGT GAGACAGTTA AAACAGCCTG TGGGTTGATC
1081 CCACCCACAG GCCCATTGGG CGCTAGCACT CTGGTATCAC GGTACCTTTG TGCGCCTGTT
1141 TTATACCCCC TCCCCCAACT GTAACTTAGA AGTAACACAC ACCGATCAAC AGTCAGCGTG
1201 GCACACCAGC CACGTTTTGA TCAAGCACTT CTGTTACCCC GGACTGAGTA TCAATAGACT
1261 GCTCACGCGG TTGAAGGAGA AAGCGTTCGT TATCCGGCCA ACTACTTCGA AAAACCTAGT
1321 AACACCGTGG AAGTTGCAGA GTGTTTCGCT CAGCACTACC CCAGTGTAGA TCAGGTCGAT
1381 GAGTCACCGC ATTCCCCACG GGCGACCGTG GCGGTGGCTG CGTTGGCGGC CTGCCCATGG
1441 GGAAACCCAT GGGACGCTCT AATACAGACA TGGTGCGAAG AGTCTATTGA GCTAGTTGGT
1501 AGTCCTCCGG CCCCTGAATG CGGCTAATCC TAACTGCGGA GCACACACCC TCAAGCCAGA
1561 GGGCAGTGTG TCGTAACGGG CAACTCTGCA GCGGAACCGA CTACTTTGGG TGTCCGTGTT
1621 TCATTTTATT CCTATACTGG CTGCTTATGG TGACAATTGA GAGATCGTTA CCATATAGCT
1681 ATTGGATTGG CCATCCGGTG ACTAATAGAG CTATTATATA TCCCTTTGTT GGGTTTATAC
1741 CACTTAGCTT GAAAGAGGTT AAAACATTAC AATTCATTGT TAAGTTGAAT ACAGCAAATA
1801 CATGACCGGC TCTAACTCAC ATATCACCAT CCTTACTTT AACATTAACG GCCTCAACTC
1861 AGCTATCAAG CGCCATCGGC TGGCCAGCTG GATCAAATCA CAGGATCCAA GCGTTTGTTG
1921 CATCCAAGAG ACCCACCTGA CCTGTAGAGA TACTCACCGC TCAAGATCA AGGGATGGCG
1981 AAAGATTTAT CAGGCGAACG GTAAGCAGAA GAAAGCCGGA GTCGCAATTC TGGTCTCAGA
2041 CAAGACGGAT TTCAAGCCCA CCAAAATTAA GCGTGATAAG GAAGGTCACT ATATTATGGT
2101 GAAAGGCAGC ATACAGCAGG AAGAACTTAC CATATTGAAC ATCTACGCGC CAAACACCGG
2161 CGCACCTCGC TTTATCAAAC AGGTCCTGTC CGATCTGCAG CGAGATCTGG ATTCTCATAC
2221 GTTGATTATG GGTGATTTCA ATACACCATT GAGCACCCTG GATCGCAGCA CCAGGCAAAA
2281 GGTAAATAAA GACACGCAAG AGTCAATAG CGCACTGCAT CAGGCAGATC TCATTGATAT
2341 TTATCGCACT CTTCATCCTA AGAGTACCGA GTACACATTC TTCAGCGCCC CACATCATAC
2401 ATACTCAAAG ATCGATCATA TCGTCGGCTC AAAGGCTCTG CTGTCAAAGT GCAAGCGCAC
2461 AGAGATAATT ACAAATTACC TGTCAGATCA TAGCGCGATC AAGCTCGAGC TGAGAATCAA
2521 GAACCTGACC CAGAGCCGGA GTACCACTTG GAAGCTTAAT AACCTGCTGC TCAACGATTA
2581 TTGGGTCCAC AATGAGATGA AGGCAGAGAT TAAAATGTTC TTCGAAACAA ATGAGAATAA
2641 GGATACTACC TATCAAAACC TTTGGGATGC CTTTAAGGCC GTCTGCAGAG GCAAGTTCAT
2701 CGCCCTCAAC GCCTATAAAA GAAAACAAGA GAGATCTAAG ATCGATACTC TCACCTCTCA
2761 GCTGAAGGAG TTGGAGAAAC AGGAACAGAC CCACTCCAAG GCGTCAAGAC GGCAGGAGAT
2821 CACAAAGATT CGCGCCGAGT TGAAAGAGAT CAAGAACCGA AAGACTCTTC AGAAAATTAA
2881 CGAGTCTCGT AGTTGGTTCT TCGAGCGGAT TAATAAGATA GACAGACCTC TGGCACGACT
2941 GATTAAGAAG AAGCGCGAAA AGAACCAGAT TGATACCATC AAGAACGACA AGGGCGACAT
3001 CACTACTGAC CCGACCGAGA TCCAGACCAC TATTCGGGAG TATTATAAGC ATTTGTATGC
3061 TAACAAGCTT GAGAACCTGG AAGAGATGGA CACTTTTCTG GATACCTATA CTCTGCCACG
3121 GCTTAATCAA GAGGAAGTCG AGTCCCTCAA CCGCCCAATT ACAGGAAGCG AGATTGTGGC
3181 CATAATTAAC TCCCTGCCGA CAAAGAAATC TCCTGGTCCG GACGGGTTTA CAGCTGAGTT
3241 TTATCAACGG TATATGGAAG AGCTTGTACC GTTTCTGCTC AAGCTCTTTC AGTCTATAGA
3301 AAAGGAAGGC ATCTTGCCCA ATTCCTTCTA CGAAGCTTCT ATAATACTTG TCCCAAACC
3361 AGGACGCGAT ACCACAAAGA AGGAAAACTT CCGGCCCATT AGTCTCATGA ATATCGACGC
3421 TAAAATATTG AACAAGATTC TCGCCAACAG AATCAACAA CATATTAAGA AATTGATACA
3481 TCACGACCAG GTGGGGTTTA TACCTGGCAT GCAGGGCTGG TTTAACATCC GGAAGAGTAT
3541 TAACGTCATT CAACACATTA ATAGAGCTAA GGATAAGAAT CATATGATCA TCTCTATAGA
3601 CGCGGAAAAG GCATTCGATA AGATTCAGCA GCCATTTATG CTCAAGACTC TGAACAAACT
3661 CGGCATCGAC GGAACATATT TTAAGATTAT TCGCGCAATT ACGATAAGC CGACTGCTAA
3721 CATTATCCTT AACGGCCAAA AGCTCGAGGC CTTTCCGCTC AAGACTGGAA CCCGCCAAGG
3781 CTGTCCCCTC TCCCCGCTTT TGTTTAATAT TGTACTCGAG GTGCTGGCTA GGGCTATTCG
3841 TCAAGAGAAA GAGATTAAAG GGATACAGCT CGGGAAGGAA GAGGTCAAGC TTTCCTTGTT
3901 CGCCGATGAT ATGATTGTGT ACCTGGAGAA TCCTATTGTG TCTGCTCAGA ACCTTCTTAA
3961 ACTTATTTCT AACTTTAGCA AGGTCAGCGG CTATAAGATT AACGTCCAGA AATCTCAGGC
4021 CTTTCTGTAC ACAAATAATC GACAGACCGA ATCCCAGATA ATGGGTGAGC TTCCGTTTGT
4081 CATAGCCAGC AAAAGGATAA AGTATCTCGG AATCCAGCTG ACACGAGACG TTAAAGATTT
4141 GTTTAAGGAA AATTACAAGC CTCTCCTGAA AGAGATTAAG GAAGATACTA ATAAGTGGAA
4201 GAATATCCCC TGTTCATGGG TTGGCAGAAT CAACATAGTG AAGATGGCAA TACTTCCTAA
4261 AGTGATATAT CGCTTTAACG CCATCCCAAT TAAACTGCCT ATGACCTTCT TTACGGAGCT
4321 CGAGAAAACA ACCCTTAAAT TTATATGGAA TCAAAAGAGA GCAAGAATAG CGAAGTCCAT
4381 CTTGAGCCAG AAGAATAAGG CCGGTGGGAT TACTTTGCCT GATTTTAAGT TGTATTATAA
4441 AGCCACAGTA ACTAAGCACG CCTGGTATTG GTATCAGAAT AGAGACATCG ACCAGTGGAA
4501 TCGGACCGAA CCATCAGAGA TAATGCCCCA CATCTATAAT TACCTTATAT CGATAAGCC
4561 AGAAAAGAAT AAACAGTGGG GCAAAGACAG CCTCTTCAAC AAGTGGTGTT GGGAGAATTG
4621 GCTGCCCATA TGCCGGAAAC TCAAGCTCGA CCCCTTTCTT ACACCCTACA CTAAAATCAA
4681 CAGTAGGTGG ATCAAGGACT TGAATGTCAA GCCAAAGACT ATAAGACAC TGGAAGAGAA
4741 TCTTGGGATC ACAATACAAG ATATAGGCGT CGGCAAAGAT TTTATGTCAA AGACGCCCAA
4801 GGCCATGGCC ACTAAGGATA AGATTGATAA GTGGGACCTT ATTAAGCTCA AAAGCTTCTG
4861 TACTGCCAAG GAGACCACGA TCAGAGTTAA TAGGCAGCCC ACTACATGGG AAAAGATTTT
4921 CGCCACTTAT TCATCAGATA AGGGGTTGAT AAGCAGAATA TATAACGAGC TGAAGCAGAT
4981 CTACAAGAAG AAAACGAATA ATCCCATCAA GAAGTGGGCA AAGATATGA ACAGGCATTT
5041 TAGCAAAGAG GATATCTACG CCGCGAAGAA GCATATGAAG AAGTGTAGTT CAAGCTTGGA
5101 CATTCGTGAG ATGCAGATTA AGACGACCAT GGCGATACAC CTTACCCCAG TGAGGATGGC
5161 AATTATCAAG AAATCTGGCA ATAATAGATG TTGGCGGGGC TGTGGCGAGA TTGGCACCCT
5221 GCTCCATTGC TGGTGGGATT GCAAGCTGGT GCAGCCGCTT TGGAAATCAG TCTGGCGCTT
5281 TCTGAGGGAC CTCGAGCTTG AGATTCCCTT CGATCCCGCA ATTCCCTTGC TCGGAATCTA
5341 TCCTAACGAA TACAAGAGCT GTTGTTACAA GGATACGTGT ACCCGGATGT TCATCGCGGC
```

TABLE 8-continued

Plasmid and mRNA construct sequences

```
5401 CTTGTTTACG ATAGCTAAGA CGTGGAATCA GCCTAAGTGC CCCACAATGA TCGATTGGAT
5461 CAAGAAAATG TGGCATATTT ATACCATGGA GTATTACGCA GCAATTAAGA ATGACGAATT
5521 TATTTCCTTC GTTGGGACCT GGATGAAGCT GGAGACTATT ATTCTGAGCA AGCTGTCTCA
5581 GGAGCAAAAG ACAAAGCATA GAATCTTCTC TCTCATTGGT GGTAACGACT ACAAAGACGA
5641 TGACGACAAG TAAAGCGCTT CTAGAAGTTG TCTCCTCCTG CACTGACTGA CTGATACAAT
5701 CGATTTCTGG ATCCGCAGGC CTAATCAACC TCTGGATTAC AAAATTTGTG AAAGATTGAC
5761 TGGTATTCTT AACTATGTTG CTCCTTTTAC GCTATGTGGA TACGCTGCTT TAATGCCTTT
5821 GTATCATGCT ATTGCTTCCC GTATGGCTTT CATTTTCTCC TCCTTGTATA AATCCTGGTT
5881 GCTGTCTCTT TATGAGGAGT TGTGGCCCGT TGTCAGGCAA CGTGGCGTGG TGTGCACTGT
5941 GTTTGCTGAC GCAACCCCCA CTGGTTGGGG CATTGCCACC ACCTGTCAGC TCCTTTCCGG
6001 GACTTTCGCT TTCCCCCTCC CTATTGCCAC GGCGGAACTC ATCGCCGCCT GCCTTGCCCG
6061 CTGCTGGACA GGGGCTCGGC TGTTGGGCAC TGACAATTCC GTGGTGTTGT CGGGGAAGCT
6121 GACGTCCTTT CCATGGCTGC TCGCCTGTGT TGCCACCTGG ATTCTGCGCG GGACGTCCTT
6181 CTGCTACGTC CCTTCGGCCC TCAATCCAGC GGACCTTCCT TCCCGCGAAC AAACGACCCA
6241 ACACCCGTGC GTTTTATTCT GTCTTTTTAT TGCCGATCCC CTCAGAAGAA CTCGTCAAGA
6301 AGGCGATAGA AGGCGATGCG CTGCGAATCG GGAGCGGCGA TACCGTAAAG CACGAGGAAG
6361 CGGTCAGCCC ATTCGCCGCC AAGCTCTTCA GCAATATCAC GGGTAGCCAA CGCTATGTCC
6421 TGATAGCGGT CGGCCGCTTT ACTTGTACAG CTCGTCCATG CCGAGAGTGA TCCCGGCGGC
6481 GGTCACGAAC TCCAGCAGGA CCATGTGATC GCGCTTCTCG TTGGGGTCTT TGCTCAGGGC
6541 GGACTGGGTG CTCAGGTAGT GGTTGTCGGG CAGCAGCACG GGGCCGTCGC CGATGGGGGT
6601 GTTCTGCTGG TAGTGGTCGG CCAGGTGAGT CCAGGAGATG TTTCAGCACT GTTGCCTTTA
6661 GTCTCGAGGC AACTTAGACA ACTGAGTATT GATCTGAGCA CAGCAGGGTG TGAGCTGTTT
6721 GAAGATACTG GGGTTGGGGG TGAAGAAACT GCAGAGGACT AACTGGGCTG AGACCCAGTG
6781 GCAATGTTTT AGGGCCTAAG GAATGCCTCT GAAAATCTAG ATGGACAACT TTGACTTTGA
6841 GAAAAGAGAG GTGGAAATGA GGAAAATGAC TTTTCTTTAT TAGATTTCGG TAGAAAGAAC
6901 TTTCATCTTT CCCCTATTTT TGTTATTCGT TTTAAAACAT CTATCTGGAG GCAGGACAAG
6961 TATGGTCATT AAAAAGATGC AGGCAGAAGG CATATATTGG CTCAGTCAAA GTGGGGAACT
7021 TTGGTGGCCA AACATACATT GCTAAGGCTA TTCCTATATC AGCTGGACAC ATATAAAATG
7081 CTGCTAATGC TTCATTACAA ACTTATATCC TTTAATTCCA GATGGGGGCA AAGTATGTCC
7141 AGGGGTGAGG AACAATTGAA ACATTTGGGC TGGAGTAGAT TTTGAAAGTC AGCTCTGTGT
7201 GTGTGTGTGT GTGTGTGTGT GTGAGAGCGT GTGTTTCTTT TAACGTTTTC AGCCTACAGC
7261 ATACAGGGTT CATGGTGGCA AGAAGATAAC AAGATTTAAA TTATGCCAG TGACTAGTGC
7321 TGCAAGAAGA ACAACTACCT GCATTTAATG GGAAAGCAAA ATCTCAGGCT TTGAGGGAAG
7381 TTAACATAGG CTTGATTCTG GGTGGAAGCT GGGTGTGTAG TTATCTGGAG GCCAGGCTGG
7441 AGCTCTCAGC TCACTATGGG TTCATCTTTA TTGTCTCCTT TCATCTCAAC AGCTGCACGC
7501 TGCCGTCCTC GATGTTGTGG CGGATCTTGA AGTTCACCTT GATGCCGTTC TTCTGCTTGT
7561 CGGCCATGAT ATAGACGTTG TGGCTGTTGT AGTTGTACTC CAGCTTGTGC CCCAGGATGT
7621 TGCCGTCCTC CTTGAAGTCG ATGCCCTTCA GCTCGATGCG GTTCACCAGG GTGTCGCCCT
7681 CGAACTTCAC CTCGGCGCGG GTCTTGTAGT TGCCGTCGTC CTTGAAGAAG ATGGTGCGCT
7741 CCTGGACGTA GCCTTCGGGC ATGGCGGACT TGAAGAAGTC GTGCTGCTTC ATGTGGTCGG
7801 GGTAGCGGCT GAAGCACTGC ACGCCGTAGG TCAGGGTGGT CACGAGGGTG GCCAGGGCA
7861 CGGGCAGCTT GCCGGTGGTG CAGATGAACT TCAGGGTCAG CTTGCCGTAG GTGGCATCGC
7921 CCTCGCCCTC GCCGGACACG CTGAACTTGT GGCCGTTTAC GTCGCCGTCC AGCTCGACCA
7981 GGATGGGCAC CACCCCGGTG AACAGCTCCT CGCCCTTGCT CACCATGGTG GCGAATTCGA
8041 AGCTTGAGCA CGAGATCTGA GTCCGGTAGG CCTAGCGGAT CTGACGGTTC ACTAAACCAG
8101 CTCTGCTTAT ATAGACCTCC CACCGTACAC GCCTACCGCC CATTTGCGTC AATGGGGCGG
8161 AGTTGTTACG ACATTTTGGA AAGTCCCGTT GATTTTGGTG CCAAAACAAA CTCCCATTGA
8221 CGTCAATGGG GTGGAGACTT GGAAATCCCC GTGAGTCAAA CCGCTATCCA CGCCCATTGA
8281 TGTACTGCCA AAACCGCATC ACCATGGTAA TAGCGATGAC TAATACGTAG ATGTACTGCC
8341 AAGTAGGAAA GTCCCATAAG GTCATGTACT GGGCATAATG CCAGGCGGGC CATTTACCGT
8401 CATTGACGTC AATAGGGGGC GTACTTGGCA TATGATACAC TTGATGTACT GCCAAGTGGG
8461 CAGTTTACCG TAAATACTCC ACCCATTGAC GTCAATGGAA AGTCCCTATT GGCGTTACTA
8521 TGGGAACATA CGTCATTATT GACGTCAATG GGCGGGGGTC GTTGGGCGGT CAGCCAGGCG
8581 GGCCATTTAC CGTAAGTTAT GTAACGGGCC TGCTGCCGGC TCTGCGGCCT CTTCCGCGTC
8641 TTCGCCTTCG CCCTCAGACG AGTCGGATCT CCCTTTGGGC CGCCTCCCCG CCTGTCTAGC
8701 TTGACTGACT GAGATACAGC GTACCTTCAG CTCACAGACA TGATAAGATA CATTGATGAG
8761 TTTGGACAAA CCACAACTAG AATGCAGTGA AAAAAATGCT TTATTTGTGA AATTTGTGAT
8821 GCTATTGCTT TATTTGTAAC CATTATAAGC TGCAATAAAC AAGTTAACAA CAACAATTGC
8881 ATTCATTTTA TGTTTCAGGT TCAGGGGGAG GTGTGGGAGG TTTTTTAAAG CAAGTAAAAC
8941 CTCTACAAAT GTGGTATTGG CCCATCTCTA TCGGTATCGT AGCATAACCC CTTGGGGCCT
9001 CTAAACGGGT CTTGAGGGGT TTTTTGTGCC CCTCGGGCCG GATTGCTATC TACCGGCATT
9061 GGCGCAGAAA AAAATGCCTG ATGCGACGCT GCGCGTCTTA TACTCCCACA TATGCCAGAT
9121 TCAGCAACGG ATACGGCTTC CCCAACTTGC CCACTTCCAT ACGTGTCCTC CTTACCAGAA
9181 ATTTATCCTT AAGGTCGTCA GCTATCCTGC AGGCGATCTC TCGATTTCGA TCAAGACATT
9241 CCTTTAATGG TCTTTTCTGG ACACCACTAG GAGTCAGAAG TAGTTCATCA AACTTTCTTC
9301 CCTCCCTAAT CTCATTGGTT ACCTTGGGCT ATCGAAACTT AATTAAGCGA TCTGCATCTC
9361 AATTAGTCAG CAACCATAGT CCCGCCCCTA ACTCCGCCCA TCCCGCCCCT AACTCCGCCC
9421 AGTTCCGCCC ATTCTCCGCC CCATCGCTGA CTAATTTTTT TTATTTATGC AGAGGCCGAG
9481 GCCGCCTCGG CCTCTGAGCT ATTCCAGAAG TAGTGAGGAG GCTTTTTTGG AGGCCTAGGC
9541 TTTTGCAAAG GAGGTAGCCA ACATGATTGA ACAAGATGGA TTGCACGCAG GTTCTCCCGC
9601 CGCTTGGGTG GAGAGGCTAT TCGGCTATGA CTGGGCACAA CAGACAATCG GCTGCTCTGA
9661 TGCCGCCGTG TTCCGGCTGT CAGCGCAGGG GCGCCCGGTT CTTTTTGTCA AGACCGACCT
9721 GTCCGGTGCC CTGAATGAAC TCCAGGACGA GGCAGCGCGG CTATCGTGGC TGGCCACGAC
9781 GGGCGTTCCT TGCGCAGCTG TGCTCGACGT TGTCACTGAA GCGGGAAGGG ACTGGCTGCT
9841 ATTGGGCGAA GTGCCGGGGC AGGATCTCCT GTCATCTCAC CTTGCTCCTG CCGAGAAAGT
9901 ATCCATCATG GCTGATGCAA TGCGGCGGCT GCATACGCTT GATCCGGCTA CCTGCCCATT
9961 CGACCACCAA GCGAAACATC GCATCGAGCG AGCACGTACT CGGATGGAAG CCGGTCTTGT
10021 CGATCAGGAT GATCTGGACG AAGAGCATCA GGGGCTCGCG CCAGCCGAAC TGTTCGCCAG
```

TABLE 8-continued

Plasmid and mRNA construct sequences

```
10081 GCTCAAGGCG CGGATGCCCG ACGGCGAGGA TCTCGTCGTG ACCCACGGCG ATGCCTGCTT
10141 GCCGAATATC ATGGTGGAAA ATGGCCGCTT TTCTGGATTC ATCGACTGTG GCCGGCTGGG
10201 TGTGGCGGAC CGCTATCAGG ACATAGCGTT GGCTACCCGT GATATTGCTG AAGAGCTTGG
10261 CGGCGAATGG GCTGACCGCT TCCTCGTGCT TTACGGTATC GCCGCTCCCG ATTCGCAGCG
10321 CATCGCCTTC TATCGCCTTC TTGACGAGTT CTTCTAGTAT GTAAGCCCTG TGCCTTCTAG
10381 TTGCCAGCCA TCTGTTGTTT GCCCCTCCCC CGTGCCTTCC TTGACCCTGG AAGGTGCCAC
10441 TCCCACTGTC CTTTCCTAAT AAAATGAGGA AATTGCATCG CATTGTCTGA GTAGGTGTCA
10501 TTCTATTCTG GGGGGTGGGG TGGGGCAGGA CAGCAAGGGG GAGGATTGGG AAGACAATAG
10561 CAGGCATGCT GGGGATGCGG TGGGCTCTAT GGTTAATTAA CCAGTCAAGT CAGCTACTTG
10621 GCGAGATCGA CTTGTCTGGG TTTCGACTAC GCTCAGAATT GCGTCAGTCA AGTTCGATCT
10681 GGTCCTTGCT ATTGCACCCG TTCTCCGATT ACGAGTTTCA TTTAAATCAT GTGAGCAAAA
10741 GGCCAGCAAA AGGCCAGGAA CCGTAAAAAG GCCGCGTTGC TGGCGTTTTT CCATAGGCTC
10801 CGCCCCCCTG ACGAGCATCA CAAAAATCGA CGCTCAAGTC AGAGGTGGCG AAACCCGACA
10861 GGACTATAAA GATACCAGGC GTTTCCCCCT GGAAGCTCCC TCGTGCGCTC TCCTGTTCCG
10921 ACCCTGCCGC TTACCGGATA CCTGTCCGCC TTTCTCCCTT CGGGAAGCGT GGCGCTTTCT
10981 CATAGCTCAC GCTGTAGGTA TCTCAGTTCG GTGTAGGTCG TTCGCTCCAA GCTGGGCTGT
11041 GTGCACGAAC CCCCCGTTCA GCCCGACCGC TGCGCCTTAT CCGGTAACTA TCGTCTTGAG
11101 TCCAACCCGG TAAGACACGA CTTATCGCCA CTGGCAGCAG CCACTGGTAA CAGGATTAGC
11161 AGAGCGAGGT ATGTAGGCGG TGCTACAGAG TTCTTGAAGT GGTGGCCTAA CTACGGCTAC
11221 ACTAGAAGAA CAGTATTTGG TATCTGCGCT CTGCTGAAGC CAGTTACCTT CGGAAAAAGA
11281 GTTGGTAGCT CTTGATCCGG CAAACAAACC ACCGCTGGTA GCGGTGGTTT TTTTGTTTGC
11341 AAGCAGCAGA TTACGCGCAG AAAAAAAGGA TCTCAAGAAG ATCCTTTGAT CTTTTCTACG
11401 GGGTCTGACG CTCAGTGGAA CGAAAACTCA CGTTAAGGGA TTTTGGTCAT GAGATTATCA
11461 AAAAGGATCT TCACCTAGAT CCTTTTAAAT TAAAAATGAA GTTTTAAATC AATCTAAAGT
11521 ATATATGAGT AAACTTGGTC TGACAGTTAC CAATGCTTAA TCAGTGAGGC ACCTATCTCA
11581 GCGATCTGTC TATTTCGTTC ATCCATAGTT GCATTTAAAT TTCCGAACTC TCCAAGGCCC
11641 TCGTCGGAAA ATCTTCAAAC CTTTCGTCCG ATCCATCTTG CAGGCTACCT CTCGAACGAA
11701 CTATCGCAAG TCTCTTGGCC GGCCTTGCGC CTTGGCTATT GCTTGGCAGC GCCTATCGCC
11761 AGGTATTACT CCAATCCCGA ATATCGAGA TCGGGATCAC CCGAGAGAAG TTCAACCTAC
11821 ATCCTCAATC CCGATCTATC CGAGATCCGA GGAATATCGA AATCGGGGCG CGCCTGGTGT
11881 ACCGAGAACG ATCCTCTCGA TGCGAGTCTC GACGATCCAT ATCGTTGCTT GGCAGTCAGC
11941 CAGTCGGAAT CCAGCTTGGG ACCCAGGAAG TCCAATCGTC AGATATTGTA CTCAAGCCTG
12001 GTCACGGCAG CGTACCGATC TGTTTAAACC TAGATATTGA TAGTCTGATC GGTCAACGTA
12061 TAATCGAGTC CTAGCTTTTG CAAACATCTA TCAAGAGACA GGATCAGCAG GAGGCTTTCG
12121 CATGAGTATT CAACATTTCC GTGTCGCCCT TATTCCCTTT TTTGCGGCAT TTTGCCTTCC
12181 TGTTTTTGCT CACCCAGAAA CGCTGGTGAA AGTAAAAGAT GCTGAAGATC AGTTGGGTGC
12241 GCGAGTGGGT TACATCGAAC TGGATCTCAA CAGCGGTAAG ATCCTTGAGA GTTTTCGCCC
12301 CGAAGAACGC TTTCCAATGA TGAGCACTTT TAAAGTTCTG CTATGTGGCG CGGTATTATC
12361 CCGTATTGAC GCCGGGCAAG AGCAACTCGG TCGCCGCATA CACTATTCTC AGAATGACTT
12421 GGTTGAGTAT TCACCAGTCA CAGAAAAGCA TCTTACGGAT GGCATGACAG TAAGAGAATT
12481 ATGCAGTGCT GCCATAACCA TGAGTGATAA CACTGCGGCC AACTTACTTC TGACAACGAT
12541 TGGAGGACCG AAGGAGCTAA CCGCTTTTTT GCACAACATG GGGGATCATG TAACTCGCCT
12601 TGATCGTTGG GAACCGGAGC TGAATGAAGC CATACCAAAC GACGAGCGTG ACACCACGAT
12661 GCCTGTAGCA ATGGCAACAA CCTTGCGTAA ACTATTAACT GGCGAACTAC TTACTCTAGC
12721 TTCCCGGCAA CAGTTGATAG ACTGGATGGA GGCGGATAAA GTTGCAGGAC CACTTCTGCG
12781 CTCGGCCCTT CCGGCTGGCT GGTTTATTGC TGATAAATCT GGAGCCGGTG AGCGTGGGTC
12841 TCGCGGTATC ATTGCAGCAC TGGGGCCAGA TGGTAAGCCC TCCCGTATCG TAGTTATCTA
12901 CACGACGGGG AGTCAGGCAA CTATGGATGA ACGAAATAGA CAGATCGCTG AGATAGGTGC
12961 CTCACTGATT AAGCATTGGT AACCGATTCT AGGTGCATTG GCGCAGAAAA AAATGCCTGA
13021 TGCGACGCTG CGCGTCTTAT ACTCCCACAT ATGCCAGATT CAGCAACGGA TACGGCTTCC
13081 CCAACTTGCC CACTTCCATA CGTGTCCTCC TTACCAGAAA TTTATCCTTA AGATCGTTTA
13141 AACTCGACTC TGGCTCTATC GAATCTCCGT CGTTTCGAAC TTACGCGAAC GCCGTGGCGG
13201 CTCATTTGCT CGTCGGGCAT CGAATCTCGT CAGCTATCGT CAGCTTACCT TTTTGGCAGC
13261 GATCGCGGCT CCCGACATCT TGGACCATTA GCTCCACAGG TATCTTCTTC CCTCTAGTGG
13321 TCATAACAGC AGCTTCAGCT ACCTCTCAAT TCAAAAAACC CCTCAAGACC CGTTTAGAGG
13381 CCCCAAGGGG TTATGCTATC AATCGTTGCG TTACACACAA AAAAACCAA CACACATCCA
13441 TCTTCGATGG ATAGCGATTT TATTATCTAA CTGCTGATCG AGTGTAGCCA GATCTAGTAA
13501 TCAATTACGG GGTCATTAGT TCATAGCCCA TATATGGAGT TCCGCGTTAC ATAACTTACG
13561 GTAAATGGCC CGCCTGGCTG ACCGCCCAAC GACCCCCGCC CATTGACGTC AATAATGACG
13621 TATGTTCCCA TAGTAACGCC AATAGGGACT TTCCATTGAC GTCAATGGGT GGAGTATTTA
13681 CGGTAAACTG CCCACTTGGC AGTACATCAA GTGTATCATA TGCCAAGTAC GCCCCCTATT
13741 GACGTCAATG ACGGTAAATG GCCCGCCTGG CATTATGCCC AGTACATGAC CTTATGGGAC
13801 TTTCCTACTT GGCAGTACAT CTACGTATTA GTCATCGCTA TTACCATGCT GATGCGGTTT
13861 TGGCAGTACA TCAATGGGCG TGGATAGCGG TTTGACTCAC GGGGATTTCC AAGTCTCCAC
13921 CCCATTGACG TCAATGGGAG TTTGTTTTGG CACCAAAATC AACGGGACTT TCCAAAATGT
13981 CGTAACAACT CCGCCCCATT GACGCAAATG GGCGGTAGGC GTGTACGGTG GGAGGTCTAT
14041 ATAAGCAGAG CTGGTTTAGT GAACCGTCAG ATCAGATCTT TGTCGATCCT ACCATCCACT
14101 CGACACACCC GCCAGCGGCC GC (SEQ ID NO: 44)
```

LINE-1 Plasmid EV71 IRES (SEQ ID NO: 45)

```
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
```

TABLE 8-continued

Plasmid and mRNA construct sequences

```
 481  TTTGGGATTA CGTCAAGAGG CCTAACCTGC GGTTGATCGG CGTCCCCGAG AGCGACGTAG
 541  AAAACGGGAC TAAACTGGAG AATACACTTC AAGACATCAT TCAAGAAAAT TTTCCAAACC
 601  TGGCTCGGCA AGCTAATGTG CAAATCCAAG AGATCCAACG CACACCCCAG CGGTATAGCT
 661  CTCGGCGTGC CACCCCTAGG CATATTATCG TGCGCTTTAC TAAGGTGGAG ATGAAAGAGA
 721  AGATGCTGCG AGCCGCTCGG GAAAAGGGAA GGGTGACTTT GAAGGGCAAA CCTATTCGGC
 781  TGACGGTTGA CCTTAGCGCG GAGACACTCC AGGCACGCCG GGAATGGGGC CCCATCTTTA
 841  ATATCCTGAA GGAGAAGAAC TTCCAGCCAC GAATCTCTTA CCCTGCAAAG TTGAGTTTTA
 901  TCTCCGAGGG TGAGATTAAG TATTTCATCG ATAAACAGAT GCTGCGAGAC TTCGTGACAA
 961  CTCGCCCAGC TCTCAAGGAA CTGCTCAAAG AGGCTCTTAA TATGGAGCGC AATAATAGAT
1021  ATCAACCCTT GCAGAACCAC GCAAAGATGT GAGACAGTTA AAACAGCTGT GGGTTGTCAC
1081  CCACCCACAG GGTCCACTGG GCGCTAGTAC ACTGGTATCT CGGTACCTTT GTACGCCTGT
1141  TTTATACCCC CTCCCTGATT TGCAACTTAG AAGCAACGCA AACCAGATCA ATAGTAGGTG
1201  TGACATACCA GTCGCATCTT GATCAAGCAC TTCTGTATCC CCGGACCGAG TATCAATAGA
1261  CTGTGCACAC GGTTGAAGGA GAAAACGTCC GTTACCCGGC TAACTACTTC GAGAAGCCTA
1321  GTAACGCCAT TGAAGTTGCA GAGTGTTTCG CTCAGCACTC CCCCGTGTA GATCAGGTCG
1381  ATGAGTCACC GCATTCCCCA CGGGCGACCG TGGCGGTGGC TGCGTTGGCG GCCTGCCTAT
1441  GGGGTAACCC ATAGGACGCT CTAATACGGA CATGGCGTGA AGAGTCTATT GAGCTAGTTA
1501  GTAGTCCTCC GGCCCCTGAA TGCGGCTAAT CCTAACTGCG GAGCACATAC CCTTAATCCA
1561  AAGGGCAGTG TGTCGTAACG GGCAACTCTG CAGCGGAACC GACTACTTTG GGTGTCCGTG
1621  TTTCTTTTTA TTCTTGTATT GGCTGCTTAT GGTGACAATT AAAGAATTGT TACCATATAG
1681  CTATTGGATT GGCCATCCAG TGTCAAACAG AGCTATTGTA TATCTCTTTG TTGGATTCAC
1741  ACCTCTCACT CTTGAAACGT TACACACCCT CAATTACATT ATACTGCTGA ACACGAAGCG
1801  TACATGACCG GCTCTAACTC ACATATCACC ATCCTTACAC TTAACATTAA CGGCCTCAAC
1861  TCAGCTATCA AGCGCCATCG GCTGGCCAGC TGGATCAAAT CACAGGATCC AAGCGTTTGT
1921  TGCATCCAAG AGACCCACCT GACCTGTAGA GATACTCACC GCCTCAAGAT CAAGGGATGG
1981  CGAAAGATTT ATCAGGCGAA CGGTAAGCAG AAGAAAGCCG GAGTCGCAAT TCTGGTCTCA
2041  GACAAGACGG ATTTCAAGCC CACCAAAATT GACGTGATAA AGGAAGGTCA CTATATTATG
2101  GTGAAAGGCA GCATACAGCA GGAAGAACTT ACCATATTGA ACATCTACGC GCCAAACACC
2161  GGCGCACCTC GCTTTATCAA ACAGGTCCTG TCCGATCTGC AGCGAGATCT GGATTCTCAT
2221  ACGTTGATTA TGGGTGATTT CAATACACCA TTGAGCACCC TGGATCGCAG CACCAGGCAA
2281  AAGGTAAATA AAGACACGCA AGAGCTCAAT AGCGCACTGC ATCAGGCAGA TCTCATTGAT
2341  ATTTATCGCA CTCTTCATCC TAAGAGTACC GAGTACACAT TCTTCAGCGC CCCACATCAT
2401  ACATACTCAA AGATCGATCA TATCGTCGGC TCAAAGGCTC TGCTGTCAAA GTGCAAGCGC
2461  ACAGAGATAA TTACAAATTA CCTGTCAGAT CATAGCGCGA TCAAGCTCGA GCTGAGAATC
2521  AAGAACCTGA CCCAGAGCCG GAGTACCACT TGGAAGCTTA ATAACCTGCT GCTCAACGAT
2581  TATTGGGTCC ACAATGAGAT GAAGGCAGAG ATTAAAATGT TCTTCGAAAC AAATGAGAAT
2641  AAGGATACTA CCTATCAAAA CCTTTGGGAT GCCTTTAAGG CCGTCTGCAG AGGCAAGTTC
2701  ATCGCCCTCA ACGCCTATAA AGAAAACAA GAGAGATCTA AGATCGATAC TCTCACCTCT
2761  CAGCTGAAGG AGTTGGAGAA ACAGGAACAG ACCCACTCCA AGGCGTCAAG ACGGCAGGAG
2821  ATCACAAAGA TTCGCGCCGA GTTGAAAGAG ATCGAAAACT AAAAGACTCT TCAGAAAATT
2881  AACGAGTCTC GTAGTTGGTT CTTCGAGCGG ATTAATAAGA TAGACAGACC TCTGGCACGA
2941  CTGATTAAGA AGAAGCGCGA AAAGAACCAG ATTGATACCA TCAAGAACGA CAAGGGCGAC
3001  ATCACTACTG ACCCGACCGA GATCCAGACC ACTATTCGGG AGTATTATAA GCATTTGTAT
3061  GCTAACAAGC TTGAGAACCT GGAAGAGATG GACACTTTTC TGGATACCTA TACTCTGCCA
3121  CGGCTTAATC AAGAGGAAGT CGAGTCCCTC AACCGCCCAA TTACAGGAAG CGAGATTGTG
3181  GCCATAATTA ACTCCCTGCC GACAAAGAAA TCTCCTGGTC CGGACGGGTT TACAGCTGAG
3241  TTTTATCAAC GGTATATGGA AGAGCTTGTA CCGTTCTGC TCAAGCTCTT TCAGTCTATA
3301  GAAAAGGAAG GCATCTTGCC CAATTCCTTC TACGAAGCTT CTATAATACT TATTCCCAAA
3361  CCAGGACGCG ATACCACAAA GAAGGAAAAC TTCCGGCCCA TTAGTCTCAT GAATATCGAC
3421  GCTAAAATAT TGAACAAGAT TCTCGCCAAC AGAATCCAAC AACATATTAA GAAATTGATA
3481  CATCACGACC AGGTGGGGTT TATACCTGGC ATGCAGGGCT GGTTTAACAT CCGGAAGAGT
3541  ATTAACGTCA TTCAACACAT TAATAGAGCT AAGGATAAGA ATCATATGAT CATCTCTATA
3601  GACGCGGAAA AGGCATTCGA TAAGATTCAG CAGCCATTTA TGCTCAAGAC TCTGAACAAA
3661  CTCGGCATCG ACGGAACATA TTTTAAGATT ATTCGCGCAA TTTACGATAA GCCGACTGCT
3721  AACATTATCC TTAACGGCCA AAAGCTCGAG GCCTTTCCGC TCAAGACTGG AACCCGCCAA
3781  GGCTGTCCCC TCTCCCCGCT TTTGTTTAAT ATTGTACTCG AGGTGCTGGC TAGGGCTATT
3841  CGTCAAGAGA AAGAGATTAA AGGGATACAG CTCGGGAAGG AAGAGGTCAA GCTTTCCTTG
3901  TTCGCCGATG ATATGATTGT GTACCTGGAG AATCCTATTG TGTCTGCTCA GAACCTTCTT
3961  AAACTTATTT CTAACTTTAG CAAGGTCAGC GGCTATAAGA TTAACGTCCA GAAATCTCAG
4021  GCCTTTCTGT ACACAAATAA TCGACAGACC GAATCCCAGA TAATGGGTGA GCTTCCGTTT
4081  GTCATAGCCA GCAAAAGGAT AAAGTATCTC GGAATCCAGC TGACACGAGA CGTTAAAGAT
4141  TTGTTTAAGG AAAATTACAA GCCTCTCCTG AAAGAGATTA AGGAAGATAC TAATAAGTGG
4201  AAGAATATCC CCTGTTCATG GGTTGGCAGA ATCAACATAG TGAAGATGGC AATACTTCCT
4261  AAAGTGATAT ATCGCTTTAA CGCCATCCCA ATTAAACTGC CTATGACCTT CTTTACGGAG
4321  CTCGAGAAAA CAACCCTTAA ATTTATATGG AATCAAAAGA GAGCAAGAAT ACGCAAGTCC
4381  ATCTTGAGCC AGAAGAATAA GGCCGGTGGG ATTACTTTGC CTGATTTTAA GTTGTATTAT
4441  AAAGCCACAG TAACTAAGAC AGCCTGGTAT TGGTATCAGA ATAGAGACAT CGACCAGTGG
4501  AATCGGACCG AACCATCAGA GATAATGCCC CACATCTATA ATTACCTTAT ATTCGATAAG
4561  CCAGAAAAGA ATAAACAGTG GGGCAAAGAC CCCTCTTCA ACAAGTGGTG TTGGGAGAAT
4621  TGGCTGGCCA TATGCCGGAA ACTCAAGCTC GACCCCTTTC TTACACCCTA CACTAAAATC
4681  AACAGTAGGT GGATCAAGGA CTTGAATGTC AAGCCAAAGA CTATAAAGAC ACTGGAAGAG
4741  AATCTTGGGA TCACAATACA AGATATAGGC GTCGGCAAAG ATTTTATGTC AAAGACGCCC
4801  AAGGCCATGG CCACTAAGGA TAAGATTGAT AAGTGGGACT TTATTAAGCT CAAAGCTTC
4861  TGTACTGCCA AGGAGACCAC GATCAGAGTT AATAGGCAGC CCACTACATG GGAAAAGATT
4921  TTCGCCACTT ATTCATCAGA TAAGGGGTTG ATAAGCAGAA TATATAACGA GCTGAAGCAG
4981  ATCTACAAGA AGAAACGAA TAATCCCATC AAGAAGTGGG CAAAAGATAT GAACAGGCAT
5041  TTTAGCAAAG AGGATATCTA CGCGCGAAG AAGCATATGA AGAAGTGTAG TTCAAGCTTG
5101  GCCATTCGTG AGATGCAGAT TAAGACGACC ATGCGATACC ACCTTACCCC AGTGAGGATG
```

TABLE 8-continued

Plasmid and mRNA construct sequences

```
5161  GCAATTATCA AGAAATCTGG CAATAATAGA TGTTGGCGGG GCTGTGGCGA GATTGGCACC
5221  CTGCTCCATT GCTGGTGGGA TTGCAAGCTG GTGCAGCCGC TTTGGAAATC AGTCTGGCGC
5281  TTTCTGAGGG ACCTCGAGCT TGAGATTCCC TTCGATCCCG CAATTCCCTT GCTCGGAATC
5341  TATCCTAACG AATACAAGAG CTGTTGTTAC AAGGATACGT GTACCCGGAT GTTCATCGCG
5401  GCCTTGTTTA CGATAGCTAA GACGTGGAAT CAGCCTAAGT GCCCCACAAT GATCGATTGG
5461  ATCAAGAAAA TGTGGCATAT TTATACCATG GAGTATTACG CAGCAATTAA GAATGACGAA
5521  TTTATTTCCT TCGTTGGGAC CTGGATGAAG CTGGAGACTA TTATTCTGAG CAAGCTGTCT
5581  CAGGAGCAAA AGACAAAGCA TAGAATCTTC TCTCTCATTG GTGGTAACGA CTACAAAGAC
5641  GATGACGACA AGTAAAGCGC TTCTAGAAGT TGTCTCCTCC TGCACTGACT GACTGATACA
5701  ATCGATTTCT GGATCCGCAG GCCTAATCAA CCTCTGGATT ACAAAATTTG TGAAAGATTG
5761  ACTGGTATTC TTAACTATGT TGCTCCTTTT ACGCTATGTG GATACGCTGC TTTAATGCCT
5821  TTGTATCATG CTATTGCTTC CCGTATGGCT TTCATTTTCT CCTCCTTGTA TAAATCCTGG
5881  TTGCTGTCTC TTTATGAGGA GTTGTGGCCC GTTGTCAGGC AACGTGGCGT GGTGTGCACT
5941  GTGTTTGCTG ACGCAACCCC CACTGGTTGG GGCATTGCCA CCACCTGTCA GCTCCTTTCC
6001  GGGACTTTCG CTTTCCCCCT CCCTATTGCC ACGGCGGAAC TCATCGCCGC CTGCCTTGCC
6061  CGCTGCTGGA CAGGGGCTCG GCTGTTGGGC ACTGACAATT CCGTGGTGTT GTCGGGGAAG
6121  CTGACGTCCT TTCCATGGCT GCTCGCCTGT GTTGCCACCT GGATTCTGCG CGGGACGTCC
6181  TTCTGCTACG TCCCTTCGGC CCTCAATCCA GCGGACCTTC CTTCCCGCGA CAAACGACC
6241  CAACACCCGT GCGTTTTATT CTGTCTTTTT ATTGCCGATC CCCTCAGAAG AACTCGTCAA
6301  GAAGGCGATA GAAGGCGATG CGCTGCGAAT CGGGAGCGGC GATACCGTAA AGCACGAGGA
6361  AGCGGTCAGC CCATTCGCCG CCAAGCTCTT CAGCAATATC ACGGGTAGCC AACGCTATGT
6421  CCTGATAGCG GTCGGCCGCT TACTTGTAC AGCTCGTCCA TGCCGAGAGT GATCCCGGCG
6481  GCGGTCACGA ACTCCAGCAG GACCATGTGA TCGCGCTTCT CGTTGGGGTC TTTGCTCAGG
6541  GCGGACTGGG TGCTCAGGTA GTGGTTGTCG GGCAGCAGCA CGGGGCCGTC GCCGATGGGG
6601  GTGTTCTGCT GGTAGTGGTC GGCCAGGTGA GTCCAGGAGA TGTTTCAGCA CTGTTGCCTT
6661  TAGTCTCGAG GCAACTTAGA CAACTGAGTA TTGATCTGAG CACAGCAGGG TGTGAGCTGT
6721  TTGAAGATAC TGGGGTTGGG GGTGAAGAAA CTGCAGAGGA CTAACTGGGC TGAGACCCAG
6781  TGGCAATGTT TTAGGGCCTA AGGAATGCCT CTGAAAATCT AGATGGACAA CTTTGACTTT
6841  GAGAAAAGAG AGGTGGAAAT GAGGAAAATG ACTTTTCTTT ATTAGATTTC GGTAGAAAGA
6901  ACTTTCATCT TTCCCCTATT TTTGTTATTC GTTTTAAAAC ATCTATCTGG AGGCAGGACA
6961  AGTATGGTCA TTAAAAAGAT GCAGGCAGAA GCATATATT GGCTCAGTCA AAGTGGGGAA
7021  CTTTGGTGGC CAAACATACA TTGCTAAGGC TATTCCTATA TCAGCTGGAC ACATATAAAA
7081  TGCTGCTAAT GCTTCATTAC AAACTTATAT CCTTTAATTC CAGATGGGGG CAAAGTATGT
7141  CCAGGGGTGA GGAACAATTG AAACATTTGG GCTGGAGTAG ATTTTGAAAG TCAGCTCTGT
7201  GTGTGTGTGT GTGTGTGTGT GTGTGAGAGC GTGTGTTTCT TTTAACGTTT TCAGCCTACA
7261  GCATACAGGG TTCATGGTGG CAAGAAGATA ACAAGATTTA AATTATGGCC AGTGACTAGT
7321  GCTGCAAGAA GAACAACTAC CTGCATTTAA TGGGAAAGCA AAATCTCAGG CTTTGAGGGA
7381  AGTTAACATA GGCTTGATTC TGGGTGGAAG CTGGGTGTGT AGTTATCTGG AGGCCAGGCT
7441  GGAGCTCTCA GCTCACTATG GGTTCATCTT TATTGTCTCC TTTCATCTCA ACAGCTGCAC
7501  GCTGCCGTCC TCGATGTTGT GGCGGATCTT GAAGTTCACC TTGATGCCGT TCTTCTGCTT
7561  GTCGGCCATG ATATAGACGT TGTGGCTGTT GTAGTTGTAC TCCAGCTTGT GCCCCAGGAT
7621  GTTGCCGTCC TCCTTGAAGT CGATGCCCTT CAGCTCGATG CGGTTCACCA GGGTGTCGCC
7681  CTCGAACTTC ACCTCGGCGC GGGTCTTGTA GTTGCCGTCG TCCTTGAAGA AGATGGTGCG
7741  CTCCTGGACG TAGCCTTCGG GCATGGCGGA CTTGAAGAAG TCGTGCTGCT TCATGGTGGTC
7801  GGGGTAGCGG CTGAAGCACT GCACGCCGTA GGTCAGGGTG GTCACGAGGG TGGGCCAGGG
7861  CACGGGCAGC TTGCCGGTGG TGCAGATGAA CTTCAGGGTC AGCTTGCCGT AGGTGGCATC
7921  GCCCTCGCCC TCGCCGGACA CGCTGAACTT GTGGCCGTTT ACGTCGCCGT CCAGCTCGAC
7981  CAGGATGGGC ACCACCCCGG TGAACAGCTC CTCGCCCTTG CTCACCATGG TGGCGAATTC
8041  GAAGCTTGAG CACGAGATCT GAGTCCGGTA GGCCTAGCGG ATCTGACGGT TCACTAAACC
8101  AGCTCTGCTT ATATAGACCT CCCACCGTAC ACGCCTACCG CCCATTTGCG TCAATGGGGC
8161  GGAGTTGTTA CGACATTTTG GAAAGTCCCG TTGATTTTGG TGCCAAAACA AACTCCCATT
8221  GACGTCAATG GGGTGGAGAC TTGGAAATCC CCGTGAGTCA AACCGCTATC CACGCCCATT
8281  GATGTACTGC CAAAACCGCA TCACCATGGT AATAGCGATG ACTAATACGT AGATGTACTG
8341  CCAAGTAGGA AAGTCCCATA AGGTCATGTA CTGGGCATAA TGCCAGGCGG GCCATTTACC
8401  GTCATTGACG TCAATAGGGG GCGTACTTGG CATATGATAC ACTTGATGTA CTGCCAAGTG
8461  GGCAGTTTAC CGTAAATACT CCACCCATTG ACGTCAATGG AAAGTCCCTA TTGGCGTTAC
8521  TATGGGAACA TACGTCATTA TTGACGTCAA TGGGCGGGGG TCGTTGGGCG GTCAGCCAGG
8581  CGGGCCATTT ACCGTAAGTT ATGTAACGGG CCTGCTGCCG GCTCTGCGGC CTCTTCCGCG
8641  TCTTCGCCTT CGCCCTCAGA CGAGTCGGAT CTCCCTTTGG GCCGCCTCCC CGCCTGTCTA
8701  GCTTGACTGA CTGAGATACA GCGTACCTTC AGCTCACAGA CATGATAAGA TACATTGATG
8761  AGTTTGGACA AACCACAACT AGAATGCAGT GAAAAAAATG CTTTATTTGT GAAATTTGTG
8821  ATGCTATTGC TTTATTTGTA ACCATTATAA GCTGCAATAA ACAAGTTAAC AACAACAATT
8881  GCATTCATTT TATGTTTCAG GTTCAGGGGG AGGTGTGGGA GGTTTTTTAA AGCAAGTAAA
8941  ACCTCTACAA ATGTGGTATT GGCCCATCTC TATCGGTATC GTAGCATAAC CCCTTGGGGC
9001  CTCTAAACGG GTCTTGAGGG GTTTTTTGTG CCCCTCGGGC CGGATTGCTA TCTACCGGCA
9061  TTGGCGCAGA AAAAAATGCC TGATGCGACG CTGCGCGTCT TATACTCCCA CATATGCCAG
9121  ATTCAGCAAC GGATACGGCT TCCCCAACTT GCCCACTTCC ATACGTGTCC TCCTTACCAG
9181  AAATTTATCC TTAAGGTCGT CAGCTATCCT GCAGGCGATC TCTCGATTTC GATCAAGACA
9241  TTCCTTTAAT GGTCTTTTCT GGACACCACT AGGGGTAGA AGTAGTTCAT TAAACTTTCT
9301  TCCCTCCCTA ATCTCATTGG TTACCTTGGG CTATCGAAAC TTAATTAAGC GATCTGCATC
9361  TCAATTAGTC AGCAACCATA GTCCCGCCCC TAACTCCGCC CATCCCGCCC CTAACTCCGC
9421  CCAGTTCCGC CCATTCTCCG CCCCATCGCT GACTAATTTT TTTTATTTAT GCAGAGGCCG
9481  AGGCCGCCTC GGCCTCTGAG CTATTCCAGA AGTAGTGAGG AGGCTTTTTT GGAGGCCTAG
9541  GCTTTTGCAA AGGAGGTAGC CAACATGATT GAACAAGATG GATTGCACGC AGGTTCTCCC
9601  GCCGCTTGGG TGGAGAGGCT ATTCGGCTAT GACTGGGCAC AACAGACAAT CGGCTGCTCT
9661  GATGCCGCCG TGTTCCGGCT GTCAGCGCAG GGGCGCCCGG TTCTTTTTGT CAAGACCGAC
9721  CTGTCCGGTG CCCTGAATGA ACTCCAGGAC GAGGCAGCGC GGCTATCGTG GCTGGCCACG
9781  ACGGGCGTTC CTTGCGCAGC TGTGCTCGAC GTTGTCACTG AAGCGGGAAG GGACTGGCTG
```

TABLE 8-continued

Plasmid and mRNA construct sequences

```
 9841 CTATTGGGCG AAGTGCCGGG GCAGGATCTC CTGTCATCTC ACCTTGCTCC TGCCGAGAAA
 9901 GTATCCATCA TGGCTGATGC AATGCGGCGG CTGCATACGC TTGATCCGGT TACCTGCCCA
 9961 TTCGACCACC AAGCGAAACA TCGCATCGAG CGAGCACGTA CTCGGATGGA AGCCGGTCTT
10021 GTCGATCAGG ATGATCTGGA CGAAGAGCAT CAGGGGCTCG CGCCAGCCGA ACTGTTCGCC
10081 AGGCTCAAGG CGCGGATGCC CGACGGCGAG GATCTCGTCG TGACCCACGG CGATGCCTGC
10141 TTGCCGAATA TCATGGTGGA AAATGGCCGC TTTTCTGGAT TCATCGACTG TGGCCGGCTG
10201 GGTGTGGCGG ACCGCTATCA GGACATAGCG TTGGCTACCC GTGATATTGC TGAAGAGCTT
10261 GGCGGCGAAT GGGCTGACCG CTTCCTCGTG CTTTACGGTA TCGCCGCTCC CGATTCGCAG
10321 CGCATCGCCT TCTATCGCCT TCTTGACGAG TTCTTCTAGT ATGTAAGCCC TGTGCCTTCT
10381 AGTTGCCAGC CATCTGTTGT TTGCCCCTCC CCCGTGCCTT CCTTGACCCT GGAAGGTGCC
10441 ACTCCCACTG TCCTTTCCTA ATAAAATGAG GAAATTGCAT CGCATTGTCT GAGTAGGTGT
10501 CATTCTATTC TGGGGGGTGG GGTGGGGCAG GACAGCAAGG GGGAGGATTG GGAAGACAAT
10561 AGCAGGCATG CTGGGGATGC GGTGGGCTCT ATGGTTAATT AACCAGTCAA GTCAGCTACT
10621 TGGCGAGATC GACTTGTCTG GGTTTCGACT ACGCTCAGAA TTGCGTCAGT CAAGTTCGAT
10681 CTGGTCCTTG CTATTGCACC CGTTCTCCGA TTACGAGTTT CATTTAAATC ATGTGAGCAA
10741 AAGGCCAGCA AAAGGCCAGG AACCGTAAAA AGGCCGCGTT GCTGGCGTTT TTCCATAGGC
10801 TCCGCCCCCC TGACGAGCAT CACAAAAATC GACGCTCAAG TCAGAGGTGG CGAAACCCGA
10861 CAGGACTATA AAGATACCAG GCGTTTCCCC CTGGAAGCTC CCTCGTGCGC TCTCCTGTTC
10921 CGACCCTGCC GCTTACCGGA TACCTGTCCG CCTTTCTCCC TTCGGGAAGC GTGGCGCTTT
10981 CTCATAGCTC ACGCTGTAGG TATCTCAGTT CGGTGTAGGT CGTTCGCTCC AAGCTGGGCT
11041 GTGTGCACGA ACCCCCCGTT CAGCCCGACC GCTGCGCCTT ATCCGGTAAC TATCGTCTTG
11101 AGTCCAACCC GGTAAGACAC GACTTATCGC CACTGGCAGC AGCCACTGGT AACAGGATTA
11161 GCAGAGCGAG GTATGTAGGC GGTGCTACAG AGTTCTTGAA GTGGTGGCCT AACTACGGCT
11221 ACACTAGAAG AACAGTATTT GGTATCTGCG CTCTGCTGAA GCCAGTTACC TTCGGAAAAA
11281 GAGTTGGTAG CTCTTGATCC GGCAAACAAA CCACCGCTGG TAGCGGTGGT TTTTTTGTTT
11341 GCAAGCAGCA GATTACGCGC AGAAAAAAAG GATCTCAAGA AGATCCTTTG ATCTTTTCTA
11401 CGGGGTCTGA CGCTCAGTGG AACGAAAACT CACGTTAAGG GATTTTGGTC ATGAGATTAT
11461 CAAAAAGGAT CTTCACCTAG ATCCTTTTAA ATTAAAAATG AAGTTTTAAA TCAATCTAAA
11521 GTATATATGA GTAAACTTGG TCTGACAGTT ACCAATGCTT AATCAGTGAG GCACCTATCT
11581 CAGCGATCTG TCTATTTCGT TCATCCATAG TTGCATTTAA ATTTCCGAAC TCTCCAAGGC
11641 CCTCGTCGGA AAATCTTCAA ACCTTTCGTC CGATCCATCT TGCAGGCTAC CTCTCGAACG
11701 AACTATCGCA AGTCTCTTGG CCGGCCTTGC GCCTTGGCTA TTGCTTGGCA GCGCCTATCG
11761 CCAGGTATTA CTCCAATCCC GAATATCCGA GATCGGGATC ACCCGAGAGA AGTTCAACCT
11821 ACATCCTCAA TCCCGATCTA TCCGAGATCC GAGGAATATC GAAATCGGGG CGCGCCTGGT
11881 GTACCGAGAA CGATCCTCTC AGTGCGAGTC TCGACGACTC ATATCGTTGC TTGGCAGTCA
11941 GCCAGTCGGA ATCCAGCTTG GGACCCAGGA AGTCCAATCG TCAGATATTG TACTCAAGCC
12001 TGGTCACGGC AGCGTACCGA TCTGTTTAAA CCTAGATATT GATAGTCTGA TCGGTCAACG
12061 TATAATCGAG TCCTAGCTTT TGCAAACATC TATCAAGAGA CAGGATCAGC AGGAGGCTTT
12121 CGCATGAGTA TTCAACATTT CCGTGTCGCC CTTATTCCCT TTTTTGCGGC ATTTTGCCTT
12181 CCTGTTTTTG CTCACCCAGA AACGCTGGTG AAAGTAAAAG ATGCTGAAGA TCAGTTGGGT
12241 GCGCGAGTGG GTTACATCGA ACTGGATCTC AACAGCGGTA AGATCCTTGA GAGTTTTCGC
12301 CCCGAAGAAC GCTTTCCAAT GATGAGCACT TTTAAAGTTC TGCTATGTGG CGCGGTATTA
12361 TCCCGTATTG ACGCCGGGCA AGAGCAACTC GGTCGCCGCA TACACTATTC TCAGAATGAC
12421 TTGGTTGAGT ATTCACCAGT CACAGAAAAG CATCTTACGG ATGGCATGAC AGTAAGAGAA
12481 TTATGCAGTG CTGCCATAAC CATGAGTGAT AACACTGCGG CCAACTTACT TCTGACAACG
12541 ATTGGAGGAC CGAAGGAGCT AACCGCTTTT TTGCACAACA TGGGGGATCA TGTAACTCGC
12601 CTTGATCGTT GGGAACCGGA GCTGAATGAA GCCATACCAA ACGACGAGCG TGACACCACG
12661 ATGCCTGTAG CAATGGCAAC AACCTTGCGT AAACTATTAA CTGGCGAACT ACTTACTCTA
12721 GCTTCCCGGC AACAGTTGAT AGACTGGATG GAGGCGGATA AAGTTGCAGG ACCACTTCTG
12781 CGCTCGGCCC TTCCGGCTGG CTGGTTTATT GCTGATAAAT CTGGAGCCGG TGAGCGTGGG
12841 TCTCGCGGTA TCATTGCAGC ACTGGGGCCA GATGGTAAGC CCTCCCGTAT CGTAGTTATC
12901 TACACGACGG GGAGTCAGGC AACTATGGAT GAACGAAATA GACAGATCGC TGAGATAGGT
12961 GCCTCACTGA TTAAGCATTG GTAACCGATT CTAGGTGCAT TGGCGCAGAA AAAAATGCCT
13021 GATGCGACGC TGCGCGTCTT ATACTCCCAC ATATGCCAGA TTCAGCAACG GATACGGCTT
13081 CCCCAACTTG CCCACTTCCA TACGTGTCCT CCTTACCAGA AATTTATCCT TAAGATCGTT
13141 TAAACTCGAC TCTGGCTCTA TCGAATCTCC GTCGTTTCGA GCTTACGCGA ACAGCCGTGG
13201 CGCTCATTTG CTCGTCGGGC ATCGAATCTC GTCAGCTATC GTCAGCTTAC CTTTTTGGCA
13261 GCGATCGCGC CTCCCGACAT CTTGGACCAT AGCTCCACA GGTATCTTCT TCCCTCTAGT
13321 GGTCATAACA GCAGCTTCAG CTACCTCTCA ATTCAAAAAA CCCCTCAAGA CCCGTTTAGA
13381 GGCCCCAAGG GGTTATGCTA TCAATCGTTG CGTTACACAC ACAAAAAACC AACACACATC
13441 CATCTTCGAT GGATAGCGAT TTTATTATCT AATGCTGAT CGAGTGTAGC CAGATCTAGT
13501 AATCAATTAC GGGGTCATTA GTTCATAGCC CATATATGGA GTTCCGCGTT ACATAACTTA
13561 CGGTAAATGG CCCGCCTGGC TGACCGCCCA ACGACCCCCG CCCATTGACG TCAATAATGA
13621 CGTATGTTCC CATAGTAACG CCAATAGGGA CTTTCCATTG ACGTCAATGG GTGGAGTATT
13681 TACGGTAAAC TGCCCACTTG GCAGTACATC AAGTGTATCA TATGCCAAGT ACGCCCCCTA
13741 TTGACGTCAA TGACGGTAAA TGGCCCGCCT GGCATTATGC CCAGTACATG ACCTTATGGG
13801 ACTTTCCTAC TTGGCAGTAC ATCTACGTAT TAGTCATCGC TATTACCATG CTGATGCGGT
13861 TTTGGCAGTA CATCAATGGG CGTGGATAGC GGTTTGACTC ACGGGGATTT CCAAGTCTCC
13921 ACCCCATTGA CGTCAATGGG AGTTTGTTTT GGCACCAAAA TCAACGGGAC TTTCCAAAAT
13981 GTCGTAACAA CTCCGCCCCA TTGACGCAAA TGGGCGGTAG GCGTGTACGG TGGGAGGTCT
14041 ATATAAGCAG AGCTGGTTTA GTGAACCGTC AGATCAGATC TTTGTCGATC CTACCATCCA
14101 CTCGACACAC CCGCCAGCGG CCGC (SEQ ID NO: 45)

LINE-1 plasmid ORF 1-E2A-ORF2 GFP (SEQ ID NO: 46)
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
```

TABLE 8-continued

Plasmid and mRNA construct sequences

```
 241 TCGAGAAGAA CCTCGAGGAG TGCATCACCC GTATCACAAA CACTGAGAAA TGTCTCAAAG
 301 AACTCATGGA ACTTAAGACA AAAGCCAGGG AGCTTCGAGA GGAGTGTCGG AGTCTGAGAT
 361 CCAGGTGTGA CCAGCTCGAG GAGCGCGTGA GCGCGATGGA AGACGAGATG AACGAGATGA
 421 AAAGAGAGGG CAAATTCAGG GAGAAGCGCA TTAAGAGGAA CGAACAGAGT CTGCAGGAGA
 481 TTTGGGATTA CGTCAAGAGG CCTAACCTGC GGTTGATCGG CGTCCCCGAG AGCGACGTAG
 541 AAAACGGGAC TAAACTGGAG AATACACTTC AAGACATCAT TCAAGAAAAT TTTCCAAACC
 601 TGGCTCGGCA AGCTAATGTG CAAATCCAAG AGATCCAACG CACACCCCAG CGGTATAGCT
 661 CTCGGCGTGC CACCCCTAGG CATATTATCG TGCGCTTTAC TAAGGTGGAG ATGAAAGAGA
 721 AGATGCTGCG AGCCGCTCGG GAAAAGGGAA GGGTGACTTT GAAGGGCAAA CCTATTCGGC
 781 TGACGGTTGA CCTTAGCGCC GAGACACTCC AGGCACGCCG GGAATGGGGC CCCATCTTTA
 841 ATATCCTGAA GGAGAAGAAC TTCCAGCCAC GAATCTCTTA CCCTGCAAAG TTGAGTTTTA
 901 TCTCCGAGGG TGAGATTAAG TATTTCATCG ATAAACAGAT GCTGCGAGAC TTCGTGACAA
 961 CTCGCCCAGC TCTCAAGGAA CTGCTCAAAG AGGCTCTTAA TATGGAGCGC AATAATAGAT
1021 ATCAACCCTT GCAGAACCAC GCAAAGATGG GAAGCGGACA GTGTACTAAT TATGCTCTCT
1081 TGAAATTGGC TGGAGATGTT GAGAGCAACC CTGACCTAT GACCGGCTCT AACTCACATA
1141 TCACCATCCT TACACTTAAC ATTAACGGCC TCAACTCAGC TATCAAGCGC CATCGGCTGG
1201 CCAGCTGGAT CAAATCACAG GATCCAAGCG TTTGTTCAT CCAAGAGACC CACCTGACCT
1261 GTAGAGATAC TCACCGCCTC AAGATCAAGG GATGGCGAAA GATTTATCAG GCGAACGGTA
1321 AGCAGAAGAA AGCCGGAGTC GCAATTCTGG TCTCAGACAA GACGGATTTC AAGCCCACCA
1381 AAATTAAGCG TGATAAGGAA GGTCACTATA TTATGGTGAA AGGCAGCATA CAGCAGGAAG
1441 AACTTACCAT ATTGAACATC TACGCGCCAA ACACCGGCGC ACCTCGCTTT ATCAAACAGG
1501 TCCTGTCCGA TCTGCAGCGA GATCTGGATT CTCATACGTT GATTATGGGT GATTTCAATA
1561 CACCATTGAG CACCCTGGAT CGCAGCACCA GGCAAAAGGT AAATAAAGAC ACGCAAGAGC
1621 TCAATAGCGC ACTGCATCAG GCAGATCTCA TTGATATTTA TCGCACTCTT CATCCTAAGA
1681 GTACCGAGTA CACATTCTTC AGCGCCCAC ATCATACATA CTCAAAGATC GATCATATCG
1741 TCGGCTCAAA GGCTCTGCTG TCAAAGTGCA AGCGCACAGA GATAATTACA AATTACCTGT
1801 CAGATCATAG CGCGATCAAG CTCGAGCTGA GAATCAAGAA CCTGACCCAG AGCCGGAGTA
1861 CCACTTGGAA GCTTAATAAC CTGCTGCTCA ACGATTATTG GGTCCACAAT GAGATGAAGG
1921 CAGAGATTAA AATGTTCTTC GAAACAAATG AGAATAAGGA TACTACCTAT CAAAACCTTT
1981 GGGATGCCTT TAAGGCCGTC TGCAGAGGCA AGTTCATCGC CCTCAACGCC TATAAAAGAA
2041 AACAAGAGAG ATCTAAGATC GATACTCTCA CCTCTCAGCT GAAGGAGTTG GAGAAACAGG
2101 AACGACCCA CTCCAAGGCG TCAAGACGGC AGGAGATACAC AAAGATTCGC GCCGAGTTGA
2161 AAGAGATCGA AACCCAAAAG ACTCTTCAGA AAATTAACGA GTCTCGTAGT TGGTTCTTCG
2221 AGCGGATTAA TAAGATAGAC AGACCTCTGG CACGACTGAT TAAGAAGAAG CGCGAAAAGA
2281 ACCAGATTGA TACCATCAAG AACGACAAGG GCGACATCAA TACTGACCCG ACCGAGATCC
2341 AGACCACTAT TCGGGAGTAT TATAAGCATT TGTATGCTAA CAAGCTTGAG AACCTGGAAG
2401 AGATGGACAC TTTTCTGGAT ACCTATACTC TGCCACGGCT TAATCAAGAG GAAGTCGAGT
2461 CCCTCAACCG CCCAATTACA GGAAGCGAGA TTGTGGCCAT AATTAACTCC CTGCCGACAA
2521 AGAAATCTCC TGGTCCGGAC GGGTTTACAG CTGAGTTTTA TCAACGGTAT ATGGAAGAGC
2581 TTGTACCGTT TCTGCTCAAG CTCTTTCAGT CTATAGAAAG GGAAGGACTC TTGCCCAATT
2641 CCTTCTACGA AGCTTCTATA ATACTTATTC CCAAACCAGG ACGCGATACC ACAAAGAAGG
2701 AAAACTTCCG GCCCATTAGT CTCATGAATA TCGACGCTAA AATATTGAAC AAGATTCTCG
2761 CCAACAGAAT CCAACAACAT ATTAAGAAAT TGATACATCA CGACCAGGTG GGGTTTATAC
2821 CTGGCATGCA GGGCTGGTTT AACATCCGGA AGAGTATTAA CGTCATTCAA CACATTATTA
2881 GAGCTAAGGA TAAGAATCAT ATGATCATCT CTATAGACGC GGAAAAGGCA TTCGATAAGA
2941 TTCAGCAGCC ATTTATGCTC AAGACTCTGA ACAAACTCGG CATCGACGGA ACATATTTTA
3001 AGATTATTCG CGCAATTTAC GATAAGCCGA CTGCTAACAT TATCCTTAAC GGCCAAAAGC
3061 TCGAGGCCTT TCCGCTCAAG ACTGGAACCC GCCAAGGCTG TCCCCTCTCC CCGCTTTTGT
3121 TTAATATTGT ACTCGAGGTG CTGGCTAGGG CTATTCGTCA AGAGAAAGAG ATTAAAGGGA
3181 TACAGCTCGG GAAGGAAGAG GTCAAGCTTT CCTTGTTCGC CGATGATATG ATTGTGTACC
3241 TGGAGAATCC TATTGTGTCT GCTCAGAACC TTCTTAAACT TATTTCTAAC TTTAGCAAGG
3301 TCAGCGGCTA TAAGATTAAC GTCCAGAAAT CTCAGGCCTT TCTGTACACA AATAATCGAC
3361 AGACCGAATC CCAGATAATG GGTGAGCTTC CGTTTGTCAT AGCCAGCAAA AGGATAAAGT
3421 ATCTCGGAAT CCAGCTGACA CGAGACGTTA AGATTTGTT TAAGGAAAAT TACAAGCCTC
3481 TCCTGAAAGA GATTAAGGAA GATACTAATA AGTGGAAGAA TATCCCCTGT TCATGGGTTG
3541 GCAGAATCAA CATAGTGAAG ATGGCAATAC TTCCTAAAGT GATATATCGC TTTAACGCCA
3601 TCCCAATTAA ACTGCCTATG ACCTTCTTTA CGGAGCTCGA GAAAACAACC CTTAAATTTA
3661 TATGGAATCA AAAGAGAGCA AGAATAGCGA AGTCCATCTT GAGCCAGAAG AATAAGGCCG
3721 GTGGGATTAC TTTGCCTGAT TTTAAGTTGT ATTATAAAGC CACAGTAACT AAGACAGCCT
3781 GGTATTGGTA TCAGAATAGA GACATCGACC AGTGGAATCG GACCGAACCA TCAGAGATAA
3841 TGCCCCACAT CTATAATTAC CTTATATTCG ATAAGCCAGA AAAGAATAAA CAGTGGGGCA
3901 AAGACAGCCT CTTCAACAAG TGGTGTTGGG AGAATTGGCT GGCCATATGC CGGAAACTCA
3961 AGCTCGACCC CTTTCTTACA CCCTACACTA AAATCAACAG TAGGTGGATC AAGGACTTGA
4021 ATGTCAAGCC AAAGACTATA AAGCACTGG AAGAGAATCT TGGGATCACA ATACAAGATA
4081 TAGGCGTCGG CAAAGATTTT ATGTCAAAGA CGCCCAAGGC CATGGCCACT AAGGATAGAA
4141 TTGATAAGTG GGACCTTATT AAGCTCAAAA GCTTCTGTAC TGCCAAGGAG ACCACGATCA
4201 GAGTTAATAG GCAGCCCACT ACATGGGAAA AGATTTTCGC CACTTATTCA TCAGATAAGG
4261 GGTTGATAAG CAGAATATAT AACGAGCTGA AGCAGATCTA CAAGAAGAAA ACGAATAATC
4321 CCATCAAGAA GTGGGCAAAA GATATGAACA GGCATTTTAG CAAGAGGAT ATCTACGCCG
4381 CGAAGAAGCA TATGAAGAAG TGTAGTTCAA GCTTGGCCAT TCGTGAGATG CAGATTAAGA
4441 CGACCATGCG ATACCACCTT ACCCCAGTGA GGATGGCAAT TATCAAGAAA TCTGGCAATA
4501 ATAGATGTTG GCGGGGCTGT GGCGAGATTG GCACCCTGCT CCATTGCTGG TGGGATTGCA
4561 AGCTGGTGCA GCCGCTTTGG AAATCAGTCT GCGCGTTTCT GAGGGACCTC GGCTTCAATT
4621 TTCCCTTCGA TCCCGCAATT CCCTTGCTCG GAATCTATCC TAACGAATAC AAGAGCTGTT
4681 GTTACAAGGA TACGTGTACC CGGATGTTCA TCGCGGCCTT GTTTACGATA GCTAAGACGT
4741 GGAATCAGCC TAAGTGCCCC ACAATGATCG ATTGGATCAA GAAAATGTGG CATATTTATA
4801 CCATGGAGTA TTACGCAGCA ATTAAGAATG ACGAATTTAT TTCCTTCGTT GGGACCTGGA
4861 TGAAGCTGGA GACTATTATT CTGAGCAAGC TGTCTCAGGA GCAAAAGACA AAGCATAGAA
```

TABLE 8-continued

Plasmid and mRNA construct sequences

```
4921  TCTTCTCTCT CATTGGTGGT AACGACTACA AAGACGATGA CGACAAGTAA AGCGCTTCTA
4981  GAAGTTGTCT CCTCCTGCAC TGACTGACTG ATACAATCGA TTTCTGGATC CGCAGGCCTA
5041  ATCAACCTCT GGATTACAAA ATTTGTGAAA GATTGACTGG TATTCTTAAC TATGTTGCTC
5101  CTTTTACGCT ATGTGGATAC GCTGCTTTAA TGCCTTTGTA TCATGCTATT GCTTCCCGTA
5161  TGGCTTTCAT TTTCTCCTCC TTGTATAAAT CCTGGTTGCT GTCTCTTTAT GAGGAGTTGT
5221  GGCCCGTTGT CAGGCAACGT GGCGTGGTGT GCACTGTGTT TGCTGACGCA ACCCCCACTG
5281  GTTGGGGCAT TGCCACCACC TGTCAGCTCC TTTCCGGGAC TTTCGCTTTC CCCCTCCCTA
5341  TTGCCACGGC GGAACTCATC GCCGCCTGCC TTGCCCGCTG CTGGACAGGG GCTCGGCTGT
5401  TGGGCACTGA CAATTCCGTG GTGTTGTCGG GGAAGCTGAC GTCCTTTCCA TGGCTGCTCG
5461  CCTGTGTTGC CACCTGGATT CTGCGCGGGA CGTCCTTCTG CTACGTCCCT TCGGCCCTCA
5521  ATCCAGCGGA CCTTCCTTCC CGCGAACAAA CGACCCAACA CCCGTGCGTT TTATTCTGTC
5581  TTTTTATTGC CGATCCCCTC AGAAGAACTC GTCAAGAAGG CGATAGAAGG CGATGCGCTG
5641  CGAATCGGGA GCGGCGATAC CGTAAAGCAC GAGGAAGCGG TCAGCCCATT CGCCGCCAAG
5701  CTCTTCAGCA ATATCACGGG TAGCCAACGC TATGTCCTGA TAGCGGTCGG CCGCTTTACT
5761  TGTACAGCTC GTCCATGCCG AGAGTGATCC CGGCGGCGGT CACGAACTCC AGCAGGACCA
5821  TGTGATCGCG CTTCTCGTTG GGGTCTTTGC TCAGGGCGGA CTGGGTGCTC AGGTAGTGGT
5881  TGTCGGGCAG CAGCACGGGG CCGTCGCCGA TGGGGGTGTT CTGCTGGTAG TGGTCGGCCA
5941  GGTGAGTCCA GGAGATGTTT CAGCACTGTT GCCTTTAGTC TCGAGGCAAC TTAGACAACT
6001  GAGTATTGAT CTGAGCACAG CAGGGTGTGA GCTGTTTGAA GATACTGGGG TTGGGGGTGA
6061  AGAAACTGCA GAGGACTAAC TGGGCTGAGA CCCAGTGGCA ATGTTTTAGG GCCTAAGGAA
6121  TGCCTCTGAA AATCTAGATG GACAACTTTG ACTTTGAGAA AAGAGAGGTG GAAATGAGGA
6181  AAATGACTTT TCTTTATTAG ATTTCGGTAG AAAGAACTTT CATCTTTCCC CTATTTTTGT
6241  TATTCGTTTT AAAACATCTA TCTGGAGGCA GACAAGTAT GGTCATTAAA AAGATGCAGG
6301  CAGAAGGCAT ATATTGGCTC AGTCAAAGTG GGGAACTTTG GTGGCCAAAC ATACATTGCT
6361  AAGGCTATTC CTATATCAGC TGGACACATA TAAAATGCTG CTAATGCTTC ATTACAAACT
6421  TATATCCTTT AATTCCAGAT GGGGGCAAAG TATGTCCAGG GGTGAGGAAC AATTGAAACA
6481  TTTGGGCTGG AGTAGATTTT GAAAGTCAGC TCTGTGTGTG TGTGTGTGTG TGTGTGTGTG
6541  AGAGCGTGTG TTTCTTTTAA CGTTTTCAGC CTACAGCATA CAGGGTTCAT GGTGGCAAGA
6601  AGATAACAAG ATTTAAATTA TGGCCAGTGA CTAGTGCTGC AAGAAGAACA ACTACCTGCA
6661  TTTAATGGGA AAGCAAAATC TCAGGCTTTG AGGGAAGTTA ACATAGGCTT GATTCTGGGT
6721  GGAAGCTGGG TGTGTAGTTA TCTGGAGGCC AGGCTGGAGC TCTCAGCTCA CTATGGGTTC
6781  ATCTTTATTG TCTCCTTTCA TCTCAACAGC TGCACGCTGC CGTCCTCGAT GTTGTGGCGG
6841  ATCTTGAAGT TCACCTTGAT GCCGTTCTTC TGCTTGTCGG CCATGATATA GACGTTGTGG
6901  CTGTTGTAGT TGTACTCCAG CTTGTGCCCC AGGATGTTGC CGTCCTCCTT GAAGTCGATG
6961  CCCTTCAGCT CGATGCGGTT CACCAGGGTG TCGCCCTCGA ACTTCACCTC GGCGCGGGTC
7021  TTGTAGTTGC CGTCGTCCTT GAAGAAGATG GTGCGCTCCT GGACGTAGCC TTCGGGCATG
7081  GCGGACTTGA AGAAGTCGTG CTGCTTCATG TGGTCGGGGT AGCGGCTGAA GCACTGCACG
7141  CCGTAGGTCA GGGTGGTCAC GAGGGTGGGC CAGGGCACGG GCAGCTTGCC GGTGGTGCAG
7201  ATGAACTTCA GGGTCAGCTT GCCGTAGGTG GCATCGCCCT CGCCCTCGCC GGACACGCTG
7261  AACTTGTGGC CGTTTACGTC GCGTCCAGC TCGACCAGGA TGGGCACCAC CCCGGTGAAC
7321  AGCTCCTCGC CCTTGCTCAC CATGGTGGCG AATTCGAAGC TTGAGCACGA GATCTGAGTC
7381  CGGTAGGCCT AGCGGATCTG ACGGTTCACT AAACCAGCTC TGCTTATATA GACCTCCCAC
7441  CGTACACGCC TACCGCCCAT TTGCGTCAAT GGGGCGGAGT TGTTACGACA TTTTGGAAAG
7501  TCCCGTTGAT TTTGGTGCCA AAACAAACTC CCATTGACGT CAATGGGTGG GAGACTTGGA
7561  AATCCCCGTG AGTCAAACCG CTATCCACGC CCATTGATGT ACTGCCAAAA CCGCATCACC
7621  ATGGTAATAG CGATGACTAA TACGTAGATG TACTGCCAAG TAGGAAAGTC CCATAAGGTC
7681  ATGTACTGGG CATAATGCCA GGCGGGCCAT TTACCGTCAT TGACGTCAAT AGGGGGCGTA
7741  CTTGGCATAT GATACACTTG ATGTACTGCC AAGTGGGCAG TTTACCGTAA ATACTCCACC
7801  CATTGACGTC AATGGAAAGT CCCTATTGGC GTTACTATGG GAACATACGT CATTATTGAC
7861  GTCAATGGGC GGGGGTCGTT GGGCGGTCAG CCAGGCGGGC CATTTACCGT AAGTTATGTA
7921  ACGGGCCTGC TGCCGGCTCT GCGGCCTCTT CCGCGTCTTC GCCTTCGCCC TCAGACGAGT
7981  CGGATCTCCC TTTGGGCCGC CTCCCCGCCT GTCTAGCTTG ACTGACTGGA ATACAGCGTA
8041  CCTTCAGCTC ACAGACATGA TAAGATACAT TGATGAGTTT GGACAAACCA CAACTAGAAT
8101  GCAGTGAAAA AAATGCTTTA TTTGTGAAAT TTGTGATGCT ATTGCTTTAT TTGTAACCAT
8161  TATAAGCTGC AATAAACAAG TTAACAACAA CAATTGCATT CATTTTATGT TTCAGGTTCA
8221  GGGGGAGGTG TGGGAGGTTT TTTAAAGCAA GTAAAACCTC TACAAATGTG GTATTGGCCC
8281  ATCTCTATCG GTATCGTAGC ATAACCCCTT GGGGCCTCTA AACGGGTCTT GAGGGGTTTT
8341  TTGTGCCCCT CGGGCCGGAT TGCTATCTAC CGGCATTGGC GCAGAAAAAA ATGCCTGATG
8401  CGACGCTGCG CGTCTTATAC TCCCACATAT GCCAGATTCA GCAACGGATA CGGCTTCCCC
8461  AACTTGCCCA CTTCCATACG TGTCCTCCTT ACCAGAAATT TATCCTTAAG GTCGTCAGCT
8521  ATCCTGCAGG CGATCTCTCG ATTTCGATCA AGACATTCCT TTAATGGTCT TTTCTGGACA
8581  CCACTAGGGG TCAGAAGTAG TTCATCAAAC TTTCTTCCCT CCCTAATCTC ATTGGTTACC
8641  TTGGGCTATC GAAACTTAAT TAAGCGATCT GCATCTCAAT TAGTCAGCAA CCATAGTCCC
8701  GCCCCTAACT CCGCCCATCC CGCCCCTAAC TCCGCCCAGT TCCGCCCATT CTCCGCCCCA
8761  TCGCTGACTA ATTTTTTTTA TTTATGCAGA GGCCGAGGCC GCCTCGGCCT CTGAGCTATT
8821  CCAGAAGTAG TGAGGAGGCT TTTTTGGAGG CCTAGGCTTT TGCAAAGGAG GTAGCCAACA
8881  TGATTGAACA AGATGGATTG CACGCAGGTT CTCCCGCCGC TTGGGTGGAG AGGCTATTCG
8941  GCTATGACTG GGCACAACAG ACAATCGGCT GCTCTGATGC CGCCGTGTTC CGGCTGTCAG
9001  CGCAGGGGCG CCCGGTTCTT TTTGTCAAGA CCGACCTGTC CGGTGCCCTG AATGAACTCC
9061  AGGACGAGGC AGCGCGGCTA TCGTGGCTGG CCACGACGGG CGTTCCTTGC GCAGCTGTGC
9121  TCGACGTTGT CACTGAAGCG GGAAGGGACT GGCTGCTATT GGGCGAAGTG CCGGGGCAGG
9181  ATCTCCTGTC ATCTCACCTT GCTCCTGCCG AGAAAGTATC CATCATGGCT GATGCAATGC
9241  GGCGGCTGCA TACGCTTGAT CCGGCTACCT GCCCATTCGA CCACCAAGCG AAACATCGCA
9301  TCGAGCGAGC ACGTACTCGG ATGGAAGCCG GTCTTGTCGA TCAGGATGAT CTGGACGAAG
9361  AGCATCAGGG GCTCGCGCCA GCCGAACTGT TCGCCAGGCT CAAGGCGCGG ATGCCCGACG
9421  GCGAGGATCT CGTCGTGACC CACGGCGATG CCTGCTTGCC GAATATCATG GTGGAAAATG
9481  GCCGCTTTTC TGGATTCATC GACTGTGGCC GGCTGGGTGT GGCGGACCGC TATCAGGACA
9541  TAGCGTTGGC TACCCGTGAT ATTGCTGAAG AGCTTGGCGG CGAATGGGCT GACCGCTTCC
```

TABLE 8-continued

Plasmid and mRNA construct sequences

```
 9601 TCGTGCTTTA CGGTATCGCC GCTCCCGATT CGCAGCGCAT CGCCTTCTAT CGCCTTCTTG
 9661 ACGAGTTCTT CTAGTATGTA AGCCCTGTGC CTTCTAGTTG CCAGCCATCT GTTGTTTGCC
 9721 CCTCCCCCGT GCCTTCCTTG ACCCTGGAAG GTGCCACTCC CACTGTCCTT TCCTAATAAA
 9781 ATGAGGAAAT TGCATCGCAT TGTCTGAGTA GGTGTCATTC TATTCTGGGG GGTGGGGTGG
 9841 GGCAGGACAG CAAGGGGGAG GATTGGGAAG ACAATAGCAG GCATGCTGGG GATGCGGTGG
 9901 GCTCTATGGT TAATTAACCA GTCAAGTCAG CTACTTGGGG AGATCGATTT GTCTGGGTTT
 9961 CGACTACGCT CAGAATTGCG TCAGTCAAGT TCGATCTGGT CCTTGCTATT GCACCCGTTC
10021 TCCGATTACG AGTTTCATTT AAATCATGTG AGCAAAAGGC CAGCAAAAGG CCAGGAACCG
10081 TAAAAAGGCC GCGTTGCTGG CGTTTTTCCA TAGGCTCCGC CCCCCTGACG AGCATCACAA
10141 AAATCGACGC TCAAGTCAGA GGTGGCGAAA CCCGACAGGA CTATAAAGAT ACCAGGCGTT
10201 TCCCCCTGGA AGCTCCCTCG TGCGCTCTCC TGTTCCGACC CTGCCGCTTA CCGGATACCT
10261 GTCCGCCTTT CTCCCTTCGG GAAGCGTGGC GCTTTCTCAT AGCTCACGCT GTAGGTATCT
10321 CAGTTCGGTG TAGGTCGTTC GCTCCAAGCT GGGCTGTGTG CACGAACCCC CCGTTCAGCC
10381 CGACCGCTGC GCCTTATCCG GTAACTATCG TCTTGAGTCC AACCCGGTAA GACACGACTT
10441 ATCGCCACTG GCAGCAGCCA CTGGTAACAG GATTAGCAGA GCGAGGTATG TAGGCGGTGC
10501 TACAGAGTTC TTGAAGTGGT GGCCTAACTA CGGCTACACT AGAAGAACAG TATTTGGTAT
10561 CTGCGCTCTG CTGAAGCCAG TTACCTTCGG AAAAAGAGTT GGTAGCTCTT GATCCGGCAA
10621 ACAAACCACC GCTGGTAGCG GTGGTTTTTT TGTTTGCAAG CAGCAGATTA CGCGCAGAAA
10681 AAAAGGATCT CAAGAAGATC CTTTGATCTT TTCTACGGGG TCTGACGCTC AGTGGAACGA
10741 AAACTCACGT TAAGGGATTT TGGTCATGAG ATTATCAAAA AGGATCTTCA CCTAGATCCT
10801 TTTAAATTAA AAATGAAGTT TTAAATCAAT CTAAAGTATA TATGAGTAAA CTTGGTCTGA
10861 CAGTTACCAA TGCTTAATCA GTGAGGCACC TATCTCAGCG ATCTGTCTAT TTCGTTCATC
10921 CATAGTTGCA TTTAAATTTC CGAACTCTCC AAGGCCCTCG TCGGAAAATC TTCAAACCTT
10981 TCGTCCGATC CATCTTGCAG GCTACCTCTC GAACGAACTA TCGCAAGTCT CTTGGCCGGC
11041 CTTGCGCCTT GGCTATTGCT TGGCAGCGCC TATCGCCAGG TATTACTCCA ATCCCGAATA
11101 TCCGAGATCG GGATCACCCG AGAGAAGTTC AACCTACATC CTCAATCCCG ATCTATCCGA
11161 GATCCGAGGA ATATCGAAAT CGGGGCGCGC CTGGTGTACC GAGAACGATC CTCTCAGTGC
11221 GAGTCTCGAC GATCCATATC GTTGCTTGGC AGTCAGCCAG TCGGAATCCA GCTTGGGACC
11281 CAGGAAGTCC AATCGTCAGA TATTGTACTC AAGCCTGGTC ACGGCAGCGT ACCGATCTGT
11341 TTAAACCTAG ATATTGATAG TCTGATCGGT CAACGTAAA TCGAGTCCTA GCTTTTGCAA
11401 ACATCTATCA AGAGACAGGA TCAGCAGGAG GCTTTCGCAT GAGTATTCAA CATTTCCGTG
11461 TCGCCCTTAT TCCCTTTTTT GCGGCATTTT GCCTTCCTGT TTTTGCTCAC CCAGAAACGC
11521 TGGTGAAAGT AAAAGATGCT GAAGATCAGT TGGGTGCGCG AGTGGGTTAC ATCGAACTGG
11581 ATCTCAACAG CGGTAAGATC CTTGAGAGTT TTCGCCCCGA AGAACGCTTT CCAATGATGA
11641 GCACTTTTAA AGTTCTGCTA TGTGGCGCGG TATTATCCCG TATTGACGCC GGGCAAGAGC
11701 AACTCGGTCG CCGCATACAC TATTCTCAGA ATGACTTGGT TGAGTATTCA CCAGTCACAG
11761 AAAAGCATCT TACGGATGGC ATGACAGTAA GAGAATTATG CAGTGCTGCC ATAACCATGA
11821 GTGATAACAC TGCGGCCAAC TTACTTCTGA CAACGATTGG AGGACCGAAG GAGCTAACCG
11881 CTTTTTTGCA CAACATGGGG GATCATGTAA CTCGCCTTGA TCGTTGGGAA CCGGAGCTGA
11941 ATGAAGCCAT ACCAAACGAC GAGCGTGACA CCACGATGCC TGTAGCAATG GCAACAACCT
12001 TGCGTAAACT ATTAACTGGC GAACTACTTA CTCTAGCTTC CCGGCAACAG TTGATAGACT
12061 GGATGGAGGC GGATAAAGTT GCAGGACCAC TTCTGCGCTC GGCCCTTCCG GCTGGCTGGT
12121 TTATTGCTGA TAAATCTGGA GCCGGTGAGC GTGGGTCTCG CGGTATCATT GCAGCACTGG
12181 GGCCAGATGG TAAGCCCTCC CGTATCGTAG TTATCTACAC GACGGGGAGT CAGGCAACTA
12241 TGGATGAACG AAATAGACAG ATCGCTGAGA TAGGTGCCTC ACTGATTAAG CATTGGTAAC
12301 CGATTCTAGG TGCATTGGCG CAGAAAAAAA TGCCTGATGC GACGCTGCGC GTCTTATACT
12361 CCCACATATG CCAGATTCAG CAACGGATAC GGCTTCCCCA ACTTGCCCAC TTCCATACGT
12421 GTCCTCCTTA CCAGAAATTT ATCCTTAAGA TCGTTTAAAC TCGACTCTGG CTCTATCGAA
12481 TCTCCGTCGT TTCGAGCTTA CGCGAACAGC CGTGGCGCTC ATTTGCTCGT CGGGCATCGA
12541 ATCTCGTCAG CTATCGTCAG CTTACCTTTT TGGCAGCGAT CGCGGCTCCC GACATCTTGG
12601 ACCATTAGCT CCACAGGTAT CTTCTTCCCT CTAGTGGTCA TAACAGCAGC TTCAGCTACC
12661 TCTCAATTCA AAAAACCCCT CAAGACCCGT TTAGAGGCCC CAAGGGGTTA TGCTATCAAT
12721 CGTTGCGTTA CACACACAAA AAACCAACAC ACATCCATCT TCGATGGATA GCGATTTTAT
12781 TATCTAACTG CTGATCGAGT GTAGCCAGAT CTAGTAATCA ATTACGGGGT CATTAGTTCA
12841 TAGCCCATAT ATGGAGTTCC GCGTTACATA ACTTACGGTA AATGGCCCGC CTGGCTGACC
12901 GCCCAACGAC CCCCGCCCAT TGACGTCAAT AATGACGTAT GTTCCCATAG TAACGCCAAT
12961 AGGGACTTTC CATTGACGTC AATGGGTGGA GTATTTACGG TAAACTGCCC ACTTGGCAGT
13021 ACATCAAGTG TATCATATGC CAAGTACGCC CCCTATTGAC GTCAATGACG GTAAATGGCC
13081 CGCCTGGCAT TATGCCCAGT ACATGACCTT ATGGGACTTT CCTACTTGGC AGTACATCTA
13141 CGTATTAGTC ATCGCTATTA CCATGCTGAT GCGGTTTTGG CAGTACATCA ATGGGCGTGG
13201 ATAGCGGTTT GACTCACGGG GATTTCCAAG TCTCCACCCC ATTGACGTCA ATGGGAGTTT
13261 GTTTTGGCAC CAAAATCAAC GGGACTTTCC AAAATGTCGT AACAACTCCG CCCCATTGAC
13321 GCAAATGGGC GGTAGGCGTG TACGGTGGGA GGTCTATATA AGCAGAGCTG GTTTAGTGAA
13381 CCGTCAGATC AGATCTTTGT CGATCCTACC ATCCACTCGA CACACCCGCC AGCGGCCGC
       (SEQ ID NO: 46)
```

LINE-1 plasmid ORF 1-P2A-ORF2 GFP (SEQ ID NO: 47)

```
   1 TAATACGACT CACTATAGGG AGAAGTACTG CCACCATGGG CAAGAAGCAA AATCGCAAGA
  61 CGGGGAATTC CAAGACACAA TCCGCTAGCC CACCACCTAA AGAGCGTTCT AGCTCCCCTG
 121 CTACTGAGCA GTCCTGGATG GAAAACGACT TCGATGAACT CCGGGAAGAG GGATTTAGGC
 181 GATCCAACTA TTCAGAACTC CGCGAAGATA TCCAGACAAA GGGGAAGGAA GTCGAGAATT
 241 TCGAGAAGAA CCTCGAGGAG TGCATCACCC GTATCACAAA CACTGAGAAA TGTCTCAAAG
 301 AACTCATGGA ACTTAAGACA AAAGCCAGGG AGCTTCAGGA GGAGTGTCGG AGTCTGAGAT
 361 CCAGGTGTGA CCAGCTCGAG GAGCGCGTGA GCGCGATGGA AGACGAGATG AACGAGATGA
 421 AAAGAGAGGG CAAATTCAGG GAGAAGCGCA TTAAGAGGAA CGAACAGAGT CTGCAGGAGA
 481 TTTGGGATTA CGTCAAGAGG CCTAACCTGC GGTTGATCGG CGTCCCCGAG AGCGACGTAG
 541 AAAACGGGAC TAAACTGGAG AATACACTTC AAGACATCAT TCAAGAAAAT TTTCCAAACC
 601 TGGCTCGGCA AGCTAATGTG CAAATCCAAG AGATCCAACG CACACCCCAG CGGTATAGCT
```

TABLE 8-continued

Plasmid and mRNA construct sequences

```
 661 CTCGGCGTGC CACCCCTAGG CATATTATCG TGCGCTTTAC TAAGGTGGAG ATGAAAGAGA
 721 AGATGCTGCG AGCCGCTCGG GAAAAGGGAA GGGTGACTTT GAAGGGCAAA CCTATTCGGC
 781 TGACGGTTGA CCTTAGCGCC GAGACACTCC AGGCACGCCG GGAATGGGGC CCCATCTTTA
 841 ATATCCTGAA GGAGAAGAAC TTCCAGCCAC GAATCTCTTA CCCTGCAAAG TTGAGTTTTA
 901 TCTCCGAGGG TGAGATTAAG TATTTCATCG ATAAACAGAT GCTGCGAGAC TTCGTGACAA
 961 CTCGCCCAGC TCTCAAGGAA CTGCTCAAAG AGGCTCTTAA TATGGAGCGC AATAATAGAT
1021 ATCAACCCTT GCAGAACCAC GCAAAGATGG GAAGCGGAGC TACTAACTTC AGCCTGCTGA
1081 AGCAGGCTGG AGACGTGGAG GAGAACCCTG GACCTATGAC CGGCTCTAAC TCACATATCA
1141 CCATCCTTAC ACTTAACATT AACGGCCTCA ACTCAGCTAT CAAGCGCCAT CGGCTGGCCA
1201 GCTGGATCAA ATCACAGGAT CCAAGCGTTT GTTGCATCCA AGAGACCCAC CTGACCTGTA
1261 GAGATACTCA CCGCCTCAAG ATCAAGGGAT GGCGAAAGAT TTATCAGGCG AACGGTAAGC
1321 AGAAGAAAGC CGGAGTCGCA ATTCTGGTCT CAGACAAGAC GGATTTCAAG CCCACCAAAA
1381 TTAAGCGTGA TAAGGAAGGT CACTATATTA TGGTGAAAGG CAGCATACAG CAGGAAGAAC
1441 TTACCATATT GAACATCTAC GCGCCAAACA CCGGCGCACC TCGCTTTATC AAACAGGTCC
1501 TGTCCGATCT GCAGCGAGAT CTGGATTCTC ATACGTTGAT TATGGGTGAT TTCAATACAC
1561 CATTGAGCAC CCTGGATCGC AGCACCAGGC AAAAGGTAAA TAAAGACACG CAAGAGCTCA
1621 ATAGCGCACT GCATCAGGCA GATCTCATTG ATATTTATCG CACTCTTCAT CCTAAGAGTA
1681 CCGAGTACAC ATTCTTCAGC GCCCCACATC ATACACTACTC AAAGATCGAT CATATCGTCG
1741 GCTCAAAGGC TCTGCTGTCA AAGTGCAAGC GCACAGAGAT AATTACAAAT TACCTGTCAG
1801 ATCATAGCGC GATCAAGCTC GAGCTGAGAA TCAAGAACCT GACCCAGAGC CGGAGTACCA
1861 CTTGGAAGCT TAATAACCTG CTGCTCAACG ATTATTGGGT CCACAATGAG ATGAAGGCAG
1921 AGATTAAAAT GTTCTTCGAA ACAAATGAGA ATAAGGATAC TACCTATCAA AACCTTTGGG
1981 ATGCCTTTAA GGCCGTCTGC AGAGGCAAGT TCATCGCCCT CAACGCCTAT AAAAGAAAAC
2041 AAGAGAGATC TAAGATCGAT ACTCTCACCT CTCAGCTGAA GGAGTTGGAG AAACAGGAAC
2101 AGACCCACTC CAAGGCGTCA AGACGGCAGG AGATCACAAA GATTCGCGCC GAGTTGAAAG
2161 AGATCGAAAC CCAAAAGACT CTTCAGAAAA TTAACGAGTC TCGTAGTTGG TTCTTCGAGC
2221 GGATTAATAA GATAGACAGA CCTCTGGCAC GACTGATTAA GAAGAAGCGC GAAAAGAACC
2281 AGATTGATAC CATCAAGAAC GACAAGGGCG ACATCACTAC TGACCCGACC GAGATCCAGA
2341 CCACTATTCG GGAGTATTAT AAGCATTTGT ATGCTAACAA GCTTGAGAAC CTGGAAGAGA
2401 TGGACACTTT TCTGGATACC TATACTCTGC CACGGCTTAA TCAAGAGGAA GTCGAGTCCC
2461 TCAACCGCCC AATTACAGGA AGCGAGATTG TGGCCATAAT TAACTCCCTG CCGACAAAGA
2521 AATCTCCTGG TCCGGACGGG TTTACAGCTG AGTTTTATCA ACGGTATATG GAAGAGCTTG
2581 TACCGTTTCT GCTCAAGCTC TTTCAGTCTA TAGAAAAGGA AGGCATCTTG CCCAATTCCT
2641 TCTACGAAGC TTCTATAATA CTTATTCCCA AACCAGGACG CGATACCACA AAGAAGGAAA
2701 ACTTCCGGCC CATTAGTCTC ATGAATATCG ACGCTAAAAT ATTGAACAAG ATTCTCGCCA
2761 ACAGAATCCA ACAACATATT AAGAAATTGA TACATCACGA CCAGGTGGGG TTTATACCTG
2821 GCATGCAGGG CTGGTTTAAC ATCCGGAAGA GTATTAACGT CATTCAACAC ATTAATAGAG
2881 CTAAGGATAA GAATCATATG ATCATCTCTA TAGACGCGGA AAAGGCATTC GATAAGATTC
2941 AGCAGCCATT TATGCTCAAG ACTCTGAACA AACTCGGCAT CGACGGAACA TATTTTAAGA
3001 TTATTCGCGC AATTTACGAT AAGCCGACTG CTAACATTAT CCTTAACGGC CAAAAGCTCG
3061 AGGCCTTTCC GCTCAAGACT GGAACCCGCC AAGGCTGTCC CCTCTCCCCG CTTTTGTTTA
3121 ATATTGTACT CGAGGTGCTG GCTAGGGCTA TTCGTCAAGA GAAAGAGATT AAAGGGATAC
3181 AGCTCGGGAA GGAAGAGGTC AAGCTTTCCT TGTTCGCCGA TGATATGATT GTGTACCTGG
3241 AGATCCTAT TGTGTCTGCT CAGAACCTTC TTAAACTTAT TTCTAACTTT AGCAAGGTCA
3301 GCGGCTATAA GATTAACGTC CAGAAATCTC AGGCCTTTCT GTACACAAAT AATCGACAGA
3361 CCGAATCCCA GATAATGGGT GAGCTTCCGT TTGTCATAGC CAGCAAAAGG ATAAAGTATC
3421 TCGGAATCCA GCTGACACGA GACGTTAAAG ATTTGTTTAA GGAAATTAC AAGCCTCTCC
3481 TGAAAGAGAT TAAGGAAGAT ACTAATAAGT GGAAGAATAT CCCCTGTTCA TGGGTTGGCA
3541 GAATCAACAT AGTGAAGATG GCAATACTTC CTAAAGTGAT ATATCGCTTT AACGCCATCC
3601 CAATTAAACT GCCTATGACC TTCTTTACGG AGCTCGAGAA AACAACCCTT AAATTTATAT
3661 GGAATCAAAA GAGAGCAAGA ATAGCGAAGT CCATCTTGAG CCAGAAGAAT AAGGCCGGTG
3721 GGATTACTTT GCCTGATTTT AAGTTGTATT ATAAAGCCAC AGTAACTAAG ACAGCCTGGT
3781 ATTGGTATCA GAATAGAGAC ATCGACCAGT GGAATCGGAC CGAACCATCA AGGATAATGC
3841 CCCACATCTA TAATTACCTT ATATTCGATA AGCCAGAAAA GAATAAACAG TGGGGCAAAG
3901 ACAGCCTCTT CAACAAGTGG TGTTGGGAGA ATTGGCTGGC CATATGCCGG AAACTCAAGC
3961 TCGACCCCTT TCTTACACCC TACACTAAAA TCAACAGTAG GTGGATCAAG GACTTGAATG
4021 TCAAGCCAAA GACTATAAAG ACACTGGAAG AGAATCTTGG GATCACAATA CAAGATATAG
4081 GCGTCGGCAA AGATTTTATG TCAAAGACGC CAAGGCCAT GGCCACTAAG GATAAGATTG
4141 ATAAGTGGGA CCTTATTAAG CTCAAAAGCT TCTGTACTGC CAAGGAGACC ACGATCAGAG
4201 TTAATAGGCA GCCCACTACA TGGGAAAGA TTTTCGCCAC TTATTCATCA GATAAGGGGT
4261 TGATAAGCAG AATATATAAC GAGTCGAAGC AGATCTACAA GAAGAAAACG AATAATCCCA
4321 TCAAGAAGTG GGCAAAAGAT ATGAACAGGC ATTTTAGCAA AGAGGATATC TACGCCGCGA
4381 AGAAGCATAT GAAGAAGTGT AGTTCAAGCT TGGCCATTCG TGAGATGCAG ATTAAGACGA
4441 CCATGCGATA CCACCTTACC CCAGTGAGGA TGGCAATTAT CAAGAAATCT GGCAATAATA
4501 GATGTTGGCG GGGCTGTGGC GAGATTGGCA CCCTGCTCCA TTGCTGGTGG GATTGCAAGC
4561 TGGTGCAGCC GCTTTGGAAA TCAGTCTGGC GCTTTCTGAG GGACCTCGAG CTTGAGATTC
4621 CCTTCGATCC CGCAATTCCC TTGCTCGGAA TCTATCCTAA CGAATACAAG AGCTGTTGTT
4681 ACAAGGATAC GTGTACCCGG ATGTTCATCG CGGCCTTGTT TACGATAGCT AAGACGTGGA
4741 ATCAGCCTAA GTGCCCCACA ATGATCGATT GGATCAAGAA AATGTGGCAT ATTTATACCA
4801 TGGAGTATTA CGCAGCAATT AAGAATGACG AATTTATTC CTTCGTTGGG ACCTGGATGA
4861 AGCTGGAGAC TATTATTCTG AGCAAGCTGT CTCAGGAGCA AAAGACAAAG CATAGAATCT
4921 TCTCTCTCAT TGGTGGTAAC GACTACAAAG ACGATGACGA CAAGTAAAGC GCTTCTAGAA
4981 GTTGTCTCCT CCTGCACTGA CTGACTGATA CAATCCATTT CTGGATCCGC AGGCCTAATC
5041 AACCTCTGGA TTACAAAATT TGTGAAAGAT TGACTGGTAT TCTTAACTAT GTTGCTCCTT
5101 TTACGCTATG TGGATACGCT GCTTTAATGC CTTTGTATCA TGCTATTGCT TCCCGTATGG
5161 CTTTCATTTT CTCCTCCTTG TATAAATCCT GGTTGCTGTC TCTTTATGAG GAGTTGTGGC
5221 CCGTTGTCAG GCAACGTGGC GTGGTGTGCA CTGTGTTTGC TGACGCAACC CCCACTGGTT
5281 GGGGCATTGC CACCACCTGT CAGCTCCTTT CCGGGACTTT CGCTTTCCCC CTCCCTATTG
```

TABLE 8-continued

Plasmid and mRNA construct sequences

```
5341  CCACGGCGGA ACTCATCGCC GCCTGCCTTG CCCGCTGCTG GACAGGGGCT CGGCTGTTGG
5401  GCACTGACAA TTCCGTGGTG TTGTCGGGGA AGCTGACGTC CTTTCCATGG CTGCTCGCCT
5461  GTGTTGCCAC CTGGATTCTG CGCGGGACGT CCTTCTGCTA CGTCCCTTCG GCCCTCAATC
5521  CAGCGGACCT TCCTTCCCGC GAACAAACGA CCCAACACCC GTGCGTTTTA TTCTGTCTTT
5581  TTATTGCCGA TCCCCTCAGA AGAACTCGTC AAGAAGGCGA TAGAAGGCGA TGCGCTGCGA
5641  ATCGGGAGCG GCGATACCGT AAAGCACGAG GAAGCGGTCA GCCCATTCGC CGCCAAGCTC
5701  TTCAGCAATA TCACGGGTAG CCAACGCTAT GTCCTGATAG CGGTCGGCCG CTTTACTTTG
5761  ACAGCTCGTC CATGCCGAGA GTGATCCCGG CGGCGGTCAC GAACTCCAGC AGGACCATGT
5821  GATCGCGCTT CTCGTTGGGG TCTTTGCTCA GGGCGGACTG GGTGCTCAGG TAGTGGTTGT
5881  CGGGCAGCAG CACGGGGCCG TCGCCGATGG GGGTGTTCTG CTGGTAGTGG TCGGCCAGGT
5941  GAGTCCAGGA GATGTTTCAG CACTGTTGCC TTTAGTCTCG AGGCAACTTA GACAACTGAG
6001  TATTGATCTG AGCACAGCAG GGTGTGAGCT GTTTGAAGAT ACTGGGGTTG GGGGTGAAGA
6061  AACTGCAGAG GACTAACTGG GCTGAGACCC AGTGGCAATG TTTTAGGGCC TAAGGAATGC
6121  CTCTGAAAAT CTAGATGGAC AACTTTGACT TGAGAAAAG AGAGGTGGAA ATGAGGAAAA
6181  TGACTTTTCT TTATTAGATT TCGGTAGAAA GAACTTTCAT CTTTCCCCTA TTTTTGTTAT
6241  TCGTTTTAAA ACATCTATCT GGAGGCAGGA CAAGTATGGT CATTAAAAAG ATGCAGGCAG
6301  AAGGCATATA TTGGCTCAGT CAAAGTGGGG AACTTTGGTG GCCAAACATA CATTGCTAAG
6361  GCTATTCCTA TATCAGCTGG ACACATATAA AATGCTGCTA ATGCTTCATT ACAAACTTAT
6421  ATCCTTTAAT TCCAGATGGG GGCAAAGTAT GTCCAGGGGT GAGGAACAAT TGAAACATTT
6481  GGGCTGGAGT AGATTTGAA AGTCAGCTCT GTGTGTGTGT GTGTGTGTGT GTGTGTGAGA
6541  GCGTGTGTTT CTTTTAACGT TTTCAGCCTA CAGCATACAG GGTTCATGGT GGCAAGAAGA
6601  TAACAAGATT TAAATTATGG CCAGTGACTA GTGCTGCAAG AAGAACAACT ACCTGCATTT
6661  AATGGGAAAG CAAAATCTCA GGCTTTGAGG GAAGTTAACA TAGGCTTGAT TCTGGGTGGA
6721  AGCTGGGTGT GTAGTTATCT GGAGGCCAGG CTGGAGCTCT CAGCTCACTA TGGGTTCATC
6781  TTTATTGTCT CCTTTCATCT CAACAGCTGC ACGCTGCCGT CCTCGATGTT GTGGCGGATC
6841  TTGAAGTTCA CCTTGATGCC GTTCTTCTGC TTGTCGGCCA TGATATAGAC GTTGTGGCTG
6901  TTGTAGTTGT ACTCCAGCTT GTGCCCCAGG ATGTTGCCGT CCTCCTTGAA GTCGATGCCC
6961  TTCAGCTCGA TGCGGTTCAC CAGGGTGTCG CCCTCGAACT TCACCTCGGC GCGGGTCTTG
7021  TAGTTGCCGT CGTCCTTGAA GAAGATGGTG CGCTCCTGGA CGTAGCCTTC GGGCATGGCG
7081  GACTTGAAGA AGTCGTGCTG CTTCATGTGG TCGGGGTAGC GGCTGAAGCA CTGCACGCCG
7141  TAGGTCAGGG TGGTCACGAG GGTGGGCCAG GGCACGGGCA GCTTGCCGGT GGTGCAGATG
7201  AACTTCAGGG TCAGCTTGCC GTAGGTGGCA TCGCCCTCGC CCTCGCCGGA CACGCTGAAC
7261  TTGTGGCCGT TTACGTCGCC GTCCAGCTCG ACCAGGATGG GCACCACCCC GGTGAACAGC
7321  TCCTCGCCCT TGCTCACCAT GGTGGCGAAT TCGAAGCTTG AGCACGAGAT CTGAGTCCGG
7381  TAGGCCTAGC GGATCTGACG GTTCACTAAA CCAGCTCTGC TTATATAGAC CTCCCACCGT
7441  ACACGCCTAC CGCCCATTTG CGTCAATGGG GCGGAGTTGT TACGACATTT TGGAAAGTCC
7501  CGTTGATTTT GGTGCCAAAA CAAACTCCCA TTGACGTCAA TGGGGTGGAG ACTTGGAAAT
7561  CCCCGTGAGT CAAACCGCTA TCCACGCCCA TTGATGTACT GCCAAAACCG CATCACCATG
7621  GTAATAGCGA TGACTAATAC GTAGATGTAC TGCCAAGTAG GAAAGTCCCA TAAGGTCATG
7681  TACTGGGCAT AATGCCAGGC GGGCCATTTA CCGTCATTGA CGTCAATAGG GGGCGTACTT
7741  GGCATATGAT ACACTTGATG TACTGCCAAG TGGGCAGTTT ACCGTAAATA CTCCACCCAT
7801  TGACGTCAAT GGAAAGTCCC TATTGGCGTT ACTATGGGAA CATACGTCAT TATTGACGTC
7861  AATGGGCGGG GGTCGTTGGG CGGTCAGCCA GGCGGGCCAT TTACCGTAAG TTATGTAACG
7921  GGCCTGCTGC CGGCTCTGCG GCCTCTTCCG CGTCTTCGCC TTCGCCCTCA GACGAGTCGG
7981  ATCTCCCTTT GGGCCGCCTC CCCGCCTGTC TAGCTTGACT GACTGAGATA CAGCGTACCT
8041  TCAGCTCACA GACATGATAA GATACATTGA TGAGTTTGGA CAAACCACAA CTAGAATGCA
8101  GTGAAAAAAA TGCTTTATTT GTGAAATTTG TGATGCTATT GCTTTATTTG TAACCATTAT
8161  AAGCTGCAAT AAACAAGTTA ACAACAACAA TTGCATTCAT TTTATGTTTC AGGTTCAGGG
8221  GGAGGTGTGG GAGGTTTTTT AAAGCAAGTA AAACCTCTAC AAATGTGGTA TTGGCCCATC
8281  TCTATCGGTA TCGTAGCATA ACCCCTTGGG GCCTCTAAAC GGGTCTTGAG GGGTTTTTTG
8341  TGCCCCTCGG GCCGGATTGC TATCTACCGG CATTGGCGCA GAAAAAAATG CCTGATGCGA
8401  CGCTGCGCGT CTTATACTCC CACATATGCC AGATTCAGCA ACGGATACGG CTTCCCCAAC
8461  TTGCCCACTT CCATACGTGT CCTCCTTACC AGAAATTTAT CCTTAAGGTC GTCAGCTATC
8521  CTGCAGGCGA TCTCTCGATT TCGATCAAGA CATTCCTTTA ATGGTCTTTT CTGGACACCA
8581  CTAGGGGTCA GAAGTAGTTC ATCAAACTTT CTTCCCTCCC TAATCTCATT GGTTACCTTG
8641  GGCTATCGAA ACTTAATTAA GCGATCTGCA TCTCAATTAG TCAGCAACCA TAGTCCCGCC
8701  CCTAACTCCG CCCATCCCGC CCCTAACTCC GCCCAGTTCC GCCCATTCTC CGCCCCATCG
8761  CTGACTAATT TTTTTTATTT ATGCAGAGGC CGAGGCCGCC TCGGCCTCTG AGCTATTCCA
8821  GAAGTAGTGA GGAGGCTTTT TTGGAGGCCT AGGCTTTTGC AAAGGAGGTA GCCAACATGA
8881  TTGAACAAGA TGGATTGCAC GCAGGTTCTC CCGCCGCTTG GGTGGAGAGG CTATTCGGCT
8941  ATGACTGGGC ACAACAGACA ATCGGCTGCT CTGATGCCGC CGTGTTCCGG CTGTCAGCGC
9001  AGGGGCGCCC GGTTCTTTTT GTCAAGACCG ACCTGTCCGG TGCCCTGAAT GAACTCCAGG
9061  ACGAGGCAGC GCGGCTATCG TGGCTGGCCA CGACGGGCGT TCCTTGCGCA GCTGTGCTCG
9121  ACGTTGTCAC TGAAGCGGGA AGGGACTGGC TGCTATTGGG CGAAGTGCCG GGGCAGGATC
9181  TCCTGTCATC TCACCTTGCT CCTGCCGAGA AAGTATCCAT CATGGCTGAT GCAATGCGGC
9241  GGCTGCATAC GCTTGATCCG GCTACCTGCC CATTCGACCA CCAAGCGAAA CATCGCATCG
9301  AGCGAGCACG TACTCGGATG AAGCCGGTC TTGTCGATCA GGATGATCTG GACGAAGAGC
9361  ATCAGGGGCT CGCGCCAGCC GAACTGTTCG CCAGGCTCAA GGCGCGGATG CCCGACGGCG
9421  AGGATCTCGT CGTGACCCAC GGCGATGCCT GCTTGCCGAA TATCATGGTG GAAAATGGCC
9481  GCTTTTCTGG ATTCATCGAC TGTGGCCGGC TGGGTGTGGC GGACCGCTAT CAGGACATAG
9541  CGTTGGCTAC CCGTGATATT GCTGAAGAGC TTGGCGGCGA ATGGGCTGAC CGCTTCCTCG
9601  TGCTTTACGG TATCGCCGCT CCCGATTCGC AGCGCATCGC CTTCTATCGC CTTCTTGACG
9661  AGTTCTTCTA GTATGTAAGC CCTGTGCCTT CTAGTTGCCA GCCATCTGTT GTTTGCCCCT
9721  CCCCCGTGCC TTCCTTGACC CTGGAAGGTG CCACTCCCAC TGTCCTTTCC TAATAAAATG
9781  AGGAAATTGC ATCGCATTGT CTGAGTAGGT GTCATTCTAT TCTGGGGGGT GGGGTGGGGC
9841  AGGACAGCAA GGGGGAGGAT TGGGAAGACA ATAGCAGGCA TGCTGGGGAT GCGGTGGGCT
9901  CTATGGTTAA TTAACCAGTC AAGTCAGCTA CTTGGCGAGA TCGACTTGTC TGGGTTTCGA
9961  CTACGCTCAG AATTGCGTCA GTCAAGTTCG ATCTGGTCCT TGCTATTGCA CCCGTTCTCC
```

TABLE 8-continued

Plasmid and mRNA construct sequences

```
10021 GATTACGAGT TTCATTTAAA TCATGTGAGC AAAAGGCCAG CAAAAGGCCA GGAACCGTAA
10081 AAAGGCCGCG TTGCTGGCGT TTTTCCATAG GCTCCGCCCC CCTGACGAGC ATCACAAAAA
10141 TCGACGCTCA AGTCAGAGGT GGCGAAACCC GACAGGACTA TAAAGATACC AGGCGTTTCC
10201 CCCTGGAAGC TCCCTCGTGC GCTCTCCTGT TCCGACCCTG CCGCTTACCG GATACCTGTC
10261 CGCCTTTCTC CCTTCGGGAA GCGTGGCGCT TTCTCATAGC TCACGCTGTA GGTATCTCAG
10321 TTCGGTGTAG GTCGTTCGCT CCAAGCTGGG CTGTGTGCAC GAACCCCCCG TTCAGCCCGA
10381 CCGCTGCGCC TTATCCGGTA ACTATCGTCT TGAGTCCAAC CCGGTAAGAC ACGACTTATC
10441 GCCACTGGCA GCAGCCACTG GTAACAGGAT TAGCAGAGCG AGGTATGTAG GCGGTGCTAC
10501 AGAGTTCTTG AAGTGGTGGC CTAACTACGG CTACACTAGA AGAACAGTAT TTGGTATCTG
10561 CGCTCTGCTG AAGCCAGTTA CCTTCGGAAA AAGAGTTGGT AGCTCTTGAT CCGGCAAACA
10621 AACCACCGCT GGTAGCGGTG GTTTTTTTGT TTGCAAGCAG CAGATTACGC GCAGAAAAAA
10681 AGGATCTCAA GAAGATCCTT TGATCTTTTC TACGGGGTCT GACGCTCAGT GGAACGAAAA
10741 CTCACGTTAA GGGATTTTGG TCATGAGATT ATCAAAAAGG ATCTTCACCT AGATCCTTTT
10801 AAATTAAAAA TGAAGTTTTA AATCAATCTA AAGTATATAT GAGTAAACTT GGTCTGACAG
10861 TTACCAATGC TTAATCAGTG AGGCACCTAT CTCAGCGATC TGTCTATTTC GTTCATCCAT
10921 AGTTGCATTT AAATTTCCGA ACTCTCCAAG GCCCTCGTCG GAAAATCTTC AAACCTTTCG
10981 TCCGATCCAT CTTGCAGGCT ACCTCTCGAA CGAACTATCG CAAGTCTCTT GGCCGGCCTT
11041 GCGCCTTGGC TATTGCTTGG CAGCGCCTAT CGCCAGGTAT TACTCCAATC CCGAATATCC
11101 GAGATCGGGA CTCACCCGAG GAAGTTCAAC TACATCCTCA AATCCCGATC TATCCGAGAT
11161 CCGAGGAATA TCGAAATCGG GGCGCGCCTG GTGTACCGAG AACGATCCTC TCAGTGCGAG
11221 TCTCGACGAT CCATATCGTT GCTTGGCAGT CAGCCAGTCG GAATCCAGCT TGGGACCCAG
11281 GAAGTCCAAT CGTCAGATAT TGTACTCAAG CCTGGTCACG GCAGCGTACC GATCTGTTTA
11341 AACCTAGATA TTGATAGTCT GATCGGTCAA CGTATATCA AGTCCTAGCT TTTGCAAACA
11401 TCTATCAAGA GACAGGATCA GCAGGAGGCT TTCGCATGAG TATTCAACAT TTCCGTGTCG
11461 CCCTTATTCC CTTTTTTGCG GCATTTTGCC TTCCTGTTTT TGCTCACCCA GAAACGCTGG
11521 TGAAAGTAAA AGATGCTGAA GATCAGTTGG GTGCGCGAGT GGGTTACATC GAACTGGATC
11581 TCAACAGCGG TAAGATCCTT GAGAGTTTTC GCCCCGAAGA ACGCTTTCCA ATGATGAGCA
11641 CTTTTAAAGT TCTGCTATGT GGCGCGGTAT TATCCCGTAT TGACGCCGGG CAAGAGCAAC
11701 TCGGTCGCCG CATACACTAT TCTCAGAATG ACTTGGTTGA GTATTCACCA GTCACAGAAA
11761 AGCATCTTAC GGATGGCATG ACAGTAAGAG AATTATGCAG TGCTGCCATA ACCATGAGTG
11821 ATAACACTGC GGCCAACTTA CTTCTGACAA CGATTGGAGG ACCGAAGGAG CTAACCGCTT
11881 TTTTGCACAA CATGGGGGAT CATGTAACTC GCCTTGATCG TTGGGAACCG GAGCTGAATG
11941 AAGCCATACC AAACGACGAG CGTGACACCA CGATGCCTGT AGCAATGGCA ACAACCTTGC
12001 GTAAACTATT AACTGGCGAA CTACTTACTC TAGCTTCCCG GCAACAGTTG ATAGACTGGA
12061 TGGAGGCGGA TAAAGTTGCA GGACCACTTC TGCGCTCGGC CCTTCCGGCT GGCTGGTTTA
12121 TTGCTGATAA ATCTGGAGCC GGTGAGCGTG GGTCTCGCGG TATCATTGCA GCACTGGGGC
12181 CAGATGGTAA GCCCTCCCGT ATCGTAGTTA TCTACACGAC GGGGAGTCAG GCAACTATGG
12241 ATGAACGAAA TAGACAGATC GCTGAGATAG GTGCCTCACT GATTAAGCAT TGGTAACCGA
12301 TTCTAGGTGC ATTGGCGCAG AAAAAAATGC CTGATGCGAC GCTGCGCGTC TTATACTCCC
12361 ACATATGCCA GATTCAGCAA CGGATACGGC TTCCCCAACT TGCCCACTTC CATACGTGTC
12421 CTCCTTACCA GAAATTTATC CTTAAGATCG TTTAAACTCG ACTCTGGCTC TATCGAATCT
12481 CCGTCGTTTC GAGCTTACGC GAACAGCCGT GGCGCTCATT TGCTCGTCGG GCATCGAATC
12541 TCGTCAGCTA TCGTCAGCTT ACCTTTTTGG CAGCGATCGC GGCTCCCGAC ATCTTGGACC
12601 ATTAGCTCCA CAGGTATCTT CTTCCCTCTA GTGGTCATAA CAGCAGCTTC AGCTACCTCT
12661 CAATTCAAAA AACCCCTCAA GACCCGTTTA GAGGCCCCAA GGGGTTATGC TATCAATCGT
12721 TGCGTTACAC ACACAAAAAA CCAACACACA TCCATCTTCG ATGGATAGCG ATTTTATTAT
12781 CTAACTGCTG ATCGAGTGTA GCCAGATCTA GTAATCAATT ACGGGGTCAT TAGTTCATAG
12841 CCCATATATG GAGTTCCGCG TTACATAACT TACGGTAAAT GGCCCGCCTG GCTGACCGCC
12901 CAACGACCCC CGCCCATTGA CGTCAATAAT GACGTATGTT CCCATAGTAA CGCCAATAGG
12961 GACTTTCCAT TGACGTCAAT GGGTGGAGTA TTTACGGTAA ACTGCCCACT TGGCAGTACA
13021 TCAAGTGTAT CATATGCCAA GTACGCCCCC TATTGACGTC AATGACGGTA AATGGCCCGC
13081 CTGGCATTAT GCCCAGTACA TGACCTTATG GGACTTTCCT ACTTGGCAGT ACATCTACGT
13141 ATTAGTCATC GCTATTACCA TGCTGATGCG GTTTTGGCAG TACATCAATG GGCGTGGATA
13201 GCGGTTTGAC TCACGGGGAT TTCCAAGTCT CCACCCCATT GACGTCAATG GGAGTTTGTT
13261 TTGGCACCAA AATCAACGGG ACTTTCCAAA ATGTCGTAAC AACTCCGCCC CATTGACGCA
13321 AATGGGCGGT AGGCGTGTAC GGTGGGAGGT CTATATAAGC AGAGCTGGTT TAGTGAACCG
13381 TCAGATCAGA TCTTTGTCGA TCCTACCATC CACTCGACAC ACCCGCCAGC GGCCGC
      (SEQ ID NO: 47)
```

LINE-1 plasmid ORF1-T2A ORF2 GFP (SEQ ID NO: 48)

```
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGAGGAA CGAACAGAGT CTGCAGGAGA
  481 TTTGGGATTA CGTCAAGAGG CCTAACCTGC GGTTGATCGG CGTCCCCGAG AGCGACGTAG
  541 AAAACGGGAC TAAACTGGAG AATACACTTC AAGACATCAT TCAAGAAAAT TTTCCAAACC
  601 TGGCTCGCA AGCTAATGTG CAAATCCAAG ATCCAACG CACACCCCAG CGGTATAGCT
  661 CTCGGCGTGC CACCCCTAGG CATATTATCG TGCGCTTTAC TAAGGTGGAG ATGAAAGAGA
  721 AGATGCTGCG AGCCGCTCGG GAAAAGGGAA GGGTGACTTT GAAGGGCAAA CCTATTCGGC
  781 TGACGGTTGA CCTTAGCGCC GAGACACTCC AGGCACGCCG GGAATGGGGC CCCATCTTTA
  841 ATATCCTGAA GGAGAAGAAC TTCCAGCCAC GAATCTCTTA CCCTGCAAAG TTGAGTTTTA
  901 TCTCCGAGGG TGAGATTAAG TATTTCATCG ATAAACAGAT GCTGCGAGAC TTCGTGACAA
  961 CTCGCCCAGC TCTCAAGGAA CTGCTCAAAG AGGCTCTTAA TATGGAGCGC AATAATAGAT
 1021 ATCAACCCTT GCAGAACCAC GCAAAGATGG GAAGCGGAGA GGGCAGAGGA AGTCTGCTAA
```

TABLE 8-continued

| Plasmid and mRNA construct sequences |
|---|

```
1081 CATGCGGTGA CGTCGAGGAG AATCCTGGAC CTATGACCGG CTCTAACTCA CATATCACCA
1141 TCCTTACACT TAACATTAAC GGCCTCAACT CAGCTATCAA GCGCCATCGG CTGGCCAGCT
1201 GGATCAAATC ACAGGATCCA AGCGTTTGTT GCATCCAAGA GACCCACCTG ACCTGTAGAG
1261 ATACTCACCG CCTCAAGATC AAGGGATGGC GAAAGATTTA TCAGGCGAAC GGTAAGCAGA
1321 AGAAAGCCGG AGTCGCAATT CTGGTCTCAG ACAAGACGGA TTTCAAGCCC ACCAAAATTA
1381 AGCGTGATAA GGAAGGTCAC TATATTATGG TGAAAGGCAG CATACAGCAG GAAGAACTTA
1441 CCATATTGAA CATCTACGCG CCAAACACCG GCGCACCTCG CTTTATCAAA CAGGTCCTGT
1501 CCGATCTGCA GCGAGATCTG GATTCTCATA CGTTGATTAT GGGTGATTTC AATACACCAT
1561 TGAGCACCCT GGATCGCAGC ACCAGGCAAA AGGTAAATAA AGACACGCAA GAGCTCAATA
1621 GCGCACTGCA TCAGGCAGAT CTCATTGATA TTTATCGCAC TCTTCATCCT AAGAGTACCG
1681 AGTACACATT CTTCAGCGCC CCACATCATA CATACTCAAA GATCGATCAT ATCGTCGGCT
1741 CAAAGGCTCT GCTGTCAAAG TGCAAGCGCA CAGAGATAAT TACAAATTAC CTGTCAGATC
1801 ATAGCGCGAT CAAGCTCGAG CTGAGAATCA AGAACCTGAC CCAGAGCCGG AGTACCACTT
1861 GGAAGCTTAA TAACCTGCTG CTCAACGATT ATTGGGTCCA CAATGAGATG AAGGCAGAGA
1921 TTAAAATGTT CTTCGAAACA AATGAGAATA AGGATACTAC CTATCAAAAC CTTTGGGATG
1981 CCTTTAAGGC CGTCTGCAGA GGCAAGTTCA TCGCCCTCAA CGCCTATAAA AGAAAACAAG
2041 AGAGATCTAA GATCGATACT CTCACCTCTC AGCTGAAGGA GTTGGAGAAA CAGGAACAGA
2101 CCCACTCCAA GGCGTCAAGA CGGCAGGAGA TCACAAAGAT TCGCGCCGAG TTGAAAGAGA
2161 TCGAAACCCA AAAGACTCTT CAGAAAATTA ACGAGTCTCG TAGTTGGTTC TTCGAGCGGA
2221 TTAATAAGAT AGACAGACCT CTGGCACGAC TGATTAAGAA GAAGCGCGAA AAGAACCAGA
2281 TTGATACCAT CAAGAACGAC AAGGGCGACA TCACTACTGA CCCGACCGAG ATCCAGACCA
2341 CTATTCGGGA GTATTATAAG CATTTGTATG CTAACAAGCT TGAGAACCTG GAAGAGATGG
2401 ACACTTTTCT GGATACCTAT ACTCTGCCAC GGCTTAATCA AGAGGAAGTC GAGTCCCTCA
2461 ACCGCCCAAT TACAGGAAGC GAGATTGTGG CCATAATTAA CTCCCTGCCG ACAAAGAAAT
2521 CTCCTGGTCC GGACGGGTTT ACAGCTGAGT TTTATCAACG GTATATGGAA GAGCTTGTAC
2581 CGTTTCTGCT CAAGCTCTTT CAGTCTATAG AAAGGAAGG CATCTTGCCC AATTCCTTCT
2641 ACGAAGCTTC TATAATACTT ATTCCCAAAC CAGGACGCGA TACCACAAAG AAGGAAAACT
2701 TCCGGCCCAT TAGTCTCATG AATATCGACG CTAAAATATT GAACAAGATT CTCGCCAACA
2761 GAATCCAACA ACATATTAAG AAATTGATAC ATCACGACCA GGTGGGGTTT ATACCTGGCA
2821 TGCAGGGCTG GTTTAACATC CGGAAGAGTA TTAACGTCAT TCAACACATT AATAGAGCTA
2881 AGGATAAGAA TCATATGATC ATCTCTATAG ACGCGGAAAA GGCATTCGAT AAGATTCAGC
2941 AGCCATTTAT GCTCAAGACT CTGAACAAAC TCGGCATCGA CGGAACATAT TTTAAGATTA
3001 TTCGCGCAAT TTACGATAAG CCGACTGCTA ACATTATCCT TAACGGCCAA AAGCTCGAGG
3061 CCTTTCCGCT CAAGACTGGA ACCCGCCAAG GCTGTCCCCT CTCCCCGCTT TTGTTTAATA
3121 TTGTACTCGA GGTGCTGGCT AGGGCTATTC GTCAAGAGAA AGAGATTAAA GGGATACAGC
3181 TCGGGAAGGA AGAGGTCAAG CTTTCCTTGT TCGCCGATGA TATGATTGTG TACCTGGAGA
3241 ATCCTATTGT GTCTGCTCAG AACCTTCTTA AACTTATTTC TAACTTTAGC AAGGTCAGCG
3301 GCTATAAGAT TAACGTCCAG AAATCTCAGG CCTTTCTGTA CACAAATAAT CGACAGACCG
3361 AATCCCAGAT AATGGGTGAG CTTCCGTTTG TCATAGCCAG CAAAAGGATA AAGTATCTCG
3421 GAATCCAGCT GACACGAGAC GTTAAAGATT TGTTTAAGGA AAATTACAAG CCTCTCCTGA
3481 AAGAGATTAA GGAAGATACT AATAAGTGGA AGAATATCCC CTGTTCATGG GTTGGCAGAA
3541 TCAACATAGT GAAGATGGCA ATACTTCCTA AAGTGATATA TCGCTTTAAC GCCATCCCAA
3601 TTAAACTGCC TATGACCTTC TTTACGGAGC TCGAGAAAAC AACCCTTAAA TTTATATGGA
3661 ATCAAAAGAG AGCAAGAATA GCGAAGTCCA TCTTGAGCCA GAAGAATAAG GCCGGTGGGA
3721 TTACTTTGCC TGATTTTAAG TTGTATTATA AAGCCACAGT AACTAAGACA GCCTGGTATT
3781 GGTATCAGAA TAGAGACATC GACCAGTGGA ATCGGACCGA ACCATCAGAG ATAATGCCCC
3841 ACATCTATAA TTACCTTATA TTCGATAAGC CAGAAAAGAA TAAACAGTGG GGCAAAGACA
3901 GCCTCTTCAA CAAGTGGTGT TGGGAGAATT GGCTGGCCAT ATGCCGGAAA CTCAAGCTCG
3961 ACCCCTTTCT TACACCCTAC ACTAAAATCA ACAGTAGGTG GATCAAGGAC TTGAATGTCA
4021 AGCCAAAGAC TATAAAGACA CTGGAAGAGA ATCTTGGGAT CACAATACAA GATATAGGCG
4081 TCGGCAAAGA TTTTATGTCA AAGACGCCCA AGGCCATGGC CACTAAGGAT AAGATTGATA
4141 AGTGGGACCT TATTAAGCTC AAAAGCTTCT GTACTGCCAC GGAGACCACG ATCAGAGTTA
4201 ATAGGCAGCC CACTACATGG GAAAAGATTT TCGCCACTTA TTCATCAGAT AAGGGGTTGA
4261 TAAGCAGAAT ATATAACGAG CTGAAGCAGA TCTACAAGAA GAAAACGAAT AATCCCATCA
4321 AGAAGTGGGC AAAAGATATG AACAGGCATT TTAGCAAAGA GGATATCTAC GCCGCGAAGA
4381 AGCATATGAA GAAGTGTAGT TCAAGCTTGG CCATTCGTGA GATGCAGATT AAGACGACCA
4441 TGCGATACCA CCTTACCCCA GTGAGGATGG CAATTATCAA GAAATCTGGC AATAATAGAT
4501 GTTGGCGGGG CTGTGGCGAG ATTGGCACCC TGCTCCATTG CTGGTGGGAT TGCAAGCTGG
4561 TGCAGCCGCT TTGGAAATCA GTCTGGCGCT TTCTGAGGGA CCTCGAGCTT GAGATTCCCT
4621 TCGATCCCGC AATTCCCTTG CTCGGAATCT ATCCTAACGA ATACAAGAGC TGTTCGTTACA
4681 AGGATACGTG TACCCGGATG TTCATCGCGG CCTTGTTTAC GATAGCTAAG ACGTGGAATC
4741 AGCCTAAGTG CCCCACAATG ATCGATTGGA TCAAGAAAAT GTGGCATATT TATACCATGG
4801 AGTATTACGC AGCAATTAAG AATGACGAAT TTATTTCCTT CGTTGGGACC TGGATGAAGC
4861 TGGAGACTAT TATTCTGAGC AAGCTGTCTC AGGAGCAAAA GACAAAGCAT AGAATCTTCT
4921 CTCTCATTGG TGGTAACGAC TACAAAGACG ATGACGACAA GTCTAGAAGTT
4981 GTCTCCTCCT GCACTGACTG ACTGATACAA TCGATTTCTG GATCCGCAGG CCTAATCAAC
5041 CTCTGGATTA CAAAATTTGT GAAAGATTGA CTGGTATTCT TAACTATGTT GCTCCTTTTA
5101 CGCTATGTGG ATACGCTGCT TTAATGCCTT TGTATCATGC TATTGCTTCC CGTATGGCTT
5161 TCATTTTCTC CTCCTTGTAT AAATCCTGGT TGCTGTCTCT TTATGAGGAG TTGTGGCCCG
5221 TTGTCAGGCA ACGTGGCGTG GTGTGCACTG TGTTTGCTGA CGCAACCCCC ACTGGTTGGG
5281 GCATTGCCAC CACCTGTCAG CTCCTTTCCG GGACTTTCGC TTTCCCCCTC CCTATTGCCA
5341 CGGCGGAACT CATCGCCGCC TGCCTTGCCC GCTGCTGGAC AGGGGCTCGG CTGTTGGGCA
5401 CTGACAATTC CGTGGTGTTG TCGGGGAAGC TGACGTCCTT TCCATGGCTG CTCGCCTGTG
5461 TTGCCACCTG GATTCTGCGC GGGACGTCCT TCTGCTACGT CCCTTCGGCC CTCAATCCAG
5521 CGGACCTTCC TTCCCGCGAA CAAACGACCC AACACCCGTG CGTTTTATTC TGTCTTTTTA
5581 TTGCCGATCC CCTCAGAAGA ACTCGTCAAG AAGGCGATAG AAGGCGATGC GCTGCGAATC
5641 GGGAGCGGCG ATACCGTAAA GCACGAGGAA GCGGTCAGCC CATTCGCCGC CAAGCTCTTC
5701 AGCAATATCA CGGGTAGCCA ACGCTATGTC CTGATAGCGG TCGGCCGCTT TACTTGTACA
```

TABLE 8-continued

Plasmid and mRNA construct sequences

```
 5761 GCTCGTCCAT GCCGAGAGTG ATCCCGGCGG CGGTCACGAA CTCCAGCAGG ACCATGTGAT
 5821 CGCGCTTCTC GTTGGGGTCT TTGCTCAGGG CGGACTGGTAG GCTCAGGTAG TGGTTGTCGG
 5881 GCAGCAGCAC GGGGCCGTCG CCGATGGGGG TGTTCTGCTG GTAGTGGTCG GCCAGGTGAG
 5941 TCCAGGAGAT GTTTCAGCAC TGTTGCCTTT AGTCTCGAGG CAACTTAGAC AACTGAGTAT
 6001 TGATCTGAGC ACAGCAGGGT GTGAGCTGTT TGAAGATACT GGGGTTGGGG GTGAAGAAAC
 6061 TGCAGAGGAC TAACTGGGCT GAGACCCAGT GGCAATGTTT TAGGGCCTAA GGAATGCCTC
 6121 TGAAAATCTA GATGGACAAC TTTGACTTTG AGAAAAGAGA GGTGGAAATG AGGAAAATGA
 6181 CTTTTCTTTA TTAGATTTCG GTAGAAAGAA CTTTCATCTT TCCCCTATTT TTGTTATTCG
 6241 TTTTAAAACA TCTATCTGGA GGCAGGACAA GTATGGTCAT TAAAAAGATG CAGGCAGAAG
 6301 GCATATATTG GCTCAGTCAA AGTGGGGAAC TTTGGTGGCC AAACATACAT TGCTAAGGCT
 6361 ATTCCTATAT CAGCTGGACA CATATAAAAT GCTGCTAATG CTTCATTACA AACTTATATC
 6421 CTTTAATTCC AGATGGGGGC AAAGTATGTC CAGGGGTGAG GAACAATTGA ACATTTGGG
 6481 CTGGAGTAGA TTTTGAAAGT CAGCTCTGTG TGTGTGTGTG TGTGTGTGTG TGTGAGAGCG
 6541 TGTGTTTCTT TTAACGTTTT CAGCCTACAG CATACAGGGT TCATGGTGGC AAGAAGATAA
 6601 CAAGATTTAA ATTATGCCA GTGACTAGTG CTGCAAGAAG AACAACTACC TGCATTTAAT
 6661 GGGAAAGCAA AATCTCAGGC TTTGAGGGAA GTTAACATAG GCTTGATTCT GGGTGGAAGC
 6721 TGGGTGTGTA GTTATCTGGA GGCCAGGCTG GAGCTCTCAG CTCACTATGG GTTCATCTTT
 6781 ATTGTCTCCT TTCATCTCAA CAGCTGCACG CTGCCGTCCT CGATGTTGTG GCGGATCTTG
 6841 AAGTTCACCT TGATGCCGTT CTTCTGCTTG TCGGCCATGA TATAGACGTT GTGGCTGTTG
 6901 TAGTTGTACT CCAGCTTGTG CCCCAGGATG TTGCCGTCCT CCTTGAAGTC GATGCCCTTC
 6961 AGCTCGATGC GGTTCACCAG GGTGTCGCCC TCGAACTTCA CCTCGGCGCG GGTCTTGTAG
 7021 TTGCCGTCGT CCTTGAAGAA GATGGTGCGC TCCTGGACGT AGCCTTCGGG CATGGCGGAC
 7081 TTGAAGAAGT CGTGCTGCTT CATGTGGTCG GGGTAGCGGC TGAAGCACTG CACGCCGTAG
 7141 GTCAGGGTGG TCACGAGGGT GGGCCAGGGC ACGGGCAGCT TGCCGGTGGT GCAGATGAAC
 7201 TTCAGGGTCA GCTTGCCGTA GGTGGCATCG CCCTCGCCCT CGCCGGACAC GCTGAACTTG
 7261 TGGCCGTTTA CGTCGCCGTC CAGCTCGACC AGGATGGGCA CCACCCCGGT GAACAGCTCC
 7321 TCGCCCTTGC TCACCATGGT GGCGAATTCG AAGCTTGAGC ACGAGATCTG AGTCCGGTAG
 7381 GCCTAGCGGA TCTGACGGTT CACTAAACCA GCTCTGCTTA TATAGACCTC CCACCGTACA
 7441 CGCCTACCGC CCATTTGCGT CAATGGGCG GAGTTGTTAC GACATTTTGG AAAGTCCCGT
 7501 TGATTTTGGT GCCAAAACAA ACTCCCATTG ACGTCAATGG GGTGGAGACT TGGAAATCCC
 7561 CGTGAGTCAA ACCGCTATCC ACGCCCATTG ATGTACTGCC AAAACCGCAT CACCATGGTA
 7621 ATAGCGATGA CTAATACGTA GATGTACTGC CAAGTAGGAA AGTCCCATAA GGTCATGTAC
 7681 TGGGCATAAT GCCAGGCGGG CCATTTACCG TCATTGACGT CAATAGGGGG CGTACTTGGC
 7741 ATATGATACA CTTGATGTAC TGCCAAGTGG GCAGTTTACC GTAAATACTC CACCCATTGA
 7801 CGTCAATGGA AAGTCCCTAT TGGCGTTACT ATGGGAACAT ACGTCATTAT TGACGTCAAT
 7861 GGGCGGGGGT CGTTGGGCGG TCAGCCAGGC GGGCCATTTA CCGTAAGTTA TGTAACGGGC
 7921 CTGCTGCCGG CTCTGCGGCC TCTTCCGCGT CTTCGCCTTC GCCCTCAGAC GAGTCGGATC
 7981 TCCCTTTGGG CCGCCTCCCC GCCTGTCTAG CTTGACTGAC TGAGATACAG CGTACCTTCA
 8041 GCTCACAGAC ATGATAAGAT ACATTGATGA GTTTGGACAA ACCACAACTA GAATGCAGTG
 8101 AAAAAAATGC TTTATTTGTG AAATTTGTGA TGCTATTGCT TTATTTGTAA CCATTATAAG
 8161 CTGCAATAAA CAAGTTAACA ACAACAATTG CATTCATTTT ATGTTTCAGG TTCAGGGGGA
 8221 GGTGTGGGAG GTTTTTTAAA GCAAGTAAAA CCTCTACAAA TGTGGTATTG GCCCATCTCT
 8281 ATCGGTATCG TAGCATAACC CCTTGGGGCC TCTAAACGGG TCTTGAGGGG TTTTTTGTGC
 8341 CCCTCGGGCC GGATTGCTAT CTACCGGCAT TGGCGCAGAA AAAAATGCCT GGCGACGC
 8401 TGCGCGTCTT ATACTCCCAC ATATGCCAGA TTCAGCAACG GATACGGCTT CCCCAACTTG
 8461 CCCACTTCCA TACGTGTCCT CCTTACCAGA AATTTATCCT TAAGGTCGTC AGCTATCCTG
 8521 CAGGCGATCT CTCGATTTCG ATCAAGACAT TCCTTTAATG GTCTTTTCTG GACACCACTA
 8581 GGGGTCAGAA GTAGTTCATC AAACTTTCTT CCCTCCCTAA TCTCATTGGT TACCTTGGGC
 8641 TATCGAAACT TAATTAAGCG ATCTGCATCT CAATTAGTCA GCAACCATAG TCCCGCCCCT
 8701 AACTCCGCCC ATCCCGCCCC TAACTCCGCC CAGTTCCGCC CATTCTCCGC CCCATCGCTG
 8761 ACTAATTTTT TTTATTTATG CAGAGGCCGA GGCCGCCTCG GCCTCTGAGC TATTCCAGAA
 8821 GTAGTGAGGA GGCTTTTTTG GAGGCCTAGG CTTTTGCAAA GGAGGTAGCC TTCGGCTATG
 8881 AACAAGATGG ATTGCACGCA GGTTCTCCCG CCGCTTGGGT GGAGAGGCTA TTCGGCTATG
 8941 ACTGGGCACA ACAGACAATC GGCTGCTCTG ATGCCGCCGT GTTCCGGCTG TCAGCGCAGG
 9001 GGCGCCCGGT TCTTTTTGTC AAGACCGACC TGTCCGGTGC CCTGAATGAA CTCCAGGACG
 9061 AGGCAGCGCG GCTATCGTGG CTGGCCACGA CGGGCGTTCC TTGCGCAGCT GTGCTCGACG
 9121 TTGTCACTGA AGCGGGAAGG GACTGGCTGC TATTGGGCGA AGTGCCGGGG CAGGATCTCC
 9181 TGTCATCTCA CCTTGCTCCT GCCGAGAAAG TATCCATCAT GGCTGATGCA ATGCGGCGGC
 9241 TGCATACGCT TGATCCGGCT ACCTGCCCAT TCGACCACCA AGCGAAACAT CGCATCGAGC
 9301 GAGCACGTAC TCGGATGGAA GCCGGTCTTG TCGATCAGGA TGATCTGGAC GAAGAGCATC
 9361 AGGGGCTCGC GCCAGCCGAA CTGTTCGCCA GGCTCAAGGC GCGGATGCCC GACGGCGAGG
 9421 ATCTCGTCGT GACCCACGGC GATGCCTGCT TGCCGAATAT CATGGTGGAA AATGGCCGCT
 9481 TTTCTGGATT CATCGACTGT GGCCGGCTGG GTGTGGCGGA CCGCTATCAG GACATAGCGT
 9541 TGGCTACCCG TGATATTGCT GAAGAGCTTG GCGGCGAATG GGCTGACCGC TTCCTCGTGC
 9601 TTTACGGTAT CGCCGCTCCC GATTCGCAGC GCATCGCCTT CTATCGCCTT CTTGACGAGT
 9661 TCTTCTAGTA TGTAAGCCCT GTGCCTTCTA GTTGCCAGCC ATCTGTTGTT TGCCCCTCCC
 9721 CCGTGCCTTC CTTGACCCTG GAAGGTGCCA CTCCCACTGT CCTTTCCTAA TAAAATGAGG
 9781 AAATTGCATC GCATTGTCTG AGTAGGTGTC ATTCTATTCT GGGGGGTGGG GTGGGGCAGG
 9841 ACAGCAAGGG GGAGGATTGG GAAGACAATA GCAGGCATGC TGGGGATGCG GTGGGCTCTA
 9901 TGGTTAATTA ACCAGTCAAG TCAGCTACTT GGCGAGATCG ACTTGTCTGG GTTTCGACTA
 9961 CGCTCAGAAT TGCGTCAGTC AAGTTCGATC TGGTCCTTGC TATTGCACCC GTTCTCCGAT
10021 TACGAGTTTC ATTTAAATCA TGTGAGCAAA AGGCCAGCAA AAGGCCAGGA ACCGTAAAAA
10081 GGCCGCGTTG CTGGCGTTTT TCCATAGGCT CCGCCCCCCT GACGAGCATC ACAAAAATCG
10141 ACGCTCAAGT CAGAGGTGGC GAAACCCGAC AGGACTATAA AGATACCAGG CGTTTCCCCC
10201 TGGAAGCTCC CTCGTGCGCT CTCCTGTTCC GACCCTGCCG CTTACCGGAT ACCTGTCCGC
10261 CTTTCTCCCT TCGGGAAGCG TGGCGCTTTC TCATAGCTCA CGCTGTAGGT ATCTCAGTTC
10321 GGTGTAGGTC GTTCGCTCCA AGCTGGGCTG TGTGCACGAA CCCCCCGTTC AGCCCGACCG
10381 CTGCGCCTTA TCCGGTAACT ATCGTCTTGA GTCCAACCCG GTAAGACACG ACTTATCGCC
```

TABLE 8-continued

Plasmid and mRNA construct sequences

```
10441 ACTGGCAGCA GCCACTGGTA ACAGGATTAG CAGAGCGAGG TATGTAGGCG GTGCTACAGA
10501 GTTCTTGAAG TGGTGGCCTA ACTACGGCTA CACTAGAAGA ACAGTATTTG GTATCTGCGC
10561 TCTGCTGAAG CCAGTTACCT TCGGAAAAAG AGTTGGTAGC TCTTGATCCG GCAAACAAAC
10621 CACCGCTGGT AGCGGTGGTT TTTTTGTTTG CAAGCAGCAG ATTACGCGCA GAAAAAAAGG
10681 ATCTCAAGAA GATCCTTTGA TCTTTTCTAC GGGGTCTGAC GCTCAGTGGA ACGAAAACTC
10741 ACGTTAAGGG ATTTTGGTCA TGAGATTATC AAAAAGGATC TTCACCTAGA TCCTTTTAAA
10801 TTAAAAATGA AGTTTTAAAT CAATCTAAAG TATATATGAG TAAACTTGGT CTGACAGTTA
10861 CCAATGCTTA ATCAGTGAGG CACCTATCTC AGCGATCTGT CTATTTCGTT CATCCATAGT
10921 TGCATTTAAA TTTCCGAACT CTCCAAGGCC CTCGTCGAAA AATCTTCAAA CCTTTCGTCC
10981 GATCCATCTT GCAGGCTACC TCTCGAACGA ACTATCGCAA GTCTCTTGGC CGGCCTTGCG
11041 CCTTGGCTAT TGCTTGGCAG CGCCTATCGC CAGGTATTAC TCCAATCCCG AATATCCGAG
11101 ATCGGGATCA CCCGAGAGAA GTTCAACCTA CATCCTCAAT CCCGATCTAT CCGAGATCCG
11161 AGGAATATCG AAATCGGGGC GCGCCTGGTG TACCGAGAAC GATCCTCTCA GTGCGAGTCT
11221 CGACGATCCA TATCGTTGCT TGGCAGTCAG CCAGTCGGAA TCCAGCTTGG GACCCAGGAA
11281 GTCCAATCGT CAGATATTGT ACTCAAGCCT GGTCACGGCA GCGTACCGAT CTGTTTAAAC
11341 CTAGATATTG ATAGTCTGAT CGGTCAACGT ATAATCGAGT CCTAGCTTTT GCAAACATCT
11401 ATCAAGAGAC AGGATCAGCA GGAGGCTTTC GCATGAGTAT TCAACATTTC CGTGTCGCCC
11461 TTATTCCCTT TTTTGCGGCA TTTTGCCTTC CTGTTTTTGC TCACCCAGAA ACGCTGGTGA
11521 AAGTAAAAGA TGCTGAAGAT CAGTTGGGTG CGCGAGTGGG TTACATCGAA CTGGATCTCA
11581 ACAGCGGTAA GATCCTTGAG AGTTTTCGCC CCGAAGAACG CTTTCCAATG ATGAGCACTT
11641 TTAAAGTTCT GCTATGTGGC GCGGTATTAT CCCGTATTGA CGCCGGGCAA GAGCAACTCG
11701 GTCGCCGCAT ACACTATTCT CAGAATGACT TGGTTGAGTA TTCACCAGTC ACAGAAAAGC
11761 ATCTTACGGA TGGCATGACA GTAAGAGAAT TATGCAGTGC TGCCATAACC ATGAGTGATA
11821 ACACTGCGGC CAACTTACTT CTGACAACGA TTGGAGGACC GAAGGAGCTA ACCGCTTTTT
11881 TGCACAACAT GGGGGATCAT GTAACTCGCC TTGATCGTTG GGAACCGGAG CTGAATGAAG
11941 CCATACCAAA CGACGAGCGT GACACCACGA TGCCTGTAGC AATGGCAACA ACCTTGCGTA
12001 AACTATTAAC TGGCGAACTA CTTACTCTAG CTTCCCGGCA ACAGTTGATA GACTGGATGA
12061 AGGCGGATAA AGTTGCAGGA CCACTTCTGC GCTCGGCCCT TCCGGCTGGC TGGTTTATTG
12121 CTGATAAATC TGGAGCCGGT GAGCGTGGGT CTCGCGGTAT CATTGCAGCA CTGGGGCCAG
12181 ATGGTAAGCC CTCCCGTATC GTAGTTATCT ACACGACGGG GAGTCAGGCA ACTATGGATG
12241 AACGAAATAG ACAGATCGCT GAGATAGGTG CCTCACTGAT TAAGCATTGG TAACCGATTC
12301 TAGGTGCATT GGCGCAGAAA AAAATGCCTG ATGCGACGCT GCGCGTCTTA TACTCCCACA
12361 TATGCCAGAT TCAGCAACGG ATACGGCTTC CCCAACTTGC CCACTTCCAT ACGTGTCCTC
12421 CTTACCAGAA ATTTATCCTT AAGATCGTTT AAACTCGACT CTGGCTCTAT CGAATCTCCG
12481 TCGTTTCGAG CTTACGCGAA CAGCCGTGGC GCTCATTTGC TCGTCGGGCA TCGAATCTCG
12541 TCAGCTATCG TCAGCTTACC TTTTTGGCAG CGATCGCGGC TCCCGACATC TTGGACCATT
12601 AGCTCCACAG GTATCTTCTT CCCTCTAGTG GTCATAACAG CAGCTTCAGC TACCTCTCAA
12661 TTCAAAAAAC CCCTCAAGAC CCGTTTAGAG GCCCCAAGGG GTTATGCTAT CAATCGTTGC
12721 GTTACACACA CAAAAAACCA ACACACATCC ATCTTCGATG GATAGCGATT TTATTATCTA
12781 ACTGCTGATC GAGTGTAGCC AGATCTAGTA TCAATTACG GGGTCATTAG TTCATAGCCC
12841 ATATATGGAG TTCCGCGTTA CATAACTTAC GGTAAATGGC CCGCCTGGCT GACCGCCCAA
12901 CGACCCCCGC CCATTGACGT CAATAATGAC GTATGTTCCC ATAGTAACGC CAATAGGGAC
12961 TTTCCATTGA CGTCAATGGG TGGAGTATTT ACGGTAAACT GCCCACTTGG CAGTACATCA
13021 AGTGTATCAT ATGCCAAGTA CGCCCCCTAT TGACGTCAAT GACGGTAAAT GGCCCGCCTG
13081 GCATTATGCC CAGTACATGA CCTTATGGGA CTTTCCTACT TGGCAGTACA TCTACGTATT
13141 AGTCATCGCT ATTACCATGC TGATGCGGTT TTGGCAGTAC ATCAATGGGC GTGGATAGCG
13201 GTTTGACTCA CGGGGATTTC CAAGTCTCCA CCCCATTGAC GTCAATGGGA GTTTGTTTTG
13261 GCACCAAAAT CAACGGGACT TTCCAAAATG TCGTAACAAC TCCGCCCCAT TGACGCAAAT
13321 GGGCGGTAGG CGTGTACGGT GGGAGGTCTA TATAAGCAGA GCTGGTTTAG TGAACCGTCA
13381 GATCAGATCT TTGTCGATCC TACCATCCAC TCGACACACC CGCCAGCGGC CGC
       (SEQ ID NO: 48)

LINE-1_ORF2-MCP_MS2_mRNA (SEQ ID NO: 49)
    1 TAATACGACT CACTATAGGG AGAAGTACTG CCACCATGGG CAAGAAGCAA AATCGCAAGA
   61 CGGGGAATTC CAAGACACAA TCCGCTAGCC CACCACCTAA AGAGCGTTCT AGCTCCCCTG
  121 CTACTGAGCA GTCCTGGATG GAAAACGACT TCGATGAACT CCGGGAAGAG GGATTTAGGC
  181 GATCCAACTA TTCAGAACTC CGCGAAGATA TCCAGACAAA GGGGAAGGAA GTCGAGAATT
  241 TCGAGAAGAA CCTCGAGGAG TGCATCACCC GTATCACAAA CACTGAGAAA TGTCTCAAAG
  301 AACTCATGGA ACTTAAGACA AAAGCCAGGG AGCTTCGAGA GGAGTGTCGG AGTCTGAGAT
  361 CCAGGTGTGA CCAGCTCGAG GAGCGCGTGA GCGCGATGGA AGACGAGATG AACGAGATGA
  421 AAAGAGAGGG CAAATTCAGG GAGAAGCGCA TTAAGGAGGA CGAACGAGT CTGCAGGAGA
  481 TTTGGGATTA CGTCAAGAGG CCTAACCTGC GGTTGATCGG CGTCCCCGAG AGCGACGTAG
  541 AAAACGGGAC TAAACTGGAG AATACACTTC AAGACATCAT TCAAGAAAAT TTTCCAAACC
  601 TGGCTCGGCA AGCTAATGTG CAAATCCAAG AGATCCAACG CACACCCCAG CGGTATAGCT
  661 CTCGGCGTGC CACCCCTAGG CATATATCG TGCGCTTTAC TAAGGTGGAG ATGAAAGAGA
  721 AGATGCTGCG AGCGCTCCGG GAAAAGGGAA GGGTGACTTT GAAGGGCAAA CCTATTCGGC
  781 TGACGGTTGA CCTTAGCGCC GAGACACTCC AGGCACGCCG GGAATGGGGC CCCATCTTTA
  841 ATATCCTGAA GGAGAAGAAC TTCCAGCCAC GAATCTCTTA CCCTGCAAAG TTGAGTTTTA
  901 TCTCCGAGGG TGAGATTAAG TATTTCATCG ATAAACAGAT GCTGCAGAC TTCGTGACAA
  961 CTCGCCCAGC TCTCAAGGAA CTGCTCAAAG AGGCTCTTAA TATGGAGCGC AATAATAGAT
 1021 ATCAACCCTT GCAGAACCAC GCAAAGATGT GAGACAGCCG TCAGACCATC AAGACTAGGA
 1081 AGAAACTGCA TCAACTAATG AGCAAAATCA CCAGCTAACA TCATAGTATA CATGACCGGC
 1141 TCTAACTCAC ATATACCAT CCTTACTT AACATTAACG GCCTCAACTC AGCTATCAAG
 1201 CGCCATCGGC TGGCCAGCTG GATCAAATCA CAGGATCCAA GCGTTTGTTG CATCCAAGAG
 1261 ACCCACCTGA CCTGTAGAGA TACTCACCGC CTCAAGATCA AGGGATGGCG AAAGATTTAT
 1321 CAGGCGAACG GTAAGCAGAA GAAAGCCGGA GTCGCAATTC TGGTCTCAGA CAAGACGGAT
 1381 TTCAAGCCCA CCAAAATTAA GCGTGATAAG GAAGGTCACT ATATTATGGT GAAAGGCAGC
 1441 ATACAGCAGG AAGAACTTAC CATATTGAAC ATCTACGCGC CAAACACCGG CGCACCTCGC
```

TABLE 8-continued

Plasmid and mRNA construct sequences

```
1501 TTTATCAAAC AGGTCCTGTC CGATCTGCAG CGAGATCTGG ATTCTCATAC GTTGATTATG
1561 GGTGATTTCA ATACACCATT GAGCACCCTG GATCGCGACA CCAGGCAAAA GGTAAATAAA
1621 GACACGCAAG AGCTCAATAG CGCACTGCAT CAGGCAGATC TCATTGATAT TTATCGCACT
1681 CTTCATCCTA AGAGTACCGA GTACACATTC TTCAGCGCCC CACATCATAC ATACTCAAAG
1741 ATCGATCATA TCGTCGGCTC AAAGGCTCTG CTGTCAAAGT GCAAGCGCAC AGAGATAATT
1801 ACAAATTACC TGTCAGATCA TAGCGCGATC AAGCTCGAGC TGAGAATCAA GAACCTGACC
1861 CAGAGCCGGA GTACCACTTG GAAGCTTAAT AACCTGCTGC TCAACGATTA TTGGGTCCAC
1921 AATGAGATGA AGGCAGAGAT TAAAATGTTC TTCGAAACAA ATGAGAATAA GGATACTACC
1981 TATCAAAACC TTTGGGATGC CTTTAAGGCC GTCTGCAGAG GCAAGTTCAT CGCCCTCAAC
2041 GCCTATAAAA GAAAACAAGA GAGATCTAAG ATCGATACTC TCACCTCTCA GCTGAAGGAG
2101 TTGGAGAAAC AGGAACAGAC CCACTCCAAG GCGTCAAGAC GGCAGGAGAT CACAAAGATT
2161 CGCGCCGAGT TGAAAGAGAT CGAAACCCAA AAGACTCTTC AGAAAATTAA CGAGTCTCGT
2221 AGTTGGTTCT TCGAGCGGAT TAATAAGATA GACAGACCTC TGGCACGACT GATTAAGAAG
2281 AAGCGCGAAA AGAACCGAT TGATACCATC AAGAACGACA AGGGCGACAT CACTACTGAC
2341 CCGACCGAGA TCCAGACCAC TATTCGGAG TATTATAAGC ATTTGTATGC TAACAAGCTT
2401 GAGAACCTGG AAGAGATGGA CACTTTTCTG GATACCTATA CTCTGCCACG GCTTAATCAA
2461 GAGGAAGTCG AGTCCCTCAA CCGCCCAATT ACAGGAAGCG AGATTGTGGC CATAATTAAC
2521 TCCCTGCCGA CAAAGAAATC TCCTGGTCCG GACGGGTTTA CAGCTGAGTT TTATCAACGG
2581 TATATGGAAG AGCTTGTACC GTTTCTGCTC AAGCTCTTTC AGTCTATAGA AAAGGAAGGC
2641 ATCTTGCCCA ATTCCTTCTA CGAAGCTTCT ATAATACTTA TTCCCAAACC AGGACGCGAT
2701 ACCACAAAGA AGGAAAACTT CCGGCCCATT AGTCTCATGA ATATCGACGC TAAAATATTG
2761 AACAAGATTC TCGCCAACAG AATCCAACAA CATATTAAGA AATTGATACA TCACGACCAG
2821 GTGGGGTTTA TACCTGGCAT GCAGGGCTGG TTTAACATCC GGAAGAGTAT TAACGTCATT
2881 CAACACATTA ATAGAGCTAA GGATAAGAAT CATATGATCA TCTCTATAGA CGCGGAAAAG
2941 GCATTCGATA AGATTCAGCA GCCATTTATG CTCAAGACTC TGAACAAACT CGGCATCGAC
3001 GGAACATATT TTAAGATTAT TCGCGCAATT TACGATAAGC CGACTGCTAA CATTATCCTT
3061 AACGGCCAAA AGCTCGAGGC CTTTCCGCTC AAGACTGAGA CCCGCCAAGG CTGTCCCCTC
3121 TCCCCGCTTT TGTTTAATAT TGTACTCGAG GTGCTGGCTA GGGCTATTCG TCAAGAGAAA
3181 GAGATTAAAG GGATACAGCT CGGGAAGGAA GAGGTCAAGC TTTCCTTGTT CGCCGATGAT
3241 ATGATTGTGT ACCTGGAGAA TCCTATTGTG TCTGCTCAGA ACCTTCTTAA ACTTATTTCT
3301 AACTTTAGCA AGGTCAGCGG CTATAAGATT AACGTCCAGA AATCTCAGGC CTTTCTGTAC
3361 ACAAATAATC GACAGACCGA ATCCCAGATA ATGGGTGAGC TTCCGTTTGT CATAGCCAGC
3421 AAAAGGATAA AGTATCTCGG AATCCAGCTG ACACGAGACG TTAAAGATTT GTTTAAGGAA
3481 AATTACAAGC CTCTCCTGAA AGAGATTAAG GAAGATACTA ATAAGTGGAA GAATATCCCC
3541 TGTTCATGGG TTGGCAGAAT CAACATAGTG AAGATGGCAA TACTTCCTAA AGTGATATAT
3601 CGCTTTAACG CCATCCCAAT TAAACTGCCT ATGACCTTCT TTACGGAGCT CGAGAAAACA
3661 ACCCTTAAAT TTATATGGAA TCAAAAGAGA GCAAGAATAG CGAAGTCCAT CTTGAGCCAG
3721 AAGAATAAGG CCGGTGGGAT TACTTTGCCT GATTTTAAGT TGTATTATAA AGCCACAGTA
3781 ACTAAGACAG CCTGGTATTG GTATCAGAAT AGAGACATCG ACCAGTGGAA TCGGACCGAA
3841 CCATCAGAGA TAATGCCCCA CATCTATAAT TACCTTTATAT TCGATAAGCC AGAAAAGAAT
3901 AAACAGTGGG GCAAAGACAG CCTCTTCAAC AAGTGGTGTT GGGAGAATTG GCTGGCCATA
3961 TGCCGGAAAC TCAAGCTCGA CCCCCTTTCTT ACACCCTACA CTAAAATCAA CAGTAGGTGG
4021 ATCAAGGACT TGAATGTCAA GCCAAAGACT ATAAAGACAC TGGAAGAGAA TCTTGGGATC
4081 ACAATACAAG ATATAGGCG CGGCAAAGAT TTTATGTCAA AGACGCCCAA GGCCATGGCC
4141 ACTAAGGATA AGATTGATAA GTGGGACCTT ATTAAGCTCA AAAGCTTCTG TACTGCCAAG
4201 GAGACCACGA TCAGAGTTAA TAGGCAGCCC ACTACATGGG AAAAGATTTT CGCCACTTAT
4261 TCATCAGATA AGGGGTTGAT AAGCAGAATA TATAACGAGC TGAAGCAGAT CTACAAGAAG
4321 AAAACGAATA ATCCCATCAA GAAGTGGGCA AAAGATATGA ACAGGCATTT TAGCAAAGAG
4381 GATATCTACG CCGCGAAGAA GCATATGAAG AAGTGTAGTT CAAGCTTGGC CATTCGTGAG
4441 ATGCAGATTA AGACGACCAT GCGATACCAC CTTACCCCAG TGAGGATGGC AATTATCAAG
4501 AAATCTGGCA ATAATAGATG TTGGCGGGC TGTGGCGAGA TTGGCACCCT GCTCCATTGC
4561 TGGTGGGATT GCAAGCTGGT GCAGCCGCTT TGGAAATCAG TCTGGCGCTT TCTGAGGGAC
4621 CTCGAGCTTG AGATTCCCTT CGATCCCGCA ATTCCCTTGC TCGGAATCTA TCCTAACGAA
4681 TACAAGAGCT GTTGTTACAA GGATACGTGT ACCCGGATGT TCATCGCGGC CTTGTTTACG
4741 ATAGCTAAGA CGTGGAATCA GCCTAAGTGC CCCACAATGA TCGATTGGAT CAAGAAAATG
4801 TGGCATATTT ATACCATGGA GTATTACGCA GCAATTAAGA ATGACGAATT TATTTCCTTC
4861 GTTGGGACCT GGATGAAGCT GGAGACTATT ATTCTGAGCA AGCTGTCTCA GGAGCAAAAG
4921 ACAAAGCATA GAATCTTCTC TCTCATTGGT GGTAACGCTT CTAACTTTAC TCAGTTCGTT
4981 CTCGTCGACA ATGGCGGAAC TGGCGACGTG ACTGTCGCCC AAGCAACTTT CGCTAACGGG
5041 ATCGCTGAAT GGATCAGCTC TAACTCGCGT TCACAGGCTT ACAAAGTAAC CTGTAGCGTT
5101 CGTCAGAGCT CTGCGCAGAA TCGCAAATAC ACCATCAAGA TCGAGGTGCC TAAAGGCGCC
5161 TGGCGTTCGT ACTTAAATAT GGAACTAACC ATTCCAATTT TCGCCACGAA TTCCGACTGC
5221 GAGCTTATTG TTAAGGCAAT GCAAGGTCTC TAAAAGATG GAAACCCGAT TCCCTCAGCA
5281 ATCGCAGCAA ACTCCGGCAT CTACGCCATG GCCAGCAACT TCACCCAGTT CGTGCTGGTG
5341 GACAACGGCG GCACCGGCGA CGTGACCGTG GCCCCCAGCA ACTTCGCCAA CGGCATCGCC
5401 GAGTGGATCA GCAGCAACAG CAGAAGCCAG GCCTACAAGG TGACCTGCAG CGTGAGACAG
5461 AGCAGCGCCC AGAACAGAAA GTACACCATC AAGGTGGAGG TGCCCAAGGG CGCCTGGAGA
5521 AGCTACCTGA ACATGGAGCT GACCATCCCC ATCTTCGCCA CCAACAGCGA CTGCGAGCTG
5581 ATCGTGAAGG CCATGCAGGG CCTGCTGAAG GACGGCAACC CCATCCCCAG CGCCATCGCC
5641 GCCAACAGCG GCATCTACGA CTACAAAGAC GATGACGATA AGTAAAGCAA CCTACAAACG
5701 GGTGGAGGAT CACCCCACCC GACACTTCAC AATCAAGGGG TACAATACAC AAGGGTGGAG
5761 GAACACCCCA CCCTCCAGAC ACATTACACA GAAATCCAAT CAAACAGAAG CACCATCAGG
5821 GCTTCTGCTA CCAAATTTAT CTCAAAAAAC TACAACAAGG AATCCACATA AGGGATTCCC
5881 TGTGCAATAT ACGTCAAACG AGGGCCACGA CGGGAGGACG ATCACGCCTC CGAATATCG
5941 GCATGTCTGG CTTTCGAATT CAGTGCGTGG AGCATCAGCC CACGCAGCCA ATCAGAGTCG
6001 AATACAAGTC GACTTTCGCG AAGAGCATCA GCCTTCGCGC CATTCTTACA CAAACCACAC
6061 TCTCCCCTAC AGGAACAGCA TCAGCGTTCC TGCCCAGTAC CCAACTCAAG AAAATTTATG
6121 TCCCCATGCA GCATCAGCGC ATGGGCCCCA AGAATACATC CCCAACAAAA TCACATCCGA
```

TABLE 8-continued

Plasmid and mRNA construct sequences

```
6181  GCACCAACAG GGCTCGGAGT GTTGTTTCTT GTCCAACTGG ACAAACCCTC CATGGACCAT
6241  CAGGCCATGG ACTCTCACCA ACAAGACAAA AACTACTCTT CTCGAAGCAG CATCAGCGCT
6301  TCGAAACACT CGAGCATACA TTGTGCCTAT TTCTTGGGTG GACGATCACG CCACCCATGC
6361  TCTCACGAAT TCAAAACAC GGACAAGGAC GAGCACCACC AGGGCTCGTC GTTCCACGTC
6421  CAATACGATT ACTTACCTTT CGGGATCACG ATCACGGATC CCGCAGCTAC ATCACTTCCA
6481  CTCAGGACAT TCAAGCATGC ACGATCACGG CATGCTCACC AAGTCTCAAC CACAGAAACT
6541  ACCAAATGGG TTCAGCACCA GCGAACCCAC TCCTACCTCA AACCTCTTCC CACAAAACTG
6601  GCAAGCAGGA TCACCGCTTG CCCATTCCAA CATACCAAAT CAAAAACAAT TACTGGTACA
6661  GCATCAGCGT ACCAGCCCAC ATCTCTCACT ACTATCAAAA ACCAAACCGT TCAGCAACAG
6721  CGAACGGTAC ACACGGAAAA ATCAACTGGT TTACAAATAC GAAAGACGAT CACGCTTTCG
6781  TCCAGCGCAA ACTATTACGA AAAACATCCG ACGGGAAGAG CAACAGCCTT CCCGCGGCGG
6841  AAAACCTCAC AAAAACACGA CAAACGGATG CACGAACACG GCATCCGCCG ACAACCCACA
6901  AACTTACAAC CAGGCAAACG GTGCAGGATC ACCGCACCGT ACATCAAACA CCTCAGATCT
6961  CATGCTTCTA GAAGTTGTCT CCTCCTGCAC TGACTGACTG ATACAATCGA TTTCTGGATC
7021  CGCAGGCCTA ATCAACCTCT GGATTACAAA ATTTGTGAAA GATTGACTGG TATTCTTAAC
7081  TATGTTGCTC CTTTTACGCT ATGTGGATAC GCTGCTTTAA TGCCTTTGTA TCATGCTATT
7141  GCTTCCCGTA TGGCTTTCAT TTTCTCCTCC TTGTATAAAT CCTGGTTGCT GTCTCTTTAT
7201  GAGGAGTTGT GGCCCGTTGT CAGGCAACGT GGCGTGGTGT GCACTGTGTT TGCTGACGCA
7261  ACCCCCACTG GTTGGGGCAT TGCCACCACC TGTCAGCTCC TTTCCGGGAC TTTCGCTTTC
7321  CCCCTCCCTA TTGCCACGGC GGAACTCATC GCCGCCTGCC TTGCCCGCTG CTGGACAGGG
7381  GCTCGGCTGT TGGGCACTGA CAATTCCGTG GTGTTGTCGG GGAAGCTGAC GTCCTTTCCA
7441  TGGCTGCTCG CCTGTGTTGC CACCTGGATT CTGCGCGGGA CGTCCTTCTG CTACGTCCCT
7501  TCGGCCCTCA ATCCAGCGGA CCTTCCTTCC CGCTGAGAGA CACAAAAAAT TCCAACACAC
7561  TATTGCAATG AAAATAAATT TCCTTTATTA GCCAGAAGTC AGATGCTCAA GGGGCTTCAT
7621  GATGTCCCCA TAATTTTTGG CAGAGGGAAA AAGATCTCAG TGGTATTTGT GAGCCAGGGC
7681  ATTGGCCTTC TGATAGGCAG CCTGCACCTG AGGAGTGCGG CCGCTTTACT TGTACAGCTC
7741  GTCCATGCCG AGAGTGATCC CGGCGGCGGT CACGAACTCC AGCAGGACCA TGTGATCGCG
7801  CTTCTCGTTG GGGTCTTTGC TCAGGGCGGA CTGGGTGCTC AGGTAGTGGT TGTCGGGCAG
7861  CAGCACGGGG CCGTCGCCGA TGGGGGTGTT CTGCTGGTAG TGGTCGGCGA GCTGCACGCT
7921  GCCGTCCTCG ATGTTGTGGC GGATCTTGAA GTTCACCTTG ATGCCGTTCT TCTGCTTGTC
7981  GGCCATGATA TAGACGTTGT GGCTGTTGTA GTTGTACTCC AGCTTGTGCC CCAGGATGTT
8041  GCCGTCCTCC TTGAAGTCGA TGCCCTTCAG CTCGATGCGG TTCACCAGGG TGTCGCCCTC
8101  GAACTTCACC TCGGCGCGGG TCTTGTAGTT GCCGTCGTCC TTGAAGAAGA TGGTGCGCTC
8161  CTGGACGTAG CCTTCGGGCA TGGCGGACTT GAAGAAGTCG TGCTGCTTCA TGTGGTCGGG
8221  GTAGCGGCTG AAGCACTGCA CGCCGTAGGT CAGGGTGGTC ACGAGGGTGG GCCAGGGCAC
8281  GGGCAGCTTG CCGGTGGTGC AGATGAACTT CAGGGTCGAC TTGCCGTAGG TGGCATCGCC
8341  CTCGCCCTCG CCGGACACGC TGAACTTGTG GCCGTTTACG TCGCCGTCCA GCTCGACCAG
8401  GATGGGCACC ACCCCGGTGA ACAGCTCCTC GCCCTTGCTC ACCATGGTGG CGGGATCTGA
8461  CGGTTCACTA AACCAGCTCT GCTTATATAG ACCTCCCACC GTACACGCCT ACCGCCCATT
8521  TGCGTCAATG GGGCGGAGTT GTTACGACAT TTTGGAAAGT CCCGTTGATT TTGGTGCCAA
8581  AACAAACTCC CATTGACGTC AATGGGGTGG AGACTTGAAA ATCCCCGTGA GTCAAACCGC
8641  TATCCACGCC CATTGATGTA CTGCCAAAAC CGCATCACCA TGGTAATAGC GATGACTAAT
8701  ACGTAGATGT ACTGCCAAGT AGGAAAGTCC CATAAGGTCA TGTACTGGGC ATAATGCCAG
8761  GCGGGCCATT TACCGTCATT GACGTCAATA GGGGGCGTAC TTGGCATATG ATACACTTGA
8821  TGTACTGCCA AGTGGGCAGT TTACCGTAAA TACTCCACCC ATTGACGTCA ATGGAAAGTC
8881  CCTATTGGCG TTACTATGGG AACATACGTC ATTATTGACG TCAATGGGCG GGGTCGTTG
8941  GGCGGTCAGC CAGGCGGGCC ATTTACCGTA AGTTATGTAA CGGGCCTGCT GCCGGCTCTG
9001  CGGCCTCTTC CGCGTCTTCG CCTTCGCCCT CAGCAGCGTC GGATCTCCCT TTGGGCCGCC
9061  TCCCCGCCTG TCTAGCTTGA CTGACTGAGA TACAGCGTAC CTTCAGCTCA CAGACATGAT
9121  AAGATACATT GATGAGTTTG GACAAACCAC AACTAGAATG CAGTGAAAAA AATGCTTTAT
9181  TTGTGAAATT TGTGATGCTA TTGCTTTATT TGTAACCATT ATAAGCTGCA ATAAACAAGT
9241  T (SEQ ID NO: 49)
```

LINE 1 ORF2-minke mRNA GFP (SEQ ID NO: 50)
```
   1  TAATACGACT CACTATAGGG AGAAGTACTG CCACCATGGG CAAGAAGCAA AATCGCAAGA
  61  CGGGGAATTC CAAGACACAA TCCGCTAGCC CACCACCTAA AGAGCGTTCT AGCTCCCCTG
 121  CTACTGAGCA GTCCTGGATG GAAAACGACT TCGATGAACT CCGGGAAGAG GGATTTAGGC
 181  GATCCAACTA TTCAGAACTC CGCAAGATA TCCAGACAAA GGGGAAGGAA GTCGAGAATT
 241  TCGAGAAGAA CCTCAGGAGG TGCATCACCC GTATCACAAA CACTGAGAAA TGTCTCAAAG
 301  AACTCATGGA ACTTAAGACA AAAGCCAGGG AGCTTCGAGA GGAGTGTCGG AGTCTGAGAT
 361  CCAGGTGTGA CCAGCTCGAG GAGCGCGTGA GCGCGATGGA AGACGAGGA AACGAGATGA
 421  AAAGAGAGGG CAAATTCAGG GAGAAGCGCA TTAAGAGGAA CGAACAGAGT CTGCAGGAGA
 481  TTTGGGATTA CGTCAAGAGG CCTAACCTGC GGTTGATCGG CGTCCCCGAG AGCGACGTAG
 541  AAAACGGGAC TAAACTGGAG AATACACTTC AAGACATCAT TCAAGAAAAT TTTCCAAACC
 601  TGGCTCGGCA AGCTAATGTG CAAATCCAAG AGATCCAACG CACACCCCAG CGGTATAGCT
 661  CTCGGCGTGC CACCCCTAGG CATATTATCG TGCGCTTTAC TAAGGTGGAG ATGAAAGAGA
 721  AGATGCTGCG AGCCGCTCGG GAAAAGGGAA GGGTGACTTT GAAGGGCAAA CCTATTCGGC
 781  TGACGGTTGA CCTTAGCGCC GAGACACTCC AGGCACGCCG GAATGGGGC CCCATCTTTA
 841  ATATCCTGAA GGAGAAGAAC TTCCAGCCAC GAATCTCTTA CCCTGCAAAG TTGAGTTTTA
 901  TCTCCGAGGG TGAGATTAAG TATTTCATCG ATAAACAGAT GCTGCGAGAC TTCGTGACAA
 961  CTCGCCCAGC TCTCAAGGAA CTGCTCAAAG AGGCTCTTAA TATGGAGCGC AATAATAGAT
1021  ATCAACCCTT GCAGAACCAC GCAAAGATGT GAGACAGCCG TCAGACCATC AAGACTAGGA
1081  AGAAACTGCA TCAACTAATG AGCAAAATCA CCAGCTAACA TCATAGTATA CATGGTACTA
1141  GGAACTTACA TTTCGATTAT TACCTTAAAC GTGAATGGGT TAAATGCCCC AACCAAGAGA
1201  CATCGGCTGG CTGAATGGAT TCAGAACAG GACCCCTATA TTTGCTGTCT GCAGGAGACC
1261  CACTTCCGTC CTCGCGACAC ATACAGACTG AAAGTGAGGG GCTGGAAAAA GATCTTCCAT
1321  GCCAATGGAA ATCAAAAGAA AGCTGGAGTG CTATTCTCA TCTCAGATAA AATTGACTTC
1381  AAAATAAAGA ATGTTACTCG AGATAAGGAG GGACACTACA TAATGATCCA GGGGTCCATC
```

TABLE 8-continued

Plasmid and mRNA construct sequences

```
1441 CAAGAAGAGG ATATAACTAT TATTAATATT TATGCACCCA ACATTGGCGC CCCTCAGTAC
1501 ATCAGGCAGC TGCTTACAGC TATCAAGGAG GAAATGACA GTAACACGAT TATCGTGGGG
1561 GACTTTAACA CCAGCCTTAC TCCGATGGAT AGATCATCCA AAATGAAAAT AAATAAGGAA
1621 ACAGAGGCTC TTAATGACAC CATTGACCAG ATAGATCTGA TTGATATATA TAGGACATTC
1681 CATCCAAAAA CTGCCGATTA CACTTTCTTC AGCAGTGCGC ATGGAACCTT CTCCAGGATA
1741 GATCACATCT TGGGTCACAA AAGTAGCCTC AGTAAGTTTA AGAAAATTGA AATCATTAGC
1801 AGCATCTTTT CTGACCATAA CGCTATGCGC CTGGAGATGA ATCACAGGGA GAAGAACGTA
1861 AAGAAGACAA ACACCTGGAG GCTGAACAAT ACGCTGCTAA ATAACCAAGA GATCACTGAG
1921 GAAATCAAAC AGGAAATAAA AAAATACTTG GAGACAAATG ACAATGAAAA CACGACCACC
1981 CAGAACTTGT GGGATGCAGC TAAAGCGGTT CTGAGAGGGA AGTTTATAGC TATTCAAGCC
2041 TACCTTAAGA AACAGGAAAA ATCTCAAGTG AACAATTTGA CCTTACACCT AAAGAAACTG
2101 GAGAAGGAGG AGCAGACCAA ACCCAAAGTG AGCAGGAGGA AAGAAATCAT CAAGATCAGA
2161 GCCGAAATCA ATGAAATAGA AACTAAGAAG ACAATTGCCA AGATCAATAA AACTAAATCC
2221 TGGTTCTTTG AGAAGATCAA CAAAATTGAT AAGCCATTAG CCAGACTCAT CAAGAAAAAG
2281 AGGGAGAGGA CTCAGATCAA TAAGATCAGA ATGAGAAGG GGGAAGTTAC AACCGACACG
2341 GCGGAGATTC AGAACATCCT GAGAGACTAC TACAAGCAAC TTTATGCCAA TAAAATGGAC
2401 AACCTGGAAG AAATGGACAA ATTCCTGGAA AGGTATAACC TTCCCCGGCT GAACCAGGAG
2461 GAGACTGAAA ATATCAACCG CCCAATCACA AGTAATGAGA TTGAGACTGT GATTAAGAAT
2521 CTTCCAACTA ACAAAGTCC CGGCCCCGAT GGCTTCACAG GTGAATTCTA TCAGACCTTT
2581 CGGGAGGAGT TGACACCCAT CCTTCTCAAG CTCTTCCAAA AAATTGCAGA GGAGGGCACA
2641 CTCCCGAACT CATTCTATGA GGCCACCATC ACCCTGATCC CAAAGCCCGA CAAGGACACT
2701 ACAAAGAAAG AAAATTACCG ACCAATTTCC CTGATGAATA TCGATGCCAA GATCCTCAAC
2761 AAAATCTTGG CAAACAGAAT CCAGCAGCAC ATTAAGAGGA TCATACACCA CGATCAGGTG
2821 GGCTTTATCC CGGGGATGCA AGGATTCTTC AATATCCGCA AATCAATCAA TGTGATCCAC
2881 CATATTAACA AGTTGAAGAA GAAGAACCAT ATGATCATCT CCATCGATGC AGAGAAAGCT
2941 TTTGACAAAA TTCAACACCC ATTTATGATC AAAACTCTCC AGAAGGTGGG CATCGAGGGG
3001 ACCTACCTCA ACATAATTAA GGCCATCTAT GATAAGCCCA CAGCCAACAT CATTCTCAAT
3061 GGTGAAAAGC TGAAGGCATT TCCTCTGCGG TCCGGAACGA GACAGGGATG TCCTCTCTCT
3121 CCTCTTCTGT TCAACATCGT TCTGGAAGTC CTAGCCACCG CTATCCGCGA GGAAAAGGAA
3181 ATTAAGGCA TACAGATTGG AAAGGAAGAG GTAAAACTGT CTCTGTTTGC GGATGATATG
3241 ATACTGTACA TAGAGAATCC TAAAACTGCC ACCCGGAACG TGTTGGAGCT CTCTTGCTTT
3301 TATGGTAAGG TCGCCGGTTA CAAGATTAAT GCTCAGAAGT CTCTTGCTTT CCTGTACACT
3361 AATGATGAAA AGTCTGAACG GGAAATTATG GAGACACTCC CCTTTACCAT TGCAACCAAA
3421 CGTATTAAAT ACCTTGGCAT TAACCTGCCT AAGGAGACAA AAGACCTGTA TGCTGAAAAC
3481 TATAAGACAC TGATGAAAGA GATTAAAGAT GATACCAACC GGTGGCGGGA TATCCCATGT
3541 TCTTGGATTG GCAGAATCAA CATTGTGAAG ATGAGCATCC TGCCCAAGGC CATCTACAGA
3601 TTCAATGCCA TCCCTATCAA ATTACCTATG GCATTTTTTA CGGAGCTGGA ACAGATCATC
3661 TTAAAATTTG TGTGGCGCCA CAAGCGGCCC CGAATCGCCA AAGCGGTCTT GAGGCAGAAG
3721 AATGGCGCTG GGGGAATCCG ACTCCCTGAC TTCAGATTGT ACTACAAAGC TACCGTCATC
3781 AAGACAATCT GGTACTGGCA CAAGAACAGA AACATCGATC AGTGGAACAA GATCGAAAGC
3841 CCTGAGATTA ACCCCCGCAC CTATGGTCAA CTGATCTATG ACAAAGGGGG CAAGGATATA
3901 CAATGGCGCA AGGACGCCT CTTCAATAAG TGGTGCTGGG AAAACTGGAC AGCCACCTGC
3961 AAGCGTATGA AGCTGGAGTA CTCCCTGACA CCATACACAA AAATAAACTC AAAGTGGATT
4021 CGAGACCTCA ATATCGGCT GGACACTATA AAACTCCTGG AGGAGAACAT TGGGCGTACA
4081 CTCTTTGACA TTAATCATAG CAAGATCTTT TTCGATCCCC CTCCTCGTGT AATGGAAATA
4141 AAAACAAAAA TAAACAAGTG GGATCTGATG AAACTTCAGA GCTTTTGCAC CGCAAAGGAG
4201 ACCATAAACA AGACGAAGCG CCAACCCTCA GAATGGGAGA AAATATTTGC GAATGAGTCT
4261 ACGGACAAAG GCTTAATCTC CAAAATATAT AAGCAGCTCA TTCAGCTCAA TATCAAGGAA
4321 ACAAACACCC CGATCCAAAA GTGGGCAGAG GACCTAAATC GGCATTTCTC CAAGGAAGAC
4381 ATCCAGACGG CCACGAAGCA CATGAAGCGA TGCTCAACTT CCCTGATTAT TCGCGAAATG
4441 CAGATCAAGA CTACTATGCG CTATCACCTC ACTCCTGTTC GGATGGGCAT CATCCGGAAA
4501 TCTACAAACA ACAAGTGCTG GAGAGGGTGT GGCGAAAAGG GAACCCTCTT GCATTGTTGG
4561 TGGGAGTGTA AGTTGATCCA GCCACTATGG CGGACCATAT GGAGGTTCCT TAAAAAACTG
4621 AAGATTGAGC TGCCATATGA CCCAGCAATC CCACTGCTGG GCATATACCC GGAGAAAACC
4681 GTGATTCAGA AAGACACTTG CACCCGAATG TTCATTGCAG CATTGTTTAC AATAGCCAGG
4741 TCATGGAAGC AGCCTAAGTG CCCCTCGACA GACGAGTGGA TCAAGAAGAT GTGGTACATT
4801 TATACTATGG AATATTACAG CGCCATCAAA CGCAACGAAA TTGGGTCTTT TCTGGAGACG
4861 TGGATGATC TAGAGACTGT CATCCAGAGT GAGGTAAGTC AGAAAGAGAA GAACAAATAT
4921 CGTATTTTAA CGCATATTTG TGGAACCTGG AAGAATGGTA CAGATGAGCC GGTCTGCCGA
4981 ACCGAGATTG AGACCCAGAT GGACTACAAA GACGATGACG ACAAGTGAAG CGCTTCTAGA
5041 AGTTGTCTCC TCCTGCACTG ACTGATGAT ACAATCGATT TCTGGATCCG CAGGCCTAAT
5101 CAACCTCTGG ATTACAAAAT TTGTGAAAGA TTGACTGGTA TTCTTAACTA TGTTGCTCCT
5161 TTTACGCTAT GTGGATACGC TGCTTTAATG CCTTTGTATC ATGCTATTGC TTCCCGTATG
5221 GCTTTCATTT TCTCCTCCTT GTATAAATCC TGGTTGCTGT CTCTTTATGA GGAGTTGTGG
5281 CCCGTTGTCA GGCAACGTGG CGTGGTGTGC ACTGTGTTTG CTGACGCAAC CCCCACTGGT
5341 TGGGGCATTG CCACCACCTG TCAGCTCCTT TCCGGGACTT TCGCTTTCCC CCTCCCTATT
5401 GCCACGGCGG AACTCATCGC CGCCTGCCTT GCCCGCTGCT GGACAGGGGC TCGGCTGTTG
5461 GGCACTGACA ATTCCGTGGT GTTGTCGGGG AAGCTGACGT CCTTTCCATG GCTGCTCGCC
5521 TGTGTTGCCA CCTGGATTCT GCGCGGGACG TCCTTCTGCT ACGTCCCTTC GGCCCTCAAT
5581 CCAGCGGACC TTCCTTCCCG CTGAGAGACA CAAAAAATTC CAACACACTA TTGCAATGAA
5641 AATAAATTTC CTTTATTAGC CAGAAGTCAG ATGCTCAAGG GCTTCATGA TGTCCCCATA
5701 ATTTTTGGCA GAGGGAAAAA GATCTCAGTG GTATTTGTGA GCCAGGGCAT TGGCCTTCTG
5761 ATAGGCAGCC TGCACCTGAG GAGTGCGGCC GCTTTACTTG TACAGCTCGT CCATGCCGAG
5821 AGTGATCCCG GCGGCGGTCA CGAACTCCAG CAGGACCATG TGATCGCGCT TCTCGTTGGG
5881 GTCTTTGCTC AGGGCGGACT GGGTGCTCAG GTAGTGGTTG TCGGGCAGCA GCACGGGGCC
5941 GTCGCCGATG GGGGTGTTCT GCTGGTAGTG GTCGGCGAGC TGCACGCTGC CGTCCTCGAT
6001 GTTGTGGCGG ATCTTGAAGT TCACCTTGAT GCCGTTCTTC TGCTTGTCGG CCATGATATA
6061 GACGTTGTGG CTGTTGTAGT TGTACTCCAG CTTGTGCCCC AGGATGTTGC CGTCCTCCTT
```

TABLE 8-continued

Plasmid and mRNA construct sequences

```
6121  GAAGTCGATG  CCCTTCAGCT  CGATGCGGTT  CACCAGGGTG  TCGCCCTCGA  ACTTCACCTC
6181  GGCGCGGGTC  TTGTAGTTGC  CGTCGTCCTT  GAAGAAGATG  GTGCGCTCCT  GGACGTAGCC
6241  TTCGGGCATG  GCGGACTTGA  AGAAGTCGTG  CTGCTTCATG  TGGTCGGGGT  AGCGGCTGAA
6301  GCACTGCACG  CCGTAGGTCA  GGGTGGTCAC  GAGGGTGGGC  CAGGGCACGG  GCAGCTTGCC
6361  GGTGGTGCAG  ATGAACTTCA  GGGTCAGCTT  GCCGTAGGTG  GCATCGCCCT  CGCCCTCGCC
6421  GGACACGCTG  AACTTGTGGC  CGTTTACGTC  GCCGTCCAGC  TCGACCAGGA  TGGGCACCAC
6481  CCCGGTGAAC  AGCTCCTCGC  CCTTGCTCAC  CATGGTGGCG  GGATCTGACG  GTTCACTAAA
6541  CCAGCTCTGC  TTATATAGAC  CTCCCACCGT  ACACGCCTAC  CGCCCATTTG  CGTCAATGGG
6601  GCGGAGTTGT  TACGACATTT  TGGAAAGTCC  CGTTGATTTT  GGTGCCAAAA  CAAACTCCCA
6661  TTGACGTCAA  TGGGGTGGAG  ACTTGGAAAT  CCCCGTGAGT  CAAACCGCTA  TCCACGCCCA
6721  TTGATGTACT  GCCAAAACCG  CATCACCATG  GTAATAGCGA  TGACTAATAC  GTAGATGTAC
6781  TGCCAAGTAG  GAAAGTCCCA  TAAGGTCATG  TACTGGGCAT  AATGCCAGGC  GGGCCATTTA
6841  CCGTCATTGA  CGTCAATAGG  GGGCGTACTT  GGCATATGAT  ACACTTGATG  TACTGCCAAG
6901  TGGGCAGTTT  ACCGTAAATA  CTCCACCCAT  TGACGTCAAT  GGAAAGTCCC  TATTGGCGTT
6961  ACTATGGGAA  CATACGTCAT  TATTGACGTC  AATGGGCGGG  GGTCGTTGGG  CGGTCAGCCA
7021  GGCGGGCCAT  TTACCGTAAG  TTATGTAACG  GGCCTGCTGC  CGGCTCTGCG  GCCTCTTCCG
7081  CGTCTTCGCC  TTCGCCCTCA  GACGAGTCGG  ATCTCCCTTT  GGGCCGCCTC  CCCGCCTGTC
7141  TAGCTTGACT  GACTGAGATA  CAGCGTACCT  TCAGCTCACA  GACATGATAA  GATACATTGA
7201  TGAGTTTGGA  CAAACCACAA  CTAGAATGCA  GTGAAAAAAA  TGCTTTATTT  GTGAAATTTG
7261  TGATGCTATT  GCTTTATTTG  TAACCATTAT  AAGCTGCAAT  AAACAAGTT
      (SEQ ID NO: 50)
```

Example 17. Enriching Stably Retrotransposed Cells

Figure 40:
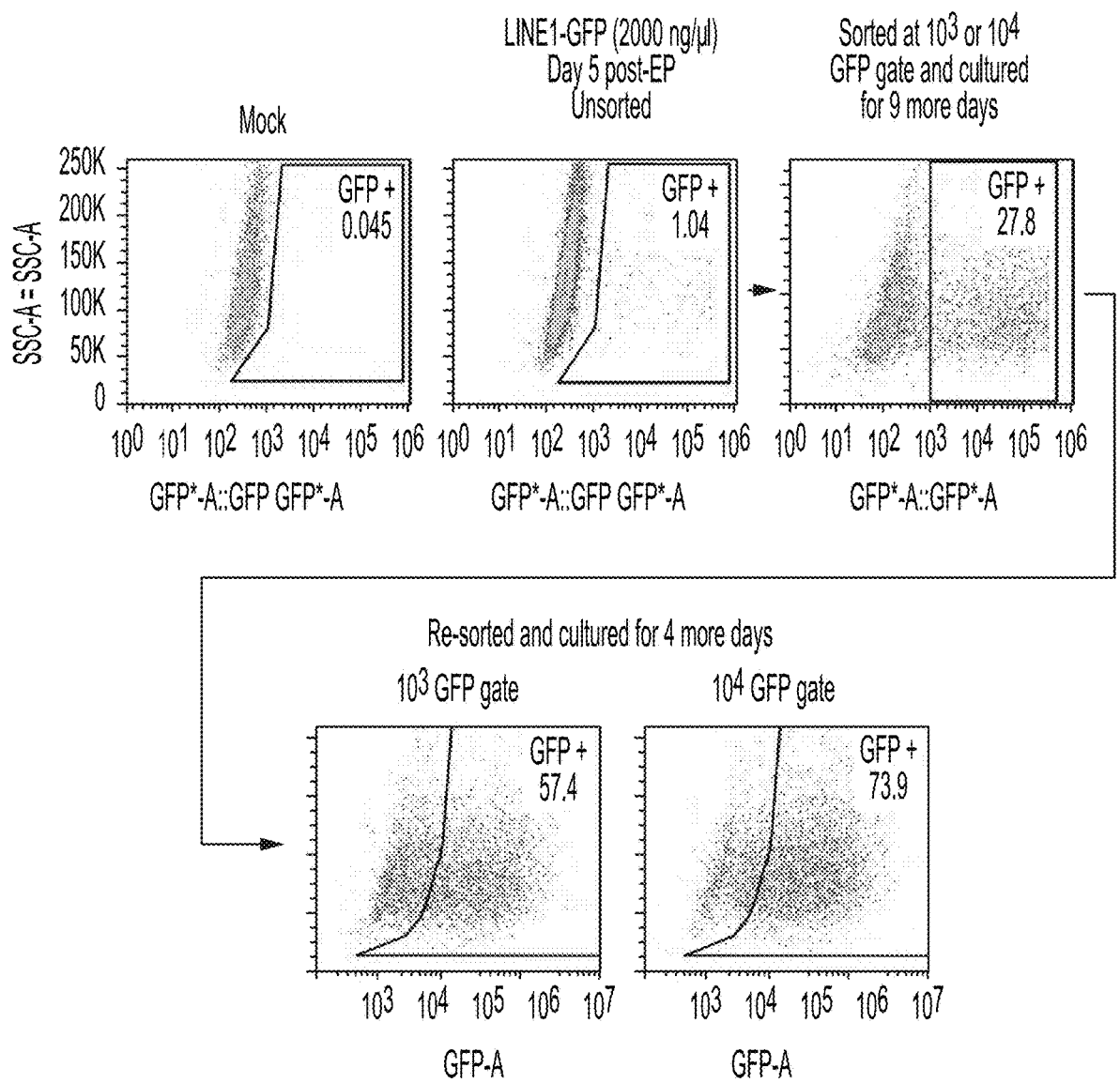
FIG. 40 depicts exemplary flow cytometry data showing sorting and enriching GFP+293T cells electroporated with 2000 ng/4 LINE1-GFP mRNA. The first panel shows flow cytometry data for mock electroporated cells in the absence of LINE1-GFP mRNA. The second panel shows flow cytometry data collected 5 days post electroporation for unsorted cells electroporated with LINE1-GFP mRNA. The GFP+ cells from the second panel were sorted and the flow cytometry data are shown in the third panel. The GFP+ cells from the third panel were cultured for 9 days post sorting and resorted using 10^3 or 10^4 GFP fluorescence intensity gate. The fourth panel shows flow cytometry data for cells resorted using GFP+ at 10^3 GFP gate collected 4 days after resorting. The fifth panel shows flow cytometry data for cells resorted using GFP+ at 10^3 GFP gate collected 4 days after resorting.

In an effort to increase the cell yield having stably integrated nucleic acid sequence a method of sorting and culturing was attempted, as described in this example. 293T cells were electroporated with LINE1-GFP mRNA produced by IVT and cultured in vitro for at least 3 days. Expression of GFP was determined periodically using flow cytometry, as shown in FIG. 40. Genomic integration per genome was evaluated using quantitative PCR. Interpolations of nucleic acid encoding GFP in the genome per genome were evaluated using standard curves for GFP and a housekeeping gene (FAU). In a sorting and enrichment culture of GFP positive cells, shown in FIG. 40, it was evident that integration was stable for multiple cell passages (at least 18 days post EP), and considerable enrichment was possible. GFP expression was detectable in ~1% of 293T cells 5 days post-EP. GFP+ cells were enriched to ~28% after first sorting and was further enriched up to ~74% of cells after 2nd sorting. (FIG. 40, FIG. 41C).

Figures 41A, 41B:
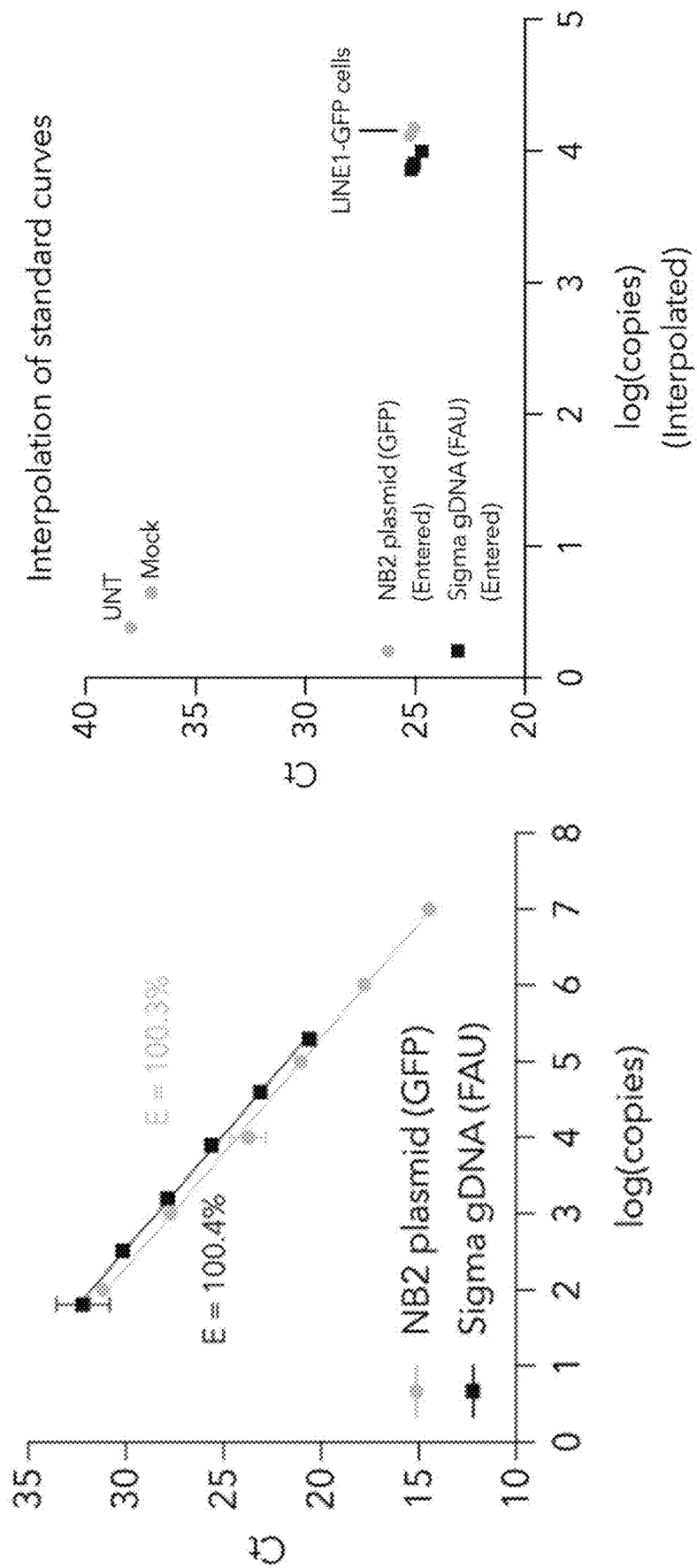
FIG. 41A shows a standard curve for GFP (NB2 plasmid) and a housekeeping gene (FAU) for evaluating genomic integration of GFP-encoding nucleic acid per cell using quantitative PCR.
FIG. 41B shows results of an exemplary graph depicting interpolation of the standard curves of FIG. 41A for quantitation of genomic integration.
Figure 41C:
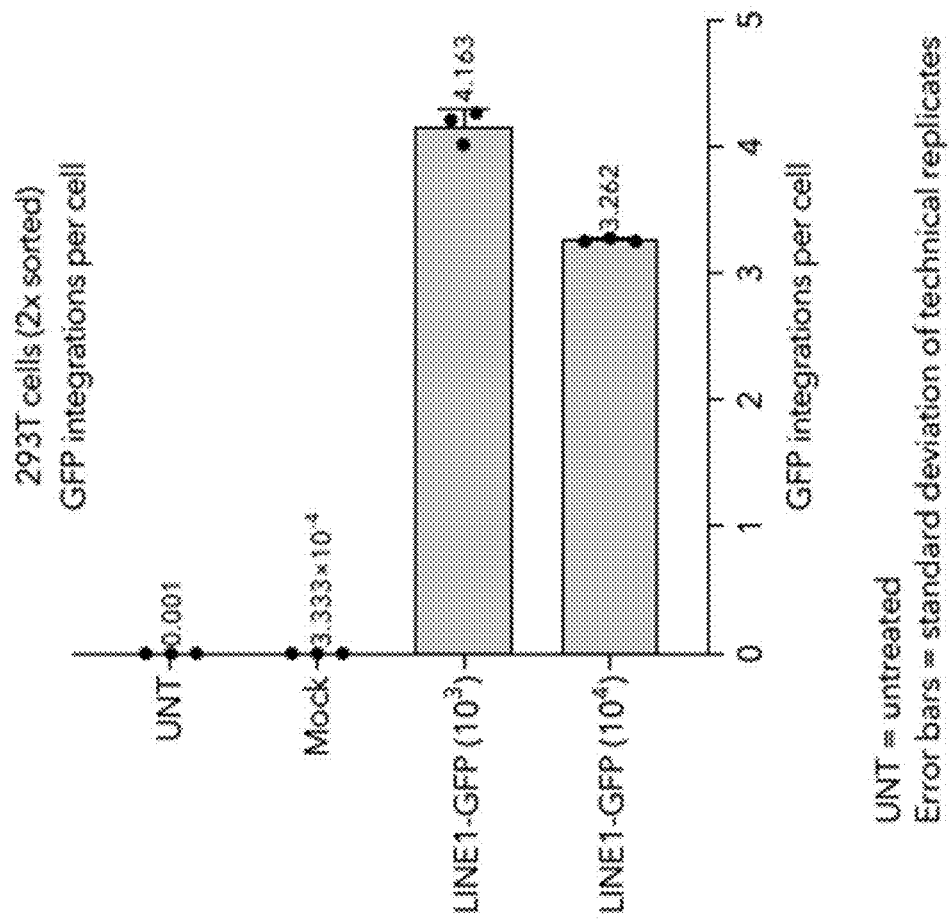
FIG. 41C shows the number of the GFP gene integrated into genome of 293T cells following LINE1-GFP mRNA electroporation and double sorting as shown in FIG. 40. The average number of GFP integrations per cell when gated at 10^3 GFP+ cells and at 10^4 GFP+ cells according to qPCR are shown.

Standard curves and exemplary quantitation of genomic integrations are shown in FIGS. 41A and 41B respectively. FIG. 41C shows average number of GFP integrations per genome when gated at 10^3 units of GFP fluorescence intensity and at 10^4 units of GFP fluorescence intensity.

Figure 42:
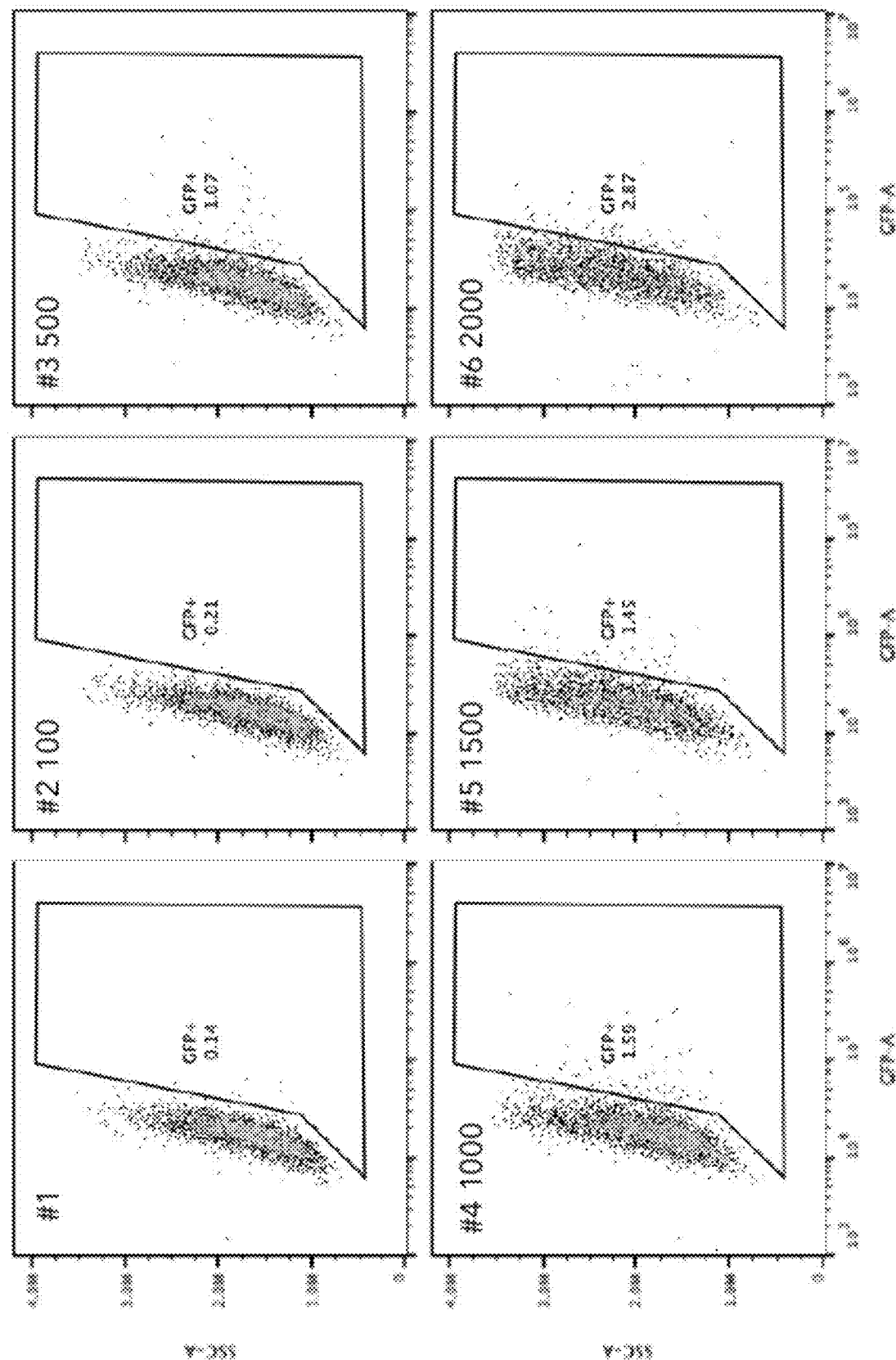
FIG. 42 depicts exemplary flow cytometry data showing GFP+293T cells electroporated with the indicated titrated amounts of LINE1-GFP mRNA, in ng/4 in electroporation solution, after culturing for 3 days post-electroporation.
Figure 43:
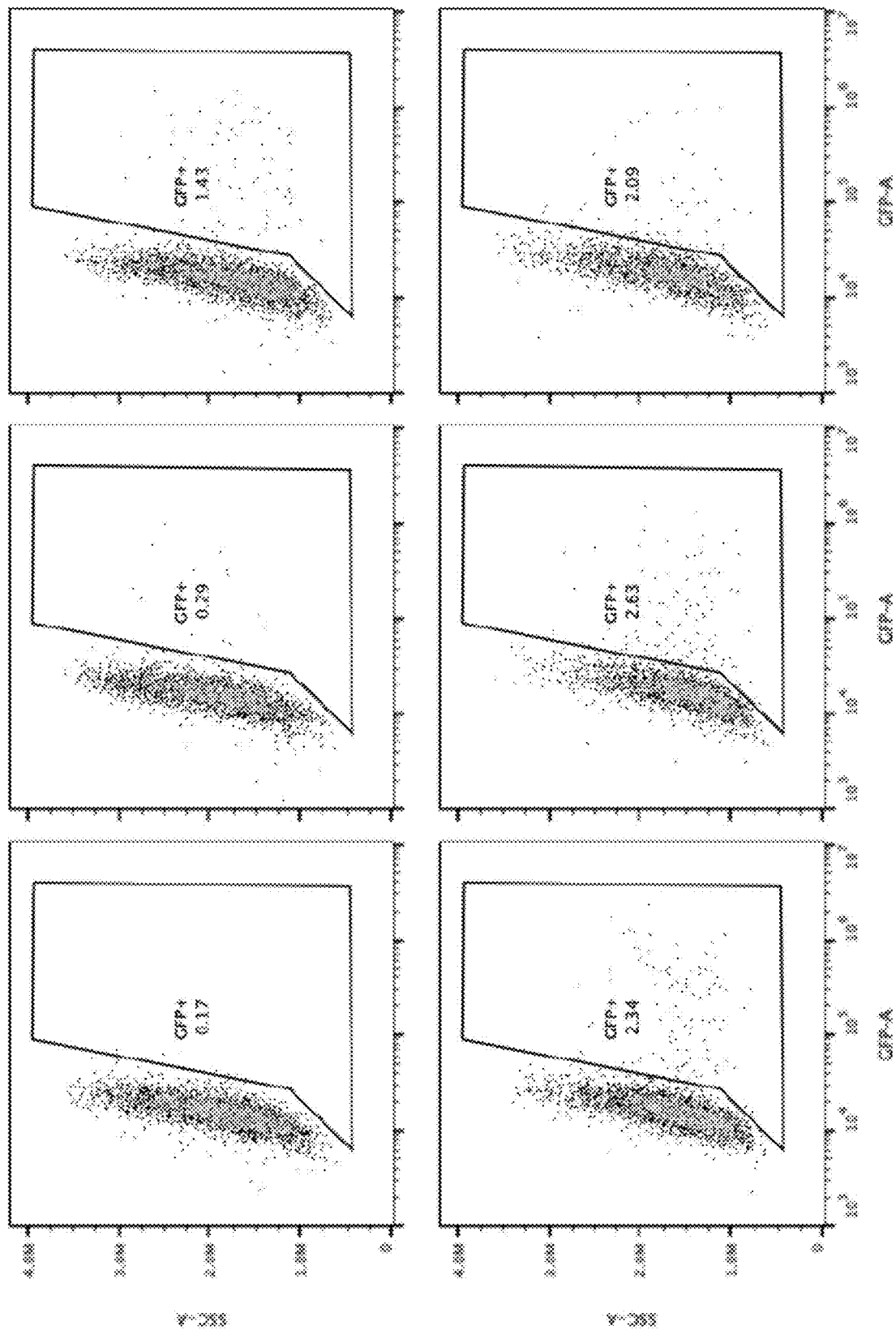
FIG. 43 depicts exemplary flow cytometry data showing GFP+293T cells electroporated with the indicated titrated amounts of LINE1-GFP mRNA, in ng/4 in electroporation solution, after culturing for 5 days post-electroporation.
Figure 44:
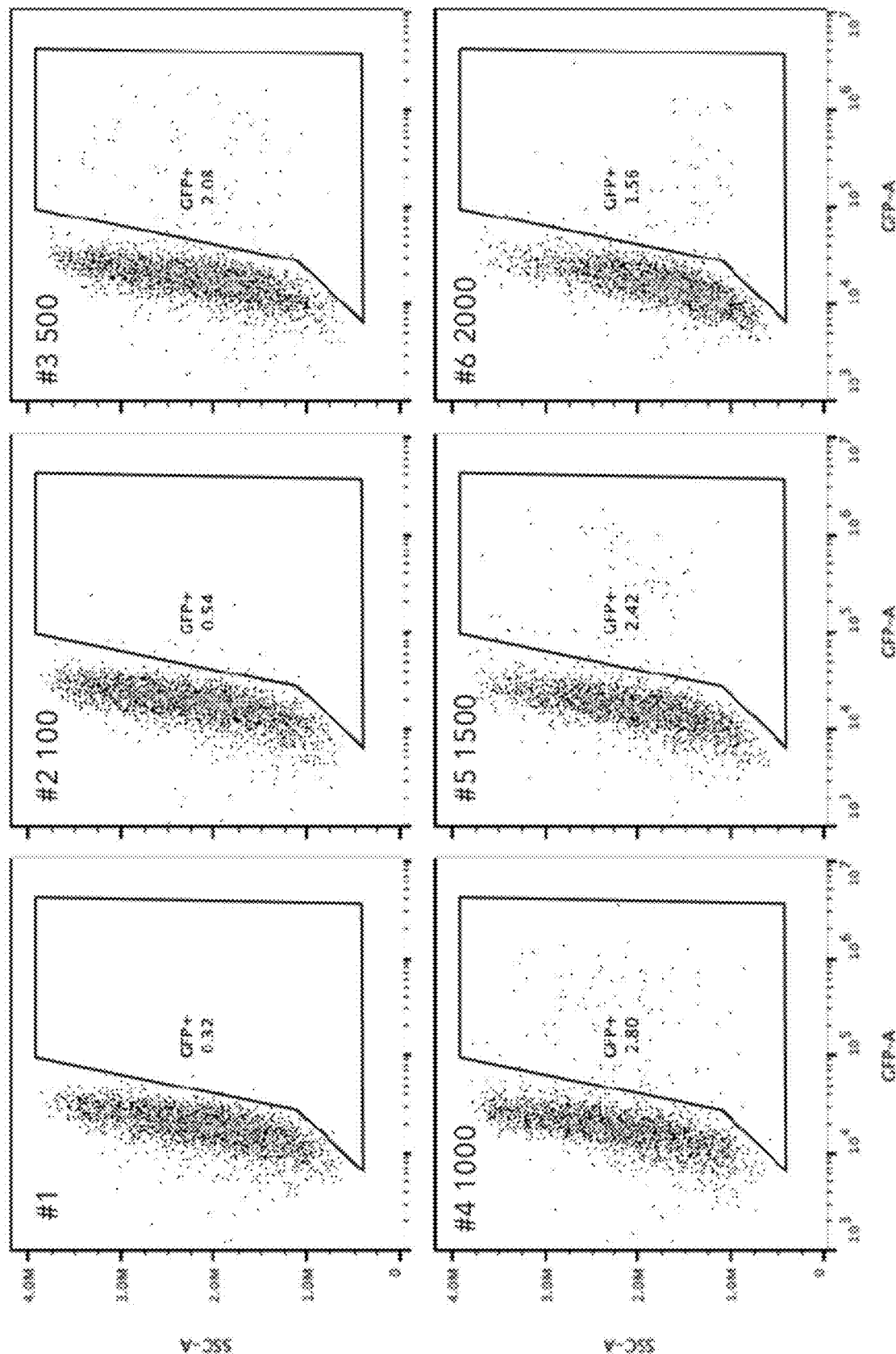
FIG. 44 depicts exemplary flow cytometry data showing GFP+293T cells electroporated with the indicated titrated amounts of LINE1-GFP mRNA, in ng/µL in electroporation solution, after culturing for 7 days post-electroporation.
Figure 45:
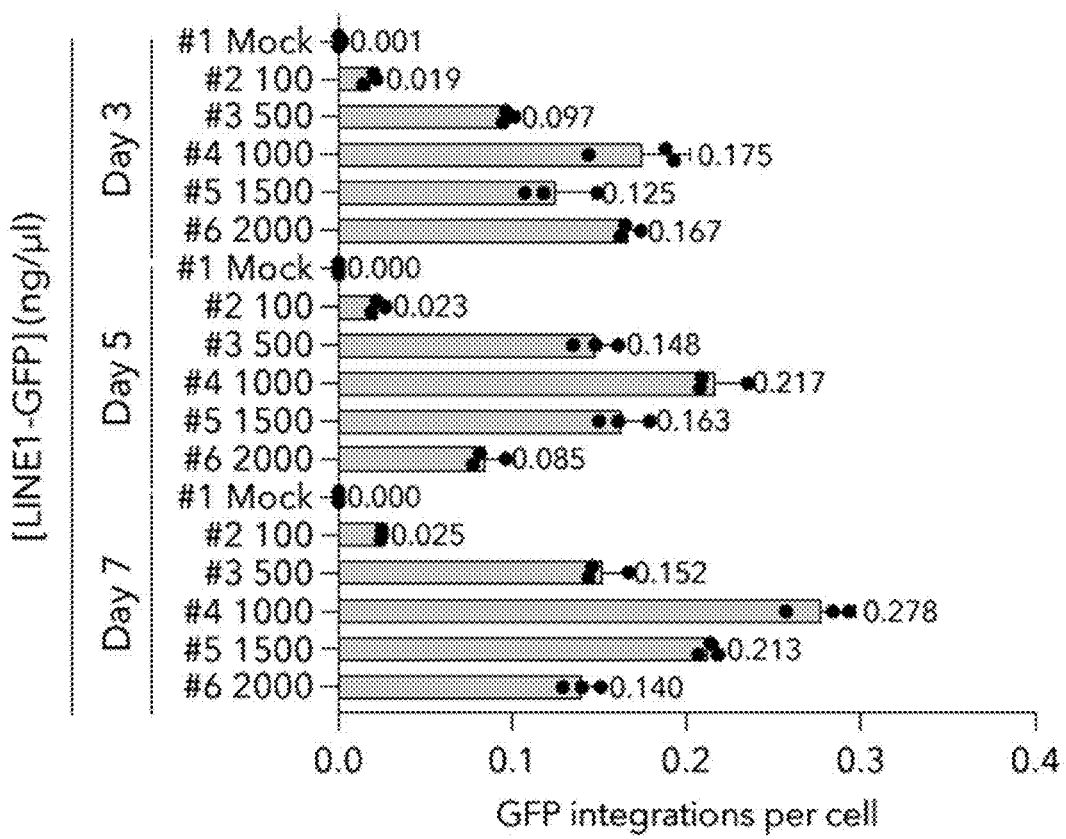
FIG. 45 shows a graph of the number of GFP integrations per genome of 293T cells electroporated with the indicated titrated amounts of LINE1-GFP mRNA, in ng/µL in electroporation solution, according to qPCR after culturing for 3, 5 or 7 days post-electroporation according to FIGS. 42-44 (top) and a graph of the integration kinetics (bottom) according to the data from FIGS. 42-44.
Figure 45:
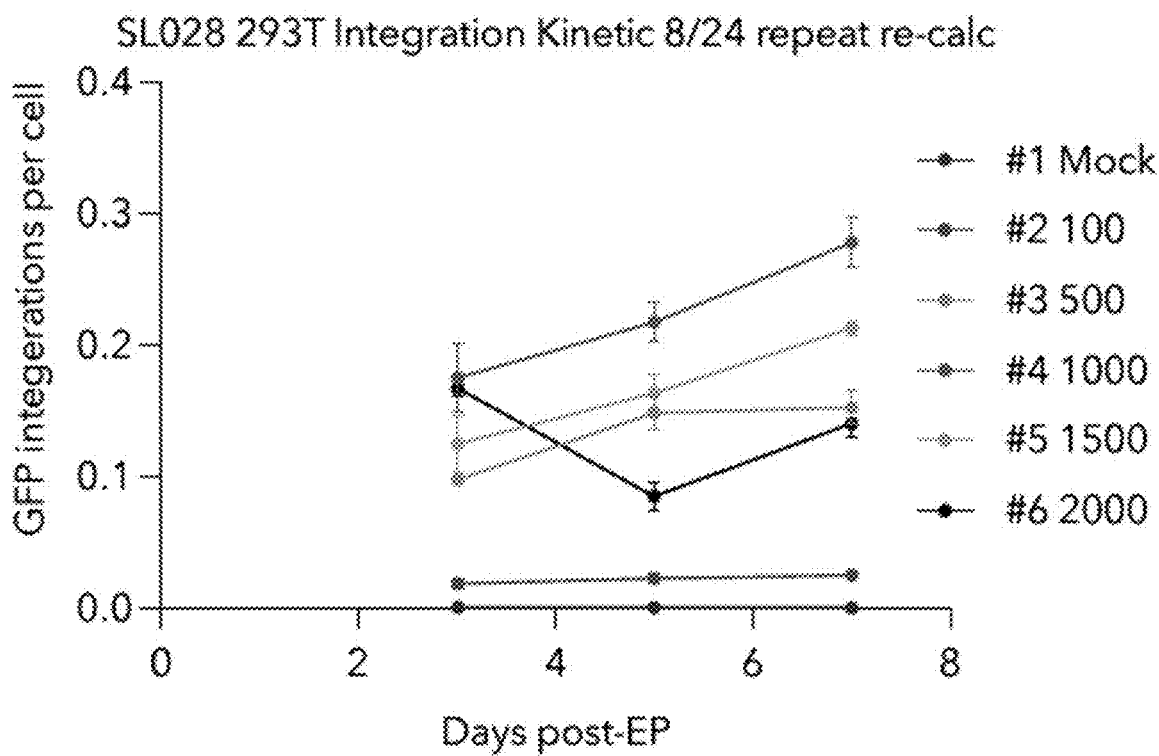
Figure 46:
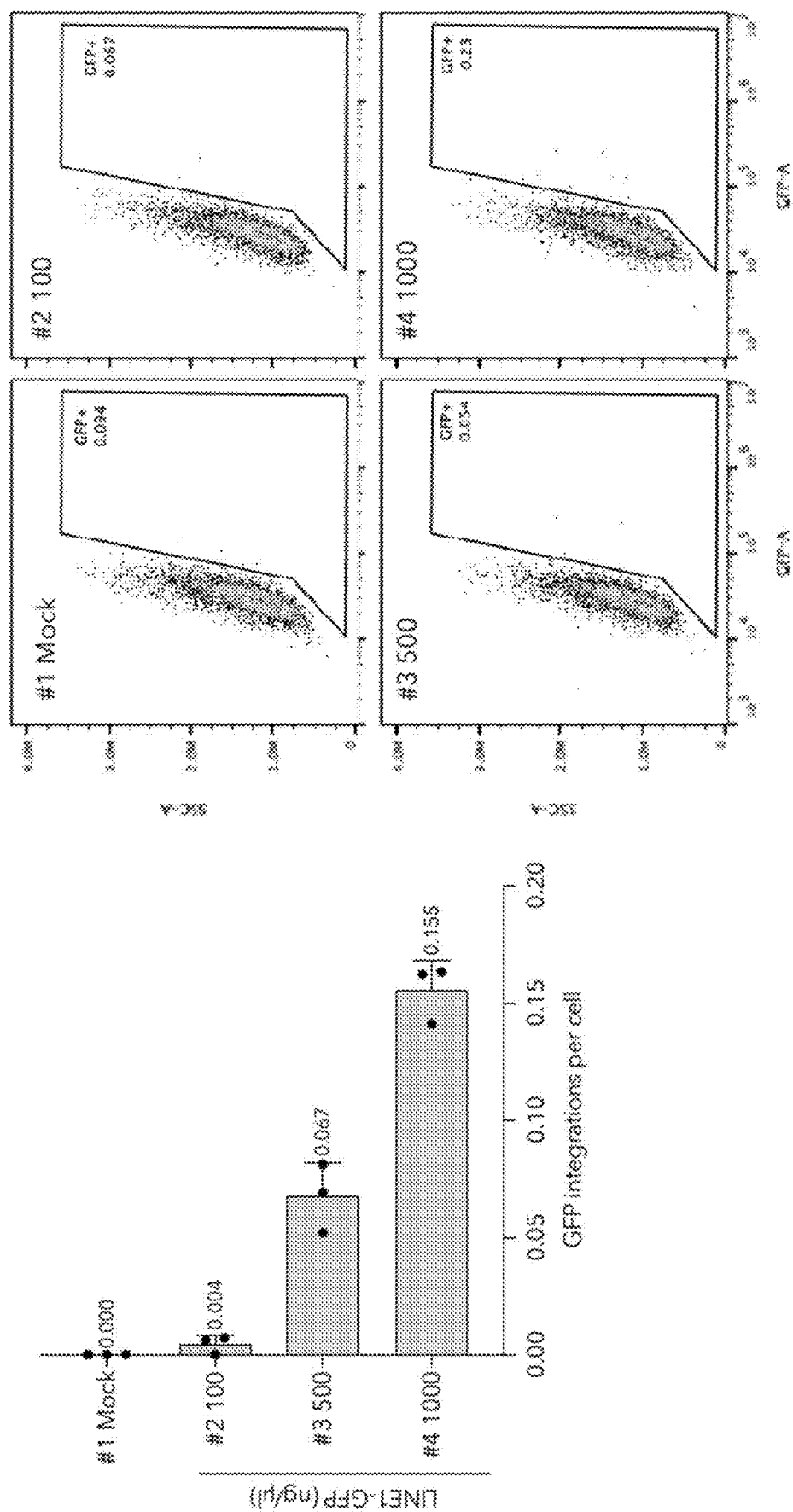
FIG. 46 depicts exemplary flow cytometry data (right) showing GFP+K562 cells electroporated with the indicated titrated amounts of LINE1-GFP mRNA, in ng/µL in electroporation solution, after culturing for 6 days post-electroporation, and a graph of the number of GFP integrations per genome according to qPCR (left).
Figure 47:
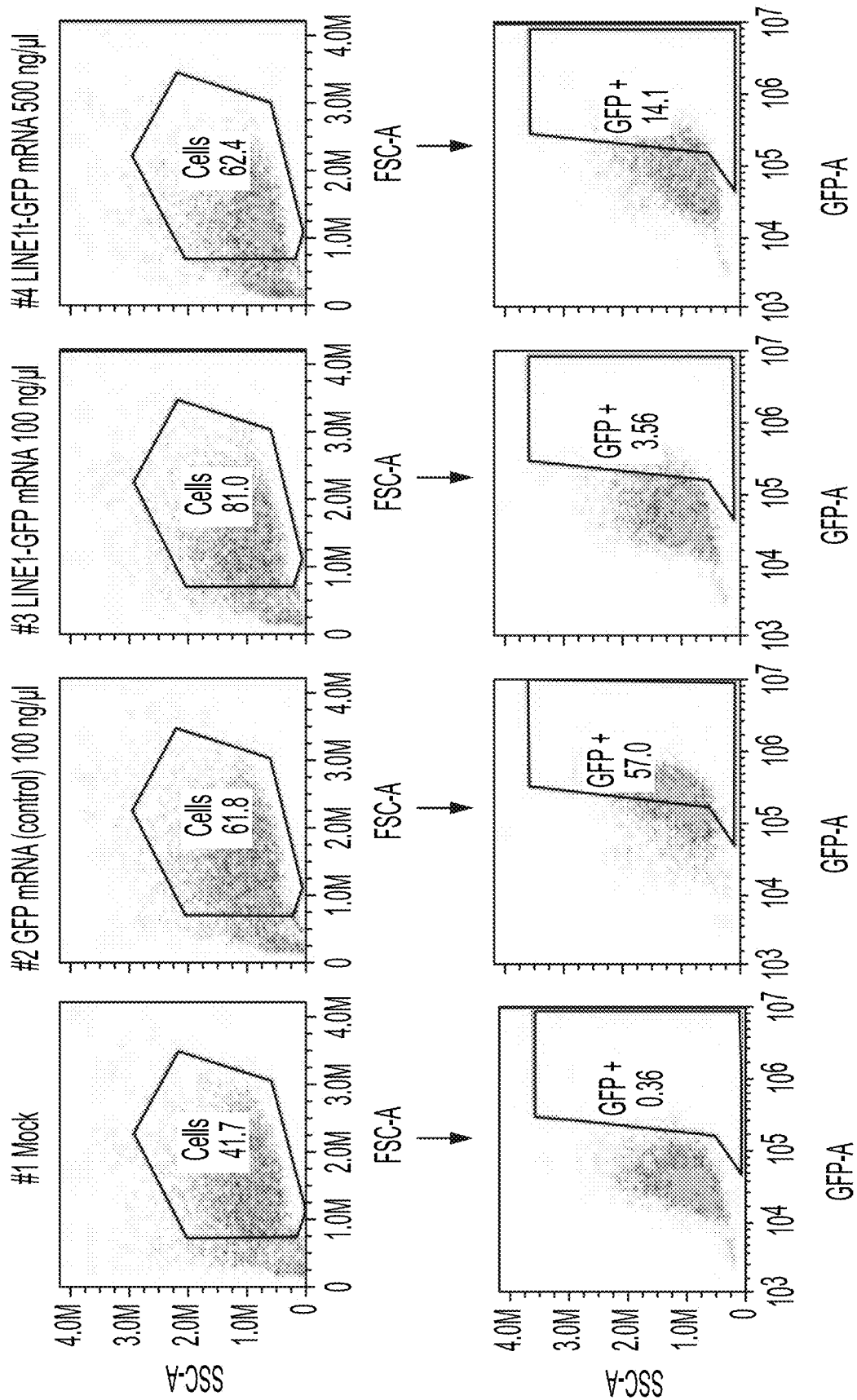
FIG. 47 depicts exemplary flow cytometry data (top) showing GFP+human primary monocytes electroporated with the indicated titrated amounts of LINE1-GFP mRNA after culturing for 3 days post-electroporation, and a graph of the number of GFP integrations per genome according to qPCR (bottom).
Figure 47:
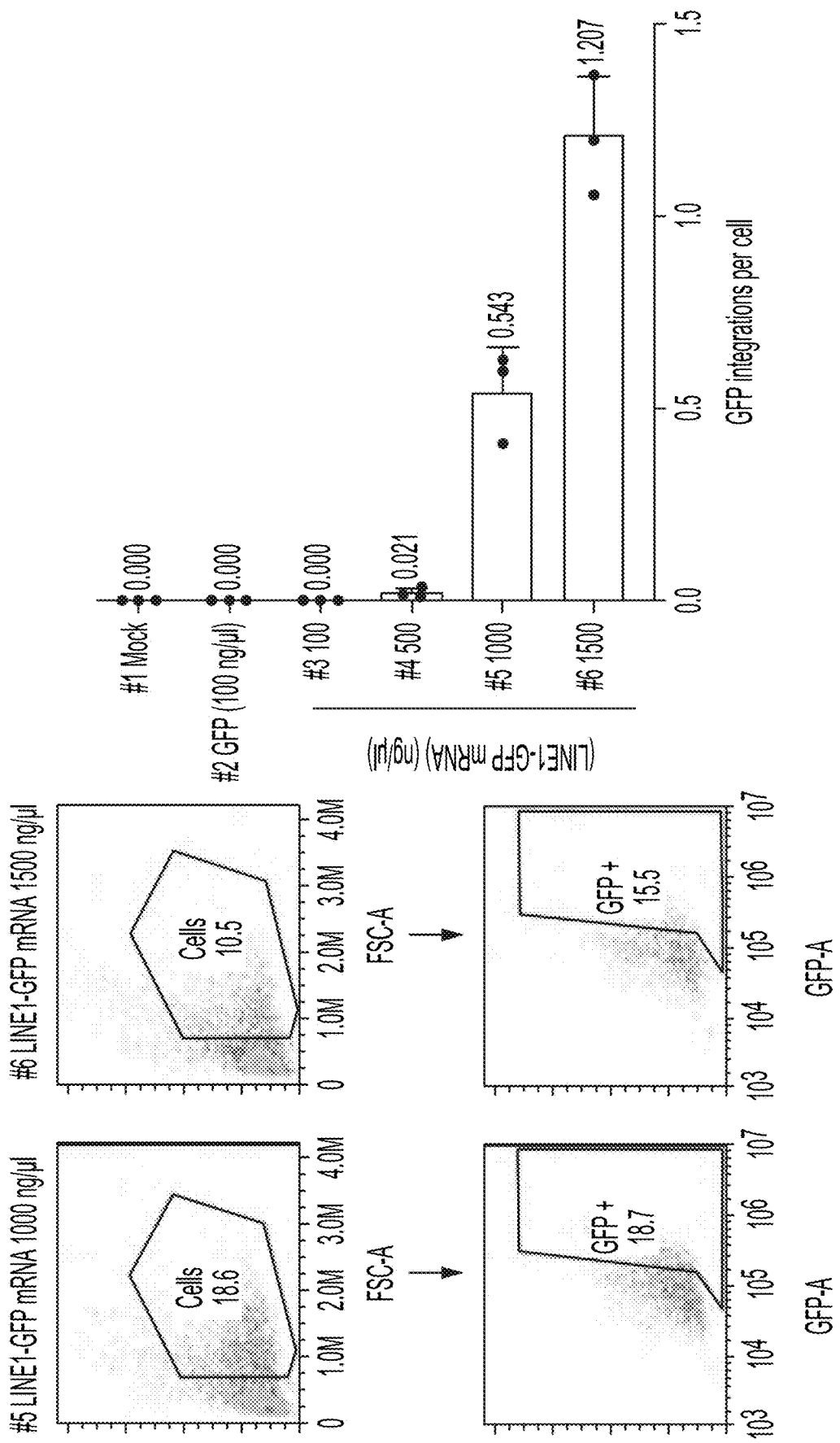
Figure 48:
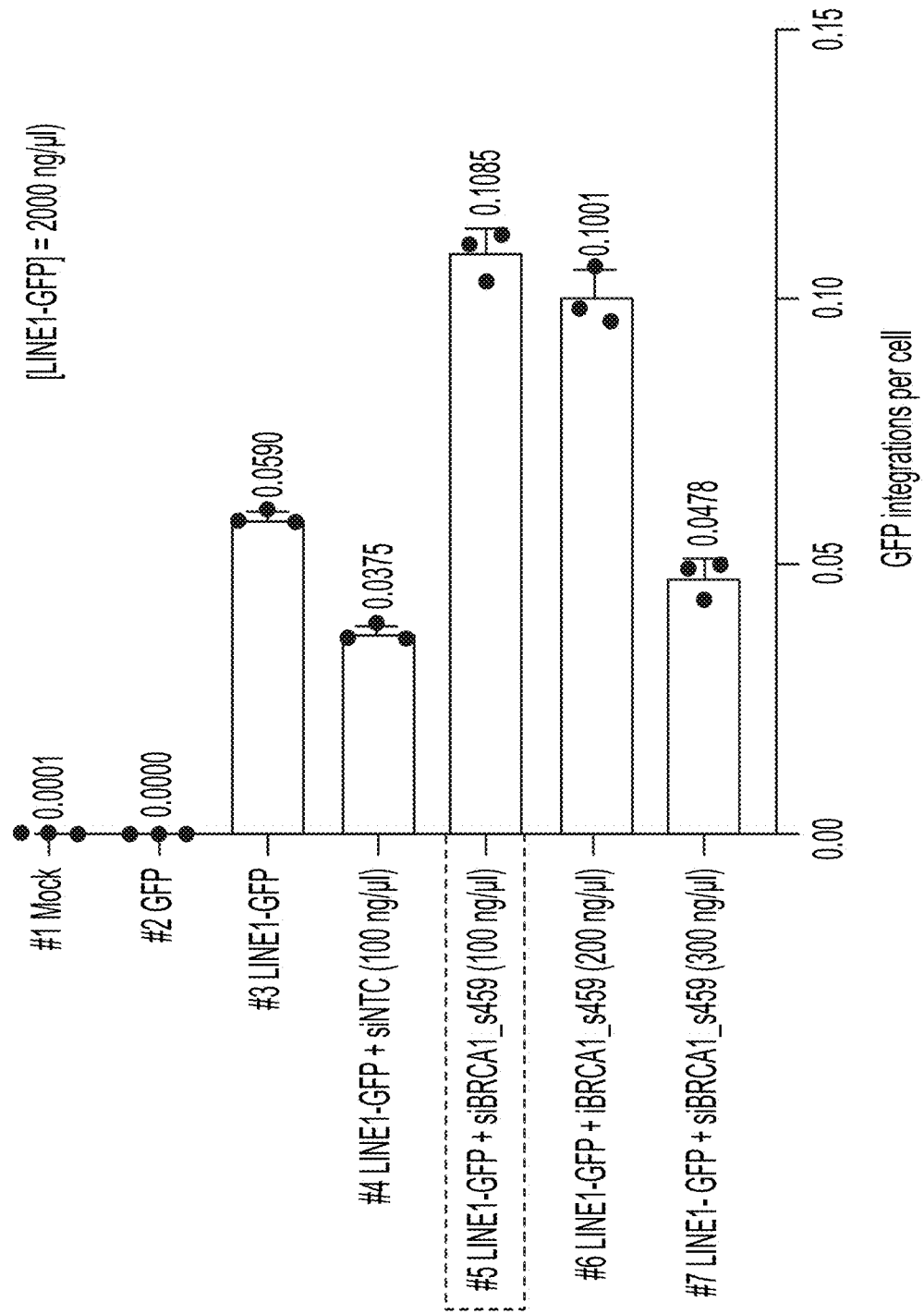
FIG. 48 depicts exemplary flow cytometry data (bottom) showing GFP+293T cells electroporated with 2000 ng/µL LINE1-GFP mRNA and 100 ng/µL, 200 ng/µL or 300 ng/µL of an siRNA targeting BRCA1 (siBRCA1) after culturing for 4 days post-electroporation and a graph of the number of GFP integrations per genome according to qPCR (top).
Figure 48:
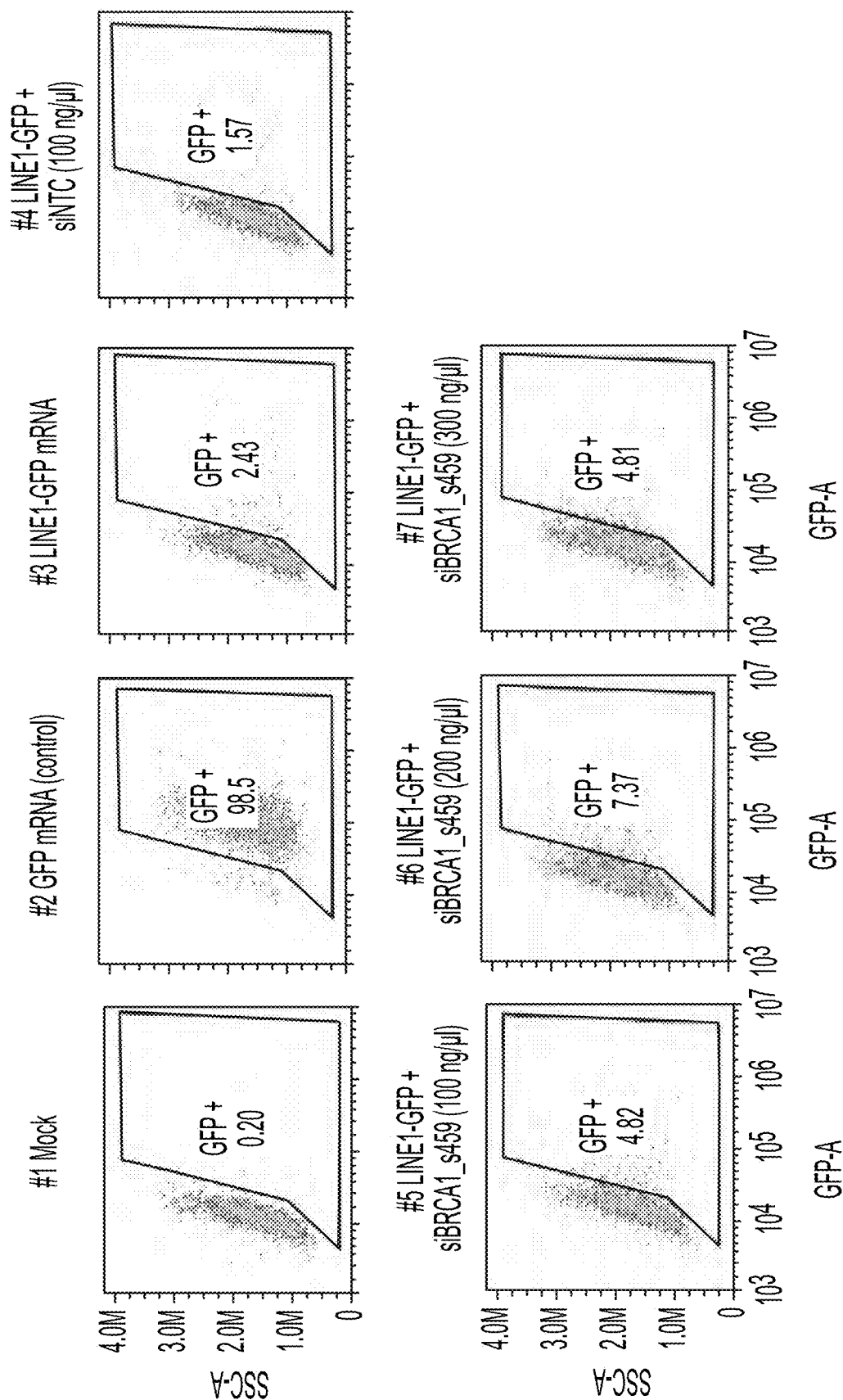
Figure 49:
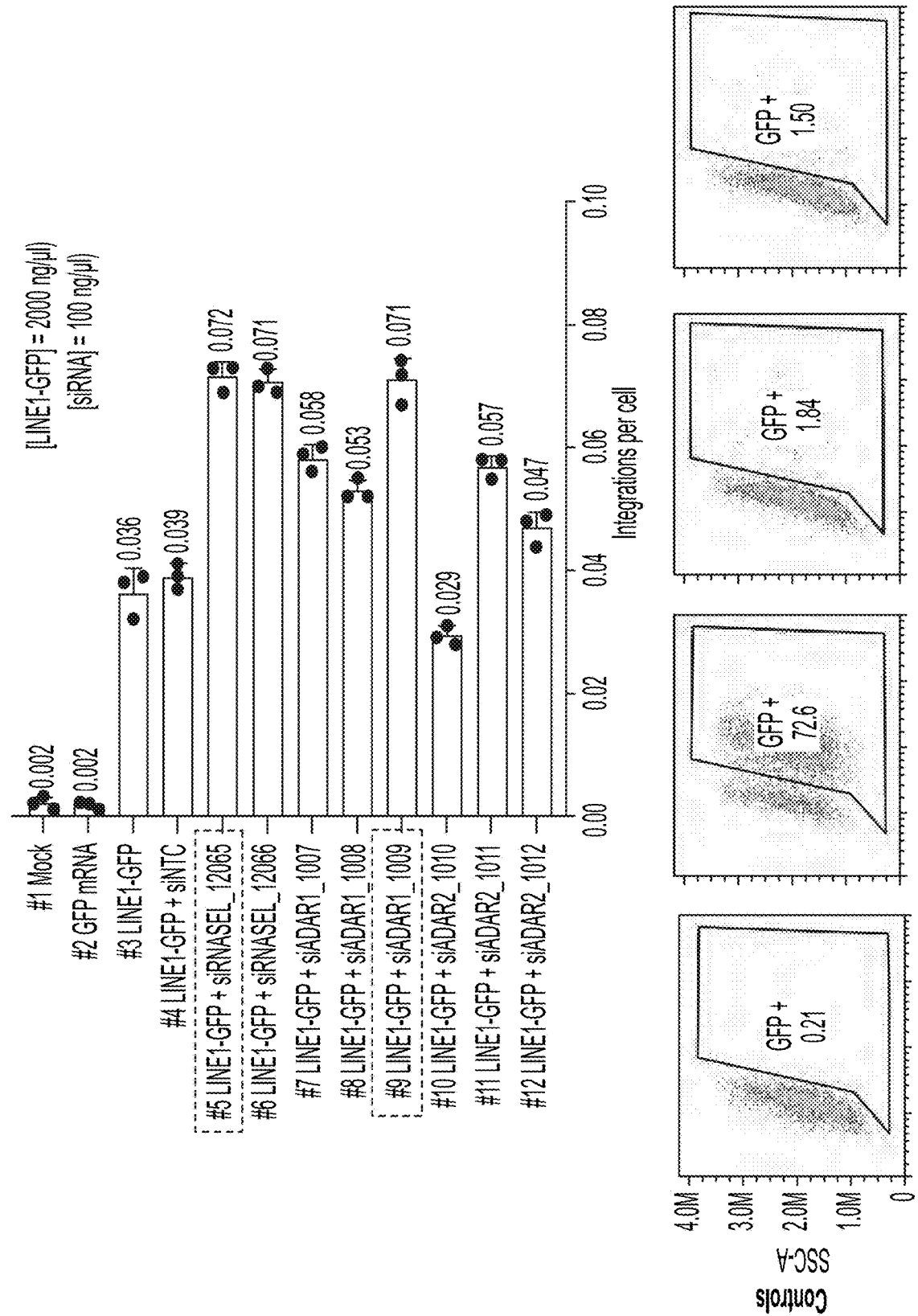
FIG. 49 depicts exemplary flow cytometry data (bottom) showing GFP+293T cells electroporated with 2000 ng/µL LINE1-GFP mRNA and 100 ng/µL of an siRNA targeting RNASEL (siRNASEL), ADAR1 (siADAR1), or ADAR2 (siADAR2) after culturing for 6 days post-electroporation and a graph of the number of GFP integrations per genome according to qPCR (top).
Figure 49:
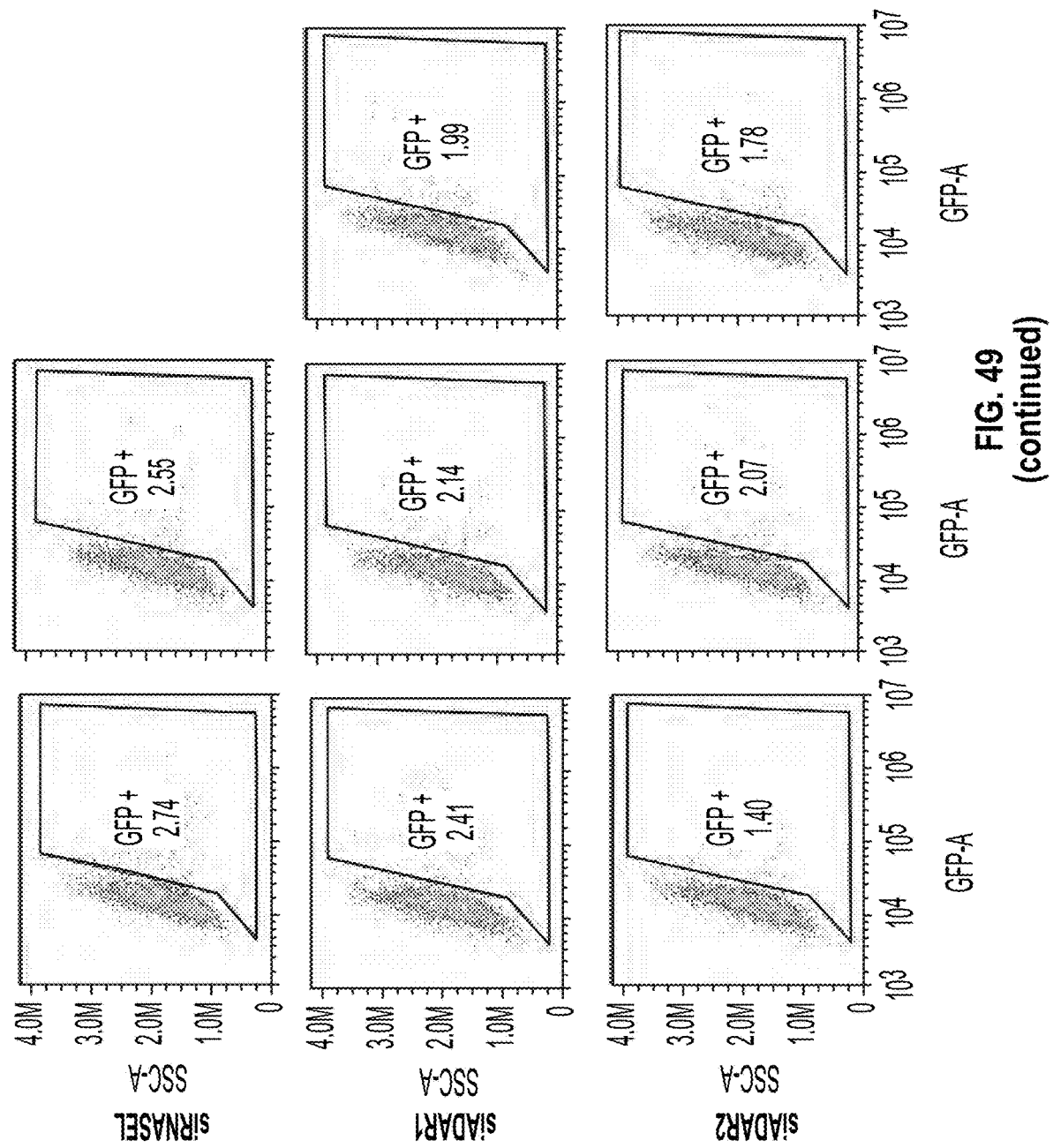
Figure 50:
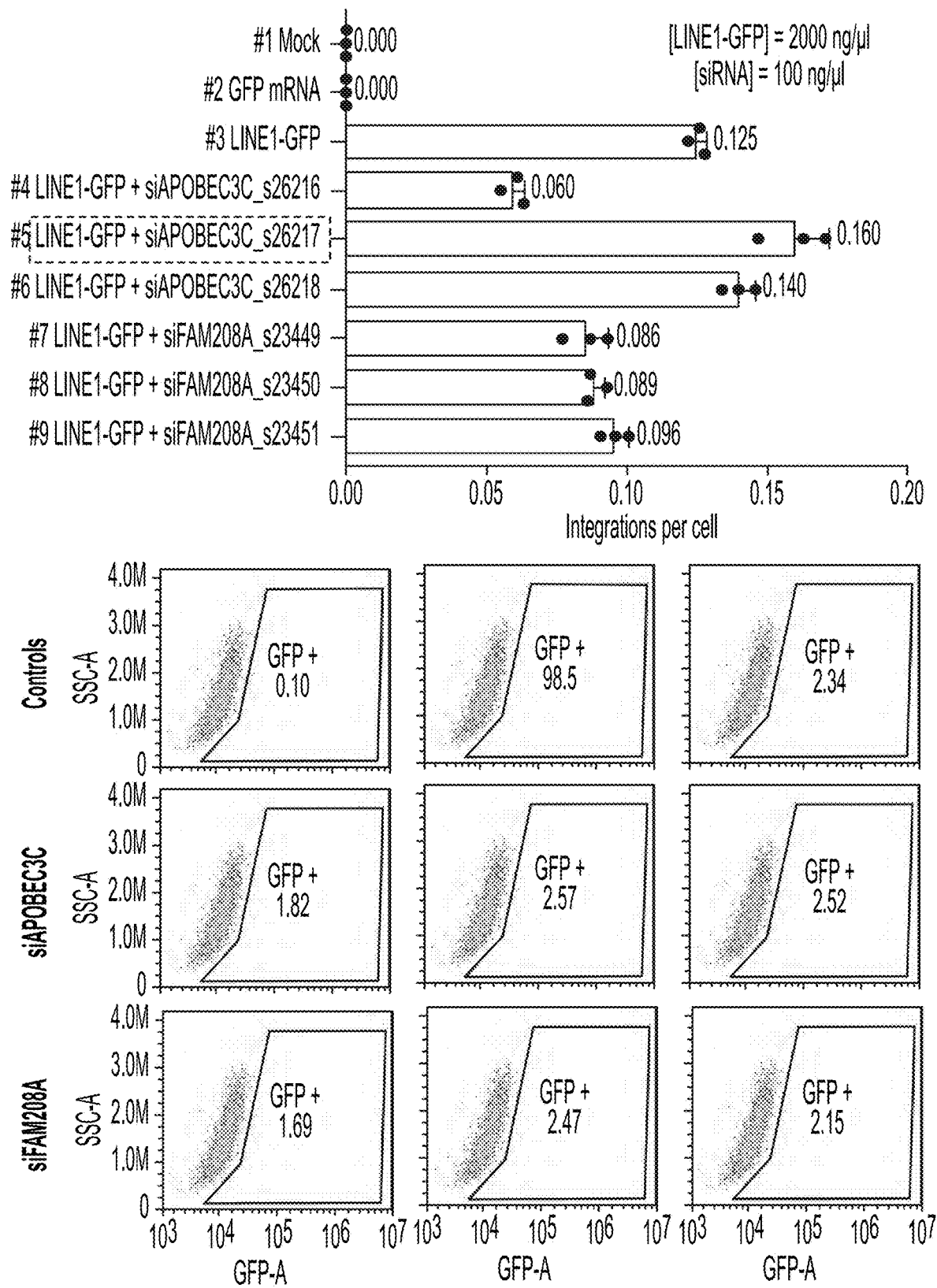
FIG. 50 depicts exemplary flow cytometry data (bottom) showing GFP+293T cells electroporated with 2000 ng/µL LINE1-GFP mRNA and 100 ng/µL of an siRNA targeting APOBEC3C (siAPOBEC3C) or FAM208A (siFAM208A) after culturing for 6 days post-electroporation and a graph of the number of GFP integrations per genome according to qPCR (top).

Example 18. Titration of mRNA Concentration for Increased Transposon Mediated Integration The concentration of LINE1-GFP mRNA used for electroporation was titrated for optimum genomic integration per cell in different cell types, 293T cells, K562 and THP-1 cells (FIGS. 42-46). 100, 500, 1000, 1500 and 2000 ng/μL of mRNA were tested for GFP expression and number of integrations per cell. Concentrations higher than 1000 ng/μl cause cell death. From the results shown in FIGS. 42, 43 and 44 that 1000 ng/μl causes a higher and long-term expression of GFP encoded by the retrotransposed integrated nucleic acid. Integrated DNA encoded protein expression starts to be detectable at day 3 and peaks around day 6-7 (FIG. 45). However, genomic integration and expression of the LINE-1 GFP mRNA in K562 and THP-1 was quite low; integration was detected at about 0.067-0.155 per cell in K562 cells (FIG. 46). (THP-1 data not shown). Higher LINE1-GFP mRNA concentrations (1500 and 2000 ng/μl) caused cell death in these cells. GFP mRNA expression in PD-0015 monocytes was detected at day 3 post electroporation, with detectable integration per cell. (FIG. 47). Steps were to be taken for more extensive DNase 1 treatment, and test mRNA batches were to be evaluated for residual plasmid before electroporation. Accuracy in determination of integration levels in the genome could be improved by first enriching for integrated DNA sequence by PCR followed by paired end sequencing leading to mapping the integration sites within the genome. Next generation sequencing is considered the gold standard in this respect, which involves gDNA extraction→shearing by sonication→DNA linkers ligated onto DNA ends→nested PCR (1: one primer for linker, second to integrated DNA, 2: Illumina sequencing adapters added)→paired-end sequencing.

Example 19. Improvement of Integration Efficiency by Knockdown of Candidates that Prevent Transposon Mediated Integration In this example, a number of endogenous candidates were knocked down using siRNA to determine if the knockdown could result in higher integration of test nucleic acid encoding GFP. Candidates included inhibitors of LINE1 retrotransposition: ADAR1, ADAR2 (ADAR1B), APOBEC3C, BRCA1, let-7 miRNA, RNase L, TASOR (HUSH complex). siRNAs (3 per target candidate) were made, electroporated in test cells along with LINE1-GFP mRNA and tested for alteration of the LINE-1 GFP expression by flow cytometry and its genome integration by qPCR and a cocktail of the siRNA that help increase LINE-1 GFP integration and expression was selected for further titration. Results from the different siRNAs tested are shown in FIGS. 48-51. Knockdown of ADAR1, BRCA and RNASEL tested individually induced about 2-fold increase in integration of LINE1-GFP. ADAR2 and APOEBEC3C each led to less than 1.5-fold increase, and let7 miRNA and TASOR each led to no increase. In the study shown in FIG. 48, LINE-1 GFP (2000 ng/μL) was electroporated with an siBRCA at 100, 200 and 300 ng/μL in 293 cells, data shown at 4 days post electroporation. With 100 ng/μL, the integration rate was approximately ~0.06 GFP copies per cell, and siBRCA1_s459 (100 ng/μl) increases integration by ~2-fold. Data shown in FIG. 49 demonstrates that at day 6 post electroporation, each of siRNASEL and siADAR1 siRNAs separately increased integration about 2-fold. On the other hand, siAPOBEC3C_s2617 increases GFP integration <1.5-fold (FIG. 50) at 6 days post electroporation.

TABLE 11

Effect of specific knockdowns on genomic integration rate.

Figure 51:
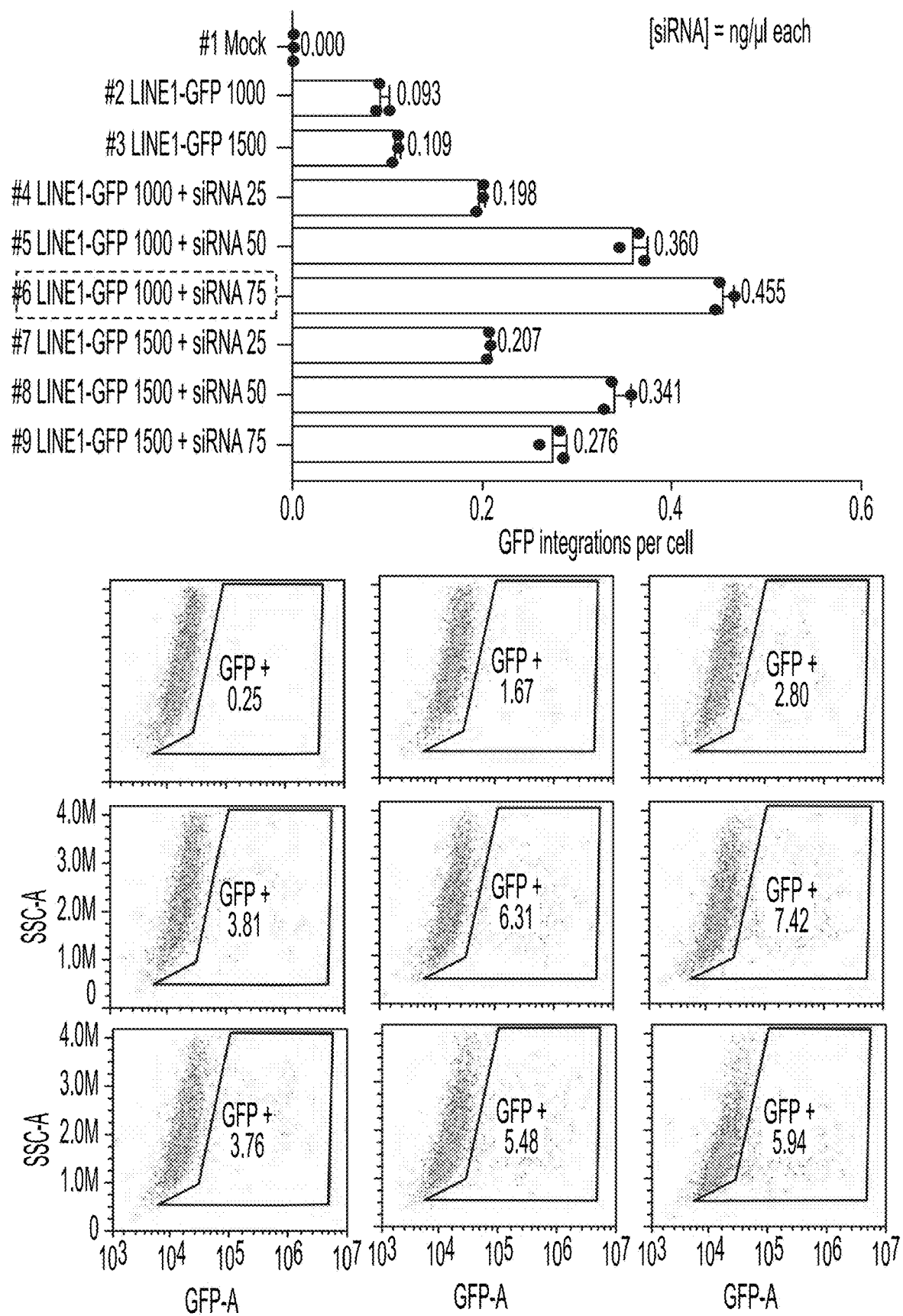
FIG. 51 depicts exemplary flow cytometry data (bottom) showing GFP+293T cells electroporated with 1000 ng/µL or 1500 ng/µL LINE1-GFP mRNA and an siRNA cocktail with 25 ng/µL, 50 ng/µL or 75 ng/µL of each siRNA targeting RNASEL (siRNASEL), ADAR1 (siADAR1), ADAR2 (siADAR2) and BRCA1 (siBRCA1) after culturing for 6 days post-electroporation and a graph of the number of GFP integrations per genome according to qPCR (top).
Figure 52:
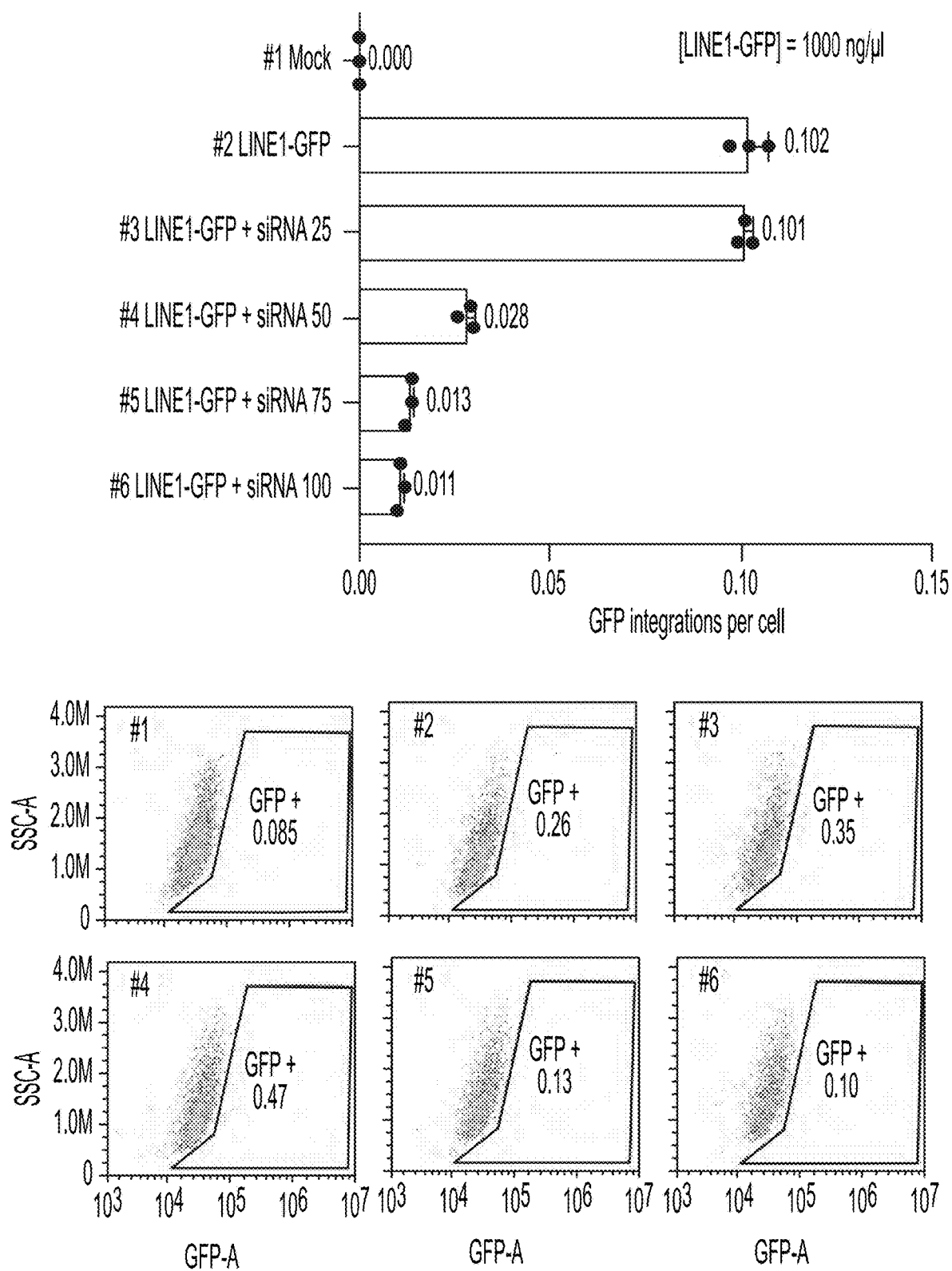
FIG. 52 depicts exemplary flow cytometry data (bottom) showing GFP+K562 cells electroporated with 1000 ng/µL LINE1-GFP mRNA and an siRNA cocktail with 25 ng/µL, 50 ng/µL or 75 ng/µL of each siRNA targeting RNASEL (siRNASEL), ADAR1 (siADAR1), ADAR2 (siADAR2) and BRCA1 (siBRCA1) after culturing for 5 days post-electroporation and a graph of the number of GFP integrations per cell according to qPCR (top).
Figure 53:
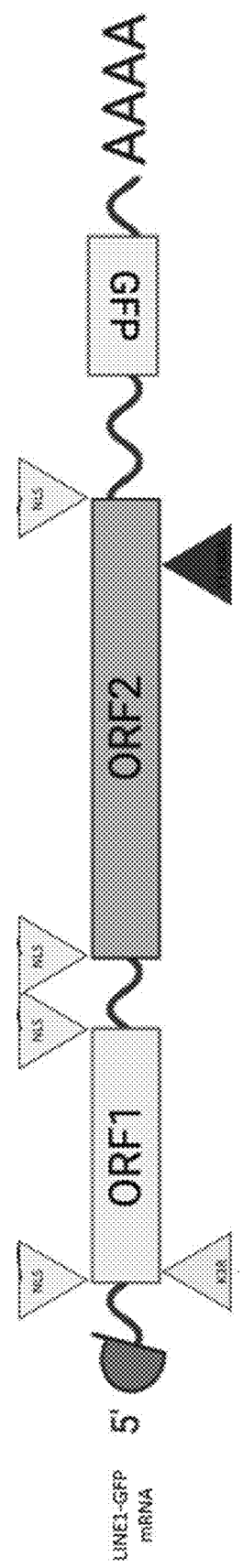
FIG. 53 depicts a schematic showing exemplary locations of extraneous nuclear localization sequences (NLS) and exemplary ORF1p and ORF2p mutations of an exemplary LINE1-GFP mRNA construct.

| Target | GFP integration fold change in 293T cells |
|---|---|
| ADAR1 | ~2 fold increase |
| ADAR2 | <1.5-fold increase |
| APOEBEC3C | <1.5-fold increase |
| BRCA | ~2 fold increase |
| Let7 miRNA | No increase |
| RNASEL | ~2 fold increase |
| TASOR (Hush complex) | No increase | siRNA against ADAR, APOEBEC3C, BRCA and RNASEL were chosen for the siRNA cocktail. Using 1000 ng/μL and 1500 ng/μL LINE1-GFP mRNA in two sets of experiments, the concentration of the siRNAs for electroporation was titrated next. It was observed that LINE1-GFP mRNA at 1500 ng/μL was slightly toxic (FIG. 51). With 1000 ng/μL, 75 ng/uL of each siRNA resulted in ~5-fold improvement of integration of GFP in 293T cells. These results were highly encouraging and support further development. Results from a similar experiment in K562 cells are shown in FIG. 52.

What is claimed is:

1. A method of expressing an exogenous human therapeutic polypeptide from a genomically integrated DNA sequence of a target human cell, the method comprising:
   (a) contacting a composition to a population of human cells comprising the target human cell, the composition comprising one or more RNA molecules comprising a first RNA sequence and a second RNA sequence, wherein the ratio of the first RNA sequence to the second RNA sequence in the composition is at least 2:1, wherein the target human cell uptakes the one or more RNA molecules, and wherein:
      (i) the first RNA sequence comprises a sequence that encodes a human ORF1p polypeptide, and
      (ii) the second RNA sequence comprises (A) a sequence that encodes a human ORF2p polypeptide and (B) a sequence that is a reverse complement of a sequence encoding the exogenous human therapeutic polypeptide;
   (b) translating the sequence of the first RNA sequence encoding the that encodes a human ORF1p polypeptide, thereby producing the human ORF1p polypeptide; and translating the sequence of the second RNA sequence encoding the human ORF2p polypeptide, thereby producing the human ORF2p polypeptide;
   (c) reverse transcribing the sequence of (a)(ii)(B) via target-primed reverse transcription (TPRT) activity of the human ORF2p polypeptide translated in step (b), thereby producing a DNA sequence encoding the exogenous human therapeutic polypeptide;
   (d) integrating the DNA sequence encoding the exogenous human therapeutic polypeptide produced in step (c) into genomic DNA of the target human cell; and
   (e) expressing the exogenous human therapeutic polypeptide in the target human cell, wherein the exogenous human therapeutic polypeptide is expressed from the DNA sequence integrated into the genomic DNA of the target human cell in step (d).

2. The method of claim 1, wherein the one or more RNA molecules comprise:
   (a) a first RNA molecule comprising the sequence of the first RNA sequence encoding the human ORF1p polypeptide,
   (b) and a second RNA molecule comprising (A) the sequence of the second RNA sequence encoding the human ORF2p polypeptide and (B) the sequence of the second RNA sequence that is the reverse complement of the sequence encoding the exogenous human therapeutic polypeptide;
   wherein the ratio of the first RNA molecule to the second RNA molecule in the composition is at least 2:1.

3. The method of claim 2, wherein the second RNA molecule has a total length of from 3 kb to 20 kb.

4. The method of claim 1, wherein the one or more RNA molecules comprise a single RNA molecule comprising:
   (a) the sequence of the first RNA sequence encoding the human ORF1p polypeptide,
   (b) the sequence of the second RNA sequence encoding the human ORF2p polypeptide, and
   (c) the sequence of the second RNA sequence that is the reverse complement of the sequence encoding the exogenous human therapeutic polypeptide.

5. The method of claim 1, wherein step (e) comprises expressing the exogenous human therapeutic polypeptide in at least 2% of the cells in the population of human cells.

6. The method of claim 5, wherein step (e) comprises expressing the exogenous human therapeutic polypeptide in at least 10% of the cells in the population of human cells.

7. The method of claim 5, wherein step (e) comprises expressing the exogenous human therapeutic polypeptide in at least 20% of the cells in the population of human cells.

8. The method of claim 1, wherein step (d) comprises integrating the DNA sequence encoding the exogenous human therapeutic polypeptide produced in step (c) into the genomic DNA at a poly T site via endonuclease activity of the human ORF2p polypeptide translated in step (b).

9. The method of claim 1, wherein the target human cell is a primary cell, a neuron, a fibroblast, a muscle cell, an epithelial cell, a retinal pigmented epithelial cell, a cardiac cell, a stem cell, or a hematopoietic cell.

10. The method of claim 1, wherein the one or more RNA molecules comprise homology arms complementary to a sequence comprising a target site in the genomic DNA.

11. The method of claim 1, wherein step (d) comprises integrating the DNA sequence encoding the exogenous human therapeutic polypeptide produced in step (c) into non-ribosomal genomic DNA of the target human cell or at a locus that is not an rDNA locus.

12. The method of claim 1, wherein the composition further comprises (i) one or more siRNAs and/or (ii) an RNA guide sequence or a polynucleic acid encoding the RNA guide sequence, and wherein the RNA guide sequence targets a DNA target site of the genomic DNA and the DNA sequence encoding the exogenous human therapeutic polypeptide produced in step (c) is integrated into the genomic DNA at the DNA target site of the genomic DNA in step (d).

13. The method of claim 1, wherein step (a) comprises administering the composition to a human subject.

14. The method of claim 1, wherein the exogenous human therapeutic polypeptide is selected from the group consisting of a ligand, an antibody, a receptor, an enzyme, a transport protein, a structural protein, a hormone, a contractile protein, a storage protein and a transcription factor.

15. The method of claim 14, wherein the exogenous human therapeutic polypeptide is a receptor selected from the group consisting of a chimeric antigen receptor (CAR) and a T cell receptor (TCR).

16. The method of claim 1, wherein the composition is a pharmaceutical composition formulated for systemic administration to a human subject.

17. The method of claim 1, wherein the ratio of the first RNA sequence to the second RNA sequence in the composition is at most 5:1.

18. The method of claim 1, wherein the ratio of the first RNA sequence to the second RNA sequence in the composition is about 3:1.

19. The method of claim 1, wherein the human ORF2p polypeptide comprises a nuclear localization signal (NLS).

20. The method of claim 19, wherein the NLS comprises a C-terminal NLS, an N-terminal NLS, or both.

21. The method of claim 1, wherein the one or more RNA molecules comprises a 5' UTR sequence and a 3' UTR sequence, wherein
   (a) the 5' UTR comprises a 5' UTR from LINE-1; and/or
   (b) the 3' UTR comprises a 3' UTR from LINE-1.

22. The method of claim 1, wherein the sequence encoding the exogenous human therapeutic polypeptide does not comprise introns.

23. The method of claim 1, wherein the target human cell is an immune cell selected from the group consisting of a T cell, a B cell, a myeloid cell, a monocyte, a macrophage and a dendritic cell.

24. The method of claim 1, wherein the human ORF1p polypeptide comprises a sequence with at least 80% sequence identity to SEQ ID NO: 53.

25. The method of claim 1, wherein the one or more RNA molecules
   (i) is formulated in a nanoparticle selected from the group consisting of a lipid nanoparticle and a polymeric nanoparticle; and/or
   (ii) comprise a glycosylated RNA molecule, a circular RNA molecule or a self-replicating RNA molecule.

26. The method of claim 1, wherein the human ORF2p polypeptide comprises a sequence with at least 80% sequence identity to SEQ ID NO: 55.

* * * * *

UNITED STATES PATENT AND TRADEMARK OFFICE
CERTIFICATE OF CORRECTION

| | |
|---|---|
| PATENT NO. | : 11,672,874 B2 |
| APPLICATION NO. | : 17/499232 |
| DATED | : June 13, 2023 |
| INVENTOR(S) | : Daniel Getts et al. |

It is certified that error appears in the above-identified patent and that said Letters Patent is hereby corrected as shown below:

In the Claims

Column 461, Line 34:
"encoding the that encodes a human" should read --encoding the human--

Signed and Sealed this
Fifth Day of September, 2023

Katherine Kelly Vidal
*Director of the United States Patent and Trademark Office*